US011312783B2

(12) United States Patent
Prinz et al.

(10) Patent No.: US 11,312,783 B2
(45) Date of Patent: Apr. 26, 2022

(54) ANTIBODY MOLECULES TO CD73 AND USES THEREOF

(71) Applicants: Novartis AG, Basel (CH); SURFACE ONCOLOGY, INC., Cambridge, MA (US)

(72) Inventors: Bianka Prinz, Lebanon, NH (US); Jerry M. Thomas, Lebanon, NH (US); Ansgar Brock, San Diego, CA (US); Scott Chappel, Cambridge, MA (US); Andrew Lake, Cambridge, MA (US); Alison Paterson, Cambridge, MA (US); Rachel W. O'Connor, Cambridge, MA (US); Michael Warren, Cambridge, MA (US); Pamela Holland, Cambridge, MA (US); Dirksen Bussiere, Emeryville, CA (US); Mikias Woldegiorgis, Oakland, CA (US); Wei Shu, Danville, CA (US); John Delmas Venable, San Diego, CA (US); Michael Gladstone, Cambridge, MA (US); Jonathan Hill, Cambridge, MA (US); Christine Miller, Cambridge, MA (US)

(73) Assignees: Novartis AG, Basel (CH); SURFACE ONCOLOGY, INC., Cambridge, MA (US)

( * ) Notice: Subject to any disclaimer, the term of this patent is extended or adjusted under 35 U.S.C. 154(b) by 599 days.

(21) Appl. No.: 16/014,744

(22) Filed: Jun. 21, 2018

(65) Prior Publication Data

US 2019/0031766 A1 Jan. 31, 2019

Related U.S. Application Data

(60) Provisional application No. 62/636,510, filed on Feb. 28, 2018, provisional application No. 62/523,481, filed on Jun. 22, 2017.

(51) Int. Cl.

| | |
|---|---|
| ***C07K 16/28*** | (2006.01) |
| ***A61K 39/395*** | (2006.01) |
| ***A61K 31/495*** | (2006.01) |
| ***A61K 39/40*** | (2006.01) |
| ***A61P 35/00*** | (2006.01) |
| ***A61K 45/06*** | (2006.01) |
| ***G01N 33/68*** | (2006.01) |
| *A61K 39/00* | (2006.01) |

(52) U.S. Cl.

CPC ........ *C07K 16/2896* (2013.01); *A61K 31/495* (2013.01); *A61K 39/395* (2013.01); *A61K 39/3955* (2013.01); *A61K 39/39533* (2013.01); *A61K 39/40* (2013.01); *A61K 45/06* (2013.01); *A61P 35/00* (2018.01); *C07K 16/2818* (2013.01); *G01N 33/68* (2013.01); *A61K 2039/505* (2013.01); *A61K 2039/507* (2013.01); *A61K 2039/545* (2013.01); *C07K 2317/34* (2013.01); *C07K 2317/76* (2013.01); *C07K 2317/90* (2013.01); *C07K 2317/92* (2013.01); *C07K 2317/94* (2013.01); *G01N 2333/70596* (2013.01)

(58) Field of Classification Search

CPC .......... A61K 2039/505; A61K 39/3955; A61K 2039/507; A61K 39/395; A61P 35/00; C07K 2317/76; C07K 2317/92; C07K 2317/34; C07K 16/2896; C07K 2317/94; C07K 2317/90

See application file for complete search history.

(56) References Cited

U.S. PATENT DOCUMENTS

| | | | | |
|---|---|---|---|---|
| 9,605,080 | B2 * | 3/2017 | Lonberg | A61P 35/04 |
| 9,938,356 | B2 | 4/2018 | Hay et al. | |
| 10,100,129 | B2 * | 10/2018 | Lonberg | G01N 33/573 |
| 10,167,343 | B2 * | 1/2019 | Lonberg | C07K 16/30 |
| 10,287,362 | B2 | 5/2019 | Hay et al. | |
| 10,556,968 | B2 | 2/2020 | Hay et al. | |
| 10,766,966 | B2 | 9/2020 | Perrot et al. | |
| 10,864,269 | B2 | 12/2020 | Sachsenmeier et al. | |
| 2013/0109645 | A1 | 5/2013 | Gahl et al. | |
| 2016/0129108 | A1 | 5/2016 | Sachsenmeier et al. | |
| 2016/0145350 | A1 | 5/2016 | Lonberg et al. | |
| 2016/0194407 | A1 | 7/2016 | Hay et al. | |
| 2017/0253665 | A1 | 9/2017 | Lonberg et al. | |
| 2018/0030144 | A1 | 2/2018 | Chanteux et al. | |
| 2018/0125973 | A1 | 5/2018 | Sachsenmeier et al. | |
| 2018/0127513 | A1 | 5/2018 | Lonberg et al. | |
| 2018/0194858 | A1 | 7/2018 | Hay et al. | |
| 2018/0237536 | A1 | 8/2018 | Perrot et al. | |
| 2019/0055320 | A1 | 2/2019 | Lonberg et al. | |
| 2019/0062456 | A1 | 2/2019 | Lonberg et al. | |

(Continued)

FOREIGN PATENT DOCUMENTS

| | | | |
|---|---|---|---|
| EP | 0118311 | B1 | 9/1984 |
| EP | 3218406 | B1 | 9/2017 |

(Continued)

OTHER PUBLICATIONS

Geoghegan et al, "Inhibition of CD73 AMP hydrolysis by a therapeutic antibody with a dual, non-competitive mechanism of action" mAbs (2016) vol. 8, No. 3, pp. 454-467.

(Continued)

*Primary Examiner* — Zachary C Howard
(74) *Attorney, Agent, or Firm* — Lando & Anastasi, LLP

(57) ABSTRACT

Antibody molecules that bind to CD73 are disclosed. The anti-CD73 antibody molecules can be used to treat, prevent and/or diagnose cancer.

26 Claims, 40 Drawing Sheets

Specification includes a Sequence Listing.

(56) References Cited

U.S. PATENT DOCUMENTS

2019/0225703 A1 7/2019 Caux et al.
2019/0284293 A1 9/2019 Lonberg et al.
2019/0292274 A1 9/2019 Hay et al.
2019/0352420 A1 11/2019 Hofmann et al.
2020/0079877 A1 3/2020 Hay et al.
2020/0392243 A1 12/2020 Perrot et al.

FOREIGN PATENT DOCUMENTS

WO 2009036379 A2 3/2009
WO 2010105256 A1 9/2010
WO 2011123518 A1 10/2011
WO 2012009568 A2 1/2012
WO 2012031320 A1 3/2012
WO 2016055609 A1 4/2016
WO 2016075099 A1 5/2016
WO 2016075176 A1 5/2016
WO 2016081748 A2 5/2016
WO 2016131950 A1 8/2016
WO 2016185016 A1 11/2016
WO 2017064043 A1 4/2017
WO 2017152085 A1 9/2017
WO 2018013611 A1 1/2018
WO 2019224025 A2 11/2019
WO 2019232244 A2 12/2019
WO 2021032173 A1 2/2021
WO 2021097223 A2 5/2021

OTHER PUBLICATIONS

Invitation to Pay Additional Fees and Partial Search Report for International Application No. PCT/US2018/038775 dated Aug. 30, 2018.
Terp et al., "Anti-Human CD73 Monoclonal Antibody Inhibits Metastasis Formation in Human Breast Cancer by Inducing Clustering and Internalization of CD73 Expressed on the Surface of Cancer Cells" The Journal of Immunology (2013) vol. 191, pp. 4165-4173.
Allard et al., "Targeting CD73 Enhances the Antitumor Activity of Anti-PD-1 and Anti-CTLA-4 mAbs," Clin Cancer Res (2013) vol. 19, No. 20, pp. 5626-5635.
Hay et al. "Targeting CD73 in the tumor microenvironment with MEDI9447" Oncoimmunology (2016) vol. 5, No. 8, e1208875, pp. 1-10.
Huang et al., "Levels and Enzyme Activity of CD73 in Primary Samples From Cancer Patients," AACR Annual Meeting Abstracts (2015) Abstract #1538.
International Search Report and Written Opinion for International Application No. PCT/US2019/034706 dated Jan. 24, 2020.
International Search Report and Written Opinion issued in PCT/US2018-038805, dated Nov. 12, 2018.
Invitation to Pay Adiditional Fees from International Application No. PCT/US2019/034706 dated Nov. 26, 2019.
Rudikoff et al. "Single amino acid substitution altering antigen-binding specificity" PNAS (1982) vol. 79, pp. 1979-1983.
Siu et al. "Abstract CT180: Preliminary phase 1 profile of BMS-986179, an anti-CD73 antibody, in combination with nivolumab in patients with advanced solid tumors" Cancer Research (2018) vol. 78, No. 13, Supp S, pp. CT180.
Allard et al., "Targeting CD73 and downstream adenosine receptor signaling in triple-negative breast cancer" Expert Opin Ther Targets (2014) vol. 18, pp. 863-881.
Allard, et al., "CD73-adenosine: a next-generation target in immuno-oncology" Immunotherapy (2016) vol. 8, pp. 145-163.
Allard, et al., "Immunosuppressive activities of adenosine in cancer" Curr Opin Pharmacol (2016) vol. 29, pp. 7-16.
Chalmers et al., "Probing protein ligand interactions by automated hydrogen/deuterium exchange mass spectrometry" Anal. Chem (2006) vol. 78, No. 4, pp. 1005-1014.
Colgan et al., "Physiological roles for ecto-5'-nucleotidase (CD73)" Prinergic Signal (2006)vol. 2, pp. 351-360.
Estep et al, "High throughput solution-based measurement of antibody-antigen affinity and epitope binning" Mabs (2013) vol. 5, No. 2, pp. 270-278.
Gaudreau et al., "CD73-adenosine reduces immune responses and survival in ovarian cancer patients" Oncoimmunology (2016) vol. 5, No. 5, e1127496.
Inoue et al., "Prognostic impact of CD73 and A2A adenosine receptor expression in non-small-cell lung cancer" Oncotarget. (2017) vol. 8, No. 5, pp. 8738-8751 ).
Jin et al., "CD73 on tumor cells impairs antitumor T-cell responses: a novel mechanism of tumor-induced immune suppression" Cancer Research (2010) vol. 70, pp. 2245-2255.
Knapp et al., "Crystal structure of the human ecto-5'-nucleotidase (CD73): insights into the regulation of purinergic signaling" Structure (2012) vol. 20, pp. 2161-2173.
Leclerc et al., "CD73 Expression Is an Independent Prognostic Factor in Prostate Cancer" Clin Cancer Res (2016) vol. 22, pp. 158-166.
Ohta et al., "A2A adenosine receptor protects tumors from antitumor T cells" PNAS (2006) vol. 103, No. 35, pp. 13132-13137.
Park et al., "Estimation of Hydrogen-Exchange Protection Factors from MD Simulation Based on Amide Hydrogen Bonding Analysis" J. Chem. Inf. Model (2015) vol. 55, No. 9, pp. 1914-1925.
Ren et al., "CD73 as a novel marker for poor prognosis of oral squamous cell carcinoma" Oncol Lett (2016) vol. 12, pp. 556-562.
Ren et al., "CD73 is associated with poor prognosis in HNSCC" Oncotarget (2016)vol. 7, pp. 61690-61702.
Resta et al., "Ecto-enzyme and signaling functions of lymphocyte CD 7 3" Immunol Rev (1998) vol. 161 pp. 95-109.
Siegel et al, "High efficiency recovery and epitope-specific sorting of an scFv yeast display library" J Immunol Methods (2004) vol. 286, No. 1-2, pp. 141-153.
Stagg et al., "Anti-CD73 antibody therapy inhibits breast tumor growth and metastasis" PNAS (2010) vol. 107, pp. 1547-1552.
Turcotte et al., "CD73 is associated with poor prognosis in high-grade serous ovarian cancer" Cancer Res (2015) vol. 75, pp. 4494-4503.
Venable et al, "Isotope-Coded Labeling for Accelerated Protein Interaction Profiling Using MS" Analytical Chemistry (2015) vol. 87, No. 15, pp. 7540-7544.
Vesley et al., "Natural innate and adaptive immunity to cancer" Annu Rev Immunol (2011) vol. 29, pp. 235-271.
Wu et al., "High expression of CD73 as a poor prognostic biomarker in human colorectal cancer" Journal of Surgical Oncology (2012) vol. 106, No. 2, pp. 130-137.
Xu et al, "Addressing polyspecificity of antibodies selected from an in vitro yeast presentation system: a FACS-based, high-throughput selection and analytical tool" PEDS (2013) vol. 26, No. 10, pp. 663-670.
Young et al., "Targeting cancer-derived adenosine: new therapeutic approaches" Cancer Discovery (2014) vol. 4, No. 8, pp. 879-888.
Zhang, "CD73: a novel target for cancer immunotherapy" Cancer Research (2010) vol. 70, pp. 6407-6411.
Young, et al. "Co-inhibition of CD73 and A2AR Adenosine Signaling Improves Anti-tumor Immune Responses" Cancer Cell (2016) vol. 30, pp. 391-403.
Singapore Written Opinion for Singapore Application No. 11201912473P dated Jun. 25, 2021.
Brown et al. "Tolerance of single, but not multiple, amino acid replacements in antibody VH CDR 2: a means of minimizing B cell wastage from somatic hypermutation?" The Journal of Immunology (1996) vol. 156, No. 9, pp. 3285-3291.
"Monoclonal Antibody to CD73 (Clone: ABM40E2)" Facebook Post by Abgenex dated May 24, 2016; https://www.facebook.com/Abgenex/posts/1777266845893656?comment_id=1777266915893649&usg=AOvVaw2IH-RXjtWawBceFKoRYbFv; Retrieved from the internet Nov. 21, 2021.
Abgenex.com "Monoclonal Antibody to CD73 (Clone: ABM40E2)" Product code: 10-4106; https://abgenex.com/10-4106/Monoclonal-Antibody-to-CD73-Clone-ABM40E2?fbclid=IwAR1BXiEskeUA9

(56) References Cited

OTHER PUBLICATIONS

6MV6Db7dbKI1GPvLoBBgtAuaqhdsceed8mxAwitmxUn_ws; Retrieved from the internet Nov. 21, 2021.
Airas et al. "Differential regulation and function of CD73, a glycosyl-phosphatidylinositol-linked 70-kD adhesion molecule, on lymphocytes and endothelial cells" The Journal of Cell Biology (1997) vol. 136, No. 2, pp. 421-431.
Barry et al. "The SH-3 and SH-4 antibodies recognize distinct epitopes on CD73 from human mesenchymal stem cells" Biochem Biophys Res Commun. (2001) vol. 289, No. 2, pp. 519-524.
Chen et al. "Smooth Muscle Cell Reprogramming in Aortic Aneurysms" Cell Stem Cell (2020) vol. 26, No. 4, pp. 542-557, e11.
Cinti et al. "Simultaneous Overexpression of Functional Human HO-1, E5NT and ENTPD1 Protects Murine Fibroblasts against TNF-?-Induced Injury In Vitro" PLoS One (2015) vol. 10, No. 10, e0141933, pp. 1-23.
Crane et al. "Ecto-5'-nucleotidase and intestinal ion secretion by enteropathogenic *Escherichia coli*" Purinergic signalling (2007) vol. 3, No. 3, pp. 233-246.
Delcourt et al. "Targeted identification of sialoglycoproteins in hypoxic endothelial cells and validation in zebrafish reveal roles for proteins in angiogenesis" The Journal of Biological Chemistry (2015) vol. 290, No. 6, pp. 3405-3417.
Fausther et al. "NT5E mutations that cause human disease are associated with intracellular mistrafficking of NT5E protein" PLoS One (2014) vol. 9, No. 6, e98568, pp. 1-11.
Garcia-Esparcia et al. "Purine metabolism gene deregulation in Parkinson's disease" Neuropathology and Applied Neurobiology (2015) vol. 41, No. 7, pp. 926-940.
Goudenege et al. "Myoblasts Derived From Normal hESCs and Dystrophic hiPSCs Efficiently Fuse With Existing Muscle Fibers Following Transplantation" Molecular Therapy (2012) vol. 20, No. 11, pp. 2153-2167.
Grozio et al. "CD73 protein as a source of extracellular precursors for sustained NAD+ biosynthesis in FK866-treated tumor cells" J Biol Chem (2013) vol. 288, No. 36, pp. 25938-25949.
Hausler et al. "Anti-CD39 and anti-CD73 antibodies A1 and 7G2 improve targeted therapy in ovarian cancer by blocking adenosine-dependent immune evasion" Am J Transl Res (2014) vol. 6, No. 2, pp. 129-139.
Kruger et al. "Expression of ecto-5'-nucleotidase (CD73) in normal mammary gland and in breast carcinoma" Br J Cancer (1991) vol. 63, No. 1, pp. 114-118.
Kummer et al. "Development and Properties of a Monoclonal Antibody Specific for Human Ecto-5'-Nucleotidase" Immunobiology (1984) vol. 166, No. 2, pp. 203-211.
Kummer et al. "Production and Properties of Monoclonal Antibodies against Human Ecto-5?-Nucleotidase" Purine and Pyrimidine Metabolism in Man V. Advances in Experimental Medicine and Biology (1986) vol. 195B, pp. 385-389.
Misumi et al. "Primary structure of human placental 5'-nucleotidase and identification of the glycolipid anchor in the mature form" Eur. J. Biochem. (1990) vol. 191, No. 3, pp. 563-569.
Ntokou et al. "Characterization of the platelet-derived growth factor receptor-a-positive cell lineage during murine late lung development" Am J Physiol Lung Cell Mol Physiol (2015) vol. 309, No. 9, pp. L942-L958.
Supernat et al. "CD73 expression as a potential marker of good prognosis in breast carcinoma" Applied Immunohistochemistry & Molecular Morphology (2012) vol. 20, No. 2, pp. 103-107.
Thompson et al. "Antibodies to 5'-nucleotidase (CD73), a glycosyl-phosphatidylinositol-anchored protein, cause human peripheral blood T cells to proliferate" J Immunol. (1989) vol. 143, No. 6, pp. 1815-1821.
Thompson et al. "Crucial role for ecto-5'-nucleotidase (CD73) in vascular leakage during hypoxia" The Journal of Experimental Medicine (2004) vol. 200, No. 11, pp. 1395-1405.
Thomson et al. "Production and characterization of monoclonal antibodies to the glycosyl phosphatidylinositol-anchored lymphocyte differentiation antigen ecto-5'-nucleotidase (CD73)" Tissue antigens (1990) vol. 35, No. 1, pp. 9-19.
ABIN1724945; NT5E antibody from antibodies—online; https://www.antibodypedia.com/gene/3007/NT5E/antibody/1489049/ABIN1724945; Retrieved from the internet Nov. 22, 2021.
CD73 Antikörper (2B6): sc-130006; https://www.scbt.com/p/cd73-antibody-2b6?productCanUrl=cd73-antibody-2b6&_requestid=62460; Retrieved from the internet Nov. 22, 2021.
ABIN316595; NT5E antibody from antibodies—online; https://www.antibodypedia.com/gene/3007/NT5E/antibody/1459269/ABIN316595; Retrieved from the internet Nov. 22, 2021.
ABIN2472417; NT5E antibody from antibodies—online; https://www.antibodypedia.com/gene/3007/NT5E/antibody/2313953/ABIN2472417; Retrieved from the internet Nov. 22, 2021.
ABIN562052; NT5E antibody from antibodies—online; https://www.antibodypedia.com/gene/3007/NT5E/antibody/746177/ABIN562052; Retrieved from the internet Nov. 22, 2021.
Anti-CD73 antibody [7G2] (ab54217) from Abcam; https://www.abcam.com/cd73-antibody-7g2-ab54217.html; Retrieved from the internet Nov. 22, 2021.
5'-Nucleotidase/CD73 Antibody (4G4) [NBP1-60135]from Novus Biologicals; https://www.novusbio.com/products/5-nucleotidase-cd73-antibody-4g4_nbp1-60135#reviews-publications; Retrieved from the internet Nov. 22, 2021.
NT5E monoclonal antibody (M01), clone 4C4-2B5 [H00004907-M01] from Abnova; http://www.abnova.com/products/products_detail.asp?catalog_id=H00004907-M01; Retrived from the internet Nov. 22, 2021.
NT5E/CD73 (D7F9A) Rabbit mAb #13160 from Cell Signaling; https://www.cellsignal.com/products/primary-antibodies/nt5e-cd73-d7f9a-rabbit-mab/13160; Retrieved from the internet Nov. 22, 2021.
CD73 Monoclonal Antibody (AD2), APC, eBioscience [17-0739-42] from ThermoFisher Scientific; https://www.thermofisher.com/antibody/product/CD73-Antibody-clone-AD2-Monoclonal/17-0739-42; Retrieved from the internet Nov. 22, 2021.
CD73 Antikörper (IE9): sc-32299; https://www.scbt.com/de/p/cd73-antibody-ie9; Retrieved from the internet Nov. 22, 2021.
NBP2-46259; NT5E antibody from Novus Biologicals; https://www.antibodypedia.com/gene/3007/NT5E/antibody/2368629/NBP2-46259; Retrieved from the internet Nov. 22, 2021.
Dondelinger et al., "Understanding the Significance and Implications of Antibody Numbering and Antigen-Binding Surface/Residue Definition," Frontiers in Immunology (2018) vol. 9, Article 2278, 15 pages.

* cited by examiner

MCPRAARAPATLLLALGAVLWPAAGAWELTILHTNDVHSRLEQTSEDSSKCVNASRC
MGGVARLFTKVQQIRRAEPNVLLLDAGDQYQGTIWFTVYKGAEVAHFMNALRYDA
MALGNHEFDNGVEGLIEPLLKEAKFPILSANIKAKGPLASQISGLYLPYKVLPVGDEVVG
IVGYTSKETPFLSNPGTNLVFEDEITALQPEVDKLKTLNVNKIIALGHSGFEMDKLIAQKV
RGVDVVVGGHSNTFLYTGNPPSKEVPAGKYPFIVTSDDGRKVPVVQAYAFGKYLGYLKI
EFDERGNVISSHGNPILLNSSIPEDPSIKADINKWRIKLDNYSTQELGKTIVYLDGSSQSC
RFRECNMGNLICDAMINNNLRHADETFWNHVSMCILNGGGIRSPIDERNNGTITWE
NLAAVLPFGGTFDLVQLKGSTLKKAFEHSVHRYGQSTGEFLQVGGIHVVYDLSRKPGD
RVVKLDVLCTKCRVPSYDPLKMDEVYKVILPNFLANGGDGFQMIKDELLRHDSGDQDI
NVVSTYISKMKVIYPAVEGRIKHHHHHH (SEQ ID NO: 332)

FIG. 26A

MCPRAARAPATLLLALGAVLWPAAGAWELTILHTNDVHSRLEQTSEDSSKCVNASRC
MGGVARLFTKVQQIRRAEPNVLLLDAGDQYQGTIWFTVYKGAEVAHFMNALRYDA
MALGNHEFDNGVEGLIEPLLKEA*KFP*ILSANIKAKGPLASQI*SGLYLPYKVLPVGDEV*V
GIVGYTSKETPFLSNPGTNLVFEDEITALQPEVDKLKTLNVNKIIALGHSGFEMDKLIAQK
VRGVDVVVGGHSNTFLYTGNPPSKEVPAGKYPFIVTSDDGRKVPVVQAYAFGKYLGYL
KIEFDERGNVISSHGNPILLNSSIPEDPSIKADINKWRIKLDNYSTQELGKTIVYLDGSSQS
CRFRECNMGNLICDAMINNNLRHADETFWNHVSMCILNGGGIRSPIDERNNGTITW
ENLAAVLPFGGTFDLVQLKGSTLKKAFEHSVHRYGQSTGEFLQVGGIHVVYDLSRKPG
DRVVKLDVLCTKCRVPSYDPLKMDEVYKVILPNFLANGGDGFQMIKDELLRHDSGDQ
DINVVSTYISKMKVIYPAVEGRIKHHHHHH (SEQ ID NO: 332)

FIG. 26B

QVQLQESGPGLVKPSETLSLTCTVSGGSIERYYWSWIRQPPGKGLEWIGYIYGRGS
TNYNPSLKSRVTISVDTSKNQFSLKLSSVTAADTAVYYCARESQESPYNNWFDPW
GQGTLVTVSSASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKVDKRVESKYG
P (SEQ ID NO: 331)

FIG. 26C

QVQLQESGPGLVKPSETLSLTCTVSGGSIERYYWSWIRQPPGKGLEWIGYIYGRGS
TNYNPSLKSRVTISVDTSKNQFSLKLSSVTAADTAVYYCARESQESPYNNWFDPW
GQGTLVTVSSASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKVDKRVESKYG
P (SEQ ID NO: 331)

FIG. 26D

MCPRAARAPATLLLALGAVLWPAAGAWELTILHTNDVHSRLEQTSEDSSKCVNASRC
MGGVARLFTKVQQIRRAEPNVLLLDAGDQYQGTIWFTVYKGAEVAHFMNALRYDA
MALGNHEFDNGVEGLIEPLLKEAKFPILSANIKAKGPLASQISGLYLPYKVLPVGDEVVG
IVGYTSKETPFLSNPGTNLVFEDEITALQPEVDKLKTLNVNKIIALGHSGFEMDKLIAQKV
RGVDVVVGGHSNTFLYTGNPPSKEVPAGKYPFIVTSDDGRKVPVVQAYAFGKYLGYLKI
EFDERGNVISSHGNPILLNSSIPEDPSIKADINKWRIKLDNYSTQELGKTIVYLDGSSQSC
RFRECNMGNLICDAMINNNLRHADETFWNHVSMCILNGGGIRSPIDERNNGTITWE
NLAAVLPFGGTFDLVQLKGSTLKKAFEHSVHRYGQSTGEFLQVGGIHVVYDLSRKPGD
RVVKLDVLCTKCRVPSYDPLKMDEVYKVILPNFLANGGDGFQMIKDELLRHDSGDQDI
NVVSTYISKMKVIYPAVEGRIKHHHHHH (SEQ ID NO: 332)

FIG. 26E

MCPRAARAPATLLLALGAVLWPAAGAWELTILHTNDVHSRLEQTSEDSSKCVNASRC
MGGVARLFTKVQQIRRAEPNVLLLDAGDQYQGTIWFTVYKGAEVAHFMNALRYDA
MALGNHEFDNGVEGLIEPLLKEAKFPILSANIKAKGPLASQISGLYLPYKVLPVGDEVVG
IVGYTSKETPFLSNPGTNLVFEDEITALQPEVDKLKTLNVNKIIALGHSGFEMDKLIAQKV
RGVDVVVGGHSNTFLYTGNPPSKEVPAGKYPFIVTSDDGRKVPVVQAYAFGKYLGYLKI
EFDERGNVISSHGNPILLNSSIPEDPSIKADINKWRIKLDNYSTQELGKTIVYLDGSSQSC
RFRECNMGNLICDAMINNNLRHADETFWNHVSMCILNGGGIRSPIDERNNGTITWE
NLAAVLPFGGTFDLVQLKGSTLKKAFEHSVHRYGQSTGEFLQVGGIHVVYDLSRKPGD
RVVKLDVLCTKCRVPSYDPLKMDEVYKVILPNFLANGGDGFQMIKDELLRHDSGDQDI
NVVSTYISKMKVIYPAVEGRIKHHHHHH (SEQ ID NO: 332)

FIG. 26F

DIQMTQSPSSVSASVGDRVTITCRASQGISS*W*LAWYQQKPGKAPKLLIYAASSLQSG
VPSRFSGSGSGTDFTLTISSLQPEDFATYYCQQGNSFPRTFGGGTKVEIKRTVAAPSVF
IFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO: 23)

FIG. 26G

DIQMTQSPSSVSASVGDRVTITCRASQGI*S*S*W*LAWYQQKPGKAPKLLIYAASSLQSG
VPSRFSGSGSGTDFTLTISSLQPEDFATYYCQQGNSFPRTFGGGTKVEIKRTVAAPSVF
IFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO: 23)

FIG. 26H

SEQUENCE LISTING

```
<160> NUMBER OF SEQ ID NOS: 922

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Gly Ser Ile Ser Gly Arg Tyr Trp Ser
1               5                   10


<210> SEQ ID NO 2
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Tyr Ile Tyr Gly Thr Gly Ser Thr Asn Tyr Asn Pro Ser Leu Lys Ser
1               5                   10                  15


<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3
```

```
Glu Ser Gln Glu Ser Pro Tyr Asn Asn Trp Phe Asp Pro
1               5                   10


<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Arg Tyr Trp Ser
1               5


<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Gly Ser Ile Ser Gly Arg
1               5


<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Tyr Gly Thr Gly Ser
1               5


<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Gly Ser Ile Ser Gly Arg Tyr
1               5


<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ile Tyr Gly Thr Gly Ser Thr
1               5
```

<210> SEQ ID NO 9
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 9

```
Ala Arg Glu Ser Gln Glu Ser Pro Tyr Asn Asn Trp Phe Asp Pro
1               5                   10                  15
```

<210> SEQ ID NO 10
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Arg
            20                  25                  30

Tyr Trp Ser Trp Ile Arg Gln Pro Pro Gly Lys Gly Leu Glu Trp Ile
        35                  40                  45

Gly Tyr Ile Tyr Gly Thr Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Gln Glu Ser Pro Tyr Asn Asn Trp Phe Asp Pro Trp Gly
            100                 105                 110

Gln Gly Thr Leu Val Thr Val Ser Ser
        115                 120
```

<210> SEQ ID NO 11
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11

```
caagtgcagc tgcaggaatc tggccctggc ctggtcaagc cctccgagac actgtccctg     60

acctgcaccg tgtccggcgg ctccatctcc ggccggtact ggtcttggat ccggcagcct    120

cccggcaagg gcctggaatg gatcggctac atctacggca ccggctccac caactacaac    180

cccagcctga agtccagagt gaccatctcc gtggacacct ccaagaacca gttctccctg    240

aagctgtcct ccgtgaccgc cgctgacacc gccgtgtact actgcgccag agagtcccag    300

gaatcccctt acaacaattg gttcgacccc tggggccagg gcaccctggt caccgtgtcc    360

tct                                                                   363
```

<210> SEQ ID NO 12
<211> LENGTH: 448

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (448)..(448)
<223> OTHER INFORMATION: /replace=" "
<220> FEATURE:
<221> NAME/KEY: MISC_FEATURE
<222> LOCATION: (1)..(448)
<223> OTHER INFORMATION: /note="Variant residues given in the sequence
      have no preference with respect to those in the annotations
      for variant positions"

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Arg
            20                  25                  30

Tyr Trp Ser Trp Ile Arg Gln Pro Pro Gly Lys Gly Leu Glu Trp Ile
        35                  40                  45

Gly Tyr Ile Tyr Gly Thr Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Gln Glu Ser Pro Tyr Asn Asn Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320
```

-continued

```
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 13
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: Variation
<222> LOCATION: (1342)..(1344)
<223> OTHER INFORMATION: /replace=" "
<220> FEATURE:
<221> NAME/KEY: misc_feature
<222> LOCATION: (1)..(1344)
<223> OTHER INFORMATION: /note="Variant nucleotides given in the sequence have no preference with respect to those in the annotations for variant positions"

<400> SEQUENCE: 13

```
caagtgcagc tgcaggaatc tggccctggc ctggtcaagc cctccgagac actgtccctg     60

acctgcaccg tgtccggcgg ctccatctcc ggccggtact ggtcttggat ccggcagcct    120

cccggcaagg gcctggaatg gatcggctac atctacggca ccggctccac caactacaac    180

cccagcctga agtccagagt gaccatctcc gtggacacct ccaagaacca gttctccctg    240

aagctgtcct ccgtgaccgc cgctgacacc gccgtgtact actgcgccag agagtcccag    300

gaatcccctt acaacaattg gttcgacccc tggggccagg gcaccctggt caccgtgtcc    360

tctgcttcca ccaagggccc ctccgtgttc cctctggccc cttgctcccg gtccacctcc    420

gagtctaccg ccgctctggg ctgcctcgtg aaggactact tccccgagcc cgtgaccgtg    480

tcctggaact ctggcgccct gacctccggc gtgcacacct tccctgccgt gctgcagtcc    540

tccggcctgt actccctgtc cagcgtcgtg accgtgccct cctccagcct gggcaccaag    600

acctacacct gtaacgtgga ccacaagccc tccaacacca aagtggacaa gcgggtggaa    660

tctaagtacg gccctccctg ccctccttgc cctgcccctg agttcctggg cggaccttcc    720

gtgttcctgt tccctccaaa gcccaaggac accctgatga tctcccggac ccctgaagtg    780

acctgcgtgg tggtggacgt gtcccaggaa gatcccgaag tccagttcaa ttggtacgtg    840

gacggcgtgg aagtgcacaa cgccaagacc aagcccagag aggaacagtt caactccacc    900

taccgggtgg tgtccgtgct gaccgtgctg caccaggact ggctgaacgg caaagagtac    960

aagtgcaaag tgtccaacaa gggcctgccc tccagcatcg aaaagaccat ctccaaggcc   1020
```

```
aagggccagc cccgcgagcc ccaagtgtac accctgcctc ccagccagga agagatgacc   1080

aagaatcaag tgtccctgac ttgtctggtc aagggcttct accccctccga tatcgccgtg   1140

gagtgggagt ccaacggcca gcccgagaac aactacaaga ccacccctcc cgtgctggac   1200

tccgacggct ccttcttcct gtactctcgg ctgaccgtgg acaagtcccg gtggcaggaa   1260

ggcaacgtct tctcctgctc cgtgatgcac gaggccctgc acaaccacta cacccagaag   1320

tccctgtccc tgtctctggg caag                                          1344


<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Arg Ala Ser Gln Gly Ile Ser Ser Trp Leu Ala
1               5                   10


<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ala Ala Ser Ser Leu Gln Ser
1               5


<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gln Gln Gly Asn Ser Phe Pro Arg Thr
1               5


<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Gln Gly Ile Ser Ser Trp
1               5


<210> SEQ ID NO 18
<211> LENGTH: 3
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 18

Ala Ala Ser
1


<210> SEQ ID NO 19
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly Asn Ser Phe Pro Arg
1               5


<210> SEQ ID NO 20
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gln Gly Ile Ser Ser Trp
1               5


<210> SEQ ID NO 21
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ser Phe Pro Arg
                85                  90                  95

Thr Phe Gly Gly Gly Thr Lys Val Glu Ile Lys
            100                 105


<210> SEQ ID NO 22
<211> LENGTH: 321
<212> TYPE: DNA
<213> ORGANISM: Artificial Sequence
<220> FEATURE:
<221> NAME/KEY: source
```

<223> OTHER INFORMATION: /note="Description of Artificial Sequence: Synthetic polynucleotide"

<400> SEQUENCE: 22
gacatccaga tgacccagag cccctcctcc gtgtccgcct ccgtgggcga cagagtgacc 60
atcacctgtc gggcctccca gggcatctcc agctggctgg cctggtatca gcagaagccc 120
ggcaaggccc ctaagctgct gatctacgcc gcctccagcc tgcagtccgg cgtgccctcc 180
agattctccg gctctggctc cggcaccgac ttcaccctga ccatcagctc cctgcagccc 240
gaggacttcg ccacctacta ctgccagcag ggcaactcct tccctcggac cttcggcgga 300
ggcaccaaag tggaaatcaa g 321

<210> SEQ ID NO 23
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ser Phe Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 24
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 24
gacatccaga tgacccagag cccctcctcc gtgtccgcct ccgtgggcga cagagtgacc 60
atcacctgtc gggcctccca gggcatctcc agctggctgg cctggtatca gcagaagccc 120
ggcaaggccc ctaagctgct gatctacgcc gcctccagcc tgcagtccgg cgtgccctcc 180
agattctccg gctctggctc cggcaccgac ttcaccctga ccatcagctc cctgcagccc 240
gaggacttcg ccacctacta ctgccagcag ggcaactcct tccctcggac cttcggcgga 300
ggcaccaaag tggaaatcaa gcgtacggtg gccgctccct ccgtgttcat cttcccaccc 360
tccgacgagc agctgaagtc cggcaccgcc tccgtcgtgt gcctgctgaa caacttctac 420
cctcgcgagg ccaaagtgca gtggaaagtg gacaacgccc tgcagtccgg caactcccag 480
gaatccgtca ccgagcagga ctccaaggac agcacctact ccctgtcctc caccctgacc 540
ctgtccaagg ccgactacga gaagcacaaa gtgtacgcct gcgaagtgac ccaccagggc 600
ctgtccagcc ccgtgaccaa gtccttcaac cggggcgagt gc 642

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 25

Gly Gly Ser Ile Glu Gly Arg Tyr Trp Ser
1 5 10

<210> SEQ ID NO 26
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 26

Tyr Ile Tyr Gly Ser Gly Ser Thr Lys Tyr Asn Pro Ser Leu Lys Ser
1 5 10 15

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 27

Gly Gly Ser Ile Glu Gly Arg
1 5

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 28

Tyr Gly Ser Gly Ser
1 5

<210> SEQ ID NO 29
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

Gly Gly Ser Ile Glu Gly Arg Tyr
1 5

<210> SEQ ID NO 30
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 30

Ile Tyr Gly Ser Gly Ser Thr
1 5

<210> SEQ ID NO 31
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Glu Gly Arg
20 25 30

Tyr Trp Ser Trp Ile Arg Gln Pro Pro Gly Lys Gly Leu Glu Trp Ile
35 40 45

Gly Tyr Ile Tyr Gly Ser Gly Ser Thr Lys Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Ser Gln Glu Ser Pro Tyr Asn Asn Trp Phe Asp Pro Trp Gly
100 105 110

Gln Gly Thr Leu Val Thr Val Ser Ser
115 120

<210> SEQ ID NO 32
<211> LENGTH: 363
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic polynucleotide"

<400> SEQUENCE: 32
caagtgcagc tgcaggaatc tggccctggc ctggtcaagc cctccgagac actgtccctg 60
acctgcaccg tgtccggcgg ctctatcgag ggccggtact ggtcctggat ccggcagcct 120
cctggcaagg gcctggaatg gatcggctac atctacggct ccggctccac caagtacaac 180
cccagcctga agtccagagt gaccatctcc gtggacacct ccaagaacca gttctccctg 240
aagctgtcct ccgtgaccgc cgctgacacc gccgtgtact actgcgccag agagtcccag 300
gaatcccctt acaacaattg gttcgacccc tggggccagg gcaccctggt caccgtgtcc 360
tct 363

<210> SEQ ID NO 33
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"
<220> FEATURE:
<221> NAME/KEY: VARIANT
<222> LOCATION: (448)..(448)
<223> OTHER INFORMATION: /replace=" "
<220> FEATURE:
<221> NAME/KEY: MISC_FEATURE
<222> LOCATION: (1)..(448)
<223> OTHER INFORMATION: /note="Variant residues given in the sequence
have no preference with respect to those in the annotations
for variant positions"

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu Gly Arg
            20                  25                  30

Tyr Trp Ser Trp Ile Arg Gln Pro Pro Gly Lys Gly Leu Glu Trp Ile
        35                  40                  45

Gly Tyr Ile Tyr Gly Ser Gly Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Gln Glu Ser Pro Tyr Asn Asn Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His

```
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

```
<210> SEQ ID NO 34
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (1342)..(1344)
<223> OTHER INFORMATION: /replace=" "
<220> FEATURE:
<221> NAME/KEY: misc_feature
<222> LOCATION: (1)..(1344)
<223> OTHER INFORMATION: /note="Variant nucleotides given in the
      sequence have no preference with respect to those in the
      annotations for variant positions"

<400> SEQUENCE: 34

caagtgcagc tgcaggaatc tggccctggc ctggtcaagc cctccgagac actgtccctg      60

acctgcaccg tgtccggcgg ctctatcgag ggccggtact ggtcctggat ccggcagcct     120

cctggcaagg gcctggaatg gatcggctac atctacggct ccggctccac caagtacaac     180

cccagcctga agtccagagt gaccatctcc gtggacacct ccaagaacca gttctccctg     240

aagctgtcct ccgtgaccgc cgctgacacc gccgtgtact actgcgccag agagtcccag     300
```

-continued

```
gaatcccctt acaacaattg gttcgacccc tggggccagg gcaccctggt caccgtgtcc    360

tctgcctcca ccaagggccc ctccgtgttc cctctggccc cttgctcccg gtccacctcc    420

gagtctaccg ccgctctggg ctgcctcgtg aaggactact tccccgagcc cgtgaccgtg    480

tcctggaact ctggcgccct gacctccggc gtgcacacct tccctgccgt gctgcagtcc    540

tccggcctgt actccctgtc cagcgtcgtg accgtgccct cctccagcct gggcaccaag    600

acctacacct gtaacgtgga ccacaagccc tccaacacca aagtggacaa gcgggtggaa    660

tctaagtacg gccctccctg ccctccttgc cctgcccctg agttcctggg cggaccttcc    720

gtgttcctgt tccctccaaa gcccaaggac accctgatga tctcccggac ccctgaagtg    780

acctgcgtgg tggtggacgt gtcccaggaa gatcccgaag tccagttcaa ttggtacgtg    840

gacggcgtgg aagtgcacaa cgccaagacc aagcccagag aggaacagtt caactccacc    900

taccgggtgg tgtccgtgct gaccgtgctg caccaggact ggctgaacgg caaagagtac    960

aagtgcaaag tgtccaacaa gggcctgccc tccagcatcg aaaagaccat ctccaaggcc   1020

aagggccagc cccgcgagcc ccaagtgtac accctgcctc ccagccagga agagatgacc   1080

aagaatcaag tgtccctgac ttgtctggtc aagggcttct acccctccga tatcgccgtg   1140

gagtgggagt ccaacggcca gcccgagaac aactacaaga ccacccctcc cgtgctggac   1200

tccgacggct ccttcttcct gtactctcgg ctgaccgtgg acaagtcccg gtggcaggaa   1260

ggcaacgtct tctcctgctc cgtgatgcac gaggccctgc acaaccacta cacccagaag   1320

tccctgtccc tgtctctggg caag                                          1344
```

```
<210> SEQ ID NO 35
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Phe Thr Phe His Arg Tyr Ala Met Ser
1               5                   10


<210> SEQ ID NO 36
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ala Ile Ser Gly Ser Gly Met Asn Thr Tyr Tyr Ala Asp Ser Val Lys
1               5                   10                  15

Gly


<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37
```

-continued

Gly Gly Leu Tyr Gly Ser Gly Ser Tyr Leu Ser Asp Phe Asp Leu
1 5 10 15

<210> SEQ ID NO 38
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Arg Tyr Ala Met Ser
1 5

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

Gly Phe Thr Phe His Arg Tyr
1 5

<210> SEQ ID NO 40
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 40

Ser Gly Ser Gly Met Asn
1 5

<210> SEQ ID NO 41
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 41

Gly Phe Thr Phe His Arg Tyr Ala
1 5

<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 42

Ile Ser Gly Ser Gly Met Asn Thr
1 5

<210> SEQ ID NO 43
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 43

Ala Arg Gly Gly Leu Tyr Gly Ser Gly Ser Tyr Leu Ser Asp Phe Asp
1 5 10 15

Leu

<210> SEQ ID NO 44
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 44

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe His Arg Tyr
20 25 30

Ala Met Ser Trp Val Arg Gln Ala Pro Gly Lys Gly Leu Glu Trp Val
35 40 45

Ser Ala Ile Ser Gly Ser Gly Met Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Leu Tyr Gly Ser Gly Ser Tyr Leu Ser Asp Phe Asp
100 105 110

Leu Trp Gly Arg Gly Thr Leu Val Thr Val Ser Ser
115 120

<210> SEQ ID NO 45
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45
gaagtgcagc tgctggaatc tggcggcgga ctggtgcagc ctggcggctc cctgagactg 60
tcttgcgccg cctccggctt caccttccac agatacgcca tgtcctgggt ccgacaggcc 120
cctggcaagg gcctggagtg ggtgtccgcc atctccggct ccggcatgaa cacctactac 180
gccgactccg tgaagggccg gttcaccatc tcccgggaca actccaagaa caccctgtac 240
ctgcagatga actccctgcg ggccgaggac accgccgtgt actactgtgc cagaggcggc 300
ctgtacggct ccggctccta cctgtccgac ttcgacctgt ggggcagagg caccctggtc 360
accgtgtcct cc 372

<210> SEQ ID NO 46
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (451)..(451)
<223> OTHER INFORMATION: /replace=" "
<220> FEATURE:
<221> NAME/KEY: MISC_FEATURE
<222> LOCATION: (1)..(451)
<223> OTHER INFORMATION: /note="Variant residues given in the sequence have no preference with respect to those in the annotations for variant positions"

<400> SEQUENCE: 46

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe His Arg Tyr
20 25 30

Ala Met Ser Trp Val Arg Gln Ala Pro Gly Lys Gly Leu Glu Trp Val
35 40 45

Ser Ala Ile Ser Gly Ser Gly Met Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Leu Tyr Gly Ser Gly Ser Tyr Leu Ser Asp Phe Asp
100 105 110

Leu Trp Gly Arg Gly Thr Leu Val Thr Val Ser Ser Ala Ser Thr Lys
115 120 125

Gly Pro Ser Val Phe Pro Leu Ala Pro Cys Ser Arg Ser Thr Ser Glu
130 135 140

Ser Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Lys Thr Tyr Thr Cys Asn
195 200 205

Val Asp His Lys Pro Ser Asn Thr Lys Val Asp Lys Arg Val Glu Ser
210 215 220

Lys Tyr Gly Pro Pro Cys Pro Pro Cys Pro Ala Pro Glu Phe Leu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser Gln
260 265 270

Glu Asp Pro Glu Val Gln Phe Asn Trp Tyr Val Asp Gly Val Glu Val
275 280 285

His Asn Ala Lys Thr Lys Pro Arg Glu Glu Gln Phe Asn Ser Thr Tyr
290 295 300

```
Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 47
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (1351)..(1353)
<223> OTHER INFORMATION: /replace=" "
<220> FEATURE:
<221> NAME/KEY: misc_feature
<222> LOCATION: (1)..(1353)
<223> OTHER INFORMATION: /note="Variant nucleotides given in the
      sequence have no preference with respect to those in the
      annotations for variant positions"

<400> SEQUENCE: 47

gaagtgcagc tgctggaatc tggcggcgga ctggtgcagc ctggcggctc cctgagactg     60

tcttgcgccg cctccggctt caccttccac agatacgcca tgtcctgggt ccgacaggcc    120

cctggcaagg gcctggagtg ggtgtccgcc atctccggct ccggcatgaa cacctactac    180

gccgactccg tgaagggccg gttcaccatc tcccgggaca actccaagaa caccctgtac    240

ctgcagatga actccctgcg ggccgaggac accgccgtgt actactgtgc cagaggcggc    300

ctgtacggct ccggctccta cctgtccgac ttcgacctgt ggggcagagg caccctggtc    360

accgtgtcct ccgcctccac aaagggcccc tccgtgttcc ctctggcccc ttgctcccgg    420

tccacctccg agtctaccgc cgctctgggc tgcctcgtga aggactactt ccccgagccc    480

gtgaccgtgt cctggaactc tggcgccctg acctccggcg tgcacacctt ccctgccgtg    540

ctgcagtcct ccggcctgta ctccctgtcc agcgtcgtga ccgtgccctc ctccagcctg    600

ggcaccaaga cctacacctg taacgtggac cacaagccct ccaacaccaa agtggacaag    660

cgggtggaat ctaagtacgg ccctccctgc cctccttgcc ctgcccctga gttcctgggc    720

ggaccttccg tgttcctgtt ccctccaaag cccaaggaca ccctgatgat ctcccggacc    780

cctgaagtga cctgcgtggt ggtggacgtg tcccaggaag atcccgaagt ccagttcaat    840
```

-continued

```
tggtacgtgg acggcgtgga agtgcacaac gccaagacca agcccagaga ggaacagttc    900

aactccacct accgggtggt gtccgtgctg accgtgctgc accaggactg gctgaacggc    960

aaagagtaca agtgcaaagt gtccaacaag ggcctgccct ccagcatcga aaagaccatc   1020

tccaaggcca agggccagcc ccgcgagccc caagtgtaca ccctgcctcc cagccaggaa   1080

gagatgacca agaatcaagt gtccctgact tgtctggtca agggcttcta cccctccgat   1140

atcgccgtgg agtgggagtc caacggccag cccgagaaca actacaagac cacccctccc   1200

gtgctggact ccgacggctc cttcttcctg tactctcggc tgaccgtgga caagtcccgg   1260

tggcaggaag gcaacgtctt ctcctgctcc gtgatgcacg aggccctgca caaccactac   1320

acccagaagt ccctgtccct gtctctgggc aag                                1353
```

```
<210> SEQ ID NO 48
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Arg Ala Ser Gln Ser Val Gly Ser Asn Leu Ala
1               5                   10


<210> SEQ ID NO 49
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Ala Ser Thr Arg Ala Thr
1               5


<210> SEQ ID NO 50
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gln Gln His Asn Ala Phe Pro Tyr Thr
1               5


<210> SEQ ID NO 51
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Ser Gln Ser Val Gly Ser Asn
1               5
```

<210> SEQ ID NO 52
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 52

Gly Ala Ser
1

<210> SEQ ID NO 53
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 53

His Asn Ala Phe Pro Tyr
1 5

<210> SEQ ID NO 54
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 54

Gln Ser Val Gly Ser Asn
1 5

<210> SEQ ID NO 55
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

Glu Ile Val Leu Thr Gln Ser Pro Ala Thr Leu Ser Val Ser Pro Gly
1 5 10 15

Glu Arg Ala Thr Leu Ser Cys Arg Ala Ser Gln Ser Val Gly Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln His Asn Ala Phe Pro Tyr
85 90 95

Thr Phe Gly Gly Gly Thr Lys Val Glu Ile Lys
100 105

<210> SEQ ID NO 56
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56

```
gagatcgtgc tgacacagtc ccctgccacc ctgtctgtgt ctcccggcga gagagccacc      60

ctgagctgca gagcctccca gtccgtgggc tccaacctgg cctggtatca gcagaagccc     120

ggccaggccc ctcggctgct gatctacggc gcctctacca gagccaccgg catccctgcc     180

agattctccg gctctggctc cggcaccgag ttcaccctga ccatctccag cctgcagtcc     240

gaggacttcg ccgtgtacta ctgccagcag cacaacgcct tcccttacac cttcggcgga     300

ggcaccaaag tggaaatcaa g                                               321
```

<210> SEQ ID NO 57
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Asn Ala Phe Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 58

<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58
gagatcgtgc tgacacagtc ccctgccacc ctgtctgtgt ctcccggcga gagagccacc 60
ctgagctgca gagcctccca gtccgtgggc tccaacctgg cctggtatca gcagaagccc 120
ggccaggccc ctcggctgct gatctacggc gcctctacca gagccaccgg catccctgcc 180
agattctccg gctctggctc cggcaccgag ttcaccctga ccatctccag cctgcagtcc 240
gaggacttcg ccgtgtacta ctgccagcag cacaacgcct tcccttacac cttcggcgga 300
ggcaccaaag tggaaatcaa gcgtacggtg gccgctccct ccgtgttcat cttcccaccc 360
tccgacgagc agctgaagtc cggcaccgcc tccgtcgtgt gcctgctgaa caacttctac 420
cctcgcgagg ccaaagtgca gtggaaagtg gacaacgccc tgcagtccgg caactcccag 480
gaatccgtca ccgagcagga ctccaaggac agcacctact ccctgtcctc caccctgacc 540
ctgtccaagg ccgactacga gaagcacaaa gtgtacgcct gcgaagtgac ccaccagggc 600
ctgtccagcc ccgtgaccaa gtccttcaac cggggcgagt gc 642

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

Gly Gly Ser Ile Glu Arg Tyr Tyr Trp Ser
1 5 10

<210> SEQ ID NO 60
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 60

Tyr Ile Tyr Gly Arg Gly Ser Thr Asn Tyr Asn Pro Ser Leu Lys Ser
1 5 10 15

<210> SEQ ID NO 61
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 61

Arg Tyr Tyr Trp Ser
1 5

<210> SEQ ID NO 62

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Gly Ser Ile Glu Arg Tyr
1               5


<210> SEQ ID NO 63
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Tyr Gly Arg Gly Ser
1               5


<210> SEQ ID NO 64
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gly Gly Ser Ile Glu Arg Tyr Tyr
1               5


<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Ile Tyr Gly Arg Gly Ser Thr
1               5


<210> SEQ ID NO 66
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu Arg Tyr
            20                  25                  30

Tyr Trp Ser Trp Ile Arg Gln Pro Pro Gly Lys Gly Leu Glu Trp Ile
        35                  40                  45
```

Gly Tyr Ile Tyr Gly Arg Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Ser Gln Glu Ser Pro Tyr Asn Asn Trp Phe Asp Pro Trp Gly
100 105 110

Gln Gly Thr Leu Val Thr Val Ser Ser
115 120

<210> SEQ ID NO 67
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67
caagtgcagc tgcaggaatc tggccctggc ctggtcaagc cctccgagac actgtccctg 60
acctgcaccg tgtccggcgg ctccatcgag cggtactact ggtcctggat ccggcagcct 120
cccggcaagg gcctggaatg gatcggctac atctacggca gaggctccac caactacaac 180
cccagcctga agtccagagt gaccatctcc gtggacacct ccaagaacca gttctccctg 240
aagctgtcct ccgtgaccgc cgctgacacc gccgtgtact actgcgccag agagtcccag 300
gaatcccctt acaacaattg gttcgacccc tggggccagg gcaccctggt caccgtgtcc 360
tct 363

<210> SEQ ID NO 68
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (448)..(448)
<223> OTHER INFORMATION: /replace=" "
<220> FEATURE:
<221> NAME/KEY: MISC_FEATURE
<222> LOCATION: (1)..(448)
<223> OTHER INFORMATION: /note="Variant residues given in the sequence have no preference with respect to those in the annotations for variant positions"

<400> SEQUENCE: 68

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Glu Arg Tyr
20 25 30

Tyr Trp Ser Trp Ile Arg Gln Pro Pro Gly Lys Gly Leu Glu Trp Ile
35 40 45

Gly Tyr Ile Tyr Gly Arg Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala

```
                85                  90                  95

Arg Glu Ser Gln Glu Ser Pro Tyr Asn Asn Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 69
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: Variation
<222> LOCATION: (1342)..(1344)
<223> OTHER INFORMATION: /replace=" "
<220> FEATURE:
<221> NAME/KEY: misc_feature
<222> LOCATION: (1)..(1344)
<223> OTHER INFORMATION: /note="Variant nucleotides given in the sequence have no preference with respect to those in the annotations for variant positions"

<400> SEQUENCE: 69

```
caagtgcagc tgcaggaatc tggccctggc ctggtcaagc cctccgagac actgtccctg     60
acctgcaccg tgtccggcgg ctccatcgag cggtactact ggtcctggat ccggcagcct    120
cccggcaagg gcctggaatg gatcggctac atctacggca gaggctccac caactacaac    180
cccagcctga agtccagagt gaccatctcc gtggacacct ccaagaacca gttctccctg    240
aagctgtcct ccgtgaccgc cgctgacacc gccgtgtact actgcgccag agagtcccag    300
gaatcccctt acaacaattg gttcgacccc tggggccagg gcaccctggt caccgtgtcc    360
tctgcctcca ccaagggccc ctccgtgttc cctctggccc cttgctcccg gtccacctcc    420
gagtctaccg ccgctctggg ctgcctcgtg aaggactact tccccgagcc cgtgaccgtg    480
tcctggaact ctggcgccct gacctccggc gtgcacacct tccctgccgt gctgcagtcc    540
tccggcctgt actccctgtc cagcgtcgtg accgtgccct cctccagcct gggcaccaag    600
acctacacct gtaacgtgga ccacaagccc tccaacacca aagtggacaa gcgggtggaa    660
tctaagtacg gccctccctg ccctccttgc cctgcccctg agttcctggg cggaccttcc    720
gtgttcctgt tccctccaaa gcccaaggac accctgatga tctcccggac ccctgaagtg    780
acctgcgtgg tggtggacgt gtcccaggaa gatcccgaag tccagttcaa ttggtacgtg    840
gacggcgtgg aagtgcacaa cgccaagacc aagcccagag aggaacagtt caactccacc    900
taccgggtgg tgtccgtgct gaccgtgctg caccaggact ggctgaacgg caaagagtac    960
aagtgcaaag tgtccaacaa gggcctgccc tccagcatcg aaaagaccat ctccaaggcc   1020
aagggccagc cccgcgagcc ccaagtgtac accctgcctc ccagccagga agagatgacc   1080
aagaatcaag tgtccctgac ttgtctggtc aagggcttct acccctccga tatcgccgtg   1140
gagtgggagt ccaacggcca gcccgagaac aactacaaga ccacccctcc cgtgctggac   1200
tccgacggct ccttcttcct gtactctcgg ctgaccgtgg acaagtcccg gtggcaggaa   1260
ggcaacgtct tctcctgctc cgtgatgcac gaggccctgc acaaccacta cacccagaag   1320
tccctgtccc tgtctctggg caag                                          1344
```

<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 70

```
Gly Phe Thr Phe Ser Tyr Asn Ala Met Ser
1               5                   10
```

<210> SEQ ID NO 71
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 71

Ser Ile Ser Gly Thr Gly Gly Ser Thr Tyr Tyr Ala Asp Ser Val Lys
1 5 10 15

Gly

<210> SEQ ID NO 72
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 72

Tyr Asn Ala Met Ser
1 5

<210> SEQ ID NO 73
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 73

Gly Phe Thr Phe Ser Tyr Asn
1 5

<210> SEQ ID NO 74
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 74

Ser Gly Thr Gly Gly Ser
1 5

<210> SEQ ID NO 75
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 75

Gly Phe Thr Phe Ser Tyr Asn Ala
1 5

<210> SEQ ID NO 76
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 76

Ile Ser Gly Thr Gly Gly Ser Thr
1 5

<210> SEQ ID NO 77
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Tyr Asn
20 25 30

Ala Met Ser Trp Val Arg Gln Ala Pro Gly Lys Gly Leu Glu Trp Val
35 40 45

Ser Ser Ile Ser Gly Thr Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Leu Tyr Gly Ser Gly Ser Tyr Leu Ser Asp Phe Asp
100 105 110

Leu Trp Gly Arg Gly Thr Leu Val Thr Val Ser Ser
115 120

<210> SEQ ID NO 78
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 78
gaagtgcagc tgctggaatc tggcggcgga ctggtgcagc ctggcggctc cctgagactg 60
tcttgcgccg cctccggctt caccttctcc tacaacgcca tgtcctgggt ccgacaggcc 120
cctggcaagg gcctggagtg ggtgtcctcc atctccggca ccggcggctc cacctactac 180
gccgactctg tgaagggccg gttcaccatc tcccgggaca actccaagaa caccctgtac 240
ctgcagatga actccctgcg ggccgaggac accgccgtgt actactgtgc cagaggcggc 300
ctgtacggct ccggctccta cctgtccgac ttcgacctgt ggggcagagg caccctggtc 360
accgtgtcct cc 372

<210> SEQ ID NO 79
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT

```
<222> LOCATION: (451)..(451)
<223> OTHER INFORMATION: /replace=" "
<220> FEATURE:
<221> NAME/KEY: MISC_FEATURE
<222> LOCATION: (1)..(451)
<223> OTHER INFORMATION: /note="Variant residues given in the sequence
      have no preference with respect to those in the annotations
      for variant positions"

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Asn
            20                  25                  30

Ala Met Ser Trp Val Arg Gln Ala Pro Gly Lys Gly Leu Glu Trp Val
        35                  40                  45

Ser Ser Ile Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 80
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (1351)..(1353)
<223> OTHER INFORMATION: /replace=" "
<220> FEATURE:
<221> NAME/KEY: misc_feature
<222> LOCATION: (1)..(1353)
<223> OTHER INFORMATION: /note="Variant nucleotides given in the
      sequence have no preference with respect to those in the
      annotations for variant positions"

<400> SEQUENCE: 80

gaagtgcagc tgctggaatc tggcggcgga ctggtgcagc ctggcggctc cctgagactg      60

tcttgcgccg cctccggctt caccttctcc tacaacgcca tgtcctgggt ccgacaggcc     120

cctggcaagg gcctggagtg ggtgtcctcc atctccggca ccggcggctc cacctactac     180

gccgactctg tgaagggccg gttcaccatc tcccgggaca actccaagaa caccctgtac     240

ctgcagatga actccctgcg ggccgaggac accgccgtgt actactgtgc cagaggcggc     300

ctgtacggct ccggctccta cctgtccgac ttcgacctgt ggggcagagg caccctggtc     360

accgtgtcct ccgcctccac aaagggcccc tccgtgttcc ctctggcccc ttgctcccgg     420

tccacctccg agtctaccgc cgctctgggc tgcctcgtga aggactactt ccccgagccc     480

gtgaccgtgt cctggaactc tggcgccctg acctccggcg tgcacacctt ccctgccgtg     540

ctgcagtcct ccggcctgta ctccctgtcc agcgtcgtga ccgtgccctc ctccagcctg     600

ggcaccaaga cctacacctg taacgtggac cacaagccct ccaacaccaa agtggacaag     660

cgggtggaat ctaagtacgg ccctccctgc cctccttgcc ctgcccctga gttcctgggc     720

ggaccttccg tgttcctgtt ccctccaaag cccaaggaca ccctgatgat ctcccggacc     780

cctgaagtga cctgcgtggt ggtggacgtg tcccaggaag atcccgaagt ccagttcaat     840

tggtacgtgg acggcgtgga agtgcacaac gccaagacca agcccagaga ggaacagttc     900

aactccacct accgggtggt gtccgtgctg accgtgctgc accaggactg gctgaacggc     960

aaagagtaca agtgcaaagt gtccaacaag ggcctgccct ccagcatcga aaagaccatc    1020

tccaaggcca agggccagcc ccgcgagccc caagtgtaca ccctgcctcc cagccaggaa    1080

gagatgacca agaatcaagt gtccctgact tgtctggtca agggcttcta cccctccgat    1140
```

-continued

```
atcgccgtgg agtgggagtc caacggccag cccgagaaca actacaagac cacccctccc   1200

gtgctggact ccgacggctc cttcttcctg tactctcggc tgaccgtgga caagtcccgg   1260

tggcaggaag gcaacgtctt ctcctgctcc gtgatgcacg aggccctgca caaccactac   1320

acccagaagt ccctgtccct gtctctgggc aag                                1353


<210> SEQ ID NO 81
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Gly Phe Thr Phe Ser Arg Tyr Ala Met Ser
1               5                   10


<210> SEQ ID NO 82
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gly Phe Thr Phe Ser Arg Tyr
1               5


<210> SEQ ID NO 83
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gly Phe Thr Phe Ser Arg Tyr Ala
1               5


<210> SEQ ID NO 84
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ser Ile Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
            100                 105                 110

Leu Trp Gly Arg Gly Thr Leu Val Thr Val Ser Ser
        115                 120


<210> SEQ ID NO 85
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85

gaagtgcagc tgctggaatc tggcggcgga ctggtgcagc ctggcggctc cctgagactg      60

tcttgcgccg cctccggctt caccttctcc agatacgcca tgtcctgggt ccgacaggcc     120

cctggcaagg gcctggagtg ggtgtcctcc atctccggca ccggcggctc cacctactac     180

gccgactctg tgaagggccg gttcaccatc tcccgggaca actccaagaa caccctgtac     240

ctgcagatga actccctgcg ggccgaggac accgccgtgt actactgtgc cagaggcggc     300

ctgtacggct ccggctccta cctgtccgac ttcgacctgt ggggcagagg caccctggtc     360

accgtgtcct cc                                                         372


<210> SEQ ID NO 86
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (451)..(451)
<223> OTHER INFORMATION: /replace=" "
<220> FEATURE:
<221> NAME/KEY: MISC_FEATURE
<222> LOCATION: (1)..(451)
<223> OTHER INFORMATION: /note="Variant residues given in the sequence
      have no preference with respect to those in the annotations
      for variant positions"

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ser Ile Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
            100                 105                 110
```

```
Leu Trp Gly Arg Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 87
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: Variation
<222> LOCATION: (1351)..(1353)
<223> OTHER INFORMATION: /replace=" "
```

<220> FEATURE:
<221> NAME/KEY: misc_feature
<222> LOCATION: (1)..(1353)
<223> OTHER INFORMATION: /note="Variant nucleotides given in the sequence have no preference with respect to those in the annotations for variant positions"

<400> SEQUENCE: 87

```
gaagtgcagc tgctggaatc tggcggcgga ctggtgcagc ctggcggctc cctgagactg      60

tcttgcgccg cctccggctt caccttctcc agatacgcca tgtcctgggt ccgacaggcc     120

cctggcaagg gcctggagtg ggtgtcctcc atctccggca ccggcggctc cacctactac     180

gccgactctg tgaagggccg gttcaccatc tcccgggaca actccaagaa caccctgtac     240

ctgcagatga actccctgcg ggccgaggac accgccgtgt actactgtgc cagaggcggc     300

ctgtacggct ccggctccta cctgtccgac ttcgacctgt ggggcagagg caccctggtc     360

accgtgtcct ccgcctccac aaagggcccc tccgtgttcc ctctggcccc ttgctcccgg     420

tccacctccg agtctaccgc cgctctgggc tgcctcgtga aggactactt ccccgagccc     480

gtgaccgtgt cctggaactc tggcgccctg acctccggcg tgcacacctt ccctgccgtg     540

ctgcagtcct ccggcctgta ctccctgtcc agcgtcgtga ccgtgccctc ctccagcctg     600

ggcaccaaga cctacacctg taacgtggac cacaagccct ccaacaccaa agtggacaag     660

cgggtggaat ctaagtacgg ccctccctgc cctccttgcc ctgcccctga gttcctgggc     720

ggaccttccg tgttcctgtt ccctccaaag cccaaggaca ccctgatgat ctcccggacc     780

cctgaagtga cctgcgtggt ggtggacgtg tcccaggaag atcccgaagt ccagttcaat     840

tggtacgtgg acggcgtgga agtgcacaac gccaagacca agcccagaga ggaacagttc     900

aactccacct accgggtggt gtccgtgctg accgtgctgc accaggactg gctgaacggc     960

aaagagtaca agtgcaaagt gtccaacaag ggcctgccct ccagcatcga aaagaccatc    1020

tccaaggcca agggccagcc ccgcgagccc caagtgtaca ccctgcctcc cagccaggaa    1080

gagatgacca agaatcaagt gtccctgact tgtctggtca agggcttcta cccctccgat    1140

atcgccgtgg agtgggagtc caacggccag cccgagaaca actacaagac cacccctccc    1200

gtgctggact ccgacggctc cttcttcctg tactctcggc tgaccgtgga caagtcccgg    1260

tggcaggaag gcaacgtctt ctcctgctcc gtgatgcacg aggccctgca caaccactac    1320

acccagaagt ccctgtccct gtctctgggc aag                                 1353
```

<210> SEQ ID NO 88
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Tyr" or "Ser"
<220> FEATURE:
<221> NAME/KEY: VARIANT
<222> LOCATION: (2)..(2)
<223> OTHER INFORMATION: /replace="Asn"
<220> FEATURE:
<221> NAME/KEY: MISC_FEATURE
<222> LOCATION: (1)..(5)
<223> OTHER INFORMATION: /note="Variant residues given in the sequence have no preference with respect to those in the annotations for variant positions"

<400> SEQUENCE: 88

Arg Tyr Ala Met Ser
1 5

<210> SEQ ID NO 89
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: VARIANT
<222> LOCATION: (3)..(3)
<223> OTHER INFORMATION: /replace="Thr"
<220> FEATURE:
<221> NAME/KEY: VARIANT
<222> LOCATION: (5)..(5)
<223> OTHER INFORMATION: /replace="Thr"
<220> FEATURE:
<221> NAME/KEY: VARIANT
<222> LOCATION: (7)..(7)
<223> OTHER INFORMATION: /replace="Gly" or "Ser"
<220> FEATURE:
<221> NAME/KEY: VARIANT
<222> LOCATION: (8)..(8)
<223> OTHER INFORMATION: /replace="Ser" or "Leu" or "Tyr"
<220> FEATURE:
<221> NAME/KEY: MISC_FEATURE
<222> LOCATION: (1)..(17)
<223> OTHER INFORMATION: /note="Variant residues given in the sequence have no preference with respect to those in the annotations for variant positions"

<400> SEQUENCE: 89

Ala Ile Ser Gly Ser Gly Met Asn Thr Tyr Tyr Ala Asp Ser Val Lys
1 5 10 15

Gly

<210> SEQ ID NO 90
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Gly" or "Ser"
<220> FEATURE:
<221> NAME/KEY: VARIANT
<222> LOCATION: (2)..(2)
<223> OTHER INFORMATION: /replace="Arg"
<220> FEATURE:
<221> NAME/KEY: MISC_FEATURE
<222> LOCATION: (1)..(5)
<223> OTHER INFORMATION: /note="Variant residues given in the sequence have no preference with respect to those in the annotations for variant positions"

<400> SEQUENCE: 90

Arg Tyr Tyr Trp Ser
1 5

<210> SEQ ID NO 91

<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (5)..(5)
<223> OTHER INFORMATION: /replace="Ser" or "Thr"
<220> FEATURE:
<221> NAME/KEY: VARIANT
<222> LOCATION: (9)..(9)
<223> OTHER INFORMATION: /replace="Lys"
<220> FEATURE:
<221> NAME/KEY: MISC_FEATURE
<222> LOCATION: (1)..(16)
<223> OTHER INFORMATION: /note="Variant residues given in the sequence have no preference with respect to those in the annotations for variant positions"

<400> SEQUENCE: 91

```
Tyr Ile Tyr Gly Arg Gly Ser Thr Asn Tyr Asn Pro Ser Leu Lys Ser
1               5                   10                  15
```

<210> SEQ ID NO 92
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 92

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

-continued

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 93
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325


<210> SEQ ID NO 94
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 95
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 95

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325


<210> SEQ ID NO 96
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 97
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305 310 315 320

Gln Lys Ser Leu Ser Leu Ser Pro Gly
325

<210> SEQ ID NO 98
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 98

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

```
Gln Lys Ser Leu Ser Leu Ser Pro Gly Lys
                325                 330


<210> SEQ ID NO 99
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 100
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 100

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 101
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 101

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Ala Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 102
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 102

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val Glu Pro Lys Ser Cys Asp Lys Thr His Thr Cys Pro Pro Cys
100 105 110

Pro Ala Pro Glu Ala Ala Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 103
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 103

Ala Ser Thr Lys Gly Pro Ser Val Phe Pro Leu Ala Pro Ser Ser Lys

```
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 104
<211> LENGTH: 107
<212> TYPE: PRT
<213> ORGANISM: Homo sapiens

<400> SEQUENCE: 104

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

```
Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 105
<211> LENGTH: 574
<212> TYPE: PRT
<213> ORGANISM: Homo sapiens

<400> SEQUENCE: 105

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320
```

Lys Ala Asp Ile Asn Lys Trp Arg Ile Lys Leu Asp Asn Tyr Ser Thr
325 330 335

Gln Glu Leu Gly Lys Thr Ile Val Tyr Leu Asp Gly Ser Ser Gln Ser
340 345 350

Cys Arg Phe Arg Glu Cys Asn Met Gly Asn Leu Ile Cys Asp Ala Met
355 360 365

Ile Asn Asn Asn Leu Arg His Ala Asp Glu Thr Phe Trp Asn His Val
370 375 380

Ser Met Cys Ile Leu Asn Gly Gly Gly Ile Arg Ser Pro Ile Asp Glu
385 390 395 400

Arg Asn Asn Gly Thr Ile Thr Trp Glu Asn Leu Ala Ala Val Leu Pro
405 410 415

Phe Gly Gly Thr Phe Asp Leu Val Gln Leu Lys Gly Ser Thr Leu Lys
420 425 430

Lys Ala Phe Glu His Ser Val His Arg Tyr Gly Gln Ser Thr Gly Glu
435 440 445

Phe Leu Gln Val Gly Gly Ile His Val Val Tyr Asp Leu Ser Arg Lys
450 455 460

Pro Gly Asp Arg Val Val Lys Leu Asp Val Leu Cys Thr Lys Cys Arg
465 470 475 480

Val Pro Ser Tyr Asp Pro Leu Lys Met Asp Glu Val Tyr Lys Val Ile
485 490 495

Leu Pro Asn Phe Leu Ala Asn Gly Gly Asp Gly Phe Gln Met Ile Lys
500 505 510

Asp Glu Leu Leu Arg His Asp Ser Gly Asp Gln Asp Ile Asn Val Val
515 520 525

Ser Thr Tyr Ile Ser Lys Met Lys Val Ile Tyr Pro Ala Val Glu Gly
530 535 540

Arg Ile Lys Phe Ser Thr Gly Ser His Cys His Gly Ser Phe Ser Leu
545 550 555 560

Ile Phe Leu Ser Leu Trp Ala Val Ile Phe Val Leu Tyr Gln
565 570

<210> SEQ ID NO 106
<211> LENGTH: 574
<212> TYPE: PRT
<213> ORGANISM: Homo sapiens

<400> SEQUENCE: 106

Met Cys Pro Arg Ala Ala Arg Ala Pro Ala Thr Leu Leu Leu Ala Leu
1 5 10 15

Gly Ala Val Leu Trp Pro Ala Ala Gly Ala Trp Glu Leu Thr Ile Leu
20 25 30

His Thr Asn Asp Val His Ser Arg Leu Glu Gln Thr Ser Glu Asp Ser
35 40 45

Ser Lys Cys Val Asn Ala Ser Arg Cys Met Gly Gly Val Ala Arg Leu
50 55 60

Phe Thr Lys Val Gln Gln Ile Arg Arg Ala Glu Pro Asn Val Leu Leu
65 70 75 80

Leu Asp Ala Gly Asp Gln Tyr Gln Gly Thr Ile Trp Phe Thr Val Tyr
85 90 95

Lys Gly Ala Glu Val Ala His Phe Met Asn Ala Leu Arg Tyr Asp Ala
100 105 110

Met Ala Leu Gly Asn His Glu Phe Asp Asn Gly Val Glu Gly Leu Ile

```
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
    370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540
```

```
Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570


<210> SEQ ID NO 107
<211> LENGTH: 524
<212> TYPE: PRT
<213> ORGANISM: Homo sapiens

<400> SEQUENCE: 107

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
```

340 345 350

Cys Arg Phe Arg Glu Cys Asn Met Gly Asn Leu Ile Cys Asp Ala Met
355 360 365

Ile Asn Asn Asn Leu Arg His Thr Asp Glu Met Phe Trp Asn His Val
370 375 380

Ser Met Cys Ile Leu Asn Gly Gly Gly Ile Arg Ser Pro Ile Asp Glu
385 390 395 400

Arg Asn Asn Gly Ile His Val Val Tyr Asp Leu Ser Arg Lys Pro Gly
405 410 415

Asp Arg Val Val Lys Leu Asp Val Leu Cys Thr Lys Cys Arg Val Pro
420 425 430

Ser Tyr Asp Pro Leu Lys Met Asp Glu Val Tyr Lys Val Ile Leu Pro
435 440 445

Asn Phe Leu Ala Asn Gly Gly Asp Gly Phe Gln Met Ile Lys Asp Glu
450 455 460

Leu Leu Arg His Asp Ser Gly Asp Gln Asp Ile Asn Val Val Ser Thr
465 470 475 480

Tyr Ile Ser Lys Met Lys Val Ile Tyr Pro Ala Val Glu Gly Arg Ile
485 490 495

Lys Phe Ser Thr Gly Ser His Cys His Gly Ser Phe Ser Leu Ile Phe
500 505 510

Leu Ser Leu Trp Ala Val Ile Phe Val Leu Tyr Gln
515 520

<210> SEQ ID NO 108
<211> LENGTH: 15
<212> TYPE: PRT
<213> ORGANISM: Homo sapiens

<400> SEQUENCE: 108

Tyr Leu Pro Tyr Lys Val Leu Pro Val Gly Asp Glu Val Val Gly
1 5 10 15

<210> SEQ ID NO 109
<211> LENGTH: 10
<212> TYPE: PRT
<213> ORGANISM: Homo sapiens

<400> SEQUENCE: 109

Lys Leu Lys Thr Leu Asn Val Asn Lys Ile
1 5 10

<210> SEQ ID NO 110
<211> LENGTH: 20
<212> TYPE: PRT
<213> ORGANISM: Homo sapiens

<400> SEQUENCE: 110

Met Ile Asn Asn Asn Leu Arg His Ala Asp Glu Thr Phe Trp Asn His
1 5 10 15

Val Ser Met Cys
20

<210> SEQ ID NO 111
<211> LENGTH: 18
<212> TYPE: PRT
<213> ORGANISM: Homo sapiens

<400> SEQUENCE: 111

```
Tyr Gln Gly Thr Ile Trp Phe Thr Val Tyr Lys Gly Ala Glu Val Ala
1               5                   10                  15

His Phe


<210> SEQ ID NO 112
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (448)..(448)
<223> OTHER INFORMATION: /replace=" "
<220> FEATURE:
<221> NAME/KEY: MISC_FEATURE
<222> LOCATION: (1)..(448)
<223> OTHER INFORMATION: /note="Variant residues given in the sequence
      have no preference with respect to those in the annotations
      for variant positions"

<400> SEQUENCE: 112

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Arg
            20                  25                  30

Tyr Trp Ser Trp Ile Arg Gln Pro Pro Gly Lys Gly Leu Glu Trp Ile
        35                  40                  45

Gly Tyr Ile Tyr Gly Thr Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Gln Glu Ser Pro Tyr Asn Asn Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
```

```
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 113
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (448)..(448)
<223> OTHER INFORMATION: /replace=" "
<220> FEATURE:
<221> NAME/KEY: MISC_FEATURE
<222> LOCATION: (1)..(448)
<223> OTHER INFORMATION: /note="Variant residues given in the sequence
      have no preference with respect to those in the annotations
      for variant positions"

<400> SEQUENCE: 113

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu Gly Arg
            20                  25                  30

Tyr Trp Ser Trp Ile Arg Gln Pro Pro Gly Lys Gly Leu Glu Trp Ile
        35                  40                  45

Gly Tyr Ile Tyr Gly Ser Gly Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Gln Glu Ser Pro Tyr Asn Asn Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
```

```
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 114
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (451)..(451)
<223> OTHER INFORMATION: /replace=" "
<220> FEATURE:
<221> NAME/KEY: MISC_FEATURE
<222> LOCATION: (1)..(451)
<223> OTHER INFORMATION: /note="Variant residues given in the sequence
      have no preference with respect to those in the annotations
      for variant positions"
```

<400> SEQUENCE: 114

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Arg Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Met Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415
```

```
Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 115
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (448)..(448)
<223> OTHER INFORMATION: /replace=" "
<220> FEATURE:
<221> NAME/KEY: MISC_FEATURE
<222> LOCATION: (1)..(448)
<223> OTHER INFORMATION: /note="Variant residues given in the sequence
      have no preference with respect to those in the annotations
      for variant positions"

<400> SEQUENCE: 115

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Glu Arg Tyr
            20                  25                  30

Tyr Trp Ser Trp Ile Arg Gln Pro Pro Gly Lys Gly Leu Glu Trp Ile
        35                  40                  45

Gly Tyr Ile Tyr Gly Arg Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Gln Glu Ser Pro Tyr Asn Asn Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Glu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 116
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (451)..(451)
<223> OTHER INFORMATION: /replace=" "
<220> FEATURE:
<221> NAME/KEY: MISC_FEATURE
<222> LOCATION: (1)..(451)
<223> OTHER INFORMATION: /note="Variant residues given in the sequence
      have no preference with respect to those in the annotations
      for variant positions"

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Asn
            20                  25                  30

Ala Met Ser Trp Val Arg Gln Ala Pro Gly Lys Gly Leu Glu Trp Val
        35                  40                  45

Ser Ser Ile Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
            100                 105                 110
```

```
Leu Trp Gly Arg Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450
```

<210> SEQ ID NO 117
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: VARIANT
<222> LOCATION: (451)..(451)

```
<223> OTHER INFORMATION: /replace=" "
<220> FEATURE:
<221> NAME/KEY: MISC_FEATURE
<222> LOCATION: (1)..(451)
<223> OTHER INFORMATION: /note="Variant residues given in the sequence
      have no preference with respect to those in the annotations
      for variant positions"

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ser Ile Ser Gly Thr Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 118
<211> LENGTH: 13
<212> TYPE: PRT
<213> ORGANISM: Homo sapiens

<400> SEQUENCE: 118

Arg Gly Asn Val Ile Ser Ser His Gly Asn Pro Ile Leu
1               5                   10


<210> SEQ ID NO 119
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 120
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 121
<211> LENGTH: 20
<212> TYPE: PRT
<213> ORGANISM: Homo sapiens

<400> SEQUENCE: 121

Met Ile Asn Asn Asn Leu Arg His Thr Asp Glu Met Phe Trp Asn His
1               5                   10                  15

Val Ser Met Cys
            20


<210> SEQ ID NO 122
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Ser" or "Arg" or "Lys"
<220> FEATURE:
<221> NAME/KEY: VARIANT
<222> LOCATION: (6)..(6)
<223> OTHER INFORMATION: /replace="Tyr" or "Ser"
<220> FEATURE:
<221> NAME/KEY: VARIANT
<222> LOCATION: (7)..(7)
<223> OTHER INFORMATION: /replace="Asn"
<220> FEATURE:
<221> NAME/KEY: MISC_FEATURE
<222> LOCATION: (1)..(7)
<223> OTHER INFORMATION: /note="Variant residues given in the sequence
      have no preference with respect to those in the annotations
      for variant positions"

<400> SEQUENCE: 122

Gly Phe Thr Phe His Arg Tyr
1               5


<210> SEQ ID NO 123
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
```

<222> LOCATION: (1)..(1)
<223> OTHER INFORMATION: /replace="Thr"
<220> FEATURE:
<221> NAME/KEY: VARIANT
<222> LOCATION: (3)..(3)
<223> OTHER INFORMATION: /replace="Thr"
<220> FEATURE:
<221> NAME/KEY: VARIANT
<222> LOCATION: (5)..(5)
<223> OTHER INFORMATION: /replace="Gly" or "Ser"
<220> FEATURE:
<221> NAME/KEY: VARIANT
<222> LOCATION: (6)..(6)
<223> OTHER INFORMATION: /replace="Ser" or "Leu" or "Tyr"
<220> FEATURE:
<221> NAME/KEY: MISC_FEATURE
<222> LOCATION: (1)..(6)
<223> OTHER INFORMATION: /note="Variant residues given in the sequence have no preference with respect to those in the annotations for variant positions"

<400> SEQUENCE: 123

Ser Gly Ser Gly Met Asn
1 5

<210> SEQ ID NO 124
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: VARIANT
<222> LOCATION: (6)..(6)
<223> OTHER INFORMATION: /replace="Gly" or "Ser"
<220> FEATURE:
<221> NAME/KEY: VARIANT
<222> LOCATION: (7)..(7)
<223> OTHER INFORMATION: /replace="Arg"
<220> FEATURE:
<221> NAME/KEY: MISC_FEATURE
<222> LOCATION: (1)..(7)
<223> OTHER INFORMATION: /note="Variant residues given in the sequence have no preference with respect to those in the annotations for variant positions"

<400> SEQUENCE: 124

Gly Gly Ser Ile Glu Arg Tyr
1 5

<210> SEQ ID NO 125
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (3)..(3)
<223> OTHER INFORMATION: /replace="Ser" or "Thr"
<220> FEATURE:
<221> NAME/KEY: MISC_FEATURE
<222> LOCATION: (1)..(5)

<223> OTHER INFORMATION: /note="Variant residues given in the sequence
      have no preference with respect to those in the annotations
      for variant positions"

<400> SEQUENCE: 125

Tyr Gly Arg Gly Ser
1               5

<210> SEQ ID NO 126
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Ser" or "Arg" or "Lys"
<220> FEATURE:
<221> NAME/KEY: VARIANT
<222> LOCATION: (6)..(6)
<223> OTHER INFORMATION: /replace="Tyr" or "Ser"
<220> FEATURE:
<221> NAME/KEY: VARIANT
<222> LOCATION: (7)..(7)
<223> OTHER INFORMATION: /replace="Asn"
<220> FEATURE:
<221> NAME/KEY: MISC_FEATURE
<222> LOCATION: (1)..(10)
<223> OTHER INFORMATION: /note="Variant residues given in the sequence
      have no preference with respect to those in the annotations
      for variant positions"

<400> SEQUENCE: 126

Gly Phe Thr Phe His Arg Tyr Ala Met Ser
1               5                   10

<210> SEQ ID NO 127
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: VARIANT
<222> LOCATION: (6)..(6)
<223> OTHER INFORMATION: /replace="Gly" or "Ser"
<220> FEATURE:
<221> NAME/KEY: VARIANT
<222> LOCATION: (7)..(7)
<223> OTHER INFORMATION: /replace="Arg"
<220> FEATURE:
<221> NAME/KEY: MISC_FEATURE
<222> LOCATION: (1)..(10)
<223> OTHER INFORMATION: /note="Variant residues given in the sequence
      have no preference with respect to those in the annotations
      for variant positions"

<400> SEQUENCE: 127

Gly Gly Ser Ile Glu Arg Tyr Tyr Trp Ser
1               5                   10

<210> SEQ ID NO 128
<211> LENGTH: 8
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: VARIANT
<222> LOCATION: (5)..(5)
<223> OTHER INFORMATION: /replace="Ser" or "Arg" or "Lys"
<220> FEATURE:
<221> NAME/KEY: VARIANT
<222> LOCATION: (6)..(6)
<223> OTHER INFORMATION: /replace="Tyr" or "Ser"
<220> FEATURE:
<221> NAME/KEY: VARIANT
<222> LOCATION: (7)..(7)
<223> OTHER INFORMATION: /replace="Asn"
<220> FEATURE:
<221> NAME/KEY: MISC_FEATURE
<222> LOCATION: (1)..(8)
<223> OTHER INFORMATION: /note="Variant residues given in the sequence
have no preference with respect to those in the annotations
for variant positions"

<400> SEQUENCE: 128

Gly Phe Thr Phe His Arg Tyr Ala
1 5

<210> SEQ ID NO 129
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: VARIANT
<222> LOCATION: (2)..(2)
<223> OTHER INFORMATION: /replace="Thr"
<220> FEATURE:
<221> NAME/KEY: VARIANT
<222> LOCATION: (4)..(4)
<223> OTHER INFORMATION: /replace="Thr"
<220> FEATURE:
<221> NAME/KEY: VARIANT
<222> LOCATION: (6)..(6)
<223> OTHER INFORMATION: /replace="Gly" or "Ser"
<220> FEATURE:
<221> NAME/KEY: VARIANT
<222> LOCATION: (7)..(7)
<223> OTHER INFORMATION: /replace="Ser" or "Leu" or "Tyr"
<220> FEATURE:
<221> NAME/KEY: MISC_FEATURE
<222> LOCATION: (1)..(8)
<223> OTHER INFORMATION: /note="Variant residues given in the sequence
have no preference with respect to those in the annotations
for variant positions"

<400> SEQUENCE: 129

Ile Ser Gly Ser Gly Met Asn Thr
1 5

<210> SEQ ID NO 130
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: VARIANT
<222> LOCATION: (5)..(5)
<223> OTHER INFORMATION: /replace="Ser"

```
<220> FEATURE:
<221> NAME/KEY: VARIANT
<222> LOCATION: (6)..(6)
<223> OTHER INFORMATION: /replace="Gly" or "Ser"
<220> FEATURE:
<221> NAME/KEY: VARIANT
<222> LOCATION: (7)..(7)
<223> OTHER INFORMATION: /replace="Arg"
<220> FEATURE:
<221> NAME/KEY: MISC_FEATURE
<222> LOCATION: (1)..(8)
<223> OTHER INFORMATION: /note="Variant residues given in the sequence
      have no preference with respect to those in the annotations
      for variant positions"

<400> SEQUENCE: 130

Gly Gly Ser Ile Glu Arg Tyr Tyr
1               5


<210> SEQ ID NO 131
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(3)
<223> OTHER INFORMATION: /replace="Ser"
<220> FEATURE:
<221> NAME/KEY: VARIANT
<222> LOCATION: (4)..(4)
<223> OTHER INFORMATION: /replace="Ser" or "Thr"
<220> FEATURE:
<221> NAME/KEY: MISC_FEATURE
<222> LOCATION: (1)..(7)
<223> OTHER INFORMATION: /note="Variant residues given in the sequence
      have no preference with respect to those in the annotations
      for variant positions"

<400> SEQUENCE: 131

Ile Tyr Gly Arg Gly Ser Thr
1               5


<210> SEQ ID NO 132
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95
```

-continued

```
Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

<210> SEQ ID NO 133
<211> LENGTH: 465
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Lys Gln
        355                 360                 365

Gly Gln Asn Gln Leu Tyr Asn Glu Leu Asn Leu Gly Arg Arg Glu Glu
    370                 375                 380
```

```
Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465


<210> SEQ ID NO 134
<211> LENGTH: 521
<212> TYPE: PRT
<213> ORGANISM: Homo sapiens

<400> SEQUENCE: 134

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205

Gly Val Asp Val Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
```

```
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Ala Asp Glu
            340                 345                 350

Thr Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
    450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys
        515                 520


<210> SEQ ID NO 135
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Gly Phe Thr Phe Arg Ser Tyr Ala Met Ser
1               5                   10


<210> SEQ ID NO 136
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Ala Ile Thr Gly Ser Gly Gly Leu Thr Tyr Tyr Ala Asp Ser Val Lys
1               5                   10                  15

Gly
```

<210> SEQ ID NO 137
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 137

Ser Tyr Ala Met Ser
1 5

<210> SEQ ID NO 138
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 138

Gly Phe Thr Phe Arg Ser Tyr
1 5

<210> SEQ ID NO 139
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 139

Thr Gly Ser Gly Gly Leu
1 5

<210> SEQ ID NO 140
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 140

Gly Phe Thr Phe Arg Ser Tyr Ala
1 5

<210> SEQ ID NO 141
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 141

Ile Thr Gly Ser Gly Gly Leu Thr
1 5

<210> SEQ ID NO 142
<211> LENGTH: 124
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 142

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Thr Gly Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
            100                 105                 110

Leu Trp Gly Arg Gly Thr Leu Val Thr Val Ser Ser
        115                 120
```

<210> SEQ ID NO 143
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 143

```
gaggtgcagc tgttggagtc tgggggaggc ttggtacagc ctggggggtc cctgagactc     60

tcctgtgcag cctctggatt cacctttcgt agctatgcca tgagctgggt ccgccaggct    120

ccagggaagg ggctggagtg ggtctcagct attacgggaa gtggtggttt gacatactac    180

gcagactccg tgaagggccg gttcaccatc tccagagaca attccaagaa cacgctgtat    240

ctgcaaatga acagcctgag agccgaggac acggcggtgt actactgcgc cagaggtgga    300

ttgtacggaa gcggaagcta cttgagtgac ttcgacctat gggggagagg taccttggtc    360

accgtctcct ca                                                        372
```

<210> SEQ ID NO 144
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144

```
gaaatagtgt tgacgcagtc tccagccacc ctgtctgtgt ctccagggga aagagccacc     60

ctctcctgca gggccagtca gagtgttggc agcaacttag cctggtacca gcagaaacct    120

ggccaggctc ccaggctcct catctatggt gcatccacca gggccactgg tatcccagcc    180

aggttcagtg gcagtgggtc tgggacagag ttcactctca ccatcagcag cctgcagtct    240

gaagattttg cagtttatta ctgtcagcag cacaatgcct tcccttacac ttttggcgga    300
```

```
gggaccaagg ttgagatcaa a                                            321


<210> SEQ ID NO 145
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Gly Phe Thr Phe Lys Ser Tyr Ala Met Ser
1               5                   10


<210> SEQ ID NO 146
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Ala Ile Ser Gly Ser Gly Ser Tyr Thr Tyr Tyr Ala Asp Ser Val Lys
1               5                   10                  15

Gly


<210> SEQ ID NO 147
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Gly Phe Thr Phe Lys Ser Tyr
1               5


<210> SEQ ID NO 148
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Ser Gly Ser Gly Ser Tyr
1               5


<210> SEQ ID NO 149
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 149

Gly Phe Thr Phe Lys Ser Tyr Ala
1               5
```

```
<210> SEQ ID NO 150
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Ile Ser Gly Ser Gly Ser Tyr Thr
1               5


<210> SEQ ID NO 151
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 151

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
            100                 105                 110

Leu Trp Gly Arg Gly Thr Leu Val Thr Val Ser Ser
        115                 120


<210> SEQ ID NO 152
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 152

gaggtgcagc tgttggagtc tgggggaggc ttggtacagc ctggggggtc cctgagactc      60

tcctgtgcag cctctggatt cacctttaag agctatgcca tgagttgggt ccgccaggct     120

ccagggaagg ggctggagtg ggtctcagct attagtggaa gtggttcgta tacatactac     180

gcagactccg tgaagggccg gttcaccatc tccagagaca attccaagaa cacgctgtat     240

ctgcaaatga acagcctgag agccgaggac acggcggtgt actactgcgc cagaggtgga     300

ttgtacggaa gcggaagcta cttgagtgac ttcgacctat gggggagagg taccttggtc     360

accgtctcct ca                                                         372
```

<210> SEQ ID NO 153
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 153

Gly Phe Thr Phe Ser Ser Tyr Ala Met Ser
1 5 10

<210> SEQ ID NO 154
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 154

Ala Ile Ser Gly Ser Gly Gly Ser Thr Tyr Tyr Ala Asp Ser Val Lys
1 5 10 15

Gly

<210> SEQ ID NO 155
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 155

Gly Phe Thr Phe Ser Ser Tyr
1 5

<210> SEQ ID NO 156
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 156

Ser Gly Ser Gly Gly Ser
1 5

<210> SEQ ID NO 157
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 157

Gly Phe Thr Phe Ser Ser Tyr Ala
1 5

<210> SEQ ID NO 158
<211> LENGTH: 8

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 158

Ile Ser Gly Ser Gly Gly Ser Thr
1 5

<210> SEQ ID NO 159
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 159

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Leu Tyr Gly Ser Gly Ser Tyr Leu Ser Asp Phe Asp
100 105 110

Leu Trp Gly Arg Gly Thr Leu Val Thr Val Ser Ser
115 120

<210> SEQ ID NO 160
<211> LENGTH: 372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 160
gaggtgcagc tgttggagtc tgggggaggc ttggtacagc ctgggggggtc cctgagactc 60 tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggcggtgt actactgcgc cagaggtgga 300
ttgtacggaa gcggaagcta cttgagtgac ttcgacctat gggggagagg taccttggtc 360
accgtctcct ca 372

<210> SEQ ID NO 161
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 161

Gly Gly Ser Ile Ser Ser Tyr Tyr Trp Ser
1 5 10

<210> SEQ ID NO 162
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 162

Tyr Ile Tyr Ser Ser Gly Ser Thr Asn Tyr Asn Pro Ser Leu Lys Ser
1 5 10 15

<210> SEQ ID NO 163
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 163

Ser Tyr Tyr Trp Ser
1 5

<210> SEQ ID NO 164
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 164

Gly Gly Ser Ile Ser Ser Tyr
1 5

<210> SEQ ID NO 165
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 165

Tyr Ser Ser Gly Ser
1 5

<210> SEQ ID NO 166
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 166

Gly Gly Ser Ile Ser Ser Tyr Tyr
1               5

<210> SEQ ID NO 167
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 167

Ile Tyr Ser Ser Gly Ser Thr
1               5

<210> SEQ ID NO 168
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 168

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Ser Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Gln Glu Ser Pro Tyr Asn Asn Trp Phe Asp Pro Trp Gly
            100                 105                 110

Gln Gly Thr Leu Val Thr Val Ser Ser
        115                 120

<210> SEQ ID NO 169
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 169
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaagg gactggagtg gattgggtat atctatagta gtgggagcac caactacaac    180
ccctccctca agagtcgagt caccatatca gtagacacgt ccaagaacca gttctccctg    240
aagctgagtt ctgtgaccgc cgcagacacg gcggtgtact actgcgccag agaatctcag    300

```
gagagtccat acaacaattg gttcgaccca tggggacagg gtacattggt caccgtctcc    360

tca                                                                  363


<210> SEQ ID NO 170
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 170

gacatccaga tgacccagtc tccatcttcc gtgtctgcat ctgtaggaga cagagtcacc     60

atcacttgtc gggcgagtca gggtattagc agctggttag cctggtatca gcagaaacca    120

gggaaagccc ctaagctcct gatctatgct gcatccagtt tgcaaagtgg ggtcccatca    180

aggttcagcg gcagtggatc tgggacagat ttcactctca ccatcagcag cctgcagcct    240

gaagattttg caacttatta ctgtcagcag ggaaacagtt tccctaggac ttttggcgga    300

gggaccaagg ttgagatcaa a                                              321


<210> SEQ ID NO 171
<211> LENGTH: 527
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Trp Glu Leu Thr Ile Leu His Thr Asn Asp Val His Ser Arg Leu Glu
1               5                   10                  15

Gln Thr Ser Glu Asp Ser Ser Lys Cys Val Asn Ala Ser Arg Cys Met
            20                  25                  30

Gly Gly Val Ala Arg Leu Phe Thr Lys Val Gln Gln Ile Arg Arg Ala
        35                  40                  45

Glu Pro Asn Val Leu Leu Leu Asp Ala Gly Asp Gln Tyr Gln Gly Thr
    50                  55                  60

Ile Trp Phe Thr Val Tyr Lys Gly Ala Glu Val Ala His Phe Met Asn
65                  70                  75                  80

Ala Leu Arg Tyr Asp Ala Met Ala Leu Gly Asn His Glu Phe Asp Asn
                85                  90                  95

Gly Val Glu Gly Leu Ile Glu Pro Leu Leu Lys Glu Ala Lys Phe Pro
            100                 105                 110

Ile Leu Ser Ala Asn Ile Lys Ala Lys Gly Pro Leu Ala Ser Gln Ile
        115                 120                 125

Ser Gly Leu Tyr Leu Pro Tyr Lys Val Leu Pro Val Gly Asp Glu Val
    130                 135                 140

Val Gly Ile Val Gly Tyr Thr Ser Lys Glu Thr Pro Phe Leu Ser Asn
145                 150                 155                 160

Pro Gly Thr Asn Leu Val Phe Glu Asp Glu Ile Thr Ala Leu Gln Pro
                165                 170                 175

Glu Val Asp Lys Leu Lys Thr Leu Asn Val Asn Lys Ile Ile Ala Leu
            180                 185                 190

Gly His Ser Gly Phe Glu Met Asp Lys Leu Ile Ala Gln Lys Val Arg
        195                 200                 205
```

Gly Val Asp Val Val Val Gly Gly His Ser Asn Thr Phe Leu Tyr Thr
    210                 215                 220

Gly Asn Pro Pro Ser Lys Glu Val Pro Ala Gly Lys Tyr Pro Phe Ile
225                 230                 235                 240

Val Thr Ser Asp Asp Gly Arg Lys Val Pro Val Val Gln Ala Tyr Ala
                245                 250                 255

Phe Gly Lys Tyr Leu Gly Tyr Leu Lys Ile Glu Phe Asp Glu Arg Gly
            260                 265                 270

Asn Val Ile Ser Ser His Gly Asn Pro Ile Leu Leu Asn Ser Ser Ile
        275                 280                 285

Pro Glu Asp Pro Ser Ile Lys Ala Asp Ile Asn Lys Trp Arg Ile Lys
    290                 295                 300

Leu Asp Asn Tyr Ser Thr Gln Glu Leu Gly Lys Thr Ile Val Tyr Leu
305                 310                 315                 320

Asp Gly Ser Ser Gln Ser Cys Arg Phe Arg Glu Cys Asn Met Gly Asn
                325                 330                 335

Leu Ile Cys Asp Ala Met Ile Asn Asn Asn Leu Arg His Ala Asp Glu
            340                 345                 350

Thr Phe Trp Asn His Val Ser Met Cys Ile Leu Asn Gly Gly Gly Ile
        355                 360                 365

Arg Ser Pro Ile Asp Glu Arg Asn Asn Gly Thr Ile Thr Trp Glu Asn
    370                 375                 380

Leu Ala Ala Val Leu Pro Phe Gly Gly Thr Phe Asp Leu Val Gln Leu
385                 390                 395                 400

Lys Gly Ser Thr Leu Lys Lys Ala Phe Glu His Ser Val His Arg Tyr
                405                 410                 415

Gly Gln Ser Thr Gly Glu Phe Leu Gln Val Gly Gly Ile His Val Val
            420                 425                 430

Tyr Asp Leu Ser Arg Lys Pro Gly Asp Arg Val Val Lys Leu Asp Val
        435                 440                 445

Leu Cys Thr Lys Cys Arg Val Pro Ser Tyr Asp Pro Leu Lys Met Asp
    450                 455                 460

Glu Val Tyr Lys Val Ile Leu Pro Asn Phe Leu Ala Asn Gly Gly Asp
465                 470                 475                 480

Gly Phe Gln Met Ile Lys Asp Glu Leu Leu Arg His Asp Ser Gly Asp
                485                 490                 495

Gln Asp Ile Asn Val Val Ser Thr Tyr Ile Ser Lys Met Lys Val Ile
            500                 505                 510

Tyr Pro Ala Val Glu Gly Arg Ile Lys His His His His His His
        515                 520                 525

<210> SEQ ID NO 172
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met

```
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 173

<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 173

```
Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 174
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 174

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Leu Trp Glu Val Arg Ala Leu Pro Ser Val Tyr Trp Gly
            100                 105                 110

Gln Gly Thr Leu Val Thr Val Ser Ser
        115                 120


<210> SEQ ID NO 175
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 175

Ser Tyr Glu Leu Thr Gln Pro Pro Ser Val Ser Val Ala Pro Gly Gln
1               5                   10                  15

Thr Ala Arg Ile Thr Cys Gly Ala Asn Asp Ile Gly Ser Lys Ser Val
            20                  25                  30

His Trp Tyr Gln Gln Lys Ala Gly Gln Ala Pro Val Leu Val Val Ser
        35                  40                  45

Glu Asp Ile Ile Arg Pro Ser Gly Ile Pro Glu Arg Ile Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Asp Ser Asp Gln
                85                  90                  95

Tyr Val Phe Gly Thr Gly Thr Lys Val Thr Val Leu Gly
            100                 105


<210> SEQ ID NO 176
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Arg Gly Asp Ser
1


<210> SEQ ID NO 177
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Met
        35                  40                  45

Gly Asp Ile Ile Pro Ser Asn Gly Ala Thr Phe Tyr Asn Gln Lys Phe
```

```
    50                  55                  60

Lys Gly Lys Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Leu Leu Arg Ala Ser Trp Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asp Thr Lys Val Asp Lys Lys Val Glu Pro Lys Ser Cys Asp
    210                 215                 220

Lys Thr His Thr Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Lys His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Glu Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Asp Val Ser Gly Phe Tyr Pro Ser Asp Ile Ala Val Glu Trp Glu
    370                 375                 380

Ser Asp Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Glu Gln Gly Asp Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 178
<211> LENGTH: 485
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Glu Pro
                245                 250                 255

Lys Ser Ser Asp Lys Thr His Thr Cys Pro Pro Cys Pro Ala Pro Pro
            260                 265                 270

Val Ala Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
```

```
    370                 375                 380

Gln Val Tyr Thr Leu Pro Pro Ser Arg Glu Gln Met Thr Lys Asn Gln
385                 390                 395                 400

Val Lys Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Lys
                485


<210> SEQ ID NO 179
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Asp Phe Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Thr
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 180
```

```
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Asp Thr Ser Tyr Asn Gln Lys Phe
    50                  55                  60

Gln Gly Arg Val Thr Ile Thr Ala Asp Lys Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asp Thr Lys Val Asp Lys Lys Val Glu Pro Lys Ser Cys
    210                 215                 220

Asp Lys Thr His Thr Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Lys His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Glu Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

-continued

```
Thr Cys Asp Val Ser Gly Phe Tyr Pro Ser Asp Ile Ala Val Glu Trp
    370                 375                 380

Glu Ser Asp Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Glu Gln Gly Asp Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 181
<211> LENGTH: 485
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Glu Pro
                245                 250                 255

Lys Ser Ser Asp Lys Thr His Thr Cys Pro Pro Cys Pro Ala Pro Pro
```

```
            260                 265                 270

Val Ala Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Glu Gln Met Thr Lys Asn Gln
385                 390                 395                 400

Val Lys Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Lys
                485


<210> SEQ ID NO 182
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Gln Ile Val Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Phe Gln Gln Lys Pro Gly Lys Ser Pro Lys Pro Leu Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Thr Ser Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 183
<211> LENGTH: 114
<212> TYPE: PRT
<213> ORGANISM: Homo sapiens

<400> SEQUENCE: 183

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 184
<211> LENGTH: 170
<212> TYPE: PRT
<213> ORGANISM: Homo sapiens

<400> SEQUENCE: 184

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110
```

```
Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly
                165                 170


<210> SEQ ID NO 185
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 186
<211> LENGTH: 297
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110
```

```
Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295


<210> SEQ ID NO 187
<211> LENGTH: 114
<212> TYPE: PRT
<213> ORGANISM: Homo sapiens
<220> FEATURE:
<221> NAME/KEY: VARIANT
<222> LOCATION: (93)..(93)
<223> OTHER INFORMATION: /replace="Lys"
<220> FEATURE:
<221> NAME/KEY: MISC_FEATURE
<222> LOCATION: (1)..(114)
<223> OTHER INFORMATION: /note="Variant residues given in the sequence
      have no preference with respect to those in the annotations
      for variant positions"

<400> SEQUENCE: 187

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 188
<211> LENGTH: 77
<212> TYPE: PRT
<213> ORGANISM: Homo sapiens

<400> SEQUENCE: 188

Ile Thr Cys Pro Pro Pro Met Ser Val Glu His Ala Asp Ile Trp Val
1 5 10 15

Lys Ser Tyr Ser Leu Tyr Ser Arg Glu Arg Tyr Ile Cys Asn Ser Gly
20 25 30

Phe Lys Arg Lys Ala Gly Thr Ser Ser Leu Thr Glu Cys Val Leu Asn
35 40 45

Lys Ala Thr Asn Val Ala His Trp Thr Thr Pro Ser Leu Lys Cys Ile
50 55 60

Arg Asp Pro Ala Leu Val His Gln Arg Pro Ala Pro Pro
65 70 75

<210> SEQ ID NO 189
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (4)..(4)
<223> OTHER INFORMATION: /replace="Ser" or "Arg" or "Lys"
<220> FEATURE:
<221> NAME/KEY: VARIANT
<222> LOCATION: (5)..(5)
<223> OTHER INFORMATION: /replace="Tyr" or "Ser"
<220> FEATURE:
<221> NAME/KEY: VARIANT
<222> LOCATION: (6)..(6)
<223> OTHER INFORMATION: /replace="Asn"
<220> FEATURE:
<221> NAME/KEY: MISC_FEATURE
<222> LOCATION: (1)..(9)
<223> OTHER INFORMATION: /note="Variant residues given in the sequence have no preference with respect to those in the annotations for variant positions"

<400> SEQUENCE: 189

Phe Thr Phe His Arg Tyr Ala Met Ser
1 5

<210> SEQ ID NO 190
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 190

Phe Thr Phe His Arg Tyr Ala Met Ser
1 5

<210> SEQ ID NO 191
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 191

Phe Thr Phe Ser Tyr Asn Ala Met Ser
1 5

<210> SEQ ID NO 192
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 192

Phe Thr Phe Ser Arg Tyr Ala Met Ser
1 5

<210> SEQ ID NO 193
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 193

Phe Thr Phe Arg Ser Tyr Ala Met Ser
1 5

<210> SEQ ID NO 194
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 194

Phe Thr Phe Lys Ser Tyr Ala Met Ser
1 5

<210> SEQ ID NO 195
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 195

Phe Thr Phe Ser Ser Tyr Ala Met Ser
1 5

<210> SEQ ID NO 196
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: VARIANT
<222> LOCATION: (4)..(4)
<223> OTHER INFORMATION: /replace="Ser"

<220> FEATURE:
<221> NAME/KEY: VARIANT
<222> LOCATION: (5)..(5)
<223> OTHER INFORMATION: /replace="Gly" or "Ser"
<220> FEATURE:
<221> NAME/KEY: VARIANT
<222> LOCATION: (6)..(6)
<223> OTHER INFORMATION: /replace="Arg"
<220> FEATURE:
<221> NAME/KEY: MISC_FEATURE
<222> LOCATION: (1)..(9)
<223> OTHER INFORMATION: /note="Variant residues given in the sequence have no preference with respect to those in the annotations for variant positions"

<400> SEQUENCE: 196

Gly Ser Ile Glu Arg Tyr Tyr Trp Ser
1 5

<210> SEQ ID NO 197
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 197

Gly Ser Ile Glu Arg Tyr Tyr Trp Ser
1 5

<210> SEQ ID NO 198
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 198

Gly Ser Ile Glu Gly Arg Tyr Trp Ser
1 5

<210> SEQ ID NO 199
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 199

Gly Ser Ile Ser Gly Arg Tyr Trp Ser
1 5

<210> SEQ ID NO 200
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 200

Gly Ser Ile Ser Ser Tyr Tyr Trp Ser
1 5

```
<210> SEQ ID NO 201
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Ala Ile Ser Gly Thr Gly Ile Ser Thr Tyr Tyr Ala Asp Ser Val Lys
1               5                   10                  15

Gly


<210> SEQ ID NO 202
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Ser Gly Thr Gly Ile Ser
1               5


<210> SEQ ID NO 203
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 203

Ile Ser Gly Thr Gly Ile Ser Thr
1               5


<210> SEQ ID NO 204
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 204

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ala Ile Ser Gly Thr Gly Ile Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
```

100 105 110

Leu Trp Gly Arg Gly Thr Leu Val Thr Val Ser Ser
115 120

<210> SEQ ID NO 205
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 205

Arg Ala Ser Gln Ser Ile Ser Ser Trp Leu Ala
1 5 10

<210> SEQ ID NO 206
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 206

Asp Ala Ser Ser Leu Glu Ser
1 5

<210> SEQ ID NO 207
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 207

Gln Gln Ser Asn Thr Phe Tyr Thr
1 5

<210> SEQ ID NO 208
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 208

Ser Gln Ser Ile Ser Ser Trp
1 5

<210> SEQ ID NO 209
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 209

Asp Ala Ser
1

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

-continued

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 228

Ser Asn Thr Phe Tyr
1               5

<210> SEQ ID NO 229
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 229

Gln Ser Ile Ser Ser Trp
1               5

```
<210> SEQ ID NO 230
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 230

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Thr Phe Tyr Thr
                85                  90                  95

Phe Gly Gly Gly Thr Lys Val Glu Ile Lys
            100                 105


<210> SEQ ID NO 231
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Ala Ile Ser Gly Thr Gly Leu Ser Thr Tyr Tyr Ala Asp Ser Val Lys
1               5                   10                  15

Gly


<210> SEQ ID NO 232
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Ser Gly Thr Gly Leu Ser
1               5


<210> SEQ ID NO 233
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Ile Ser Gly Thr Gly Leu Ser Thr
1               5
```

<210> SEQ ID NO 234
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 234

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ala Ile Ser Gly Thr Gly Leu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Tyr Gly Ser Gly Ser Tyr Leu Ser Asp Phe Asp
            100                 105                 110

Leu Trp Gly Arg Gly Thr Leu Val Thr Val Ser Ser
        115                 120

<210> SEQ ID NO 235
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 235

Gly Tyr Thr Phe Thr Tyr Tyr Trp Met His
1               5                   10

<210> SEQ ID NO 236
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 236

Ser Ile Asn Pro Asn Ser Gly Ser Thr Asn Tyr Ala Gln Lys Phe Gln
1               5                   10                  15

Gly

<210> SEQ ID NO 237
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 237

```
Asp Thr Gly Gly Asp Lys Ser Pro Leu Thr Tyr Tyr Tyr Tyr Gly Met
1               5                   10                  15

Asp Val


<210> SEQ ID NO 238
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Tyr Tyr Trp Met His
1               5


<210> SEQ ID NO 239
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 239

Gly Tyr Thr Phe Thr Tyr Tyr
1               5


<210> SEQ ID NO 240
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Asn Pro Asn Ser Gly Ser
1               5


<210> SEQ ID NO 241
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Gly Tyr Thr Phe Thr Tyr Tyr Trp
1               5


<210> SEQ ID NO 242
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Ile Asn Pro Asn Ser Gly Ser Thr
```

1 5

<210> SEQ ID NO 243
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 243

Ala Arg Asp Thr Gly Gly Asp Lys Ser Pro Leu Thr Tyr Tyr Tyr Tyr
1 5 10 15

Gly Met Asp Val
20

<210> SEQ ID NO 244
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 244

Tyr Thr Phe Thr Tyr Tyr Trp Met His
1 5

<210> SEQ ID NO 245
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 245

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Tyr Tyr
20 25 30

Trp Met His Trp Val Arg Gln Ala Pro Gly Gln Gly Leu Glu Trp Met
35 40 45

Gly Ser Ile Asn Pro Asn Ser Gly Ser Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Thr Gly Gly Asp Lys Ser Pro Leu Thr Tyr Tyr Tyr Tyr
100 105 110

Gly Met Asp Val Trp Gly Gln Gly Thr Thr Val Thr Val Ser Ser
115 120 125

<210> SEQ ID NO 246
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 246

Arg Ala Ser Gln Gly Ile Ser Arg Trp Leu Ala
1 5 10

<210> SEQ ID NO 247
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 247

Gln Gln Ala Ile Ala Leu Pro Pro Phe Thr
1 5 10

<210> SEQ ID NO 248
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 248

Ser Gln Gly Ile Ser Arg Trp
1 5

<210> SEQ ID NO 249
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 249

Ala Ile Ala Leu Pro Pro Phe
1 5

<210> SEQ ID NO 250
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 250

Gln Gly Ile Ser Arg Trp
1 5

<210> SEQ ID NO 251
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 251

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Ala Leu Pro Pro
                85                  90                  95

Phe Thr Phe Gly Gly Gly Thr Lys Val Glu Ile Lys
            100                 105


<210> SEQ ID NO 252
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Gly Phe Thr Phe Ser Ser Tyr Trp Met Ser
1               5                   10


<210> SEQ ID NO 253
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Asn Ile Lys Gln Asp Gly Ser Glu Lys Tyr Tyr Val Asp Ser Val Lys
1               5                   10                  15

Gly


<210> SEQ ID NO 254
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 254

Ala Pro Glu Tyr Tyr Ser Thr Thr Thr Arg Leu Tyr Tyr Tyr Tyr Gly
1               5                   10                  15

Met Asp Val


<210> SEQ ID NO 255
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 255

Ser Tyr Trp Met Ser
1 5

<210> SEQ ID NO 256
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 256

Lys Gln Asp Gly Ser Glu
1 5

<210> SEQ ID NO 257
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 257

Gly Phe Thr Phe Ser Ser Tyr Trp
1 5

<210> SEQ ID NO 258
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 258

Ile Lys Gln Asp Gly Ser Glu Lys
1 5

<210> SEQ ID NO 259
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 259

Ala Arg Ala Pro Glu Tyr Tyr Ser Thr Thr Thr Arg Leu Tyr Tyr Tyr
1 5 10 15

Tyr Gly Met Asp Val
20

<210> SEQ ID NO 260
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 260

Phe Thr Phe Ser Ser Tyr Trp Met Ser
1 5

<210> SEQ ID NO 261
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 261

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Lys Gln Asp Gly Ser Glu Lys Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ala Pro Glu Tyr Tyr Ser Thr Thr Thr Arg Leu Tyr Tyr Tyr
100 105 110

Tyr Gly Met Asp Val Trp Gly Gln Gly Thr Thr Val Thr Val Ser Ser
115 120 125

<210> SEQ ID NO 262
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 262

Lys Ser Ser Gln Ser Val Leu Tyr Ser Ser Asn Asn Lys Asn Tyr Leu
1 5 10 15

Ala

<210> SEQ ID NO 263
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 263

Trp Ala Ser Thr Arg Glu Ser
1 5

<210> SEQ ID NO 264
<211> LENGTH: 9
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 264

Gln Gln Tyr Asp Ala His Pro Phe Thr
1 5

<210> SEQ ID NO 265
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 265

Ser Gln Ser Val Leu Tyr Ser Ser Asn Asn Lys Asn Tyr
1 5 10

<210> SEQ ID NO 266
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 266

Trp Ala Ser
1

<210> SEQ ID NO 267
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 267

Tyr Asp Ala His Pro Phe
1 5

<210> SEQ ID NO 268
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 268

Gln Ser Val Leu Tyr Ser Ser Asn Asn Lys Asn Tyr
1 5 10

<210> SEQ ID NO 269
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 269

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Asp Ala His Pro Phe Thr Phe Gly Gly Gly Thr Lys Val Glu Ile
100 105 110

Lys

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 287

Gly Gly Thr Phe Ser Ser Tyr Ala Ile Ser
1 5 10

<210> SEQ ID NO 288
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 288

Gly Ile Ile Pro Ile Phe Gly Thr Ala Asn Tyr Ala Gln Lys Phe Gln
1 5 10 15

Gly

<210> SEQ ID NO 289
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 289

His Tyr Tyr Asp Tyr Trp Ser Gly Tyr Tyr Thr Asn Thr Gly Ile Tyr
1 5 10 15

<210> SEQ ID NO 290
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 290

Ser Tyr Ala Ile Ser
1 5

<210> SEQ ID NO 291
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 291

Gly Gly Thr Phe Ser Ser Tyr
1 5

<210> SEQ ID NO 292
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 292

Ile Pro Ile Phe Gly Thr
1 5

<210> SEQ ID NO 293
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 293

Gly Gly Thr Phe Ser Ser Tyr Ala
1 5

<210> SEQ ID NO 294
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 294

Ile Ile Pro Ile Phe Gly Thr Ala
1 5

<210> SEQ ID NO 295
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 295

Ala Arg His Tyr Tyr Asp Tyr Trp Ser Gly Tyr Tyr Thr Asn Thr Gly
1 5 10 15

Ile Tyr

<210> SEQ ID NO 296
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 296

Gly Thr Phe Ser Ser Tyr Ala Ile Ser
1 5

<210> SEQ ID NO 297
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 297

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

```
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Tyr Asp Tyr Trp Ser Gly Tyr Tyr Thr Asn Thr Gly
            100                 105                 110

Ile Tyr Trp Gly Gln Gly Thr Leu Val Thr Val Ser Ser
        115                 120                 125


<210> SEQ ID NO 298
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Arg Ala Ser Gln Ser Val Ser Ser Asn Leu Ala
1               5                   10


<210> SEQ ID NO 299
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Gln Gln Ser Gly Ala Leu Pro Ile Thr
1               5


<210> SEQ ID NO 300
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Ser Gln Ser Val Ser Ser Asn
1               5


<210> SEQ ID NO 301
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 301

Ser Gly Ala Leu Pro Ile
1               5
```

<210> SEQ ID NO 302
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 302

Gln Ser Val Ser Ser Asn
1 5

<210> SEQ ID NO 303
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 303

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Ser Gly Ala Leu Pro Ile
85 90 95

Thr Phe Gly Gly Gly Thr Lys Val Glu Ile Lys
100 105

<210> SEQ ID NO 304
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 304

Gly Gly Ser Phe Leu Arg Tyr Tyr Trp Ser
1 5 10

<210> SEQ ID NO 305
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 305

Glu Ile Asp His Ser Gly Ser Thr Asn Tyr Asn Pro Ser Leu Lys Ser
1 5 10 15

<210> SEQ ID NO 306

-continued

<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 306

Gly Gln Asn Tyr Tyr Gly Ser Gly Ser Ala Asp Gly Phe Asp Pro
1 5 10 15

<210> SEQ ID NO 307
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 307

Gly Gly Ser Phe Leu Arg Tyr
1 5

<210> SEQ ID NO 308
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 308

Asp His Ser Gly Ser
1 5

<210> SEQ ID NO 309
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 309

Gly Gly Ser Phe Leu Arg Tyr Tyr
1 5

<210> SEQ ID NO 310
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 310

Ile Asp His Ser Gly Ser Thr
1 5

<210> SEQ ID NO 311
<211> LENGTH: 17
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 311

```
Ala Arg Gly Gln Asn Tyr Tyr Gly Ser Gly Ser Ala Asp Gly Phe Asp
1               5                   10                  15

Pro
```

<210> SEQ ID NO 312
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 312

```
Gly Ser Phe Leu Arg Tyr Tyr Trp Ser
1               5
```

<210> SEQ ID NO 313
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 313

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Leu Arg Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gln Asn Tyr Tyr Gly Ser Gly Ser Ala Asp Gly Phe Asp Pro
            100                 105                 110

Trp Gly Gln Gly Thr Leu Val Thr Val Ser Ser
        115                 120
```

<210> SEQ ID NO 314
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 314

```
Gln Gln Ala Asn Ser Phe Pro Pro Thr
1               5
```

<210> SEQ ID NO 315

-continued

<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 315

Ala Asn Ser Phe Pro Pro
1 5

<210> SEQ ID NO 316
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 316

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Pro
85 90 95

Thr Phe Gly Gly Gly Thr Lys Val Glu Ile Lys
100 105

<210> SEQ ID NO 317
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 317

Gly Gly Ser Phe Ser Gly Tyr Tyr Trp Ser
1 5 10

<210> SEQ ID NO 318
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 318

Glu Ile Asp Ala Ser Gly Ser Thr Arg Tyr Asn Pro Ser Leu Lys Ser
1 5 10 15

<210> SEQ ID NO 319
<211> LENGTH: 9

<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 319

Pro Leu Tyr Asp Ala Tyr Leu Asp Val
1 5

<210> SEQ ID NO 320
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 320

Gly Tyr Tyr Trp Ser
1 5

<210> SEQ ID NO 321
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 321

Gly Gly Ser Phe Ser Gly Tyr
1 5

<210> SEQ ID NO 322
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 322

Asp Ala Ser Gly Ser
1 5

<210> SEQ ID NO 323
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 323

Gly Gly Ser Phe Ser Gly Tyr Tyr
1 5

<210> SEQ ID NO 324
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Ile Asp Ala Ser Gly Ser Thr
1               5

<210> SEQ ID NO 325
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Ala Arg Pro Leu Tyr Asp Ala Tyr Leu Asp Val
1               5                   10

<210> SEQ ID NO 326
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Gly Ser Phe Ser Gly Tyr Tyr Trp Ser
1               5

<210> SEQ ID NO 327
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 327

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp Ala Ser Gly Ser Thr Arg Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro Leu Tyr Asp Ala Tyr Leu Asp Val Trp Gly Gln Gly Thr Met
            100                 105                 110

Val Thr Val Ser Ser
        115

<210> SEQ ID NO 328
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 328

Gln Gln Ala Pro Ile Tyr Pro Ile Thr
1 5

<210> SEQ ID NO 329
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 329

Ala Pro Ile Tyr Pro Ile
1 5

<210> SEQ ID NO 330
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 330

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Pro Ile Tyr Pro Ile
85 90 95

Thr Phe Gly Gly Gly Thr Lys Val Glu Ile Lys
100 105

<210> SEQ ID NO 331
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 331

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Glu Arg Tyr
20 25 30

Tyr Trp Ser Trp Ile Arg Gln Pro Pro Gly Lys Gly Leu Glu Trp Ile
35 40 45

```
Gly Tyr Ile Tyr Gly Arg Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ser Gln Glu Ser Pro Tyr Asn Asn Trp Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro
225


<210> SEQ ID NO 332
<211> LENGTH: 553
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 332

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
```

```
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Ala Asp Glu Thr Phe Trp Asn His Val
    370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540

Arg Ile Lys His His His His His His
545                 550
```

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
<400> SEQUENCE: 372
000

<210> SEQ ID NO 373
<400> SEQUENCE: 373
000

<210> SEQ ID NO 374
<400> SEQUENCE: 374
000

<210> SEQ ID NO 375
<400> SEQUENCE: 375
000

<210> SEQ ID NO 376
<400> SEQUENCE: 376
000

<210> SEQ ID NO 377
<400> SEQUENCE: 377
000

<210> SEQ ID NO 378
<400> SEQUENCE: 378
000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447
<400> SEQUENCE: 447
000

<210> SEQ ID NO 448
<400> SEQUENCE: 448
000

<210> SEQ ID NO 449
<400> SEQUENCE: 449
000

<210> SEQ ID NO 450
<400> SEQUENCE: 450
000

<210> SEQ ID NO 451
<400> SEQUENCE: 451
000

<210> SEQ ID NO 452
<400> SEQUENCE: 452
000

<210> SEQ ID NO 453
<400> SEQUENCE: 453
000

<210> SEQ ID NO 454
<400> SEQUENCE: 454
000

<210> SEQ ID NO 455
<400> SEQUENCE: 455
000

<210> SEQ ID NO 456
<400> SEQUENCE: 456
000

<210> SEQ ID NO 457
<400> SEQUENCE: 457
000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

000

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 501

Thr Tyr Trp Met His
1 5

<210> SEQ ID NO 502
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 502

Asn Ile Tyr Pro Gly Thr Gly Gly Ser Asn Phe Asp Glu Lys Phe Lys
1 5 10 15

Asn

<210> SEQ ID NO 503
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 503

Trp Thr Thr Gly Thr Gly Ala Tyr
1 5

<210> SEQ ID NO 504
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 504

Gly Tyr Thr Phe Thr Thr Tyr
1 5

<210> SEQ ID NO 505
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 505

Tyr Pro Gly Thr Gly Gly
1 5

<210> SEQ ID NO 506
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 506

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Thr Phe Thr Thr Tyr

```
            20                  25                  30
Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser
            115

<210> SEQ ID NO 507
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 507

gaggtgcagc tggtgcagtc aggcgccgaa gtgaagaagc ccggcgagtc actgagaatt      60

agctgtaaag gttcaggcta caccttcact acctactgga tgcactgggt ccgccaggct     120

accggtcaag gcctcgagtg gatgggtaat atctaccccg gcaccggcgg ctctaacttc     180

gacgagaagt ttaagaatag agtgactatc accgccgata agtctactag caccgcctat     240

atggaactgt ctagcctgag atcagaggac accgccgtct actactgcac taggtggact     300

accggcacag gcgcctactg gggtcaaggc actaccgtga ccgtgtctag c              351

<210> SEQ ID NO 508
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 508

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
            20                  25                  30

Trp Met His Trp Val Arg Gln Ala Thr Gly Gln Gly Leu Glu Trp Met
        35                  40                  45

Gly Asn Ile Tyr Pro Gly Thr Gly Gly Ser Asn Phe Asp Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Thr Thr Gly Thr Gly Ala Tyr Trp Gly Gln Gly Thr Thr
            100                 105                 110

Val Thr Val Ser Ser Ala Ser Thr Lys Gly Pro Ser Val Phe Pro Leu
            115                 120                 125
```

```
Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440
```

<210> SEQ ID NO 509
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 509

```
gaggtgcagc tggtgcagtc aggcgccgaa gtgaagaagc ccggcgagtc actgagaatt     60

agctgtaaag gttcaggcta caccttcact acctactgga tgcactgggt ccgccaggct    120

accggtcaag gcctcgagtg gatgggtaat atctaccccg gcaccggcgg ctctaacttc    180
```

```
gacgagaagt ttaagaatag agtgactatc accgccgata agtctactag caccgcctat    240

atggaactgt ctagcctgag atcagaggac accgccgtct actactgcac taggtggact    300

accggcacag gcgcctactg ggtcaaggc actaccgtga ccgtgtctag cgctagcact    360

aagggcccgt ccgtgttccc cctggcacct tgtagccgga gcactagcga atccaccgct    420

gccctcggct gcctggtcaa ggattacttc ccggagcccg tgaccgtgtc ctggaacagc    480

ggagccctga cctccggagt gcacaccttc cccgctgtgc tgcagagctc cgggctgtac    540

tcgctgtcgt cggtggtcac ggtgccttca tctagcctgg gtaccaagac ctacacttgc    600

aacgtggacc acaagccttc caacactaag gtggacaagc gcgtcgaatc gaagtacggc    660

ccaccgtgcc cgccttgtcc cgcgccggag ttcctcggcg gtccctcggt ctttctgttc    720

ccaccgaagc ccaaggacac tttgatgatt tcccgcaccc ctgaagtgac atgcgtggtc    780

gtggacgtgt cacaggaaga tccggaggtg cagttcaatt ggtacgtgga tggcgtcgag    840

gtgcacaacg ccaaaaccaa gccgagggag gagcagttca actccactta ccgcgtcgtg    900

tccgtgctga cggtgctgca tcaggactgg ctgaacggga aggagtacaa gtgcaaagtg    960

tccaacaagg gacttcctag ctcaatcgaa aagaccatct cgaaagccaa gggacagccc   1020

cgggaacccc aagtgtatac cctgccaccg agccaggaag aaatgactaa gaaccaagtc   1080

tcattgactt gccttgtgaa gggcttctac ccatcggata tcgccgtgga atgggagtcc   1140

aacggccagc cggaaaacaa ctacaagacc acccctccgg tgctggactc agacggatcc   1200

ttcttcctct actcgcggct gaccgtggat aagagcagat ggcaggaggg aaatgtgttc   1260

agctgttctg tgatgcatga agccctgcac aaccactaca ctcagaagtc cctgtccctc   1320

tccctggga                                                           1329
```

<210> SEQ ID NO 510
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 510

```
Lys Ser Ser Gln Ser Leu Leu Asp Ser Gly Asn Gln Lys Asn Phe Leu
1               5                   10                  15

Thr
```

<210> SEQ ID NO 511
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 511

```
Trp Ala Ser Thr Arg Glu Ser
1               5
```

<210> SEQ ID NO 512
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 512

Gln Asn Asp Tyr Ser Tyr Pro Tyr Thr
1               5

<210> SEQ ID NO 513
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 513

Ser Gln Ser Leu Leu Asp Ser Gly Asn Gln Lys Asn Phe
1               5                   10

<210> SEQ ID NO 514
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 514

Trp Ala Ser
1

<210> SEQ ID NO 515
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 515

Asp Tyr Ser Tyr Pro Tyr
1               5

<210> SEQ ID NO 516
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 516

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

```
Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 517
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 517

```
gagatcgtcc tgactcagtc acccgctacc ctgagcctga gccctggcga gcgggctaca     60

ctgagctgta aatctagtca gtcactgctg gatagcggta atcagaagaa cttcctgacc    120

tggtatcagc agaagcccgg taaagcccct aagctgctga tctactgggc ctctactaga    180

gaatcaggcg tgccctctag gtttagcggt agcggtagtg gcaccgactt caccttcact    240

atctctagcc tgcagcccga ggatatcgct acctactact gtcagaacga ctatagctac    300

ccctacacct tcggtcaagg cactaaggtc gagattaag                           339
```

<210> SEQ ID NO 518
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 518

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
```

```
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 519
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 519

gagatcgtcc tgactcagtc acccgctacc ctgagcctga gccctggcga gcgggctaca      60

ctgagctgta aatctagtca gtcactgctg gatagcggta atcagaagaa cttcctgacc     120

tggtatcagc agaagcccgg taaagcccct aagctgctga tctactgggc ctctactaga     180

gaatcaggcg tgccctctag gtttagcggt agcggtagtg gcaccgactt caccttcact     240

atctctagcc tgcagcccga ggatatcgct acctactact gtcagaacga ctatagctac     300

ccctacacct tcggtcaagg cactaaggtc gagattaagc gtacggtggc cgctcccagc     360

gtgttcatct tcccccccag cgacgagcag ctgaagagcg gcaccgccag cgtggtgtgc     420

ctgctgaaca acttctaccc ccgggaggcc aaggtgcagt ggaaggtgga caacgccctg     480

cagagcggca acagccagga gagcgtcacc gagcaggaca gcaaggactc cacctacagc     540

ctgagcagca ccctgaccct gagcaaggcc gactacgaga agcataaggt gtacgcctgc     600

gaggtgaccc accagggcct gtccagcccc gtgaccaaga gcttcaacag gggcgagtgc     660


<210> SEQ ID NO 520
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 520

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys


<210> SEQ ID NO 521
```

```
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 521

gagatcgtcc tgactcagtc acccgctacc ctgagcctga gccctggcga gcgggctaca     60

ctgagctgta aatctagtca gtcactgctg gatagcggta atcagaagaa cttcctgacc    120

tggtatcagc agaagcccgg tcaagcccct agactgctga tctactgggc ctctactaga    180

gaatcaggcg tgccctctag gtttagcggt agcggtagtg gcaccgactt caccttcact    240

atctctagcc tggaagccga ggacgccgct acctactact gtcagaacga ctatagctac    300

ccctacacct tcggtcaagg cactaaggtc gagattaag                           339


<210> SEQ ID NO 522
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 522

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 523
<211> LENGTH: 660
```

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 523
gagatcgtcc tgactcagtc acccgctacc ctgagcctga gccctggcga gcgggctaca 60
ctgagctgta aatctagtca gtcactgctg gatagcggta atcagaagaa cttcctgacc 120
tggtatcagc agaagcccgg tcaagcccct agactgctga tctactgggc ctctactaga 180
gaatcaggcg tgccctctag gtttagcggt agcggtagtg gcaccgactt caccttcact 240
atctctagcc tggaagccga ggacgccgct acctactact gtcagaacga ctatagctac 300
ccctacacct tcggtcaagg cactaaggtc gagattaagc gtacggtggc cgctcccagc 360
gtgttcatct tcccccccag cgacgagcag ctgaagagcg gcaccgccag cgtggtgtgc 420
ctgctgaaca acttctaccc ccgggaggcc aaggtgcagt ggaaggtgga caacgccctg 480
cagagcggca acagccagga gagcgtcacc gagcaggaca gcaaggactc cacctacagc 540
ctgagcagca ccctgaccct gagcaaggcc gactacgaga agcataaggt gtacgcctgc 600
gaggtgaccc accagggcct gtccagcccc gtgaccaaga gcttcaacag gggcgagtgc 660

<210> SEQ ID NO 524
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 524
acctactgga tgcac 15

<210> SEQ ID NO 525
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 525
aatatctacc ccggcaccgg cggctctaac ttcgacgaga agtttaagaa t 51

<210> SEQ ID NO 526
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 526
tggactaccg gcacaggcgc ctac 24

<210> SEQ ID NO 527
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 527
ggctacacct tcactaccta c 21

<210> SEQ ID NO 528
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
taccccggca ccggcggc 18

<210> SEQ ID NO 529
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
aaatctagtc agtcactgct ggatagcggt aatcagaaga acttcctgac c 51

<210> SEQ ID NO 530
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
tgggcctcta ctagagaatc a 21

<210> SEQ ID NO 531
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
cagaacgact atagctaccc ctacacc 27

<210> SEQ ID NO 532
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
agtcagtcac tgctggatag cggtaatcag aagaacttc 39

<210> SEQ ID NO 533
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 533 tgggcctct 9

<210> SEQ ID NO 534
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 534
gactatagct acccctac 18

<210> SEQ ID NO 535
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 535

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
```

```
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 536
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 536

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 537
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 537

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 538
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 538

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

```
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 539
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 539

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 540
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 540

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

```
Asn Arg Gly Glu Cys
    210


<210> SEQ ID NO 541
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 541

Gly Tyr Thr Phe Thr Thr Tyr Trp Met His
1               5                   10


<210> SEQ ID NO 542

<400> SEQUENCE: 542

000


<210> SEQ ID NO 543

<400> SEQUENCE: 543

000


<210> SEQ ID NO 544

<400> SEQUENCE: 544

000


<210> SEQ ID NO 545

<400> SEQUENCE: 545

000


<210> SEQ ID NO 546

<400> SEQUENCE: 546

000


<210> SEQ ID NO 547

<400> SEQUENCE: 547

000


<210> SEQ ID NO 548

<400> SEQUENCE: 548

000


<210> SEQ ID NO 549

<400> SEQUENCE: 549

000


<210> SEQ ID NO 550

<400> SEQUENCE: 550
```

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 601

```
Ser Tyr Trp Met Tyr
1               5
```

<210> SEQ ID NO 602
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 602

```
Arg Ile Asp Pro Asn Ser Gly Ser Thr Lys Tyr Asn Glu Lys Phe Lys
1               5                   10                  15

Asn
```

<210> SEQ ID NO 603
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 603

```
Asp Tyr Arg Lys Gly Leu Tyr Ala Met Asp Tyr
1               5                   10


<210> SEQ ID NO 604
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 604

Gly Tyr Thr Phe Thr Ser Tyr
1               5


<210> SEQ ID NO 605
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 605

Asp Pro Asn Ser Gly Ser
1               5


<210> SEQ ID NO 606
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 606

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120


<210> SEQ ID NO 607
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 607
gaagtgcagc tggtgcagtc aggcgccgaa gtgaagaaac ccggcgctac cgtgaagatt 60
agctgtaaag tctcaggcta caccttcact agctactgga tgtactgggt ccgacaggct 120
agagggcaaa gactggagtg gatcggtaga atcgacccta atagcggctc tactaagtat 180
aacgagaagt ttaagaatag gttcactatt agtagggata actctaagaa caccctgtac 240
ctgcagatga atagcctgag agccgaggac accgccgtct actactgcgc tagagactat 300
agaaagggcc tgtacgctat ggactactgg ggtcaaggca ctaccgtgac cgtgtcttca 360

<210> SEQ ID NO 608
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 608

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Val Arg Gln Ala Arg Gly Gln Arg Leu Glu Trp Ile
35 40 45

Gly Arg Ile Asp Pro Asn Ser Gly Ser Thr Lys Tyr Asn Glu Lys Phe
50 55 60

Lys Asn Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys

```
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 609
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 609

Lys Ala Ser Gln Asp Val Gly Thr Ala Val Ala
1               5                   10


<210> SEQ ID NO 610
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 610

Trp Ala Ser Thr Arg His Thr
1               5


<210> SEQ ID NO 611
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 611

Gln Gln Tyr Asn Ser Tyr Pro Leu Thr
1               5


<210> SEQ ID NO 612
```

<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 612

Ser Gln Asp Val Gly Thr Ala
1 5

<210> SEQ ID NO 613
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 613

Trp Ala Ser
1

<210> SEQ ID NO 614
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 614

Tyr Asn Ser Tyr Pro Leu
1 5

<210> SEQ ID NO 615
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 615
gaagtgcagc tggtgcagtc aggcgccgaa gtgaagaaac ccggcgctac cgtgaagatt 60
agctgtaaag tctcaggcta caccttcact agctactgga tgtactgggt ccgacaggct 120
agagggcaaa gactggagtg gatcggtaga atcgacccta atagcggctc tactaagtat 180
aacgagaagt ttaagaatag gttcactatt agtagggata actctaagaa caccctgtac 240
ctgcagatga atagcctgag agccgaggac accgccgtct actactgcgc tagagactat 300
agaaagggcc tgtacgctat ggactactgg ggtcaaggca ctaccgtgac cgtgtcttca 360
gctagcacta agggcccgtc cgtgttcccc ctggcacctt gtagccggag cactagcgaa 420
tccaccgctg ccctcggctg cctggtcaag gattacttcc cggagcccgt gaccgtgtcc 480
tggaacagcg gagccctgac ctccggagtg cacaccttcc ccgctgtgct gcagagctcc 540
gggctgtact cgctgtcgtc ggtggtcacg gtgccttcat ctagcctggg taccaagacc 600
tacacttgca acgtggacca caagccttcc aacactaagg tggacaagcg cgtcgaatcg 660
aagtacggcc caccgtgccc gccttgtccc gcgccggagt tcctcggcgg tccctcggtc 720

-continued

```
tttctgttcc caccgaagcc caaggacact ttgatgattt cccgcacccc tgaagtgaca    780

tgcgtggtcg tggacgtgtc acaggaagat ccggaggtgc agttcaattg gtacgtggat    840

ggcgtcgagg tgcacaacgc caaaaccaag ccgagggagg agcagttcaa ctccacttac    900

cgcgtcgtgt ccgtgctgac ggtgctgcat caggactggc tgaacgggaa ggagtacaag    960

tgcaaagtgt ccaacaaggg acttcctagc tcaatcgaaa agaccatctc gaaagccaag   1020

ggacagcccc gggaacccca agtgtatacc ctgccaccga gccaggaaga aatgactaag   1080

aaccaagtct cattgacttg ccttgtgaag ggcttctacc catcggatat cgccgtggaa   1140

tgggagtcca acggccagcc ggaaaacaac tacaagacca cccctccggt gctggactca   1200

gacggatcct tcttcctcta ctcgcggctg accgtggata agagcagatg gcaggaggga   1260

aatgtgttca gctgttctgt gatgcatgaa gccctgcaca accactacac tcagaagtcc   1320

ctgtccctct ccctggga                                                 1338
```

<210> SEQ ID NO 616
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 616

```
Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105
```

<210> SEQ ID NO 617
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 617

```
gctattcagc tgactcagtc acctagtagc ctgagcgcta gtgtgggcga tagagtgact     60

atcacctgta aagcctctca ggacgtgggc accgccgtgg cctggtatct gcagaagcct    120

ggtcaatcac ctcagctgct gatctactgg gcctctacta gacacaccgg cgtgccctct    180

aggtttagcg gtagcggtag tggcaccgac ttcaccttca ctatctcttc actggaagcc    240

gaggacgccg ctacctacta ctgtcagcag tataatagct acccccctgac cttcggtcaa    300

ggcactaagg tcgagattaa g                                              321
```

<210> SEQ ID NO 618
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 618

Ala Ile Gln Leu Thr Gln Ser Pro Ser Ser Leu Ser Ala Ser Val Gly
1 5 10 15

Asp Arg Val Thr Ile Thr Cys Lys Ala Ser Gln Asp Val Gly Thr Ala
20 25 30

Val Ala Trp Tyr Leu Gln Lys Pro Gly Gln Ser Pro Gln Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Phe Thr Ile Ser Ser Leu Glu Ala
65 70 75 80

Glu Asp Ala Ala Thr Tyr Tyr Cys Gln Gln Tyr Asn Ser Tyr Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 619
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 619
gctattcagc tgactcagtc acctagtagc ctgagcgcta gtgtgggcga tagagtgact 60
atcacctgta aagcctctca ggacgtgggc accgccgtgg cctggtatct gcagaagcct 120
ggtcaatcac ctcagctgct gatctactgg gcctctacta gacacaccgg cgtgccctct 180
aggtttagcg gtagcggtag tggcaccgac ttcaccttca ctatctcttc actggaagcc 240
gaggacgccg ctacctacta ctgtcagcag tataatagct accccctgac cttcggtcaa 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420

```
ccccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642
```

<210> SEQ ID NO 620
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 620

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Thr Gly Gln Gly Leu Glu Trp Met
        35                  40                  45

Gly Arg Ile Asp Pro Asn Ser Gly Ser Thr Lys Tyr Asn Glu Lys Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120
```

<210> SEQ ID NO 621
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 621

```
gaagtgcagc tggtgcagtc aggcgccgaa gtgaagaaac ccggcgctac cgtgaagatt     60

agctgtaaag tctcaggcta caccttcact agctactgga tgtactgggt ccgacaggct    120

accggtcaag gcctggagtg gatgggtaga atcgacccta atagcggctc tactaagtat    180

aacgagaagt ttaagaatag agtgactatc accgccgata agtctactag caccgcctat    240

atggaactgt ctagcctgag atcagaggac accgccgtct actactgcgc tagagactat    300

agaaagggcc tgtacgctat ggactactgg ggtcaaggca ctaccgtgac cgtgtcttca    360
```

<210> SEQ ID NO 622
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

-continued

<400> SEQUENCE: 622

Glu Val Gln Leu Val Gln Ser Gly Ala Glu Val Lys Lys Pro Gly Ala
1 5 10 15

Thr Val Lys Ile Ser Cys Lys Val Ser Gly Tyr Thr Phe Thr Ser Tyr
20 25 30

Trp Met Tyr Trp Val Arg Gln Ala Thr Gly Gln Gly Leu Glu Trp Met
35 40 45

Gly Arg Ile Asp Pro Asn Ser Gly Ser Thr Lys Tyr Asn Glu Lys Phe
50 55 60

Lys Asn Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Tyr Arg Lys Gly Leu Tyr Ala Met Asp Tyr Trp Gly Gln
100 105 110

Gly Thr Thr Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Phe Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Arg Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly
435 440 445

<210> SEQ ID NO 623
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 623
gaagtgcagc tggtgcagtc aggcgccgaa gtgaagaaac ccggcgctac cgtgaagatt 60
agctgtaaag tctcaggcta caccttcact agctactgga tgtactgggt ccgacaggct 120
accggtcaag gcctggagtg gatgggtaga atcgacccta atagcggctc tactaagtat 180
aacgagaagt ttaagaatag agtgactatc accgccgata agtctactag caccgcctat 240
atggaactgt ctagcctgag atcagaggac accgccgtct actactgcgc tagagactat 300
agaaagggcc tgtacgctat ggactactgg ggtcaaggca ctaccgtgac cgtgtcttca 360
gctagcacta agggcccgtc cgtgttcccc ctggcacctt gtagccggag cactagcgaa 420
tccaccgctg ccctcggctg cctggtcaag gattacttcc cggagcccgt gaccgtgtcc 480
tggaacagcg gagccctgac ctccggagtg cacaccttcc ccgctgtgct gcagagctcc 540
gggctgtact cgctgtcgtc ggtggtcacg gtgccttcat ctagcctggg taccaagacc 600
tacacttgca acgtggacca caagccttcc aacactaagg tggacaagcg cgtcgaatcg 660
aagtacggcc caccgtgccc gccttgtccc gcgccggagt tcctcggcgg tccctcggtc 720
tttctgttcc caccgaagcc caaggacact ttgatgattt cccgcacccc tgaagtgaca 780
tgcgtggtcg tggacgtgtc acaggaagat ccggaggtgc agttcaattg gtacgtggat 840
ggcgtcgagg tgcacaacgc caaaaccaag ccgagggagg agcagttcaa ctccacttac 900
cgcgtcgtgt ccgtgctgac ggtgctgcat caggactggc tgaacgggaa ggagtacaag 960
tgcaaagtgt ccaacaaggg acttcctagc tcaatcgaaa agaccatctc gaaagccaag 1020
ggacagcccc gggaacccca agtgtatacc ctgccaccga gccaggaaga aatgactaag 1080
aaccaagtct cattgacttg ccttgtgaag ggcttctacc catcggatat cgccgtggaa 1140
tgggagtcca acggccagcc ggaaaacaac tacaagacca cccctccggt gctggactca 1200
gacggatcct tcttcctcta ctcgcggctg accgtggata agagcagatg gcaggaggga 1260
aatgtgttca gctgttctgt gatgcatgaa gccctgcaca accactacac tcagaagtcc 1320
ctgtccctct ccctggga 1338

<210> SEQ ID NO 624
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 624

Asp Val Val Met Thr Gln Ser Pro Leu Ser Leu Pro Val Thr Leu Gly
1 5 10 15

```
Gln Pro Ala Ser Ile Ser Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105
```

<210> SEQ ID NO 625
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 625

```
gacgtcgtga tgactcagtc acccctgagc ctgcccgtga ccctggggca gcccgcctct      60

attagctgta aagcctctca ggacgtgggc accgccgtgg cctggtatca gcagaagcca     120

gggcaagccc ctagactgct gatctactgg gcctctacta gacacaccgg cgtgccctct     180

aggtttagcg gtagcggtag tggcaccgag ttcaccctga ctatctcttc actgcagccc     240

gacgacttcg ctacctacta ctgtcagcag tataatagct accccctgac cttcggtcaa     300

ggcactaagg tcgagattaa g                                               321
```

<210> SEQ ID NO 626
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 626

```
Asp Val Val Met Thr Gln Ser Pro Leu Ser Leu Pro Val Thr Leu Gly
1               5                   10                  15

Gln Pro Ala Ser Ile Ser Cys Lys Ala Ser Gln Asp Val Gly Thr Ala
            20                  25                  30

Val Ala Trp Tyr Gln Gln Lys Pro Gly Gln Ala Pro Arg Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 627
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 627

gacgtcgtga tgactcagtc acccctgagc ctgcccgtga ccctggggca gcccgcctct     60

attagctgta aagcctctca ggacgtgggc accgccgtgg cctggtatca gcagaagcca    120

gggcaagccc ctagactgct gatctactgg gcctctacta gacacaccgg cgtgccctct    180

aggtttagcg gtagcggtag tggcaccgag ttcaccctga ctatctcttc actgcagccc    240

gacgacttcg ctacctacta ctgtcagcag tataatagct acccccctgac cttcggtcaa    300

ggcactaagg tcgagattaa gcgtacggtg gccgctccca gcgtgttcat cttccccccc    360

agcgacgagc agctgaagag cggcaccgcc agcgtggtgt gcctgctgaa caacttctac    420

ccccgggagg ccaaggtgca gtggaaggtg gacaacgccc tgcagagcgg caacagccag    480

gagagcgtca ccgagcagga cagcaaggac tccacctaca gcctgagcag caccctgacc    540

ctgagcaagg ccgactacga gaagcataag gtgtacgcct gcgaggtgac ccaccagggc    600

ctgtccagcc ccgtgaccaa gagcttcaac aggggcgagt gc                       642


<210> SEQ ID NO 628
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628

agctactgga tgtac                                                      15


<210> SEQ ID NO 629
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629

agaatcgacc ctaatagcgg ctctactaag tataacgaga agtttaagaa t              51
```

<210> SEQ ID NO 630
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 630
gactatagaa agggcctgta cgctatggac tac 33

<210> SEQ ID NO 631
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 631
ggctacacct tcactagcta c 21

<210> SEQ ID NO 632
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 632
gaccctaata gcggctct 18

<210> SEQ ID NO 633
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 633
aaagcctctc aggacgtggg caccgccgtg gcc 33

<210> SEQ ID NO 634
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 634
tgggcctcta ctagacacac c 21

<210> SEQ ID NO 635
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 635
cagcagtata atagctaccc cctgacc 27

<210> SEQ ID NO 636
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 636
tctcaggacg tgggcaccgc c 21

<210> SEQ ID NO 637
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 637 tgggcctct 9

<210> SEQ ID NO 638
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 638
tataatagct accccctg 18

<210> SEQ ID NO 639
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 639

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Arg His Trp Pro Gly Gly Phe Asp Tyr Trp Gly Gln Gly Thr

```
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 640
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 640

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 641
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 641

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

-continued

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 642
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 642

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Tyr Val Ser Trp Tyr Gln Gln His Pro Gly Lys Ala Pro Lys Leu

```
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 643
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 643

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 644
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 644

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60
```

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 645
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 645

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120


<210> SEQ ID NO 646
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 646

Glu Ile Val Leu Thr Gln Ser Pro Ala Thr Leu Ser Leu Ser Pro Gly
```

-continued

```
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105
```

<210> SEQ ID NO 647
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 647

```
Gly Tyr Thr Phe Thr Ser Tyr Trp Met Tyr
1               5                   10
```

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666
<400> SEQUENCE: 666
000

<210> SEQ ID NO 667
<400> SEQUENCE: 667
000

<210> SEQ ID NO 668
<400> SEQUENCE: 668
000

<210> SEQ ID NO 669
<400> SEQUENCE: 669
000

<210> SEQ ID NO 670
<400> SEQUENCE: 670
000

<210> SEQ ID NO 671
<400> SEQUENCE: 671
000

<210> SEQ ID NO 672
<400> SEQUENCE: 672
000

<210> SEQ ID NO 673
<400> SEQUENCE: 673
000

<210> SEQ ID NO 674
<400> SEQUENCE: 674
000

<210> SEQ ID NO 675
<400> SEQUENCE: 675
000

<210> SEQ ID NO 676
<400> SEQUENCE: 676
000

<210> SEQ ID NO 677
<400> SEQUENCE: 677
000

<210> SEQ ID NO 678
<400> SEQUENCE: 678
000

<210> SEQ ID NO 679
<400> SEQUENCE: 679
000

<210> SEQ ID NO 680
<400> SEQUENCE: 680
000

<210> SEQ ID NO 681
<400> SEQUENCE: 681
000

<210> SEQ ID NO 682
<400> SEQUENCE: 682
000

<210> SEQ ID NO 683
<400> SEQUENCE: 683
000

<210> SEQ ID NO 684
<400> SEQUENCE: 684
000

<210> SEQ ID NO 685
<400> SEQUENCE: 685
000

<210> SEQ ID NO 686
<400> SEQUENCE: 686
000

<210> SEQ ID NO 687
<400> SEQUENCE: 687
000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 701

Asn Tyr Gly Met Asn
1 5

<210> SEQ ID NO 702
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 702

Trp Ile Asn Thr Asp Thr Gly Glu Pro Thr Tyr Ala Asp Asp Phe Lys
1 5 10 15

Gly

<210> SEQ ID NO 703
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 703

Asn Pro Pro Tyr Tyr Tyr Gly Thr Asn Asn Ala Glu Ala Met Asp Tyr
1 5 10 15

<210> SEQ ID NO 704
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 704

Gly Phe Thr Leu Thr Asn Tyr
1 5

<210> SEQ ID NO 705
<211> LENGTH: 6
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic peptide"

<400> SEQUENCE: 705

Asn Thr Asp Thr Gly Glu
1 5

<210> SEQ ID NO 706
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 706

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Leu Thr Asn Tyr
20 25 30

Gly Met Asn Trp Val Arg Gln Ala Arg Gly Gln Arg Leu Glu Trp Ile
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser
115 120 125

<210> SEQ ID NO 707
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 707
caagtgcagc tggtgcagtc gggagccgaa gtgaagaagc ctggagcctc ggtgaaggtg 60
tcgtgcaagg catccggatt caccctcacc aattacggga tgaactgggt cagacaggcc 120
cggggtcaac ggctggagtg gatcggatgg attaacaccg acaccgggga gcctacctac 180
gcggacgatt tcaagggacg gttcgtgttc tccctcgaca cctccgtgtc caccgcctac 240
ctccaaatct cctcactgaa agcggaggac accgccgtgt actattgcgc gaggaacccg 300
ccctactact acggaaccaa caacgccgaa gccatggact actggggcca gggcaccact 360
gtgactgtgt ccagc 375

<210> SEQ ID NO 708
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 708
caggtgcagc tggtgcagtc tggcgccgaa gtgaagaaac ctggcgcctc cgtgaaggtg 60
tcctgcaagg cctctggctt caccctgacc aactacggca tgaactgggt gcgacaggcc 120
aggggccagc ggctggaatg gatcggctgg atcaacaccg acaccggcga gcctacctac 180
gccgacgact tcaagggcag attcgtgttc tccctggaca cctccgtgtc caccgcctac 240
ctgcagatct ccagcctgaa ggccgaggat accgccgtgt actactgcgc ccggaacccc 300
ccttactact acggcaccaa caacgccgag gccatggact attggggcca gggcaccacc 360
gtgaccgtgt cctct 375

<210> SEQ ID NO 709
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 709

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Leu Thr Asn Tyr
20 25 30

Gly Met Asn Trp Val Arg Gln Ala Arg Gly Gln Arg Leu Glu Trp Ile
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Arg Asn Pro Pro Tyr Tyr Tyr Gly Thr Asn Asn Ala Glu Ala Met
100 105 110

Asp Tyr Trp Gly Gln Gly Thr Thr Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Lys Thr Tyr Thr Cys
195 200 205

Asn Val Asp His Lys Pro Ser Asn Thr Lys Val Asp Lys Arg Val Glu
210 215 220

Ser Lys Tyr Gly Pro Pro Cys Pro Pro Cys Pro Ala Pro Glu Phe Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser

```
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450


<210> SEQ ID NO 710
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 710

Ser Ser Ser Gln Asp Ile Ser Asn Tyr Leu Asn
1               5                   10


<210> SEQ ID NO 711
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 711

Tyr Thr Ser Thr Leu His Leu
1               5


<210> SEQ ID NO 712
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 712
```

Gln Gln Tyr Tyr Asn Leu Pro Trp Thr
1 5

<210> SEQ ID NO 713
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 713

Ser Gln Asp Ile Ser Asn Tyr
1 5

<210> SEQ ID NO 714
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 714

Tyr Thr Ser
1

<210> SEQ ID NO 715
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 715

Tyr Tyr Asn Leu Pro Trp
1 5

<210> SEQ ID NO 716
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 716
caagtgcagc tggtgcagtc gggagccgaa gtgaagaagc ctggagcctc ggtgaaggtg 60
tcgtgcaagg catccggatt caccctcacc aattacggga tgaactgggt cagacaggcc 120
cggggtcaac ggctggagtg gatcggatgg attaacaccg acaccgggga gcctacctac 180
gcggacgatt tcaagggacg gttcgtgttc tccctcgaca cctccgtgtc caccgcctac 240
ctccaaatct cctcactgaa agcggaggac accgccgtgt actattgcgc gaggaacccg 300
ccctactact acggaaccaa caacgccgaa gccatggact actggggcca gggcaccact 360
gtgactgtgt ccagcgcgtc cactaagggc ccgtccgtgt tcccccctggc accttgtagc 420 cggagcacta gcgaatccac cgctgccctc ggctgcctgg tcaaggatta cttcccggag 480
cccgtgaccg tgtcctggaa cagcggagcc ctgacctccg gagtgcacac cttccccgct 540

```
gtgctgcaga gctccgggct gtactcgctg tcgtcggtgg tcacggtgcc ttcatctagc    600

ctgggtacca agacctacac ttgcaacgtg gaccacaagc cttccaacac taaggtggac    660

aagcgcgtcg aatcgaagta cggcccaccg tgcccgcctt gtcccgcgcc ggagttcctc    720

ggcggtccct cggtctttct gttcccaccg aagcccaagg acactttgat gatttcccgc    780

acccctgaag tgacatgcgt ggtcgtggac gtgtcacagg aagatccgga ggtgcagttc    840

aattggtacg tggatggcgt cgaggtgcac aacgccaaaa ccaagccgag ggaggagcag    900

ttcaactcca cttaccgcgt cgtgtccgtg ctgacggtgc tgcatcagga ctggctgaac    960

gggaaggagt acaagtgcaa agtgtccaac aagggacttc ctagctcaat cgaaaagacc   1020

atctcgaaag ccaagggaca gccccgggaa ccccaagtgt ataccctgcc accgagccag   1080

gaagaaatga ctaagaacca agtctcattg acttgccttg tgaagggctt ctacccatcg   1140

gatatcgccg tggaatggga gtccaacggc cagccggaaa acaactacaa gaccacccct   1200

ccggtgctgg actcagacgg atccttcttc ctctactcgc ggctgaccgt ggataagagc   1260

agatggcagg agggaaatgt gttcagctgt tctgtgatgc atgaagccct gcacaaccac   1320

tacactcaga agtccctgtc cctctccctg gga                                1353


<210> SEQ ID NO 717
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 717

caggtgcagc tggtgcagtc tggcgccgaa gtgaagaaac ctggcgcctc cgtgaaggtg     60

tcctgcaagg cctctggctt caccctgacc aactacggca tgaactgggt gcgacaggcc    120

aggggccagc ggctggaatg gatcggctgg atcaacaccg acaccggcga gcctacctac    180

gccgacgact tcaagggcag attcgtgttc tccctggaca cctccgtgtc caccgcctac    240

ctgcagatct ccagcctgaa ggccgaggat accgccgtgt actactgcgc ccggaacccc    300

ccttactact acggcaccaa caacgccgag gccatggact attggggcca gggcaccacc    360

gtgaccgtgt cctctgcttc taccaagggg cccagcgtgt tcccccctggc cccctgctcc    420

agaagcacca gcgagagcac agccgccctg ggctgcctgg tgaaggacta cttccccgag    480

cccgtgaccg tgtcctggaa cagcggagcc ctgaccagcg gcgtgcacac cttccccgcc    540

gtgctgcaga gcagcggcct gtacagcctg agcagcgtgg tgaccgtgcc cagcagcagc    600

ctgggcacca agacctacac ctgtaacgtg gaccacaagc ccagcaacac caaggtggac    660

aagagggtgg agagcaagta cggcccaccc tgccccccct gcccagcccc cgagttcctg    720

ggcggaccca gcgtgttcct gttccccccc aagcccaagg acaccctgat gatcagcaga    780

acccccgagg tgacctgtgt ggtggtggac gtgtcccagg aggaccccga ggtccagttc    840

aactggtacg tggacggcgt ggaggtgcac aacgccaaga ccaagcccag agaggagcag    900

tttaacagca cctaccgggt ggtgtccgtg ctgaccgtgc tgcaccagga ctggctgaac    960

ggcaaagagt acaagtgtaa ggtctccaac aagggcctgc caagcagcat cgaaaagacc   1020

atcagcaagg ccaagggcca gcctagagag ccccaggtct acaccctgcc acccagccaa   1080

gaggagatga ccaagaacca ggtgtccctg acctgtctgg tgaagggctt ctacccaagc   1140

gacatcgccg tggagtggga gagcaacggc cagcccgaga acaactacaa gaccaccccc   1200
```

ccagtgctgg acagcgacgg cagcttcttc ctgtacagca ggctgaccgt ggacaagtcc 1260
agatggcagg agggcaacgt ctttagctgc tccgtgatgc acgaggccct gcacaaccac 1320
tacacccaga agagcctgag cctgtccctg ggc 1353

<210> SEQ ID NO 718
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 718

Asp Ile Gln Met Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Leu Gln Lys Pro Gly Gln Ser Pro Gln Leu Leu Ile
35 40 45

Tyr Tyr Thr Ser Thr Leu His Leu Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Tyr Asn Leu Pro Trp
85 90 95

Thr Phe Gly Gln Gly Thr Lys Val Glu Ile Lys
100 105

<210> SEQ ID NO 719
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 719
gatattcaga tgactcagtc acctagtagc ctgagcgcta gtgtgggcga tagagtgact 60
atcacctgta gctctagtca ggatatctct aactacctga actggtatct gcagaagccc 120
ggtcaatcac ctcagctgct gatctactac actagcaccc tgcacctggg cgtgccctct 180
aggtttagcg gtagcggtag tggcaccgag ttcaccctga ctatctctag cctgcagccc 240
gacgacttcg ctacctacta ctgtcagcag tactataacc tgccctggac cttcggtcaa 300
ggcactaagg tcgagattaa g 321

<210> SEQ ID NO 720
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 720
gacatccaga tgacccagtc cccctccagc ctgtctgctt ccgtgggcga cagagtgacc 60
atcacctgtt cctccagcca ggacatctcc aactacctga actggtatct gcagaagccc 120

```
ggccagtccc ctcagctgct gatctactac acctccaccc tgcacctggg cgtgccctcc    180

agattttccg gctctggctc tggcaccgag tttaccctga ccatcagctc cctgcagccc    240

gacgacttcg ccacctacta ctgccagcag tactacaacc tgccctggac cttcggccag    300

ggcaccaagg tggaaatcaa g                                              321


<210> SEQ ID NO 721
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 721

Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Leu Gln Lys Pro Gly Gln Ser Pro Gln Leu Leu Ile
        35                  40                  45

Tyr Tyr Thr Ser Thr Leu His Leu Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asn Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 722
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 722

gatattcaga tgactcagtc acctagtagc ctgagcgcta gtgtgggcga tagagtgact     60

atcacctgta gctctagtca ggatatctct aactacctga actggtatct gcagaagccc    120
```

ggtcaatcac ctcagctgct gatctactac actagcaccc tgcacctggg cgtgccctct 180
aggtttagcg gtagcggtag tggcaccgag ttcaccctga ctatctctag cctgcagccc 240
gacgacttcg ctacctacta ctgtcagcag tactataacc tgccctggac cttcggtcaa 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 723
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 723
gacatccaga tgacccagtc cccctccagc ctgtctgctt ccgtgggcga cagagtgacc 60
atcacctgtt cctccagcca ggacatctcc aactacctga actggtatct gcagaagccc 120
ggccagtccc ctcagctgct gatctactac acctccaccc tgcacctggg cgtgccctcc 180
agattttccg gctctggctc tggcaccgag tttaccctga ccatcagctc cctgcagccc 240
gacgacttcg ccacctacta ctgccagcag tactacaacc tgccctggac cttcggccag 300
ggcaccaagg tggaaatcaa gcgtacggtg gccgctccca gcgtgttcat cttcccccca 360
agcgacgagc agctgaagag cggcaccgcc agcgtggtgt gtctgctgaa caacttctac 420
cccagggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac aggggcgagt gc 642

<210> SEQ ID NO 724
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 724

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Leu Thr Asn Tyr
20 25 30

Gly Met Asn Trp Val Arg Gln Ala Pro Gly Gln Gly Leu Glu Trp Met
35 40 45

Gly Trp Ile Asn Thr Asp Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

```
Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser
        115                 120                 125


<210> SEQ ID NO 725
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 725

caggtgcagc tggtgcagtc aggcgccgaa gtgaagaaac ccggcgctag tgtgaaagtc      60

agctgtaaag ctagtggctt caccctgact aactacggga tgaactgggt ccgccaggcc     120

ccaggtcaag gcctcgagtg gatgggctgg attaacaccg acaccggcga gcctacctac     180

gccgacgact ttaagggcag attcgtgttt agcctggaca ctagtgtgtc taccgcctac     240

ctgcagatct ctagcctgaa ggccgaggac accgccgtct actactgcgc tagaaacccc     300

ccctactact acggcactaa caacgccgag gctatggact actggggtca aggcactacc     360

gtgaccgtgt ctagc                                                      375


<210> SEQ ID NO 726
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 726

caggtgcagc tggtgcagtc tggcgccgaa gtgaagaaac ctggcgcctc cgtgaaggtg      60

tcctgcaagg cctctggctt caccctgacc aactacggca tgaactgggt gcgacaggcc     120

cctggacagg gcctggaatg gatgggctgg atcaacaccg acaccggcga gcctacctac     180

gccgacgact tcaagggcag attcgtgttc tccctggaca cctccgtgtc caccgcctac     240

ctgcagatct ccagcctgaa ggccgaggat accgccgtgt actactgcgc ccggaacccc     300

ccttactact acggcaccaa caacgccgag gccatggact attggggcca gggcaccacc     360

gtgaccgtgt cctct                                                      375


<210> SEQ ID NO 727
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 727

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Leu Thr Asn Tyr
            20                  25                  30
```

```
Gly Met Asn Trp Val Arg Gln Ala Pro Gly Gln Gly Leu Glu Trp Met
        35                  40                  45

Gly Trp Ile Asn Thr Asp Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Pro Tyr Tyr Tyr Gly Thr Asn Asn Ala Glu Ala Met
            100                 105                 110

Asp Tyr Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
```

450

<210> SEQ ID NO 728
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 728
caggtgcagc tggtgcagtc aggcgccgaa gtgaagaaac ccggcgctag tgtgaaagtc 60
agctgtaaag ctagtggctt caccctgact aactacggga tgaactgggt ccgccaggcc 120
ccaggtcaag gcctcgagtg gatgggctgg attaacaccg acaccggcga gcctacctac 180
gccgacgact ttaagggcag attcgtgttt agcctggaca ctagtgtgtc taccgcctac 240
ctgcagatct ctagcctgaa ggccgaggac accgccgtct actactgcgc tagaaacccc 300
ccctactact acggcactaa caacgccgag gctatggact actggggtca aggcactacc 360
gtgaccgtgt ctagcgctag cactaagggc ccgtccgtgt tcccccctggc accttgtagc 420 cggagcacta gcgaatccac cgctgccctc ggctgcctgg tcaaggatta cttcccggag 480
cccgtgaccg tgtcctggaa cagcggagcc ctgacctccg gagtgcacac cttccccgct 540
gtgctgcaga gctccgggct gtactcgctg tcgtcggtgg tcacggtgcc ttcatctagc 600
ctgggtacca agacctacac ttgcaacgtg gaccacaagc cttccaacac taaggtggac 660
aagcgcgtcg aatcgaagta cggcccaccg tgcccgcctt gtcccgcgcc ggagttcctc 720
ggcggtccct cggtctttct gttcccaccg aagcccaagg acactttgat gatttcccgc 780
acccctgaag tgacatgcgt ggtcgtggac gtgtcacagg aagatccgga ggtgcagttc 840
aattggtacg tggatggcgt cgaggtgcac aacgccaaaa ccaagccgag ggaggagcag 900
ttcaactcca cttaccgcgt cgtgtccgtg ctgacggtgc tgcatcagga ctggctgaac 960
gggaaggagt acaagtgcaa agtgtccaac aagggacttc ctagctcaat cgaaaagacc 1020
atctcgaaag ccaagggaca gccccgggaa ccccaagtgt ataccctgcc accgagccag 1080
gaagaaatga ctaagaacca agtctcattg acttgccttg tgaagggctt ctacccatcg 1140
gatatcgccg tggaatggga gtccaacggc cagccggaaa acaactacaa gaccacccct 1200
ccggtgctgg actcagacgg atccttcttc ctctactcgc ggctgaccgt ggataagagc 1260
agatggcagg agggaaatgt gttcagctgt tctgtgatgc atgaagccct gcacaaccac 1320
tacactcaga agtccctgtc cctctccctg gga 1353

<210> SEQ ID NO 729
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 729
caggtgcagc tggtgcagtc tggcgccgaa gtgaagaaac ctggcgcctc cgtgaaggtg 60
tcctgcaagg cctctggctt caccctgacc aactacggca tgaactgggt gcgacaggcc 120
cctggacagg gcctggaatg gatgggctgg atcaacaccg acaccggcga gcctacctac 180
gccgacgact tcaagggcag attcgtgttc tccctggaca cctccgtgtc caccgcctac 240

-continued

```
ctgcagatct ccagcctgaa ggccgaggat accgccgtgt actactgcgc ccggaacccc    300

ccttactact acggcaccaa caacgccgag gccatggact attggggcca gggcaccacc    360

gtgaccgtgt cctctgcttc taccaagggg cccagcgtgt tcccccctggc cccctgctcc    420

agaagcacca gcgagagcac agccgccctg ggctgcctgg tgaaggacta cttccccgag    480

cccgtgaccg tgtcctggaa cagcggagcc ctgaccagcg gcgtgcacac cttccccgcc    540

gtgctgcaga gcagcggcct gtacagcctg agcagcgtgg tgaccgtgcc cagcagcagc    600

ctgggcacca agacctacac ctgtaacgtg gaccacaagc ccagcaacac caaggtggac    660

aagagggtgg agagcaagta cggcccaccc tgccccccct gcccagcccc cgagttcctg    720

ggcggaccca gcgtgttcct gttcccccc aagcccaagg acaccctgat gatcagcaga    780

acccccgagg tgacctgtgt ggtggtggac gtgtcccagg aggaccccga ggtccagttc    840

aactggtacg tggacggcgt ggaggtgcac aacgccaaga ccaagcccag agaggagcag    900

tttaacagca cctaccgggt ggtgtccgtg ctgaccgtgc tgcaccagga ctggctgaac    960

ggcaaagagt acaagtgtaa ggtctccaac aagggcctgc caagcagcat cgaaaagacc   1020

atcagcaagg ccaagggcca gcctagagag ccccaggtct acaccctgcc acccagccaa   1080

gaggagatga ccaagaacca ggtgtccctg acctgtctgg tgaagggctt ctacccaagc   1140

gacatcgccg tggagtggga gagcaacggc cagcccgaga acaactacaa gaccaccccc   1200

ccagtgctgg acagcgacgg cagcttcttc ctgtacagca ggctgaccgt ggacaagtcc   1260

agatggcagg agggcaacgt ctttagctgc tccgtgatgc acgaggccct gcacaaccac   1320

tacacccaga agagcctgag cctgtccctg ggc                                 1353
```

<210> SEQ ID NO 730
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 730

```
Asp Ile Gln Met Thr Gln Ser Pro Ser Ser Leu Ser Ala Ser Val Gly
1               5                   10                  15

Asp Arg Val Thr Ile Thr Cys Ser Ser Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Leu Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln Tyr Tyr Asn Leu Pro Trp
                85                  90                  95

Thr Phe Gly Gln Gly Thr Lys Val Glu Ile Lys
            100                 105
```

<210> SEQ ID NO 731
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 731
gatattcaga tgactcagtc acctagtagc ctgagcgcta gtgtgggcga tagagtgact 60
atcacctgta gctctagtca ggatatctct aactacctga actggtatca gcagaagccc 120
ggtaaagccc ctaagctgct gatctactac actagcaccc tgcacctggg aatcccccct 180
aggtttagcg gtagcggcta cggcaccgac ttcaccctga ctattaacaa tatcgagtca 240
gaggacgccg cctactactt ctgtcagcag tactataacc tgccctggac cttcggtcaa 300
ggcactaagg tcgagattaa g 321

<210> SEQ ID NO 732
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 732
gacatccaga tgacccagtc cccctccagc ctgtctgctt ccgtgggcga cagagtgacc 60
atcacctgtt cctccagcca ggacatctcc aactacctga actggtatca gcagaagccc 120
ggcaaggccc ccaagctgct gatctactac acctccaccc tgcacctggg catccccccct 180 agattctccg gctctggcta cggcaccgac ttcaccctga ccatcaacaa catcgagtcc 240
gaggacgccg cctactactt ctgccagcag tactacaacc tgccctggac cttcggccag 300
ggcaccaagg tggaaatcaa g 321

<210> SEQ ID NO 733
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 733

Asp Ile Gln Met Thr Gln Ser Pro Ser Ser Leu Ser Ala Ser Val Gly
1 5 10 15

Asp Arg Val Thr Ile Thr Cys Ser Ser Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Thr Leu His Leu Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln Tyr Tyr Asn Leu Pro Trp
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 734
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 734
gatattcaga tgactcagtc acctagtagc ctgagcgcta gtgtgggcga tagagtgact 60
atcacctgta gctctagtca ggatatctct aactacctga actggtatca gcagaagccc 120
ggtaaagccc ctaagctgct gatctactac actagcaccc tgcacctggg aatcccccct 180
aggtttagcg gtagcggcta cggcaccgac ttcaccctga ctattaacaa tatcgagtca 240
gaggacgccg cctactactt ctgtcagcag tactataacc tgccctggac cttcggtcaa 300
ggcactaagg tcgagattaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 735
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 735
gacatccaga tgacccagtc cccctccagc ctgtctgctt ccgtgggcga cagagtgacc 60
atcacctgtt cctccagcca ggacatctcc aactacctga actggtatca gcagaagccc 120
ggcaaggccc ccaagctgct gatctactac acctccaccc tgcacctggg catccccccct 180 agattctccg gctctggcta cggcaccgac ttcaccctga ccatcaacaa catcgagtcc 240
gaggacgccg cctactactt ctgccagcag tactacaacc tgccctggac cttcggccag 300
ggcaccaagg tggaaatcaa gcgtacggtg gccgctccca gcgtgttcat cttcccccca 360
agcgacgagc agctgaagag cggcaccgcc agcgtggtgt gtctgctgaa caacttctac 420
cccagggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcacaag gtgtacgcct gtgaggtgac ccaccagggc 600
ctgtccagcc ccgtgaccaa gagcttcaac aggggcgagt gc 642

<210> SEQ ID NO 736
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 736
aattacggga tgaac 15

<210> SEQ ID NO 737
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 737
aactacggca tgaac 15

<210> SEQ ID NO 738
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 738
tggattaaca ccgacaccgg ggagcctacc tacgcggacg atttcaaggg a 51

<210> SEQ ID NO 739
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 739
tggatcaaca ccgacaccgg cgagcctacc tacgccgacg acttcaaggg c 51

<210> SEQ ID NO 740
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 740
aacccgccct actactacgg aaccaacaac gccgaagcca tggactac 48

<210> SEQ ID NO 741
<211> LENGTH: 48
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 741 aaccccccctt actactacgg caccaacaac gccgaggcca tggactat 48

<210> SEQ ID NO 742
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 742
ggattcaccc tcaccaatta c 21

<210> SEQ ID NO 743
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 743
ggcttcaccc tgaccaacta c 21

<210> SEQ ID NO 744
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 744
aacaccgaca ccggggag 18

<210> SEQ ID NO 745
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 745
aacaccgaca ccggcgag 18

<210> SEQ ID NO 746
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 746
agctctagtc aggatatctc taactacctg aac 33

<210> SEQ ID NO 747
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 747
tcctccagcc aggacatctc caactacctg aac 33

<210> SEQ ID NO 748
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 748
tacactagca ccctgcacct g 21

<210> SEQ ID NO 749
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 749
tacacctcca ccctgcacct g 21

<210> SEQ ID NO 750
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 750
cagcagtact ataacctgcc ctggacc 27

<210> SEQ ID NO 751
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 751
cagcagtact acaacctgcc ctggacc 27

<210> SEQ ID NO 752
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 752
agtcaggata tctctaacta c 21

<210> SEQ ID NO 753
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 753
agccaggaca tctccaacta c 21

<210> SEQ ID NO 754
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 754 tacactagc 9

<210> SEQ ID NO 755
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 755 tacacctcc 9

<210> SEQ ID NO 756
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 756
tactataacc tgccctgg 18

<210> SEQ ID NO 757
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 757
tactacaacc tgccctgg 18

<210> SEQ ID NO 758
<211> LENGTH: 15

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758

aactacggga tgaac                                                          15

<210> SEQ ID NO 759
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759

tggattaaca ccgacaccgg cgagcctacc tacgccgacg actttaaggg c                   51

<210> SEQ ID NO 760
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760

aaccccccct actactacgg cactaacaac gccgaggcta tggactac                      48

<210> SEQ ID NO 761
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761

ggcttcaccc tgactaacta c                                                   21

<210> SEQ ID NO 762
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 762
```

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Ser Thr Asn Ser Asn Pro Ser Leu Lys
    50                  55                  60

Ser Arg Val Thr Leu Ser Leu Asp Thr Ser Lys Asn Gln Phe Ser Leu
65                  70                  75                  80

```
Lys Leu Arg Ser Val Thr Ala Ala Asp Thr Ala Val Tyr Tyr Cys Ala
                85                  90                  95

Phe Gly Tyr Ser Asp Tyr Glu Tyr Asn Trp Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 763
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 763

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 764
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 764

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asn Trp Val Arg Gln Pro Pro Gly Lys Gly Leu Glu Trp Leu
        35                  40                  45

Gly Met Ile Trp Asp Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Glu Gly Asp Val Ala Phe Asp Tyr Trp Gly Gln Gly Thr Thr Leu
            100                 105                 110

Thr Val Ser Ser Ala Ser Thr Lys Gly Pro Ser Val Phe Pro Leu Ala
```

```
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 765
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 765

```
Asp Ile Val Met Thr Gln Ser Pro Ser Ser Leu Ala Val Ser Val Gly
1               5                   10                  15

Gln Lys Val Thr Met Ser Cys Lys Ser Ser Gln Ser Leu Leu Asn Gly
            20                  25                  30
```

```
Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Asp Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Leu Gln
                85                  90                  95

His Phe Gly Thr Pro Pro Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 766
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 766

Gly Phe Thr Leu Thr Asn Tyr Gly Met Asn
1               5                   10


<210> SEQ ID NO 767

<400> SEQUENCE: 767

000


<210> SEQ ID NO 768

<400> SEQUENCE: 768

000


<210> SEQ ID NO 769

<400> SEQUENCE: 769

000


<210> SEQ ID NO 770

<400> SEQUENCE: 770

000
```

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793

<400> SEQUENCE: 793

000

<210> SEQ ID NO 794

<400> SEQUENCE: 794

000

<210> SEQ ID NO 795

<400> SEQUENCE: 795

000

<210> SEQ ID NO 796

<400> SEQUENCE: 796

000

<210> SEQ ID NO 797

<400> SEQUENCE: 797

000

<210> SEQ ID NO 798

<400> SEQUENCE: 798

000

<210> SEQ ID NO 799

<400> SEQUENCE: 799

000

<210> SEQ ID NO 800

<400> SEQUENCE: 800

000

<210> SEQ ID NO 801
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 801

Ser Tyr Asn Met His
1               5

<210> SEQ ID NO 802
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 802

```
Asp Ile Tyr Pro Gly Asn Gly Asp Thr Ser Tyr Asn Gln Lys Phe Lys
1               5                   10                  15

Gly


<210> SEQ ID NO 803
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 803

Val Gly Gly Ala Phe Pro Met Asp Tyr
1               5


<210> SEQ ID NO 804
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 804

Gly Tyr Thr Phe Thr Ser Tyr
1               5


<210> SEQ ID NO 805
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 805

Tyr Pro Gly Asn Gly Asp
1               5


<210> SEQ ID NO 806
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 806

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
```

```
                85                  90                  95

Ala Arg Val Gly Gly Ala Phe Pro Met Asp Tyr Trp Gly Gln Gly Thr
            100                 105                 110

Thr Val Thr Val Ser Ser
        115


<210> SEQ ID NO 807
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 807

caggtgcagc tggtgcagtc aggcgccgaa gtgaagaaac ccggctctag cgtgaaagtt      60

tcttgtaaag ctagtggcta caccttcact agctataata tgcactgggt tcgccaggcc     120

ccagggcaag gcctcgagtg gatgggcgat atctaccccg ggaacggcga cactagttat     180

aatcagaagt ttaagggtag agtcactatc accgccgata agtctactag caccgtctat     240

atggaactga gttccctgag gtctgaggac accgccgtct actactgcgc tagagtgggc     300

ggagccttcc ctatggacta ctggggtcaa ggcactaccg tgaccgtgtc tagc           354


<210> SEQ ID NO 808
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 808

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Asp Ile Tyr Pro Gly Asn Gly Asp Thr Ser Tyr Asn Gln Lys Phe
    50                  55                  60

Lys Gly Arg Val Thr Ile Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

```
Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440
```

<210> SEQ ID NO 809
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 809

```
caggtgcagc tggtgcagtc aggcgccgaa gtgaagaaac ccggctctag cgtgaaagtt      60

tcttgtaaag ctagtggcta caccttcact agctataata tgcactgggt tcgccaggcc     120

ccagggcaag gcctcgagtg gatgggcgat atctaccccg ggaacggcga cactagttat     180

aatcagaagt ttaagggtag agtcactatc accgccgata agtctactag caccgtctat     240

atggaactga gttccctgag gtctgaggac accgccgtct actactgcgc tagagtgggc     300

ggagccttcc ctatggacta ctggggtcaa ggcactaccg tgaccgtgtc tagcgctagc     360

actaagggcc cgtccgtgtt ccccctggca ccttgtagcc ggagcactag cgaatccacc     420

gctgccctcg gctgcctggt caaggattac ttcccggagc ccgtgaccgt gtcctggaac     480

agcggagccc tgacctccgg agtgcacacc ttccccgctg tgctgcagag ctccgggctg     540
```

```
tactcgctgt cgtcggtggt cacggtgcct tcatctagcc tgggtaccaa gacctacact    600

tgcaacgtgg accacaagcc ttccaacact aaggtggaca agcgcgtcga atcgaagtac    660

ggcccaccgt gcccgccttg tcccgcgccg gagttcctcg gcggtccctc ggtctttctg    720

ttcccaccga agcccaagga cactttgatg atttcccgca cccctgaagt gacatgcgtg    780

gtcgtggacg tgtcacagga agatccggag gtgcagttca attggtacgt ggatggcgtc    840

gaggtgcaca acgccaaaac caagccgagg gaggagcagt tcaactccac ttaccgcgtc    900

gtgtccgtgc tgacggtgct gcatcaggac tggctgaacg ggaaggagta caagtgcaaa    960

gtgtccaaca agggacttcc tagctcaatc gaaaagacca tctcgaaagc caagggacag   1020

ccccgggaac cccaagtgta taccctgcca ccgagccagg aagaaatgac taagaaccaa   1080

gtctcattga cttgccttgt gaagggcttc tacccatcgg atatcgccgt ggaatgggag   1140

tccaacggcc agccggaaaa caactacaag accacccctc cggtgctgga ctcagacgga   1200

tccttcttcc tctactcgcg gctgaccgtg gataagagca gatggcagga gggaaatgtg   1260

ttcagctgtt ctgtgatgca tgaagccctg cacaaccact acactcagaa gtccctgtcc   1320

ctctccctgg ga                                                       1332
```

<210> SEQ ID NO 810
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 810

```
Arg Ala Ser Glu Ser Val Glu Tyr Tyr Gly Thr Ser Leu Met Gln
1               5                   10                  15
```

<210> SEQ ID NO 811
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 811

```
Ala Ala Ser Asn Val Glu Ser
1               5
```

<210> SEQ ID NO 812
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 812

```
Gln Gln Ser Arg Lys Asp Pro Ser Thr
1               5
```

<210> SEQ ID NO 813
<211> LENGTH: 11
<212> TYPE: PRT
<213> ORGANISM: Artificial Sequence
<220> FEATURE:

<221> NAME/KEY: source
<223> OTHER INFORMATION: /note="Description of Artificial Sequence: Synthetic peptide"

<400> SEQUENCE: 813

Ser Glu Ser Val Glu Tyr Tyr Gly Thr Ser Leu
1 5 10

<210> SEQ ID NO 814
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 814

Ala Ala Ser
1

<210> SEQ ID NO 815
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 815

Ser Arg Lys Asp Pro Ser
1 5

<210> SEQ ID NO 816
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 816

Ala Ile Gln Leu Thr Gln Ser Pro Ser Ser Leu Ser Ala Ser Val Gly
1 5 10 15

Asp Arg Val Thr Ile Thr Cys Arg Ala Ser Glu Ser Val Glu Tyr Tyr
20 25 30

Gly Thr Ser Leu Met Gln Trp Tyr Gln Gln Lys Pro Gly Lys Ala Pro
35 40 45

Lys Leu Leu Ile Tyr Ala Ala Ser Asn Val Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Phe Cys Gln Gln Ser Arg
85 90 95

Lys Asp Pro Ser Thr Phe Gly Gly Gly Thr Lys Val Glu Ile Lys
100 105 110

<210> SEQ ID NO 817
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 817
gctattcagc tgactcagtc acctagtagc ctgagcgcta gtgtgggcga tagagtgact 60
atcacctgta gagctagtga atcagtcgag tactacggca ctagcctgat gcagtggtat 120
cagcagaagc ccgggaaagc ccctaagctg ctgatctacg ccgcctctaa cgtggaatca 180
ggcgtgccct ctaggtttag cggtagcggt agtggcaccg acttcaccct gactatctct 240
agcctgcagc ccgaggactt cgctacctac ttctgtcagc agtctaggaa ggaccctagc 300
accttcggcg gaggcactaa ggtcgagatt aag 333

<210> SEQ ID NO 818
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 818

Ala Ile Gln Leu Thr Gln Ser Pro Ser Ser Leu Ser Ala Ser Val Gly
1 5 10 15

Asp Arg Val Thr Ile Thr Cys Arg Ala Ser Glu Ser Val Glu Tyr Tyr
20 25 30

Gly Thr Ser Leu Met Gln Trp Tyr Gln Gln Lys Pro Gly Lys Ala Pro
35 40 45

Lys Leu Leu Ile Tyr Ala Ala Ser Asn Val Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Phe Cys Gln Gln Ser Arg
85 90 95

Lys Asp Pro Ser Thr Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 819
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 819
gctattcagc tgactcagtc acctagtagc ctgagcgcta gtgtgggcga tagagtgact 60
atcacctgta gagctagtga atcagtcgag tactacggca ctagcctgat gcagtggtat 120
cagcagaagc ccgggaaagc ccctaagctg ctgatctacg ccgcctctaa cgtggaatca 180
ggcgtgccct ctaggtttag cggtagcggt agtggcaccg acttcaccct gactatctct 240
agcctgcagc ccgaggactt cgctacctac ttctgtcagc agtctaggaa ggaccctagc 300
accttcggcg gaggcactaa ggtcgagatt aagcgtacgg tggccgctcc cagcgtgttc 360
atcttccccc ccagcgacga gcagctgaag agcggcaccg ccagcgtggt gtgcctgctg 420
aacaacttct acccccggga ggccaaggtg cagtggaagg tggacaacgc cctgcagagc 480
ggcaacagcc aggagagcgt caccgagcag gacagcaagg actccaccta cagcctgagc 540
agcaccctga ccctgagcaa ggccgactac gagaagcata aggtgtacgc ctgcgaggtg 600
acccaccagg gcctgtccag ccccgtgacc aagagcttca acaggggcga gtgc 654

<210> SEQ ID NO 820
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 820

Asp Ile Tyr Pro Gly Gln Gly Asp Thr Ser Tyr Asn Gln Lys Phe Lys
1 5 10 15

Gly

<210> SEQ ID NO 821
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 821

Tyr Pro Gly Gln Gly Asp
1 5

<210> SEQ ID NO 822
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 822

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Asn Met His Trp Val Arg Gln Ala Pro Gly Gln Gly Leu Glu Trp Ile
35 40 45

```
Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser
        115
```

<210> SEQ ID NO 823
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 823

```
caggtgcagc tggtgcagtc aggcgccgaa gtgaagaaac ccggcgctag tgtgaaagtt      60

agctgtaaag ctagtggcta tactttcact tcttataata tgcactgggt ccgccaggcc     120

ccaggtcaag gcctcgagtg gatcggcgat atctaccccg gtcaaggcga cacttcctat     180

aatcagaagt ttaagggtag agctactatg accgccgata agtctacttc taccgtctat     240

atggaactga gttccctgag gtctgaggac accgccgtct actactgcgc tagagtgggc     300

ggagccttcc caatggacta ctggggtcaa ggcaccctgg tcaccgtgtc tagc           354
```

<210> SEQ ID NO 824
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 824

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Ile
        35                  40                  45

Gly Asp Ile Tyr Pro Gly Gln Gly Asp Thr Ser Tyr Asn Gln Lys Phe
    50                  55                  60

Lys Gly Arg Ala Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Gly Ala Phe Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
```

```
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440
```

<210> SEQ ID NO 825
<211> LENGTH: 1332
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 825

```
caggtgcagc tggtgcagtc aggcgccgaa gtgaagaaac ccggcgctag tgtgaaagtt     60

agctgtaaag ctagtggcta tactttcact tcttataata tgcactgggt ccgccaggcc    120

ccaggtcaag gcctcgagtg gatcggcgat atctaccccg gtcaaggcga cacttcctat    180

aatcagaagt ttaagggtag agctactatg accgccgata agtctacttc taccgtctat    240

atggaactga gttccctgag gtctgaggac accgccgtct actactgcgc tagagtgggc    300

ggagccttcc caatggacta ctggggtcaa ggcaccctgg tcaccgtgtc tagcgctagc    360
```

```
actaagggcc cgtccgtgtt ccccctggca ccttgtagcc ggagcactag cgaatccacc    420

gctgccctcg gctgcctggt caaggattac ttcccggagc ccgtgaccgt gtcctggaac    480

agcggagccc tgacctccgg agtgcacacc ttccccgctg tgctgcagag ctccgggctg    540

tactcgctgt cgtcggtggt cacggtgcct tcatctagcc tgggtaccaa gacctacact    600

tgcaacgtgg accacaagcc ttccaacact aaggtggaca agcgcgtcga atcgaagtac    660

ggcccaccgt gcccgccttg tcccgcgccg gagttcctcg gcggtccctc ggtctttctg    720

ttcccaccga agcccaagga cactttgatg atttcccgca cccctgaagt gacatgcgtg    780

gtcgtggacg tgtcacagga agatccggag gtgcagttca attggtacgt ggatggcgtc    840

gaggtgcaca acgccaaaac caagccgagg gaggagcagt tcaactccac ttaccgcgtc    900

gtgtccgtgc tgacggtgct gcatcaggac tggctgaacg ggaaggagta caagtgcaaa    960

gtgtccaaca agggacttcc tagctcaatc gaaaagacca tctcgaaagc caagggacag   1020

ccccgggaac cccaagtgta taccctgcca ccgagccagg aagaaatgac taagaaccaa   1080

gtctcattga cttgccttgt gaagggcttc tacccatcgg atatcgccgt ggaatgggag   1140

tccaacggcc agccggaaaa caactacaag accacccctc cggtgctgga ctcagacgga   1200

tccttcttcc tctactcgcg gctgaccgtg gataagagca gatggcagga gggaaatgtg   1260

ttcagctgtt ctgtgatgca tgaagccctg cacaaccact acactcagaa gtccctgtcc   1320

ctctccctgg ga                                                       1332
```

```
<210> SEQ ID NO 826
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 826

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys
            100                 105                 110


<210> SEQ ID NO 827
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 827
```

```
gatatcgtcc tgactcagtc acccgatagc ctggccgtca gcctgggcga gcgggctact     60

attaactgta gagctagtga atcagtcgag tactacggca ctagcctgat gcagtggtat    120

cagcagaagc ccggtcaacc ccctaagctg ctgatctacg ccgcctctaa cgtggaatca    180

ggcgtgcccg ataggtttag cggtagcggt agtggcaccg acttcaccct gactattagt    240

agcctgcagg ccgaggacgt ggccgtctac tactgtcagc agtctaggaa ggaccctagc    300

accttcggcg gaggcactaa ggtcgagatt aag                                 333
```

<210> SEQ ID NO 828
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 828

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Asp Pro Ser Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 829
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 829

```
gatatcgtcc tgactcagtc acccgatagc ctggccgtca gcctgggcga gcgggctact     60

attaactgta gagctagtga atcagtcgag tactacggca ctagcctgat gcagtggtat    120

cagcagaagc ccggtcaacc ccctaagctg ctgatctacg ccgcctctaa cgtggaatca    180

ggcgtgcccg ataggtttag cggtagcggt agtggcaccg acttcaccct gactattagt    240

agcctgcagg ccgaggacgt ggccgtctac tactgtcagc agtctaggaa ggaccctagc    300

accttcggcg gaggcactaa ggtcgagatt aagcgtacgg tggccgctcc cagcgtgttc    360

atcttccccc ccagcgacga gcagctgaag agcggcaccg ccagcgtggt gtgcctgctg    420

aacaacttct acccccggga ggccaaggtg cagtggaagg tggacaacgc cctgcagagc    480

ggcaacagcc aggagagcgt caccgagcag gacagcaagg actccaccta cagcctgagc    540

agcaccctga ccctgagcaa ggccgactac gagaagcata aggtgtacgc ctgcgaggtg    600

acccaccagg gcctgtccag ccccgtgacc aagagcttca acaggggcga gtgc          654
```

<210> SEQ ID NO 830
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 830

```
Glu Val Gln Leu Leu Glu Ser Gly Gly Gly Leu Val Gln Pro Gly Gly
1               5                   10                  15

Ser Leu Arg Leu Ser Cys Ala Ala Ala Ser Gly Phe Thr Phe Ser Ser
            20                  25                  30

Tyr Asp Met Ser Trp Val Arg Gln Ala Pro Gly Lys Gly Leu Asp Trp
        35                  40                  45

Val Ser Thr Ile Ser Gly Gly Gly Thr Tyr Thr Tyr Tyr Gln Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ser Met Asp Tyr Trp Gly Gln Gly Thr Thr Val Thr Val Ser
            100                 105                 110

Ser Ala
```

<210> SEQ ID NO 831
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 831

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
            20                  25                  30

Leu Asn Trp Tyr His Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
```

50 55 60

Ser Gly Ser Gly Thr Asp Phe Thr Leu Thr Ile Ser Ser Leu Gln Pro
65 70 75 80

Glu Asp Phe Ala Val Tyr Tyr Cys Gln Gln Ser His Ser Ala Pro Leu
85 90 95

Thr Phe Gly Gly Gly Thr Lys Val Glu Ile Lys Arg
100 105

<210> SEQ ID NO 832
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 832

Glu Val Gln Val Leu Glu Ser Gly Gly Gly Leu Val Gln Pro Gly Gly
1 5 10 15

Ser Leu Arg Leu Tyr Cys Val Ala Ser Gly Phe Thr Phe Ser Gly Ser
20 25 30

Tyr Ala Met Ser Trp Val Arg Gln Ala Pro Gly Lys Gly Leu Glu Trp
35 40 45

Val Ser Ala Ile Ser Gly Ser Gly Gly Ser Thr Tyr Tyr Ala Asp Ser
50 55 60

Val Lys Gly Arg Phe Thr Ile Ser Arg Asp Asn Ser Lys Asn Thr Leu
65 70 75 80

Tyr Leu Gln Met Asn Ser Leu Arg Ala Glu Asp Thr Ala Val Tyr Tyr
85 90 95

Cys Ala Lys Lys Tyr Tyr Val Gly Pro Ala Asp Tyr Trp Gly Gln Gly
100 105 110

Thr Leu Val Thr Val Ser Ser Gly
115 120

<210> SEQ ID NO 833
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 833

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Val Leu Tyr Ser
20 25 30

Ser Asn Asn Lys Asn Tyr Leu Ala Trp Tyr Gln His Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Ser Pro Leu Thr Phe Gly Gly Gly Thr Lys Ile Glu Val
100 105 110

Lys

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880

000

<210> SEQ ID NO 881

<400> SEQUENCE: 881

000

<210> SEQ ID NO 882

<400> SEQUENCE: 882

000

<210> SEQ ID NO 883

<400> SEQUENCE: 883

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

```
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 901

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Val
        35                  40                  45

Gly Val Ile Trp Gly Gly Gly Gly Thr Tyr Tyr Ala Ser Ser Leu Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Ala Tyr Gly His Asp Gly Gly Phe Ala Met Asp Tyr Trp Gly
            100                 105                 110

Gln Gly Thr Leu Val Thr Val Ser Ser
        115                 120


<210> SEQ ID NO 902
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 902

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ser Asn
            20                  25                  30

Val Ala Trp Tyr Gln Gln Arg Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Tyr Ser Tyr Pro Phe
                85                  90                  95

Thr Phe Gly Gln Gly Thr Lys Leu Glu Ile Lys
            100                 105


<210> SEQ ID NO 903
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 903
```

```
Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Val
        35                  40                  45

Gly Val Ile Trp Gly Gly Gly Gly Thr Tyr Tyr Ala Ser Ser Leu Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Ala Tyr Gly His Asp Gly Gly Phe Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

```
            420                 425                 430

His Glu Ala Leu His Asn His Tyr Thr Gln Lys Ser Leu Ser Leu Ser
        435                 440                 445

Pro Gly Lys
    450


<210> SEQ ID NO 904
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 904

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ser Asn
            20                  25                  30

Val Ala Trp Tyr Gln Gln Arg Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Tyr Ser Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 905
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 905

gaggtgcagc tggtggaatc tggcggcgga ctggtgcagt ccggcggctc tctgagactg     60

tcttgcgctg cctccggctt ctccctgtcc tcttacggcg tggactgggt gcgacaggcc    120

cctggcaagg gcctggaatg ggtgggagtg atctggggcg gaggcggcac ctactacgcc    180
```

tcttccctga tgggccggtt caccatctcc cgggacaact ccaagaacac cctgtacctg 240
cagatgaact ccctgcgggc cgaggacacc gccgtgtact actgcgccag acacgcctac 300
ggccacgacg gcggcttcgc catggattat tggggccagg gcaccctggt gacagtgtcc 360
tcc 363

<210> SEQ ID NO 906
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 906
gagatcgtga tgacccagtc ccccgccacc ctgtctgtgt ctcccggcga gagagccacc 60
ctgagctgca gagcctccga gtccgtgtcc tccaacgtgg cctggtatca gcagagacct 120
ggtcaggccc ctcggctgct gatctacggc gcctctaacc gggccaccgg catccctgcc 180
agattctccg gctccggcag cggcaccgac ttcaccctga ccatctcccg gctggaaccc 240
gaggacttcg ccgtgtacta ctgcggccag tcctactcat accccttcac cttcggccag 300
ggcaccaagc tggaaatcaa g 321

<210> SEQ ID NO 907
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 907
gaggtgcagc tggtggaatc tggcggcgga ctggtgcagt ccggcggctc tctgagactg 60
tcttgcgctg cctccggctt ctccctgtcc tcttacggcg tggactgggt gcgacaggcc 120
cctggcaagg gcctggaatg ggtgggagtg atctggggcg gaggcggcac ctactacgcc 180
tcttccctga tgggccggtt caccatctcc cgggacaact ccaagaacac cctgtacctg 240
cagatgaact ccctgcgggc cgaggacacc gccgtgtact actgcgccag acacgcctac 300
ggccacgacg gcggcttcgc catggattat tggggccagg gcaccctggt gacagtgtcc 360
tccgctagca ccaagggccc aagtgtgttt cccctggccc ccagcagcaa gtctacttcc 420
ggcggaactg ctgccctggg ttgcctggtg aaggactact tccccgagcc cgtgacagtg 480
tcctggaact ctggggctct gacttccggc gtgcacacct tccccgccgt gctgcagagc 540
agcggcctgt acagcctgag cagcgtggtg acagtgccct ccagctctct gggaacccag 600
acctatatct gcaacgtgaa ccacaagccc agcaacacca aggtggacaa gagagtggag 660
cccaagagct gcgacaagac ccacacctgc ccccctgcc cagctccaga actgctggga 720
gggccttccg tgttcctgtt cccccccaag cccaaggaca ccctgatgat cagcaggacc 780
cccgaggtga cctgcgtggt ggtggacgtg tcccacgagg acccagaggt gaagttcaac 840
tggtacgtgg acggcgtgga ggtgcacaac gccaagacca agcccagaga ggagcagtac 900
aacagcacct acagggtggt gtccgtgctg accgtgctgc accaggactg gctgaacggc 960
aaagaataca agtgcaaagt ctccaacaag gccctgccag ccccaatcga aaagacaatc 1020
agcaaggcca agggccagcc acgggagccc caggtgtaca ccctgccccc cagccgggag 1080
gagatgacca agaaccaggt gtccctgacc tgtctggtga agggcttcta ccccagcgat 1140
atcgccgtgg agtgggagag caacggccag cccgagaaca actacaagac cacccccccca 1200 gtgctggaca gcgacggcag cttcttcctg tacagcaagc tgaccgtgga caagtccagg 1260
tggcagcagg gcaacgtgtt cagctgcagc gtgatgcacg aggccctgca caaccactac 1320
acccagaagt ccctgagcct gagccccggc aag 1353

<210> SEQ ID NO 908
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 908
gagatcgtga tgacccagtc ccccgccacc ctgtctgtgt ctcccggcga gagagccacc 60
ctgagctgca gagcctccga gtccgtgtcc tccaacgtgg cctggtatca gcagagacct 120
ggtcaggccc ctcggctgct gatctacggc gcctctaacc gggccaccgg catccctgcc 180
agattctccg gctccggcag cggcaccgac ttcaccctga ccatctcccg gctggaaccc 240
gaggacttcg ccgtgtacta ctgcggccag tcctactcat accccttcac cttcggccag 300
ggcaccaagc tggaaatcaa gcgtacggtg gccgctccca gcgtgttcat cttccccccc 360
agcgacgagc agctgaagag cggcaccgcc agcgtggtgt gcctgctgaa caacttctac 420
ccccgggagg ccaaggtgca gtggaaggtg gacaacgccc tgcagagcgg caacagccag 480
gagagcgtca ccgagcagga cagcaaggac tccacctaca gcctgagcag caccctgacc 540
ctgagcaagg ccgactacga gaagcataag gtgtacgcct gcgaggtgac ccaccagggc 600
ctgtccagcc ccgtgaccaa gagcttcaac aggggcgagt gc 642

<210> SEQ ID NO 909
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 909

Ser Tyr Gly Val Asp
1 5

<210> SEQ ID NO 910
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 910

Gly Phe Ser Leu Ser Ser Tyr
1 5

<210> SEQ ID NO 911
<211> LENGTH: 16

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 911

Val Ile Trp Gly Gly Gly Gly Thr Tyr Tyr Ala Ser Ser Leu Met Gly
1 5 10 15

<210> SEQ ID NO 912
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 912

Trp Gly Gly Gly Gly
1 5

<210> SEQ ID NO 913
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 913

His Ala Tyr Gly His Asp Gly Gly Phe Ala Met Asp Tyr
1 5 10

<210> SEQ ID NO 914
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 914

Arg Ala Ser Glu Ser Val Ser Ser Asn Val Ala
1 5 10

<210> SEQ ID NO 915
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 915

Ser Glu Ser Val Ser Ser Asn
1 5

<210> SEQ ID NO 916
<211> LENGTH: 7
<212> TYPE: PRT
<213> ORGANISM: Artificial Sequence
<220> FEATURE:
<221> NAME/KEY: source -continued

```
<223> OTHER INFORMATION: /note="Description of Artificial Sequence:
      Synthetic peptide"

<400> SEQUENCE: 916

Gly Ala Ser Asn Arg Ala Thr
1               5


<210> SEQ ID NO 917
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 917

Gly Ala Ser
1


<210> SEQ ID NO 918
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 918

Gly Gln Ser Tyr Ser Tyr Pro Phe Thr
1               5


<210> SEQ ID NO 919
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 919

Ser Tyr Ser Tyr Pro Phe
1               5


<210> SEQ ID NO 920
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 920

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Gly Ser Met Val Arg Gly Asp Tyr Tyr Tyr Gly Met Asp
            100                 105                 110

Val Trp Gly Gln Gly Thr Thr Val Thr Val Ser Ser
        115                 120


<210> SEQ ID NO 921
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 921

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105


<210> SEQ ID NO 922
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 922

His His His His His His
1               5
```

ANTIBODY MOLECULES TO CD73 AND USES THEREOF

RELATED APPLICATIONS

This application claims priority to U.S. Ser. No. 62/523,481 filed on Jun. 22, 2017, and U.S. Ser. No. 62/636,510 filed on Feb. 28, 2018, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 15, 2018, is named N2067-7123WO_SL.txt and is 497,959 bytes in size.

BACKGROUND

Cluster of Differentiation 73 (CD73), also known as ecto-5'-nucleotidase (ecto-5'NT), is a glycosyl-phosphatidylinositol (GPI)-linked cell surface enzyme found in most tissues, and particularly expressed in endothelial cells and subsets of hematopoietic cells (Resta et al., Immunol Rev 161:95-109 (1998) and Colgan et al., Prinergic Signal 2:351-60 (2006)). CD73 catalyzes the conversion of adenosine monophosphate (AMP) to adenosine. Adenosine is a signaling molecule which mediates its biological effects through several receptors, including the Adenosine A1, A2A, A2B, and A3 receptors. The A2A receptor has received particular attention due to its broad expression on immune cells. Adenosine has pleiotropic effects in the tumor microenvironment, including expansion of regulatory T cells (Tregs), inhibition of effector T cell (Teff) responses mediated by interferon (IFN)-γ, and expansion of myeloid derived suppressor cells (MDSCs). See, e.g., Allard B, et al., Curr Opin Pharmacol 29:7-16 (2016) and Allard D, et al., Immunotherapy 8:145-163 (2016).

CD73 is also expressed on cancer cells, including colon, lung, pancreas, ovary, bladder, leukemia, glioma, glioblastoma, melanoma, thyroid, esophageal, prostate, and breast (Jin et al., Cancer Res 70:2245-55 (2010) and Stagg et al., PNAS 107: 1547-52 (2010); Zhang et al., Cancer Res 70:6407-11 (2010)). High CD73 expression has been reported to correlate with poor outcome across various cancer indications, such as lung, melanoma, triple-negative breast, squamous head and neck and colorectal cancers. See, e.g., Allard B, et al., Expert Opin Ther Targets 18:863-881 (2014); Leclerc B G, et al., Clin Cancer Res 22:158-166 (2016); Ren Z H, et al., Oncotarget 7:61690-61702 (2016); Ren Z H, et al., Oncol Lett 12:556-562 (2016); and Turcotte M, et al., Cancer Res 75:4494-4503 (2015).

Given the ongoing need for improved strategies for targeting diseases such as cancer, new compositions and methods for regulating CD73 activity and related therapeutic agents are highly desirable.

SUMMARY

Disclosed herein are antibody molecules that bind to CD73 (Cluster of Differentiation 73) with high affinity and specificity. Nucleic acid molecules encoding the antibody molecules, expression vectors, host cells and methods for making the antibody molecules are also provided. Immunoconjugates, multi- or bispecific antibody molecules and pharmaceutical compositions comprising the antibody molecules are also provided. The anti-CD73 antibody molecules disclosed herein can be used (alone or in combination with other agents or therapeutic modalities) to treat, prevent and/or diagnose disorders, including immune disorders and cancer. Thus, compositions and methods for treating and/or diagnosing various disorders, including cancer and immune disorders, using the anti-CD73 antibody molecules are disclosed herein.

Accordingly, in certain aspects, this disclosure provides an antibody molecule (e.g., an isolated or recombinant antibody molecule) having one or more (e.g., 2, 3, 4, 5, 6, 7, 8, 9, 10, 11, 12, 13, 14, 15, 16, 17, 18, 19, 20, 21, 22, 23, 24, 25, or more, e.g., all) of the following properties:

(i) binds to CD73, e.g., human CD73, with high affinity, e.g., with a dissociation constant ($K_D$) of less than about 100 nM, e.g., less than about 10 nM, 1 nM, 0.1 nM, or 0.01 nM, e.g., when the antibody molecule is tested as a bivalent antibody molecule using Octet;

(ii) binds to soluble human CD73 or membrane-bound human CD73, or both;

(iii) binds substantially to a non-human primate CD73, e.g., cynomolgus CD73, with a dissociation constant ($K_D$) of less than about 100 nM, e.g., less than about 10 nM, 1 nM, 0.1 nM, or 0.01 nM, e.g., when the antibody molecule is tested as a bivalent antibody molecule using Octet;

(iv) does not bind to murine CD73, e.g., as determined using Octet, e.g., as described in Example 1;

(v) inhibits or reduces the enzymatic activity of CD73 (e.g., soluble human CD73 or membrane-bound human CD73), e.g., inhibits or reduces human CD73 mediated conversion of adenosine monophosphate (AMP) to adenosine, e.g., as measured by a method described herein, e.g., when the antibody molecule is tested as a bivalent antibody in a malachite green (MG) phosphate assay or a modified Cell Titer Glo (CTG) assay, e.g., as described in Example 1;

(vi) increases proliferation of anti-CD3/anti-CD28 stimulated T cells, e.g., CD4+ T cells, in the presence of adenosine monophosphate (AMP), e.g., as measured by a method described herein, e.g., when the antibody molecule is tested as a bivalent antibody in a CellTrace Violet (CTV) cell proliferation assay, e.g., as described in Example 1;

(vii) increases internalization of human CD73 into a cell when bound to human CD73 expressed on the cell surface, e.g., increases internalization of human CD73 into a cell by at least 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold.

(viii) binds to an epitope on CD73, e.g., the same or similar epitope as the epitope recognized by an antibody molecule described herein, e.g., a human anti-CD73 antibody molecule as described herein, e.g., an antibody molecule of Table 1;

(ix) binds the same (or substantially the same) or an overlapping (or substantially overlapping) epitope with a second antibody molecule to CD73, wherein the second antibody molecule is an antibody molecule described herein, e.g., an antibody molecule shown in Table 1;

(x) inhibits, e.g., competitively inhibits, the binding of a second antibody molecule to CD73 wherein the second antibody molecule is an antibody molecule described herein, e.g., an antibody molecule shown in Table 1;

(xi) shows the same or similar binding affinity or specificity, or both, as an antibody molecule described in Table 1, e.g., an antibody molecule comprising a heavy chain variable region and/or a light chain variable region shown in Table 1;

(xii) binds to the N-terminal domain of human CD73;

(xiii) binds to the A-loop and/or B-loop of human CD73;

(xiv) reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, e.g., when the antibody molecule is tested as a bivalent antibody molecule using hydrogen deuterium-exchange mass spectrometry;

(xv) when bound to a protein comprising the amino acid sequence of residues 27-547 of SEQ ID NO: 105 (e.g., a protein consisting of the amino acid sequence of SEQ ID NO: 171), induces a conformational change in residues 368-387 of SEQ ID NO: 105;

(xvi) contacts, e.g., directly or indirectly, at least one, two, three, or four residues within residues 158-172 of SEQ ID NO: 105;

(xvii) contacts, e.g., directly or indirectly, at least one, two, three, four or five residues within residues 206-215 of SEQ ID NO: 105;

(xviii) contacts, e.g., directly or indirectly, at least one, two, three, four or five residues within residues 368-387 of SEQ ID NO: 105 or 106;

(xix) contacts, e.g., directly or indirectly, at least one, two, three, four or five residues within residues 87-104 of SEQ ID NO: 105;

(xx) binds to a human CD73 dimer, said dimer consisting of a first CD73 monomer and a second CD73 monomer, wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography;

(xxi) preferentially binds to an open conformation, e.g., a catalytically inactive conformation, of CD73 over a closed conformation, e.g., a catalytically active conformation, of CD73, e.g., does not bind to or binds to the closed conformation, e.g., the catalytically active conformation, of CD73 with lower affinity, e.g., 50%, 60%, 70%, 80%, 90%, 95%, or 99% lower affinity than when the antibody molecule binds to the open conformation, e.g., the catalytically inactive conformation, of CD73;

(xxii) locks human CD73 in a catalytically inactive open conformation;

(xxiii) prevents or reduces the conversion of human CD73 from a catalytically inactive open conformation to a catalytically active closed conformation, e.g., reduces the conversion by at least 1.5-fold, 2-fold, 5-fold, 10-fold, 20-fold, 30-fold, 40-fold, 50-fold, 60-fold, 70-fold, 80-fold, 90-fold, or 100-fold;

(xxiv) has one or more biological properties of an antibody molecule described herein, e.g., an antibody molecule shown in Table 1;

(xxv) has one or more pharmacokinetic properties of an antibody molecule described herein, e.g., an antibody molecule shown in Table 1; or (xxvi) modulates (e.g., inhibits) one or more activities of CD73, e.g., results in one or more of: inhibiting or reducing the enzymatic activity of CD73; inhibiting or reducing the conversion of adenosine monophosphate (AMP) to adenosine; increasing proliferation of anti-CD3/anti-CD28 stimulated T cells, e.g., CD4+ T cells, in the presence of adenosine monophosphate (AMP); inhibiting proliferation of regulatory T cells; increasing effector T cell responses; and/or inhibiting migration, infiltration, or expansion of myeloid derived suppressor cells.

In one aspect, disclosed herein is an antibody molecule that binds to a human CD73 dimer, said dimer consisting of a first CD73 monomer and a second CD73 monomer, wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography. In one embodiment, the first or second CD73 monomer comprises the amino acid sequence of residues 27-547 of SEQ ID NO: 105. In one embodiment, the first or second CD73 monomer consists of the amino acid sequence of SEQ ID NO: 171.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at least 30%, 35%, or 40% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2. In one embodiment, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at least 30%, 35%, or 40% of the antibody molecules in said composition bind to the CD73 dimer to form a complex, wherein each of said complex consists of one antibody molecule and one CD73 dimer, e.g., when measured using a size exclusion chromatography (SEC) assay comprising the following steps:

(i) incubating a sample containing an equimolar amount of the bivalent antibody molecule and the CD73 monomer overnight at 4° C.;

(ii) running the sample through a SEC column (e.g., a Shodex Protein KW-803 column (8×300 mm ID)) at room temperature in a buffer containing 90% 2×PBS and 10% isopropanol by volume; and (iii) analyzing SEC peaks to obtain the relative percentage values of distinguishable antibody CD73 species by determining the amount of the antibody molecules in the complex relative to the total amount of the antibody molecules binding to CD73 (excluding unbound antibody molecules).

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at least 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2. In one embodiment, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at least 70%, 75%, or 80% of the antibody molecules in said composition bind to the CD73 dimer to form a complex, wherein each of said complex consists of one antibody molecule and one CD73 dimer, e.g., when measured using a size exclusion chromatography (SEC) assay comprising the following steps:

(i) incubating a sample containing an equimolar amount of the bivalent antibody molecule and the CD73 monomer overnight at 4° C.;

(ii) running the sample through a SEC column (e.g., a Shodex Protein KW-803 column (8×300 mm ID)) at room temperature in a buffer containing 90% 2×PBS and 10% isopropanol by volume; and (iii) analyzing SEC peaks to obtain the relative percentage values of distinguishable antibody CD73 species by determining the amount of the antibody molecules in the complex relative to the total amount of the antibody molecules binding to CD73 (excluding unbound antibody molecules).

In one aspect, disclosed herein is a plurality of an antibody molecule that binds to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at most 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2. In one embodiment, disclosed herein is a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at most 60%, 65%, or 70% of the antibody molecules in said composition bind to the CD73 dimer to form a complex, wherein each of said complex comprises two or more antibody molecules and two or more CD73 dimers, e.g., when measured using a size exclusion chromatography (SEC) assay comprising the following steps:

(i) incubating a sample containing an equimolar amount of the bivalent antibody molecule and the CD73 monomer overnight at 4° C.;

(ii) running the sample through a SEC column (e.g., a Shodex Protein KW-803 column (8×300 mm ID)) at room temperature in a buffer containing 90% 2×PBS and 10% isopropanol by volume; and (iii) analyzing SEC peaks to obtain the relative percentage values of distinguishable antibody CD73 species by determining the amount of the antibody molecules in the complex relative to the total amount of the antibody molecules binding to CD73 (excluding unbound antibody molecules).

In one aspect, disclosed herein is a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at most 20%, 25%, or 30% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2. In one embodiment, disclosed herein is a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at most 20%, 25%, or 30% of the antibody molecules in said composition bind to the CD73 dimer to form a complex, wherein each of said complex comprises two or more antibody molecules and two or more CD73 dimers, e.g., when measured using a size exclusion chromatography (SEC) assay comprising the following steps:

(i) incubating a sample containing an equimolar amount of the bivalent antibody molecule and the CD73 monomer overnight at 4° C.;

(ii) running the sample through a SEC column (e.g., a Shodex Protein KW-803 column (8×300 mm ID)) at room temperature in a buffer containing 90% 2×PBS and 10% isopropanol by volume; and (iii) analyzing SEC peaks to obtain the relative percentage values of distinguishable antibody CD73 species by determining the amount of the antibody molecules in the complex relative to the total amount of the antibody molecules binding to CD73 (excluding unbound antibody molecules).

In one aspect, disclosed herein is an antibody molecule that binds to human CD73, the antibody molecule preferentially binds to an open conformation, e.g., a catalytically inactive conformation, of CD73 over a closed conformation, e.g., a catalytically active conformation, of CD73, e.g., does not bind to or binds to the closed conformation, e.g., the catalytically active conformation, of CD73 with lower affinity, e.g., 50%, 60%, 70%, 80%, 90%, 95%, or 99% lower affinity than when the antibody molecule binds to the open conformation, e.g., the catalytically inactive conformation, of CD73.

In one aspect, disclosed herein is an antibody molecule that binds to human CD73, wherein the antibody molecule prevents or reduces the conversion of human CD73 from a catalytically inactive open conformation to a catalytically active closed conformation, e.g., reduces the conversion by at least 1.5-fold, 2-fold, 5-fold, 10-fold, 20-fold, 30-fold, 40-fold, 50-fold, 60-fold, 70-fold, 80-fold, 90-fold, or 100-fold, compared to the conversion in the absence of the antibody molecule.

In one aspect, disclosed herein is an antibody molecule that binds to human CD73, wherein the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is an antibody molecule that binds to human CD73, wherein the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at $X_C$ residue(s) selected from core region C (residues 368-387 of SEQ ID NO: 105) to a greater extent than at $X_A$ residue(s) selected from core region A (residues 158-172 of SEQ ID NO: 105), $X_B$ residue(s) selected from core region B (residues 206-215 of SEQ ID NO: 105), or $X_D$ residue(s) selected from core region D (residues 297-309 of SEQ ID NO: 105), e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature, wherein:

$X_C$ is equal to 1, 2, 3, 4, 5, 6, 7, 8, 9, 10, 15, or 20, $X_A$ is equal to 1, 2, 3, 4, 5, 6, 7, 8, 9, 10, 11, 12, 13, or 14, $X_B$ is equal to 1, 2, 3, 4, 5, 6, 7, 8, 9, or 10, and $X_D$ is equal to 1, 2, 3, 4, 5, 6, 7, 8, 9, 10, 11, 12, or 13.

In one embodiment, the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at 20 residues selected from core region C to a greater extent than at:

(i) 14 residues selected from core region A, (ii) 10 residues selected from core region B, or (iii) 13 residues selected from core region D, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature. In one embodiment, antibody binding reduces the average hydrogen-deuterium exchange at core region C to a greater extent than at core region A. In one embodiment, antibody binding reduces the average hydrogen-deuterium exchange at core region C to a greater extent than at core region B. In one embodiment, antibody binding reduces the average hydrogen-deuterium exchange at core region C to a greater extent than at core region D. In one embodiment, antibody binding reduces the average hydrogen-deuterium exchange at core region C to a greater extent than at core region A and core region B. In one embodiment, antibody binding reduces the average hydrogen-deuterium exchange at core region C to a greater extent than at core region A and core region D. In one embodiment, antibody binding reduces the average hydrogen-deuterium exchange at core region C to a greater extent than at core region B and core region D. In one embodiment, antibody binding reduces the average hydrogen-deuterium exchange at core region C to a greater extent than at core region A, core region B, and core region D.

In one embodiment, the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at 15 residues selected from core region C to a greater extent than at:

(i) 10 residues selected from core region A, (ii) 8 residues selected from core region B, or (iii) 10 residues selected from core region D, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature. In one embodiment, antibody binding reduces the average hydrogen-deuterium exchange at core region C to a greater extent than at core region A. In one embodiment, antibody binding reduces the average hydrogen-deuterium exchange at core region C to a greater extent than at core region B. In one embodiment, antibody binding reduces the average hydrogen-deuterium exchange at core region C to a greater extent than at core region D. In one embodiment, antibody binding reduces the average hydrogen-deuterium exchange at core region C to a greater extent than at core region A and core region B. In one embodiment, antibody binding reduces the average hydrogen-deuterium exchange at core region C to a greater extent than at core region A and core region D. In one embodiment, antibody binding reduces the average hydrogen-deuterium exchange at core region C to a greater extent than at core region B and core region D. In one embodiment, antibody binding reduces the average hydrogen-deuterium exchange at core region C to a greater extent than at core region A, core region B, and core region D.

In one embodiment, the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at 10 residues selected from core region C to a greater extent than at:

(i) 7 residues selected from core region A, (ii) 5 residues selected from core region B, or (iii) 7 residues selected from core region D, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature. In one embodiment, antibody binding reduces the average hydrogen-deuterium exchange at core region C to a greater extent than at core region A. In one embodiment, antibody binding reduces the average hydrogen-deuterium exchange at core region C to a greater extent than at core region B. In one embodiment, antibody binding reduces the average hydrogen-deuterium exchange at core region C to a greater extent than at core region D. In one embodiment, antibody binding reduces the average hydrogen-deuterium exchange at core region C to a greater extent than at core region A and core region B. In one embodiment, antibody binding reduces the average hydrogen-deuterium exchange at core region C to a greater extent than at core region A and core region D. In one embodiment, antibody binding reduces the average hydrogen-deuterium exchange at core region C to a greater extent than at core region B and core region D. In one embodiment, antibody binding reduces the average hydrogen-deuterium exchange at core region C to a greater extent than at core region A, core region B, and core region D.

In one aspect, disclosed herein is an antibody molecule that binds to human CD73, wherein the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature. In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is an antibody molecule that binds to human CD73, wherein the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at $X_A$ residue(s) selected from core region A (residues 158-172 of SEQ ID NO: 105) to a greater extent than at $X_B$ residue(s) selected from core region B (residues 206-215 of SEQ ID NO: 105), $X_C$ residue(s) selected from core region C (residues 368-387 of SEQ ID NO: 105), or $X_D$ residue(s) selected from core region D (residues 297-309 of SEQ ID NO: 105), e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature, wherein:

$X_A$ is equal to 1, 2, 3, 4, 5, 6, 7, 8, 9, 10, 11, 12, 13, or 14,
$X_B$ is equal to 1, 2, 3, 4, 5, 6, 7, 8, 9, or 10,
$X_C$ is equal to 1, 2, 3, 4, 5, 6, 7, 8, 9, 10, 15, or 20, and
$X_D$ is equal to 1, 2, 3, 4, 5, 6, 7, 8, 9, 10, 11, 12, or 13.

In one embodiment, the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at 14 residues selected from core region A to a greater extent than at:
(i) 10 residues selected from core region B,
(ii) 20 residues selected from core region C, or
(iii) 13 residues selected from core region D,
e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature. In one embodiment, antibody binding reduces the average hydrogen-deuterium exchange at core region A to a greater extent than at core region B. In one embodiment, antibody binding reduces the average hydrogen-deuterium exchange at core region A to a greater extent than at core region C. In one embodiment, antibody binding reduces the average hydrogen-deuterium exchange at core region A to a greater extent than at core region D. In one embodiment, antibody binding reduces the average hydrogen-deuterium exchange at core region A to a greater extent than at core region B and core region C. In one embodiment, antibody binding reduces the average hydrogen-deuterium exchange at core region A to a greater extent than at core region B and core region D. In one embodiment, antibody binding reduces the average hydrogen-deuterium exchange at core region A to a greater extent than at core region C and core region D. In one embodiment, antibody binding reduces the average hydrogen-deuterium exchange at core region A to a greater extent than at core region B, core region C, and core region D.

In one embodiment, the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at 10 residues selected from core region A to a greater extent than at:
(i) 8 residues selected from core region B,
(ii) 15 residues selected from core region C, or
(iii) 10 residues selected from core region D, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature. In one embodiment, antibody binding reduces the average hydrogen-deuterium exchange at core region A to a greater extent than at core region B. In one embodiment, antibody binding reduces the average hydrogen-deuterium exchange at core region A to a greater extent than at core region C. In one embodiment, antibody binding reduces the average hydrogen-deuterium exchange at core region A to a greater extent than at core region D. In one embodiment, antibody binding reduces the average hydrogen-deuterium exchange at core region A to a greater extent than at core region B and core region C. In one embodiment, antibody binding reduces the average hydrogen-deuterium exchange at core region A to a greater extent than at core region B and core region D. In one embodiment, antibody binding reduces the average hydrogen-deuterium exchange at core region A to a greater extent than at core region C and core region D. In one embodiment, antibody binding reduces the average hydrogen-deuterium exchange at core region A to a greater extent than at core region B, core region C, and core region D.

In one embodiment, the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at 7 residues selected from core region A to a greater extent than at:

(i) 5 residues selected from core region B, (ii) 10 residues selected from core region C, or (iii) 7 residues selected from core region D, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature. In one embodiment, antibody binding reduces the average hydrogen-deuterium exchange at core region A to a greater extent than at core region B. In one embodiment, antibody binding reduces the average hydrogen-deuterium exchange at core region A to a greater extent than at core region C. In one embodiment, antibody binding reduces the average hydrogen-deuterium exchange at core region A to a greater extent than at core region D. In one embodiment, antibody binding reduces the average hydrogen-deuterium exchange at core region A to a greater extent than at core region B and core region C. In one embodiment, antibody binding reduces the average hydrogen-deuterium exchange at core region A to a greater extent than at core region B and core region D. In one embodiment, antibody binding reduces the average hydrogen-deuterium exchange at core region A to a greater extent than at core region C and core region D. In one embodiment, antibody binding reduces the average hydrogen-deuterium exchange at core region A to a greater extent than at core region B, core region C, and core region D.

In one aspect, disclosed herein is an antibody molecule that binds to human CD73, wherein the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature. In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is an antibody molecule that binds to human CD73, wherein the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is an antibody molecule that binds to human CD73, wherein the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is an antibody molecule that binds to human CD73, wherein the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is an antibody molecule that binds to human CD73, wherein the antibody molecule contacts, e.g., directly or indirectly, at least one, two, three, or four residues within residues 158-172 of SEQ ID NO: 105. In one aspect, disclosed herein is an antibody molecule that binds to human CD73, wherein the antibody molecule contacts, e.g., directly or indirectly, at least one, two, three, four or five residues within residues 206-215 of SEQ ID NO: 105. In one aspect, disclosed herein is an antibody molecule that binds to human CD73, wherein the antibody molecule contacts, e.g., directly or indirectly, at least one, two, three, four or five residues within residues 368-387 of SEQ ID NO: 105 or 106. In one aspect, disclosed herein is an antibody molecule that binds to human CD73, wherein the antibody molecule contacts, e.g., directly or indirectly, at least one, two, three, four or five residues within residues 87-104 of SEQ ID NO: 105.

In one embodiment, the antibody molecule binds to at least one, two, three, or four residues within residues 158-172 of SEQ ID NO: 105. In one embodiment, the antibody molecule binds to at least one, two, three, four or five residues within residues 206-215 of SEQ ID NO: 105.

Alternatively, or in combination of an embodiment described herein, the antibody molecule reduces tandem mass tag (TMT) labeling at residue K136 (numbered according to SEQ ID NO: 105) of a protein comprising the amino acid sequence of residues 27-547 of SEQ ID NO: 105 when bound thereto, e.g., when the antibody molecule is tested as a bivalent antibody molecule using TMT isotope labeling, e.g., using methods described in Example 9, e.g., using TMT isotope labeling conducted for 30s labeling time, optionally wherein the antibody molecule further reduces TMT labeling at one or more of residues K133, K162, K179, K206, K214, K285, K291, and K341 (numbered according to SEQ ID NO: 105) of the protein, e.g., at one or more of residues K162, K206, K214, K285, K291 and K341 (numbered according to SEQ ID NO: 105) of the protein. In one embodiment, the antibody molecule increases TMT labeling at one or both of residues K262 and K274 (numbered according to SEQ ID NO: 105) of the protein when bound thereto, e.g., when the antibody molecule is tested as a bivalent antibody molecule using TMT isotope labeling, e.g., using methods described in Example 9, e.g., using TMT isotope labeling conducted for 30s labeling time. In one embodiment, the antibody molecule reduces tandem mass tag (TMT) labeling at residues K206 and K214 (numbered according to SEQ ID NO: 105) of a protein comprising the amino acid sequence of residues 27-547 of SEQ ID NO: 105 when bound thereto, wherein the reduction at residue K214 is no less than 90, 80, 70, 60, or 50% of the reduction at residue K206, e.g., when the antibody molecule is tested as a bivalent antibody molecule using TMT isotope labeling, e.g., using methods described in Example 9, e.g., wherein the reduction at residue K214 is no less than 90, 80, 70, 60, or 50% of the reduction at residue K206 using TMT isotope labeling conducted for 30s labeling time, e.g., wherein the reduction at residue K214 is no less than 90, 80, 70, 60, 50, 40, or 30% of the reduction at residue K206 using TMT isotope labeling conducted for 300s labeling time. In one embodiment, the antibody molecule reduces tandem mass tag (TMT) labeling at residue K162 (numbered according to SEQ ID NO: 105) of a protein comprising the amino acid sequence of residues 27-547 of SEQ ID NO: 105 when bound thereto, when the antibody molecule is tested using TMT isotope labeling conducted for 30s labeling time, wherein:

(i) the antibody molecule does not reduce TMT labeling at residue K162 when tested using TMT isotope labeling conducted for 300s labeling time, or (ii) the antibody molecule reduces TMT labeling at residue K162 when tested using TMT isotope labeling conducted for 300s labeling time, wherein the reduction at residue K162 under 300s labeling time is no more than 20, 30, 40, or 50% of the reduction at residue K162 under 30s labeling time, e.g., when the antibody molecule is tested as a bivalent antibody molecule, e.g., using methods described in Example 9.

Alternatively, or in combination of an embodiment described herein, the antibody molecule binds to one or more residues of CD73, e.g., via an electrostatic interaction and/or a hydrogen-bond, wherein the one or more residues are selected from the group consisting of residues Y110, K136, L132, L157, K162, S155, and T209, numbered according to SEQ ID NO: 105, e.g., as measured using crystal structure analysis, e.g., using methods described in Example 8. In one embodiment, the antibody molecule comprises a heavy chain variable region and a light chain variable region, wherein the antibody molecule has one or more (e.g., 1, 2, 3, 4, or all) of the following properties:

(i) the antibody molecule (e.g., the heavy chain variable region, e.g., R54 of the heavy chain variable region, numbered according to Kabat numbering) binds to Y110 (e.g., the backbone carbonyl of Y110) or K136 (e.g., the backbone carbonyl of K136) of CD73 (numbered according to SEQ ID NO: 105), e.g., via an electrostatic interaction, e.g., as measured using crystal structure analysis, e.g., using methods described in Example 8, (ii) the antibody molecule (e.g., the heavy chain variable region, e.g., R31 of the heavy chain variable region, numbered according to Kabat numbering) binds to L132 (e.g., the backbone carbonyl of L132) or L157 (e.g., the backbone carbonyl of L157) of CD73 (numbered according to SEQ ID NO: 105), e.g., via an electrostatic interaction, e.g., as measured using crystal structure analysis, e.g., using methods described in Example 8, (iii) the antibody molecule (e.g., the heavy chain variable region, e.g., S99 (e.g., the backbone carbonyl of S99), R31 (e.g., the backbone carbonyl of R31), or E95 (e.g., the sidechain of E95) of the heavy chain variable region, numbered according to Kabat numbering) binds to K162 (e.g., the sidechain of K162) of CD73 (numbered according to SEQ ID NO: 105), e.g., via an electrostatic interaction, e.g., as measured using crystal structure analysis, e.g., using methods described in Example 8, (iv) the antibody molecule (e.g., the heavy chain variable region, e.g., E98 of the heavy chain variable region, numbered according to Kabat numbering) binds to S155 (e.g., the sidechain of S155) of CD73 (numbered according to SEQ ID NO: 105), e.g., via a hydrogen-bond, e.g., as measured using crystal structure analysis, e.g., using methods described in Example 8, and (v) the antibody molecule (e.g., the light chain variable region, e.g., W32 (e.g., the sidechain of W32) of the light chain variable region, numbered according to Kabat numbering) binds to T209 (e.g., the sidechain of T209) of CD73 (numbered according to SEQ ID NO: 105), e.g., via a hydrogen-bond, e.g., as measured using crystal structure analysis, e.g., using methods described in Example 8.

In one embodiment, the antibody molecule binds to one or more regions of CD73, e.g., via shape complementarity and/or a Van der Waal interaction, wherein the one or more regions are selected from the group consisting of residues 155-170, 136-138, and 209-210, numbered according to SEQ ID NO: 105, e.g., as measured using crystal structure analysis, e.g., using methods described in Example 8. In one embodiment, the antibody molecule comprises a heavy chain variable region and a light chain variable region, wherein the antibody molecule has one or more (e.g., 1, 2, or all) of the following properties:

(i) the antibody molecule (e.g., the heavy chain variable region, e.g., residue 33, 50, 52, 56, 97, 98, 100, or 100a of the heavy chain variable region, numbered according to Kabat numbering) binds to residues 155-170 of CD73 (numbered according to SEQ ID NO: 105), e.g., via shape complementarity and/or a Van der Waal interaction, e.g., as measured using crystal structure analysis, e.g., using methods described in Example 8, (ii) the antibody molecule (e.g., the heavy chain variable region, e.g., residue 30 or 31 of the heavy chain variable region, numbered according to Kabat numbering) binds to residues 136-138 of CD73 (numbered according to SEQ ID NO: 105), e.g., via shape complementarity and/or a Van der Waal interaction, e.g., as measured using crystal structure analysis, e.g., using methods described in Example 8, and (iii) the antibody molecule (e.g., the light chain variable region, e.g., residue 30 or 32 of the light chain variable region, numbered according to Kabat numbering) binds to residues 209-210 of CD73 (numbered according to SEQ ID NO: 105), e.g., as measured using crystal structure analysis, e.g., using methods described in Example 8.

In one aspect, disclosed herein is an antibody molecule that binds to human CD73, wherein the antibody molecule comprises at least one, two, three, four, five or six complementarity determining regions (CDRs) (or collectively all of the CDRs) from a heavy variable region and/or a light chain variable region comprising an amino acid sequence shown in Table 1 (e.g., from the heavy and light chain variable region sequences of an antibody disclosed in Table 1, e.g., the antibody 918, 350, 356, 358, 930, 373, 374, 376, 377, 379, 363, 366, 407, 893, 939, 430, or 398), or encoded by a nucleotide sequence shown in Table 1. In some embodiments, the CDRs are according to the Kabat definition (e.g., as set out in Table 1). In some embodiments, the CDRs are according to the Chothia definition (e.g., as set out in Table 1). In some embodiments, the CDRs are according to the combined definition based on the Kabat definition and the Chothia definition (e.g., as set out in Table 1). In some embodiments, the CDRs are according to the IMGT definition (e.g., as set out in Table 1). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 1, or encoded by a nucleotide sequence shown in Table 1.

In one aspect, disclosed herein is an antibody molecule that binds to human CD73, comprising a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is an antibody molecule that binds to human CD73, comprising:

(i) a heavy chain variable region (VH) comprising one, two, or three of: a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1$I$X_2$G$X_3$G$X_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and/or (ii) a light chain variable region (VL) comprising one, two, or three of: a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In some embodiments, the anti-CD73 antibody molecule comprises:

(i) a VH comprising one, two, or three of: a VHCDR1 amino acid sequence of SEQ ID NO: 38, a VHCDR2 amino acid sequence of SEQ ID NO: 36, and a VHCDR3 amino acid sequence of SEQ ID NO: 37 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 48, a VLCDR2 amino acid sequence of SEQ ID NO: 49, and a VLCDR3 amino acid sequence of SEQ ID NO: 50 (or a sequence having at least about 85%, 90%, 95%, or 99% sequence identity thereto, and/or having one, two, three or more substitutions, insertions or deletions, e.g., conserved substitutions);

(ii) a VH comprising one, two, or three of: a VHCDR1 amino acid sequence of SEQ ID NO: 72, a VHCDR2 amino acid sequence of SEQ ID NO: 71, and a VHCDR3 amino acid sequence of SEQ ID NO: 37 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 48, a VLCDR2 amino acid sequence of SEQ ID NO: 49, and a VLCDR3 amino acid sequence of SEQ ID NO: 50 (or a sequence having at least about 85%, 90%, 95%, or 99% sequence identity thereto, and/or having one, two, three or more substitutions, insertions or deletions, e.g., conserved substitutions);

(iii) a VH comprising one, two, or three of: a VHCDR1 amino acid sequence of SEQ ID NO: 38, a VHCDR2 amino acid sequence of SEQ ID NO: 71, and a VHCDR3 amino acid sequence of SEQ ID NO: 37 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 48, a VLCDR2 amino acid sequence of SEQ ID NO: 49, and a VLCDR3 amino acid sequence of SEQ ID NO: 50 (or a sequence having at least about 85%, 90%, 95%, or 99% sequence identity thereto, and/or having one, two, three or more substitutions, insertions or deletions, e.g., conserved substitutions);

(iv) a VH comprising one, two, or three of: a VHCDR1 amino acid sequence of SEQ ID NO: 137, a VHCDR2 amino acid sequence of SEQ ID NO: 136, and a VHCDR3 amino acid sequence of SEQ ID NO: 37 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 48, a VLCDR2 amino acid sequence of SEQ ID NO: 49, and a VLCDR3 amino acid sequence of SEQ ID NO: 50 (or a sequence having at least about 85%, 90%, 95%, or 99% sequence identity thereto, and/or having one, two, three or more substitutions, insertions or deletions, e.g., conserved substitutions);

(v) a VH comprising one, two, or three of: a VHCDR1 amino acid sequence of SEQ ID NO: 137, a VHCDR2 amino acid sequence of SEQ ID NO: 146, and a VHCDR3 amino acid sequence of SEQ ID NO: 37 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 48, a VLCDR2 amino acid sequence of SEQ ID NO: 49, and a VLCDR3 amino acid sequence of SEQ ID NO: 50 (or a sequence having at least about 85%, 90%, 95%, or 99% sequence identity thereto, and/or having one, two, three or more substitutions, insertions or deletions, e.g., conserved substitutions); or (vi) a VH comprising one, two, or three of: a VHCDR1 amino acid sequence of SEQ ID NO: 137, a VHCDR2 amino acid sequence of SEQ ID NO: 154, and a VHCDR3 amino acid sequence of SEQ ID NO: 37 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 48, a VLCDR2 amino acid sequence of SEQ ID NO: 49, and a VLCDR3 amino acid sequence of SEQ ID NO: 50 (or a sequence having at least about 85%, 90%, 95%, or 99% sequence identity thereto, and/or having one, two, three or more substitutions, insertions or deletions, e.g., conserved substitutions).

In some embodiments, the anti-CD73 antibody molecule comprises a heavy chain variable region comprising the amino acid sequence of SEQ ID NO: 44, 77, 84, 142, 151, or 159, or an amino acid sequence having at least about 85%, 90%, 95%, or 99% sequence identity to SEQ ID NO: 44, 77, 84, 142, 151, or 159.

In some embodiments, the anti-CD73 antibody molecule comprises a light chain variable region comprising the amino acid sequence of SEQ ID NO: 55, or an amino acid sequence having at least about 85%, 90%, 95%, or 99% sequence identity to SEQ ID NO: 55.

In some embodiments, the anti-CD73 antibody molecule comprises a heavy chain comprising the amino acid sequence of SEQ ID NO: 46, 79, 86, 114, 116, or 117, or an amino acid sequence having at least about 85%, 90%, 95%, or 99% sequence identity to SEQ ID NO: 46, 79, 86, 114, 116, or 117.

In some embodiments, the anti-CD73 antibody molecule comprises a light chain comprising the amino acid sequence of SEQ ID NO: 57, or an amino acid sequence having at least about 85%, 90%, 95%, or 99% sequence identity to SEQ ID NO: 57.

In some embodiments, the anti-CD73 antibody molecule comprises:

(i) a heavy chain variable region comprising the amino acid sequence of SEQ ID NO: 44 (or a sequence having at least about 85%, 90%, 95%, or 99% sequence identity thereto) and a light chain variable region comprising the amino acid sequence of SEQ ID NO: 55 (or a sequence having at least about 85%, 90%, 95%, or 99% sequence identity thereto);

(ii) a heavy chain variable region comprising the amino acid sequence of SEQ ID NO: 77 (or a sequence having at least about 85%, 90%, 95%, or 99% sequence identity thereto) and a light chain variable region comprising the amino acid sequence of SEQ ID NO: 55 (or a sequence having at least about 85%, 90%, 95%, or 99% sequence identity thereto);

(iii) a heavy chain variable region comprising the amino acid sequence of SEQ ID NO: 84 (or a sequence having at least about 85%, 90%, 95%, or 99% sequence identity thereto) and a light chain variable region comprising the amino acid sequence of SEQ ID NO: 55 (or a sequence having at least about 85%, 90%, 95%, or 99% sequence identity thereto);

(iv) a heavy chain variable region comprising the amino acid sequence of SEQ ID NO: 142 (or a sequence having at least about 85%, 90%, 95%, or 99% sequence identity thereto) and a light chain variable region comprising the amino acid sequence of SEQ ID NO: 55 (or a sequence having at least about 85%, 90%, 95%, or 99% sequence identity thereto);

(v) a heavy chain variable region comprising the amino acid sequence of SEQ ID NO: 151 (or a sequence having at least about 85%, 90%, 95%, or 99% sequence identity thereto) and a light chain variable region comprising the amino acid sequence of SEQ ID NO: 55 (or a sequence having at least about 85%, 90%, 95%, or 99% sequence identity thereto); or (vi) a heavy chain variable region comprising the amino acid sequence of SEQ ID NO: 159 (or a sequence having at least about 85%, 90%, 95%, or 99% sequence identity thereto) and a light chain variable region comprising the amino acid sequence of SEQ ID NO: 55 (or a sequence having at least about 85%, 90%, 95%, or 99% sequence identity thereto).

In some embodiments, the anti-CD73 antibody molecule comprises:

(i) a heavy chain comprising the amino acid sequence of SEQ ID NO: 46 (or a sequence having at least about 85%, 90%, 95%, or 99% sequence identity thereto) and a light chain comprising the amino acid sequence of SEQ ID NO: 57 (or a sequence having at least about 85%, 90%, 95%, or 99% sequence identity thereto);

(ii) a heavy chain comprising the amino acid sequence of SEQ ID NO: 114 (or a sequence having at least about 85%, 90%, 95%, or 99% sequence identity thereto) and a light chain comprising the amino acid sequence of SEQ ID NO: 57 (or a sequence having at least about 85%, 90%, 95%, or 99% sequence identity thereto);

(iii) a heavy chain comprising the amino acid sequence of SEQ ID NO: 79 (or a sequence having at least about 85%, 90%, 95%, or 99% sequence identity thereto) and a light chain comprising the amino acid sequence of SEQ ID NO: 57 (or a sequence having at least about 85%, 90%, 95%, or 99% sequence identity thereto);

(iv) a heavy chain comprising the amino acid sequence of SEQ ID NO: 116 (or a sequence having at least about 85%, 90%, 95%, or 99% sequence identity thereto) and a light chain comprising the amino acid sequence of SEQ ID NO: 57 (or a sequence having at least about 85%, 90%, 95%, or 99% sequence identity thereto);

(v) a heavy chain comprising the amino acid sequence of SEQ ID NO: 86 (or a sequence having at least about 85%, 90%, 95%, or 99% sequence identity thereto) and a light chain comprising the amino acid sequence of SEQ ID NO: 57 (or a sequence having at least about 85%, 90%, 95%, or 99% sequence identity thereto); or (vi) a heavy chain comprising the amino acid sequence of SEQ ID NO: 117 (or a sequence having at least about 85%, 90%, 95%, or 99% sequence identity thereto) and a light chain comprising the amino acid sequence of SEQ ID NO:

57 (or a sequence having at least about 85%, 90%, 95%, or 99% sequence identity thereto).

In one aspect, disclosed herein is an antibody molecule that binds to human CD73, comprising a heavy chain variable region (VH) comprising a VHCDR3 amino acid sequence of ESQESPYNNWFDP (SEQ ID NO: 3).

In one aspect, disclosed herein is an antibody molecule that binds to human CD73, comprising:

(i) a heavy chain variable region (VH) comprising a heavy chain complementarity determining region 1 (VHCDR1) amino acid sequence of $X_1X_2$YWS (SEQ ID NO: 90), wherein $X_1$ is R, G, or S, and $X_2$ is Y or R; a VHCDR2 amino acid sequence of YIY$X_1X_2$GST$X_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and/or (ii) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSF-PRT (SEQ ID NO: 16).

In some embodiments, the anti-CD73 antibody molecule comprises:

(i) a VH comprising one, two, or three of: a VHCDR1 amino acid sequence of SEQ ID NO: 61, a VHCDR2 amino acid sequence of SEQ ID NO: 60, and a VHCDR3 amino acid sequence of SEQ ID NO: 3 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 14, a VLCDR2 amino acid sequence of SEQ ID NO: 15, and a VLCDR3 amino acid sequence of SEQ ID NO: 16 (or a sequence having at least about 85%, 90%, 95%, or 99% sequence identity thereto, and/or having one, two, three or more substitutions, insertions or deletions, e.g., conserved substitutions);

(ii) a VH comprising one, two, or three of: a VHCDR1 amino acid sequence of SEQ ID NO: 4, a VHCDR2 amino acid sequence of SEQ ID NO: 26, and a VHCDR3 amino acid sequence of SEQ ID NO: 3 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 14, a VLCDR2 amino acid sequence of SEQ ID NO: 15, and a VLCDR3 amino acid sequence of SEQ ID NO: 16 (or a sequence having at least about 85%, 90%, 95%, or 99% sequence identity thereto, and/or having one, two, three or more substitutions, insertions or deletions, e.g., conserved substitutions);

(iii) a VH comprising one, two, or three of: a VHCDR1 amino acid sequence of SEQ ID NO: 4, a VHCDR2 amino acid sequence of SEQ ID NO: 2, and a VHCDR3 amino acid sequence of SEQ ID NO: 3 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 14, a VLCDR2 amino acid sequence of SEQ ID NO: 15, and a VLCDR3 amino acid sequence of SEQ ID NO: 16 (or a sequence having at least about 85%, 90%, 95%, or 99% sequence identity thereto, and/or having one, two, three or more substitutions, insertions or deletions, e.g., conserved substitutions); or (iv) a VH comprising one, two, or three of: a VHCDR1 amino acid sequence of SEQ ID NO: 163, a VHCDR2 amino acid sequence of SEQ ID NO: 162, and a VHCDR3 amino acid sequence of SEQ ID NO: 3 (or a sequence having at least about 85%, 90%, 95%, or 99% sequence identity thereto, and/or having one, two, three or more substitutions, insertions or deletions, e.g., conserved substitutions); and a VL comprising one, two, or three of: a VLCDR1 amino acid sequence of SEQ ID NO: 14, a VLCDR2 amino acid sequence of SEQ ID NO: 15, and a VLCDR3 amino acid sequence of SEQ ID NO: 16 (or a sequence having at least about 85%, 90%, 95%, or 99% sequence identity thereto, and/or having one, two, three or more substitutions, insertions or deletions, e.g., conserved substitutions).

In some embodiments, the anti-CD73 antibody molecule comprises a heavy chain variable region comprising the amino acid sequence of SEQ ID NO: 66, 31, 10, or 168, or an amino acid sequence having at least about 85%, 90%, 95%, or 99% sequence identity to SEQ ID NO: 66, 31, 10, or 168.

In some embodiments, the anti-CD73 antibody molecule comprises a light chain variable region comprising the amino acid sequence of SEQ ID NO: 21, or an amino acid sequence having at least about 85%, 90%, 95%, or 99% sequence identity to SEQ ID NO: 21.

In some embodiments, the anti-CD73 antibody molecule comprises a heavy chain comprising the amino acid sequence of SEQ ID NO: 68, 33, 12, 115, 113, or 112, or an amino acid sequence having at least about 85%, 90%, 95%, or 99% sequence identity to SEQ ID NO: 68, 33, 12, 115, 113, or 112.

In some embodiments, the anti-CD73 antibody molecule comprises a light chain comprising the amino acid sequence of SEQ ID NO: 23, or an amino acid sequence having at least about 85%, 90%, 95%, or 99% sequence identity to SEQ ID NO: 23.

In some embodiments, the anti-CD73 antibody molecule comprises:

(i) a heavy chain variable region comprising the amino acid sequence of SEQ ID NO: 66 (or a sequence having at least about 85%, 90%, 95%, or 99% sequence identity thereto) and a light chain variable region comprising the amino acid sequence of SEQ ID NO: 21 (or a sequence having at least about 85%, 90%, 95%, or 99% sequence identity thereto);

(ii) a heavy chain variable region comprising the amino acid sequence of SEQ ID NO: 31 (or a sequence having at least about 85%, 90%, 95%, or 99% sequence identity thereto) and a light chain variable region comprising the amino acid sequence of SEQ ID NO: 21 (or a sequence having at least about 85%, 90%, 95%, or 99% sequence identity thereto);

(iii) a heavy chain variable region comprising the amino acid sequence of SEQ ID NO: 10 (or a sequence having at least about 85%, 90%, 95%, or 99% sequence identity thereto) and a light chain variable region comprising the amino acid sequence of SEQ ID NO: 21 (or a sequence having at least about 85%, 90%, 95%, or 99% sequence identity thereto); or (iv) a heavy chain variable region comprising the amino acid sequence of SEQ ID NO: 168 (or a sequence having at least about 85%, 90%, 95%, or 99% sequence identity thereto) and a light chain variable region comprising the amino acid sequence of SEQ ID NO: 21 (or a sequence having at least about 85%, 90%, 95%, or 99% sequence identity thereto).

In some embodiments, the anti-CD73 antibody molecule comprises:

(i) a heavy chain comprising the amino acid sequence of SEQ ID NO: 68 (or a sequence having at least about 85%, 90%, 95%, or 99% sequence identity thereto) and a light chain comprising the amino acid sequence of SEQ ID NO: 23 (or a sequence having at least about 85%, 90%, 95%, or 99% sequence identity thereto);

(ii) a heavy chain comprising the amino acid sequence of SEQ ID NO: 115 (or a sequence having at least about 85%, 90%, 95%, or 99% sequence identity thereto) and a light chain comprising the amino acid sequence of SEQ ID NO: 23 (or a sequence having at least about 85%, 90%, 95%, or 99% sequence identity thereto);

(iii) a heavy chain comprising the amino acid sequence of SEQ ID NO: 33 (or a sequence having at least about 85%, 90%, 95%, or 99% sequence identity thereto) and a light chain comprising the amino acid sequence of SEQ ID NO: 23 (or a sequence having at least about 85%, 90%, 95%, or 99% sequence identity thereto);

(iv) a heavy chain comprising the amino acid sequence of SEQ ID NO: 113 (or a sequence having at least about 85%, 90%, 95%, or 99% sequence identity thereto) and a light chain comprising the amino acid sequence of SEQ ID NO: 23 (or a sequence having at least about 85%, 90%, 95%, or 99% sequence identity thereto);

(v) a heavy chain comprising the amino acid sequence of SEQ ID NO: 12 (or a sequence having at least about 85%, 90%, 95%, or 99% sequence identity thereto) and a light chain comprising the amino acid sequence of SEQ ID NO: 23 (or a sequence having at least about 85%, 90%, 95%, or 99% sequence identity thereto); or (vi) a heavy chain comprising the amino acid sequence of SEQ ID NO: 112 (or a sequence having at least about 85%, 90%, 95%, or 99% sequence identity thereto) and a light chain comprising the amino acid sequence of SEQ ID NO: 23 (or a sequence having at least about 85%, 90%, 95%, or 99% sequence identity thereto).

In certain embodiments, the anti-CD73 antibody molecule comprises a heavy chain variable region having an amino acid sequence derived from a human VH3-23 germline sequence. In certain embodiments, the anti-CD73 antibody molecule comprises a light chain variable region having an amino acid sequence derived from a human VK3-15 germline sequence. In certain embodiments, the anti-CD73 antibody molecule comprises a heavy chain variable region having an amino acid sequence derived from a human VH3-23 germline sequence, and a light chain variable region having an amino acid sequence derived from a human VK3-15 germline sequence.

In certain embodiments, the anti-CD73 antibody molecule comprises a heavy chain variable region having an amino acid sequence derived from a human VH4-59 germline sequence. In certain embodiments, the anti-CD73 antibody molecule comprises a light chain variable region having an amino acid sequence derived from a human VK1-12 germline sequence. In certain embodiments, the anti-CD73 antibody molecule comprises a heavy chain variable region having an amino acid sequence derived from a human VH4-59 germline sequence, and a light chain variable region having an amino acid sequence derived from a human VK1-12 germline sequence.

In certain embodiments, the anti-CD73 antibody molecule comprises a heavy chain variable region having an amino acid sequence derived from a human VH3-23 germline sequence. In certain embodiments, the anti-CD73 antibody molecule comprises a light chain variable region having an amino acid sequence derived from a human VK1-05 germline sequence. In certain embodiments, the anti-CD73 antibody molecule comprises a heavy chain variable region having an amino acid sequence derived from a human VH3-23 germline sequence, and a light chain variable region having an amino acid sequence derived from a human VK1-05 germline sequence.

In certain embodiments, the anti-CD73 antibody molecule comprises a heavy chain variable region having an amino acid sequence derived from a human VH1-02 germline sequence. In certain embodiments, the anti-CD73 antibody molecule comprises a light chain variable region having an amino acid sequence derived from a human VK1-12 germline sequence. In certain embodiments, the anti-CD73 antibody molecule comprises a heavy chain variable region having an amino acid sequence derived from a human VH1-02 germline sequence, and a light chain variable region having an amino acid sequence derived from a human VK1-12 germline sequence.

In certain embodiments, the anti-CD73 antibody molecule comprises a heavy chain variable region having an amino acid sequence derived from a human VH3-07 germline sequence. In certain embodiments, the anti-CD73 antibody molecule comprises a light chain variable region having an amino acid sequence derived from a human VK4-01 germline sequence. In certain embodiments, the anti-CD73 antibody molecule comprises a heavy chain variable region having an amino acid sequence derived from a human VH3-07 germline sequence, and a light chain variable region having an amino acid sequence derived from a human VK4-01 germline sequence.

In certain embodiments, the anti-CD73 antibody molecule comprises a heavy chain variable region having an amino acid sequence derived from a human VH1-69 germline sequence. In certain embodiments, the anti-CD73 antibody molecule comprises a light chain variable region having an amino acid sequence derived from a human VK3-15 germline sequence. In certain embodiments, the anti-CD73 antibody molecule comprises a heavy chain variable region having an amino acid sequence derived from a human VH1-69 germline sequence, and a light chain variable region having an amino acid sequence derived from a human VK3-15 germline sequence.

In certain embodiments, the anti-CD73 antibody molecule comprises a heavy chain variable region having an amino acid sequence derived from a human VH4-34 germline sequence. In certain embodiments, the anti-CD73 antibody molecule comprises a light chain variable region having an amino acid sequence derived from a human VK1-12 germline sequence. In certain embodiments, the anti-CD73 antibody molecule comprises a heavy chain variable region having an amino acid sequence derived from a human VH4-34 germline sequence, and a light chain variable region having an amino acid sequence derived from a human VK1-12 germline sequence.

In certain embodiments, the anti-CD73 antibody molecule is a monoclonal antibody or an antibody with single specificity. In certain embodiments, the anti-CD73 antibody molecule is a bispecific or multispecific antibody. The heavy and light chains of the anti-CD73 antibody molecule can be full-length (e.g., an antibody can include at least one or at least two complete heavy chains, and at least one or at least two complete light chains) or can include an antigen-binding fragment (e.g., a Fab, F(ab')2, Fv, a single chain Fv fragment, a single domain antibody, a diabody (dAb), a bivalent or bispecific antibody or fragment thereof, a single domain variant thereof, or a camelid antibody).

In certain embodiments, the anti-CD73 antibody molecule has a heavy chain constant region (Fc) chosen from, e.g., the heavy chain constant regions of IgG, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG4. In some embodiments, the heavy chain constant region is human IgG4. In some embodiments, the anti-CD73 antibody molecule has a light chain constant region chosen from, e.g., the light chain constant regions of kappa or lambda. In some embodiments, the light chain constant region is kappa (e.g., human kappa). In some embodiments, the constant region is altered, e.g., mutated, to modify the properties of the anti-CD73 antibody molecule (e.g., to increase or decrease one or more of: Fc receptor binding, antibody glycosylation, the number of cysteine residues, effector cell function, or complement function). In some embodiments, the heavy chain constant region of an IgG4, e.g., a human IgG4, is mutated at position 228 according to Eu numbering (e.g., S to P), e.g., as shown in Table 3. In certain embodiments, the anti-CD73 antibody molecules comprises a human IgG4 mutated at position 228 according to Eu numbering (e.g., S to P), e.g., as shown in Table 3; and a kappa light chain constant region, e.g., as shown in Table 3. In some embodiments, the heavy chain constant region of an IgG4, e.g., a human IgG4, is mutated at position 228 (e.g., S to P) and position 235 (e.g., L to E) according to Eu numbering, e.g., as shown in Table 3. In certain embodiments, the anti-CD73 antibody molecules comprises a human IgG4 mutated at position 228 (e.g., S to P) and position 235 (e.g., L to E) according to Eu numbering, e.g., as shown in Table 3; and a kappa light chain constant region, e.g., as shown in Table 3. In still another embodiment, the heavy chain constant region of an IgG1, e.g., a human IgG1, is mutated at one or more of position 297 (e.g., N to A), position 265 (e.g., D to A), position 329 (e.g., P to A), position 234 (e.g., L to A), or position 235 (e.g., L to A), all according to Eu numbering, e.g., as shown in Table 3. In certain embodiments, the anti-CD73 antibody molecules comprises a human IgG1 mutated at one or more of the aforesaid positions, e.g., as shown in Table 3; and a kappa light chain constant region, e.g., as shown in Table 3.

In some embodiments, the anti-CD73 antibody molecule comprises a heavy chain constant region selected from IgG1, IgG2, IgG3, and IgG4, and a light chain constant region chosen from the light chain constant regions of kappa or lambda. In some embodiments, the anti-CD73 antibody molecule comprises a heavy chain constant region comprising an amino acid sequence selected from the group consisting of SEQ ID NOs: 92-103, 119, and 120, and a light chain constant region comprising the amino acid sequence of SEQ ID NO: 104.

In one aspect, the invention features an antibody molecule that competes with a monoclonal antibody, e.g., an antibody molecule described herein, for binding to human CD73. The invention also features an antibody molecule that binds to the same (or substantially the same) or an overlapping (or substantially overlapping) epitope as a monoclonal antibody, e.g., an antibody molecule described herein, to human CD73.

In one embodiment, the monoclonal antibody comprises a heavy chain variable region (VH) comprising a heavy chain complementarity determining region 3 (VHCDR3) amino acid sequence of GGLYGSGSYLSDFDL (SEQ ID NO: 37).

In certain embodiments, the monoclonal antibody comprises:

(i) a heavy chain variable region (VH) comprising a heavy chain complementarity determining region 1 (VHCDR1) amino acid sequence of $X_1X_2AMS$ (SEQ ID NO: 88), wherein $X_1$ is R, Y, or S, and $X_2$ is Y or N; a VHCDR2 amino acid sequence of $X_1IX_2GX_3GX_4X_5TYYADSVKG$ (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and/or (ii) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In certain embodiments, the monoclonal antibody comprises:

(i) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(ii) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(iii) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(iv) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(v) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (vi) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one embodiment, the monoclonal antibody comprises a heavy chain variable region (VH) comprising a heavy chain complementarity determining region 3 (VHCDR3) amino acid sequence of ESQESPYNNWFDP (SEQ ID NO: 3).

In certain embodiments, the monoclonal antibody comprises:

(i) a heavy chain variable region (VH) comprising a heavy chain complementarity determining region 1 (VHCDR1) amino acid sequence of $X_1X_2$YWS (SEQ ID NO: 90), wherein $X_1$ is R, G, or S, and $X_2$ is Y or R; a VHCDR2 amino acid sequence of YIY$X_1X_2$GST$X_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and/or (ii) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSFPRT (SEQ ID NO: 16).

In certain embodiments, the monoclonal antibody comprises:

(i) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(ii) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(iii) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (iv) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one aspect, the invention features a nucleic acid molecule that comprise one or both nucleotide sequences that encode heavy and light chain variable regions, CDRs, hypervariable loops, framework regions of the anti-CD73 antibody molecules, as described herein. In certain embodiments, the nucleotide sequence that encodes the anti-CD73 antibody molecule is codon optimized. For example, the invention features a first and second nucleic acid encoding heavy and light chain variable regions, respectively, of an anti-CD73 antibody molecule chosen from, e.g., any of 918, 350, 356, 358, 930, 373, 374, 376, 377, 379, 363, 366, 407, 893, 939, 430, or 398, as summarized in Table 1, or a sequence substantially identical thereto. For example, the nucleic acid can comprise a nucleotide sequence as set forth in Table 1, or a sequence substantially identical thereto (e.g., a sequence having at least about 85%, 90%, 95%, or 99% sequence identity thereto, or which differs by no more than 3, 6, 15, 30, or 45 nucleotides from the sequences shown in Table 1).

In one aspect, nucleic acids comprising nucleotide sequences that encode heavy and light chain variable regions and CDRs of the anti-CD73 antibody molecules, as described herein, are disclosed. For example, the disclosure provides a first and second nucleic acid encoding heavy and light chain variable regions, respectively, of an anti-CD73 antibody molecule according to Table 1 or a sequence substantially identical thereto. For example, the nucleic acid can comprise a nucleotide sequence encoding an anti-CD73 antibody molecule according to Table 1, or a sequence substantially identical to that nucleotide sequence (e.g., a sequence having at least about 85%, 90%, 95%, or 99% sequence identity thereto, or which differs by no more than 3, 6, 15, 30, or 45 nucleotides from the aforementioned nucleotide sequence).

In certain embodiments, the nucleic acid can comprise a nucleotide sequence encoding at least one, two, or three CDRs, or hypervariable loops, from a heavy chain variable region having an amino acid sequence as set forth in Table 1, or a sequence substantially homologous thereto (e.g., a sequence having at least about 85%, 90%, 95%, or 99% sequence identity thereto, and/or having one, two, three or more substitutions, insertions or deletions, e.g., conserved substitutions).

In certain embodiments, the nucleic acid can comprise a nucleotide sequence encoding at least one, two, or three CDRs, or hypervariable loops, from a light chain variable region having an amino acid sequence as set forth in Table 1, or a sequence substantially homologous thereto (e.g., a sequence having at least about 85%, 90%, 95%, or 99% sequence identity thereto, and/or having one, two, three or more substitutions, insertions or deletions, e.g., conserved substitutions).

In certain embodiments, the nucleic acid can comprise a nucleotide sequence encoding at least one, two, three, four, five, or six CDRs, or hypervariable loops, from heavy and light chain variable regions having an amino acid sequence as set forth in Table 1, or a sequence substantially homologous thereto (e.g., a sequence having at least about 85%, 90%, 95%, or 99% sequence identity thereto, and/or having one, two, three or more substitutions, insertions or deletions, e.g., conserved substitutions).

In certain embodiments, the nucleic acid encodes a heavy chain variable region, wherein the nucleic acid comprises the nucleotide sequence of SEQ ID NO: 45, 78, 85, 143, 152, 160, 67, 32, 11, or 169, or a nucleotide sequence having at least about 85%, 90%, 95%, or 99% sequence identity to SEQ ID NO: 45, 78, 85, 143, 152, 160, 67, 32, 11, or 169.

In certain embodiments, the nucleic acid encodes a heavy chain, wherein the nucleic acid comprises the nucleotide sequence of SEQ ID NO: 47, 80, 87, 69, 34, or 13, or a nucleotide sequence having at least about 85%, 90%, 95%, or 99% sequence identity to SEQ ID NO: 47, 80, 87, 69, 34, or 13.

In certain embodiments, the nucleic acid encodes a light chain variable region, wherein the nucleic acid comprises the nucleotide sequence of SEQ ID NO: 56, 144, 22, or 170, or a nucleotide sequence having at least about 85%, 90%, 95%, or 99% sequence identity to SEQ ID NO: 56, 144, 22, or 170.

In certain embodiments, the nucleic acid encodes a light chain, wherein the nucleic acid comprises the nucleotide sequence of SEQ ID NO: 58 or 24, or a nucleotide sequence having at least about 85%, 90%, 95%, or 99% sequence identity to SEQ ID NO: 58 or 24.

In one aspect, this disclosure features host cells and vectors containing the nucleic acids described herein. The nucleic acids may be present in a single vector or separate vectors present in the same host cell or separate host cell. Also provided herein is a method of producing an anti-C73 antibody molecule, the method comprising culturing a host cell disclosed herein under conditions suitable for gene expression.

In one aspect, the present disclosure provides a method of providing an antibody molecule described herein. The method may include: providing a CD73 antigen (e.g., an antigen comprising at least a portion of a CD73 epitope, e.g., the N-terminal domain of a CD73 antigen); obtaining an antibody molecule that binds to the CD73 antigen; and evaluating if the antibody molecule binds to the CD73 antigen, or evaluating efficacy of the antibody molecule in modulating, e.g., stimulating or inhibiting, the activity of CD73. The method can further include administering the antibody molecule to a subject, e.g., a human or non-human animal.

In one aspect, the disclosure provides, compositions, e.g., pharmaceutical compositions, which include a pharmaceutically acceptable carrier, excipient or stabilizer, and at least one of the anti-CD73 antibody molecules described herein. In one embodiment, the composition, e.g., the pharmaceutical composition, includes a combination of the antibody molecule and one or more agents, e.g., a therapeutic agent or other antibody molecule, as described herein. In some embodiments, the antibody molecule is conjugated to a label or a therapeutic agent. In some embodiments, the compositions, e.g., the pharmaceutical compositions, comprise a combination of the antibody molecule and a second agent, e.g., a therapeutic agent, or two or more of the aforesaid antibody molecules, as further described herein.

The anti-CD73 antibody molecules disclosed herein can inhibit, reduce or neutralize one or more activities of CD73, e.g., inhibiting or reducing the enzymatic activity of CD73; inhibiting or reducing the conversion of adenosine monophosphate (AMP) to adenosine; increasing proliferation of anti-CD3/anti-CD28 stimulated T cells, e.g., CD4+ T cells, in the presence of adenosine monophosphate (AMP); inhibiting proliferation of regulatory T cells; increasing effector T cell responses; and/or inhibiting migration, infiltration, or expansion of myeloid derived suppressor cells. Thus, such antibody molecules can be used to treat or prevent disorders where enhancing an immune response in a subject is desired.

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105.

In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule binds to at least one, two, three, or four residues within residues 158-172 of SEQ ID NO: 105, and/or at least one, two, three, four or five residues within residues 206-215 of SEQ ID NO: 105.

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1$I$X_2$G$X_3$G$X_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule comprises:

(a) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(b) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(c) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(d) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(e) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (f) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule comprises a heavy chain variable region (VH) comprising a heavy chain complementarity determining region 3 (VHCDR3) amino acid sequence of ESQESPYNNWFDP (SEQ ID NO: 3).

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule comprises:

(a) a heavy chain variable region (VH) comprising a heavy chain complementarity determining region 1 (VHCDR1) amino acid sequence of $X_1X_2$YWS (SEQ ID NO: 90), wherein $X_1$ is R, G, or S, and $X_2$ is Y or R; a VHCDR2 amino acid sequence of YIY$X_1X_2$GST$X_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSFPRT (SEQ ID NO: 16).

In one aspect, disclosed herein is an antibody molecule that binds to human CD73, wherein:

(i) the antibody molecule binds to a human CD73 dimer, said dimer consisting of a first CD73 monomer and a second CD73 monomer (e.g., each monomer comprising the amino acid sequence of residues 27-547 of SEQ ID NO: 105, e.g., each monomer consists of the amino acid sequence of SEQ ID NO: 171), wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography; and (ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule binds to at least one, two, three, or four residues within residues 158-172 of SEQ ID NO: 105, and/or at least one, two, three, four or five residues within residues 206-215 of SEQ ID NO: 105.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1$I$X_2$G$X_3$G$X_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises:

(a) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(b) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(c) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(d) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(e) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (f) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises a heavy chain variable region (VH) comprising a heavy chain complementarity determining region 3 (VHCDR3) amino acid sequence of ESQESPYNNWFDP (SEQ ID NO: 3).

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises:

(a) a heavy chain variable region (VH) comprising a heavy chain complementarity determining region 1 (VHCDR1) amino acid sequence of $X_1X_2$YWS (SEQ ID NO: 90), wherein $X_1$ is R, G, or S, and $X_2$ is Y or R; a VHCDR2 amino acid sequence of YIY$X_1X_2$GST$X_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSFPRT (SEQ ID NO: 16).

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule binds to at least one, two, three, or four residues within residues 158-172 of SEQ ID NO: 105, and/or at least one, two, three, four or five residues within residues 206-215 of SEQ ID NO: 105.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO:

105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1IX_2GX_3GX_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises:

(a) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(b) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(c) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(d) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(e) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (f) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises a heavy chain variable region (VH) comprising a heavy chain complementarity determining region 3 (VHCDR3) amino acid sequence of ESQESPYNNWFDP (SEQ ID NO: 3).

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises:

(a) a heavy chain variable region (VH) comprising a heavy chain complementarity determining region 1 (VHCDR1) amino acid sequence of $X_1X_2$YWS (SEQ ID NO: 90), wherein $X_1$ is R, G, or S, and $X_2$ is Y or R; a VHCDR2 amino acid sequence of YIY$X_1X_2$GST$X_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSFPRT (SEQ ID NO: 16).

In one aspect, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein:

(i) when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g., as described in Example 2; and (ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is an antibody molecule that binds to human CD73, wherein:

(i) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one aspect, disclosed herein is an antibody molecule that binds to human CD73, wherein:

(i) the antibody molecule binds to at least one, two, three, or four residues within residues 158-172 of SEQ ID NO: 105, and/or at least one, two, three, four or five residues within residues 206-215 of SEQ ID NO: 105; and (ii) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is an antibody molecule that binds to human CD73, wherein:

(i) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is an antibody molecule that binds to human CD73, wherein:

(i) the antibody molecule binds to at least one, two, three, or four residues within residues 158-172 of SEQ ID NO: 105, and/or at least one, two, three, four or five residues within residues 206-215 of SEQ ID NO: 105; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1$I$X_2$G$X_3$G$X_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1$I$X_2$G$X_3$G$X_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is an antibody molecule that binds to human CD73, wherein:

(i) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1$I$X_2$G$X_3$G$X_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1$I$X_2$G$X_3$G$X_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1$I$X_2$G$X_3$G$X_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one aspect, disclosed herein is an antibody molecule that binds to human CD73, wherein:

(i) the antibody molecule binds to at least one, two, three, or four residues within residues 158-172 of SEQ ID NO: 105, and/or at least one, two, three, four or five residues within residues 206-215 of SEQ ID NO: 105; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1IX_2GX_3GX_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(b) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(c) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(d) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(e) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (f) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(b) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(c) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(d) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(e) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (f) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is an antibody molecule that binds to human CD73, wherein:

(i) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(b) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(c) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(d) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(e) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (f) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(b) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(c) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(d) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(e) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (f) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is an antibody molecule that binds to human CD73, wherein:

(i) the antibody molecule binds to at least one, two, three, or four residues within residues 158-172 of SEQ ID NO: 105, and/or at least one, two, three, four or five residues within residues 206-215 of SEQ ID NO: 105; and (ii) the antibody molecule comprises:

(a) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(b) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(c) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(d) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(e) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (f) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of ESQESPYNNWFDP (SEQ ID NO: 3).

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of ESQESPYNNWFDP (SEQ ID NO: 3).

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is an antibody molecule that binds to human CD73, wherein:

(i) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of ESQESPYNNWFDP (SEQ ID NO: 3).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of ESQESPYNNWFDP (SEQ ID NO: 3).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises a heavy chain variable region (VH) comprising a heavy chain complementarity determining region 3 (VHCDR3) amino acid sequence of ESQESPYNNWFDP (SEQ ID NO: 3).

In one aspect, disclosed herein is an antibody molecule that binds to human CD73, wherein:

(i) the antibody molecule binds to at least one, two, three, or four residues within residues 158-172 of SEQ ID NO: 105, and/or at least one, two, three, four or five residues within residues 206-215 of SEQ ID NO: 105; and (ii) the antibody molecule comprises a heavy chain variable region (VH) comprising a heavy chain complementarity determining region 3 (VHCDR3) amino acid sequence of ESQESPYNNWFDP (SEQ ID NO: 3).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2YWS$ (SEQ ID NO: 90), wherein $X_1$ is R, G, or S, and $X_2$ is Y or R; a VHCDR2 amino acid sequence of YIYX$_1$X$_2$GSTX$_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSFPRT (SEQ ID NO: 16).

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2YWS$ (SEQ ID NO: 90), wherein $X_1$ is R, G, or S, and $X_2$ is Y or R; a VHCDR2 amino acid sequence of YIYX$_1$X$_2$GSTX$_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSFPRT (SEQ ID NO: 16).

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is an antibody molecule that binds to human CD73, wherein:

(i) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2YWS$ (SEQ ID NO: 90), wherein $X_1$ is R, G, or S, and $X_2$ is Y or R; a VHCDR2 amino acid sequence of YIYX$_1$X$_2$GSTX$_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSF-PRT (SEQ ID NO: 16).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2$YWS (SEQ ID NO: 90), wherein $X_1$ is R, G, or S, and $X_2$ is Y or R; a VHCDR2 amino acid sequence of YIY$X_1X_2$GST$X_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSF-PRT (SEQ ID NO: 16).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a heavy chain variable region (VH) comprising a heavy chain complementarity determining region 1 (VHCDR1) amino acid sequence of $X_1X_2$YWS (SEQ ID NO: 90), wherein $X_1$ is R, G, or S, and $X_2$ is Y or R; a VHCDR2 amino acid sequence of YIY$X_1X_2$GST$X_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSF-PRT (SEQ ID NO: 16).

In one aspect, disclosed herein is an antibody molecule that binds to human CD73, wherein:

(i) the antibody molecule binds to at least one, two, three, or four residues within residues 158-172 of SEQ ID NO: 105, and/or at least one, two, three, four or five residues within residues 206-215 of SEQ ID NO: 105; and (ii) the antibody molecule comprises:

(a) a heavy chain variable region (VH) comprising a heavy chain complementarity determining region 1 (VHCDR1) amino acid sequence of $X_1X_2$YWS (SEQ ID NO: 90), wherein $X_1$ is R, G, or S, and $X_2$ is Y or R; a VHCDR2 amino acid sequence of YIY$X_1X_2$GST$X_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSF-PRT (SEQ ID NO: 16).

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydro-gen-deuterium exchange at residues 368-387 of SEQ ID NO: 105 to a greater extent than at residues 158-172, residues 206-215, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry con-ducted for 1-minute in-exchange at pH 7-8 (e.g., pH 7.5) and room temperature; and (ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one embodiment, antibody binding reduces the average hydrogen-deuterium exchange at residues 368-387 of SEQ ID NO: 105 to a greater extent than at residues 158-172 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105. In one embodiment, antibody binding reduces the average hydrogen-deuterium exchange at residues 368-387 of SEQ ID NO: 105 to a greater extent than at residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 206-215 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 368-387 of SEQ ID NO: 105 to a greater extent than at residues 158-172 of SEQ ID NO: 105, residues 206-215 of SEQ ID NO: 105, and residues 297-309 of SEQ ID NO: 105.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), reduces the average hydrogen-deuterium exchange at residues 158-172 of SEQ ID NO: 105 to a greater extent than at residues 206-215 of SEQ ID NO: 105, residues 368-387 of SEQ ID NO: 105, or residues 297-309 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one embodiment, antibody binding reduces the average hydrogen-deuterium exchange at residues 158-172 of SEQ ID NO: 105 to a greater extent than at residues 206-215 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105. In one embodiment, antibody binding reduces the average hydrogen-deuterium exchange at residues 158-172 of SEQ ID NO: 105 to a greater extent than at residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 368-387 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 368-387 of SEQ ID NO: 105 and residues 297-309 of SEQ ID NO: 105. In one embodiment, antibody binding reduces the average hydrogen-deuterium exchange at residues 158-172 of SEQ ID NO: 105 to a greater extent than at residues 206-215 of SEQ ID NO: 105, residues 368-387 of SEQ ID NO: 105, and residues 297-309 of SEQ ID NO: 105.

In one aspect, disclosed herein is an antibody molecule that binds to human CD73, wherein:

(i) the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, wherein the region having the greatest reduction in the average hydrogen-deuterium exchange among the one or more regions is not residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of more than, e.g., 0.02, 0.03, 0.04, 0.05, or 0.06 Da per residue at residues 368-387 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one aspect, disclosed herein is an antibody molecule that binds to human CD73, wherein:

(i) the antibody molecule, when bound to a protein comprising the amino acid sequence of residues 27-547 of SEQ ID NO: 105 (e.g., a protein consisting of the amino acid sequence of SEQ ID NO: 171), leads to a reduction in the average hydrogen-deuterium exchange of less than, e.g., 0.05, 0.04, 0.03, or 0.02 Da per residue at residues 206-215 of SEQ ID NO: 105, e.g., when the antibody molecule is tested as a bivalent antibody molecule using hydrogen deuterium-exchange mass spectrometry, e.g., as described in Example 2, e.g., hydrogen deuterium-exchange mass spectrometry conducted for 1-minute in-exchange at pH 7-8 (e.g., pH 7.5) and room temperature; and (ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one aspect, disclosed herein is an antibody molecule that binds to human CD73, wherein:

(i) the antibody molecule binds to at least one, two, three, or four residues within residues 158-172 of SEQ ID NO: 105, and/or at least one, two, three, four or five residues within residues 206-215 of SEQ ID NO: 105; and (ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one aspect, disclosed herein is an antibody molecule that binds to human CD73, wherein:

(i) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1; and (ii) the antibody molecule comprises a heavy chain variable region (VH) comprising a heavy chain complementarity determining region 3 (VHCDR3) amino acid sequence of GGLYGSGSYLSDFDL (SEQ ID NO: 37).

In one aspect, disclosed herein is an antibody molecule that binds to human CD73, wherein:

(i) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1; and (ii) the antibody molecule comprises:

(a) a heavy chain variable region (VH) comprising a heavy chain complementarity determining region 1 (VHCDR1) amino acid sequence of $X_1X_2$AMS (SEQ ID NO: 88), wherein $X_1$ is R, Y, or S, and $X_2$ is Y or N; a VHCDR2 amino acid sequence of $X_1$I$X_2$G$X_3$G$X_4X_5$TYYADSVKG (SEQ ID NO: 89), wherein $X_1$ is A or S, $X_2$ is S or T, $X_3$ is S or T, $X_4$ is M, G, or S, and $X_5$ is N, S, L, or Y; and a VHCDR3 amino acid sequence of GGLYGSGSYLSDFDL (SEQ ID NO: 37); and (b) a light chain variable region (VL) comprising a light chain complementarity determining region 1 (VLCDR1) amino acid sequence of RASQSVGSNLA (SEQ ID NO: 48); a VLCDR2 amino acid sequence of GASTRAT (SEQ ID NO: 49); and a VLCDR3 amino acid sequence of QQHNAFPYT (SEQ ID NO: 50).

In one aspect, disclosed herein is an antibody molecule that binds to human CD73, wherein:

(i) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1; and (ii) the antibody molecule comprises:

(a) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(b) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(c) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(d) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(e) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (f) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

In one aspect, disclosed herein is an antibody molecule that binds to human CD73, wherein:

(i) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1; and;

(ii) the antibody molecule comprises a heavy chain variable region (VH) comprising a heavy chain complementarity determining region 3 (VHCDR3) amino acid sequence of ESQESPYNNWFDP (SEQ ID NO: 3).

In one aspect, disclosed herein is an antibody molecule that binds to human CD73, wherein:

(i) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1; and (ii) the antibody molecule comprises:

(a) a heavy chain variable region (VH) comprising a heavy chain complementarity determining region 1 (VHCDR1) amino acid sequence of $X_1X_2$YWS (SEQ ID NO: 90), wherein $X_1$ is R, G, or S, and $X_2$ is Y or R; a VHCDR2 amino acid sequence of YIY$X_1X_2$GST$X_3$YNPSLKS (SEQ ID NO: 91), wherein $X_1$ is G or S, $X_2$ is R, S, or T, and $X_3$ is N or K; and a VHCDR3 amino acid sequence of ESQESPYNNWFDP (SEQ ID NO: 3); and/or (b) a light chain variable region (VL) comprising a light chain complementarity determining region 1 (VLCDR1) amino acid sequence of RASQGISSWLA (SEQ ID NO: 14); a VLCDR2 amino acid sequence of AASSLQS (SEQ ID NO: 15); and a VLCDR3 amino acid sequence of QQGNSFPRT (SEQ ID NO: 16).

In one aspect, disclosed herein is an antibody molecule that binds to human CD73, wherein:

(i) the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1; and;

(ii) the antibody molecule comprises:

(a) a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(b) a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16;

(c) a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16; or (d) a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

Uses of the Anti-CD73 Antibody Molecules

The antibody molecules disclosed herein can modulate (e.g., enhance, stimulate, increase, inhibit, reduce or neutralize) one or more activities of CD73. In some embodiments, the antibody molecule results in one or more of: inhibiting or reducing the enzymatic activity of CD73; inhibiting or reducing the conversion of adenosine monophosphate (AMP) to adenosine; and increasing proliferation of anti-CD3/anti-CD28 stimulated T cells, e.g., CD4+ T cells, in the presence of adenosine monophosphate (AMP).

In some embodiments, the antibody molecule inhibits or reduces the enzymatic activity of CD73 (e.g., soluble human CD73 or membrane-bound human CD73), e.g., human CD73 mediated conversion of adenosine monophosphate (AMP) to adenosine, e.g., as measured by a method described herein, e.g., a malachite green (MG) phosphate assay or a modified Cell Titer Glo (CTG) assay, e.g., as described in Example 1.

In some embodiments, the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay, e.g., as described in Example 1.

In one embodiment, the antibody molecule inhibits at least about 60%, 70%, 80%, or 90% of the enzymatic activity of membrane-bound human CD73, e.g., when the antibody molecule is tested as a bivalent antibody molecule using a modified Cell Titer Glo (CTG) assay comprising the following steps:

(i) incubating a dose titration of the antibody molecule (e.g., 1000 ng/ml) with 20,000 cells/ml of a human cancer cell line expressing human CD73 (e.g., the human breast cancer cell line MDA-MB-231 or the human ovarian cancer cell line SKOV3) for 240 minutes at 37° C. in the presence of 100 μM AMP;

(ii) measuring disappearance of AMP using a modified Cell Titer Glo (CTG) assay as described in Example 1; and (iii) calculating the percentage of inhibition mediated by the antibody molecule using time zero control as 100% inhibition and no antibody control as 0% inhibition.

In some embodiments, the antibody molecule increases proliferation of anti-CD3/anti-CD28 stimulated T cells, e.g., CD4+ T cells, in the presence of adenosine monophosphate (AMP), e.g., as measured by a method described herein, e.g., a CellTrace Violet (CTV) cell proliferation assay, e.g., an assay of Example 1.

In certain aspects, a method of modulating (e.g., stimulating or inhibiting) an immune response in a subject is provided. The method comprises administering to the subject an anti-CD73 antibody molecule disclosed herein, (e.g., a therapeutically effective amount of an anti-CD73 antibody molecule), alone or in combination with one or more agents or procedures (e.g., in combination with anti-tumor therapies, e.g., chemotherapies, radiation therapies, and/or other immunomodulatory agents), such that the immune response in the subject is modulated. In some embodiments, the antibody molecule inhibits, reduces, or neutralizes an immune response in a subject.

The subject can be a mammal, e.g., a monkey, a primate, preferably a higher primate, e.g., a human (e.g., a patient having, or at risk of having, a disorder described herein). In some embodiments, the subject is in need of enhancing an immune response, and in some embodiments, the subject is in need of inhibiting an immune response. In one embodiment, the subject has, or is at risk of, having a disorder described herein, e.g., a cancer as described herein. In certain embodiments, the subject is, or is at risk of being, immunocompromised. For example, the subject is undergoing or has undergone a chemotherapeutic treatment and/or radiation therapy.

In one aspect, a method of stimulating an immune response in a subject is provided. The method comprises administering to the subject an anti-CD73 antibody molecule described herein, e.g., a therapeutically effective amount of an anti-CD73 antibody molecule, alone or in combination with one or more agents or procedures.

In one aspect, a method of treating (e.g., one or more of reducing, inhibiting, or delaying progression) a cancer or a tumor in a subject is provided. The method comprises administering to the subject an anti-CD73 antibody molecule described herein, e.g., a therapeutically effective amount of an anti-CD73 antibody molecule, alone or in combination with one or more agents or procedures.

In some embodiments, the antibody molecule is administered in combination with a second therapeutic agent or procedure. In some embodiments, the second therapeutic agent or procedure is chosen from one or more of chemotherapy, a targeted anti-cancer therapy, an oncolytic drug, a cytotoxic agent, an immune-based therapy, a cytokine, surgical procedure, a radiation procedure, an activator of a costimulatory molecule, an inhibitor of an inhibitory molecule (e.g., an inhibitor of a checkpoint inhibitor), a vaccine, or a cell therapy. In some embodiments, the second therapeutic agent is chosen from one or more of: 1) a protein kinase C (PKC) inhibitor; 2) a heat shock protein 90 (HSP90) inhibitor; 3) an inhibitor of a phosphoinositide 3-kinase (PI3K) and/or target of rapamycin (mTOR); 4) an inhibitor of cytochrome P450 (e.g., a CYP17 inhibitor or a 17alpha-Hydroxylase/C17-20 Lyase inhibitor); 5) an iron chelating agent; 6) an aromatase inhibitor; 7) an inhibitor of p53, e.g., an inhibitor of a p53/Mdm2 interaction; 8) an apoptosis inducer; 9) an angiogenesis inhibitor; 10) an aldosterone synthase inhibitor; 11) a smoothened (SMO) receptor inhibitor; 12) a prolactin receptor (PRLR) inhibitor; 13) a Wnt signaling inhibitor; 14) a CDK4/6 inhibitor; 15) a fibroblast growth factor receptor 2 (FGFR2)/fibroblast growth factor receptor 4 (FGFR4) inhibitor; 16) an inhibitor of macrophage colony-stimulating factor (M-CSF); 17) an inhibitor of one or more of c-KIT, histamine release, Flt3 (e.g., FLK2/STK1) or PKC; 18) an inhibitor of one or more of VEGFR-2 (e.g., FLK-1/KDR), PDGFRbeta, c-KIT or Raf kinase C; 19) a somatostatin agonist and/or a growth hormone release inhibitor; 20) an anaplastic lymphoma kinase (ALK) inhibitor; 21) an insulin-like growth factor 1 receptor (IGF-1R) inhibitor; 22) a P-Glycoprotein 1 inhibitor; 23) a vascular endothelial growth factor receptor (VEGFR) inhibitor; 24) a BCR-ABL kinase inhibitor; 25) an FGFR inhibitor; 26) an inhibitor of CYP11B2; 27) a HDM2 inhibitor, e.g., an inhibitor of the HDM2-p53 interaction; 28) an inhibitor of a tyrosine kinase; 29) an inhibitor of c-MET; 30) an inhibitor of JAK; 31) an inhibitor of DAC; 32) an inhibitor of 11β-hydroxylase; 33) an inhibitor of IAP; 34) an inhibitor of PIM kinase; 35) an inhibitor of Porcupine; 36) an inhibitor of BRAF, e.g., BRAF V600E or wild-type BRAF; 37) an inhibitor of HER3; 38) an inhibitor of MEK; or 39) an inhibitor of a lipid kinase.

In some embodiments, the anti-CD73 antibody molecule is administered in combination with a PD-1 inhibitor. In some embodiments, the PD-1 inhibitor is selected from the group consisting of PDR001, Nivolumab, Pembrolizumab, Pidilizumab, MEDI0680, REGN2810, TSR-042, PF-06801591, and AMP-224. In some embodiments, the PD-1 inhibitor is an anti-PD-1 antibody molecule. In some embodiments, the anti-PD-1 antibody molecule is administered, e.g., intravenously, at a dose of about 250 mg to 350 mg, about 350 mg to 450 mg, or about 450 mg to 550 mg, e.g., at a dose of about 300 mg or about 400 mg, e.g., once every three weeks (Q3W) or once every four weeks (Q4W), e.g., at a dose of about 300 mg Q3W, or at a dose of about 400 mg Q4W. In one embodiment, the anti-PD-1 antibody molecule is administered, e.g., by infusion, over a period of 30 minutes, or a period of up to 2 hours. In some embodiments, the anti-CD73 antibody molecule is administered, e.g., intravenously, at a dose of about 5 mg to 100 mg, about 100 mg to 500 mg, about 500 mg to 1000 mg, about 1000 mg to 1500 mg, about 1500 mg to 2000 mg, about 2000 mg to 2500 mg, about 2500 mg to 3000 mg, about 3000 mg to 3500 mg, or about 3500 mg to 4000 mg, e.g., at a dose of about 6 mg, about 20 mg, about 60 mg, about 200 mg, about 600 mg, about 1200 mg, about 2400 mg, about 3000 mg, or about 3600 mg, e.g., once every week (QW), once every two weeks (Q2W), or once every four weeks (Q4W), e.g., Q2W. In one embodiment, the anti-CD73 antibody molecule is administered, e.g., by infusion, over a period of 30 minutes, a period of 1 hour, or a period of up to 2 hours. In some embodiments, the anti-CD73 antibody molecule is administered, e.g., intravenously, at a dose of about 5 mg to 100 mg, e.g., 20 mg, Q2W, and the anti-PD-1 antibody molecule is administered, e.g., intravenously, at a dose of about 350 mg to 450 mg, e.g., 400 mg, Q4W. In some embodiments, the anti-CD73 antibody molecule is administered, e.g., intravenously, at a dose of about 5 mg to 100 mg, e.g., 60 mg, Q2W, and the anti-PD-1 antibody molecule is administered, e.g., intravenously, at a dose of about 350 mg to 450 mg, e.g., 400 mg, Q4W. In some embodiments, the anti-CD73 antibody molecule is administered, e.g., intravenously, at a dose of about 100 mg to 500 mg, e.g., 200 mg, Q2W, and the anti-PD-1 antibody molecule is administered, e.g., intravenously, at a dose of about 350 mg to 450 mg, e.g., 400 mg, Q4W. In some embodiments, the anti-CD73 antibody molecule is administered, e.g., intravenously, at a dose of about 500 mg to 1000 mg, e.g., 600 mg, Q2W, and the anti-PD-1 antibody molecule is administered, e.g., intravenously, at a dose of about 350 mg to 450 mg, e.g., 400 mg, Q4W. In some embodiments, the anti-CD73 antibody molecule is administered, e.g., intravenously, at a dose of about 1000 mg to 1500 mg, e.g., 1200 mg, Q2W, and the anti-PD-1 antibody molecule is administered, e.g., intravenously, at a dose of about 350 mg to 450 mg, e.g., 400 mg, Q4W. In some embodiments, the anti-CD73 antibody molecule is administered, e.g., intravenously, at a dose of about 2000 mg to 2500 mg, e.g., 2400 mg, Q2W, and the anti-PD-1 antibody molecule is administered, e.g., intravenously, at a dose of about 350 mg to 450 mg, e.g., 400 mg, Q4W. In some embodiments, the anti-CD73 antibody molecule is administered, e.g., intravenously, at a dose of about 3000 mg to 3500 mg, e.g., 3000 mg, Q2W, and the anti-PD-1 antibody molecule is administered, e.g., intravenously, at a dose of about 350 mg to 450 mg, e.g., 400 mg, Q4W. In some embodiments, the anti-CD73 antibody molecule is administered, e.g., intravenously, at a dose of about 3500 mg to 4000 mg, e.g., 3600 mg, Q2W, and the anti-PD-1 antibody molecule is administered, e.g., intravenously, at a dose of about 350 mg to 450 mg, e.g., 400 mg, Q4W.

In some embodiments, the anti-CD73 antibody molecule is administered in combination with a PD-L1 inhibitor. In some embodiments, the PD-L1 inhibitor is selected from the group consisting of FAZ053, Atezolizumab, Avelumab, Durvalumab, and BMS-936559.

In some embodiments, the anti-CD73 antibody molecule is administered in combination with a CTLA-4 inhibitor. In some embodiments, the CTLA-4 inhibitor is Ipilimumab or Tremelimumab.

In some embodiments, the anti-CD73 antibody molecule is administered in combination with a TIM-3 inhibitor. In some embodiments, the TIM-3 inhibitor is chosen from MGB453, TSR-022, or LY3321367.

In some embodiments, the anti-CD73 antibody molecule is administered in combination with a LAG-3 inhibitor. In some embodiments, the LAG-3 inhibitor is selected from the group consisting of LAG525, BMS-986016, TSR-033, MK-4280, and REGN3767.

In some embodiments, the anti-CD73 antibody molecule is administered in combination with a GITR agonist. In some embodiments, the GITR agonist is selected from the group consisting of GWN323 (Novartis), BMS-986156 (BMS), MK4166 or MK-1248 (Merck), TRX518 (Leap Therapeutics), INCAGN1876 (Incyte/Agenus), AMG 228 (Amgen), and INBRX-110 (Inhibrx).

In some embodiments, the anti-CD73 antibody molecule is administered in combination with an anti-CD3 multispecific antibody molecule. In some embodiments, the anti-CD3 multispecific antibody molecule is an anti-CD3×anti-CD123 bispecific antibody molecule (e.g., XENP14045), or an anti-CD3×anti-CD20 bispecific antibody molecule (e.g., XENP13676).

In some embodiments, the anti-CD73 antibody molecule is administered in combination with a cytokine molecule. In some embodiments, the cytokine molecule is IL-15 complexed with a soluble form of IL-15 receptor alpha (IL-15Ra).

In some embodiments, the anti-CD73 antibody molecule is administered in combination with a STING agonist.

In some embodiments, the anti-CD73 antibody molecule is administered in combination with a macrophage colony-stimulating factor (M-CSF) inhibitor, optionally wherein the M-CSF inhibitor is MCS110.

In some embodiments, the anti-CD73 antibody molecule is administered in combination with a CSF-1R inhibitor, optionally wherein the CSF-1R inhibitor is BLZ945.

In some embodiments, the anti-CD73 antibody molecule is administered in combination with an inhibitor of indoleamine 2,3-dioxygenase (IDO) and/or tryptophan 2,3-dioxygenase (TDO).

In some embodiments, the anti-CD73 antibody molecule is administered in combination with a TGF-β inhibitor.

In some embodiments, the anti-CD73 antibody molecule is administered in combination with an adenosine A2AR antagonist. In some embodiments, the adenosine A2AR antagonist is selected from the group consisting of PBF509, CPI444, AZD4635, Vipadenant, GBV-2034, and AB928. In some embodiments, the adenosine A2AR antagonist is selected from the group consisting of 5-bromo-2,6-di-(1H-pyrazol-1-yl)pyrimidine-4-amine; (S)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine; (R)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine, or racemate thereof; 7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine; and 6-(2-chloro-6-methylpyridin-4-yl)-5-(4-fluorophenyl)-1,2,4-triazin-3-amine. In some embodiments, the adenosine A2AR antagonist is administered, e.g., orally, at a dose of about 20 mg to 60 mg, about 60 mg to 100 mg, about 100 mg to 140 mg, about 140 mg to 180 mg, about 180 mg to 220 mg, about 220 mg to 260 mg, about 260 mg to 300 mg, about 300 mg to 340 mg, about 340 mg to 380 mg, about 380 mg to 480 mg, about 480 mg to 580 mg, or about 580 mg to 680 mg, e.g., at a dose of about 40 mg, about 80 mg, about 160 mg, about 320 mg, about 480 mg, or about 620 mg, e.g., once a day (QD), twice a day (BID), or three times a day (TID), e.g., BID. In some embodiments, the anti-CD73 antibody molecule is administered, e.g., intravenously, at a dose of about 5 mg to 100 mg, about 100 mg to 500 mg, about 500 mg to 1000 mg, about 1000 mg to 1500 mg, about 1500 mg to 2000 mg, about 2000 mg to 2500 mg, about 2500 mg to 3000 mg, about 3000 mg to 3500 mg, or about 3500 mg to 4000 mg, e.g., at a dose of about 6 mg, about 20 mg, about 60 mg, about 200 mg, about 600 mg, about 1200 mg, about 2400 mg, about 3000 mg, or about 3600 mg, e.g., once every week (QW), once every two weeks (Q2W), or once every four weeks (Q4W), e.g., Q2W. In some embodiments, the anti-CD73 antibody molecule is administered, e.g., intravenously, at a dose of about 5 mg to 100 mg, e.g., 20 mg, Q2W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 5 mg to 100 mg, e.g., 20 mg, Q2W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 5 mg to 100 mg, e.g., 20 mg, Q2W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 5 mg to 100 mg, e.g., 20 mg, Q2W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 5 mg to 100 mg, e.g., 60 mg, Q2W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 5 mg to 100 mg, e.g., 60 mg, Q2W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 5 mg to 100 mg, e.g., 60 mg, Q2W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 5 mg to 100 mg, e.g., 60 mg, Q2W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 100 mg to 500 mg, e.g., 200 mg, Q2W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 100 mg to 500 mg, e.g., 200 mg, Q2W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 100 mg to 500 mg, e.g., 200 mg, Q2W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 100 mg to 500 mg, e.g., 200 mg, Q2W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 500 mg to 1000 mg, e.g., 600 mg, Q2W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 500 mg to 1000 mg, e.g., 600 mg, Q2W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 500 mg to 1000 mg, e.g., 600 mg, Q2W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 500 mg to 1000 mg, e.g., 600 mg, Q2W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 1000 mg to 1500 mg, e.g., 1200 mg, Q2W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 1000 mg to 1500 mg, e.g., 1200 mg, Q2W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 1000 mg to 1500 mg, e.g., 1200 mg, Q2W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 1000 mg to 1500 mg, e.g., 1200 mg, Q2W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 2000 mg to 2500 mg, e.g., 2400 mg, Q2W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 2000 mg to 2500 mg, e.g., 2400 mg, Q2W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 2000 mg to 2500 mg, e.g., 2400 mg, Q2W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 2000 mg to 2500 mg, e.g., 2400 mg, Q2W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 2000 mg to 2500 mg, e.g., 2400 mg, Q2W, and the adenosine A2AR antagonist is administered, e.g., orally, at a dose of about 480 mg to 580 mg, e.g., 480 mg, BID. In some embodiments, the anti-CD73 antibody molecule is administered, e.g., intravenously, at a dose of about 2000 mg to 2500 mg, e.g., 2400 mg, Q2W, and the adenosine A2AR antagonist is administered, e.g., orally, at a dose of about 580 mg to 680 mg, e.g., 620 mg, BID. In some embodiments, the anti-CD73 antibody molecule is administered, e.g., intravenously, at a dose of about 3000 mg to 3500 mg, e.g., 3000 mg, Q2W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 3000 mg to 3500 mg, e.g., 3000 mg, Q2W, and the adenosine A2AR antagonist is administered, e.g., orally, at a dose of about 480 mg to 580 mg, e.g., 480 mg, BID. In some embodiments, the anti-CD73 antibody molecule is administered, e.g., intravenously, at a dose of about 3000 mg to 3500 mg, e.g., 3000 mg, Q2W, and the adenosine A2AR antagonist is administered, e.g., orally, at a dose of about 580 mg to 680 mg, e.g., 620 mg, BID. In some embodiments, the anti-CD73 antibody molecule is administered, e.g., intravenously, at a dose of about 3500 mg to 4000 mg, e.g., 3600 mg, Q2W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 3500 mg to 4000 mg, e.g., 3600 mg, Q2W, and the adenosine A2AR antagonist is administered, e.g., orally, at a dose of about 480 mg to 580 mg, e.g., 480 mg, BID. In some embodiments, the anti-CD73 antibody molecule is administered, e.g., intravenously, at a dose of about 3500 mg to 4000 mg, e.g., 3600 mg, Q2W, and the adenosine A2AR antagonist is administered, e.g., orally, at a dose of about 580 mg to 680 mg, e.g., 620 mg, BID.

In some embodiments, the anti-CD73 antibody molecule is administered in combination with a PD-1 inhibitor and an adenosine A2AR antagonist. In some embodiments, the anti-CD73 antibody molecule is administered, e.g., intravenously, at a dose of about 5 mg to 100 mg, about 100 mg to 500 mg, about 500 mg to 1000 mg, about 1000 mg to 1500 mg, about 1500 mg to 2000 mg, about 2000 mg to 2500 mg, about 2500 mg to 3000 mg, about 3000 mg to 3500 mg, or about 3500 mg to 4000 mg, e.g., at a dose of about 6 mg, about 20 mg, about 60 mg, about 200 mg, about 600 mg, about 1200 mg, about 2400 mg, about 3000 mg, or about 3600 mg, e.g., once every week (QW), once every two weeks (Q2W), or once every four weeks (Q4W), e.g., Q2W. In some embodiments, the PD-1 inhibitor is an anti-PD-1 antibody molecule. In some embodiments, the anti-PD-1 antibody molecule is administered, e.g., intravenously, at a dose of about 250 mg to 350 mg, about 350 mg to 450 mg, or about 450 mg to 550 mg, e.g., at a dose of about 300 mg or about 400 mg, e.g., once every three weeks (Q3W) or once every four weeks (Q4W), e.g., at a dose of about 300 mg Q3W, or at a dose of about 400 mg Q4W. In some embodiments, the adenosine A2AR antagonist is administered, e.g., orally, at a dose of about 20 mg to 60 mg, about 60 mg to 100 mg, about 100 mg to 140 mg, about 140 mg to 180 mg, about 180 mg to 220 mg, about 220 mg to 260 mg, about 260 mg to 300 mg, about 300 mg to 340 mg, about 340 mg to 380 mg, about 380 mg to 480 mg, about 480 mg to 580 mg, or about 580 mg to 680 mg, e.g., at a dose of about 40 mg, about 80 mg, about 160 mg, about 320 mg, about 480 mg, or about 620 mg, e.g., once a day (QD), twice a day (BID), or three times a day (TID), e.g., BID. In some embodiments, the anti-CD73 antibody molecule is administered, e.g., intravenously, at a dose of about 5 mg to 100 mg, e.g., 20 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 5 mg to 100 mg, e.g., 20 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 5 mg to 100 mg, e.g., 20 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 5 mg to 100 mg, e.g., 20 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 5 mg to 100 mg, e.g., 60 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 5 mg to 100 mg, e.g., 60 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 5 mg to 100 mg, e.g., 60 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 5 mg to 100 mg, e.g., 60 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 100 mg to 500 mg, e.g., 200 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 100 mg to 500 mg, e.g., 200 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 100 mg to 500 mg, e.g., 200 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 100 mg to 500 mg, e.g., 200 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 500 mg to 1000 mg, e.g., 600 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 500 mg to 1000 mg, e.g., 600 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 500 mg to 1000 mg, e.g., 600 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 500 mg to 1000 mg, e.g., 600 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 1000 mg to 1500 mg, e.g., 1200 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 1000 mg to 1500 mg, e.g., 1200 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 1000 mg to 1500 mg, e.g., 1200 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 1000 mg to 1500 mg, e.g., 1200 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 2000 mg to 2500 mg, e.g., 2400 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 20 mg to 60 mg, e.g., 40 mg, BID. In some embodiments, the anti-CD73 antibody molecule is administered, e.g., intravenously, at a dose of about 2000 mg to 2500 mg, e.g., 2400 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 60 mg to 100 mg, e.g., 80 mg, BID. In some embodiments, the anti-CD73 antibody molecule is administered, e.g., intravenously, at a dose of about 2000 mg to 2500 mg, e.g., 2400 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 140 mg to 180 mg, e.g., 160 mg, BID. In some embodiments, the anti-CD73 antibody molecule is administered, e.g., intravenously, at a dose of about 2000 mg to 2500 mg, e.g., 2400 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 2000 mg to 2500 mg, e.g., 2400 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 480 mg to 580 mg, e.g., 480 mg, BID. In some embodiments, the anti-CD73 antibody molecule is administered, e.g., intravenously, at a dose of about 2000 mg to 2500 mg, e.g., 2400 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 580 mg to 680 mg, e.g., 620 mg, BID. In some embodiments, the anti-CD73 antibody molecule is administered, e.g., intravenously, at a dose of about 3000 mg to 3500 mg, e.g., 3000 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 3000 mg to 3500 mg, e.g., 3000 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 480 mg to 580 mg, e.g., 480 mg, BID. In some embodiments, the anti-CD73 antibody molecule is administered, e.g., intravenously, at a dose of about 3000 mg to 3500 mg, e.g., 3000 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 580 mg to 680 mg, e.g., 620 mg, BID. In some embodiments, the anti-CD73 antibody molecule is administered, e.g., intravenously, at a dose of about 3500 mg to 4000 mg, e.g., 3600 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 300 mg to 340 mg, e.g., 320 mg, BID. In some embodiments, the anti-CD73 antibody molecule is administered, e.g., intravenously, at a dose of about 3500 mg to 4000 mg, e.g., 3600 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 480 mg to 580 mg, e.g., 480 mg, BID. In some embodiments, the anti-CD73 antibody molecule is administered, e.g., intravenously, at a dose of about 3500 mg to 4000 mg, e.g., 3600 mg, Q2W, the anti-PD-1 antibody molecule is administered, e.g., intravenously, at a dose of about 350 mg to 450 mg, e.g., 400 mg, Q4W, and the adenosine A2AR antagonist is administered, e.g., orally, at a dose of about 580 mg to 680 mg, e.g., 620 mg, BID.

In some embodiments, the anti-CD73 antibody molecule is administered in combination with a PD-L1 inhibitor and an adenosine A2AR antagonist.

In some embodiments, the anti-CD73 antibody molecule is administered in combination with a chimeric antigen receptor (CAR) T-cell therapy. In some embodiments, the CAR T-cell therapy is CTL019.

In some embodiments, the anti-CD73 antibody molecule is administered in combination with one or more agents disclosed in Table 18, e.g., one or more of: 1) a protein kinase C (PKC) inhibitor; 2) a heat shock protein 90 (HSP90) inhibitor; 3) an inhibitor of a phosphoinositide 3-kinase (PI3K) and/or target of rapamycin (mTOR); 4) an inhibitor of cytochrome P450 (e.g., a CYP17 inhibitor or a 17alpha-Hydroxylase/C17-20 Lyase inhibitor); 5) an iron chelating agent; 6) an aromatase inhibitor; 7) an inhibitor of p53, e.g., an inhibitor of a p53/Mdm2 interaction; 8) an apoptosis inducer; 9) an angiogenesis inhibitor; 10) an aldosterone synthase inhibitor; 11) a smoothened (SMO) receptor inhibitor; 12) a prolactin receptor (PRLR) inhibitor; 13) a Wnt signaling inhibitor; 14) a CDK4/6 inhibitor; 15) a fibroblast growth factor receptor 2 (FGFR2)/fibroblast growth factor receptor 4 (FGFR4) inhibitor; 16) an inhibitor of macrophage colony-stimulating factor (M-CSF); 17) an inhibitor of one or more of c-KIT, histamine release, Flt3 (e.g., FLK2/STK1) or PKC; 18) an inhibitor of one or more of VEGFR-2 (e.g., FLK-1/KDR), PDGFRbeta, c-KIT or Raf kinase C; 19) a somatostatin agonist and/or a growth hormone release inhibitor; 20) an anaplastic lymphoma kinase (ALK) inhibitor; 21) an insulin-like growth factor 1 receptor (IGF-1R) inhibitor; 22) a P-Glycoprotein 1 inhibitor; 23) a vascular endothelial growth factor receptor (VEGFR) inhibitor; 24) a BCR-ABL kinase inhibitor; 25) an FGFR inhibitor; 26) an inhibitor of CYP11B2; 27) a HDM2 inhibitor, e.g., an inhibitor of the HDM2-p53 interaction; 28) an inhibitor of a tyrosine kinase; 29) an inhibitor of c-MET; 30) an inhibitor of JAK; 31) an inhibitor of DAC; 32) an inhibitor of 11β-hydroxylase; 33) an inhibitor of IAP; 34) an inhibitor of PIM kinase; 35) an inhibitor of Porcupine; 36) an inhibitor of BRAF, e.g., BRAF V600E or wild-type BRAF; 37) an inhibitor of HER3; 38) an inhibitor of MEK; or 39) an inhibitor of a lipid kinase, e.g., as described herein and in Table 18.

In certain embodiments, the cancer treated with the anti-CD73 antibody molecule, alone or in combination with a second therapeutic agent or procedure, includes but is not limited to, a solid tumor, a hematological cancer (e.g., leukemia, lymphoma, myeloma, e.g., multiple myeloma), and a metastatic lesion. In some embodiments, the cancer is chosen from lung cancer (e.g., non-small cell lung cancer), pancreas cancer (e.g., pancreatic ductal adenocarcinoma), breast cancer (e.g., triple-negative breast cancer), melanoma, head and neck cancer (e.g., squamous head and neck cancer), colorectal cancer (e.g., microsatellite stable (MSS) colorectal cancer), ovarian cancer, or renal cancer (e.g., renal cell carcinoma). In certain embodiments, the anti-CD73 antibody molecule, used alone or in combination with a second therapeutic agent or procedure, controls tumor growth, reduces metastasis, and/or improves survival.

In certain embodiments, the antibody molecule is administered at a dose of about 100 mg to 1600 mg, about 100 mg to 1400 mg, about 100 mg to 1200 mg, about 100 mg to 1000 mg, about 100 mg to 800 mg, about 100 mg to 600 mg, about 100 mg to 400 mg, about 100 mg to 200 mg, or about 100 mg, about 180 mg, or about 200 mg, e.g., once every two weeks. In one embodiment, the antibody molecule is administered at a dose of at least about 180 mg once every two weeks.

In certain embodiments, the antibody molecule is administered, e.g., intravenously, at a dose of about 5 mg to 100 mg, about 100 mg to 500 mg, about 500 mg to 1000 mg, about 1000 mg to 1500 mg, about 1500 mg to 2000 mg, about 2000 mg to 2500 mg, about 2500 mg to 3000 mg, about 3000 mg to 3500 mg, or about 3500 mg to 4000 mg, e.g., once every week (QW), once every two weeks (Q2W), or once every four weeks (Q4W). In certain embodiments, the antibody molecule is administered, e.g., intravenously, at a dose of about 6 mg, about 20 mg, about 60 mg, about 200 mg, about 600 mg, about 1200 mg, about 2400 mg, about 3000 mg, or about 3600 mg, e.g., QW, Q2W, or Q4W. In certain embodiments, the antibody molecule is administered, e.g., intravenously, at a dose of about 60 mg Q2W. In certain embodiments, the antibody molecule is administered, e.g., intravenously, at a dose of about 200 mg Q2W. In certain embodiments, the antibody molecule is administered, e.g., intravenously, at a dose of about 600 mg Q2W. In certain embodiments, the antibody molecule is administered, e.g., intravenously, at a dose of about 1200 mg Q2W. In certain embodiments, the antibody molecule is administered, e.g., intravenously, at a dose of about 2400 mg Q2W. In certain embodiments, the antibody molecule is administered, e.g., intravenously, at a dose of about 3000 mg Q2W. In certain embodiments, the antibody molecule is administered, e.g., intravenously, at a dose of about 3600 mg Q2W.

Still further, this disclosure provides methods of enhancing an immune response to an antigen in a subject, comprising administering to the subject: (i) the antigen; and (ii) an anti-CD73 antibody molecule disclosed herein, such that an immune response to the antigen in the subject is enhanced. The antigen can be, for example, a tumor antigen, a viral antigen, a bacterial antigen or an antigen from a pathogen.

The anti-CD73 antibody molecule can be administered to the subject systemically (e.g., orally, parenterally, subcutaneously, intravenously, rectally, intramuscularly, intraperitoneally, intranasally, transdermally, or by inhalation or intracavitary installation), or locally. In one embodiment, the anti-CD73 antibody molecule is administered intravenously.

The anti-CD73 antibody molecule can be used alone in unconjugated form, or can be bound to a substance, e.g., a cytotoxic agent or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the anti-CD73 antibody can be coupled to a radioactive isotope such as an α-, β-, or γ-emitter, or a β- and γ-emitter.

Dosages and therapeutic regimens of the anti-CD73 antibody molecule can be determined by a skilled artisan.

In another aspect, a method of detecting CD73 in a biological sample or in a subject is provided. In one embodiment, the method comprises (i) contacting the sample or the subject (and optionally, a reference sample or subject) with the antibody molecule of any one of claims 1-57 under conditions that allow interaction of the antibody molecule and CD73 to occur, and (ii) detecting formation of a complex between the antibody molecule and the sample or the subject (and optionally, the reference sample or subject).

The antibody molecules described herein are preferred for use in the methods described herein, although other anti-CD73 antibodies can be used instead, or in combination with an anti-CD73 antibody molecule of the invention.

BRIEF DESCRIPTION OF THE DRAWINGS

In FIG. 2A, recombinant human CD73 was incubated with the substrate AMP with buffer alone ("hCD73 Km") or in the presence of an IgG1 isotype control antibody ("ISO.C"). In FIG. 2B, recombinant CD73 was incubated with AMP with buffer alone ("hCD73 Km") or in the presence of anti-CD73 antibody 350.C at indicated concentrations ("1 μg/ml 350.C," "0.3 μg/ml 350.C," or "0.1 μg/ml 350.C").

FIG. 12A shows results from a study testing the anti-CD73 antibodies 350, 356, 358, 374, 377, and 379, all in the .B format. FIG. 12B shows results from a study using the antibodies 350 and 372, expressed in either the .A or .B format.

FIG. 14 shows results for 1-min in-exchange at pH 7.5 and room temperature.

FIG. 15 shows results for 1-min in-exchange at pH 7.5 and room temperature.

In FIG. 21A, CD73 expression is displayed as fluorescence intensity, as compared to samples stained with a matched isotype control. One representative sample is shown. In FIG. 21B, quantification of CD73 expression, measured as mean fluorescence intensity, is depicted. Each symbol represents a sample. P-values are indicated where significant. CAF=cancer associated fibroblasts.

In FIG. 22A, IgM secretion was measured using an ELISA assay in the 7-day culture supernatant. In FIG. 22B, B cell proliferation was measured on day 7 and the numbers of divided cells counted after electronically gating on the CFSE diluted population are plotted for the three different concentrations tested. In FIG. 22C, IgG secreting cells (IgG SCs) were enumerated by an ELISPOT assay at the same time point. Data were collected from two independent experiments.

FIGS. 26A and 26B show CD73 residues (bold, italic, and single-underlined) that interact with 350.A2 Fab heavy chain via direct enthalpic interactions (Y110, L132, K136, S155, L157, and K162, numbered according to SEQ ID NO: 105) (FIG. 26A) or Van der Waal and hydrophobic interactions (residues 136-138 and 155-170, numbered according to SEQ ID NO: 105) (FIG. 26B), as measured in Example 8. FIGS. 26C and 26D show 350.A2 Fab heavy chain residues (bold, italic, and single-underlined) that interact with CD73 via direct enthalpic interactions (R31, R54, E95, E98, and S99, numbered according to Kabat numbering; or R31, R54, E98, E101, and 5102, numbered according to their linear positions in SEQ ID NO: 331) (FIG. 26C) or Van der Waal and hydrophobic interactions (residues 30, 31, 33, 50, 52, 56, 97, 98, 100, and 100a, numbered according to Kabat numbering; or residues 30, 31, 33, 50, 52, 56, 100, 101, 103, and 104, numbered according to their linear positions in SEQ ID NO: 331) (FIG. 26D), as measured in Example 8. FIGS. 26E and 26F show CD73 residues (bold, italic, and single-underlined) that interact with 350.A2 Fab light chain via direct enthalpic interactions (T209, numbered according to SEQ ID NO: 105) (FIG. 26E) or Van der Waal and hydrophobic interactions (residues 209 and 210, numbered according to SEQ ID NO: 105) (FIG. 26F), as measured in Example 8. FIGS. 26G and 26H show 350.A2 Fab light chain residues (bold, italic, and single-underlined) that interact with CD73 via direct enthalpic interactions (W32, numbered according to Kabat numbering or its linear position in SEQ ID NO: 23) (FIG. 26G) or Van der Waal and hydrophobic interactions (residues 30 and 32, numbered according to Kabat numbering or their linear positions in SEQ ID NO: 23) (FIG. 26H), as measured in Example 8. The signal peptide is double-underlined in FIGS. 26A, 26B, 26E, and 26F.

BRIEF DESCRIPTION OF THE TABLES

Figure 1:
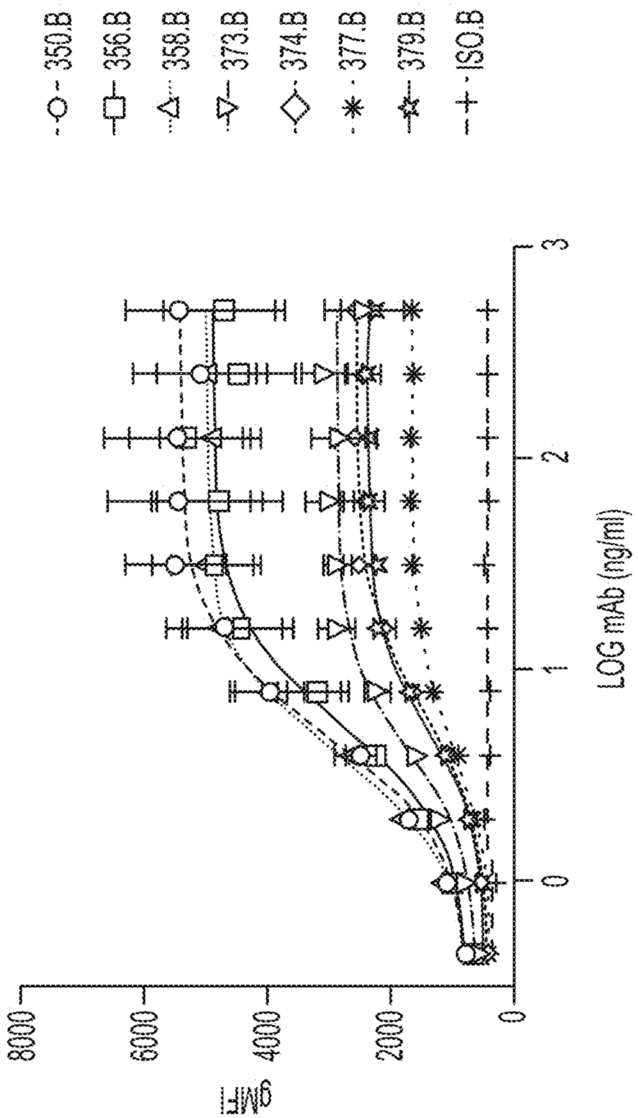
FIG. 1 is a graph showing the binding of anti-CD73 antibodies or an isotype control antibody to CD8+ T cells, measured by flow cytometry. MFI values are plotted against antibody concentrations. The antibodies tested are the anti-CD73 antibodies 350, 356, 358, 373, 374, 377, and 379, as well as an isotype control antibody, all expressed in the .B format.

Table 1 provides amino acid and nucleotide sequences for exemplary anti-CD73 antibodies.

Table 2 provides consensus CDR sequences for exemplary anti-CD73 antibodies.

Table 3 provides amino acid sequences of human IgG heavy chains and human kappa light chain.

Table 4 provides exemplary sequences of CD73.

Tables 5 and 6 provide amino acid and/or nucleotide sequences of exemplary anti-PD-1 antibody molecules.

Tables 7 and 8 provide amino acid and/or nucleotide sequences of exemplary anti-PD-L1 antibody molecules.

Tables 9 and 10 provide amino acid and/or nucleotide sequences of exemplary anti-LAG-3 antibody molecules.

Tables 11 and 12 provide amino acid and/or nucleotide sequences of exemplary anti-TIM-3 antibody molecules.

Tables 13 and 14 provide amino acid and/or nucleotide sequences of exemplary anti-GITR antibody molecules.

Table 15 provides amino acid sequences of exemplary anti-CD3 bispecific antibody molecules.

Tables 16 and 17 provide amino acid sequences of exemplary IL15/IL-15Ra complexes.

Table 18 is a summary of selected therapeutic agents that can be administered in combination with the anti-CD73 antibody molecules described herein. Table 18 provides from left to right the following: the Compound Designation of the second therapeutic agent, the Compound structure, and Patent publication(s) disclosing the Compound.

Table 19 provides nomenclatures for two lineages of anti-CD73 antibodies.

Table 20 provides affinities of anti-CD73 antibodies.

Table 21 provides affinities of anti-CD73 Fabs.

Table 22 provides provisional dose levels for 373.A.

Table 23 provides provisional dose levels for 373.A in combination with PBF509.

Table 24 provides provisional dose levels for 373.A in combination with BAP049-Clone-E.

Table 25 provides provisional dose levels for PBF509 in combination with 373.A and BAP049-Clone-E.

Table 26 provides corresponding germline sequences of anti-CD73 antibodies.

DETAILED DESCRIPTION

The term “CD73” as used herein refers to “Cluster of Differentiation 73,” also known as 5'-nucleotidase (5'-NT) or ecto-5'-nucleotidase. The term “CD73” includes mutants, fragments, variants, isoforms, and homologs of full-length wild-type CD73. In one embodiment, the protein CD73 is encoded by the NT5E gene. Exemplary CD73 sequences are available at the Uniprot database under accession numbers Q6NZX3 and P21589. Exemplary immature CD73 amino acid sequences are provided as SEQ ID NOs: 105-107. A “CD73 monomer” refers to a polypeptide comprising an extracellular domain of CD73. In one embodiment, a CD73 monomer is a full-length CD73. A “CD73 dimer” refers to two polypeptides (e.g., two non-covalently associated polypeptides) consisting of two CD73 monomers (e.g., two identical CD73 monomers) interacting with each other to form a stable dimer, e.g., a dimer formed via protein-protein interactions between the C-terminal domains of the CD73 monomers. In one embodiment, the CD73 dimer is a naturally-occurring CD73 dimer.

Without wishing to be bound by theory, human CD73 has two domains. A conserved N-terminal domain (corresponding to approximately residues 29-310 of SEQ ID NO: 105) and a conserved C-terminal domain (corresponding to approximately residues 343-513 of SEQ ID NO: 105), which are linked by a single α-helix (corresponding to approximately residues 318-336 of SEQ ID NO: 105). The active site is detected primarily in the closed conformation and is formed between C- and N-terminal domains. For enzyme catalysis, a domain motion of ~100° of the N-terminal domain with respect to the C-terminal domain can enable substrate binding and release, which occurs in the open (catalytic inactive) conformation. Human CD73 forms a dimer through protein-protein interactions between C-terminal domains. The buried surface area as well as the molecular interactions at the dimer interface are significantly different between active and inactive conformations of the enzyme. See, e.g., Knapp K, et al., Structure 20:2161-73 (2012), incorporated herein by reference in its entirety.

Accordingly, the present invention provides, at least in part, antibody molecules that bind to CD73 with high affinity and specificity. In one embodiment, disclosed herein are human antibodies that bind to CD73. In one embodiment, disclosed herein are antibody molecules that are capable of inhibiting or reducing the enzymatic activity of CD73, e.g., human CD73, e.g., soluble human CD73 or membrane-bound human CD73. In one embodiment, disclosed herein are antibody molecules that are capable of inhibiting or reducing CD73-mediated conversion of adenosine monophosphate (AMP) to adenosine. Additional aspects of the invention include nucleic acid molecules encoding the antibody molecules, expression vectors, host cells and methods for making the antibody molecules. Immunoconjugates, multi- or bispecific molecules and pharmaceutical compositions comprising the antibody molecules are also provided. The anti-CD73 antibody molecules disclosed herein can be used to treat, prevent and/or diagnose cancerous or malignant disorders, e.g., solid and liquid tumors, e.g., lung cancer (e.g., non-small cell lung cancer), pancreas cancer (e.g., pancreatic ductal adenocarcinoma), breast cancer (e.g., triple-negative breast cancer), melanoma, head and neck cancer (e.g., squamous head and neck cancer), colorectal cancer (e.g., microsatellite stable (MSS) colorectal cancer), ovarian cancer, or renal cancer (e.g., renal cell carcinoma). The anti-CD73 antibody molecules disclosed herein can be used to treat, prevent and/or diagnose an infectious disease. Thus, methods for detecting CD73, as well as methods for treating various disorders, including cancer and infectious diseases, using the anti-CD73 antibody molecules are disclosed herein.

Additional terms are defined below and throughout the application.

As used herein, the articles “a” and “an” refer to one or to more than one (e.g., to at least one) of the grammatical object of the article. As used herein, “plurality” means two or more.

The term “or” is used herein to mean, and is used interchangeably with, the term “and/or”, unless context clearly indicates otherwise.

“About” and “approximately” shall generally mean an acceptable degree of error for the quantity measured given the nature or precision of the measurements. Exemplary degrees of error are within 20 percent (%), typically, within 10%, and more typically, within 5% of a given value or range of values.

The compositions and methods disclosed herein encompass polypeptides and nucleic acids having the sequences specified, or sequences substantially identical or similar thereto, e.g., sequences having at least about 85%, 90%, or 95% sequence identity to the sequence specified. In the context of an amino acid sequence, the term “substantially identical” is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, e.g., at least 40%, 50%, 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a some embodiments, the percent identity between two amino acid sequences is determined using the Needleman and Wunsch ((1970) *J. Mol. Biol.* 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package (available at pwww.gcg.com), using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See www.ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are suitable conditions and the ones that should be used unless otherwise specified.

It is understood that the molecules of the invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide," "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

The term "Chimeric Antigen Receptor" or alternatively a "CAR" refers to a set of polypeptides, typically two in the simplest embodiments, which when in an immune effector cell, provides the cell with specificity for a target cell, typically a cancer cell, and with intracellular signal generation. In some embodiments, a CAR comprises at least an extracellular antigen binding domain, a transmembrane domain, and a cytoplasmic signaling domain (also referred to herein as "an intracellular signaling domain") comprising a functional signaling domain derived from a stimulatory molecule and/or costimulatory molecule as defined below. In some aspects, the set of polypeptides are contiguous with each other. In some embodiments, the set of polypeptides include a dimerization switch that, upon the presence of a dimerization molecule, can couple the polypeptides to one another, e.g., can couple an antigen binding domain to an intracellular signaling domain. In one aspect, the stimulatory molecule is the zeta chain associated with the T cell receptor complex. In one aspect, the cytoplasmic signaling domain further comprises one or more functional signaling domains derived from at least one costimulatory molecule as defined below. In one aspect, the costimulatory molecule is chosen from the costimulatory molecules described herein, e.g., 4-1BB (i.e., CD137), CD27 and/or CD28. In one aspect, the CAR comprises a chimeric fusion protein comprising an extracellular antigen binding domain, a transmembrane domain, and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule. In one aspect, the CAR comprises a chimeric fusion protein comprising an extracellular antigen binding domain, a transmembrane domain, and an intracellular signaling domain comprising two functional signaling domains derived from one or more costimulatory molecule(s) and a functional signaling domain derived from a stimulatory molecule. In one aspect, the CAR comprises a chimeric fusion protein comprising an extracellular antigen binding domain, a transmembrane domain and an intracellular signaling domain comprising at least two functional signaling domains derived from one or more costimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen binding domain, wherein the leader sequence is optionally cleaved from the antigen binding domain (e.g., a scFv) during cellular processing and localization of the CAR to the cellular membrane.

The term "signaling domain" refers to the functional portion of a protein which acts by transmitting information within the cell to regulate cellular activity via defined signaling pathways by generating second messengers or functioning as effectors by responding to such messengers.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

The term "zeta" or alternatively "zeta chain", "CD3-zeta" or "TCR-zeta" is defined as the protein provided as GenBank Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof.

The term a "costimulatory molecule" refers to a cognate binding partner on a T cell that binds to a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that binds to CD83.

A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that binds to CD83, and the like.

The intracellular signaling domain can comprise the entire intracellular portion, or the entire native intracellular signaling domain, of the molecule from which it is derived, or a functional fragment or derivative thereof.

The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

"Immune effector function" or "immune effector response," as that term is used herein, refers to function or response, e.g., of an immune effector cell, that enhances or promotes an immune attack of a target cell. E.g., an immune effector function or response refers a property of a T or NK cell that promotes killing or the inhibition of growth or proliferation, of a target cell. In the case of a T cell, primary stimulation and co-stimulation are examples of immune effector function or response.

The terms "cancer associated antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen is a cell surface molecule that is inappropriately synthesized in the cancer cell, for instance, a molecule that contains deletions, additions or mutations in comparison to the molecule expressed on a normal cell. In some embodiments, a tumor antigen will be expressed exclusively on the cell surface of a cancer cell, entirely or as a fragment (e.g., MHC/peptide), and not synthesized or expressed on the surface of a normal cell. In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The MHC class I complexes are constitutively expressed by all nucleated cells. In cancer, virus-specific and/or tumor-specific peptide/MHC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

Various aspects of the compositions and methods herein are described in further detail below. Additional definitions are set out throughout the specification.

Antibody Molecules

In one embodiment, the antibody molecule binds to a mammalian, e.g., human, CD73. For example, the antibody molecule binds to an epitope, e.g., linear or conformational epitope, e.g., an epitope as described herein, on CD73.

As used herein, the term "antibody molecule" refers to a protein, e.g., an immunoglobulin chain or fragment thereof, comprising at least one immunoglobulin variable domain sequence. The term "antibody molecule" includes, for example, a monoclonal antibody (including a full length antibody which has an immunoglobulin Fc region). In an embodiment, an antibody molecule comprises a full length antibody, or a full length immunoglobulin chain. In an embodiment, an antibody molecule comprises an antigen binding or functional fragment of a full length antibody, or a full length immunoglobulin chain.

As used herein, an antibody molecule "binds to" an antigen as such binding is understood by one skilled in the art. In one embodiment, an antibody binds to an antigen with a dissociation constant ($K_D$) of about $1\times10^{-3}$ M or less, $1\times10^{-4}$ M or less, or $1\times10^{-5}$ M or less.

In an embodiment, an antibody molecule is a monospecific antibody molecule and binds a single epitope, e.g., a monospecific antibody molecule having a plurality of immunoglobulin variable domain sequences, each of which binds the same epitope.

In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., different proteins (or different subunits of a multimeric protein). In an embodiment, a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule.

In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., different proteins (or different subunits of a multimeric protein). In an embodiment, a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody molecule comprises a half antibody having binding specificity for a first epitope and a half antibody having binding specificity for a second epitope. In an embodiment, a bispecific antibody molecule comprises a half antibody, or fragment thereof, having binding specificity for a first epitope and a half antibody, or fragment thereof, having binding specificity for a second epitope. In an embodiment, a bispecific antibody molecule comprises a scFv, or fragment thereof, have binding specificity for a first epitope and a scFv, or fragment thereof, have binding specificity for a second epitope.

In an embodiment, an antibody molecule comprises a diabody, and a single-chain molecule, as well as an antigen-binding fragment of an antibody (e.g., Fab, $F(ab')_2$, and Fv). For example, an antibody molecule can include a heavy (H) chain variable domain sequence (abbreviated herein as VH), and a light (L) chain variable domain sequence (abbreviated herein as VL). In an embodiment, an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', $F(ab')_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. A preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

The antibodies disclosed herein can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in *Camelidae* species, for example in camel, llama, dromedary, alpaca and guanaco. Other species besides *Camelidae* may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg).

The terms "complementarity determining region" and "CDR" as used herein refer to the sequences of amino acids within antibody variable regions which confer antigen specificity and binding affinity. In some embodiments, there are three CDRs in each heavy chain variable region (HCDR1, HCDR2, and HCDR3) and three CDRs in each light chain variable region (LCDR1, LCDR2, and LCDR3).

The precise amino acid sequence boundaries of a given CDR can be determined using any of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273, 927-948 ("Chothia" numbering scheme). As used herein, the CDRs defined according to the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Under all definitions, each VH and VL typically includes three CDRs and four FRs, arranged from amino-terminus to carboxy-terminus in the following order: FR1, CDR1, FR2, CDR2, FR3, CDR3, FR4.

Generally, unless specifically indicated, the anti-CD73 antibody molecules can include any combination of one or more Kabat CDRs, Chothia CDRs, combination of Kabat and Chothia CDRs, IMGT CDRs, and/or an alternative definition, e.g., described in Table 1.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to a CD73 polypeptide, or an epitope thereof. With respect to proteins (or protein mimetics), the antigen-binding site typically includes one or more loops (of at least, e.g., four amino acids or amino acid mimics) that form an interface that binds to a CD73 polypeptide. Typically, the antigen-binding site of an antibody molecule includes at least one or two CDRs and/or hypervariable loops, or more typically at least three, four, five or six CDRs and/or hypervariable loops.

As used herein, the term "Eu numbering" refers to the Eu numbering convention for the constant regions of an antibody, as described in Edelman, G. M. et al., Proc. Natl. Acad. USA, 63, 78-85 (1969) and Kabat et al., in "Sequences of Proteins of Immunological Interest", U.S. Dept. Health and Human Services, 5th edition, 1991.

The terms "compete" or "cross-compete" are used interchangeably herein to refer to the ability of an antibody molecule to interfere with binding of an anti-CD73 antibody molecule, e.g., an anti-CD73 antibody molecule provided herein, to a target, e.g., human CD73. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a flow cytometry assay, an ELISA or BIACORE assay. In some embodiments, a competition binding assay is a quantitative competition assay. In some embodiments, a first anti-CD73 antibody molecule is said to compete for binding to the target with a second anti-CD73 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

As used herein, the term "epitope" refers to the moieties of an antigen (e.g., human CD73) that specifically interact with an antibody molecule. Such moieties, also referred to herein as epitopic determinants, typically comprise, or are part of, elements such as amino acid side chains or sugar side chains. An epitopic determinant can be defined by methods known in the art or disclosed herein, e.g., by crystallography or by hydrogen-deuterium exchange. At least one or some of the moieties on the antibody molecule that specifically interact with an epitopic determinant are typically located in a CDR(s). Typically, an epitope has a specific three dimensional structural characteristics. Typically, an epitope has specific charge characteristics. Some epitopes are linear epitopes while others are conformational epitopes.

In an embodiment, an epitopic determinant is a moiety on the antigen, e.g., such as amino acid side chain or sugar side chain, or part thereof, which, when the antigen and antibody molecule are co-crystallized, is within a predetermined distance, e.g., within 5 Angstroms, of a moiety on the antibody molecule, referred to herein as a "crystallographic epitopic determinant." The crystallographic epitopic determinants of an epitope are collectively referred to as the "crystallographic epitope."

A first antibody molecule binds the same epitope as a second antibody molecule (e.g., a reference antibody molecule, e.g., an antibody molecule disclosed herein) if the first antibody interacts with the same epitopic determinants on the antigen as does the second or reference antibody, e.g., when interaction is measured in the same way for both the antibody and the second or reference antibody. Epitopes that overlap share at least one epitopic determinant. A first antibody molecule binds an overlapping epitope with a second antibody molecule (e.g., a reference antibody molecule, e.g., an antibody disclosed herein) when both antibody molecules interact with a common epitopic determinant. A first and a second antibody molecule (e.g., a reference antibody molecule, e.g., an antibody molecule disclosed herein) bind substantially overlapping epitopes if at least half of the epitopic determinants of the second or reference antibody are found as epitopic determinants in the epitope of the first antibody. A first and a second antibody molecule (e.g., a reference antibody molecule, e.g., an antibody molecule disclosed herein) bind substantially the same epitope if the first antibody molecule binds at least half of the core epitopic determinants of the epitope of the second or reference antibody, wherein the core epitopic determinants are defined by, e.g., crystallography or hydrogen-deuterium exchange.

As used herein, an antibody molecule "reduces hydrogen-deuterium exchange" in an antigen fragment when the hydrogen-deuterium exchange in the antigen fragment in the presence of the antibody molecule is lower than the hydrogen-deuterium exchange in the antigen fragment in the absence of the antibody molecule, as measured in a hydrogen-deuterium exchange assay.

As used herein, a reduction in "the average hydrogen-deuterium exchange" is determined by the level of normalized hydrogen-deuterium exchange (Da per residue) in an antigen fragment in the absence of an antibody minus the level of normalized hydrogen-deuterium exchange (Da per residue) in the antigen fragment in the presence of the antibody.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.,* 32:180-190 (1990)) and also because of potential allergic reactions (see, e.g., LoBuglio et al., *Hybridoma,* 5:5117-5123 (1986)).

The antibody molecule can be a polyclonal or a monoclonal antibody. In other embodiments, the antibody can be recombinantly produced, e.g., produced by yeast display, phage display, or by combinatorial methods. Alternatively, such antibodies may be selected from synthetic yeast-based antibody presentation systems, such as those described in, e.g., Y. Xu et al, Addressing polyspecificity of antibodies selected from an in vitro yeast presentation system: a FACS-based, high-throughput selection and analytical tool. *PEDS* 26.10, 663-70 (2013): WO2009036379: WO2010105256; and WO2012009568, herein incorporated by reference in their entireties.

In one embodiment, the antibody is a fully human antibody (e.g., an antibody produced by yeast display, an antibody produced by phage display, or an antibody made in a mouse which has been genetically engineered to produce an antibody from a human immunoglobulin sequence), or a non-human antibody, e.g., a rodent (mouse or rat), goat, primate (e.g., monkey), or camel antibody. Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Antibodies can be produced by any suitable recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to CD73. In some embodiments, the donor is a rodent antibody, e.g., a rat or mouse antibody, and the recipient is a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In some embodiments the antibody has effector function and can fix complement. In other embodiments the antibody does not recruit effector cells or fix complement. In certain embodiments, the antibody has reduced or no ability to bind an Fc receptor. For example, it may be an isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Amino acid mutations which stabilize antibody structure, such as S228P (Eu numbering) in human IgG4, are also contemplated. Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody molecule of the invention may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, Jgalactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecule can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule may be conjugated to another molecular entity, typically a label or a therapeutic (e.g., immunomodulatory, immunostimularoty, cytotoxic, or cytostatic) agent or moiety. Radioactive isotopes can be used in diagnostic or therapeutic applications. Radioactive isotopes that can be coupled to the anti-CD73 antibodies include, but are not limited to α-, β-, or γ-emitters, or β- and γ-emitters. Such radioactive isotopes include, but are not limited to iodine ($^{131}I$ or $^{125}I$), yttrium ($^{90}Y$), lutetium ($^{177}Lu$), actinium ($^{225}Ac$), praseodymium, astatine ($^{211}At$), rhenium ($^{186}Re$), bismuth ($^{212}Bi$ or $^{213}Bi$), indium ($^{111}In$), technetium ($^{99}mTc$), phosphorus ($^{32}P$), rhodium ($^{188}Rh$), sulfur ($^{35}S$), carbon ($^{14}C$), tritium ($^{3}H$), chromium ($^{51}Cr$), chlorine ($^{36}Cl$), cobalt ($^{57}Co$ or $^{58}Co$), iron ($^{59}Fe$), selenium ($^{75}Se$), or gallium ($^{67}Ga$). Radioisotopes useful as therapeutic agents include yttrium ($^{90}Y$), lutetium ($^{177}Lu$), actinium ($^{225}Ac$), praseodymium, astatine ($^{211}At$), rhenium ($^{186}Re$), bismuth ($^{212}Bi$ or $^{213}Bi$), and rhodium ($^{188}Rh$). Radioisotopes useful as labels, e.g., for use in diagnostics, include iodine ($^{131}I$ or $^{125}I$), indium ($^{111}In$), technetium ($^{99}mTc$), phosphorus ($^{32}P$), carbon ($^{14}C$), and tritium ($^{3}H$), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

As is discussed above, the antibody molecule can be conjugated to a therapeutic agent. Therapeutically active radioisotopes have already been mentioned. Examples of other therapeutic agents include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846, 545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclinies (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In one aspect, the invention features a method of providing a target binding molecule that binds to a CD73 receptor. For example, the target binding molecule is an antibody molecule. The method includes: providing a target protein that comprises at least a portion of non-human protein, the portion being homologous to (at least 70, 75, 80, 85, 87, 90, 92, 94, 95, 96, 97, 98, or 99% identical to) a corresponding portion of a human target protein, but differing by at least one amino acid (e.g., at least one, two, three, four, five, six, seven, eight, or nine amino acids); obtaining an antibody molecule that binds to the antigen; and evaluating efficacy of the binding agent in modulating activity of the target protein. The method can further include administering the binding agent (e.g., antibody molecule) or a derivative (e.g., a humanized antibody molecule) to a human subject.

In certain embodiments, the antibody molecule is a multispecific (e.g., a bispecific or a trispecific) antibody molecule. Protocols for generating bispecific or heterodimeric antibody molecules are known in the art; including but not limited to, for example, the "knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also disclosed creating bispecifc, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901 A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

In other embodiments, the anti-CD73 antibody molecule (e.g., a monospecific, bispecific, or multispecific antibody molecule) is covalently linked, e.g., fused, to another partner e.g., a protein e.g., one, two or more cytokines, e.g., as a fusion molecule for example a fusion protein.

A "fusion protein" and a "fusion polypeptide" refer to a polypeptide having at least two portions covalently linked together, where each of the portions is a polypeptide having a different property. The property may be a biological property, such as activity in vitro or in vivo. The property can also be simple chemical or physical property, such as binding to a target molecule, catalysis of a reaction, etc. The two portions can be linked directly by a single peptide bond or through a peptide linker, but are in reading frame with each other.

This invention provides an isolated nucleic acid molecule encoding the above antibody molecule, vectors and host cells thereof. The nucleic acid molecule includes but is not limited to RNA, genomic DNA and cDNA.

Exemplary Anti-CD73 Antibody Molecules

In some embodiments, the anti-CD73 antibody molecule comprises at least one antigen-binding region, e.g., a variable region or an antigen-binding fragment thereof, from an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences.

In certain embodiments, the anti-CD73 antibody molecule comprises at least one, two, three, or four variable regions from an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences.

In some embodiments, the anti-CD73 antibody molecule comprises at least one or two heavy chain variable regions from an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences.

In certain embodiments, the anti-CD73 antibody molecule comprises at least one or two light chain variable regions from an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences.

In one embodiment, the anti-CD73 antibody molecule includes a heavy chain constant region of an IgG4, e.g., a human IgG4. In another embodiment, the human IgG4 includes a substitution (e.g., a Ser to Pro substitution) at position 228 according to Eu numbering. In still another embodiment, the anti-CD73 antibody molecule includes a heavy chain constant region of an IgG1, e.g., a human IgG1. In one embodiment, the human IgG1 includes a substitution (e.g., an Asn to Ala substitution) at position 297 according to Eu numbering. In one embodiment, the human IgG1 includes a substitution (e.g., an Asp to Ala substitution) at position 265 according to Eu numbering, a substitution (e.g., a Pro to Ala substitution) at position 329 according to Eu numbering, or both. In one embodiment, the human IgG1 includes a substitution (e.g., a Leu to Ala substitution) at position 234 according to Eu numbering, a substitution (e.g., a Leu to Ala substitution) at position 235 according to Eu numbering, or both. In one embodiment, the heavy chain constant region comprises an amino acid sequence set forth in Table 3, or a sequence substantially identical (e.g., having at least about 80%, 85%, 90%, 92%, 95%, 97%, 98%, or 99% sequence identity) thereto.

In yet another embodiment, the anti-CD73 antibody molecule includes a kappa light chain constant region, e.g., a human kappa light chain constant region. In one embodiment, the light chain constant region comprises an amino acid sequence set forth in Table 3, or a sequence substantially identical (e.g., having at least about 80%, 85%, 90%, 92%, 95%, 97%, 98%, or 99% sequence identity) thereto.

In another embodiment, the anti-CD73 antibody molecule includes a heavy chain constant region of an IgG4, e.g., a human IgG4, and a kappa light chain constant region, e.g., a human kappa light chain constant region, e.g., a heavy and light chain constant region comprising an amino acid sequence set forth in Table 3, or a sequence substantially identical (e.g., having at least about 80%, 85%, 90%, 92%, 95%, 97%, 98%, or 99% sequence identity) thereto. In yet another embodiment, the anti-CD73 antibody molecule includes a heavy chain constant region of an IgG1, e.g., a human IgG1, and a kappa light chain constant region, e.g., a human kappa light chain constant region, e.g., a heavy and light chain constant region comprising an amino acid sequence set forth in Table 3, or a sequence substantially identical (e.g., having at least about 80%, 85%, 90%, 92%, 95%, 97%, 98%, or 99% sequence identity) thereto. In one embodiment, the human IgG1 includes a substitution at position 297 according to Eu numbering (e.g., an Asn to Ala substitution). In one embodiment, the human IgG1 includes a substitution at position 265 according to Eu numbering, a substitution at position 329 according to Eu numbering, or both (e.g., an Asp to Ala substitution at position 265 and/or a Pro to Ala substitution at position 329). In one embodiment, the human IgG1 includes a substitution at position 234 according to Eu numbering, a substitution at position 235 according to Eu numbering, or both (e.g., a Leu to Ala substitution at position 234 and/or a Leu to Ala substitution at position 235).

In another embodiment, the anti-CD73 antibody molecule includes a heavy chain variable region and a constant region, a light chain variable region and a constant region, or both, comprising the amino acid sequence of 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences.

In some embodiments, the anti-CD73 antibody molecule includes at least one, two, or three complementarity determining regions (CDRs) from a heavy chain variable region of an antibody described herein, e.g., an antibody chosen from 918, 350, 356, 358, 930, 373, 374, 376, 377, 379, 363, 366, 407, 893, 939, 430, or 398; or as described in Table 1, or encoded by a nucleotide sequence in Table 1; or a sequence substantially identical (e.g., having at least about 80%, 85%, 90%, 92%, 95%, 97%, 98%, or 99% sequence identity) to any of the aforesaid sequences.

In some embodiments, the anti-CD73 antibody molecule comprises at least one, two, or three complementarity determining regions (CDRs) from a heavy chain variable region comprising an amino acid sequence shown in Table 1, or encoded by a nucleotide sequence in Table 1. In one embodiment, one or more of the CDRs (or collectively all of the CDRs) have one, two, three, four, five or more changes, e.g., amino acid substitutions, insertions, or deletions, relative to the amino acid sequence shown in Table 1, or encoded by a nucleotide sequence shown in Table 1. In certain embodiments, the anti-CD73 antibody molecule includes a substitution in a heavy chain CDR, e.g., one or more substitutions in a CDR1, CDR2 and/or CDR3 of the heavy chain.

In some embodiments, the anti-CD73 antibody molecule includes at least one, two, or three complementarity determining regions (CDRs) from a light chain variable region of an antibody described herein, e.g., an antibody chosen from 918, 350, 356, 358, 930, 373, 374, 376, 377, 379, 363, 366, 407, 893, 939, 430, or 398; or as described in Table 1, or encoded by a nucleotide sequence in Table 1; or a sequence substantially identical (e.g., having at least about 80%, 85%, 90%, 92%, 95%, 97%, 98%, or 99% sequence identity) to any of the aforesaid sequences.

In certain embodiments, the anti-CD73 antibody molecule includes at least one, two, or three CDRs (or collectively all of the CDRs) from a light chain variable region comprising an amino acid sequence shown in Table 1, or encoded by a nucleotide sequence shown in Table 1. In some embodiments, one or more of the CDRs (or collectively all of the CDRs) have one, two, three, four, five, six or more changes, e.g., amino acid substitutions, insertions, or deletions, relative to the CDRs shown in Table 1, or encoded by a nucleotide sequence shown in Table 1. In some embodiments, the anti-CD73 antibody molecule includes at least one, two, or three CDRs (or collectively all of the CDRs) from a light chain variable region comprising an amino acid sequence shown in Table 1, or encoded by a nucleotide sequence shown in Table 1. In some embodiments, one or more of the CDRs (or collectively all of the CDRs) have one, two, three, four, five, six or more changes, e.g., amino acid substitutions, insertions, or deletions, relative to the CDRs shown in Table 1, or encoded by a nucleotide sequence shown in Table 1.

In some embodiments, the anti-CD73 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1. In some embodiments, one or more of the CDRs (or collectively all of the CDRs) have one, two, three, four, five, six or more changes, e.g., amino acid substitutions, insertions, or deletions, relative to the CDRs shown in Table 1, or encoded by a nucleotide sequence shown in Table 1.

In certain embodiments, the anti-CD73 antibody molecule includes all six CDRs from an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions). In certain embodiments, the anti-CD73 antibody molecule may include any CDR described herein. In certain embodiments, the anti-CD73 antibody molecule includes a substitution in a heavy chain CDR, e.g., one or more substitutions in a CDR1, CDR2 and/or CDR3 of the heavy chain.

In some embodiments, the anti-CD73 antibody molecule includes at least one, two, or three CDRs according to Kabat et al. (e.g., at least one, two, or three CDRs according to the Kabat definition as set out in Table 1) from a heavy chain variable region of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In certain embodiments, the anti-CD73 antibody molecule includes at least one, two, or three CDRs according to Kabat et al. (e.g., at least one, two, or three CDRs according to the Kabat definition as set out in Table 1) from a light chain variable region of an antibody described herein, e.g., an antibody chosen from 918, 350, 356, 358, 930, 373, 374, 376, 377, 379, 363, 366, 407, 893, 939, 430, or 398; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In certain embodiments, the anti-CD73 antibody molecule includes at least one, two, three, four, five, or six CDRs according to Kabat et al. (e.g., at least one, two, three, four, five, or six CDRs according to the Kabat definition as set out in Table 1) from the heavy and light chain variable regions of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Table 1.

In some embodiments, the anti-CD73 antibody molecule includes all six CDRs according to Kabat et al. (e.g., all six CDRs according to the Kabat definition as set out in Table 1) from the heavy and light chain variable regions of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. In one embodiment, the anti-CD73 antibody molecule may include any CDR described herein.

In some embodiments, the anti-CD73 antibody molecule includes at least one, two, or three Chothia hypervariable loops (e.g., at least one, two, or three hypervariable loops according to the Chothia definition as set out in Table 1) from a heavy chain variable region of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or at least the amino acids from those hypervariable loops that contact CD73; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In certain embodiments, the anti-CD73 antibody molecule includes at least one, two, or three Chothia hypervariable loops (e.g., at least one, two, or three hypervariable loops according to the Chothia definition as set out in Table 1) of a light chain variable region of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or at least the amino acids from those hypervariable loops that contact CD73; or which have at least one amino acid alteration, but not more than two, three or four alterations (e.g., substitutions, deletions, or insertions, e.g., conservative substitutions) relative to one, two, or three hypervariable loops according to Chothia et al. shown in Table 1.

In certain embodiments, the anti-CD73 antibody molecule includes at least one, two, three, four, five, or six hypervariable loops (e.g., at least one, two, three, four, five, or six hypervariable loops according to the Chothia definition as set out in Table 1) from the heavy and light chain variable regions of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or at least the amino acids from those hypervariable loops that contact CD73; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Table 1.

In some embodiments, the anti-CD73 antibody molecule includes all six hypervariable loops (e.g., all six hypervariable loops according to the Chothia definition as set out in Table 1) of an antibody described herein, e.g., an antibody chosen from 918, 350, 356, 358, 930, 373, 374, 376, 377, 379, 363, 366, 407, 893, 939, 430, or 398; or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Table 1. In one embodiment, the anti-CD73 antibody molecule may include any hypervariable loop described herein.

In still another embodiment, the anti-CD73 antibody molecule includes at least one, two, or three hypervariable loops that have the same canonical structures as the corresponding hypervariable loop of an antibody described herein, e.g., an antibody chosen from 918, 350, 356, 358, 930, 373, 374, 376, 377, 379, 363, 366, 407, 893, 939, 430, or 398, e.g., the same canonical structures as at least loop 1 and/or loop 2 of the heavy and/or light chain variable domains of an antibody described herein. See, e.g., Chothia et al., (1992) *J. Mol. Biol.* 227:799-817; Tomlinson et al., (1992) *J. Mol. Biol.* 227:776-798 for descriptions of hypervariable loop canonical structures. These structures can be determined by inspection of the tables described in these references.

In certain embodiments, the anti-CD73 antibody molecule includes a combination of CDRs or hypervariable loops defined according to the Kabat et al. and Chothia et al.

In one embodiment, the anti-CD73 antibody molecule includes at least one, two or three CDRs or hypervariable loops from a heavy chain variable region of an antibody described herein, e.g., an antibody chosen from 918, 350, 356, 358, 930, 373, 374, 376, 377, 379, 363, 366, 407, 893, 939, 430, or 398, according to the Kabat and Chothia definition (e.g., at least one, two, or three CDRs or hypervariable loops according to the Kabat and Chothia definition as set out in Table 1); or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

In another embodiment, the anti-CD73 antibody molecule includes at least one, two or three CDRs or hypervariable loops from a light chain variable region of an antibody described herein, e.g., an antibody chosen from 918, 350, 356, 358, 930, 373, 374, 376, 377, 379, 363, 366, 407, 893, 939, 430, or 398, according to the Kabat and Chothia definition (e.g., at least one, two, or three CDRs or hypervariable loops according to the Kabat and Chothia definition as set out in Table 1); or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1.

In some embodiments, the anti-CD73 antibody molecule includes at least one, two, or three CDRs according to the IMGT definition (e.g., at least one, two, or three CDRs according to the IMGT definition as set out in Table 1) from a heavy chain variable region of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to one, two, or three CDRs according to the IMGT definition shown in Table 1.

In certain embodiments, the anti-CD73 antibody molecule includes at least one, two, or three CDRs according to the IMGT definition (e.g., at least one, two, or three CDRs according to the IMGT definition as set out in Table 1) from a light chain variable region of an antibody described herein, e.g., an antibody chosen from 918, 350, 356, 358, 930, 373, 374, 376, 377, 379, 363, 366, 407, 893, 939, 430, or 398; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to one, two, or three CDRs according to the IMGT definition shown in Table 1.

In certain embodiments, the anti-CD73 antibody molecule includes at least one, two, three, four, five, or six CDRs according to the IMGT definition (e.g., at least one, two, three, four, five, or six CDRs according to the IMGT definition as set out in Table 1) from the heavy and light chain variable regions of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to the IMGT definition shown in Table 1.

In some embodiments, the anti-CD73 antibody molecule includes all six CDRs according to the IMGT definition (e.g., all six CDRs according to the IMGT definition as set out in Table 1) from the heavy and light chain variable regions of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or a sequence substantially identical (e.g., having at least about 80%, 85%, 90%, 92%, 95%, 97%, 98%, or 99% sequence identity) to any of the aforesaid sequences; or which have at least one amino acid alteration, but not more than two, three or four alterations (e.g., substitutions, deletions, or insertions, e.g., conservative substitutions) relative to all six CDRs according to the IMGT definition shown in Table 1. In one embodiment, the anti-CD73 antibody molecule may include any CDR described herein.

The anti-CD73 antibody molecule can contain any combination of CDRs or hypervariable loops according to the Kabat and Chothia definitions.

In some embodiments, the anti-CD73 antibody molecule includes at least one, two, or three Chothia hypervariable loops from a heavy chain variable region of an antibody described herein, e.g., an antibody of Table 1, or at least the amino acids from those hypervariable loops that contact CD73.

In some embodiments, the anti-CD73 antibody molecule includes at least one, two, or three Chothia hypervariable loops from a light chain variable region of an antibody described herein, e.g., an antibody of Table 1, or at least the amino acids from those hypervariable loops that contact CD73.

In some embodiments, the anti-CD73 antibody molecule includes at least one, two, or three Kabat hypervariable loops from a heavy chain variable region of an antibody described herein, e.g., an antibody of Table 1, or at least the amino acids from those hypervariable loops that contact CD73.

In some embodiments, the anti-CD73 antibody molecule includes at least one, two, or three Kabat hypervariable loops from a light chain variable region of an antibody described herein, e.g., an antibody of Table 1, or at least the amino acids from those hypervariable loops that contact CD73.

In some embodiments, the anti-CD73 antibody molecule includes at least one, two, or three IMGT hypervariable loops from a heavy chain variable region of an antibody described herein, e.g., an antibody of Table 1, or at least the amino acids from those hypervariable loops that contact CD73.

In some embodiments, the anti-CD73 antibody molecule includes at least one, two, or three IMGT hypervariable loops from a light chain variable region of an antibody described herein, e.g., an antibody of Table 1, or at least the amino acids from those hypervariable loops that contact CD73.

In certain embodiments, the anti-CD73 antibody molecule includes at least one, two, three, four, five, or six hypervariable loops from the heavy and light chain variable regions of an antibody described herein, e.g., an antibody of Table 1, or at least the amino acids from those hypervariable loops that contact CD73.

In certain embodiments, the anti-CD73 antibody molecule includes all six hypervariable loops from the heavy and light chain variable regions of an antibody described herein, e.g., an antibody of Table 1, or at least the amino acids from those hypervariable loops that contact CD73, or at least the amino acids from those hypervariable loops that contact CD73, or closely related hypervariable loops, e.g., hypervariable loops which are identical or which have at least one amino acid alteration, but not more than two, three or four alterations (e.g., substitutions, e.g., conservative substitutions, deletions, or insertions).

In some embodiments, the anti-CD73 antibody molecule includes at least one, two, or three hypervariable loops that have the same canonical structures as the corresponding hypervariable loop of an antibody described herein, e.g., an antibody of Table 1, e.g., the same canonical structures as at least loop 1 and/or loop 2 of the heavy and/or light chain variable domains of an antibody described herein. See, e.g., Chothia et al., (1992) J. Mol. Biol. 227:799-817; Tomlinson et al., (1992) J. Mol. Biol. 227:776-798 for descriptions of hypervariable loop canonical structures. These structures can be determined by inspection of the tables described in these references. In an embodiment, e.g., an embodiment comprising a variable region, CDR (e.g., Chothia, Kabat, or IMGT CDR), or other sequence referred to herein, e.g., in Table 1, the antibody molecule is a monospecific antibody molecule, a bispecific antibody molecule, or is an antibody molecule that comprises an antigen binding fragment of an antibody, e.g., a half antibody or antigen binding fragment of a half antibody.

In some embodiments, the heavy or light chain variable domain, or both, of the anti-CD73 antibody molecule includes an amino acid sequence, which is substantially identical to an amino acid disclosed herein, e.g., having at least about 80%, 85%, 90%, 92%, 95%, 97%, 98%, or 99% sequence identity to a variable region of an antibody described herein, e.g., an antibody chosen from 918, 350, 356, 358, 930, 373, 374, 376, 377, 379, 363, 366, 407, 893, 939, 430, or 398; or as described in Table 1; or encoded by a nucleotide sequence in Table 1; or which differs at least 1 or 5 residues, but less than 40, 30, 20, or 10 residues, from a variable region of an antibody described herein.

In certain embodiments, the heavy or light chain variable region, or both, of the anti-CD73 antibody molecule includes an amino acid sequence encoded by a nucleic acid sequence described herein or a nucleic acid that hybridizes to a nucleic acid sequence described herein (e.g., a nucleic acid sequence as shown in Table 1) or its complement, e.g., under low stringency, medium stringency, or high stringency, or other hybridization condition described herein.

In certain embodiments, the anti-CD73 antibody molecule comprises at least one, two, three, or four antigen-binding regions, e.g., variable regions, having an amino acid sequence as set forth in Table 1, or a sequence substantially identical thereto (e.g., a sequence having at least about 85%, 90%, 95%, or 99% sequence identity thereto, or which differs by no more than 1, 2, 5, 10, or 15 amino acid residues from the sequences shown in Table 1. In certain embodiments, the anti-CD73 antibody molecule includes a VH and/or VL domain encoded by a nucleic acid having a nucleotide sequence that encodes an antibody of Table 1, or a sequence substantially identical to any one of the nucleotide sequences (e.g., a sequence having at least about 85%, 90%, 95%, or 99% sequence identity thereto, or which differs by no more than 3, 6, 15, 30, or 45 nucleotides from the sequences shown in Table 1).

In certain embodiments, the anti-CD73 antibody molecule comprises at least one, two, or three (e.g., all) CDRs from a heavy chain variable region having an amino acid sequence as set forth in Table 1, or a sequence substantially homologous thereto (e.g., a sequence having at least about 85%, 90%, 95%, or 99% sequence identity thereto, and/or having one, two, three or more substitutions, insertions or deletions, e.g., conserved substitutions). In some embodiments, the anti-CD73 antibody molecule comprises at least one, two, or three (e.g., all) CDRs from a light chain variable region having an amino acid sequence as set forth in Table 1, or a sequence substantially homologous thereto (e.g., a sequence having at least about 85%, 90%, 95%, or 99% sequence identity thereto, and/or having one, two, three or more substitutions, insertions or deletions, e.g., conserved substitutions). In certain embodiments, the anti-CD73 antibody molecule comprises at least one, two, three, four, five or six (e.g., all) CDRs from heavy and light chain variable regions having an amino acid sequence as set forth in Table 1, or a sequence substantially homologous thereto (e.g., a sequence having at least about 85%, 90%, 95%, or 99% sequence identity thereto, and/or having one, two, three or more substitutions, insertions or deletions, e.g., conserved substitutions).

In some embodiments, the anti-CD73 antibody molecule comprises at least one, two, or three (e.g., all) CDRs and/or hypervariable loops from a heavy chain variable region having an amino acid sequence of an antibody described herein, e.g., an antibody chosen from 918, 350, 356, 358, 930, 373, 374, 376, 377, 379, 363, 366, 407, 893, 939, 430, or 398, as summarized in Table 1, or a sequence substantially identical thereto (e.g., a sequence having at least about 85%, 90%, 95%, or 99% sequence identity thereto, and/or having one, two, three or more substitutions, insertions or deletions, e.g., conserved substitutions). In certain embodiments, the anti-CD73 antibody molecule comprises at least one, two, or three (e.g., all) CDRs and/or hypervariable loops from a light chain variable region having an amino acid sequence of an antibody described herein, e.g., an antibody chosen from 918, 350, 356, 358, 930, 373, 374, 376, 377, 379, 363, 366, 407, 893, 939, 430, or 398, as summarized in Table 1, or a sequence substantially identical thereto (e.g., a sequence having at least about 85%, 90%, 95%, or 99% sequence identity thereto, and/or having one, two, three or more substitutions, insertions or deletions, e.g., conserved substitutions). In some embodiments, the anti-CD73 antibody molecule comprises all six CDRs and/or hypervariable loops described herein, e.g., described in Table 1.

In some embodiments, the antibody molecule has a variable region that is identical in sequence, or which differs by 1, 2, 3, or 4 amino acids from a variable region described herein (e.g., an FR region disclosed herein).

In one embodiment, the anti-CD73 antibody molecule comprises a heavy chain variable region (VH) comprising a VHCDR3 amino acid sequence of GGLYGSGSYLSDFDL (SEQ ID NO: 37). In one embodiment, the anti-CD73 antibody molecule comprises a heavy chain variable region (VH) comprising a VHCDR3 amino acid sequence of ESQESPYNNWFDP (SEQ ID NO: 3).

In one embodiment, the anti-CD73 antibody molecule comprises a heavy chain variable region (VH) comprising a VHCDR1 amino acid sequence of SEQ ID NO: 88, a VHCDR2 amino acid sequence of SEQ ID NO: 89, and a VHCDR3 amino acid sequence of SEQ ID NO: 37; and a light chain variable region (VL) comprising a VLCDR1 amino acid sequence of SEQ ID NO: 48, a VLCDR2 amino acid sequence of SEQ ID NO: 49, and a VLCDR3 amino acid sequence of SEQ ID NO: 50, each disclosed in Table 2. In one embodiment, the anti-CD73 antibody molecule comprises a heavy chain variable region (VH) comprising a VHCDR1 amino acid sequence of SEQ ID NO: 90, a VHCDR2 amino acid sequence of SEQ ID NO: 91, and a VHCDR3 amino acid sequence of SEQ ID NO: 3; and a light chain variable region (VL) comprising a VLCDR1 amino acid sequence of SEQ ID NO: 14, a VLCDR2 amino acid sequence of SEQ ID NO: 15, and a VLCDR3 amino acid sequence of SEQ ID NO: 16, each disclosed in Table 2.

In one embodiment, the anti-CD73 antibody molecule comprises a heavy chain variable region (VH) comprising a VHCDR1 amino acid sequence of SEQ ID NO: 122, a VHCDR2 amino acid sequence of SEQ ID NO: 123, and a VHCDR3 amino acid sequence of SEQ ID NO: 37; and a light chain variable region (VL) comprising a VLCDR1 amino acid sequence of SEQ ID NO: 51, a VLCDR2 amino acid sequence of SEQ ID NO: 52, and a VLCDR3 amino acid sequence of SEQ ID NO: 53, each disclosed in Table 2. In one embodiment, the anti-CD73 antibody molecule comprises a heavy chain variable region (VH) comprising a VHCDR1 amino acid sequence of SEQ ID NO: 124, a VHCDR2 amino acid sequence of SEQ ID NO: 125, and a VHCDR3 amino acid sequence of SEQ ID NO: 3; and a light chain variable region (VL) comprising a VLCDR1 amino acid sequence of SEQ ID NO: 17, a VLCDR2 amino acid sequence of SEQ ID NO: 18, and a VLCDR3 amino acid sequence of SEQ ID NO: 19, each disclosed in Table 2.

In one embodiment, the anti-CD73 antibody molecule comprises a heavy chain variable region (VH) comprising a VHCDR1 amino acid sequence of SEQ ID NO: 126, a VHCDR2 amino acid sequence of SEQ ID NO: 89, and a VHCDR3 amino acid sequence of SEQ ID NO: 37; and a light chain variable region (VL) comprising a VLCDR1 amino acid sequence of SEQ ID NO: 48, a VLCDR2 amino acid sequence of SEQ ID NO: 49, and a VLCDR3 amino acid sequence of SEQ ID NO: 50, each disclosed in Table 2. In one embodiment, the anti-CD73 antibody molecule comprises a heavy chain variable region (VH) comprising a VHCDR1 amino acid sequence of SEQ ID NO: 127, a VHCDR2 amino acid sequence of SEQ ID NO: 91, and a VHCDR3 amino acid sequence of SEQ ID NO: 3; and a light chain variable region (VL) comprising a VLCDR1 amino acid sequence of SEQ ID NO: 14, a VLCDR2 amino acid sequence of SEQ ID NO: 15, and a VLCDR3 amino acid sequence of SEQ ID NO: 16, each disclosed in Table 2.

In one embodiment, the anti-CD73 antibody molecule comprises a heavy chain variable region (VH) comprising a VHCDR1 amino acid sequence of SEQ ID NO: 128, a VHCDR2 amino acid sequence of SEQ ID NO: 129, and a VHCDR3 amino acid sequence of SEQ ID NO: 43; and a light chain variable region (VL) comprising a VLCDR1 amino acid sequence of SEQ ID NO: 54, a VLCDR2 amino acid sequence of SEQ ID NO: 52, and a VLCDR3 amino acid sequence of SEQ ID NO: 50, each disclosed in Table 2. In one embodiment, the anti-CD73 antibody molecule comprises a heavy chain variable region (VH) comprising a VHCDR1 amino acid sequence of SEQ ID NO: 130, a VHCDR2 amino acid sequence of SEQ ID NO: 131, and a VHCDR3 amino acid sequence of SEQ ID NO: 9; and a light chain variable region (VL) comprising a VLCDR1 amino acid sequence of SEQ ID NO: 20, a VLCDR2 amino acid sequence of SEQ ID NO: 18, and a VLCDR3 amino acid sequence of SEQ ID NO: 16, each disclosed in Table 2.

In one embodiment, the anti-CD73 antibody molecule comprises a heavy chain variable region (VH) comprising a VHCDR1 amino acid sequence of SEQ ID NO: 189, a VHCDR2 amino acid sequence of SEQ ID NO: 89, and a VHCDR3 amino acid sequence of SEQ ID NO: 43; and a light chain variable region (VL) comprising a VLCDR1 amino acid sequence of SEQ ID NO: 48, a VLCDR2 amino acid sequence of SEQ ID NO: 49, and a VLCDR3 amino acid sequence of SEQ ID NO: 50, each disclosed in Table 2. In one embodiment, the anti-CD73 antibody molecule comprises a heavy chain variable region (VH) comprising a VHCDR1 amino acid sequence of SEQ ID NO: 196, a VHCDR2 amino acid sequence of SEQ ID NO: 91, and a VHCDR3 amino acid sequence of SEQ ID NO: 9; and a light chain variable region (VL) comprising a VLCDR1 amino acid sequence of SEQ ID NO: 14, a VLCDR2 amino acid sequence of SEQ ID NO: 15, and a VLCDR3 amino acid sequence of SEQ ID NO: 16, each disclosed in Table 2.

In one embodiment, the anti-CD73 antibody molecule comprises a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 61, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16. In one embodiment, the anti-CD73 antibody molecule comprises a VH comprising a VHCDR1 amino acid sequence of SEQ ID NO: 4, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16. In one embodiment, the anti-CD73 antibody molecule comprises a VH comprising a VHCDR1 amino acid sequence of SEQ ID NO: 4, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16. In one embodiment, the anti-CD73 antibody molecule comprises a VH comprising a VHCDR1 amino acid sequence of SEQ ID NO: 163, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one embodiment, the anti-CD73 antibody molecule comprises a VH comprising a VHCDR1 amino acid sequence of SEQ ID NO: 39, a VHCDR2 amino acid sequence of SEQ ID NO: 40, and a VHCDR3 amino acid sequence of SEQ ID NO: 37; and a VL comprising a VLCDR1 amino acid sequence of SEQ ID NO: 51, a VLCDR2 amino acid sequence of SEQ ID NO: 52, and a VLCDR3 amino acid sequence of SEQ ID NO: 53. In one embodiment, the anti-CD73 antibody molecule comprises a VH comprising a VHCDR1 amino acid sequence of SEQ ID NO: 73, a VHCDR2 amino acid sequence of SEQ ID NO: 74, and a VHCDR3 amino acid sequence of SEQ ID NO: 37; and a VL comprising a VLCDR1 amino acid sequence of SEQ ID NO: 51, a VLCDR2 amino acid sequence of SEQ ID NO: 52, and a VLCDR3 amino acid sequence of SEQ ID NO: 53. In one embodiment, the anti-CD73 antibody molecule comprises a VH comprising a VHCDR1 amino acid sequence of SEQ ID NO: 82, a VHCDR2 amino acid sequence of SEQ ID NO: 74, and a VHCDR3 amino acid sequence of SEQ ID NO: 37; and a VL comprising a VLCDR1 amino acid sequence of SEQ ID NO: 51, a VLCDR2 amino acid sequence of SEQ ID NO: 52, and a VLCDR3 amino acid sequence of SEQ ID NO: 53. In one embodiment, the anti-CD73 antibody molecule comprises a VH comprising a VHCDR1 amino acid sequence of SEQ ID NO: 138, a VHCDR2 amino acid sequence of SEQ ID NO: 139, and a VHCDR3 amino acid sequence of SEQ ID NO: 37; and a VL comprising a VLCDR1 amino acid sequence of SEQ ID NO: 51, a VLCDR2 amino acid sequence of SEQ ID NO: 52, and a VLCDR3 amino acid sequence of SEQ ID NO: 53. In one embodiment, the anti-CD73 antibody molecule comprises a VH comprising a VHCDR1 amino acid sequence of SEQ ID NO: 147, a VHCDR2 amino acid sequence of SEQ ID NO: 148, and a VHCDR3 amino acid sequence of SEQ ID NO: 37; and a VL comprising a VLCDR1 amino acid sequence of SEQ ID NO: 51, a VLCDR2 amino acid sequence of SEQ ID NO: 52, and a VLCDR3 amino acid sequence of SEQ ID NO: 53. In one embodiment, the anti-CD73 antibody molecule comprises a VH comprising a VHCDR1 amino acid sequence of SEQ ID NO: 155, a VHCDR2 amino acid sequence of SEQ ID NO: 156, and a VHCDR3 amino acid sequence of SEQ ID NO: 37; and a VL comprising a VLCDR1 amino acid sequence of SEQ ID NO: 51, a VLCDR2 amino acid sequence of SEQ ID NO: 52, and a VLCDR3 amino acid sequence of SEQ ID NO: 53. In one embodiment, the anti-CD73 antibody molecule comprises a VH comprising a VHCDR1 amino acid sequence of SEQ ID NO: 62, a VHCDR2 amino acid sequence of SEQ ID NO: 63, and a VHCDR3 amino acid sequence of SEQ ID NO: 3; and a VL comprising a VLCDR1 amino acid sequence of SEQ ID NO: 17, a VLCDR2 amino acid sequence of SEQ ID NO: 18, and a VLCDR3 amino acid sequence of SEQ ID NO: 19. In one embodiment, the anti-CD73 antibody molecule comprises a VH comprising a VHCDR1 amino acid sequence of SEQ ID NO: 27, a VHCDR2 amino acid sequence of SEQ ID NO: 28, and a VHCDR3 amino acid sequence of SEQ ID NO: 3; and a VL comprising a VLCDR1 amino acid sequence of SEQ ID NO: 17, a VLCDR2 amino acid sequence of SEQ ID NO: 18, and a VLCDR3 amino acid sequence of SEQ ID NO: 19. In one embodiment, the anti-CD73 antibody molecule comprises a VH comprising a VHCDR1 amino acid sequence of SEQ ID NO: 5, a VHCDR2 amino acid sequence of SEQ ID NO: 6, and a VHCDR3 amino acid sequence of SEQ ID NO: 3; and a VL comprising a VLCDR1 amino acid sequence of SEQ ID NO: 17, a VLCDR2 amino acid sequence of SEQ ID NO: 18, and a VLCDR3 amino acid sequence of SEQ ID NO: 19. In one embodiment, the anti-CD73 antibody molecule comprises a VH comprising a VHCDR1 amino acid sequence of SEQ ID NO: 164, a VHCDR2 amino acid sequence of SEQ ID NO: 165, and a VHCDR3 amino acid sequence of SEQ ID NO: 3; and a VL comprising a VLCDR1 amino acid sequence of SEQ ID NO: 17, a VLCDR2 amino acid sequence of SEQ ID NO: 18, and a VLCDR3 amino acid sequence of SEQ ID NO: 19.

In one embodiment, the anti-CD73 antibody molecule comprises a VH comprising a VHCDR1 amino acid sequence of SEQ ID NO: 35, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 70, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 81, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 135, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 145, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 153, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 59, a VHCDR2 amino acid sequence of SEQ ID NO: 60, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16. In one embodiment, the anti-CD73 antibody molecule comprises a VH comprising a VHCDR1 amino acid sequence of SEQ ID NO: 25, a VHCDR2 amino acid sequence of SEQ ID NO: 26, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16. In one embodiment, the anti-CD73 antibody molecule comprises a VH comprising a VHCDR1 amino acid sequence of SEQ ID NO: 1, a VHCDR2 amino acid sequence of SEQ ID NO: 2, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16. In one embodiment, the anti-CD73 antibody molecule comprises a VH comprising a VHCDR1 amino acid sequence of SEQ ID NO: 161, a VHCDR2 amino acid sequence of SEQ ID NO: 162, and a VHCDR3 amino acid sequence of SEQ ID NO: 3; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In one embodiment, the anti-CD73 antibody molecule comprises a VH comprising a VHCDR1 amino acid sequence of SEQ ID NO: 41, a VHCDR2 amino acid sequence of SEQ ID NO: 42, and a VHCDR3 amino acid sequence of SEQ ID NO: 43; and a VL comprising a VLCDR1 amino acid sequence of SEQ ID NO: 54, a VLCDR2 amino acid sequence of SEQ ID NO: 52, and a VLCDR3 amino acid sequence of SEQ ID NO: 50. In one embodiment, the anti-CD73 antibody molecule comprises a VH comprising a VHCDR1 amino acid sequence of SEQ ID NO: 75, a VHCDR2 amino acid sequence of SEQ ID NO: 76, and a VHCDR3 amino acid sequence of SEQ ID NO: 43; and a VL comprising a VLCDR1 amino acid sequence of SEQ ID NO: 54, a VLCDR2 amino acid sequence of SEQ ID NO: 52, and a VLCDR3 amino acid sequence of SEQ ID NO: 50. In one embodiment, the anti-CD73 antibody molecule comprises a VH comprising a VHCDR1 amino acid sequence of SEQ ID NO: 83, a VHCDR2 amino acid sequence of SEQ ID NO: 76, and a VHCDR3 amino acid sequence of SEQ ID NO: 43; and a VL comprising a VLCDR1 amino acid sequence of SEQ ID NO: 54, a VLCDR2 amino acid sequence of SEQ ID NO: 52, and a VLCDR3 amino acid sequence of SEQ ID NO: 50. In one embodiment, the anti-CD73 antibody molecule comprises a VH comprising a VHCDR1 amino acid sequence of SEQ ID NO: 140, a VHCDR2 amino acid sequence of SEQ ID NO: 141, and a VHCDR3 amino acid sequence of SEQ ID NO: 43; and a VL comprising a VLCDR1 amino acid sequence of SEQ ID NO: 54, a VLCDR2 amino acid sequence of SEQ ID NO: 52, and a VLCDR3 amino acid sequence of SEQ ID NO: 50. In one embodiment, the anti-CD73 antibody molecule comprises a VH comprising a VHCDR1 amino acid sequence of SEQ ID NO: 149, a VHCDR2 amino acid sequence of SEQ ID NO: 150, and a VHCDR3 amino acid sequence of SEQ ID NO: 43; and a VL comprising a VLCDR1 amino acid sequence of SEQ ID NO: 54, a VLCDR2 amino acid sequence of SEQ ID NO: 52, and a VLCDR3 amino acid sequence of SEQ ID NO: 50. In one embodiment, the anti-CD73 antibody molecule comprises a VH comprising a VHCDR1 amino acid sequence of SEQ ID NO: 157, a VHCDR2 amino acid sequence of SEQ ID NO: 158, and a VHCDR3 amino acid sequence of SEQ ID NO: 43; and a VL comprising a VLCDR1 amino acid sequence of SEQ ID NO: 54, a VLCDR2 amino acid sequence of SEQ ID NO: 52, and a VLCDR3 amino acid sequence of SEQ ID NO: 50. In one embodiment, the anti-CD73 antibody molecule comprises a VH comprising a VHCDR1 amino acid sequence of SEQ ID NO: 64, a VHCDR2 amino acid sequence of SEQ ID NO: 65, and a VHCDR3 amino acid sequence of SEQ ID NO: 9; and a VL comprising a VLCDR1 amino acid sequence of SEQ ID NO: 20, a VLCDR2 amino acid sequence of SEQ ID NO: 18, and a VLCDR3 amino acid sequence of SEQ ID NO: 16. In one embodiment, the anti-CD73 antibody molecule comprises a VH comprising a VHCDR1 amino acid sequence of SEQ ID NO: 29, a VHCDR2 amino acid sequence of SEQ ID NO: 30, and a VHCDR3 amino acid sequence of SEQ ID NO: 9; and a VL comprising a VLCDR1 amino acid sequence of SEQ ID NO: 20, a VLCDR2 amino acid sequence of SEQ ID NO: 18, and a VLCDR3 amino acid sequence of SEQ ID NO: 16. In one embodiment, the anti-CD73 antibody molecule comprises a VH comprising a VHCDR1 amino acid sequence of SEQ ID NO: 7, a VHCDR2 amino acid sequence of SEQ ID NO: 8, and a VHCDR3 amino acid sequence of SEQ ID NO: 9; and a VL comprising a VLCDR1 amino acid sequence of SEQ ID NO: 20, a VLCDR2 amino acid sequence of SEQ ID NO: 18, and a VLCDR3 amino acid sequence of SEQ ID NO: 16. In one embodiment, the anti-CD73 antibody molecule comprises a VH comprising a VHCDR1 amino acid sequence of SEQ ID NO: 166, a VHCDR2 amino acid sequence of SEQ ID NO: 167, and a VHCDR3 amino acid sequence of SEQ ID NO: 9; and a VL comprising a VLCDR1 amino acid sequence of SEQ ID NO: 20, a VLCDR2 amino acid sequence of SEQ ID NO: 18, and a VLCDR3 amino acid sequence of SEQ ID NO: 16.

In one embodiment, the anti-CD73 antibody molecule comprises a VH comprising a VHCDR1 amino acid sequence of SEQ ID NO: 190, a VHCDR2 amino acid sequence of SEQ ID NO: 36, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 191, a VHCDR2 amino acid sequence of SEQ ID NO: 71, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 192, a VHCDR2 amino acid sequence of SEQ ID NO: 71, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 193, a VHCDR2 amino acid sequence of SEQ ID NO: 136, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 194, a VHCDR2 amino acid sequence of SEQ ID NO: 146, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 195, a VHCDR2 amino acid sequence of SEQ ID NO: 154, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50. In one embodiment, the anti-CD73 antibody molecule comprises a VH comprising a VHCDR1 amino acid sequence of SEQ ID NO: 197, a VHCDR2 amino acid sequence of SEQ ID NO: 60, and a VHCDR3 amino acid sequence of SEQ ID NO: 9; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16. In one embodiment, the anti-CD73 antibody molecule comprises a VH comprising a VHCDR1 amino acid sequence of SEQ ID NO: 198, a VHCDR2 amino acid sequence of SEQ ID NO: 26, and a VHCDR3 amino acid sequence of SEQ ID NO: 9; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16. In one embodiment, the anti-CD73 antibody molecule comprises a VH comprising a VHCDR1 amino acid sequence of SEQ ID NO: 199, a VHCDR2 amino acid sequence of SEQ ID NO: 2, and a VHCDR3 amino acid sequence of SEQ ID NO: 9; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16. In one embodiment, the anti-CD73 antibody molecule comprises a VH comprising a VHCDR1 amino acid sequence of SEQ ID NO: 200, a VHCDR2 amino acid sequence of SEQ ID NO: 162, and a VHCDR3 amino acid sequence of SEQ ID NO: 9; and a VL comprising a VLCDR1 amino acid sequence of SEQ ID NO: 14, a VLCDR2 amino acid sequence of SEQ ID NO: 15, and a VLCDR3 amino acid sequence of SEQ ID NO: 16.

In other embodiments, the aforesaid antibodies comprise a heavy chain variable region comprising an amino acid sequence having at least about 85% (e.g., at least 90%, 95%, 97%, 98%, 99%, or 100%) sequence identity to any of SEQ ID NOs: 44, 77, 84, 142, 151, or 159. In other embodiments, the aforesaid antibodies comprise a heavy chain variable region comprising an amino acid sequence having at least about 85% (e.g., at least 90%, 95%, 97%, 98%, 99%, or 100%) sequence identity to any of SEQ ID NOs: 66, 31, 10, or 168.

In other embodiments, the aforesaid antibodies comprise a light chain variable region comprising an amino acid sequence having at least about 85% (e.g., at least 90%, 95%, 97%, 98%, 99%, or 100%) sequence identity to any of SEQ ID NOs: 55 or 21.

In other embodiments, the aforesaid antibodies comprise a heavy chain comprising an amino acid sequence having at least about 85% (e.g., at least 90%, 95%, 97%, 98%, 99%, or 100%) sequence identity to any of SEQ ID NOs: 46, 79, 86, 114, 116, or 117. In other embodiments, the aforesaid antibodies comprise a heavy chain comprising an amino acid sequence having at least about 85% (e.g., at least 90%, 95%, 97%, 98%, 99%, or 100%) sequence identity to any of SEQ ID NOs: 68, 33, 12, 115, 113, or 112.

In other embodiments, the aforesaid antibodies comprise a light chain comprising an amino acid sequence having at least about 85% (e.g., at least 90%, 95%, 97%, 98%, 99%, or 100%) sequence identity to any of SEQ ID NOs: 57 or 23.

In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 44; and a light chain variable region comprising an amino acid sequence having at least about 85% (e.g., at least 90%, 95%, 97%, 98%, 99%, or 100%) sequence identity to SEQ ID NO: 55. In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 77; and a light chain variable region comprising an amino acid sequence having at least about 85% (e.g., at least 90%, 95%, 97%, 98%, 99%, or 100%) sequence identity to SEQ ID NO: 55. In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 84; and a light chain variable region comprising an amino acid sequence having at least about 85% (e.g., at least 90%, 95%, 97%, 98%, 99%, or 100%) sequence identity to SEQ ID NO: 55. In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 142; and a light chain variable region comprising an amino acid sequence having at least about 85% (e.g., at least 90%, 95%, 97%, 98%, 99%, or 100%) sequence identity to SEQ ID NO: 55. In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 151; and a light chain variable region comprising an amino acid sequence having at least about 85% (e.g., at least 90%, 95%, 97%, 98%, 99%, or 100%) sequence identity to SEQ ID NO: 55. In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 159; and a light chain variable region comprising an amino acid sequence having at least about 85% (e.g., at least 90%, 95%, 97%, 98%, 99%, or 100%) sequence identity to SEQ ID NO: 55. In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 66; and a light chain variable region comprising an amino acid sequence having at least about 85% (e.g., at least 90%, 95%, 97%, 98%, 99%, or 100%) sequence identity to SEQ ID NO: 21. In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 31; and a light chain variable region comprising an amino acid sequence having at least about 85% (e.g., at least 90%, 95%, 97%, 98%, 99%, or 100%) sequence identity to SEQ ID NO: 21. In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 10; and a light chain variable region comprising an amino acid sequence having at least about 85% (e.g., at least 90%, 95%, 97%, 98%, 99%, or 100%) sequence identity to SEQ ID NO: 21. In other embodiments, the antibody molecule comprises a heavy chain variable region comprising an amino acid sequence having at least about 85% (e.g., at least 90%, 95%, 97%, 98%, 99%, or 100%) sequence identity to SEQ ID NO: 168; and a light chain variable region comprising an amino acid sequence having at least about 85% (e.g., at least 90%, 95%, 97%, 98%, 99%, or 100%) sequence identity to SEQ ID NO: 21.

In other embodiments, the antibody molecule comprises a heavy chain comprising an amino acid sequence having at least about 85% (e.g., at least 90%, 95%, 97%, 98%, 99%, or 100%) sequence identity to SEQ ID NO: 46; and a light chain comprising an amino acid sequence having at least about 85% (e.g., at least 90%, 95%, 97%, 98%, 99%, or 100%) sequence identity to SEQ ID NO: 57. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 79; and a light chain comprising an amino acid sequence having at least about 85% (e.g., at least 90%, 95%, 97%, 98%, 99%, or 100%) sequence identity to SEQ ID NO: 57. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 86; and a light chain comprising an amino acid sequence having at least about 85% (e.g., at least 90%, 95%, 97%, 98%, 99%, or 100%) sequence identity to SEQ ID NO: 57. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 114; and a light chain comprising an amino acid sequence having at least about 85% (e.g., at least 90%, 95%, 97%, 98%, 99%, or 100%) sequence identity to SEQ ID NO: 57. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 116; and a light chain comprising an amino acid sequence having at least about 85% (e.g., at least 90%, 95%, 97%, 98%, 99%, or 100%) sequence identity to SEQ ID NO: 57. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 117; and a light chain comprising an amino acid sequence having at least about 85% (e.g., at least 90%, 95%, 97%, 98%, 99%, or 100%) sequence identity to SEQ ID NO: 57. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 68; and a light chain comprising an amino acid sequence having at least about 85% (e.g., at least 90%, 95%, 97%, 98%, 99%, or 100%) sequence identity to SEQ ID NO: 23. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 33; and a light chain comprising an amino acid sequence having at least about 85% (e.g., at least 90%, 95%, 97%, 98%, 99%, or 100%) sequence identity to SEQ ID NO: 23. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 12; and a light chain comprising an amino acid sequence having at least about 85% (e.g., at least 90%, 95%, 97%, 98%, 99%, or 100%) sequence identity to SEQ ID NO: 23. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 115; and a light chain comprising an amino acid sequence having at least about 85% (e.g., at least 90%, 95%, 97%, 98%, 99%, or 100%) sequence identity to SEQ ID NO: 23. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 113; and a light chain comprising an amino acid sequence having at least about 85% (e.g., at least 90%, 95%, 97%, 98%, 99%, or 100%) sequence identity to SEQ ID NO: 23. In other embodiments, the antibody molecule comprises a heavy chain comprising an amino acid sequence having at least about 85% (e.g., at least 90%, 95%, 97%, 98%, 99%, or 100%) sequence identity to SEQ ID NO: 112; and a light chain comprising an amino acid sequence having at least about 85% (e.g., at least 90%, 95%, 97%, 98%, 99%, or 100%) sequence identity to SEQ ID NO: 23.

In other embodiments, the antibody molecule comprises a VHCDR1, a VHCDR2, a VHCDR3, a VLCDR1, a VLCDR2, and a VLCDR3 comprising the amino acid sequences of SEQ ID NOs: 81, 201, 37, 205, 206, and 207, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 38, 201, 37, 205, 206, and 207, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 82, 202, 37, 208, 209, and 228, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 83, 203, 43, 229, 209, and 207, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 192, 201, 43, 205, 206, and 207, respectively. In other embodiments, the antibody molecule comprises a VH and VL comprising the amino acid sequences of SEQ ID NOs: 204 and 230, respectively (or an amino acid sequence having at least about 85% (e.g., at least 90%, 95%, 97%, 98%, 99%, or 100%) sequence identity thereof).

In other embodiments, the antibody molecule comprises a VHCDR1, a VHCDR2, a VHCDR3, a VLCDR1, a VLCDR2, and a VLCDR3 comprising the amino acid sequences of SEQ ID NOs: 81, 231, 37, 205, 206, and 207, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 38, 231, 37, 205, 206, and 207, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 82, 232, 37, 208, 209, and 228, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 83, 233, 43, 229, 209, and 207, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 192, 231, 43, 205, 206, and 207, respectively. In other embodiments, the antibody molecule comprises a VH and VL comprising the amino acid sequences of SEQ ID NOs: 234 and 230, respectively (or an amino acid sequence having at least about 85% (e.g., at least 90%, 95%, 97%, 98%, 99%, or 100%) sequence identity thereof).

In other embodiments, the antibody molecule comprises a VHCDR1, a VHCDR2, a VHCDR3, a VLCDR1, a VLCDR2, and a VLCDR3 comprising the amino acid sequences of SEQ ID NOs: 235, 236, 237, 246, 15, and 247, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 238, 236, 237, 246, 15, and 247, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 239, 240, 237, 248, 18, and 249, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 241, 242, 243, 250, 18, and 247, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 244, 236, 243, 246, 15, and 247, respectively. In other embodiments, the antibody molecule comprises a VH and VL comprising the amino acid sequences of SEQ ID NOs: 245 and 251, respectively (or an amino acid sequence having at least about 85% (e.g., at least 90%, 95%, 97%, 98%, 99%, or 100%) sequence identity thereof).

In other embodiments, the antibody molecule comprises a VHCDR1, a VHCDR2, a VHCDR3, a VLCDR1, a VLCDR2, and a VLCDR3 comprising the amino acid sequences of SEQ ID NOs: 252, 253, 254, 262, 263, and 264, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 255, 253, 254, 262, 263, and 264, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 155, 256, 254, 265, 266, and 267, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 257, 258, 259, 268, 266, and 264, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 260, 253, 259, 262, 263, and 264, respectively. In other embodiments, the antibody molecule comprises a VH and VL comprising the amino acid sequences of SEQ ID NOs: 261 and 269, respectively (or an amino acid sequence having at least about 85% (e.g., at least 90%, 95%, 97%, 98%, 99%, or 100%) sequence identity thereof).

In other embodiments, the antibody molecule comprises a VHCDR1, a VHCDR2, a VHCDR3, a VLCDR1, a VLCDR2, and a VLCDR3 comprising the amino acid sequences of SEQ ID NOs: 287, 288, 289, 298, 49, and 299, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 290, 288, 289, 298, 49, and 299, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 291, 292, 289, 300, 52, and 301, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 293, 294, 295, 302, 52, and 299, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 296, 288, 295, 298, 49, and 299, respectively. In other embodiments, the antibody molecule comprises a VH and VL comprising the amino acid sequences of SEQ ID NOs: 297 and 303, respectively (or an amino acid sequence having at least about 85% (e.g., at least 90%, 95%, 97%, 98%, 99%, or 100%) sequence identity thereof).

In other embodiments, the antibody molecule comprises a VHCDR1, a VHCDR2, a VHCDR3, a VLCDR1, a VLCDR2, and a VLCDR3 comprising the amino acid sequences of SEQ ID NOs: 304, 305, 306, 14, 15, and 314, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 61, 305, 306, 14, 15, and 314, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 307, 308, 306, 17, 18, and 315, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 309, 310, 311, 20, 18, and 314, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 312, 305, 311, 14, 15, and 314, respectively. In other embodiments, the antibody molecule comprises a VH and VL comprising the amino acid sequences of SEQ ID NOs: 313 and 316, respectively (or an amino acid sequence having at least about 85% (e.g., at least 90%, 95%, 97%, 98%, 99%, or 100%) sequence identity thereof).

In other embodiments, the antibody molecule comprises a VHCDR1, a VHCDR2, a VHCDR3, a VLCDR1, a VLCDR2, and a VLCDR3 comprising the amino acid sequences of SEQ ID NOs: 317, 318, 319, 14, 15, and 328, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 320, 318, 319, 14, 15, and 328, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 321, 322, 319, 17, 18, and 329, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 323, 324, 325, 20, 18, and 328, respectively. In other embodiments, the antibody molecule comprises a VHCDR1, a VHCDR2, a VHCDR3, a VLCDR1, a VLCDR2, and a VLCDR3 comprising the amino acid sequences of SEQ ID NOs: 326, 318, 325, 14, 15, and 328, respectively. In other embodiments, the antibody molecule comprises a VH and VL comprising the amino acid sequences of SEQ ID NOs: 327 and 330, respectively (or an amino acid sequence having at least about 85% (e.g., at least 90%, 95%, 97%, 98%, 99%, or 100%) sequence identity thereof).

In other embodiments, the aforesaid antibody molecules are chosen from a fully antibody, a bispecific antibody, Fab, F(ab'2, Fv, or a single chain Fv fragment (scFv).

In other embodiments, the aforesaid antibody molecules comprise a heavy chain constant region selected from IgG1, IgG2, IgG3, and IgG4.

In other embodiments, the aforesaid antibody molecules comprise a light chain constant region chosen from the light chain constant regions of kappa or lambda.

In some embodiments, the anti-CD73 antibody molecule comprises a heavy chain variable region, a light chain variable region, a heavy chain constant region, and/or a light chain constant region disclosed in Table 1. In some embodiments, the anti-CD73 antibody molecule comprises a heavy chain constant region, and/or a light chain constant region disclosed in Table 3. In some embodiments, the anti-CD73 antibody molecule comprises a heavy chain constant region comprising an amino acid sequence selected from the group consisting of SEQ ID NOs: 92-103, 119, and 120. In some embodiments, the anti-CD73 antibody molecule comprises a light chain constant region comprising the amino acid sequence of SEQ ID NO: 104.

Exemplary sequences of anti-CD73 antibodies are described in Tables 1 and 2 below.

TABLE 1

Amino acid and nucleotide sequences for exemplary anti-CD73 antibodies

| | | |
|---|---|---|
| 358 | | |
| SEQ ID NO: 1 (Combined) | HCDR1 | GGSISGRYWS |
| SEQ ID NO: 2 (Combined) | HCDR2 | YIYGTGSTNYNPSLKS |
| SEQ ID NO: 3 (Combined) | HCDR3 | ESQESPYNNWFDP |
| SEQ ID NO: 4 (Kabat) | HCDR1 | GRYWS |
| SEQ ID NO: 2 (Kabat) | HCDR2 | YIYGTGSTNYNPSLKS |
| SEQ ID NO: 3 (Kabat) | HCDR3 | ESQESPYNNWFDP |
| SEQ ID NO: 5 (Chothia) | HCDR1 | GGSISGR |
| SEQ ID NO: 6 (Chothia) | HCDR2 | YGTGS |
| SEQ ID NO: 3 (Chothia) | HCDR3 | ESQESPYNNWFDP |
| SEQ ID NO: 7 (IMGT) | HCDR1 | GGSISGRY |
| SEQ ID NO: 8 (IMGT) | HCDR2 | IYGTGST |
| SEQ ID NO: 9 (IMGT) | HCDR3 | ARESQESPYNNWFDP |
| SEQ ID NO: 199 (Alternative) | HCDR1 | GSISGRYWS |
| SEQ ID NO: 2 (Alternative) | HCDR2 | YIYGTGSTNYNPSLKS |
| SEQ ID NO: 9 (Alternative) | HCDR3 | ARESQESPYNNWFDP |

TABLE 1-continued

| Amino acid and nucleotide sequences for exemplary anti-CD73 antibodies | | |
|---|---|---|
| SEQ ID NO: 10 | VH | QVQLQESGPGLVKPSETLSLTCTVSGGSISGRYWSWIRQ PPGKGLEWIGYIYGTGSTNYNPSLKSRVTISVDTSKNQFS LKLSSVTAADTAVYYCARESQESPYNNWFDPWGQGTL VTVSS |
| SEQ ID NO: 11 | DNA VH | CAAGTGCAGCTGCAGGAATCTGGCCCTGGCCTGGTCA AGCCCTCCGAGACACTGTCCCTGACCTGCACCGTGTC CGGCGGCTCCATCTCCGGCCGGTACTGGTCTTGGATC CGGCAGCCTCCCGGCAAGGGCCTGGAATGGATCGGC TACATCTACGGCACCGGCTCCACCAACTACAACCCCA GCCTGAAGTCCAGAGTGACCATCTCCGTGGACACCTC CAAGAACCAGTTCTCCCTGAAGCTGTCCTCCGTGACC GCCGCTGACACCGCCGTGTACTACTGCGCCAGAGAGT CCCAGGAATCCCCTTACAACAATTGGTTCGACCCCTG GGGCCAGGGCACCCTGGTCACCGTGTCCTCT |
| SEQ ID NO: 12 | 358.A Heavy Chain | QVQLQESGPGLVKPSETLSLTCTVSGGSISGRYWSWIRQ PPGKGLEWIGYIYGTGSTNYNPSLKSRVTISVDTSKNQFS LKLSSVTAADTAVYYCARESQESPYNNWFDPWGQGTL VTVSSASTKGPSVFPLAPCSRSTSESTAALGCLVKDYFPE PVTVSWNSGALTSGVHTFPAVLQSSGLYSLSSVVTVPSS SLGTKTYTCNVDHKPSNTKVDKRVESKYGPPCPPCPAP EFLGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGX, wherein X is K or absent. |
| SEQ ID NO: 13 | 358.A DNA Heavy Chain | CAAGTGCAGCTGCAGGAATCTGGCCCTGGCCTGGTCA AGCCCTCCGAGACACTGTCCCTGACCTGCACCGTGTC CGGCGGCTCCATCTCCGGCCGGTACTGGTCTTGGATC CGGCAGCCTCCCGGCAAGGGCCTGGAATGGATCGGC TACATCTACGGCACCGGCTCCACCAACTACAACCCCA GCCTGAAGTCCAGAGTGACCATCTCCGTGGACACCTC CAAGAACCAGTTCTCCCTGAAGCTGTCCTCCGTGACC GCCGCTGACACCGCCGTGTACTACTGCGCCAGAGAGT CCCAGGAATCCCCTTACAACAATTGGTTCGACCCCTG GGGCCAGGGCACCCTGGTCACCGTGTCCTCTGCTTCC ACCAAGGGCCCCTCCGTGTTCCCTCTGGCCCCTTGCTC CCGGTCCACCTCCGAGTCTACCGCCGCTCTGGGCTGC CTCGTGAAGGACTACTTCCCCGAGCCCGTGACCGTGT CCTGGAACTCTGGCGCCCTGACCTCCGGCGTGCACAC CTTCCCTGCCGTGCTGCAGTCCTCCGGCCTGTACTCCC TGTCCAGCGTCGTGACCGTGCCCTCCTCCAGCCTGGG CACCAAGACCTACACCTGTAACGTGGACCACAAGCCC TCCAACACCAAAGTGGACAAGCGGGTGGAATCTAAG TACGGCCCTCCCTGCCCTCCTTGCCCTGCCCCTGAGTT CCTGGGCGGACCTTCCGTGTTCCTGTTCCCTCCAAAG CCCAAGGACACCCTGATGATCTCCCGGACCCCTGAAG TGACCTGCGTGGTGGTGGACGTGTCCCAGGAAGATCC CGAAGTCCAGTTCAATTGGTACGTGGACGGCGTGGAA GTGCACAACGCCAAGACCAAGCCCAGAGAGGAACAG TTCAACTCCACCTACCGGGTGGTGTCCGTGCTGACCG TGCTGCACCAGGACTGGCTGAACGGCAAAGAGTACA AGTGCAAAGTGTCCAACAAGGGCCTGCCCTCCAGCAT CGAAAAGACCATCTCCAAGGCCAAGGGCCAGCCCCG CGAGCCCCAAGTGTACACCCTGCCTCCCAGCCAGGAA GAGATGACCAAGAATCAAGTGTCCCTGACTTGTCTGG TCAAGGGCTTCTACCCCTCCGATATCGCCGTGGAGTG GGAGTCCAACGGCCAGCCCGAGAACAACTACAAGAC CACCCCTCCCGTGCTGGACTCCGACGGCTCCTTCTTCC TGTACTCTCGGCTGACCGTGGACAAGTCCCGGTGGCA GGAAGGCAACGTCTTCTCCTGCTCCGTGATGCACGAG GCCCTGCACAACCACTACACCCAGAAGTCCCTGTCCC TGTCTCTGGGC$X_1X_2X_3$, wherein $X_1$ is A, $X_2$ is A, and $X_3$ is G; or $X_1$ is absent, $X_2$ is absent, and $X_3$ is absent. |
| SEQ ID NO: 112 | 358.B Heavy Chain | QVQLQESGPGLVKPSETLSLTCTVSGGSISGRYWSWIRQ PPGKGLEWIGYIYGTGSTNYNPSLKSRVTISVDTSKNQFS LKLSSVTAADTAVYYCARESQESPYNNWFDPWGQGTL VTVSSASTKGPSVFPLAPCSRSTSESTAALGCLVKDYFPE PVTVSWNSGALTSGVHTFPAVLQSSGLYSLSSVVTVPSS SLGTKTYTCNVDHKPSNTKVDKRVESKYGPPCPPCPAP EFEGGPSVFLFPPKPKDTLMISRTPEVTCVVVDVSQEDPE |

TABLE 1-continued

| Amino acid and nucleotide sequences for exemplary anti-CD73 antibodies | | |
|---|---|---|
| | | VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGX, wherein X is K or absent |
| SEQ ID NO: 14 (Combined) | LCDR1 | RASQGISSWLA |
| SEQ ID NO: 15 (Combined) | LCDR2 | AASSLQS |
| SEQ ID NO: 16 (Combined) | LCDR3 | QQGNSFPRT |
| SEQ ID NO: 14 (Kabat) | LCDR1 | RASQGISSWLA |
| SEQ ID NO: 15 (Kabat) | LCDR2 | AASSLQS |
| SEQ ID NO: 16 (Kabat) | LCDR3 | QQGNSFPRT |
| SEQ ID NO: 17 (Chothia) | LCDR1 | SQGISSW |
| SEQ ID NO: 18 (Chothia) | LCDR2 | AAS |
| SEQ ID NO: 19 (Chothia) | LCDR3 | GNSFPR |
| SEQ ID NO: 20 (IMGT) | LCDR1 | QGISSW |
| SEQ ID NO: 18 (IMGT) | LCDR2 | AAS |
| SEQ ID NO: 16 (IMGT) | LCDR3 | QQGNSFPRT |
| SEQ ID NO: 14 (Alternative) | LCDR1 | RASQGISSWLA |
| SEQ ID NO: 15 (Alternative) | LCDR2 | AASSLQS |
| SEQ ID NO: 16 (Alternative) | LCDR3 | QQGNSFPRT |
| SEQ ID NO: 21 | VL | DIQMTQSPSSVSASVGDRVTITCRASQGISSWLAWYQQ KPGKAPKLLIYAASSLQSGVPSRFSGSGSGTDFTLTISSL QPEDFATYYCQQGNSFPRTFGGGTKVEIK |
| SEQ ID NO: 22 | DNA VL | GACATCCAGATGACCCAGAGCCCCTCCTCCGTGTCCG CCTCCGTGGGCGACAGAGTGACCATCACCTGTCGGGC CTCCCAGGGCATCTCCAGCTGGCTGGCCTGGTATCAG CAGAAGCCCGGCAAGGCCCCTAAGCTGCTGATCTACG CCGCCTCCAGCCTGCAGTCCGGCGTGCCCTCCAGATT CTCCGGCTCTGGCTCCGGCACCGACTTCACCCTGACC ATCAGCTCCCTGCAGCCCGAGGACTTCGCCACCTACT ACTGCCAGCAGGGCAACTCCTTCCCTCGGACCTTCGG CGGAGGCACCAAAGTGGAAATCAAG |
| SEQ ID NO: 23 | Light Chain | DIQMTQSPSSVSASVGDRVTITCRASQGISSWLAWYQQ KPGKAPKLLIYAASSLQSGVPSRFSGSGSGTDFTLTISSL QPEDFATYYCQQGNSFPRTFGGGTKVEIKRTVAAPSVFI FPPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC |
| SEQ ID NO: 24 | DNA Light Chain | GACATCCAGATGACCCAGAGCCCCTCCTCCGTGTCCG CCTCCGTGGGCGACAGAGTGACCATCACCTGTCGGGC CTCCCAGGGCATCTCCAGCTGGCTGGCCTGGTATCAG CAGAAGCCCGGCAAGGCCCCTAAGCTGCTGATCTACG CCGCCTCCAGCCTGCAGTCCGGCGTGCCCTCCAGATT CTCCGGCTCTGGCTCCGGCACCGACTTCACCCTGACC ATCAGCTCCCTGCAGCCCGAGGACTTCGCCACCTACT ACTGCCAGCAGGGCAACTCCTTCCCTCGGACCTTCGG CGGAGGCACCAAAGTGGAAATCAAGCGTACGGTGGC CGCTCCCTCCGTGTTCATCTTCCCACCCTCCGACGAGC AGCTGAAGTCCGGCACCGCCTCCGTCGTGTGCCTGCT GAACAACTTCTACCCTCGCGAGGCCAAAGTGCAGTGG AAAGTGGACAACGCCCTGCAGTCCGGCAACTCCCAG GAATCCGTCACCGAGCAGGACTCCAAGGACAGCACC |

TABLE 1-continued

| Amino acid and nucleotide sequences for exemplary anti-CD73 antibodies | | |
|---|---|---|
| | | TACTCCCTGTCCTCCACCCTGACCCTGTCCAAGGCCG ACTACGAGAAGCACAAAGTGTACGCCTGCGAAGTGA CCCACCAGGGCCTGTCCAGCCCCGTGACCAAGTCCTT CAACCGGGGCGAGTGC |
| 356 | | |
| SEQ ID NO: 25 (Combined) | HCDR1 | GGSIEGRYWS |
| SEQ ID NO: 26 (Combined) | HCDR2 | YIYGSGSTKYNPSLKS |
| SEQ ID NO: 3 (Combined) | HCDR3 | ESQESPYNNWFDP |
| SEQ ID NO: 4 (Kabat) | HCDR1 | GRYWS |
| SEQ ID NO: 26 (Kabat) | HCDR2 | YIYGSGSTKYNPSLKS |
| SEQ ID NO: 3 (Kabat) | HCDR3 | ESQESPYNNWFDP |
| SEQ ID NO: 27 (Chothia) | HCDR1 | GGSIEGR |
| SEQ ID NO: 28 (Chothia) | HCDR2 | YGSGS |
| SEQ ID NO: 3 (Chothia) | HCDR3 | ESQESPYNNWFDP |
| SEQ ID NO: 29 (IMGT) | HCDR1 | GGSIEGRY |
| SEQ ID NO: 30 (IMGT) | HCDR2 | IYGSGST |
| SEQ ID NO: 9 (IMGT) | HCDR3 | ARESQESPYNNWFDP |
| SEQ ID NO: 198 (Alternative) | HCDR1 | GSIEGRYWS |
| SEQ ID NO: 26 (Alternative) | HCDR2 | YIYGSGSTKYNPSLKS |
| SEQ ID NO: 9 (Alternative) | HCDR3 | ARESQESPYNNWFDP |
| SEQ ID NO: 31 | VH | QVQLQESGPGLVKPSETLSLTCTVSGGSIEGRYWSWIRQ PPGKGLEWIGYIYGSGSTKYNPSLKSRVTISVDTSKNQFS LKLSSVTAADTAVYYCARESQESPYNNWFDPWGQGTL VTVSS |
| SEQ ID NO: 32 | DNA VH | CAAGTGCAGCTGCAGGAATCTGGCCCTGGCCTGGTCA AGCCCTCCGAGACACTGTCCCTGACCTGCACCGTGTC CGGCGGCTCTATCGAGGGCCGGTACTGGTCCTGGATC CGGCAGCCTCCTGGCAAGGGCCTGGAATGGATCGGCT ACATCTACGGCTCCGGCTCCACCAAGTACAACCCCAG CCTGAAGTCCAGAGTGACCATCTCCGTGGACACCTCC AAGAACCAGTTCTCCCTGAAGCTGTCCTCCGTGACCG CCGCTGACACCGCCGTGTACTACTGCGCCAGAGAGTC CCAGGAATCCCCTTACAACAATTGGTTCGACCCCTGG GGCCAGGGCACCCTGGTCACCGTGTCCTCT |
| SEQ ID NO: 33 | 356.A Heavy Chain | QVQLQESGPGLVKPSETLSLTCTVSGGSIEGRYWSWIRQ PPGKGLEWIGYIYGSGSTKYNPSLKSRVTISVDTSKNQFS LKLSSVTAADTAVYYCARESQESPYNNWFDPWGQGTL VTVSSASTKGPSVFPLAPCSRSTSESTAALGCLVKDYFPE PVTVSWNSGALTSGVHTFPAVLQSSGLYSLSSVVTVPSS SLGTKTYTCNVDHKPSNTKVDKRVESKYGPPCPPCPAP EFLGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGX, wherein X is K or absent |
| SEQ ID NO: 34 | 356.A DNA Heavy Chain | CAAGTGCAGCTGCAGGAATCTGGCCCTGGCCTGGTCA AGCCCTCCGAGACACTGTCCCTGACCTGCACCGTGTC CGGCGGCTCTATCGAGGGCCGGTACTGGTCCTGGATC CGGCAGCCTCCTGGCAAGGGCCTGGAATGGATCGGCT ACATCTACGGCTCCGGCTCCACCAAGTACAACCCCAG CCTGAAGTCCAGAGTGACCATCTCCGTGGACACCTCC |

TABLE 1-continued

| Amino acid and nucleotide sequences for exemplary anti-CD73 antibodies | | |
|---|---|---|
| | | AAGAACCAGTTCTCCCTGAAGCTGTCCTCCGTGACCG CCGCTGACACCGCCGTGTACTACTGCGCCAGAGAGTC CCAGGAATCCCCTTACAACAATTGGTTCGACCCCTGG GGCCAGGGCACCCTGGTCACCGTGTCCTCTGCCTCCA CCAAGGGCCCCTCCGTGTTCCCTCTGGCCCCTTGCTCC CGGTCCACCTCCGAGTCTACCGCCGCTCTGGGCTGCC TCGTGAAGGACTACTTCCCCGAGCCCGTGACCGTGTC CTGGAACTCTGGCGCCCTGACCTCCGGCGTGCACACC TTCCCTGCCGTGCTGCAGTCCTCCGGCCTGTACTCCCT GTCCAGCGTCGTGACCGTGCCCTCCTCCAGCCTGGGC ACCAAGACCTACACCTGTAACGTGGACCACAAGCCCT CCAACACCAAAGTGGACAAGCGGGTGGAATCTAAGT ACGGCCCTCCCTGCCCTCCTTGCCCTGCCCCTGAGTTC CTGGGCGGACCTTCCGTGTTCCTGTTCCCTCCAAAGC CCAAGGACACCCTGATGATCTCCCGGACCCCTGAAGT GACCTGCGTGGTGGTGGACGTGTCCCAGGAAGATCCC GAAGTCCAGTTCAATTGGTACGTGGACGGCGTGGAA GTGCACAACGCCAAGACCAAGCCCAGAGAGGAACAG TTCAACTCCACCTACCGGGTGGTGTCCGTGCTGACCG TGCTGCACCAGGACTGGCTGAACGGCAAAGAGTACA AGTGCAAAGTGTCCAACAAGGGCCTGCCCTCCAGCAT CGAAAAGACCATCTCCAAGGCCAAGGGCCAGCCCCG CGAGCCCCAAGTGTACACCCTGCCTCCCAGCCAGGAA GAGATGACCAAGAATCAAGTGTCCCTGACTTGTCTGG TCAAGGGCTTCTACCCCTCCGATATCGCCGTGGAGTG GGAGTCCAACGGCCAGCCCGAGAACAACTACAAGAC CACCCCTCCCGTGCTGGACTCCGACGGCTCCTTCTTCC TGTACTCTCGGCTGACCGTGGACAAGTCCCGGTGGCA GGAAGGCAACGTCTTCTCCTGCTCCGTGATGCACGAG GCCCTGCACAACCACTACACCCAGAAGTCCCTGTCCC TGTCTCTGGGC $X_1X_2X_3$, wherein $X_1$ is A, $X_2$ is A, and $X_3$ is G; or $X_1$ is absent, $X_2$ is absent, and $X_3$ is absent. |
| SEQ ID NO: 113 | 356.B Heavy chain | QVQLQESGPGLVKPSETLSLTCTVSGGSIEGRYWSWIRQ PPGKGLEWIGYIYGSGSTKYNPSLKSRVTISVDTSKNQFS LKLSSVTAADTAVYYCARESQESPYNNWFDPWGQGTL VTVSSASTKGPSVFPLAPCSRSTSESTAALGCLVKDYFPE PVTVSWNSGALTSGVHTFPAVLQSSGLYSLSSVVTVPSS SLGTKTYTCNVDHKPSNTKVDKRVESKYGPPCPPCPAP EFEGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGX, wherein X is K or absent |
| SEQ ID NO: 14 (Combined) | LCDR1 | RASQGISSWLA |
| SEQ ID NO: 15 (Combined) | LCDR2 | AASSLQS |
| SEQ ID NO: 16 (Combined) | LCDR3 | QQGNSFPRT |
| SEQ ID NO: 14 (Kabat) | LCDR1 | RASQGISSWLA |
| SEQ ID NO: 15 (Kabat) | LCDR2 | AASSLQS |
| SEQ ID NO: 16 (Kabat) | LCDR3 | QQGNSFPRT |
| SEQ ID NO: 17 (Chothia) | LCDR1 | SQGISSW |
| SEQ ID NO: 18 (Chothia) | LCDR2 | AAS |
| SEQ ID NO: 19 (Chothia) | LCDR3 | GNSFPR |
| SEQ ID NO: 20 (IMGT) | LCDR1 | QGISSW |
| SEQ ID NO: 18 (IMGT) | LCDR2 | AAS |
| SEQ ID NO: 16 (IMGT) | LCDR3 | QQGNSFPRT |
| SEQ ID NO: 14 (Alternative) | LCDR1 | RASQGISSWLA |

TABLE 1-continued

| Amino acid and nucleotide sequences for exemplary anti-CD73 antibodies | | |
|---|---|---|
| SEQ ID NO: 15 (Alternative) | LCDR2 | AASSLQS |
| SEQ ID NO: 16 (Alternative) | LCDR3 | QQGNSFPRT |
| SEQ ID NO: 21 | VL | DIQMTQSPSSVSASVGDRVTITCRASQGISSWLAWYQQ KPGKAPKLLIYAASSLQSGVPSRFSGSGSGTDFTLTISSL QPEDFATYYCQQGNSFPRTFGGGTKVEIK |
| SEQ ID NO: 22 | DNA VL | GACATCCAGATGACCCAGAGCCCCTCCTCCGTGTCCG CCTCCGTGGGCGACAGAGTGACCATCACCTGTCGGGC CTCCCAGGGCATCTCCAGCTGGCTGGCCTGGTATCAG CAGAAGCCCGGCAAGGCCCCTAAGCTGCTGATCTACG CCGCCTCCAGCCTGCAGTCCGGCGTGCCCTCCAGATT CTCCGGCTCTGGCTCCGGCACCGACTTCACCCTGACC ATCAGCTCCCTGCAGCCCGAGGACTTCGCCACCTACT ACTGCCAGCAGGGCAACTCCTTCCCTCGGACCTTCGG CGGAGGCACCAAAGTGGAAATCAAG |
| SEQ ID NO: 23 | Light Chain | DIQMTQSPSSVSASVGDRVTITCRASQGISSWLAWYQQ KPGKAPKLLIYAASSLQSGVPSRFSGSGSGTDFTLTISSL QPEDFATYYCQQGNSFPRTFGGGTKVEIKRTVAAPSVFI FPPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC |
| SEQ ID NO: 24 | DNA Light Chain | GACATCCAGATGACCCAGAGCCCCTCCTCCGTGTCCG CCTCCGTGGGCGACAGAGTGACCATCACCTGTCGGGC CTCCCAGGGCATCTCCAGCTGGCTGGCCTGGTATCAG CAGAAGCCCGGCAAGGCCCCTAAGCTGCTGATCTACG CCGCCTCCAGCCTGCAGTCCGGCGTGCCCTCCAGATT CTCCGGCTCTGGCTCCGGCACCGACTTCACCCTGACC ATCAGCTCCCTGCAGCCCGAGGACTTCGCCACCTACT ACTGCCAGCAGGGCAACTCCTTCCCTCGGACCTTCGG CGGAGGCACCAAAGTGGAAATCAAGCGTACGGTGGC CGCTCCCTCCGTGTTCATCTTCCCACCCTCCGACGAGC AGCTGAAGTCCGGCACCGCCTCCGTCGTGTGCCTGCT GAACAACTTCTACCCTCGCGAGGCCAAAGTGCAGTGG AAAGTGGACAACGCCCTGCAGTCCGGCAACTCCCAG GAATCCGTCACCGAGCAGGACTCCAAGGACAGCACC TACTCCCTGTCCTCCACCCTGACCCTGTCCAAGGCCG ACTACGAGAAGCACAAAGTGTACGCCTGCGAAGTGA CCCACCAGGGCCTGTCCAGCCCCGTGACCAAGTCCTT CAACCGGGGCGAGTGC |
| 373 | | |
| SEQ ID NO: 35 (Combined) | HCDR1 | GFTFHRYAMS |
| SEQ ID NO: 36 (Combined) | HCDR2 | AISGSGMNTYYADSVKG |
| SEQ ID NO: 37 (Combined) | HCDR3 | GGLYGSGSYLSDFDL |
| SEQ ID NO: 38 (Kabat) | HCDR1 | RYAMS |
| SEQ ID NO: 36 (Kabat) | HCDR2 | AISGSGMNTYYADSVKG |
| SEQ ID NO: 37 (Kabat) | HCDR3 | GGLYGSGSYLSDFDL |
| SEQ ID NO: 39 (Chothia) | HCDR1 | GFTFHRY |
| SEQ ID NO: 40 (Chothia) | HCDR2 | SGSGMN |
| SEQ ID NO: 37 (Chothia) | HCDR3 | GGLYGSGSYLSDFDL |
| SEQ ID NO: 41 (IMGT) | HCDR1 | GFTFHRYA |
| SEQ ID NO: 42 (IMGT) | HCDR2 | ISGSGMNT |
| SEQ ID NO: 43 (IMGT) | HCDR3 | ARGGLYGSGSYLSDFDL |
| SEQ ID NO: 190 (Alternative) | HCDR1 | FTFHRYAMS |

TABLE 1-continued

| Amino acid and nucleotide sequences for exemplary anti-CD73 antibodies | | |
|---|---|---|
| SEQ ID NO: 36 (Alternative) | HCDR2 | AISGSGMNTYYADSVKG |
| SEQ ID NO: 43 (Alternative) | HCDR3 | ARGGLYGSGSYLSDFDL |
| SEQ ID NO: 44 | VH | EVQLLESGGGLVQPGGSLRLSCAASGFTFHRYAMSWVR QAPGKGLEWVSAISGSGMNTYYADSVKGRFTISRDNSK NTLYLQMNSLRAEDTAVYYCARGGLYGSGSYLSDFDL WGRGTLVTVSS |
| SEQ ID NO: 45 | DNA VH | GAAGTGCAGCTGCTGGAATCTGGCGGCGGACTGGTG CAGCCTGGCGGCTCCCTGAGACTGTCTTGCGCCGCCT CCGGCTTCACCTTCCACAGATACGCCATGTCCTGGGT CCGACAGGCCCCTGGCAAGGGCCTGGAGTGGGTGTC CGCCATCTCCGGCTCCGGCATGAACACCTACTACGCC GACTCCGTGAAGGGCCGGTTCACCATCTCCCGGGACA ACTCCAAGAACACCCTGTACCTGCAGATGAACTCCCT GCGGGCCGAGGACACCGCCGTGTACTACTGTGCCAG AGGCGGCCTGTACGGCTCCGGCTCCTACCTGTCCGAC TTCGACCTGTGGGGCAGAGGCACCCTGGTCACCGTGT CCTCC |
| SEQ ID NO: 46 | 373.A Heavy Chain | EVQLLESGGGLVQPGGSLRLSCAASGFTFHRYAMSWVR QAPGKGLEWVSAISGSGMNTYYADSVKGRFTISRDNSK NTLYLQMNSLRAEDTAVYYCARGGLYGSGSYLSDFDL WGRGTLVTVSSASTKGPSVFPLAPCSRSTSESTAALGCL VKDYFPEPVTVSWNSGALTSGVHTFPAVLQSSGLYSLSS VVTVPSSSLGTKTYTCNVDHKPSNTKVDKRVESKYGPP CPPCPAPEFLGGPSVFLFPPKPKDTLMISRTPEVTCVVVD VSQEDPEVQFNWYVDGVEVHNAKTKPREEQFNSTYRV VSVLTVLHQDWLNGKEYKCKVSNKGLPSSIEKTISKAK GQPREPQVYTLPPSQEEMTKNQVSLTCLVKGFYPSDIAV EWESNGQPENNYKTTPPVLDSDGSFFLYSRLTVDKSRW QEGNVFSCSVMHEALHNHYTQKSLSLSLGX, wherein X is K or absent |
| SEQ ID NO: 47 | 373.A DNA Heavy Chain | GAAGTGCAGCTGCTGGAATCTGGCGGCGGACTGGTG CAGCCTGGCGGCTCCCTGAGACTGTCTTGCGCCGCCT CCGGCTTCACCTTCCACAGATACGCCATGTCCTGGGT CCGACAGGCCCCTGGCAAGGGCCTGGAGTGGGTGTC CGCCATCTCCGGCTCCGGCATGAACACCTACTACGCC GACTCCGTGAAGGGCCGGTTCACCATCTCCCGGGACA ACTCCAAGAACACCCTGTACCTGCAGATGAACTCCCT GCGGGCCGAGGACACCGCCGTGTACTACTGTGCCAG AGGCGGCCTGTACGGCTCCGGCTCCTACCTGTCCGAC TTCGACCTGTGGGGCAGAGGCACCCTGGTCACCGTGT CCTCCGCCTCCACAAAGGGCCCCTCCGTGTTCCCTCT GGCCCCTTGCTCCCGGTCCACCTCCGAGTCTACCGCC GCTCTGGGCTGCCTCGTGAAGGACTACTTCCCCGAGC CCGTGACCGTGTCCTGGAACTCTGGCGCCCTGACCTC CGGCGTGCACACCTTCCCTGCCGTGCTGCAGTCCTCC GGCCTGTACTCCCTGTCCAGCGTCGTGACCGTGCCCT CCTCCAGCCTGGGCACCAAGACCTACACCTGTAACGT GGACCACAAGCCCTCCAACACCAAAGTGGACAAGCG GGTGGAATCTAAGTACGGCCCTCCCTGCCCTCCTTGC CCTGCCCCTGAGTTCCTGGGCGGACCTTCCGTGTTCCT GTTCCCTCCAAAGCCCAAGGACACCCTGATGATCTCC CGGACCCCTGAAGTGACCTGCGTGGTGGTGGACGTGT CCCAGGAAGATCCCGAAGTCCAGTTCAATTGGTACGT GGACGGCGTGGAAGTGCACAACGCCAAGACCAAGCC CAGAGAGGAACAGTTCAACTCCACCTACCGGGTGGT GTCCGTGCTGACCGTGCTGCACCAGGACTGGCTGAAC GGCAAAGAGTACAAGTGCAAAGTGTCCAACAAGGGC CTGCCCTCCAGCATCGAAAAGACCATCTCCAAGGCCA AGGGCCAGCCCCGCGAGCCCCAAGTGTACACCCTGCC TCCCAGCCAGGAAGAGATGACCAAGAATCAAGTGTC CCTGACTTGTCTGGTCAAGGGCTTCTACCCCTCCGAT ATCGCCGTGGAGTGGGAGTCCAACGGCCAGCCCGAG AACAACTACAAGACCACCCCTCCCGTGCTGGACTCCG ACGGCTCCTTCTTCCTGTACTCTCGGCTGACCGTGGAC AAGTCCCGGTGGCAGGAAGGCAACGTCTTCTCCTGCT CCGTGATGCACGAGGCCCTGCACAACCACTACACCCA GAAGTCCCTGTCCCTGTCTCTGGGC $X_1X_2X_3$, wherein $X_1$ is A, $X_2$ is A, and $X_3$ is G; or $X_1$ is absent, $X_2$ is absent, and $X_3$ is absent. |

TABLE 1-continued

| Amino acid and nucleotide sequences for exemplary anti-CD73 antibodies | | |
|---|---|---|
| SEQ ID NO: 114 | 373.B Heavy chain | EVQLLESGGGLVQPGGSLRLSCAASGFTFHRYAMSWVR QAPGKGLEWVSAISGSGMNTYYADSVKGRFTISRDNSK NTLYLQMNSLRAEDTAVYYCARGGLYGSGSYLSDFDL WGRGTLVTVSSASTKGPSVFPLAPCSRSTSESTAALGCL VKDYFPEPVTVSWNSGALTSGVHTFPAVLQSSGLYSLSS VVTVPSSSLGTKTYTCNVDHKPSNTKVDKRVESKYGPP CPPCPAPEFEGGPSVFLFPPKPKDTLMISRTPEVTCVVVD VSQEDPEVQFNWYVDGVEVHNAKTKPREEQFNSTYRV VSVLTVLHQDWLNGKEYKCKVSNKGLPSSIEKTISKAK GQPREPQVYTLPPSQEEMTKNQVSLTCLVKGFYPSDIAV EWESNGQPENNYKTTPPVLDSDGSFFLYSRLTVDKSRW QEGNVFSCSVMHEALHNHYTQKSLSLSLGX, wherein X is K or absent |
| SEQ ID NO: 48 (Combined) | LCDR1 | RASQSVGSNLA |
| SEQ ID NO: 49 (Combined) | LCDR2 | GASTRAT |
| SEQ ID NO: 50 (Combined) | LCDR3 | QQHNAFPYT |
| SEQ ID NO: 48 (Kabat) | LCDR1 | RASQSVGSNLA |
| SEQ ID NO: 49 (Kabat) | LCDR2 | GASTRAT |
| SEQ ID NO: 50 (Kabat) | LCDR3 | QQHNAFPYT |
| SEQ ID NO: 51 (Chothia) | LCDR1 | SQSVGSN |
| SEQ ID NO: 52 (Chothia) | LCDR2 | GAS |
| SEQ ID NO: 53 (Chothia) | LCDR3 | HNAFPY |
| SEQ ID NO: 54 (IMGT) | LCDR1 | QSVGSN |
| SEQ ID NO: 52 (IMGT) | LCDR2 | GAS |
| SEQ ID NO: 50 (IMGT) | LCDR3 | QQHNAFPYT |
| SEQ ID NO: 48 (Alternative) | LCDR1 | RASQSVGSNLA |
| SEQ ID NO: 49 (Alternative) | LCDR2 | GASTRAT |
| SEQ ID NO: 50 (Alternative) | LCDR3 | QQHNAFPYT |
| SEQ ID NO: 55 | VL | EIVLTQSPATLSVSPGERATLSCRASQSVGSNLAWYQQK PGQAPRLLIYGASTRATGIPARFSGSGSGTEFTLTISSLQS EDFAVYYCQQHNAFPYTFGGGTKVEIK |
| SEQ ID NO: 56 | DNA VL | GAGATCGTGCTGACACAGTCCCCTGCCACCCTGTCTG TGTCTCCCGGCGAGAGAGCCACCCTGAGCTGCAGAGC CTCCCAGTCCGTGGGCTCCAACCTGGCCTGGTATCAG CAGAAGCCCGGCCAGGCCCCTCGGCTGCTGATCTACG GCGCCTCTACCAGAGCCACCGGCATCCCTGCCAGATT CTCCGGCTCTGGCTCCGGCACCGAGTTCACCCTGACC ATCTCCAGCCTGCAGTCCGAGGACTTCGCCGTGTACT ACTGCCAGCAGCACAACGCCTTCCCTTACACCTTCGG CGGAGGCACCAAAGTGGAAATCAAG |
| SEQ ID NO: 57 | Light Chain | EIVLTQSPATLSVSPGERATLSCRASQSVGSNLAWYQQK PGQAPRLLIYGASTRATGIPARFSGSGSGTEFTLTISSLQS EDFAVYYCQQHNAFPYTFGGGTKVEIKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC |
| SEQ ID NO: 58 | DNA Light Chain | GAGATCGTGCTGACACAGTCCCCTGCCACCCTGTCTG TGTCTCCCGGCGAGAGAGCCACCCTGAGCTGCAGAGC CTCCCAGTCCGTGGGCTCCAACCTGGCCTGGTATCAG CAGAAGCCCGGCCAGGCCCCTCGGCTGCTGATCTACG GCGCCTCTACCAGAGCCACCGGCATCCCTGCCAGATT CTCCGGCTCTGGCTCCGGCACCGAGTTCACCCTGACC |

TABLE 1-continued

| Amino acid and nucleotide sequences for exemplary anti-CD73 antibodies | | |
|---|---|---|
| | | ATCTCCAGCCTGCAGTCCGAGGACTTCGCCGTGTACT ACTGCCAGCAGCACAACGCCTTCCCTTACACCTTCGG CGGAGGCACCAAAGTGGAAATCAAGCGTACGGTGGC CGCTCCCTCCGTGTTCATCTTCCCACCCTCCGACGAGC AGCTGAAGTCCGGCACCGCCTCCGTCGTGTGCCTGCT GAACAACTTCTACCCTCGCGAGGCCAAAGTGCAGTGG AAAGTGGACAACGCCCTGCAGTCCGGCAACTCCCAG GAATCCGTCACCGAGCAGGACTCCAAGGACAGCACC TACTCCCTGTCCTCCACCCTGACCCTGTCCAAGGCCG ACTACGAGAAGCACAAAGTGTACGCCTGCGAAGTGA CCCACCAGGGCCTGTCCAGCCCCGTGACCAAGTCCTT CAACCGGGGCGAGTGC |
| 350 | | |
| SEQ ID NO: 59 (Combined) | HCDR1 | GGSIERYYWS |
| SEQ ID NO: 60 (Combined) | HCDR2 | YIYGRGSTNYNPSLKS |
| SEQ ID NO: 3 (Combined) | HCDR3 | ESQESPYNNWFDP |
| SEQ ID NO: 61 (Kabat) | HCDR1 | RYYWS |
| SEQ ID NO: 60 (Kabat) | HCDR2 | YIYGRGSTNYNPSLKS |
| SEQ ID NO: 3 (Kabat) | HCDR3 | ESQESPYNNWFDP |
| SEQ ID NO: 62 (Chothia) | HCDR1 | GGSIERY |
| SEQ ID NO: 63 (Chothia) | HCDR2 | YGRGS |
| SEQ ID NO: 3 (Chothia) | HCDR3 | ESQESPYNNWFDP |
| SEQ ID NO: 64 (IMGT) | HCDR1 | GGSIERYY |
| SEQ ID NO: 65 (IMGT) | HCDR2 | IYGRGST |
| SEQ ID NO: 9 (IMGT) | HCDR3 | ARESQESPYNNWFDP |
| SEQ ID NO: 197 (Alternative) | HCDR1 | GSIERYYWS |
| SEQ ID NO: 60 (Alternative) | HCDR2 | YIYGRGSTNYNPSLKS |
| SEQ ID NO: 9 (Alternative) | HCDR3 | ARESQESPYNNWFDP |
| SEQ ID NO: 66 | VH | QVQLQESGPGLVKPSETLSLTCTVSGGSIERYYWSWIRQ PPGKGLEWIGYIYGRGSTNYNPSLKSRVTISVDTSKNQF SLKLSSVTAADTAVYYCARESQESPYNNWFDPWGQGT LVTVSS |
| SEQ ID NO: 67 | DNA VH | CAAGTGCAGCTGCAGGAATCTGGCCCTGGCCTGGTCA AGCCCTCCGAGACACTGTCCCTGACCTGCACCGTGTC CGGCGGCTCCATCGAGCGGTACTACTGGTCCTGGATC CGGCAGCCTCCCGGCAAGGGCCTGGAATGGATCGGC TACATCTACGGCAGAGGCTCCACCAACTACAACCCCA GCCTGAAGTCCAGAGTGACCATCTCCGTGGACACCTC CAAGAACCAGTTCTCCCTGAAGCTGTCCTCCGTGACC GCCGCTGACACCGCCGTGTACTACTGCGCCAGAGAGT CCCAGGAATCCCCTTACAACAATTGGTTCGACCCCTG GGGCCAGGGCACCCTGGTCACCGTGTCCTCT |
| SEQ ID NO: 68 | 350.A Heavy Chain | QVQLQESGPGLVKPSETLSLTCTVSGGSIERYYWSWIRQ PPGKGLEWIGYIYGRGSTNYNPSLKSRVTISVDTSKNQF SLKLSSVTAADTAVYYCARESQESPYNNWFDPWGQGT LVTVSSASTKGPSVFPLAPCSRSTSESTAALGCLVKDYFP EPVTVSWNSGALTSGVHTFPAVLQSSGLYSLSSVVTVPS SSLGTKTYTCNVDHKPSNTKVDKRVESKYGPPCPPCPAP EFLGGPSVFLFPPKPKDTLMISRTPEVTCVVVDVSQEDPE VQFNWYVDGVEVHNAKTKPREEQFNSTYRVVSVLTVL |

TABLE 1-continued

| Amino acid and nucleotide sequences for exemplary anti-CD73 antibodies | | |
|---|---|---|
| | | HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGX, wherein X is K or absent |
| SEQ ID NO: 69 | 350.A DNA Heavy Chain | CAAGTGCAGCTGCAGGAATCTGGCCCTGGCCTGGTCA AGCCCTCCGAGACACTGTCCCTGACCTGCACCGTGTC CGGCGGCTCCATCGAGCGGTACTACTGGTCCTGGATC CGGCAGCCTCCCGGCAAGGGCCTGGAATGGATCGGC TACATCTACGGCAGAGGCTCCACCAACTACAACCCCA GCCTGAAGTCCAGAGTGACCATCTCCGTGGACACCTC CAAGAACCAGTTCTCCCTGAAGCTGTCCTCCGTGACC GCCGCTGACACCGCCGTGTACTACTGCGCCAGAGAGT CCCAGGAATCCCCTTACAACAATTGGTTCGACCCCTG GGGCCAGGGCACCCTGGTCACCGTGTCCTCTGCCTCC ACCAAGGGCCCCTCCGTGTTCCCTCTGGCCCCTTGCTC CCGGTCCACCTCCGAGTCTACCGCCGCTCTGGGCTGC CTCGTGAAGGACTACTTCCCCGAGCCCGTGACCGTGT CCTGGAACTCTGGCGCCCTGACCTCCGGCGTGCACAC CTTCCCTGCCGTGCTGCAGTCCTCCGGCCTGTACTCCC TGTCCAGCGTCGTGACCGTGCCCTCCTCCAGCCTGGG CACCAAGACCTACACCTGTAACGTGGACCACAAGCCC TCCAACACCAAAGTGGACAAGCGGGTGGAATCTAAG TACGGCCCTCCCTGCCCTCCTTGCCCTGCCCCTGAGTT CCTGGGCGGACCTTCCGTGTTCCTGTTCCCTCCAAAG CCCAAGGACACCCTGATGATCTCCCGGACCCCTGAAG TGACCTGCGTGGTGGTGGACGTGTCCCAGGAAGATCC CGAAGTCCAGTTCAATTGGTACGTGGACGGCGTGGAA GTGCACAACGCCAAGACCAAGCCCAGAGAGGAACAG TTCAACTCCACCTACCGGGTGGTGTCCGTGCTGACCG TGCTGCACCAGGACTGGCTGAACGGCAAAGAGTACA AGTGCAAAGTGTCCAACAAGGGCCTGCCCTCCAGCAT CGAAAAGACCATCTCCAAGGCCAAGGGCCAGCCCCG CGAGCCCCAAGTGTACACCCTGCCTCCCAGCCAGGAA GAGATGACCAAGAATCAAGTGTCCCTGACTTGTCTGG TCAAGGGCTTCTACCCCTCCGATATCGCCGTGGAGTG GGAGTCCAACGGCCAGCCCGAGAACAACTACAAGAC CACCCCTCCCGTGCTGGACTCCGACGGCTCCTTCTTCC TGTACTCTCGGCTGACCGTGGACAAGTCCCGGTGGCA GGAAGGCAACGTCTTCTCCTGCTCCGTGATGCACGAG GCCCTGCACAACCACTACACCCAGAAGTCCCTGTCCC TGTCTCTGGGC $X_1X_2X_3$, wherein $X_1$ is A, $X_2$ is A, and $X_3$ is G; or $X_1$ is absent, $X_2$ is absent, and $X_3$ is absent. |
| SEQ ID NO: 115 | 350.B Heavy chain | QVQLQESGPGLVKPSETLSLTCTVSGGSIERYYWSWIRQ PPGKGLEWIGYIYGRGSTNYNPSLKSRVTISVDTSKNQF SLKLSSVTAADTAVYYCARESQESPYNNWFDPWGQGT LVTVSSASTKGPSVFPLAPCSRSTSESTAALGCLVKDYFP EPVTVSWNSGALTSGVHTFPAVLQSSGLYSLSSVVTVPS SSLGTKTYTCNVDHKPSNTKVDKRVESKYGPPCPPCPAP EFEGGPSVFLFPPKPKDTLMISRTPEVTCVVVDVSQEDPE VQFNWYVDGVEVHNAKTKPREEQFNSTYRVVSVLTVL HQDWLNGKEYKCKVSNKGLPSSIEKTISKAKGQPREPQ VYTLPPSQEEMTKNQVSLTCLVKGFYPSDIAVEWESNG QPENNYKTTPPVLDSDGSFFLYSRLTVDKSRWQEGNVF SCSVMHEALHNHYTQKSLSLSLGX, wherein X is K or absent |
| SEQ ID NO: 331 | 350 Fab heavy chain | QVQLQESGPGLVKPSETLSLTCTVSGGSIERYYWSWIRQ PPGKGLEWIGYIYGRGSTNYNPSLKSRVTISVDTSKNQF SLKLSSVTAADTAVYYCARESQESPYNNWFDPWGQGT LVTVSSASTKGPSVFPLAPCSRSTSESTAALGCLVKDYFP EPVTVSWNSGALTSGVHTFPAVLQSSGLYSLSSVVTVPS SSLGTKTYTCNVDHKPSNTKVDKRVESKYGP |
| SEQ ID NO: 14 (Combined) | LCDR1 | RASQGISSWLA |
| SEQ ID NO: 15 (Combined) | LCDR2 | AASSLQS |
| SEQ ID NO: 16 (Combined) | LCDR3 | QQGNSFPRT |
| SEQ ID NO: 14 (Kabat) | LCDR1 | RASQGISSWLA |

TABLE 1-continued

| Amino acid and nucleotide sequences for exemplary anti-CD73 antibodies | | |
|---|---|---|
| SEQ ID NO: 15 (Kabat) | LCDR2 | AASSLQS |
| SEQ ID NO: 16 (Kabat) | LCDR3 | QQGNSFPRT |
| SEQ ID NO: 17 (Chothia) | LCDR1 | SQGISSW |
| SEQ ID NO: 18 (Chothia) | LCDR2 | AAS |
| SEQ ID NO: 19 (Chothia) | LCDR3 | GNSFPR |
| SEQ ID NO: 20 (IMGT) | LCDR1 | QGISSW |
| SEQ ID NO: 18 (IMGT) | LCDR2 | AAS |
| SEQ ID NO: 16 (IMGT) | LCDR3 | QQGNSFPRT |
| SEQ ID NO: 14 (Alternative) | LCDR1 | RASQGISSWLA |
| SEQ ID NO: 15 (Alternative) | LCDR2 | AASSLQS |
| SEQ ID NO: 16 (Alternative) | LCDR3 | QQGNSFPRT |
| SEQ ID NO: 21 | VL | DIQMTQSPSSVSASVGDRVTITCRASQGISSWLAWYQQ KPGKAPKLLIYAASSLQSGVPSRFSGSGSGTDFTLTISSL QPEDFATYYCQQGNSFPRTFGGGTKVEIK |
| SEQ ID NO: 22 | DNA VL | GACATCCAGATGACCCAGAGCCCCTCCTCCGTGTCCG CCTCCGTGGGCGACAGAGTGACCATCACCTGTCGGGC CTCCCAGGGCATCTCCAGCTGGCTGGCCTGGTATCAG CAGAAGCCCGGCAAGGCCCCTAAGCTGCTGATCTACG CCGCCTCCAGCCTGCAGTCCGGCGTGCCCTCCAGATT CTCCGGCTCTGGCTCCGGCACCGACTTCACCCTGACC ATCAGCTCCCTGCAGCCCGAGGACTTCGCCACCTACT ACTGCCAGCAGGGCAACTCCTTCCCTCGGACCTTCGG CGGAGGCACCAAAGTGGAAATCAAG |
| SEQ ID NO: 23 | Light Chain | DIQMTQSPSSVSASVGDRVTITCRASQGISSWLAWYQQ KPGKAPKLLIYAASSLQSGVPSRFSGSGSGTDFTLTISSL QPEDFATYYCQQGNSFPRTFGGGTKVEIKRTVAAPSVFI FPPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC |
| SEQ ID NO: 24 | DNA Light Chain | GACATCCAGATGACCCAGAGCCCCTCCTCCGTGTCCG CCTCCGTGGGCGACAGAGTGACCATCACCTGTCGGGC CTCCCAGGGCATCTCCAGCTGGCTGGCCTGGTATCAG CAGAAGCCCGGCAAGGCCCCTAAGCTGCTGATCTACG CCGCCTCCAGCCTGCAGTCCGGCGTGCCCTCCAGATT CTCCGGCTCTGGCTCCGGCACCGACTTCACCCTGACC ATCAGCTCCCTGCAGCCCGAGGACTTCGCCACCTACT ACTGCCAGCAGGGCAACTCCTTCCCTCGGACCTTCGG CGGAGGCACCAAAGTGGAAATCAAGCGTACGGTGGC CGCTCCCTCCGTGTTCATCTTCCCACCCTCCGACGAGC AGCTGAAGTCCGGCACCGCCTCCGTCGTGTGCCTGCT GAACAACTTCTACCCTCGCGAGGCCAAAGTGCAGTGG AAAGTGGACAACGCCCTGCAGTCCGGCAACTCCCAG GAATCCGTCACCGAGCAGGACTCCAAGGACAGCACC TACTCCCTGTCCTCCACCCTGACCCTGTCCAAGGCCG ACTACGAGAAGCACAAAGTGTACGCCTGCGAAGTGA CCCACCAGGGCCTGTCCAGCCCCGTGACCAAGTCCTT CAACCGGGGCGAGTGC |
| 374 | | |
| SEQ ID NO: 70 (Combined) | HCDR1 | GFTFSYNAMS |
| SEQ ID NO: 71 (Combined) | HCDR2 | SISGTGGSTYYADSVKG |
| SEQ ID NO: 37 (Combined) | HCDR3 | GGLYGSGSYLSDFDL |
| SEQ ID NO: 72 (Kabat) | HCDR1 | YNAMS |

TABLE 1-continued

| Amino acid and nucleotide sequences for exemplary anti-CD73 antibodies | | |
|---|---|---|
| SEQ ID NO: 71 (Kabat) | HCDR2 | SISGTGGSTYYADSVKG |
| SEQ ID NO: 37 (Kabat) | HCDR3 | GGLYGSGSYLSDFDL |
| SEQ ID NO: 73 (Chothia) | HCDR1 | GFTFSYN |
| SEQ ID NO: 74 (Chothia) | HCDR2 | SGTGGS |
| SEQ ID NO: 37 (Chothia) | HCDR3 | GGLYGSGSYLSDFDL |
| SEQ ID NO: 75 (IMGT) | HCDR1 | GFTFSYNA |
| SEQ ID NO: 76 (IMGT) | HCDR2 | ISGTGGST |
| SEQ ID NO: 43 (IMGT) | HCDR3 | ARGGLYGSGSYLSDFDL |
| SEQ ID NO: 191 (Alternative) | HCDR1 | FTFSYNAMS |
| SEQ ID NO: 71 (Alternative) | HCDR2 | SISGTGGSTYYADSVKG |
| SEQ ID NO: 43 (Alternative) | HCDR3 | ARGGLYGSGSYLSDFDL |
| SEQ ID NO: 77 | VH | EVQLLESGGGLVQPGGSLRLSCAASGFTFSYNAMSWVR QAPGKGLEWVSSISGTGGSTYYADSVKGRFTISRDNSKN TLYLQMNSLRAEDTAVYYCARGGLYGSGSYLSDFDLW GRGTLVTVSS |
| SEQ ID NO: 78 | DNA VH | GAAGTGCAGCTGCTGGAATCTGGCGGCGGACTGGTG CAGCCTGGCGGCTCCCTGAGACTGTCTTGCGCCGCCT CCGGCTTCACCTTCTCCTACAACGCCATGTCCTGGGTC CGACAGGCCCCTGGCAAGGGCCTGGAGTGGGTGTCCT CCATCTCCGGCACCGGCGGCTCCACCTACTACGCCGA CTCTGTGAAGGGCCGGTTCACCATCTCCCGGGACAAC TCCAAGAACACCCTGTACCTGCAGATGAACTCCCTGC GGGCCGAGGACACCGCCGTGTACTACTGTGCCAGAG GCGGCCTGTACGGCTCCGGCTCCTACCTGTCCGACTT CGACCTGTGGGGCAGAGGCACCCTGGTCACCGTGTCC TCC |
| SEQ ID NO: 79 | 374.A Heavy Chain | EVQLLESGGGLVQPGGSLRLSCAASGFTFSYNAMSWVR QAPGKGLEWVSSISGTGGSTYYADSVKGRFTISRDNSKN TLYLQMNSLRAEDTAVYYCARGGLYGSGSYLSDFDLW GRGTLVTVSSASTKGPSVFPLAPCSRSTSESTAALGCLV KDYFPEPVTVSWNSGALTSGVHTFPAVLQSSGLYSLSSV VTVPSSSLGTKTYTCNVDHKPSNTKVDKRVESKYGPPC PPCPAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAKG QPREPQVYTLPPSQEEMTKNQVSLTCLVKGFYPSDIAVE WESNGQPENNYKTTPPVLDSDGSFFLYSRLTVDKSRWQ EGNVFSCSVMHEALHNHYTQKSLSLSLGX, wherein X is K or absent |
| SEQ ID NO: 80 | 374.A DNA Heavy Chain | GAAGTGCAGCTGCTGGAATCTGGCGGCGGACTGGTG CAGCCTGGCGGCTCCCTGAGACTGTCTTGCGCCGCCT CCGGCTTCACCTTCTCCTACAACGCCATGTCCTGGGTC CGACAGGCCCCTGGCAAGGGCCTGGAGTGGGTGTCCT CCATCTCCGGCACCGGCGGCTCCACCTACTACGCCGA CTCTGTGAAGGGCCGGTTCACCATCTCCCGGGACAAC TCCAAGAACACCCTGTACCTGCAGATGAACTCCCTGC GGGCCGAGGACACCGCCGTGTACTACTGTGCCAGAG GCGGCCTGTACGGCTCCGGCTCCTACCTGTCCGACTT CGACCTGTGGGGCAGAGGCACCCTGGTCACCGTGTCC TCCGCCTCCACAAAGGGCCCCTCCGTGTTCCCTCTGG CCCCTTGCTCCCGGTCCACCTCCGAGTCTACCGCCGCT CTGGGCTGCCTCGTGAAGGACTACTTCCCCGAGCCCG TGACCGTGTCCTGGAACTCTGGCGCCCTGACCTCCGG CGTGCACACCTTCCCTGCCGTGCTGCAGTCCTCCGGC CTGTACTCCCTGTCCAGCGTCGTGACCGTGCCCTCCTC CAGCCTGGGCACCAAGACCTACACCTGTAACGTGGAC CACAAGCCCTCCAACACCAAAGTGGACAAGCGGGTG GAATCTAAGTACGGCCCTCCCTGCCCTCCTTGCCCTG CCCCTGAGTTCCTGGGCGGACCTTCCGTGTTCCTGTTC CCTCCAAAGCCCAAGGACACCCTGATGATCTCCCGGA |

TABLE 1-continued

| Amino acid and nucleotide sequences for exemplary anti-CD73 antibodies | | |
|---|---|---|
| | | CCCCTGAAGTGACCTGCGTGGTGGTGGACGTGTCCCA GGAAGATCCCGAAGTCCAGTTCAATTGGTACGTGGAC GGCGTGGAAGTGCACAACGCCAAGACCAAGCCCAGA GAGGAACAGTTCAACTCCACCTACCGGGTGGTGTCCG TGCTGACCGTGCTGCACCAGGACTGGCTGAACGGCAA AGAGTACAAGTGCAAAGTGTCCAACAAGGGCCTGCC CTCCAGCATCGAAAAGACCATCTCCAAGGCCAAGGG CCAGCCCCGCGAGCCCCAAGTGTACACCCTGCCTCCC AGCCAGGAAGAGATGACCAAGAATCAAGTGTCCCTG ACTTGTCTGGTCAAGGGCTTCTACCCCTCCGATATCG CCGTGGAGTGGGAGTCCAACGGCCAGCCCGAGAACA ACTACAAGACCACCCCTCCCGTGCTGGACTCCGACGG CTCCTTCTTCCTGTACTCTCGGCTGACCGTGGACAAGT CCCGGTGGCAGGAAGGCAACGTCTTCTCCTGCTCCGT GATGCACGAGGCCCTGCACAACCACTACACCCAGAA GTCCCTGTCCCTGTCTCTGGGC $X_1X_2X_3$, wherein $X_1$ is A, $X_2$ is A, and $X_3$ is G; or $X_1$ is absent, $X_2$ is absent, and $X_3$ is absent. |
| SEQ ID NO: 116 | 374.B Heavy chain | EVQLLESGGGLVQPGGSLRLSCAASGFTFSYNAMSWVR QAPGKGLEWVSSISGTGGSTYYADSVKGRFTISRDNSKN TLYLQMNSLRAEDTAVYYCARGGLYGSGSYLSDFDLW GRGTLVTVSSASTKGPSVFPLAPCSRSTSESTAALGCLV KDYFPEPVTVSWNSGALTSGVHTFPAVLQSSGLYSLSSV VTVPSSSLGTKTYTCNVDHKPSNTKVDKRVESKYGPPC PPCPAPEFEGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAKG QPREPQVYTLPPSQEEMTKNQVSLTCLVKGFYPSDIAVE WESNGQPENNYKTTPPVLDSDGSFFLYSRLTVDKSRWQ EGNVFSCSVMHEALHNHYTQKSLSLSLGX, wherein X is K or absent |
| SEQ ID NO: 48 (Combined) | LCDR1 | RASQSVGSNLA |
| SEQ ID NO: 49 (Combined) | LCDR2 | GASTRAT |
| SEQ ID NO: 50 (Combined) | LCDR3 | QQHNAFPYT |
| SEQ ID NO: 48 (Kabat) | LCDR1 | RASQSVGSNLA |
| SEQ ID NO: 49 (Kabat) | LCDR2 | GASTRAT |
| SEQ ID NO: 50 (Kabat) | LCDR3 | QQHNAFPYT |
| SEQ ID NO: 51 (Chothia) | LCDR1 | SQSVGSN |
| SEQ ID NO: 52 (Chothia) | LCDR2 | GAS |
| SEQ ID NO: 53 (Chothia) | LCDR3 | HNAFPY |
| SEQ ID NO: 54 (IMGT) | LCDR1 | QSVGSN |
| SEQ ID NO: 52 (IMGT) | LCDR2 | GAS |
| SEQ ID NO: 50 (IMGT) | LCDR3 | QQHNAFPYT |
| SEQ ID NO: 48 (Alternative) | LCDR1 | RASQSVGSNLA |
| SEQ ID NO: 49 (Alternative) | LCDR2 | GASTRAT |
| SEQ ID NO: 50 (Alternative) | LCDR3 | QQHNAFPYT |
| SEQ ID NO: 55 | VL | EIVLTQSPATLSVSPGERATLSCRASQSVGSNLAWYQQK PGQAPRLLIYGASTRATGIPARFSGSGSGTEFTLTISSLQS EDFAVYYCQQHNAFPYTFGGGTKVEIK |
| SEQ ID NO: 56 | DNA VL | GAGATCGTGCTGACACAGTCCCCTGCCACCCTGTCTG TGTCTCCCGGCGAGAGAGCCACCCTGAGCTGCAGAGC CTCCCAGTCCGTGGGCTCCAACCTGGCCTGGTATCAG CAGAAGCCCGGCCAGGCCCCTCGGCTGCTGATCTACG |

TABLE 1-continued

| Amino acid and nucleotide sequences for exemplary anti-CD73 antibodies | | |
|---|---|---|
| | | GCGCCTCTACCAGAGCCACCGGCATCCCTGCCAGATT CTCCGGCTCTGGCTCCGGCACCGAGTTCACCCTGACC ATCTCCAGCCTGCAGTCCGAGGACTTCGCCGTGTACT ACTGCCAGCAGCACAACGCCTTCCCTTACACCTTCGG CGGAGGCACCAAAGTGGAAATCAAG |
| SEQ ID NO: 57 | Light Chain | EIVLTQSPATLSVSPGERATLSCRASQSVGSNLAWYQQK PGQAPRLLIYGASTRATGIPARFSGSGSGTEFTLTISSLQS EDFAVYYCQQHNAFPYTFGGGTKVEIKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC |
| SEQ ID NO: 58 | DNA Light Chain | GAGATCGTGCTGACACAGTCCCCTGCCACCCTGTCTG TGTCTCCCGGCGAGAGAGCCACCCTGAGCTGCAGAGC CTCCCAGTCCGTGGGCTCCAACCTGGCCTGGTATCAG CAGAAGCCCGGCCAGGCCCCTCGGCTGCTGATCTACG GCGCCTCTACCAGAGCCACCGGCATCCCTGCCAGATT CTCCGGCTCTGGCTCCGGCACCGAGTTCACCCTGACC ATCTCCAGCCTGCAGTCCGAGGACTTCGCCGTGTACT ACTGCCAGCAGCACAACGCCTTCCCTTACACCTTCGG CGGAGGCACCAAAGTGGAAATCAAGCGTACGGTGGC CGCTCCCTCCGTGTTCATCTTCCCACCCTCCGACGAGC AGCTGAAGTCCGGCACCGCCTCCGTCGTGTGCCTGCT GAACAACTTCTACCCTCGCGAGGCCAAAGTGCAGTGG AAAGTGGACAACGCCCTGCAGTCCGGCAACTCCCAG GAATCCGTCACCGAGCAGGACTCCAAGGACAGCACC TACTCCCTGTCCTCCACCCTGACCCTGTCCAAGGCCG ACTACGAGAAGCACAAAGTGTACGCCTGCGAAGTGA CCCACCAGGGCCTGTCCAGCCCCGTGACCAAGTCCTT CAACCGGGGCGAGTGC |
| 379 | | |
| SEQ ID NO: 81 (Combined) | HCDR1 | GFTFSRYAMS |
| SEQ ID NO: 71 (Combined) | HCDR2 | SISGTGGSTYYADSVKG |
| SEQ ID NO: 37 (Combined) | HCDR3 | GGLYGSGSYLSDFDL |
| SEQ ID NO: 38 (Kabat) | HCDR1 | RYAMS |
| SEQ ID NO: 71 (Kabat) | HCDR2 | SISGTGGSTYYADSVKG |
| SEQ ID NO: 37 (Kabat) | HCDR3 | GGLYGSGSYLSDFDL |
| SEQ ID NO: 82 (Chothia) | HCDR1 | GFTFSRY |
| SEQ ID NO: 74 (Chothia) | HCDR2 | SGTGGS |
| SEQ ID NO: 37 (Chothia) | HCDR3 | GGLYGSGSYLSDFDL |
| SEQ ID NO: 83 (IMGT) | HCDR1 | GFTFSRYA |
| SEQ ID NO: 76 (IMGT) | HCDR2 | ISGTGGST |
| SEQ ID NO: 43 (IMGT) | HCDR3 | ARGGLYGSGSYLSDFDL |
| SEQ ID NO: 192 (Alternative) | HCDR1 | FTFSRYAMS |
| SEQ ID NO: 71 (Alternative) | HCDR2 | SISGTGGSTYYADSVKG |
| SEQ ID NO: 43 (Alternative) | HCDR3 | ARGGLYGSGSYLSDFDL |
| SEQ ID NO: 84 | VH | EVQLLESGGGLVQPGGSLRLSCAASGFTFSRYAMSWVR QAPGKGLEWVSSISGTGGSTYYADSVKGRFTISRDNSKN TLYLQMNSLRAEDTAVYYCARGGLYGSGSYLSDFDLW GRGTLVTVSS |
| SEQ ID NO: 85 | DNA VH | GAAGTGCAGCTGCTGGAATCTGGCGGCGGACTGGTG CAGCCTGGCGGCTCCCTGAGACTGTCTTGCGCCGCCT CCGGCTTCACCTTCTCCAGATACGCCATGTCCTGGGT |

TABLE 1-continued

| Amino acid and nucleotide sequences for exemplary anti-CD73 antibodies | | |
|---|---|---|
| | | CCGACAGGCCCCTGGCAAGGGCCTGGAGTGGGTGTC CTCCATCTCCGGCACCGGCGGCTCCACCTACTACGCC GACTCTGTGAAGGGCCGGTTCACCATCTCCCGGGACA ACTCCAAGAACACCCTGTACCTGCAGATGAACTCCCT GCGGGCCGAGGACACCGCCGTGTACTACTGTGCCAG AGGCGGCCTGTACGGCTCCGGCTCCTACCTGTCCGAC TTCGACCTGTGGGGCAGAGGCACCCTGGTCACCGTGT CCTCC |
| SEQ ID NO: 86 | 379.A Heavy Chain | EVQLLESGGGLVQPGGSLRLSCAASGFTFSRYAMSWVR QAPGKGLEWVSSISGTGGSTYYADSVKGRFTISRDNSKN TLYLQMNSLRAEDTAVYYCARGGLYGSGSYLSDFDLW GRGTLVTVSSASTKGPSVFPLAPCSRSTSESTAALGCLV KDYFPEPVTVSWNSGALTSGVHTFPAVLQSSGLYSLSSV VTVPSSSLGTKTYTCNVDHKPSNTKVDKRVESKYGPPC PPCPAPEFLGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAKG QPREPQVYTLPPSQEEMTKNQVSLTCLVKGFYPSDIAVE WESNGQPENNYKTTPPVLDSDGSFFLYSRLTVDKSRWQ EGNVFSCSVMHEALHNHYTQKSLSLSLGX, wherein X is K or absent |
| SEQ ID NO: 87 | 379.A DNA Heavy Chain | GAAGTGCAGCTGCTGGAATCTGGCGGCGGACTGGTG CAGCCTGGCGGCTCCCTGAGACTGTCTTGCGCCGCCT CCGGCTTCACCTTCTCCAGATACGCCATGTCCTGGGT CCGACAGGCCCCTGGCAAGGGCCTGGAGTGGGTGTC CTCCATCTCCGGCACCGGCGGCTCCACCTACTACGCC GACTCTGTGAAGGGCCGGTTCACCATCTCCCGGGACA ACTCCAAGAACACCCTGTACCTGCAGATGAACTCCCT GCGGGCCGAGGACACCGCCGTGTACTACTGTGCCAG AGGCGGCCTGTACGGCTCCGGCTCCTACCTGTCCGAC TTCGACCTGTGGGGCAGAGGCACCCTGGTCACCGTGT CCTCCGCCTCCACAAAGGGCCCCTCCGTGTTCCCTCT GGCCCCTTGCTCCCGGTCCACCTCCGAGTCTACCGCC GCTCTGGGCTGCCTCGTGAAGGACTACTTCCCCGAGC CCGTGACCGTGTCCTGGAACTCTGGCGCCCTGACCTC CGGCGTGCACACCTTCCCTGCCGTGCTGCAGTCCTCC GGCCTGTACTCCCTGTCCAGCGTCGTGACCGTGCCCT CCTCCAGCCTGGGCACCAAGACCTACACCTGTAACGT GGACCACAAGCCCTCCAACACCAAAGTGGACAAGCG GGTGGAATCTAAGTACGGCCCTCCCTGCCCTCCTTGC CCTGCCCCTGAGTTCCTGGGCGGACCTTCCGTGTTCCT GTTCCCTCCAAAGCCCAAGGACACCCTGATGATCTCC CGGACCCCTGAAGTGACCTGCGTGGTGGTGGACGTGT CCCAGGAAGATCCCGAAGTCCAGTTCAATTGGTACGT GGACGGCGTGGAAGTGCACAACGCCAAGACCAAGCC CAGAGAGGAACAGTTCAACTCCACCTACCGGGTGGT GTCCGTGCTGACCGTGCTGCACCAGGACTGGCTGAAC GGCAAAGAGTACAAGTGCAAAGTGTCCAACAAGGGC CTGCCCTCCAGCATCGAAAAGACCATCTCCAAGGCCA AGGGCCAGCCCCGCGAGCCCCAAGTGTACACCCTGCC TCCCAGCCAGGAAGAGATGACCAAGAATCAAGTGTC CCTGACTTGTCTGGTCAAGGGCTTCTACCCCTCCGAT ATCGCCGTGGAGTGGGAGTCCAACGGCCAGCCCGAG AACAACTACAAGACCACCCCTCCCGTGCTGGACTCCG ACGGCTCCTTCTTCCTGTACTCTCGGCTGACCGTGGAC AAGTCCCGGTGGCAGGAAGGCAACGTCTTCTCCTGCT CCGTGATGCACGAGGCCCTGCACAACCACTACACCCA GAAGTCCCTGTCCCTGTCTCTGGGC $X_1X_2X_3$, wherein $X_1$ is A, $X_2$ is A, and $X_3$ is G; or $X_1$ is absent, $X_2$ is absent, and $X_3$ is absent. |
| SEQ ID NO: 117 | 379.B Heavy chain | EVQLLESGGGLVQPGGSLRLSCAASGFTFSRYAMSWVR QAPGKGLEWVSSISGTGGSTYYADSVKGRFTISRDNSKN TLYLQMNSLRAEDTAVYYCARGGLYGSGSYLSDFDLW GRGTLVTVSSASTKGPSVFPLAPCSRSTSESTAALGCLV KDYFPEPVTVSWNSGALTSGVHTFPAVLQSSGLYSLSSV VTVPSSSLGTKTYTCNVDHKPSNTKVDKRVESKYGPPC PPCPAPEFEGGPSVFLFPPKPKDTLMISRTPEVTCVVVDV SQEDPEVQFNWYVDGVEVHNAKTKPREEQFNSTYRVV SVLTVLHQDWLNGKEYKCKVSNKGLPSSIEKTISKAKG QPREPQVYTLPPSQEEMTKNQVSLTCLVKGFYPSDIAVE WESNGQPENNYKTTPPVLDSDGSFFLYSRLTVDKSRWQ EGNVFSCSVMHEALHNHYTQKSLSLSLGX, wherein X is K or absent |

TABLE 1-continued

| Amino acid and nucleotide sequences for exemplary anti-CD73 antibodies | | |
|---|---|---|
| SEQ ID NO: 48 (Combined) | LCDR1 | RASQSVGSNLA |
| SEQ ID NO: 49 (Combined) | LCDR2 | GASTRAT |
| SEQ ID NO: 50 (Combined) | LCDR3 | QQHNAFPYT |
| SEQ ID NO: 48 (Kabat) | LCDR1 | RASQSVGSNLA |
| SEQ ID NO: 49 (Kabat) | LCDR2 | GASTRAT |
| SEQ ID NO: 50 (Kabat) | LCDR3 | QQHNAFPYT |
| SEQ ID NO: 51 (Chothia) | LCDR1 | SQSVGSN |
| SEQ ID NO: 52 (Chothia) | LCDR2 | GAS |
| SEQ ID NO: 53 (Chothia) | LCDR3 | HNAFPY |
| SEQ ID NO: 54 (IMGT) | LCDR1 | QSVGSN |
| SEQ ID NO: 52 (IMGT) | LCDR2 | GAS |
| SEQ ID NO: 50 (IMGT) | LCDR3 | QQHNAFPYT |
| SEQ ID NO: 48 (Alternative) | LCDR1 | RASQSVGSNLA |
| SEQ ID NO: 49 (Alternative) | LCDR2 | GASTRAT |
| SEQ ID NO: 50 (Alternative) | LCDR3 | QQHNAFPYT |
| SEQ ID NO: 55 | VL | EIVLTQSPATLSVSPGERATLSCRASQSVGSNLAWYQQK<br>PGQAPRLLIYGASTRATGIPARFSGSGSGTEFTLTISSLQS<br>EDFAVYYCQQHNAFPYTFGGGTKVEIK |
| SEQ ID NO: 56 | DNA VL | GAGATCGTGCTGACACAGTCCCCTGCCACCCTGTCTG<br>TGTCTCCCGGCGAGAGAGCCACCCTGAGCTGCAGAGC<br>CTCCCAGTCCGTGGGCTCCAACCTGGCCTGGTATCAG<br>CAGAAGCCCGGCCAGGCCCCTCGGCTGCTGATCTACG<br>GCGCCTCTACCAGAGCCACCGGCATCCCTGCCAGATT<br>CTCCGGCTCTGGCTCCGGCACCGAGTTCACCCTGACC<br>ATCTCCAGCCTGCAGTCCGAGGACTTCGCCGTGTACT<br>ACTGCCAGCAGCACAACGCCTTCCCTTACACCTTCGG<br>CGGAGGCACCAAAGTGGAAATCAAG |
| SEQ ID NO: 57 | Light Chain | EIVLTQSPATLSVSPGERATLSCRASQSVGSNLAWYQQK<br>PGQAPRLLIYGASTRATGIPARFSGSGSGTEFTLTISSLQS<br>EDFAVYYCQQHNAFPYTFGGGTKVEIKRTVAAPSVFIFP<br>PSDEQLKSGTASVVCLLNNFYPREAKVQWKVDNALQS<br>GNSQESVTEQDSKDSTYSLSSTLTLSKADYEKHKVYAC<br>EVTHQGLSSPVTKSFNRGEC |
| SEQ ID NO: 58 | DNA Light Chain | GAGATCGTGCTGACACAGTCCCCTGCCACCCTGTCTG<br>TGTCTCCCGGCGAGAGAGCCACCCTGAGCTGCAGAGC<br>CTCCCAGTCCGTGGGCTCCAACCTGGCCTGGTATCAG<br>CAGAAGCCCGGCCAGGCCCCTCGGCTGCTGATCTACG<br>GCGCCTCTACCAGAGCCACCGGCATCCCTGCCAGATT<br>CTCCGGCTCTGGCTCCGGCACCGAGTTCACCCTGACC<br>ATCTCCAGCCTGCAGTCCGAGGACTTCGCCGTGTACT<br>ACTGCCAGCAGCACAACGCCTTCCCTTACACCTTCGG<br>CGGAGGCACCAAAGTGGAAATCAAGCGTACGGTGGC<br>CGCTCCCTCCGTGTTCATCTTCCCACCCTCCGACGAGC<br>AGCTGAAGTCCGGCACCGCCTCCGTCGTGTGCCTGCT<br>GAACAACTTCTACCCTCGCGAGGCCAAAGTGCAGTGG<br>AAAGTGGACAACGCCCTGCAGTCCGGCAACTCCCAG<br>GAATCCGTCACCGAGCAGGACTCCAAGGACAGCACC<br>TACTCCCTGTCCTCCACCCTGACCCTGTCCAAGGCCG<br>ACTACGAGAAGCACAAAGTGTACGCCTGCGAAGTGA<br>CCCACCAGGGCCTGTCCAGCCCCGTGACCAAGTCCTT<br>CAACCGGGGCGAGTGC |

TABLE 1-continued

| Amino acid and nucleotide sequences for exemplary anti-CD73 antibodies | | |
|---|---|---|
| 376 | | |
| SEQ ID NO: 135 (Combined) | HCDR1 | GFTFRSYAMS |
| SEQ ID NO: 136 (Combined) | HCDR2 | AITGSGGLTYYADSVKG |
| SEQ ID NO: 37 (Combined) | HCDR3 | GGLYGSGSYLSDFDL |
| SEQ ID NO: 137 (Kabat) | HCDR1 | SYAMS |
| SEQ ID NO: 136 (Kabat) | HCDR2 | AITGSGGLTYYADSVKG |
| SEQ ID NO: 37 (Kabat) | HCDR3 | GGLYGSGSYLSDFDL |
| SEQ ID NO: 138 (Chothia) | HCDR1 | GFTFRSY |
| SEQ ID NO: 139 (Chothia) | HCDR2 | TGSGGL |
| SEQ ID NO: 37 (Chothia) | HCDR3 | GGLYGSGSYLSDFDL |
| SEQ ID NO: 140 (IMGT) | HCDR1 | GFTFRSYA |
| SEQ ID NO: 141 (IMGT) | HCDR2 | ITGSGGLT |
| SEQ ID NO: 43 (IMGT) | HCDR3 | ARGGLYGSGSYLSDFDL |
| SEQ ID NO: 193 (Alternative) | HCDR1 | FTFRSYAMS |
| SEQ ID NO: 136 (Alternative) | HCDR2 | AITGSGGLTYYADSVKG |
| SEQ ID NO: 43 (Alternative) | HCDR3 | ARGGLYGSGSYLSDFDL |
| SEQ ID NO: 142 | VH | EVQLLESGGGLVQPGGSLRLSCAASGFTFRSYAMSWVR QAPGKGLEWVSAITGSGGLTYYADSVKGRFTISRDNSK NTLYLQMNSLRAEDTAVYYCARGGLYGSGSYLSDFDL WGRGTLVTVSS |
| SEQ ID NO: 143 | DNA VH | GAGGTGCAGCTGTTGGAGTCTGGGGGAGGCTTGGTAC AGCCTGGGGGGTCCCTGAGACTCTCCTGTGCAGCCTC TGGATTCACCTTTCGTAGCTATGCCATGAGCTGGGTC CGCCAGGCTCCAGGGAAGGGGCTGGAGTGGGTCTCA GCTATTACGGGAAGTGGTGGTTTGACATACTACGCAG ACTCCGTGAAGGGCCGGTTCACCATCTCCAGAGACAA TTCCAAGAACACGCTGTATCTGCAAATGAACAGCCTG AGAGCCGAGGACACGGCGGTGTACTACTGCGCCAGA GGTGGATTGTACGGAAGCGGAAGCTACTTGAGTGACT TCGACCTATGGGGGAGAGGTACCTTGGTCACCGTCTC CTCA |
| SEQ ID NO: 48 (Combined) | LCDR1 | RASQSVGSNLA |
| SEQ ID NO: 49 (Combined) | LCDR2 | GASTRAT |
| SEQ ID NO: 50 (Combined) | LCDR3 | QQHNAFPYT |
| SEQ ID NO: 48 (Kabat) | LCDR1 | RASQSVGSNLA |
| SEQ ID NO: 49 (Kabat) | LCDR2 | GASTRAT |
| SEQ ID NO: 50 (Kabat) | LCDR3 | QQHNAFPYT |
| SEQ ID NO: 51 (Chothia) | LCDR1 | SQSVGSN |
| SEQ ID NO: 52 (Chothia) | LCDR2 | GAS |
| SEQ ID NO: 53 (Chothia) | LCDR3 | HNAFPY |
| SEQ ID NO: 54 (IMGT) | LCDR1 | QSVGSN |

TABLE 1-continued

| Amino acid and nucleotide sequences for exemplary anti-CD73 antibodies | | |
|---|---|---|
| SEQ ID NO: 52 (IMGT) | LCDR2 | GAS |
| SEQ ID NO: 50 (IMGT) | LCDR3 | QQHNAFPYT |
| SEQ ID NO: 48 (Alternative) | LCDR1 | RASQSVGSNLA |
| SEQ ID NO: 49 (Alternative) | LCDR2 | GASTRAT |
| SEQ ID NO: 50 (Alternative) | LCDR3 | QQHNAFPYT |
| SEQ ID NO: 55 | VL | EIVLTQSPATLSVSPGERATLSCRASQSVGSNLAWYQQK PGQAPRLLIYGASTRATGIPARFSGSGSGTEFTLTISSLQS EDFAVYYCQQHNAFPYTFGGGTKVEIK |
| SEQ ID NO: 144 | DNA VL | GAAATAGTGTTGACGCAGTCTCCAGCCACCCTGTCTG TGTCTCCAGGGGAAAGAGCCACCCTCTCCTGCAGGGC CAGTCAGAGTGTTGGCAGCAACTTAGCCTGGTACCAG CAGAAACCTGGCCAGGCTCCCAGGCTCCTCATCTATG GTGCATCCACCAGGGCCACTGGTATCCCAGCCAGGTT CAGTGGCAGTGGGTCTGGGACAGAGTTCACTCTCACC ATCAGCAGCCTGCAGTCTGAAGATTTTGCAGTTTATT ACTGTCAGCAGCACAATGCCTTCCCTTACACTTTTGG CGGAGGGACCAAGGTTGAGATCAAA |
| 377 | | |
| SEQ ID NO: 145 (Combined) | HCDR1 | GFTFKSYAMS |
| SEQ ID NO: 146 (Combined) | HCDR2 | AISGSGSYTYYADSVKG |
| SEQ ID NO: 37 (Combined) | HCDR3 | GGLYGSGSYLSDFDL |
| SEQ ID NO: 137 (Kabat) | HCDR1 | SYAMS |
| SEQ ID NO: 146 (Kabat) | HCDR2 | AISGSGSYTYYADSVKG |
| SEQ ID NO: 37 (Kabat) | HCDR3 | GGLYGSGSYLSDFDL |
| SEQ ID NO: 147 (Chothia) | HCDR1 | GFTFKSY |
| SEQ ID NO: 148 (Chothia) | HCDR2 | SGSGSY |
| SEQ ID NO: 37 (Chothia) | HCDR3 | GGLYGSGSYLSDFDL |
| SEQ ID NO: 149 (IMGT) | HCDR1 | GFTFKSYA |
| SEQ ID NO: 150 (IMGT) | HCDR2 | ISGSGSYT |
| SEQ ID NO: 43 (IMGT) | HCDR3 | ARGGLYGSGSYLSDFDL |
| SEQ ID NO: 194 (Alternative) | HCDR1 | FTFKSYAMS |
| SEQ ID NO: 146 (Alternative) | HCDR2 | AISGSGSYTYYADSVKG |
| SEQ ID NO: 43 (Alternative) | HCDR3 | ARGGLYGSGSYLSDFDL |
| SEQ ID NO: 151 | VH | EVQLLESGGGLVQPGGSLRLSCAASGFTFKSYAMSWVR QAPGKGLEWVSAISGSGSYTYYADSVKGRFTISRDNSK NTLYLQMNSLRAEDTAVYYCARGGLYGSGSYLSDFDL WGRGTLVTVSS |
| SEQ ID NO: 152 | DNA VH | GAGGTGCAGCTGTTGGAGTCTGGGGGAGGCTTGGTAC AGCCTGGGGGGTCCCTGAGACTCTCCTGTGCAGCCTC TGGATTCACCTTTAAGAGCTATGCCATGAGTTGGGTC CGCCAGGCTCCAGGGAAGGGGCTGGAGTGGGTCTCA GCTATTAGTGGAAGTGGTTCGTATACATACTACGCAG ACTCCGTGAAGGGCCGGTTCACCATCTCCAGAGACAA TTCCAAGAACACGCTGTATCTGCAAATGAACAGCCTG AGAGCCGAGGACACGGCGGTGTACTACTGCGCCAGA |

TABLE 1-continued

| Amino acid and nucleotide sequences for exemplary anti-CD73 antibodies | | |
|---|---|---|
| | | GGTGGATTGTACGGAAGCGGAAGCTACTTGAGTGACT TCGACCTATGGGGGAGAGGTACCTTGGTCACCGTCTC CTCA |
| SEQ ID NO: 48 (Combined) | LCDR1 | RASQSVGSNLA |
| SEQ ID NO: 49 (Combined) | LCDR2 | GASTRAT |
| SEQ ID NO: 50 (Combined) | LCDR3 | QQHNAFPYT |
| SEQ ID NO: 48 (Kabat) | LCDR1 | RASQSVGSNLA |
| SEQ ID NO: 49 (Kabat) | LCDR2 | GASTRAT |
| SEQ ID NO: 50 (Kabat) | LCDR3 | QQHNAFPYT |
| SEQ ID NO: 51 (Chothia) | LCDR1 | SQSVGSN |
| SEQ ID NO: 52 (Chothia) | LCDR2 | GAS |
| SEQ ID NO: 53 (Chothia) | LCDR3 | HNAFPY |
| SEQ ID NO: 54 (IMGT) | LCDR1 | QSVGSN |
| SEQ ID NO: 52 (IMGT) | LCDR2 | GAS |
| SEQ ID NO: 50 (IMGT) | LCDR3 | QQHNAFPYT |
| SEQ ID NO: 48 (Alternative) | LCDR1 | RASQSVGSNLA |
| SEQ ID NO: 49 (Alternative) | LCDR2 | GASTRAT |
| SEQ ID NO: 50 (Alternative) | LCDR3 | QQHNAFPYT |
| SEQ ID NO: 55 | VL | EIVLTQSPATLSVSPGERATLSCRASQSVGSNLAWYQQK PGQAPRLLIYGASTRATGIPARFSGSGSGTEFTLTISSLQS EDFAVYYCQQHNAFPYTFGGGTKVEIK |
| SEQ ID NO: 144 | DNA VL | GAAATAGTGTTGACGCAGTCTCCAGCCACCCTGTCTG TGTCTCCAGGGGAAAGAGCCACCCTCTCCTGCAGGGC CAGTCAGAGTGTTGGCAGCAACTTAGCCTGGTACCAG CAGAAACCTGGCCAGGCTCCCAGGCTCCTCATCTATG GTGCATCCACCAGGGCCACTGGTATCCCAGCCAGGTT CAGTGGCAGTGGGTCTGGGACAGAGTTCACTCTCACC ATCAGCAGCCTGCAGTCTGAAGATTTTGCAGTTTATT ACTGTCAGCAGCACAATGCCTTCCCTTACACTTTTGG CGGAGGGACCAAGGTTGAGATCAAA |
| 930 | | |
| SEQ ID NO: 153 (Combined) | HCDR1 | GFTFSSYAMS |
| SEQ ID NO: 154 (Combined) | HCDR2 | AISGSGGSTYYADSVKG |
| SEQ ID NO: 37 (Combined) | HCDR3 | GGLYGSGSYLSDFDL |
| SEQ ID NO: 137 (Kabat) | HCDR1 | SYAMS |
| SEQ ID NO: 154 (Kabat) | HCDR2 | AISGSGGSTYYADSVKG |
| SEQ ID NO: 37 (Kabat) | HCDR3 | GGLYGSGSYLSDFDL |
| SEQ ID NO: 155 (Chothia) | HCDR1 | GFTFSSY |
| SEQ ID NO: 156 (Chothia) | HCDR2 | SGSGGS |
| SEQ ID NO: 37 (Chothia) | HCDR3 | GGLYGSGSYLSDFDL |
| SEQ ID NO: 157 (IMGT) | HCDR1 | GFTFSSYA |

TABLE 1-continued

| Amino acid and nucleotide sequences for exemplary anti-CD73 antibodies | | |
|---|---|---|
| SEQ ID NO: 158 (IMGT) | HCDR2 | ISGSGGST |
| SEQ ID NO: 43 (IMGT) | HCDR3 | ARGGLYGSGSYLSDFDL |
| SEQ ID NO: 195 (Alternative) | HCDR1 | FTFSSYAMS |
| SEQ ID NO: 154 (Alternative) | HCDR2 | AISGSGGSTYYADSVKG |
| SEQ ID NO: 43 (Alternative) | HCDR3 | ARGGLYGSGSYLSDFDL |
| SEQ ID NO: 159 | VH | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCARGGLYGSGSYLSDFDL WGRGTLVTVSS |
| SEQ ID NO: 160 | DNA VH | GAGGTGCAGCTGTTGGAGTCTGGGGGAGGCTTGGTAC AGCCTGGGGGGTCCCTGAGACTCTCCTGTGCAGCCTC TGGATTCACCTTTAGCAGCTATGCCATGAGCTGGGTC CGCCAGGCTCCAGGGAAGGGGCTGGAGTGGGTCTCA GCTATTAGTGGTAGTGGTGGTAGCACATACTACGCAG ACTCCGTGAAGGGCCGGTTCACCATCTCCAGAGACAA TTCCAAGAACACGCTGTATCTGCAAATGAACAGCCTG AGAGCCGAGGACACGGCGGTGTACTACTGCGCCAGA GGTGGATTGTACGGAAGCGGAAGCTACTTGAGTGACT TCGACCTATGGGGGAGAGGTACCTTGGTCACCGTCTC CTCA |
| SEQ ID NO: 48 (Combined) | LCDR1 | RASQSVGSNLA |
| SEQ ID NO: 49 (Combined) | LCDR2 | GASTRAT |
| SEQ ID NO: 50 (Combined) | LCDR3 | QQHNAFPYT |
| SEQ ID NO: 48 (Kabat) | LCDR1 | RASQSVGSNLA |
| SEQ ID NO: 49 (Kabat) | LCDR2 | GASTRAT |
| SEQ ID NO: 50 (Kabat) | LCDR3 | QQHNAFPYT |
| SEQ ID NO: 51 (Chothia) | LCDR1 | SQSVGSN |
| SEQ ID NO: 52 (Chothia) | LCDR2 | GAS |
| SEQ ID NO: 53 (Chothia) | LCDR3 | HNAFPY |
| SEQ ID NO: 54 (IMGT) | LCDR1 | QSVGSN |
| SEQ ID NO: 52 (IMGT) | LCDR2 | GAS |
| SEQ ID NO: 50 (IMGT) | LCDR3 | QQHNAFPYT |
| SEQ ID NO: 48 (Alternative) | LCDR1 | RASQSVGSNLA |
| SEQ ID NO: 49 (Alternative) | LCDR2 | GASTRAT |
| SEQ ID NO: 50 (Alternative) | LCDR3 | QQHNAFPYT |
| SEQ ID NO: 55 | VL | EIVLTQSPATLSVSPGERATLSCRASQSVGSNLAWYQQK PGQAPRLLIYGASTRATGIPARFSGSGSGTEFTLTISSLQS EDFAVYYCQQHNAFPYTFGGGTKVEIK |
| SEQ ID NO: 144 | DNA VL | GAAATAGTGTTGACGCAGTCTCCAGCCACCCTGTCTG TGTCTCCAGGGGAAAGAGCCACCCTCTCCTGCAGGGC CAGTCAGAGTGTTGGCAGCAACTTAGCCTGGTACCAG CAGAAACCTGGCCAGGCTCCCAGGCTCCTCATCTATG GTGCATCCACCAGGGCCACTGGTATCCCAGCCAGGTT CAGTGGCAGTGGGTCTGGGACAGAGTTCACTCTCACC ATCAGCAGCCTGCAGTCTGAAGATTTTGCAGTTTATT |

TABLE 1-continued

| Amino acid and nucleotide sequences for exemplary anti-CD73 antibodies | | |
|---|---|---|
| | | ACTGTCAGCAGCACAATGCCTTCCCTTACACTTTTGG CGGAGGGACCAAGGTTGAGATCAAA |
| 918 | | |
| SEQ ID NO: 161 (Combined) | HCDR1 | GGSISSYYWS |
| SEQ ID NO: 162 (Combined) | HCDR2 | YIYSSGSTNYNPSLKS |
| SEQ ID NO: 3 (Combined) | HCDR3 | ESQESPYNNWFDP |
| SEQ ID NO: 163 (Kabat) | HCDR1 | SYYWS |
| SEQ ID NO: 162 (Kabat) | HCDR2 | YIYSSGSTNYNPSLKS |
| SEQ ID NO: 3 (Kabat) | HCDR3 | ESQESPYNNWFDP |
| SEQ ID NO: 164 (Chothia) | HCDR1 | GGSISSY |
| SEQ ID NO: 165 (Chothia) | HCDR2 | YSSGS |
| SEQ ID NO: 3 (Chothia) | HCDR3 | ESQESPYNNWFDP |
| SEQ ID NO: 166 (IMGT) | HCDR1 | GGSISSYY |
| SEQ ID NO: 167 (IMGT) | HCDR2 | IYSSGST |
| SEQ ID NO: 9 (IMGT) | HCDR3 | ARESQESPYNNWFDP |
| SEQ ID NO: 200 (Alternative) | HCDR1 | GSISSYYWS |
| SEQ ID NO: 162 (Alternative) | HCDR2 | YIYSSGSTNYNPSLKS |
| SEQ ID NO: 9 (Alternative) | HCDR3 | ARESQESPYNNWFDP |
| SEQ ID NO: 168 | VH | QVQLQESGPGLVKPSETLSLTCTVSGGSISSYYWSWIRQ PPGKGLEWIGYIYSSGSTNYNPSLKSRVTISVDTSKNQFS LKLSSVTAADTAVYYCARESQESPYNNWFDPWGQGTL VTVSS |
| SEQ ID NO: 169 | DNA VH | CAGGTGCAGCTGCAGGAGTCGGGCCCAGGACTGGTG AAGCCTTCGGAGACCCTGTCCCTCACCTGCACTGTCT CTGGTGGCTCCATCAGTAGTTACTACTGGAGCTGGAT CCGGCAGCCCCCAGGGAAGGGACTGGAGTGGATTGG GTATATCTATAGTAGTGGGAGCACCAACTACAACCCC TCCCTCAAGAGTCGAGTCACCATATCAGTAGACACGT CCAAGAACCAGTTCTCCCTGAAGCTGAGTTCTGTGAC CGCCGCAGACACGGCGGTGTACTACTGCGCCAGAGA ATCTCAGGAGAGTCCATACAACAATTGGTTCGACCCA TGGGGACAGGGTACATTGGTCACCGTCTCCTCA |
| SEQ ID NO: 14 (Combined) | LCDR1 | RASQGISSWLA |
| SEQ ID NO: 15 (Combined) | LCDR2 | AASSLQS |
| SEQ ID NO: 16 (Combined) | LCDR3 | QQGNSFPRT |
| SEQ ID NO: 14 (Kabat) | LCDR1 | RASQGISSWLA |
| SEQ ID NO: 15 (Kabat) | LCDR2 | AASSLQS |
| SEQ ID NO: 16 (Kabat) | LCDR3 | QQGNSFPRT |
| SEQ ID NO: 17 (Chothia) | LCDR1 | SQGISSW |
| SEQ ID NO: 18 (Chothia) | LCDR2 | AAS |
| SEQ ID NO: 19 (Chothia) | LCDR3 | GNSFPR |
| SEQ ID NO: 20 (IMGT) | LCDR1 | QGISSW |

TABLE 1-continued

Amino acid and nucleotide sequences for exemplary anti-CD73 antibodies

| | | |
|---|---|---|
| SEQ ID NO: 18 (IMGT) | LCDR2 | AAS |
| SEQ ID NO: 16 (IMGT) | LCDR3 | QQGNSFPRT |
| SEQ ID NO: 14 (Alternative) | LCDR1 | RASQGISSWLA |
| SEQ ID NO: 15 (Alternative) | LCDR2 | AASSLQS |
| SEQ ID NO: 16 (Alternative) | LCDR3 | QQGNSFPRT |
| SEQ ID NO: 21 | VL | DIQMTQSPSSVSASVGDRVTITCRASQGISSWLAWYQQ KPGKAPKLLIYAASSLQSGVPSRFSGSGSGTDFTLTISSL QPEDFATYYCQQGNSFPRTFGGGTKVEIK |
| SEQ ID NO: 170 | DNA VL | GACATCCAGATGACCCAGTCTCCATCTTCCGTGTCTG CATCTGTAGGAGACAGAGTCACCATCACTTGTCGGGC GAGTCAGGGTATTAGCAGCTGGTTAGCCTGGTATCAG CAGAAACCAGGGAAAGCCCCTAAGCTCCTGATCTATG CTGCATCCAGTTTGCAAAGTGGGGTCCCATCAAGGTT CAGCGGCAGTGGATCTGGGACAGATTTCACTCTCACC ATCAGCAGCCTGCAGCCTGAAGATTTTGCAACTTATT ACTGTCAGCAGGGAAACAGTTTCCCTAGGACTTTTGG CGGAGGGACCAAGGTTGAGATCAAA |
| 363 | | |
| SEQ ID NO: 81 (Combined) | HCDR1 | GFTFSRYAMS |
| SEQ ID NO: 201 (Combined) | HCDR2 | AISGTGISTYYADSVKG |
| SEQ ID NO: 37 (Combined) | HCDR3 | GGLYGSGSYLSDFDL |
| SEQ ID NO: 38 (Kabat) | HCDR1 | RYAMS |
| SEQ ID NO: 201 (Kabat) | HCDR2 | AISGTGISTYYADSVKG |
| SEQ ID NO: 37 (Kabat) | HCDR3 | GGLYGSGSYLSDFDL |
| SEQ ID NO: 82 (Chothia) | HCDR1 | GFTFSRY |
| SEQ ID NO: 202 (Chothia) | HCDR2 | SGTGIS |
| SEQ ID NO: 37 (Chothia) | HCDR3 | GGLYGSGSYLSDFDL |
| SEQ ID NO: 83 (IMGT) | HCDR1 | GFTFSRYA |
| SEQ ID NO: 203 (IMGT) | HCDR2 | ISGTGIST |
| SEQ ID NO: 43 (IMGT) | HCDR3 | ARGGLYGSGSYLSDFDL |
| SEQ ID NO: 192 (Alternative) | HCDR1 | FTFSRYAMS |
| SEQ ID NO: 201 (Alternative) | HCDR2 | AISGTGISTYYADSVKG |
| SEQ ID NO: 43 (Alternative) | HCDR3 | ARGGLYGSGSYLSDFDL |
| SEQ ID NO: 204 | VH | EVQLLESGGGLVQPGGSLRLSCAASGFTFSRYAMSWVR QAPGKGLEWVSAISGTGISTYYADSVKGRFTISRDNSKN TLYLQMNSLRAEDTAVYYCARGGLYGSGSYLSDFDLW GRGTLVTVSS |
| SEQ ID NO: 205 (Combined) | LCDR1 | RASQSISSWLA |

TABLE 1-continued

| Amino acid and nucleotide sequences for exemplary anti-CD73 antibodies | | |
|---|---|---|
| SEQ ID NO: 206 (Combined) | LCDR2 | DASSLES |
| SEQ ID NO: 207 (Combined) | LCDR3 | QQSNTFYT |
| SEQ ID NO: 205 (Kabat) | LCDR1 | RASQSISSWLA |
| SEQ ID NO: 206 (Kabat) | LCDR2 | DASSLES |
| SEQ ID NO: 207 (Kabat) | LCDR3 | QQSNTFYT |
| SEQ ID NO: 208 (Chothia) | LCDR1 | SQSISSW |
| SEQ ID NO: 209 (Chothia) | LCDR2 | DAS |
| SEQ ID NO: 228 (Chothia) | LCDR3 | SNTFY |
| SEQ ID NO: 229 (IMGT) | LCDR1 | QSISSW |
| SEQ ID NO: 209 (IMGT) | LCDR2 | DAS |
| SEQ ID NO: 207 (IMGT) | LCDR3 | QQSNTFYT |
| SEQ ID NO: 205 (Alternative) | LCDR1 | RASQSISSWLA |
| SEQ ID NO: 206 (Alternative) | LCDR2 | DASSLES |
| SEQ ID NO: 207 (Alternative) | LCDR3 | QQSNTFYT |
| SEQ ID NO: 230 | VL | DIQMTQSPSTLSASVGDRVTITCRASQSISSWLAWYQQK PGKAPKLLIYDASSLESGVPSRFSGSGSGTEFTLTISSLQP DDFATYYCQQSNTFYTFGGGTKVEIK |
| 366 | | |
| SEQ ID NO: 81 (Combined) | HCDR1 | GFTFSRYAMS |
| SEQ ID NO: 231 (Combined) | HCDR2 | AISGTGLSTYYADSVKG |
| SEQ ID NO: 37 (Combined) | HCDR3 | GGLYGSGSYLSDFDL |
| SEQ ID NO: 38 (Kabat) | HCDR1 | RYAMS |
| SEQ ID NO: 231 (Kabat) | HCDR2 | AISGTGLSTYYADSVKG |
| SEQ ID NO: 37 (Kabat) | HCDR3 | GGLYGSGSYLSDFDL |
| SEQ ID NO: 82 (Chothia) | HCDR1 | GFTFSRY |
| SEQ ID NO: 232 (Chothia) | HCDR2 | SGTGLS |
| SEQ ID NO: 37 (Chothia) | HCDR3 | GGLYGSGSYLSDFDL |
| SEQ ID NO: 83 (IMGT) | HCDR1 | GFTFSRYA |
| SEQ ID NO: 233 (IMGT) | HCDR2 | ISGTGLST |
| SEQ ID NO: 43 (IMGT) | HCDR3 | ARGGLYGSGSYLSDFDL |
| SEQ ID NO: 192 (Alternative) | HCDR1 | FTFSRYAMS |
| SEQ ID NO: 231 (Alternative) | HCDR2 | AISGTGLSTYYADSVKG |
| SEQ ID NO: 43 (Alternative) | HCDR3 | ARGGLYGSGSYLSDFDL |

TABLE 1-continued

| Amino acid and nucleotide sequences for exemplary anti-CD73 antibodies | | |
|---|---|---|
| SEQ ID NO: 234 | VH | EVQLLESGGGLVQPGGSLRLSCAASGFTFSRYAMSWVR QAPGKGLEWVSAISGTGLSTYYADSVKGRFTISRDNSK NTLYLQMNSLRAEDTAVYYCARGGLYGSGSYLSDFDL WGRGTLVTVSS |
| SEQ ID NO: 205 (Combined) | LCDR1 | RASQSISSWLA |
| SEQ ID NO: 206 (Combined) | LCDR2 | DASSLES |
| SEQ ID NO: 207 (Combined) | LCDR3 | QQSNTFYT |
| SEQ ID NO: 205 (Kabat) | LCDR1 | RASQSISSWLA |
| SEQ ID NO: 206 (Kabat) | LCDR2 | DASSLES |
| SEQ ID NO: 207 (Kabat) | LCDR3 | QQSNTFYT |
| SEQ ID NO: 208 (Chothia) | LCDR1 | SQSISSW |
| SEQ ID NO: 209 (Chothia) | LCDR2 | DAS |
| SEQ ID NO: 228 (Chothia) | LCDR3 | SNTFY |
| SEQ ID NO: 229 (IMGT) | LCDR1 | QSISSW |
| SEQ ID NO: 209 (IMGT) | LCDR2 | DAS |
| SEQ ID NO: 207 (IMGT) | LCDR3 | QQSNTFYT |
| SEQ ID NO: 205 (Alternative) | LCDR1 | RASQSISSWLA |
| SEQ ID NO: 206 (Alternative) | LCDR2 | DASSLES |
| SEQ ID NO: 207 (Alternative) | LCDR3 | QQSNTFYT |
| SEQ ID NO: 230 | VL | DIQMTQSPSTLSASVGDRVTITCRASQSISSWLAWYQQK PGKAPKLLIYDASSLESGVPSRFSGSGSGTEFTLTISSLQP DDFATYYCQQSNTFYTFGGGTKVEIK |
| 407 | | |
| SEQ ID NO: 235 (Combined) | HCDR1 | GYTFTYYWMH |
| SEQ ID NO: 236 (Combined) | HCDR2 | SINPNSGSTNYAQKFQG |
| SEQ ID NO: 237 (Combined) | HCDR3 | DTGGDKSPLTYYYYGMDV |
| SEQ ID NO: 238 (Kabat) | HCDR1 | YYWMH |
| SEQ ID NO: 236 (Kabat) | HCDR2 | SINPNSGSTNYAQKFQG |
| SEQ ID NO: 237 (Kabat) | HCDR3 | DTGGDKSPLTYYYYGMDV |
| SEQ ID NO: 239 (Chothia) | HCDR1 | GYTFTYY |
| SEQ ID NO: 240 (Chothia) | HCDR2 | NPNSGS |
| SEQ ID NO: 237 (Chothia) | HCDR3 | DTGGDKSPLTYYYYGMDV |
| SEQ ID NO: 241 (IMGT) | HCDR1 | GYTFTYYW |
| SEQ ID NO: 242 (IMGT) | HCDR2 | INPNSGST |
| SEQ ID NO: 243 (IMGT) | HCDR3 | ARDTGGDKSPLTYYYYGMDV |
| SEQ ID NO: 244 (Alternative) | HCDR1 | YTFTYYWMH |

TABLE 1-continued

| Amino acid and nucleotide sequences for exemplary anti-CD73 antibodies | | |
|---|---|---|
| SEQ ID NO: 236 (Alternative) | HCDR2 | SINPNSGSTNYAQKFQG |
| SEQ ID NO: 243 (Alternative) | HCDR3 | ARDTGGDKSPLTYYYYGMDV |
| SEQ ID NO: 245 | VH | QVQLVQSGAEVKKPGASVKVSCKASGYTFTYYWMHW VRQAPGQGLEWMGSINPNSGSTNYAQKFQGRVTMTRD TSISTAYMELSRLRSDDTAVYYCARDTGGDKSPLTYYY YGMDVWGQGTTVTVSS |
| SEQ ID NO: 246 (Combined) | LCDR1 | RASQGISRWLA |
| SEQ ID NO: 15 (Combined) | LCDR2 | AASSLQS |
| SEQ ID NO: 247 (Combined) | LCDR3 | QQAIALPPFT |
| SEQ ID NO: 246 (Kabat) | LCDR1 | RASQGISRWLA |
| SEQ ID NO: 15 (Kabat) | LCDR2 | AASSLQS |
| SEQ ID NO: 247 (Kabat) | LCDR3 | QQAIALPPFT |
| SEQ ID NO: 248 (Chothia) | LCDR1 | SQGISRW |
| SEQ ID NO: 18 (Chothia) | LCDR2 | AAS |
| SEQ ID NO: 249 (Chothia) | LCDR3 | AIALPPF |
| SEQ ID NO: 250 (IMGT) | LCDR1 | QGISRW |
| SEQ ID NO: 18 (IMGT) | LCDR2 | AAS |
| SEQ ID NO: 247 (IMGT) | LCDR3 | QQAIALPPFT |
| SEQ ID NO: 246 (Alternative) | LCDR1 | RASQGISRWLA |
| SEQ ID NO: 15 (Alternative) | LCDR2 | AASSLQS |
| SEQ ID NO: 247 (Alternative) | LCDR3 | QQAIALPPFT |
| SEQ ID NO: 251 | VL | DIQMTQSPSSVSASVGDRVTITCRASQGISRWLAWYQQ KPGKAPKLLIYAASSLQSGVPSRFSGSGSGTDFTLTISSL QPEDFATYYCQQAIALPPFTFGGGTKVEIK |
| 893 | | |
| SEQ ID NO: 252 (Combined) | HCDR1 | GFTFSSYWMS |
| SEQ ID NO: 253 (Combined) | HCDR2 | NIKQDGSEKYYVDSVKG |
| SEQ ID NO: 254 (Combined) | HCDR3 | APEYYSTTTRLYYYYGMDV |
| SEQ ID NO: 255 (Kabat) | HCDR1 | SYWMS |
| SEQ ID NO: 253 (Kabat) | HCDR2 | NIKQDGSEKYYVDSVKG |
| SEQ ID NO: 254 (Kabat) | HCDR3 | APEYYSTTTRLYYYYGMDV |
| SEQ ID NO: 155 (Chothia) | HCDR1 | GFTFSSY |
| SEQ ID NO: 256 (Chothia) | HCDR2 | KQDGSE |
| SEQ ID NO: 254 (Chothia) | HCDR3 | APEYYSTTTRLYYYYGMDV |
| SEQ ID NO: 257 (IMGT) | HCDR1 | GFTFSSYW |
| SEQ ID NO: 258 (IMGT) | HCDR2 | IKQDGSEK |

TABLE 1-continued

| Amino acid and nucleotide sequences for exemplary anti-CD73 antibodies | | |
|---|---|---|
| SEQ ID NO: 259 (IMGT) | HCDR3 | ARAPEYYSTTTRLYYYYGMDV |
| SEQ ID NO: 260 (Alternative) | HCDR1 | FTFSSYWMS |
| SEQ ID NO: 253 (Alternative) | HCDR2 | NIKQDGSEKYYVDSVKG |
| SEQ ID NO: 259 (Alternative) | HCDR3 | ARAPEYYSTTTRLYYYYGMDV |
| SEQ ID NO: 261 | VH | EVQLVESGGGLVQPGGSLRLSCAASGFTFSSYWMSWVR QAPGKGLEWVANIKQDGSEKYYVDSVKGRFTISRDNA KNSLYLQMNSLRAEDTAVYYCARAPEYYSTTTRLYYY YGMDVWGQGTTVTVSS |
| SEQ ID NO: 262 (Combined) | LCDR1 | KSSQSVLYSSNNKNYLA |
| SEQ ID NO: 263 (Combined) | LCDR2 | WASTRES |
| SEQ ID NO: 264 (Combined) | LCDR3 | QQYDAHPFT |
| SEQ ID NO: 262 (Kabat) | LCDR1 | KSSQSVLYSSNNKNYLA |
| SEQ ID NO: 263 (Kabat) | LCDR2 | WASTRES |
| SEQ ID NO: 264 (Kabat) | LCDR3 | QQYDAHPFT |
| SEQ ID NO: 265 (Chothia) | LCDR1 | SQSVLYSSNNKNY |
| SEQ ID NO: 266 (Chothia) | LCDR2 | WAS |
| SEQ ID NO: 267 (Chothia) | LCDR3 | YDAHPF |
| SEQ ID NO: 268 (IMGT) | LCDR1 | QSVLYSSNNKNY |
| SEQ ID NO: 266 (IMGT) | LCDR2 | WAS |
| SEQ ID NO: 264 (IMGT) | LCDR3 | QQYDAHPFT |
| SEQ ID NO: 262 (Alternative) | LCDR1 | KSSQSVLYSSNNKNYLA |
| SEQ ID NO: 263 (Alternative) | LCDR2 | WASTRES |
| SEQ ID NO: 264 (Alternative) | LCDR3 | QQYDAHPFT |
| SEQ ID NO: 269 | VL | DIVMTQSPDSLAVSLGERATINCKSSQSVLYSSNNKNYL AWYQQKPGQPPKLLIYWASTRESGVPDRFSGSGSGTDF TLTISSLQAEDVAVYYCQQYDAHPFTFGGGTKVEIK |
| 939 | | |
| SEQ ID NO: 287 (Combined) | HCDR1 | GGTFSSYAIS |
| SEQ ID NO: 288 (Combined) | HCDR2 | GIIPIFGTANYAQKFQG |
| SEQ ID NO: 289 (Combined) | HCDR3 | HYYDYWSGYYTNTGIY |
| SEQ ID NO: 290 (Kabat) | HCDR1 | SYAIS |
| SEQ ID NO: 288 (Kabat) | HCDR2 | GIIPIFGTANYAQKFQG |
| SEQ ID NO: 289 (Kabat) | HCDR3 | HYYDYWSGYYTNTGIY |
| SEQ ID NO: 291 (Chothia) | HCDR1 | GGTFSSY |
| SEQ ID NO: 292 (Chothia) | HCDR2 | IPIFGT |
| SEQ ID NO: 289 (Chothia) | HCDR3 | HYYDYWSGYYTNTGIY |

TABLE 1-continued

| Amino acid and nucleotide sequences for exemplary anti-CD73 antibodies | | |
|---|---|---|
| SEQ ID NO: 293 (IMGT) | HCDR1 | GGTFSSYA |
| SEQ ID NO: 294 (IMGT) | HCDR2 | IIPIFGTA |
| SEQ ID NO: 295 (IMGT) | HCDR3 | ARHYYDYWSGYYTNTGIY |
| SEQ ID NO: 296 (Alternative) | HCDR1 | GTFSSYAIS |
| SEQ ID NO: 288 (Alternative) | HCDR2 | GIIPIFGTANYAQKFQG |
| SEQ ID NO: 295 (Alternative) | HCDR3 | ARHYYDYWSGYYTNTGIY |
| SEQ ID NO: 297 | VH | QVQLVQSGAEVKKPGSSVKVSCKASGGTFSSYAISWVR QAPGQGLEWMGGIIPIFGTANYAQKFQGRVTITADESTS TAYMELSSLRSEDTAVYYCARHYYDYWSGYYTNTGIY WGQGTLVTVSS |
| SEQ ID NO: 298 (Combined) | LCDR1 | RASQSVSSNLA |
| SEQ ID NO: 49 (Combined) | LCDR2 | GASTRAT |
| SEQ ID NO: 299 (Combined) | LCDR3 | QQSGALPIT |
| SEQ ID NO: 298 (Kabat) | LCDR1 | RASQSVSSNLA |
| SEQ ID NO: 49 (Kabat) | LCDR2 | GASTRAT |
| SEQ ID NO: 299 (Kabat) | LCDR3 | QQSGALPIT |
| SEQ ID NO: 300 (Chothia) | LCDR1 | SQSVSSN |
| SEQ ID NO: 52 (Chothia) | LCDR2 | GAS |
| SEQ ID NO: 301 (Chothia) | LCDR3 | SGALPI |
| SEQ ID NO: 302 (IMGT) | LCDR1 | QSVSSN |
| SEQ ID NO: 52 (IMGT) | LCDR2 | GAS |
| SEQ ID NO: 299 (IMGT) | LCDR3 | QQSGALPIT |
| SEQ ID NO: 298 (Alternative) | LCDR1 | RASQSVSSNLA |
| SEQ ID NO: 49 (Alternative) | LCDR2 | GASTRAT |
| SEQ ID NO: 299 (Alternative) | LCDR3 | QQSGALPIT |
| SEQ ID NO: 303 | VL | EIVMTQSPATLSVSPGERATLSCRASQSVSSNLAWYQQK PGQAPRLLIYGASTRATGIPARFSGSGSGTEFTLTISSLQS EDFAVYYCQQSGALPITFGGGTKVEIK |
| 430 | | |
| SEQ ID NO: 304 (Combined) | HCDR1 | GGSFLRYYWS |
| SEQ ID NO: 305 (Combined) | HCDR2 | EIDHSGSTNYNPSLKS |
| SEQ ID NO: 306 (Combined) | HCDR3 | GQNYYGSGSADGFDP |
| SEQ ID NO: 61 (Kabat) | HCDR1 | RYYWS |
| SEQ ID NO: 305 (Kabat) | HCDR2 | EIDHSGSTNYNPSLKS |
| SEQ ID NO: 306 (Kabat) | HCDR3 | GQNYYGSGSADGFDP |

TABLE 1-continued

| Amino acid and nucleotide sequences for exemplary anti-CD73 antibodies | | |
|---|---|---|
| SEQ ID NO: 307 (Chothia) | HCDR1 | GGSFLRY |
| SEQ ID NO: 308 (Chothia) | HCDR2 | DHSGS |
| SEQ ID NO: 306 (Chothia) | HCDR3 | GQNYYGSGSADGFDP |
| SEQ ID NO: 309 (IMGT) | HCDR1 | GGSFLRYY |
| SEQ ID NO: 310 (IMGT) | HCDR2 | IDHSGST |
| SEQ ID NO: 311 (IMGT) | HCDR3 | ARGQNYYGSGSADGFDP |
| SEQ ID NO: 312 (Alternative) | HCDR1 | GSFLRYYWS |
| SEQ ID NO: 305 (Alternative) | HCDR2 | EIDHSGSTNYNPSLKS |
| SEQ ID NO: 311 (Alternative) | HCDR3 | ARGQNYYGSGSADGFDP |
| SEQ ID NO: 313 | VH | QVQLQQWGAGLLKPSETLSLTCAVYGGSFLRYYWSWI RQPPGKGLEWIGEIDHSGSTNYNPSLKSRVTISVDTSKN QFSLKLSSVTAADTAVYYCARGQNYYGSGSADGFDPW GQGTLVTVSS |
| SEQ ID NO: 14 (Combined) | LCDR1 | RASQGISSWLA |
| SEQ ID NO: 15 (Combined) | LCDR2 | AASSLQS |
| SEQ ID NO: 314 (Combined) | LCDR3 | QQANSFPPT |
| SEQ ID NO: 14 (Kabat) | LCDR1 | RASQGISSWLA |
| SEQ ID NO: 15 (Kabat) | LCDR2 | AASSLQS |
| SEQ ID NO: 314 (Kabat) | LCDR3 | QQANSFPPT |
| SEQ ID NO: 17 (Chothia) | LCDR1 | SQGISSW |
| SEQ ID NO: 18 (Chothia) | LCDR2 | AAS |
| SEQ ID NO: 315 (Chothia) | LCDR3 | ANSFPP |
| SEQ ID NO: 20 (IMGT) | LCDR1 | QGISSW |
| SEQ ID NO: 18 (IMGT) | LCDR2 | AAS |
| SEQ ID NO: 314 (IMGT) | LCDR3 | QQANSFPPT |
| SEQ ID NO: 14 (Alternative) | LCDR1 | RASQGISSWLA |
| SEQ ID NO: 15 (Alternative) | LCDR2 | AASSLQS |
| SEQ ID NO: 314 (Alternative) | LCDR3 | QQANSFPPT |
| SEQ ID NO: 316 | VL | DIQMTQSPSSVSASVGDRVTITCRASQGISSWLAWYQQ KPGKAPKLLIYAASSLQSGVPSRFSGSGSGTDFTLTISSL QPEDFATYYCQQANSFPPTFGGGTKVEIK |
| 398 | | |
| SEQ ID NO: 317 (Combined) | HCDR1 | GGSFSGYYWS |
| SEQ ID NO: 318 (Combined) | HCDR2 | EIDASGSTRYNPSLKS |
| SEQ ID NO: 319 (Combined) | HCDR3 | PLYDAYLDV |
| SEQ ID NO: 320 (Kabat) | HCDR1 | GYYWS |

TABLE 1-continued

| Amino acid and nucleotide sequences for exemplary anti-CD73 antibodies | | |
|---|---|---|
| SEQ ID NO: 318 (Kabat) | HCDR2 | EIDASGSTRYNPSLKS |
| SEQ ID NO: 319 (Kabat) | HCDR3 | PLYDAYLDV |
| SEQ ID NO: 321 (Chothia) | HCDR1 | GGSFSGY |
| SEQ ID NO: 322 (Chothia) | HCDR2 | DASGS |
| SEQ ID NO: 319 (Chothia) | HCDR3 | PLYDAYLDV |
| SEQ ID NO: 323 (IMGT) | HCDR1 | GGSFSGYY |
| SEQ ID NO: 324 (IMGT) | HCDR2 | IDASGST |
| SEQ ID NO: 325 (IMGT) | HCDR3 | ARPLYDAYLDV |
| SEQ ID NO: 326 (Alternative) | HCDR1 | GSFSGYYWS |
| SEQ ID NO: 318 (Alternative) | HCDR2 | EIDASGSTRYNPSLKS |
| SEQ ID NO: 325 (Alternative) | HCDR3 | ARPLYDAYLDV |
| SEQ ID NO: 327 | VH | QVQLQQWGAGLLKPSETLSLTCAVYGGSFSGYYWSWI RQPPGKGLEWIGEIDASGSTRYNPSLKSRVTISVDTSKN QFSLKLSSVTAADTAVYYCARPLYDAYLDVWGQGTMV TVSS |
| SEQ ID NO: 14 (Combined) | LCDR1 | RASQGISSWLA |
| SEQ ID NO: 15 (Combined) | LCDR2 | AASSLQS |
| SEQ ID NO: 328 (Combined) | LCDR3 | QQAPIYPIT |
| SEQ ID NO: 14 (Kabat) | LCDR1 | RASQGISSWLA |
| SEQ ID NO: 15 (Kabat) | LCDR2 | AASSLQS |
| SEQ ID NO: 328 (Kabat) | LCDR3 | QQAPIYPIT |
| SEQ ID NO: 17 (Chothia) | LCDR1 | SQGISSW |
| SEQ ID NO: 18 (Chothia) | LCDR2 | AAS |
| SEQ ID NO: 329 (Chothia) | LCDR3 | APIYPI |
| SEQ ID NO: 20 (IMGT) | LCDR1 | QGISSW |
| SEQ ID NO: 18 (IMGT) | LCDR2 | AAS |
| SEQ ID NO: 328 (IMGT) | LCDR3 | QQAPIYPIT |
| SEQ ID NO: 14 (Alternative) | LCDR1 | RASQGISSWLA |
| SEQ ID NO: 15 (Alternative) | LCDR2 | AASSLQS |
| SEQ ID NO: 328 (Alternative) | LCDR3 | QQAPIYPIT |
| SEQ ID NO: 330 | VL | DIQMTQSPSSVSASVGDRVTITCRASQGISSWLAWYQQ KPGKAPKLLIYAASSLQSGVPSRFSGSGSGTDFTLTISSL QPEDFATYYCQQAPIYPITFGGGTKVEIK |

TABLE 2

| Consensus CDR sequences for exemplary anti-CD73 antibodies | | |
|---|---|---|
| Lineage 3 | | |
| SEQ ID NO: 126 (Combined) | HCDR1 | GFTF$X_1X_2X_3$AMS, wherein $X_1$ is H, S, R, or K; $X_2$ is R, Y, or S; and $X_3$ is Y or N |
| SEQ ID NO: 89 (Combined) | HCDR2 | $X_1$I$X_2$G$X_3$G$X_4X_5$TYYADSVKG, wherein $X_1$ is A or S; $X_2$ is S or T; $X_3$ is S or T; $X_4$ is M, G, or S; and $X_5$ is N, S, L, or Y |
| SEQ ID NO: 37 (Combined) | HCDR3 | GGLYGSGSYLSDFDL |
| SEQ ID NO: 48 (Combined) | LCDR1 | RASQSVGSNLA |
| SEQ ID NO: 49 (Combined) | LCDR2 | GASTRAT |
| SEQ ID NO: 50 (Combined) | LCDR3 | QQHNAFPYT |
| SEQ ID NO: 88 (Kabat) | HCDR1 | $X_1X_2$AMS, wherein $X_1$ is R, Y, or S; and $X_2$ is Y or N |
| SEQ ID NO: 89 (Kabat) | HCDR2 | $X_1$I$X_2$G$X_3$G$X_4X_5$TYYADSVKG, wherein $X_1$ is A or S; $X_2$ is S or T; $X_3$ is S or T; $X_4$ is M, G, or S; and $X_5$ is N, S, L, or Y |
| SEQ ID NO: 37 (Kabat) | HCDR3 | GGLYGSGSYLSDFDL |
| SEQ ID NO: 48 (Kabat) | LCDR1 | RASQSVGSNLA |
| SEQ ID NO: 49 (Kabat) | LCDR2 | GASTRAT |
| SEQ ID NO: 50 (Kabat) | LCDR3 | QQHNAFPYT |
| SEQ ID NO: 122 (Chothia) | HCDR1 | GFTF$X_1X_2X_3$, wherein $X_1$ is H, S, R, or K; $X_2$ is R, Y, or S; and $X_3$ is Y or N |
| SEQ ID NO: 123 (Chothia) | HCDR2 | $X_1$G$X_2$G$X_3X_4$, wherein $X_1$ is S or T; $X_2$ is S or T; $X_3$ is M, G, or S; and $X_4$ is N, S, L, or Y |
| SEQ ID NO: 37 (Chothia) | HCDR3 | GGLYGSGSYLSDFDL |
| SEQ ID NO: 51 (Chothia) | LCDR1 | SQSVGSN |
| SEQ ID NO: 52 (Chothia) | LCDR2 | GAS |
| SEQ ID NO: 53 (Chothia) | LCDR3 | HNAFPY |
| SEQ ID NO: 128 (IMGT) | HCDR1 | GFTF$X_1X_2X_3$A, wherein $X_1$ is H, S, R, or K; $X_2$ is R, Y, or S; and $X_3$ is Y or N |
| SEQ ID NO: 129 (IMGT) | HCDR2 | I$X_1$G$X_2$G$X_3X_4$T, wherein $X_1$ is S or T; $X_2$ is S or T; $X_3$ is M, G, or S; and $X_4$ is N, S, L, or Y |
| SEQ ID NO: 43 (IMGT) | HCDR3 | ARGGLYGSGSYLSDFDL |
| SEQ ID NO: 54 (IMGT) | LCDR1 | QSVGSN |

TABLE 2-continued

| Consensus CDR sequences for exemplary anti-CD73 antibodies | | |
|---|---|---|
| SEQ ID NO: 52 (IMGT) | LCDR2 | GAS |
| SEQ ID NO: 50 (IMGT) | LCDR3 | QQHNAFPYT |
| SEQ ID NO: 189 (Alternative) | HCDR1 | $FTFX_1X_2X_3AMS$, wherein $X_1$ is H, S, R, or K; $X_2$ is R, Y, or S; and $X_3$ is Y or N |
| SEQ ID NO: 89 (Alternative) | HCDR2 | $X_1IX_2GX_3GX_4X_5TYYADSVKG$, wherein $X_1$ is A or S; $X_2$ is S or T; $X_3$ is S or T; $X_4$ is M, G, or S; and $X_5$ is N, S, L, or Y |
| SEQ ID NO: 43 (Alternative) | HCDR3 | ARGGLYGSGSYLSDFDL |
| SEQ ID NO: 48 (Alternative) | LCDR1 | RASQSVGSNLA |
| SEQ ID NO: 49 (Alternative) | LCDR2 | GASTRAT |
| SEQ ID NO: 50 (Alternative) | LCDR3 | QQHNAFPYT |
| Lineage 1 | | |
| SEQ ID NO: 127 (Combined) | HCDR1 | $GGSIX_1X_2X_3YWS$, wherein $X_1$ is E or S; $X_2$ is R, G, or S; and $X_3$ is Y or R |
| SEQ ID NO: 91 (Combined) | HCDR2 | $YIYX_1X_2GSTX_3YNPSLKS$, wherein $X_1$ is G or S; $X_2$ is R, S, or T; and $X_3$ is N or K |
| SEQ ID NO: 3 (Combined) | HCDR3 | ESQESPYNNWFDP |
| SEQ ID NO: 14 (Combined) | LCDR1 | RASQGISSWLA |
| SEQ ID NO: 15 (Combined) | LCDR2 | AASSLQS |
| SEQ ID NO: 16 (Combined) | LCDR3 | QQGNSFPRT |
| SEQ ID NO: 90 (Kabat) | HCDR1 | $X_1X_2YWS$, wherein $X_1$ is R, G, or S; and $X_2$ is Y or R |
| SEQ ID NO: 91 (Kabat) | HCDR2 | $YIYX_1X_2GSTX_3YNPSLKS$, wherein $X_1$ is G or S; $X_2$ is R, S, or T; and $X_3$ is N or K |
| SEQ ID NO: 3 (Kabat) | HCDR3 | ESQESPYNNWFDP |
| SEQ ID NO: 14 (Kabat) | LCDR1 | RASQGISSWLA |
| SEQ ID NO: 15 (Kabat) | LCDR2 | AASSLQS |
| SEQ ID NO: 16 (Kabat) | LCDR3 | QQGNSFPRT |
| SEQ ID NO: 124 (Chothia) | HCDR1 | $GGSIX_1X_2X_3$, wherein $X_1$ is E or S; $X_2$ is R, G, or S; and $X_3$ is Y or R |
| SEQ ID NO: 125 (Chothia) | HCDR2 | $YX_1X_2GS$, wherein $X_1$ is G or S; and $X_2$ is R, S, or T |

TABLE 2-continued

| Consensus CDR sequences for exemplary anti-CD73 antibodies | | |
|---|---|---|
| SEQ ID NO: 3 (Chothia) | HCDR3 | ESQESPYNNWFDP |
| SEQ ID NO: 17 (Chothia) | LCDR1 | SQGISSW |
| SEQ ID NO: 18 (Chothia) | LCDR2 | AAS |
| SEQ ID NO: 19 (Chothia) | LCDR3 | GNSFPR |
| SEQ ID NO: 130 (IMGT) | HCDR1 | GGSI$X_1X_2X_3$Y, wherein $X_1$ is E or S; $X_2$ is R, G, or S; and $X_3$ is Y or R |
| SEQ ID NO: 131 (IMGT) | HCDR2 | IY$X_1X_2$GST, wherein $X_1$ is G or S; and $X_2$ is R, S, or T |
| SEQ ID NO: 9 (IMGT) | HCDR3 | ARESQESPYNNWFDP |
| SEQ ID NO: 20 (IMGT) | LCDR1 | QGISSW |
| SEQ ID NO: 18 (IMGT) | LCDR2 | AAS |
| SEQ ID NO: 16 (IMGT) | LCDR3 | QQGNSFPRT |
| SEQ ID NO: 196 (Alternative) | HCDR1 | GSI$X_1X_2X_3$YWS, wherein $X_1$ is E or S; $X_2$ is R, G, or S; and $X_3$ is Y or R |
| SEQ ID NO: 91 (Alternative) | HCDR2 | YIY$X_1X_2$GST$X_3$YNPSLKS, wherein $X_1$ is G or S; $X_2$ is R, S, or T; and $X_3$ is N or K |
| SEQ ID NO: 9 (Alternative) | HCDR3 | ARESQESPYNNWFDP |
| SEQ ID NO: 14 (Alternative) | LCDR1 | RASQGISSWLA |
| SEQ ID NO: 15 (Alternative) | LCDR2 | AASSLQS |
| SEQ ID NO: 16 (Alternative) | LCDR3 | QQGNSFPRT |

TABLE 26

Corresponding germline sequences of anti-CD73 antibodies

| Antibody | VH germline | VL germline |
|---|---|---|
| 918 | VH4-59 | VK1-12 |
| 350 | VH4-59 | VK1-12 |
| 356 | VH4-59 | VK1-12 |
| 358 | VH4-59 | VK1-12 |
| 930 | VH3-23 | VK3-15 |
| 373 | VH3-23 | VK3-15 |
| 374 | VH3-23 | VK3-15 |
| 376 | VH3-23 | VK3-15 |
| 377 | VH3-23 | VK3-15 |

TABLE 26-continued

Corresponding germline sequences of anti-CD73 antibodies

| Antibody | VH germline | VL germline |
|---|---|---|
| 379 | VH3-23 | VK3-15 |
| 363 | VH3-23 | VK1-05 |
| 366 | VH3-23 | VK1-05 |
| 407 | VH1-02 | VK1-12 |
| 893 | VH3-07 | VK4-01 |
| 939 | VH1-69 | VK3-15 |
| 430 | VH4-34 | VK1-12 |
| 398 | VH4-34 | VK1-12 |

TABLE 3

Constant region amino acid sequences of human IgG heavy chains and human kappa light chain

| SEQ ID NO | Description | Sequence |
|---|---|---|
| 92 | IgG4 (S228P) | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVD KRVESKYGPPCPPCPAPEFLGGPSVFLFPPKPKDTLMISRTPEVTCVVV |

TABLE 3-continued

Constant region amino acid sequences of human IgG heavy chains and human kappa light chain

| SEQ ID NO | Description | Sequence |
|---|---|---|
| | | DVSQEDPEVQFNWYVDGVEVHNAKTKPREEQFNSTYRVVSVLTVLH QDWLNGKEYKCKVSNKGLPSSIEKTISKAKGQPREPQVYTLPPSQEE MTKNQVSLTCLVKGFYPSDIAVEWESNGQPENNYKTTPPVLDSDGSF FLYSRLTVDKSRWQEGNVFSCSVMHEALHNHYTQKSLSLSLGK |
| 93 | IgG4 (S228P) lacking C-terminal lysine | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVD KRVESKYGPPCPPCPAPEFLGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQEE MTKNQVSLTCLVKGFYPSDIAVEWESNGQPENNYKTTPPVLDSDGSF FLYSRLTVDKSRWQEGNVFSCSVMHEALHNHYTQKSLSLSLG |
| 94 | IgG4 (S228P/L235E) | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVD KRVESKYGPPCPPCPAPEFEGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQEE MTKNQVSLTCLVKGFYPSDIAVEWESNGQPENNYKTTPPVLDSDGSF FLYSRLTVDKSRWQEGNVFSCSVMHEALHNHYTQKSLSLSLGK |
| 95 | IgG4 (S228P/L235E) lacking C-terminal lysine | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVD KRVESKYGPPCPPCPAPEFEGGPSVFLFPPKPKDTLMISRTPEVTCVVV DVSQEDPEVQFNWYVDGVEVHNAKTKPREEQFNSTYRVVSVLTVLH QDWLNGKEYKCKVSNKGLPSSIEKTISKAKGQPREPQVYTLPPSQEE MTKNQVSLTCLVKGFYPSDIAVEWESNGQPENNYKTTPPVLDSDGSF FLYSRLTVDKSRWQEGNVFSCSVMHEALHNHYTQKSLSLSLG |
| 119 | IgG1 wild type | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCV VVDVSHEDPEVKFNWYVDGVEVHNAKTKPREEQYNSTYRVVSVLT VLHQDWLNGKEYKCKVSNKALPAPIEKTISKAKGQPREPQVYTLPPS RDELTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 120 | IgG1 wild type lacking C-terminal lysine | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCV VVDVSHEDPEVKFNWYVDGVEVHNAKTKPREEQYNSTYRVVSVLT VLHQDWLNGKEYKCKVSNKALPAPIEKTISKAKGQPREPQVYTLPPS RDELTKNQVSLTCLVKGFYPSDIAVEWESNGQPENNYKTTPPVLDSD GSFFLYSKLTVDKSRWQQGNVFSCSVMHEALHNHYTQKSLSLSPG |
| 96 | IgG1 wild type | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 97 | IgG1 wild type lacking C-terminal lysine | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPG |
| 98 | IgG1 (N297A) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYASTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 99 | IgG1 (N297A) lacking C-terminal lysine | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVDVSHEDPEVKFNWYVDGVEVHNAKTKPREEQYASTYRVVSVLT VLHQDWLNGKEYKCKVSNKALPAPIEKTISKAKGQPREPQVYTLPPS |

TABLE 3-continued

| SEQ ID NO | Description | Sequence |
|---|---|---|
| Constant region amino acid sequences of human IgG heavy chains and human kappa light chain | | |
| | | REEMTKNQVSLTCLVKGFYPSDIAVEWESNGQPENNYKTTPPVLDSD GSFFLYSKLTVDKSRWQQGNVFSCSVMHEALHNHYTQKSLSLSPG |
| 100 | IgG1 (D265A/P329A) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVAVSHEDPEVKFNWYVDGVEVHNAKTKPREEQYNSTYRVVSVLT VLHQDWLNGKEYKCKVSNKALAAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 101 | IgG1 (D265A/P329A) lacking C-terminal lysine | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCV VVAVSHEDPEVKFNWYVDGVEVHNAKTKPREEQYNSTYRVVSVLT VLHQDWLNGKEYKCKVSNKALAAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPG |
| 102 | IgG1 (L234A/L235A) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEAAGGPSVFLFPPKPKDTLMISRTPEVTCV VVDVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 103 | IgG1 (L234A/L235A) lacking C-terminal lysine | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEAAGGPSVFLFPPKPKDTLMISRTPEVTCV VVDVSHEDPEVKFNWYVDGVEVHNAKTKPREEQYNSTYRVVSVLT VLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPG |
| 104 | Human kappa constant region | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTKSFNRGEC |

TABLE 4

| SEQ ID NO | Description | Sequence |
|---|---|---|
| Exemplary sequences of CD73 | | |
| 105 | Human CD73 (Q6NZX3) | MCPRAARAPATLLLALGAVLWPAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV LPVGDEVVGIVGYTSKETPFLSNPGTNLVFEDEITALQPEVD KLKTLNVNKIIALGHSGFEMDKLIAQKVRGVDVVVGGHSN TFLYTGNPPSKEVPAGKYPFIVTSDDGRKVPVVQAYAFGKY LGYLKIEFDERGNVISSHGNPILLNSSIPEDPSIKADINKWRIK LDNYSTQELGKTIVYLDGSSQSCRFRECNMGNLICDAMINN NLRHADETFWNHVSMCILNGGGIRSPIDERNNGTITWENLA AVLPFGGTFDLVQLKGSTLKKAFEHSVHRYGQSTGEFLQVG GIHVVYDLSRKPGDRVVKLDVLCTKCRVPSYDPLKMDEVY KVILPNFLANGGDGFQMIKDELLRHDSGDQDINVVSTYISK MKVIYPAVEGRIKFSTGSHCHGSFSLIFLSLWAVIFVLYQ |
| 106 | Human CD73 isoform (P21589-1) | MCPRAARAPATLLLALGAVLWPAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV LPVGDEVVGIVGYTSKETPFLSNPGTNLVFEDEITALQPEVD KLKTLNVNKIIALGHSGFEMDKLIAQKVRGVDVVVGGHSN TFLYTGNPPSKEVPAGKYPFIVTSDDGRKVPVVQAYAFGKY LGYLKIEFDERGNVISSHGNPILLNSSIPEDPSIKADINKWRIK LDNYSTQELGKTIVYLDGSSQSCRFRECNMGNLICDAMINN NLRHTDEMFWNHVSMCILNGGGIRSPIDERNNGTITWENLA |

TABLE 4-continued

Exemplary sequences of CD73

| SEQ ID NO | Description | Sequence |
|---|---|---|
| | | AVLPFGGTFDLVQLKGSTLKKAFEHSVHRYGQSTGEFLQVG GIHVVYDLSRKPGDRVVKLDVLCTKCRVPSYDPLKMDEVY KVILPNFLANGGDGFQMIKDELLRHDSGDQDINVVSTYISK MKVIYPAVEGRIKFSTGSHCHGSFSLIFLSLWAVIFVLYQ |
| 107 | Human CD73 isoform (P21589-2) | MCPRAARAPATLLLALGAVLWPAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV LPVGDEVVGIVGYTSKETPFLSNPGTNLVFEDEITALQPEVD KLKTLNVNKIIALGHSGFEMDKLIAQKVRGVDVVVGGHSN TFLYTGNPPSKEVPAGKYPFIVTSDDGRKVPVVQAYAFGKY LGYLKIEFDERGNVISSHGNPILLNSSIPEDPSIKADINKWRIK LDNYSTQELGKTIVYLDGSSQSCRFRECNMGNLICDAMINN NLRHTDEMFWNHVSMCILNGGGIRSPIDERNNGIHVVYDLS RKPGDRVVKLDVLCTKCRVPSYDPLKMDEVYKVILPNFLA NGGDGFQMIKDELLRHDSGDQDINVVSTYISKMKVIYPAVE GRIKFSTGSHCHGSFSLIFLSLWAVIFVLYQ |
| 108 | CD73 fragment (residue range 158-172 of SEQ ID NO: 105) | YLPYKVLPVGDEVVG |
| 109 | CD73 fragment (residue range 206-215 of SEQ ID NO: 105) | KLKTLNVNKI |
| 110 | CD73 fragment (residue range 368-387 of SEQ ID NO: 105) | MINNNLRHADETFWNHVSMC |
| 121 | CD73 fragment (residue range 368-387 of SEQ ID NO: 106) | MINNNLRHTDEMFWNHVSMC |
| 111 | CD73 fragment (residue range 87-104 of SEQ ID NO: 105) | YQGTIWFTVYKGAEVAHF |
| 118 | CD73 fragment (residue range 297-309 of SEQ ID NO: 105) | RGNVISSHGNPIL |
| 134 | CD73 fragment (residue range 27-547 of SEQ ID NO: 105) | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPYKVLPVGDEVVGIVGYTSKETPFLSNPGTNL VFEDEITALQPEVDKLKTLNVNKIIALGHSGFEMDKLIAQKV RGVDVVVGGHSNTFLYTGNPPSKEVPAGKYPFIVTSDDGRK VPVVQAYAFGKYLGYLKIEFDERGNVISSHGNPILLNSSIPED PSIKADINKWRIKLDNYSTQELGKTIVYLDGSSQSCRFRECN MGNLICDAMINNNLRHADETFWNHVSMCILNGGGIRSPIDE RNNGTIITWENLAAVLPFGGTFDLVQLKGSTLKKAFEHSVHR YGQSTGEFLQVGGIHVVYDLSRKPGDRVVKLDVLCTKCRV PSYDPLKMDEVYKVILPNFLANGGDGFQMIKDELLRHDSGD QDINVVSTYISKMKVIYPAVEGRIK |
| 171 | CD73 fragment (residue range 27-547 of SEQ ID NO: 105) fused to a C-terminal 6-His tag (SEQ ID NO: 922) | WELTILHTNDVHSRLEQTSEDSSKCVNASRCMGGVARLFTK VQQIRRAEPNVLLLDAGDQYQGTIWFTVYKGAEVAHFMNA LRYDAMALGNHEFDNGVEGLIEPLLKEAKFPILSANIKAKGP LASQISGLYLPYKVLPVGDEVVGIVGYTSKETPFLSNPGTNL VFEDEITALQPEVDKLKTLNVNKIIALGHSGFEMDKLIAQKV RGVDVVVGGHSNTFLYTGNPPSKEVPAGKYPFIVTSDDGRK VPVVQAYAFGKYLGYLKIEFDERGNVISSHGNPILLNSSIPED PSIKADINKWRIKLDNYSTQELGKTIVYLDGSSQSCRFRECN MGNLICDAMINNNLRHADETFWNHVSMCILNGGGIRSPIDE RNNGTIITWENLAAVLPFGGTFDLVQLKGSTLKKAFEHSVHR YGQSTGEFLQVGGIHVVYDLSRKPGDRVVKLDVLCTKCRV PSYDPLKMDEVYKVILPNFLANGGDGFQMIKDELLRHDSGD QDINVVSTYISKMKVIYPAVEGRIKHHHHHH |
| 332 | CD73 fragment (residue range 27-547 of SEQ ID NO: 105) fused to a C-terminal 6-His tag (SEQ | MCPRAARAPATLLLALGAVLWPAAGAWELTILHTNDVHSR LEQTSEDSSKCVNASRCMGGVARLFTKVQQIRRAEPNVLLL DAGDQYQGTIWFTVYKGAEVAHFMNALRYDAMALGNHEF DNGVEGLIEPLLKEAKFPILSANIKAKGPLASQISGLYLPYKV |

TABLE 4-continued

Exemplary sequences of CD73

| SEQ ID NO | Description | Sequence |
|---|---|---|
| | ID NO: 922), including a signal peptide | LPVGDEVVGIVGYTSKETPFLSNPGTNLVFEDEITALQPEVD KLKTLNVNKIIALGHSGFEMDKLIAQKVRGVDVVVGGHSN TFLYTGNPPSKEVPAGKYPFIVTSDDGRKVPVVQAYAFGKY LGYLKIEFDERGNVISSHGNPILLNSSIPEDPSIKADINKWRIK LDNYSTQELGKTIVYLDGSSQSCRFRECNMGNLICDAMINN NLRHADETFWNHVSMCILNGGGIRSPIDERNNGTITWENLA AVLPFGGTFDLVQLKGSTLKKAFEHSVHRYGQSTGEFLQVG GIHVVYDLSRKPGDRVVKLDVLCTKCRVPSYDPLKMDEVY KVILPNFLANGGDGFQMIKDELLRHDSGDQDINVVSTYISK MKVIYPAVEGRIKHHHHHH |

In other embodiments, the aforesaid antibody molecules are capable of binding to human CD73 with a dissociation constant ($K_D$) of less than about $1\times10^{-4}$ M, $1\times10^{-5}$ M, $1\times10^{-6}$ M, $1\times10^{-7}$ M, $1\times10^{-8}$ M, $1\times10^{-9}$ M, e.g., as measured by Biacore, Octet, flow cytometry, or ELISA.

In some embodiments, the antibody molecule binds to a mammalian, e.g., human or cynomolgus, CD73. For example, the antibody molecule binds to an epitope, e.g., linear or conformational epitope, (e.g., an epitope as described herein), on CD73. In certain aspects, it is advantageous to identify an antibody that binds with high affinity to the human and cynomolgus homologs of a protein of interest. This desirable cross-reactivity allows the same antibody (or two antibodies with the same CDRs or variable regions) to be tested in an animal model and then administered to human patients as a therapeutic.

In some embodiments, disclosed herein is an isolated antibody molecule that competes for binding to human CD73 with the aforesaid anti-CD73 antibody molecules.

In some embodiments, disclosed herein is an isolated antibody molecule that binds to the same epitope as, substantially the same epitope as, an epitope that overlaps with, or an epitope that substantially overlaps with, the epitope of the aforesaid anti-CD73 antibody molecules.

In some embodiments, the antibody molecule binds to the N-terminal domain of human CD73. In some embodiments, the antibody molecule binds to the A-loop and/or B-loop of human CD73. In some embodiments, the antibody molecule, when bound to human CD73, induces a conformational change in the C-loop of human CD73.

Figure 14:
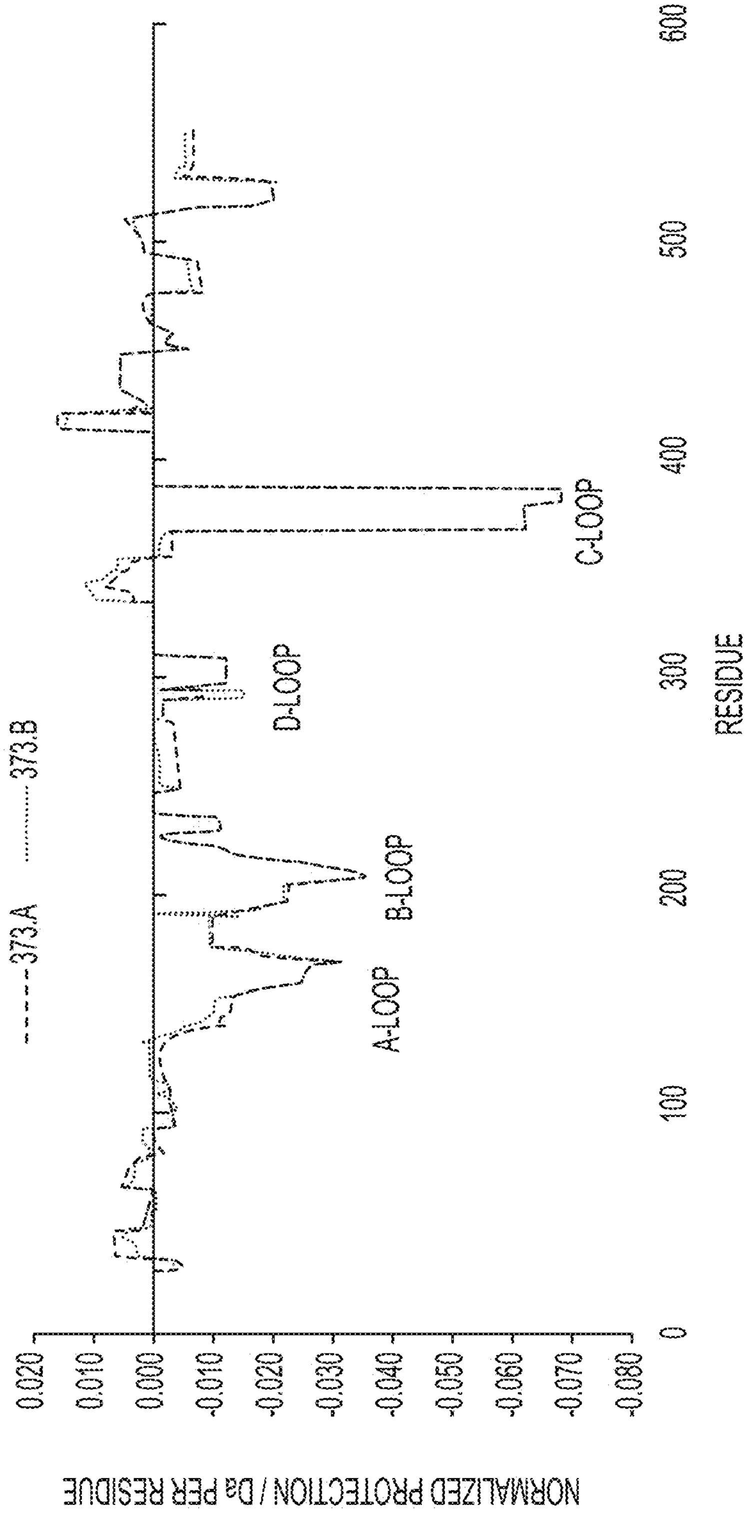
FIG. 14 is a graph showing comparison of protection profiles of 373.A and 373.B, as measured by fragmentation hydrogen deuterium-exchange mass spectrometry (HDx-MS).
Figure 15:
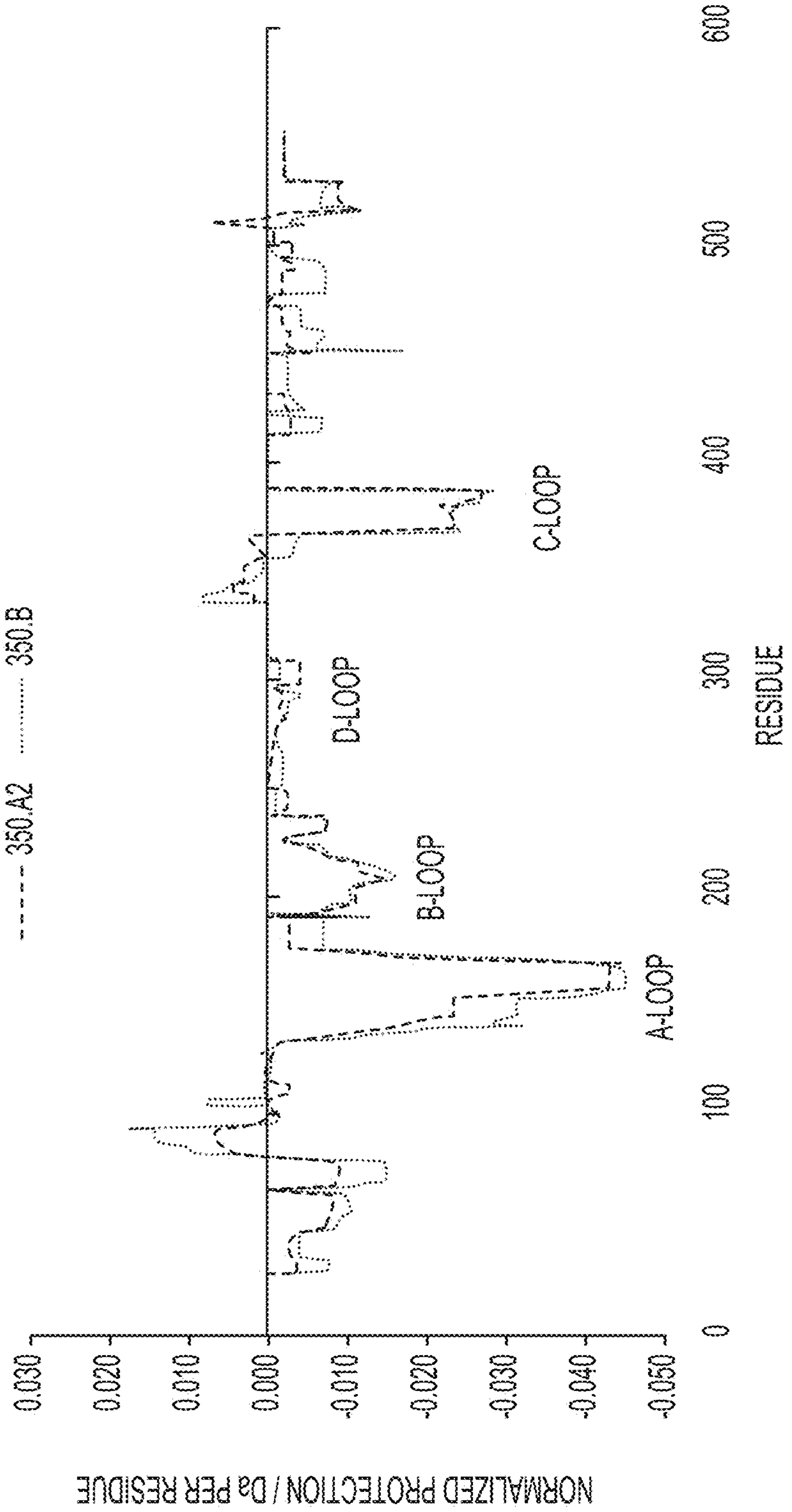
FIG. 15 is a graph showing comparison of protection profiles of 350.A2 and 350.B, as measured by fragmentation hydrogen deuterium-exchange mass spectrometry (HDx-MS).

In some embodiments, the antibody molecule reduces hydrogen-deuterium exchange at one or more regions of a protein comprising the amino acid sequence of residues 27-547 of SEQ ID NO: 105 (e.g., a protein consisting of the amino acid sequence of SEQ ID NO: 171) when bound thereto, wherein the one or more regions are selected from the group consisting of residues 158-172, residues 206-215, residues 368-387, and residues 87-104 of SEQ ID NO: 105, e.g., when the antibody molecule is tested as a bivalent antibody molecule using hydrogen deuterium-exchange mass spectrometry, e.g., the method used for FIGS. 14 and 15. Representative data are shown in FIGS. 14 and 15. In some embodiments, hydrogen-deuterium exchange is reduced by at least 10%, 20%, 30%, 40%, 50%, 60%, 70%, 80%, or 90%.

In some embodiments, the antibody molecule reduces hydrogen-deuterium exchange at one or more regions of a protein comprising the amino acid sequence of residues 27-547 of SEQ ID NO: 106 when bound thereto, wherein the one or more regions are selected from the group consisting of residues 158-172, residues 206-215, residues 368-387, and residues 87-104 of SEQ ID NO: 106, e.g., when the antibody molecule is tested as a bivalent antibody molecule using hydrogen deuterium-exchange mass spectrometry.

In some embodiments, the antibody molecule, when bound to a protein comprising the amino acid sequence of residues 27-547 of SEQ ID NO: 105 (e.g., a protein consisting of the amino acid sequence of SEQ ID NO: 171), leads to a greater reduction in hydrogen-deuterium exchange at residues 368-387 of SEQ ID NO: 105 than at residues 297-309 of SEQ ID NO: 105, e.g., as measured by a method described herein, e.g., hydrogen deuterium-exchange mass spectrometry conducted for 1-minute in-exchange at pH 7.5 and room temperature, e.g., the method used for FIGS. 14 and 15. Representative data are shown in FIGS. 14 and 15. In some embodiments, the reduction in hydrogen-deuterium exchange at residues 368-387 of SEQ ID NO: 105 is at least 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, or 4-fold of the reduction in hydrogen-deuterium exchange at residues 297-309 of SEQ ID NO: 105.

In some embodiments, the anti-CD73 antibody molecule, when bound to a protein comprising the amino acid sequence of residues 27-547 of SEQ ID NO: 106, leads to a greater reduction in hydrogen-deuterium exchange at residues 368-387 of SEQ ID NO: 106 than at residues 297-309 of SEQ ID NO: 106, e.g., as measured by a method described herein, e.g., hydrogen deuterium-exchange mass spectrometry conducted for 1-minute in-exchange at pH 7.5 and room temperature.

In some embodiments, the anti-CD73 antibody molecule, when bound to human CD73, reduces hydrogen-deuterium exchange at the C-loop of human CD73 to a greater extent than at the A-loop, B-loop, or D-loop of human CD73, e.g., as measured by a method described herein, e.g., hydrogen deuterium-exchange mass spectrometry conducted for 1-minute in-exchange at pH 7.5 and room temperature, e.g., the method used for FIGS. 14 and 15. Representative data are shown in FIGS. 14 and 15. In some embodiments, the reduction in hydrogen-deuterium exchange at the C-loop of human CD73 is at least 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, or 4-fold of the reduction in hydrogen-deuterium exchange at the A-loop, B-loop, or D-loop of human CD73.

In some embodiments, the anti-CD73 antibody molecule, when bound to a protein comprising the amino acid sequence of residues 27-547 of SEQ ID NO: 105 (e.g., a protein consisting of the amino acid sequence of SEQ ID NO: 171), reduces hydrogen-deuterium exchange at residues 368-387 of SEQ ID NO: 105 to a greater extent than at residues 158-172, residues 206-215, or residues 297-309 of SEQ ID NO: 105, e.g., as measured by a method described herein, e.g., hydrogen deuterium-exchange mass spectrometry conducted for 1-minute in-exchange at pH 7.5 and room temperature, e.g., the method used for FIGS. 14 and 15. Representative data are shown in FIGS. 14 and 15. In some embodiments, the reduction in hydrogen-deuterium exchange at residues 368-387 of SEQ ID NO: 105 is at least 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, or 4-fold of the reduction in hydrogen-deuterium exchange at residues 158-172, residues 206-215, or residues 297-309 of SEQ ID NO: 105.

In some embodiments, the anti-CD73 antibody molecule, when bound to a protein comprising the amino acid sequence of residues 27-547 of SEQ ID NO: 106, reduces hydrogen-deuterium exchange at residues 368-387 of SEQ ID NO: 106 to a greater extent than at residues 158-172, residues 206-215, or residues 297-309 of SEQ ID NO: 106, e.g., as measured by a method described herein, e.g., hydrogen deuterium-exchange mass spectrometry conducted for 1-minute in-exchange at pH 7.5 and room temperature.

In some embodiments, the anti-CD73 antibody molecule, when bound to human CD73, reduces hydrogen-deuterium exchange at the A-loop of human CD73 to a greater extent than at the B-loop, C-loop, or D-loop of human CD73, e.g., as measured by a method described herein, e.g., hydrogen deuterium-exchange mass spectrometry conducted for 1-minute in-exchange at pH 7.5 and room temperature, e.g., the method used for FIGS. 14 and 15. Representative data are shown in FIGS. 14 and 15. In some embodiments, the reduction in hydrogen-deuterium exchange at the A-loop of human CD73 is at least 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, or 4-fold of the reduction in hydrogen-deuterium exchange at the B-loop, C-loop, or D-loop of human CD73.

In some embodiments, the anti-CD73 antibody molecule, when bound to a protein comprising the amino acid sequence of residues 27-547 of SEQ ID NO: 105 (e.g., a protein consisting of the amino acid sequence of SEQ ID NO: 171), reduces hydrogen-deuterium exchange at residues 158-172 of SEQ ID NO: 105 to a greater extent than at residues 206-215, residues 368-387, or residues 297-309 of SEQ ID NO: 105, e.g., as measured by a method described herein, e.g., hydrogen deuterium-exchange mass spectrometry conducted for 1-minute in-exchange at pH 7.5 and room temperature, e.g., the method used for FIGS. 14 and 15. Representative data are shown in FIGS. 14 and 15. In some embodiments, the reduction in hydrogen-deuterium exchange at residues 158-172 of SEQ ID NO: 105 is at least 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, or 4-fold of the reduction in hydrogen-deuterium exchange at residues 206-215, residues 368-387, or residues 297-309 of SEQ ID NO: 105.

In some embodiments, the anti-CD73 antibody molecule, when bound to a protein comprising the amino acid sequence of residues 27-547 of SEQ ID NO: 105 (e.g., a protein consisting of the amino acid sequence of SEQ ID NO: 171), reduces hydrogen-deuterium exchange at residues 158-172 of SEQ ID NO: 106 to a greater extent than at residues 206-215, residues 368-387, or residues 297-309 of SEQ ID NO: 106, e.g., as measured by a method described herein, e.g., hydrogen deuterium-exchange mass spectrometry conducted for 1-minute in-exchange at pH 7.5 and room temperature.

In some embodiments, the anti-CD73 antibody molecule, when bound to a protein comprising the amino acid sequence of residues 27-547 of SEQ ID NO: 105 (e.g., a protein consisting of the amino acid sequence of SEQ ID NO: 171), is capable of reducing hydrogen-deuterium exchange at one or more regions of human CD73, wherein the one or more regions are selected from the group consisting of residues 158-172, residues 206-215, residues 368-387, and residues 87-104 of SEQ ID NO: 105, wherein the region having the greatest reduction among the one or more regions is not residues 206-215 of SEQ ID NO: 105, e.g., as measured by a method described herein, e.g., hydrogen deuterium-exchange mass spectrometry conducted for 1-minute in-exchange at pH 7.5 and room temperature, e.g., the method used for FIGS. 14 and 15. Representative data are shown in FIGS. 14 and 15.

In some embodiments, the anti-CD73 antibody molecule, when bound to a protein comprising the amino acid sequence of residues 27-547 of SEQ ID NO: 106, is capable of reducing hydrogen-deuterium exchange at one or more regions of human CD73, wherein the one or more regions are selected from the group consisting of residues 158-172, residues 206-215, residues 368-387, and residues 87-104 of SEQ ID NO: 106, wherein the region having the greatest reduction among the one or more regions is not residues 206-215 of SEQ ID NO: 106, e.g., as measured by a method described herein, e.g., hydrogen deuterium-exchange mass spectrometry conducted for 1-minute in-exchange at pH 7.5 and room temperature.

In some embodiments, the anti-CD73 antibody molecule, when bound to a protein comprising the amino acid sequence of residues 27-547 of SEQ ID NO: 105 (e.g., a protein consisting of the amino acid sequence of SEQ ID NO: 171), leads to a reduction in hydrogen-deuterium exchange of more than, e.g., 0.02, 0.03, 0.04, 0.05, or 0.06 Da per residue at residues 368-387 of SEQ ID NO: 105, e.g., as measured by a method described herein, e.g., hydrogen deuterium-exchange mass spectrometry conducted for 1-minute in-exchange at pH 7.5 and room temperature, e.g., the method used for FIGS. 14 and 15. Representative data are shown in FIGS. 14 and 15.

In some embodiments, the anti-CD73 antibody molecule, when bound to a protein comprising the amino acid sequence of residues 27-547 of SEQ ID NO: 105 (e.g., a protein consisting of the amino acid sequence of SEQ ID NO: 171), leads to a reduction in hydrogen-deuterium exchange of less than, e.g., 0.05, 0.04, 0.03, or 0.02 Da per residue at residues 206-215 of SEQ ID NO: 105, e.g., as measured by a method described herein, e.g., hydrogen deuterium-exchange mass spectrometry conducted for 1-minute in-exchange at pH 7.5 and room temperature, e.g., the method used for FIGS. 14 and 15. Representative data are shown in FIGS. 14 and 15.

Figure 17A:
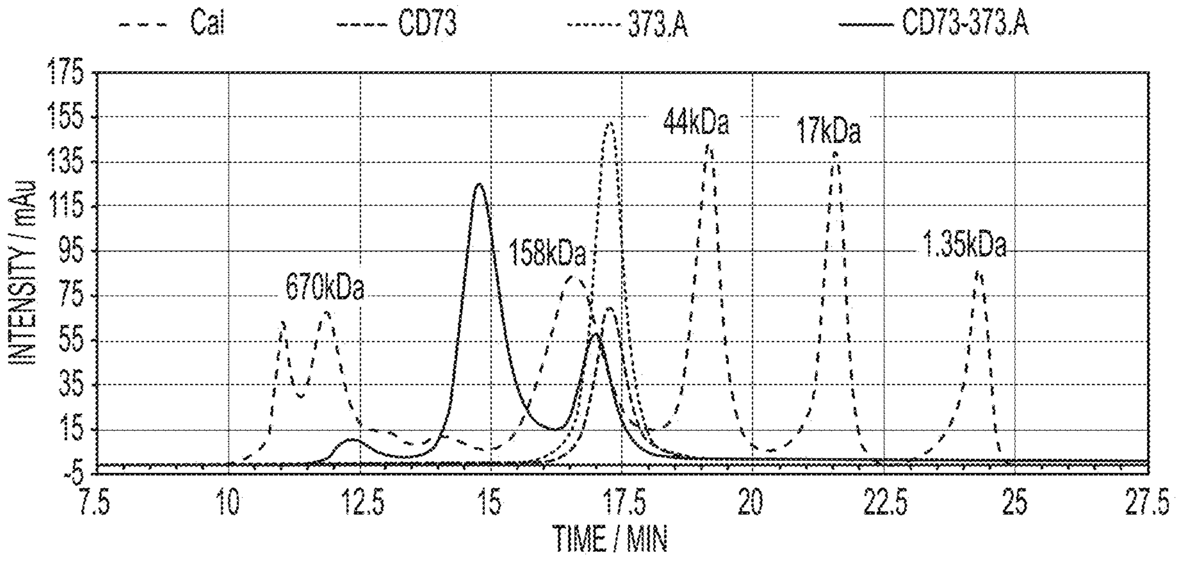
FIGS. 17A and 17B are graphs showing SEC profiles of CD73-373.A and CD73-373.B complexes, respectively.
Figure 17B:
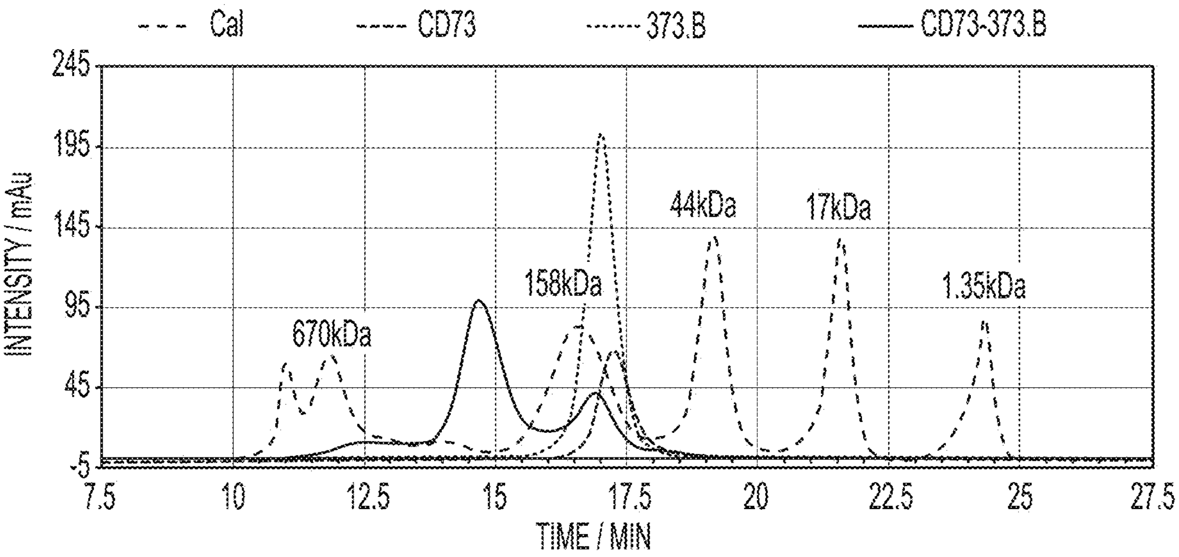

In some embodiments, the antibody molecule that binds to a human CD73 dimer, said dimer consisting of a first CD73 monomer and a second CD73 monomer, wherein when the antibody molecule comprises a first antigen binding domain and a second antigen binding domain, the first antigen binding domain binds to the first CD73 monomer and the second antigen binding domain binds to the second CD73 monomer, e.g., when tested using size exclusion chromatography, e.g., when tested using a method described herein, e.g., the method used for FIGS. 17A and 17B.

In some embodiments, disclosed herein is a composition comprising a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at least 30%, 35%, 40%, 45%, 50%, 55%, 60%, 65%, 70%, 75%, or 80% of the antibody molecules in said composition bind to the CD73 dimer to form a complex, wherein each of said complex consists of one antibody molecule and one CD73 dimer, e.g., when measured using size exclusion chromatography and the percentage value is obtained by determining the amount of the antibody molecules in the complex relative to the total amount of the antibody molecules binding to CD73 (excluding unbound antibody molecules), e.g. when tested using a method described herein, e.g., the method used for FIGS. 17A, 17B, 18A, and 18B. Representative data are shown in FIGS. 17A, 17B, 18A, and 18B.

In some embodiments, disclosed herein is a plurality of antibody molecules that bind to a human CD73 dimer, said dimer consisting of a first CD73 monomer and a second CD73 monomer, each monomer comprising the amino acid sequence of residues 27-547 of SEQ ID NO: 105 (e.g., each monomer consisting of the amino acid sequence of SEQ ID NO: 171), wherein when the antibody molecules in the plurality each comprises the same first antigen binding domain and the same second antigen binding domain, at most 20%, 25%, 30%, 35%, 40%, 45%, 50%, 55%, 60%, 65%, or 70% of the antibody molecules in said composition bind to the CD73 dimer to form a complex, wherein each of said complex comprises two or more antibody molecules and two or more CD73 dimers, e.g., when measured using size exclusion chromatography and the percentage value is obtained by determining the amount of the antibody molecules in the complex relative to the total amount of the antibody molecules binding to CD73 (excluding unbound antibody molecules), e.g. when tested using a method described herein, e.g., the method used for FIGS. 17A, 17B, 18A, and 18B. Representative data are shown in FIGS. 17A, 17B, 18A, and 18B.

In some embodiments, the anti-CD73 antibody molecule, upon binding to human CD73, does not lead to oligomerization of human CD73.

In some embodiments, the antibody molecule preferentially binds to an open conformation, e.g., a catalytically inactive conformation, of CD73 over a closed conformation, e.g., a catalytically active conformation, of CD73, e.g., does not bind to or binds to the closed conformation, e.g., the catalytically active conformation, of CD73 with lower affinity, e.g., 50%, 60%, 70%, 80%, 90%, 95%, or 99% lower affinity than when the antibody molecule binds to the open conformation, e.g., the catalytically inactive conformation, of CD73.

In some embodiments, the anti-CD73 antibody molecule prevents or reduces the conversion of human CD73 from a catalytically inactive open conformation to a catalytically active closed conformation. In some embodiments, the conversion of human CD73 from a catalytically inactive open conformation to a catalytically active closed conformation is reduced by at least 1.5-fold, 2-fold, 5-fold, 10-fold, 20-fold, 30-fold, 40-fold, 50-fold, 60-fold, 70-fold, 80-fold, 90-fold, or 100-fold, compared to the conversion in the absence of the antibody molecule.

In some embodiments, the anti-CD73 antibody molecule contacts, e.g., directly or indirectly, at least one residue within residues 158-172 of SEQ ID NO: 105. In some embodiments, the anti-CD73 antibody molecule contacts, e.g., directly or indirectly, at least one residue within residues 206-215 of SEQ ID NO: 105. In some embodiments, the anti-CD73 antibody molecule contacts, e.g., directly or indirectly, at least one residue within residues 368-387 of SEQ ID NO: 105. In some embodiments, the anti-CD73 antibody molecule contacts, e.g., directly or indirectly, at least one residue within residues 87-104 of SEQ ID NO: 105. In some embodiments, the anti-CD73 antibody molecule contacts, e.g., directly or indirectly, at least one residue within residues 368-387 of SEQ ID NO: 106.

In some embodiments, the anti-CD73 antibody molecule inhibits or reduces the enzymatic activity of CD73 (e.g., soluble human CD73 or membrane-bound human CD73), e.g., human CD73 mediated conversion of adenosine monophosphate (AMP) to adenosine, e.g., as measured by a method described herein, e.g., a malachite green (MG) phosphate assay or a modified Cell Titer Glo (CTG) assay, e.g., the method used in FIG. 2B, 3A, 3B, 3C, 4, 5, 6, 7A, 7B, 7C, 8A, 8B, 9A, 9B, 10, 11A, 11B, or 13. Representative data are shown in FIGS. 2B, 3A, 3B, 3C, 4, 5, 6, 7A, 7B, 7C, 8A, 8B, 9A, 9B, 10, 11A, 11B, and 13. In some embodiments, the enzymatic activity of CD73 (e.g., soluble human CD73 or membrane-bound human CD73) is reduced by at least 10%, 20%, 30%, 40%, 50%, 60%, 70%, 80%, 90%, or 99%.

Figure 12A:
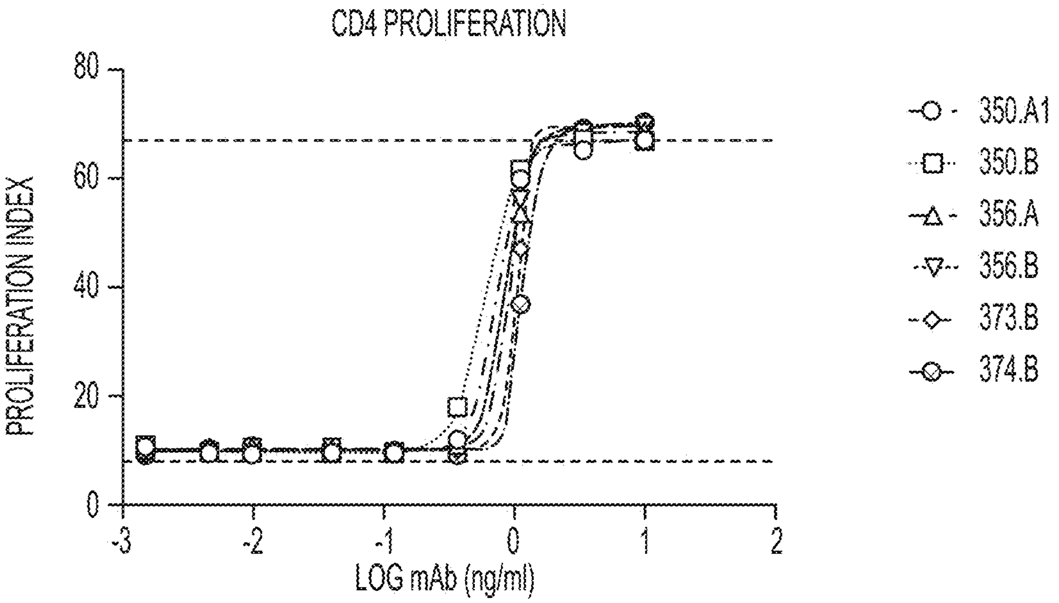
FIGS. 12A and 12B are graphs showing the proliferation of anti-CD3/28 stimulated CD4+ T cells in the presence of AMP and an anti-CD73 antibody. Proliferation index, a measure of T cell division, is plotted against a range of antibody concentrations.
Figure 12B:
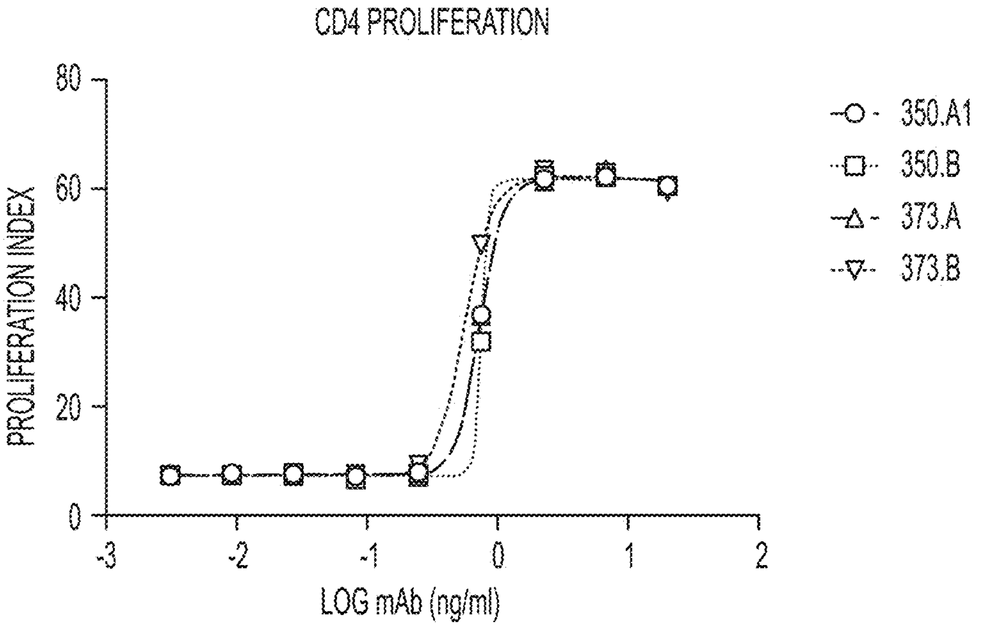

In some embodiments, the anti-CD73 antibody molecule increases proliferation of anti-CD3/anti-CD28 stimulated T cells, e.g., CD4+ T cells, in the presence of adenosine monophosphate (AMP), e.g., as measured by a method described herein, e.g., a CellTrace Violet (CTV) cell proliferation assay, e.g., the method used in FIG. 12A or 12B. Representative data are shown in FIGS. 12A and 12B. In some embodiments, anti-CD3/anti-CD28 stimulated T cell, e.g., CD4+ T cell, proliferation is increased by at least 2-fold, 3-fold, 4-fold, 5-fold, 6-fold, 7-fold, 8-fold, 9-fold, or 10-fold.

In another aspect, the invention provides an isolated nucleic acid encoding any of the aforesaid antibody molecules, vectors and host cells thereof. The nucleic acid molecule includes but is not limited to RNA, genomic DNA and cDNA.

In some embodiments, the isolated nucleic acid encodes the antibody heavy chain variable region, light chain variable region, heavy chain, and/or light chain of any of the aforesaid antibody molecules.

In some embodiments, the isolated nucleic acid encodes a heavy chain variable region, wherein the nucleic acid comprises the nucleotide sequence of SEQ ID NO: 45, 78, 85, 143, 152, 160, 67, 32, 11, or 169, or a nucleotide sequence having at least about 85%, 90%, 95%, or 99% sequence identity to SEQ ID NO: 45, 78, 85, 143, 152, 160, 67, 32, 11, or 169.

In some embodiments, the isolated nucleic acid encodes a heavy chain, wherein the nucleic acid comprises the nucleotide sequence of SEQ ID NO: 47, 80, 87, 69, 34, or 13, or a nucleotide sequence having at least about 85%, 90%, 95%, or 99% sequence identity to SEQ ID NO: 47, 80, 87, 69, 34, or 13.

In some embodiments, the isolated nucleic acid encodes a light chain variable region, wherein the nucleic acid comprises the nucleotide sequence of SEQ ID NO: 56, 144, 22, or 170, or a nucleotide sequence having at least about 85%, 90%, 95%, or 99% sequence identity to SEQ ID NO: 56, 144, 22, or 170.

In some embodiments, the isolated nucleic acid encodes a light chain, wherein the nucleic acid comprises the nucleotide sequence of SEQ ID NO: 58 or 24, or a nucleotide sequence having at least about 85%, 90%, 95%, or 99% sequence identity to SEQ ID NO: 58 or 24.

Pharmaceutical Compositions and Kits

In some aspects, this disclosure provides compositions, e.g., pharmaceutically acceptable compositions, which include an anti-CD73 antibody molecule described herein, formulated together with a pharmaceutically acceptable carrier. As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g. by injection or infusion).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In some embodiments, the antibody molecule is administered by intravenous infusion or injection. In certain embodiments, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules can be administered by a variety of methods. Several are known in the art, and for many therapeutic applications, an appropriate route/mode of administration is intravenous injection or infusion. In an embodiment, the antibody molecules can be administered by intravenous infusion at a rate of more than 20 mg/min, e.g., 20-40 mg/min. In an embodiment, the antibody molecules can be administered by intravenous infusion at a rate of greater than or equal to 40 mg/min to reach a dose of about 35 to 440 mg/m$^2$, about 70 to 310 mg/m$^2$, or about 110 to 130 mg/m$^2$. In an embodiment, the antibody molecules can be administered by intravenous infusion at a rate of less than 10 mg/min, e.g., less than or equal to 5 mg/min to reach a dose of about 1 to 100 mg/m$^2$, about 5 to 50 mg/m$^2$, about 7 to 25 mg/m$^2$, or about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody molecule can be orally administered, for example, with an inert diluent or an assimilable edible carrier. The antibody molecule (and other ingredients, if desired) may also be enclosed in a hard or soft shell gelatin capsule, compressed into tablets, or incorporated directly into the subject's diet. For oral therapeutic administration, the antibody molecule may be incorporated with excipients and used in the form of ingestible tablets, buccal tablets, troches, capsules, elixirs, suspensions, syrups, wafers, and the like. To administer an antibody molecule by other than parenteral administration, it may be necessary to coat the compound with, or co-administer the compound with, a material to prevent its inactivation. Therapeutic compositions can also be administered with medical devices known in the art.

Dosage regimens are adjusted to provide the desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic effect to be achieved, and (b) the limitations inherent in the art of compounding such an active compound for the treatment of sensitivity in individuals.

In some embodiments, an anti-CD73 antibody molecule disclosed herein is administered by injection (e.g., subcutaneously or intravenously) at a dose (e.g., a flat dose) of about 60 mg to 2400 mg, e.g., about 100 mg to 2400 mg, about 100 mg to 2200 mg, about 100 mg to 2000 mg, about 100 mg to 1800 mg, about 100 mg to 1600 mg, about 100 mg to 1400 mg, about 100 mg to 1200 mg, about 100 mg to 1000 mg, about 100 mg to 800 mg, about 100 mg to 600 mg, about 100 mg to 400 mg, about 100 mg to 200 mg, or about 100 mg, about 180 mg, or about 200 mg. The dosing schedule (e.g., flat dosing schedule) can vary from e.g., once a week to once every 2, 3, or 4 weeks. In one embodiment, an anti-CD73 antibody molecule disclosed herein is administered at a dose from about 100 mg to 200 mg once every week, once every two weeks, or once every three weeks. In one embodiment, an anti-CD73 antibody molecule disclosed herein is administered at a dose of at least about 180 mg once every two weeks.

In some embodiments, an anti-CD73 antibody molecule disclosed herein is administered by injection (e.g., subcutaneously or intravenously) at a dose (e.g., a flat dose) of about 5 mg to 100 mg, about 100 mg to 500 mg, about 500 mg to 1000 mg, about 1000 mg to 1500 mg, about 1500 mg to 2000 mg, about 2000 mg to 2500 mg, about 2500 mg to 3000 mg, about 3000 mg to 3500 mg, or about 3500 mg to 4000 mg, e.g., once every week (QW), once every two weeks (Q2W), or once every four weeks (Q4W). In certain embodiments, the antibody molecule is administered, e.g., intravenously, at a dose of about 6 mg, about 20 mg, about 60 mg, about 200 mg, about 600 mg, about 1200 mg, about 2400 mg, about 3000 mg, or about 3600 mg, e.g., QW, Q2W, or Q4W. In certain embodiments, the antibody molecule is administered, e.g., intravenously, at a dose of about 60 mg Q2W. In certain embodiments, the antibody molecule is administered, e.g., intravenously, at a dose of about 200 mg Q2W. In certain embodiments, the antibody molecule is administered, e.g., intravenously, at a dose of about 600 mg Q2W. In certain embodiments, the antibody molecule is administered, e.g., intravenously, at a dose of about 1200 mg Q2W. In certain embodiments, the antibody molecule is administered, e.g., intravenously, at a dose of about 2400 mg Q2W. In certain embodiments, the antibody molecule is administered, e.g., intravenously, at a dose of about 3000 mg Q2W. In certain embodiments, the antibody molecule is administered, e.g., intravenously, at a dose of about 3600 mg Q2W.

In one embodiment, an anti-CD73 antibody molecule disclosed herein is administered, e.g., by infusion, over a period of 30 minutes, a period of 1 hour, or a period of up to 2 hours.

An exemplary, non-limiting range for a therapeutically or prophylactically effective amount of an antibody molecule is 0.1-30 mg/kg, more preferably 1-25 mg/kg. Dosages and therapeutic regimens of the anti-CD73 antibody molecule can be determined by a skilled artisan. In certain embodiments, the anti-CD73 antibody molecule is administered by injection (e.g., subcutaneously or intravenously) at a dose of about 1 to 40 mg/kg, e.g., 1 to 30 mg/kg, e.g., about 5 to 25 mg/kg, about 10 to 20 mg/kg, about 1 to 5 mg/kg, 1 to 10 mg/kg, 5 to 15 mg/kg, 10 to 20 mg/kg, 15 to 25 mg/kg, or about 3 mg/kg. The dosing schedule can vary from e.g., once a week to once every 2, 3, or 4 weeks. In one embodiment, the anti-CD73 antibody molecule is administered at a dose from about 10 to 20 mg/kg every other week. The antibody molecule can be administered by intravenous infusion at a rate of more than 20 mg/min, e.g., 20-40 mg/min, e.g., greater than or equal to 40 mg/min to reach a dose of about 35 to 440 mg/m$^2$, about 70 to 310 mg/m$^2$, or about 110 to 130 mg/m$^2$. In embodiments, the infusion rate of about 110 to 130 mg/m$^2$ achieves a level of about 3 mg/kg. In other embodiments, the antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or about 10 mg/m$^2$. In some embodiments, the antibody is infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an antibody molecule of the invention. A "therapeutically effective amount" refers to an amount effective, at dosages and for periods of time necessary, to achieve the desired therapeutic result. A therapeutically effective amount of the modified antibody or antibody fragment may vary according to factors such as the disease state, age, sex, and weight of the individual, and the ability of the antibody or antibody portion to elicit a desired response in the individual. A therapeutically effective amount is also one in which any toxic or detrimental effects of the antibody molecule are outweighed by the therapeutically beneficial effects. A "therapeutically effective dosage" preferably inhibits a measurable parameter by at least about 20%, more preferably by at least about 40%, even more preferably by at least about 60%, and still more preferably by at least about 80% relative to untreated subjects. The measurable parameter may be, e.g., tumor growth rate or pathogen growth rate. The ability of an antibody molecule to inhibit a measurable parameter can be evaluated in an animal model system predictive of efficacy in the corresponding human disease. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention is a kit comprising an antibody molecule described herein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody molecule for administration; pharmaceutically acceptable carriers; and devices or other materials for administration to a subject.

Uses of Anti-CD73 Antibody Molecules

The anti-CD73 antibody molecules disclosed herein have in vitro and in vivo diagnostic, as well as therapeutic and prophylactic utilities. For example, these molecules can be administered to cells in culture, in vitro or ex vivo, or to a subject, e.g., a human subject, to treat, prevent, and/or diagnose a variety of disorders, such as cancers and infectious disorders.

Accordingly, in one aspect, the invention provides a method of modifying an immune response in a subject comprising administering to the subject the antibody molecule described herein, such that the immune response in the subject is modified. In one embodiment, the immune response is enhanced, stimulated or up-regulated. In one embodiment, the antibody molecules enhance an immune response in a subject by blockade of CD73.

As used herein, the term "subject" is intended to include human and non-human animals. In one embodiment, the subject is a human subject, e.g., a human patient having a disorder or condition characterized by abnormal CD73 functioning. The term "non-human animals" includes mammals and non-mammals, such as non-human primates. In one embodiment, the subject is a human. In one embodiment, the subject is a human patient in need of enhancement of an immune response. In one embodiment, the subject is immunocompromised, e.g., the subject is undergoing, or has undergone a chemotherapeutic or radiation therapy. Alternatively, or in combination, the subject is, or is at risk of being, immunocompromised as a result of an infection. The methods and compositions described herein are suitable for treating human patients having a disorder that can be treated by augmenting the T-cell mediated immune response. For example, the methods and compositions described herein can enhance a number of immune activities. In one embodiment, the subject has increased number or activity of tumour-infiltrating T lymphocytes (TILs).

Therapeutic Uses

Cancer

In one aspect, the invention relates to treatment of a subject in vivo using an anti-CD73 antibody molecule such that growth of cancerous tumors is inhibited or reduced. An anti-CD73 antibody may be used alone to inhibit the growth of cancerous tumors. Alternatively, an anti-CD73 antibody may be used in combination with one or more of: a standard of care treatment (e.g., for cancers), another antibody molecule, an immunomodulator (e.g., an activator of a costimulatory molecule or an inhibitor of a coinhibitory molecule); a vaccine, e.g., a therapeutic cancer vaccine; or other forms of cell therapy, as described below.

Accordingly, in one embodiment, the invention provides a method of inhibiting growth of tumor cells in a subject, comprising administering to the subject a therapeutically effective amount of an anti-CD73 antibody molecule described herein.

In one embodiment, the methods are suitable for the treatment of cancer in vivo. To achieve antigen-specific enhancement of immunity, the anti-CD73 antibody molecule can be administered together with an antigen of interest. When antibodies to CD73 are administered in combination with one or more agents, the combination can be administered in either order or simultaneously.

Types of Cancer

In another aspect, a method of treating a subject, e.g., reducing or ameliorating, a hyperproliferative condition or disorder (e.g., a cancer), e.g., solid tumor, a hematological cancer, soft tissue tumor, or a metastatic lesion, in a subject is provided. The method includes administering to the subject one or more anti-CD73 antibody molecules described herein, alone or in combination with other agents or therapeutic modalities.

As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, hematological cancers, soft tissue tumors, and metastatic lesions. Examples of solid tumors include malignancies, e.g., sarcomas, and carcinomas (including adenocarcinomas and squamous cell carcinomas), of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. Squamous cell carcinomas include malignancies, e.g., in the lung, esophagus, skin, head and neck region, oral cavity, anus, and cervix. In one embodiment, the cancer is a melanoma, e.g., an advanced stage melanoma. Metastatic lesions of the aforementioned cancers can also be treated or prevented using the methods and compositions of the invention.

Exemplary cancers whose growth can be inhibited using the antibodies molecules disclosed herein include cancers typically responsive to immunotherapy. Non-limiting examples of preferred cancers for treatment include melanoma (e.g., metastatic malignant melanoma), renal cancer (e.g., clear cell carcinoma), prostate cancer (e.g., hormone refractory prostate adenocarcinoma), breast cancer, colon cancer and lung cancer (e.g., non-small cell lung cancer). Additionally, refractory or recurrent malignancies can be treated using the antibody molecules described herein.

Examples of other cancers that can be treated include bone cancer, pancreatic cancer, skin cancer, cancer of the head or neck, cutaneous or intraocular malignant melanoma, uterine cancer, ovarian cancer, rectal cancer, anal cancer, gastro-esophageal, stomach cancer, testicular cancer, uterine cancer, carcinoma of the fallopian tubes, carcinoma of the endometrium, carcinoma of the cervix, carcinoma of the vagina, carcinoma of the vulva, Merkel cell cancer, Hodgkin lymphoma, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, multiple myeloma, myelodisplastic syndromes, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos (e.g., mesothelioma), and combinations of said cancers.

In some embodiments, the therapies here can be used to treat a patient that has (or is identified as having) a cancer associated with an infection, e.g., a viral or bacterial infection. Exemplary cancers include cervical cancer, anal cancer, HPV-associated head and neck squamous cell cancer, HPV-associated esophageal papillomas, HHV6-associated lymphomas, EBV-associated lymphomas (including Burkitt lymphoma), Gastric MALT lymphoma, other infection-associated MALT lymphomas, HCC, and Kaposi's sarcoma.

In other embodiments, the cancer is a hematological malignancy or cancer including but is not limited to a leukemia or a lymphoma. For example, the anti-CD73 antibody molecule can be used to treat cancers and malignancies including, but not limited to, e.g., acute leukemias including but not limited to, e.g., B-cell acute lymphoid leukemia ("BALL"), T-cell acute lymphoid leukemia ("TALL"), acute lymphoid leukemia (ALL); one or more chronic leukemias including but not limited to, e.g., chronic myelogenous leukemia (CML), chronic lymphocytic leukemia (CLL); additional hematologic cancers or hematologic conditions including, but not limited to, e.g., B cell prolymphocytic leukemia, blastic plasmacytoid dendritic cell neoplasm, Burkitt's lymphoma, diffuse large B cell lymphoma, Follicular lymphoma, Hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin lymphoma, plasmablastic lymphoma, plasmacytoid dendritic cell neoplasm, Waldenstrom macroglobulinemia, and "preleukemia" which are a diverse collection of hematological conditions united by ineffective production (or dysplasia) of myeloid blood cells, and the like.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma, e.g., clear cell renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer (e.g., microsatellite stable (MSS) colorectal cancer), ovarian cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, a non-Hogdkin's lymphoma, or a leukemia (e.g., a myeloid leukemia).

In one embodiment, the cancer is chosen from lung cancer (e.g., non-small cell lung cancer), pancreas cancer (e.g., pancreatic ductal adenocarcinoma), breast cancer (e.g., triple-negative breast cancer), melanoma, head and neck cancer (e.g., squamous head and neck cancer), colorectal cancer (e.g., microsatellite stable (MSS) colorectal cancer), ovarian cancer, or renal cancer (e.g., renal cell carcinoma).

In one embodiment, the cancer is chosen from bladder cancer, leukemia, lymphoma, glioma, glioblastoma, ovarian cancer, thyroid cancer, esophageal cancer, prostate cancer, uterine/cervical cancer, testicular cancer, esophageal cancer, gastrointestinal cancer, colon cancer, kidney cancer, stomach cancer, germ cell cancer, bone cancer, liver cancer, skin cancer, neoplasm of the central nervous system, myeloma, sarcoma, and virus-related cancer.

Combination of Anti-CD73 Antibody Molecules

The anti-CD73 antibody molecules can be used in combination with other therapies. For example, the combination therapy can include a composition of the present invention co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the antibody molecules are administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

By "in combination with," it is not intended to imply that the therapy or the therapeutic agents must be administered at the same time and/or formulated for delivery together, although these methods of delivery are within the scope described herein. The anti-CD73 antibody molecules can be administered concurrently with, prior to, or subsequent to, one or more other additional therapies or therapeutic agents. The anti-CD73 antibody molecule and the other agent or therapeutic protocol can be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

Exemplary Adenosine A2A Receptor Antagonists

In certain embodiments, the anti-CD73 molecules described herein are administered in combination with an adenosine A2A receptor (A2AR) antagonist. Exemplary A2AR antagonists include, e.g., PBF509 (Palobiofarma/Novartis), CPI444/V81444 (Corvus/Genentech), AZD4635/HTL-1071 (AstraZeneca/Heptares), Vipadenant (Redox/Juno), GBV-2034 (Globavir), AB928 (Arcus Biosciences), Theophylline, Istradefylline (Kyowa Hakko Kogyo), Tozadenant/SYN-115 (Acorda), KW-6356 (Kyowa Hakko Kogyo), ST-4206 (Leadiant Biosciences), and Preladenant/SCH 420814 (Merck/Schering).

In certain embodiments, the A2AR antagonist is PBF509. PBF509 and other A2AR antagonists are disclosed in U.S. Pat. No. 8,796,284 and WO 2017/025918, herein incorporated by reference in their entirety. PBF509 refers to 5-bromo-2,6-di-(1H-pyrazol-1-yl)pyrimidine-4-amine with the following structure:

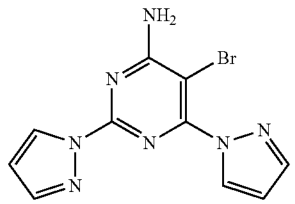 [SMILES: Nc1nc(-n2cccn2)nc(-n2cccn2)c1Br]

In certain embodiments, the A2AR antagonist is CPI444/V81444. CPI-444 and other A2AR antagonists are disclosed in WO 2009/156737, herein incorporated by reference in its entirety. In certain embodiments, the A2AR antagonist is (S)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine. In certain embodiments, the A2AR antagonist is (R)-7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine, or racemate thereof. In certain embodiments, the A2AR antagonist is 7-(5-methylfuran-2-yl)-3-((6-(((tetrahydrofuran-3-yl)oxy)methyl)pyridin-2-yl)methyl)-3H-[1,2,3]triazolo[4,5-d]pyrimidin-5-amine. In certain embodiments, the A2AR antagonist has the following structure:

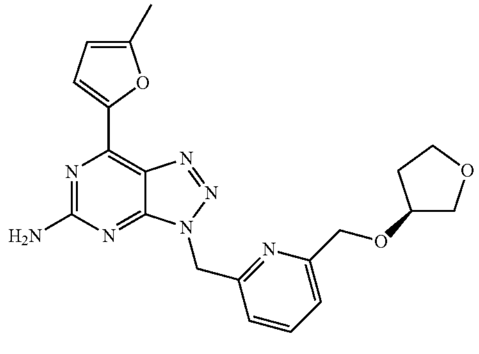 [SMILES: Cc1ccc(-c2nc(N)nc3c2nnn3Cc2cccc(CO[C@H]3CCOC3)n2)o1]

In certain embodiments, the A2AR antagonist is AZD4635/HTL-1071. A2AR antagonists are disclosed in WO 2011/095625, herein incorporated by reference in its entirety. In certain embodiments, the A2AR antagonist is 6-(2-chloro-6-methylpyridin-4-yl)-5-(4-fluorophenyl)-1,2,4-triazin-3-amine. In certain embodiments, the A2AR antagonist has the following structure:

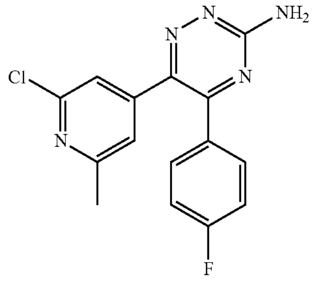 [SMILES: Cc1cc(-c2nnc(N)nc2-c2ccc(F)cc2)cc(Cl)n1]

In certain embodiments, the A2AR antagonist is ST-4206 (Leadiant Biosciences). In certain embodiments, the A2AR antagonist is an A2AR antagonist described in U.S. Pat. No. 9,133,197, herein incorporated by reference in its entirety. In certain embodiments, the A2AR antagonist has the following structure:

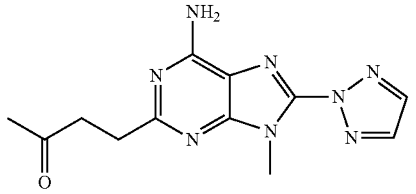 [SMILES: CC(=O)CCc1nc(N)c2nc(-n3nccn3)n(C)c2n1]

In certain embodiments, the A2AR antagonist is an A2AR antagonist described in U.S. Pat. Nos. 8,114,845, 9,029,393, US20170015758, or US20160129108, herein incorporated by reference in their entirety.

In certain embodiments, the A2AR antagonist is istradefylline (CAS Registry Number: 155270-99-8). Istradefylline is also known as KW-6002 or 8-[(E)-2-(3,4-dimethoxyphenyl)vinyl]-1,3-diethyl-7-methyl-3,7-dihydro-1H-purine-2,6-dione. Istradefylline is disclosed, e.g., in LeWitt et al. (2008) *Annals of Neurology* 63 (3): 295-302).

In certain embodiments, the A2aR antagonist is tozadenant (Biotie). Tozadenant is also known as SYN 115 or 4-hydroxy-N-(4-methoxy-7-morpholin-4-yl-1,3-benzothiazol-2-yl)-4-methylpiperidine-1-carboxamide. Tozadenant blocks the effect of endogenous adenosine at the A2a receptors, resulting in the potentiation of the effect of dopamine at the D2 receptor and inhibition of the effect of glutamate at the mGluR5 receptor. In some embodiments, the A2aR antagonist is preladenant (CAS Registry Number: 377727-87-2). Preladenant is also known as SCH 420814 or 2-(2-Furanyl)-7-[2-[4-[4-(2-methoxyethoxy)phenyl]-1-piperazinyl]ethyl]7H-pyrazolo[4,3-e][1,2,4]triazolo[1,5-c] pyrimidine-5-amine. Preladenant was developed as a drug that acted as a potent and selective antagonist at the adenosine A2A receptor.

In certain embodiments, the A2aR antagonist is vipadenan. Vipadenan is also known as BIIB014, V2006, or 3-[(4-amino-3-methylphenyl)methyl]-7-(furan-2-yl)triazolo [4,5-d]pyrimidin-5-amine.

Other exemplary A2aR antagonists include, e.g., ATL-444, MSX-3, SCH-58261, SCH-412,348, SCH-442,416, VER-6623, VER-6947, VER-7835, CGS-15943, or ZM-241,385.

In some embodiments, the A2aR antagonist is an A2aR pathway antagonist (e.g., a CD-73 inhibitor, e.g., an anti-CD73 antibody) is MEDI9447. MEDI9447 is a monoclonal antibody specific for CD73. Targeting the extracellular production of adenosine by CD73 may reduce the immunosuppressive effects of adenosine. MEDI9447 was reported to have a range of activities, e.g., inhibition of CD73 ectonucleotidase activity, relief from AMP-mediated lymphocyte suppression, and inhibition of syngeneic tumor growth. MEDI9447 can drive changes in both myeloid and lymphoid infiltrating leukocyte populations within the tumor microenvironment. These changes include, e.g., increases in CD8 effector cells and activated macrophages, as well as a reduction in the proportions of myeloid-derived suppressor cells (MDSC) and regulatory T lymphocytes.

Exemplary PD-1 Inhibitors

In certain embodiments, the anti-CD73 antibody molecule described herein is administered in combination with a PD-1 inhibitor. The PD-1 inhibitor may be an antibody, an antigen binding fragment thereof, an immunoadhesin, a fusion protein, or an oligopeptide. In some embodiments, the PD-1 inhibitor is chosen from PDR001 (Novartis), Nivolumab (Bristol-Myers Squibb), Pembrolizumab (Merck & Co), Pidilizumab (CureTech), MEDI0680 (Medimmune), REGN2810 (Regeneron), TSR-042 (Tesaro), PF-06801591 (Pfizer), BGB-A317 (Beigene), BGB-108 (Beigene), INCSHR1210 (Incyte), or AMP-224 (Amplimmune).

Exemplary Anti-PD-1 Antibody Molecules

In one embodiment, the PD-1 inhibitor is an anti-PD-1 antibody molecule. In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety.

In one embodiment, the anti-PD-1 antibody molecule comprises at least one, two, three, four, five or six complementarity determining regions (CDRs) (or collectively all of the CDRs) from a heavy and light chain variable region comprising an amino acid sequence shown in Table 5 (e.g., from the heavy and light chain variable region sequences of BAP049-Clone-E or BAP049-Clone-B disclosed in Table 5), or encoded by a nucleotide sequence shown in Table 5. In some embodiments, the CDRs are according to the Kabat definition (e.g., as set out in Table 5). In some embodiments, the CDRs are according to the Chothia definition (e.g., as set out in Table 5). In some embodiments, the CDRs are according to the combined CDR definitions of both Kabat and Chothia (e.g., as set out in Table 5). In one embodiment, the combination of Kabat and Chothia CDR of VH CDR1 comprises the amino acid sequence GYTFTTYWMH (SEQ ID NO: 541). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 5, or encoded by a nucleotide sequence shown in Table 5.

In one embodiment, the anti-PD-1 antibody molecule comprises a heavy chain variable region (VH) comprising a VHCDR1 amino acid sequence of SEQ ID NO: 501, a VHCDR2 amino acid sequence of SEQ ID NO: 502, and a VHCDR3 amino acid sequence of SEQ ID NO: 503; and a light chain variable region (VL) comprising a VLCDR1 amino acid sequence of SEQ ID NO: 510, a VLCDR2 amino acid sequence of SEQ ID NO: 511, and a VLCDR3 amino acid sequence of SEQ ID NO: 512, each disclosed in Table 5.

In one embodiment, the antibody molecule comprises a VH comprising a VHCDR1 encoded by the nucleotide sequence of SEQ ID NO: 524, a VHCDR2 encoded by the nucleotide sequence of SEQ ID NO: 525, and a VHCDR3 encoded by the nucleotide sequence of SEQ ID NO: 526; and a VL comprising a VLCDR1 encoded by the nucleotide sequence of SEQ ID NO: 529, a VLCDR2 encoded by the nucleotide sequence of SEQ ID NO: 530, and a VLCDR3 encoded by the nucleotide sequence of SEQ ID NO: 531, each disclosed in Table 5.

In one embodiment, the anti-PD-1 antibody molecule comprises a VH comprising the amino acid sequence of SEQ ID NO: 506, or an amino acid sequence having at least about 85%, 90%, 95%, or 99% sequence identity or higher to SEQ ID NO: 506. In one embodiment, the anti-PD-1 antibody molecule comprises a VL comprising the amino acid sequence of SEQ ID NO: 520, or an amino acid sequence having at least about 85%, 90%, 95%, or 99% sequence identity or higher to SEQ ID NO: 520. In one embodiment, the anti-PD-1 antibody molecule comprises a VL comprising the amino acid sequence of SEQ ID NO: 516, or an amino acid sequence having at least about 85%, 90%, 95%, or 99% sequence identity or higher to SEQ ID NO: 516. In one embodiment, the anti-PD-1 antibody molecule comprises a VH comprising the amino acid sequence of SEQ ID NO: 506 and a VL comprising the amino acid sequence of SEQ ID NO: 520. In one embodiment, the anti-PD-1 antibody molecule comprises a VH comprising the amino acid sequence of SEQ ID NO: 506 and a VL comprising the amino acid sequence of SEQ ID NO: 516.

In one embodiment, the antibody molecule comprises a VH encoded by the nucleotide sequence of SEQ ID NO: 507, or a nucleotide sequence having at least about 85%, 90%, 95%, or 99% sequence identity or higher to SEQ ID NO: 507. In one embodiment, the antibody molecule comprises a VL encoded by the nucleotide sequence of SEQ ID NO: 521 or 517, or a nucleotide sequence having at least about 85%, 90%, 95%, or 99% sequence identity or higher to SEQ ID NO: 521 or 517. In one embodiment, the antibody molecule comprises a VH encoded by the nucleotide sequence of SEQ ID NO: 507 and a VL encoded by the nucleotide sequence of SEQ ID NO: 521 or 517.

In one embodiment, the anti-PD-1 antibody molecule comprises a heavy chain comprising the amino acid sequence of SEQ ID NO: 508, or an amino acid sequence having at least about 85%, 90%, 95%, or 99% sequence identity or higher to SEQ ID NO: 508. In one embodiment, the anti-PD-1 antibody molecule comprises a light chain comprising the amino acid sequence of SEQ ID NO: 522, or an amino acid sequence having at least about 85%, 90%, 95%, or 99% sequence identity or higher to SEQ ID NO: 522. In one embodiment, the anti-PD-1 antibody molecule comprises a light chain comprising the amino acid sequence of SEQ ID NO: 518, or an amino acid sequence having at least about 85%, 90%, 95%, or 99% sequence identity or higher to SEQ ID NO: 518. In one embodiment, the anti-PD-1 antibody molecule comprises a heavy chain comprising the amino acid sequence of SEQ ID NO: 508 and a light chain comprising the amino acid sequence of SEQ ID NO: 522. In one embodiment, the anti-PD-1 antibody molecule comprises a heavy chain comprising the amino acid sequence of SEQ ID NO: 508 and a light chain comprising the amino acid sequence of SEQ ID NO: 518.

In one embodiment, the antibody molecule comprises a heavy chain encoded by the nucleotide sequence of SEQ ID NO: 509, or a nucleotide sequence having at least about 85%, 90%, 95%, or 99% sequence identity or higher to SEQ ID NO: 509. In one embodiment, the antibody molecule comprises a light chain encoded by the nucleotide sequence of SEQ ID NO: 523 or 519, or a nucleotide sequence having at least about 85%, 90%, 95%, or 99% sequence identity or higher to SEQ ID NO: 523 or 519. In one embodiment, the antibody molecule comprises a heavy chain encoded by the nucleotide sequence of SEQ ID NO: 509 and a light chain encoded by the nucleotide sequence of SEQ ID NO: 523 or 519.

The antibody molecules described herein can be made by vectors, host cells, and methods described in US 2015/0210769, incorporated by reference in its entirety.

TABLE 5

Amino acid and nucleotide sequences of exemplary anti-PD-1 antibody molecules

| | | |
|---|---|---|
| BAP049-Clone-B HC | | |
| SEQ ID NO: 501 (Kabat) | HCDR1 | TYWMH |
| SEQ ID NO: 502 (Kabat) | HCDR2 | NIYPGTGGSNFDEKFKN |
| SEQ ID NO: 503 (Kabat) | HCDR3 | WTTGTGAY |
| SEQ ID NO: 504 (Chothia) | HCDR1 | GYTFTTY |
| SEQ ID NO: 505 (Chothia) | HCDR2 | YPGTGG |
| SEQ ID NO: 503 (Chothia) | HCDR3 | WTTGTGAY |
| SEQ ID NO: 506 | VH | EVQLVQSGAEVKKPGESLRISCKGSGYTFTTYWMHWVRQATGQG LEWMGNIYPGTGGSNFDEKFKNRVTITADKSTSTAYMELSSLRSE DTAVYYCTRWTTGTGAYWGQGTTVTVSS |
| SEQ ID NO: 507 | DNA VH | GAGGTGCAGCTGGTGCAGTCAGGCGCCGAAGTGAAGAAGCCCG GCGAGTCACTGAGAATTAGCTGTAAAGGTTCAGGCTACACCTT CACTACCTACTGGATGCACTGGGTCCGCCAGGCTACCGGTCAA GGCCTCGAGTGGATGGGTAATATCTACCCCGGCACCGGCGGCT CTAACTTCGACGAGAAGTTTAAGAATAGAGTGACTATCACCGC |

TABLE 5-continued

| Amino acid and nucleotide sequences of exemplary anti-PD-1 antibody molecules | | |
|---|---|---|
| | | CGATAAGTCTACTAGCACCGCCTATATGGAACTGTCTAGCCTGA GATCAGAGGACACCGCCGTCTACTACTGCACTAGGTGGACTAC CGGCACAGGCGCCTACTGGGGTCAAGGCACTACCGTGACCGTG TCTAGC |
| SEQ ID NO: 508 | Heavy chain | EVQLVQSGAEVKKPGESLRISCKGSGYTFTTYWMHWVRQATGQG LEWMGNIYPGTGGSNFDEKFKNRVTITADKSTSTAYMELSSLRSE DTAVYYCTRWTTGTGAYWGQGTTVTVSSASTKGPSVFPLAPCSRS TSESTAALGCLVKDYFPEPVTVSWNSGALTSGVHTFPAVLQSSGL YSLSSVVTVPSSSLGTKTYTCNVDHKPSNTKVDKRVESKYGPPCPP CPAPEFLGGPSVFLFPPKPKDTLMISRTPEVTCVVVDVSQEDPEVQF NWYVDGVEVHNAKTKPREEQFNSTYRVVSVLTVLHQDWLNGKE YKCKVSNKGLPSSIEKTISKAKGQPREPQVYTLPPSQEEMTKNQVS LTCLVKGFYPSDIAVEWESNGQPENNYKTTPPVLDSDGSFFLYSRL TVDKSRWQEGNVFSCSVMHEALHNHYTQKSLSLSLG |
| SEQ ID NO: 509 | DNA heavy chain | GAGGTGCAGCTGGTGCAGTCAGGCGCCGAAGTGAAGAAGCCCG GCGAGTCACTGAGAATTAGCTGTAAAGGTTCAGGCTACACCTT CACTACCTACTGGATGCACTGGGTCCGCCAGGCTACCGGTCAA GGCCTCGAGTGGATGGGTAATATCTACCCCGGCACCGGCGGCT CTAACTTCGACGAGAAGTTTAAGAATAGAGTGACTATCACCGC CGATAAGTCTACTAGCACCGCCTATATGGAACTGTCTAGCCTGA GATCAGAGGACACCGCCGTCTACTACTGCACTAGGTGGACTAC CGGCACAGGCGCCTACTGGGGTCAAGGCACTACCGTGACCGTG TCTAGCGCTAGCACTAAGGGCCCGTCCGTGTTCCCCCTGGCACC TTGTAGCCGGAGCACTAGCGAATCCACCGCTGCCCTCGGCTGCC TGGTCAAGGATTACTTCCCGGAGCCCGTGACCGTGTCCTGGAAC AGCGGAGCCCTGACCTCCGGAGTGCACACCTTCCCCGCTGTGCT GCAGAGCTCCGGGCTGTACTCGCTGTCGTCGGTGGTCACGGTGC CTTCATCTAGCCTGGGTACCAAGACCTACACTTGCAACGTGGAC CACAAGCCTTCCAACACTAAGGTGGACAAGCGCGTCGAATCGA AGTACGGCCCACCGTGCCCGCCTTGTCCCGCGCCGGAGTTCCTC GGCGGTCCCTCGGTCTTTCTGTTCCCACCGAAGCCCAAGGACAC TTTGATGATTTCCCGCACCCCTGAAGTGACATGCGTGGTCGTGG ACGTGTCACAGGAAGATCCGGAGGTGCAGTTCAATTGGTACGT GGATGGCGTCGAGGTGCACAACGCCAAAACCAAGCCGAGGGA GGAGCAGTTCAACTCCACTTACCGCGTCGTGTCCGTGCTGACGG TGCTGCATCAGGACTGGCTGAACGGGAAGGAGTACAAGTGCAA AGTGTCCAACAAGGGACTTCCTAGCTCAATCGAAAAGACCATC TCGAAAGCCAAGGGACAGCCCCGGGAACCCCAAGTGTATACCC TGCCACCGAGCCAGGAAGAAATGACTAAGAACCAAGTCTCATT GACTTGCCTTGTGAAGGGCTTCTACCCATCGGATATCGCCGTGG AATGGGAGTCCAACGGCCAGCCGGAAAACAACTACAAGACCA CCCCTCCGGTGCTGGACTCAGACGGATCCTTCTTCCTCTACTCG CGGCTGACCGTGGATAAGAGCAGATGGCAGGAGGGAAATGTGT TCAGCTGTTCTGTGATGCATGAAGCCCTGCACAACCACTACACT CAGAAGTCCCTGTCCCTCTCCCTGGGA |
| BAP049-Clone-B LC | | |
| SEQ ID NO: 510 (Kabat) | LCDR1 | KSSQSLLDSGNQKNFLT |
| SEQ ID NO: 511 (Kabat) | LCDR2 | WASTRES |
| SEQ ID NO: 512 (Kabat) | LCDR3 | QNDYSYPYT |
| SEQ ID NO: 513 (Chothia) | LCDR1 | SQSLLDSGNQKNF |
| SEQ ID NO: 514 (Chothia) | LCDR2 | WAS |
| SEQ ID NO: 515 (Chothia) | LCDR3 | DYSYPY |
| SEQ ID NO: 516 | VL | EIVLTQSPATLSLSPGERATLSCKSSQSLLDSGNQKNFLTWYQQKP GKAPKLLIYWASTRESGVPSRFSGSGSGTDFTFTISSLQPEDIATYY CQNDYSYPYTFGQGTKVEIK |
| SEQ ID NO: 517 | DNA VL | GAGATCGTCCTGACTCAGTCACCCGCTACCCTGAGCCTGAGCCC TGGCGAGCGGGCTACACTGAGCTGTAAATCTAGTCAGTCACTG CTGGATAGCGGTAATCAGAAGAACTTCCTGACCTGGTATCAGC AGAAGCCCGGTAAAGCCCCTAAGCTGCTGATCTACTGGGCCTC TACTAGAGAATCAGGCGTGCCCTCTAGGTTTAGCGGTAGCGGT AGTGGCACCGACTTCACCTTCACTATCTCTAGCCTGCAGCCCGA GGATATCGCTACCTACTACTGTCAGAACGACTATAGCTACCCCT ACACCTTCGGTCAAGGCACTAAGGTCGAGATTAAG |

TABLE 5-continued

| Amino acid and nucleotide sequences of exemplary anti-PD-1 antibody molecules | | |
|---|---|---|
| SEQ ID NO: 518 | Light chain | EIVLTQSPATLSLSPGERATLSCKSSQSLLDSGNQKNFLTWYQQKP GKAPKLLIYWASTRESGVPSRFSGSGSGTDFTFTISSLQPEDIATYY CQNDYSYPYTFGQGTKVEIKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC |
| SEQ ID NO: 519 | DNA light chain | GAGATCGTCCTGACTCAGTCACCCGCTACCCTGAGCCTGAGCCC TGGCGAGCGGGCTACACTGAGCTGTAAATCTAGTCAGTCACTG CTGGATAGCGGTAATCAGAAGAACTTCCTGACCTGGTATCAGC AGAAGCCCGGTAAAGCCCCTAAGCTGCTGATCTACTGGGCCTC TACTAGAGAATCAGGCGTGCCCTCTAGGTTTAGCGGTAGCGGT AGTGGCACCGACTTCACCTTCACTATCTCTAGCCTGCAGCCCGA GGATATCGCTACCTACTACTGTCAGAACGACTATAGCTACCCCT ACACCTTCGGTCAAGGCACTAAGGTCGAGATTAAGCGTACGGT GGCCGCTCCCAGCGTGTTCATCTTCCCCCCCAGCGACGAGCAGC TGAAGAGCGGCACCGCCAGCGTGGTGTGCCTGCTGAACAACTT CTACCCCCGGGAGGCCAAGGTGCAGTGGAAGGTGGACAACGCC CTGCAGAGCGGCAACAGCCAGGAGAGCGTCACCGAGCAGGAC AGCAAGGACTCCACCTACAGCCTGAGCAGCACCCTGACCCTGA GCAAGGCCGACTACGAGAAGCATAAGGTGTACGCCTGCGAGGT GACCCACCAGGGCCTGTCCAGCCCCGTGACCAAGAGCTTCAAC AGGGGCGAGTGC |
| BAP049-Clone-E HC | | |
| SEQ ID NO: 501 (Kabat) | HCDR1 | TYWMH |
| SEQ ID NO: 502 (Kabat) | HCDR2 | NIYPGTGGSNFDEKFKN |
| SEQ ID NO: 503 (Kabat) | HCDR3 | WTTGTGAY |
| SEQ ID NO: 504 (Chothia) | HCDR1 | GYTFTTY |
| SEQ ID NO: 505 (Chothia) | HCDR2 | YPGTGG |
| SEQ ID NO: 503 (Chothia) | HCDR3 | WTTGTGAY |
| SEQ ID NO: 506 | VH | EVQLVQSGAEVKKPGESLRISCKGSGYTFTTYWMHWVRQATGQG LEWMGNIYPGTGGSNFDEKFKNRVTITADKSTSTAYMELSSLRSE DTAVYYCTRWTTGTGAYWGQGTTVTVSS |
| SEQ ID NO: 507 | DNA VH | GAGGTGCAGCTGGTGCAGTCAGGCGCCGAAGTGAAGAAGCCCG GCGAGTCACTGAGAATTAGCTGTAAAGGTTCAGGCTACACCTT CACTACCTACTGGATGCACTGGGTCCGCCAGGCTACCGGTCAA GGCCTCGAGTGGATGGGTAATATCTACCCCGGCACCGGCGGCT CTAACTTCGACGAGAAGTTTAAGAATAGAGTGACTATCACCGC CGATAAGTCTACTAGCACCGCCTATATGGAACTGTCTAGCCTGA GATCAGAGGACACCGCCGTCTACTACTGCACTAGGTGGACTAC CGGCACAGGCGCCTACTGGGGTCAAGGCACTACCGTGACCGTG TCTAGC |
| SEQ ID NO: 508 | Heavy chain | EVQLVQSGAEVKKPGESLRISCKGSGYTFTTYWMHWVRQATGQG LEWMGNIYPGTGGSNFDEKFKNRVTITADKSTSTAYMELSSLRSE DTAVYYCTRWTTGTGAYWGQGTTVTVSSASTKGPSVFPLAPCSRS TSESTAALGCLVKDYFPEPVTVSWNSGALTSGVHTFPAVLQSSGL YSLSSVVTVPSSSLGTKTYTCNVDHKPSNTKVDKRVESKYGPPCPP CPAPEFLGGPSVFLFPPKPKDTLMISRTPEVTCVVVDVSQEDPEVQF NWYVDGVEVHNAKTKPREEQFNSTYRVVSVLTVLHQDWLNGKE YKCKVSNKGLPSSIEKTISKAKGQPREPQVYTLPPSQEEMTKNQVS LTCLVKGFYPSDIAVEWESNGQPENNYKTTPPVLDSDGSFFLYSRL TVDKSRWQEGNVFSCSVMHEALHNHYTQKSLSLSLG |
| SEQ ID NO: 509 | DNA heavy chain | GAGGTGCAGCTGGTGCAGTCAGGCGCCGAAGTGAAGAAGCCCG GCGAGTCACTGAGAATTAGCTGTAAAGGTTCAGGCTACACCTT CACTACCTACTGGATGCACTGGGTCCGCCAGGCTACCGGTCAA GGCCTCGAGTGGATGGGTAATATCTACCCCGGCACCGGCGGCT CTAACTTCGACGAGAAGTTTAAGAATAGAGTGACTATCACCGC CGATAAGTCTACTAGCACCGCCTATATGGAACTGTCTAGCCTGA GATCAGAGGACACCGCCGTCTACTACTGCACTAGGTGGACTAC CGGCACAGGCGCCTACTGGGGTCAAGGCACTACCGTGACCGTG TCTAGCGCTAGCACTAAGGGCCCGTCCGTGTTCCCCCTGGCACC TTGTAGCCGGAGCACTAGCGAATCCACCGCTGCCCTCGGCTGCC TGGTCAAGGATTACTTCCCGGAGCCCGTGACCGTGTCCTGGAAC AGCGGAGCCCTGACCTCCGGAGTGCACACCTTCCCCGCTGTGCT GCAGAGCTCCGGGCTGTACTCGCTGTCGTCGGTGGTCACGGTGC |

TABLE 5-continued

| Amino acid and nucleotide sequences of exemplary anti-PD-1 antibody molecules | | |
|---|---|---|
| | | CTTCATCTAGCCTGGGTACCAAGACCTACACTTGCAACGTGGAC CACAAGCCTTCCAACACTAAGGTGGACAAGCGCGTCGAATCGA AGTACGGCCCACCGTGCCCGCCTTGTCCCGCGCCGGAGTTCCTC GGCGGTCCCTCGGTCTTTCTGTTCCCACCGAAGCCCAAGGACAC TTTGATGATTTCCCGCACCCCTGAAGTGACATGCGTGGTCGTGG ACGTGTCACAGGAAGATCCGGAGGTGCAGTTCAATTGGTACGT GGATGGCGTCGAGGTGCACAACGCCAAAACCAAGCCGAGGGA GGAGCAGTTCAACTCCACTTACCGCGTCGTGTCCGTGCTGACGG TGCTGCATCAGGACTGGCTGAACGGGAAGGAGTACAAGTGCAA AGTGTCCAACAAGGGACTTCCTAGCTCAATCGAAAAGACCATC TCGAAAGCCAAGGGACAGCCCCGGGAACCCCAAGTGTATACCC TGCCACCGAGCCAGGAAGAAATGACTAAGAACCAAGTCTCATT GACTTGCCTTGTGAAGGGCTTCTACCCATCGGATATCGCCGTGG AATGGGAGTCCAACGGCCAGCCGGAAAACAACTACAAGACCA CCCCTCCGGTGCTGGACTCAGACGGATCCTTCTTCCTCTACTCG CGGCTGACCGTGGATAAGAGCAGATGGCAGGAGGGAAATGTGT TCAGCTGTTCTGTGATGCATGAAGCCCTGCACAACCACTACACT CAGAAGTCCCTGTCCCTCTCCCTGGGA |
| BAP049-Clone-E LC | | |
| SEQ ID NO: 510 (Kabat) | LCDR1 | KSSQSLLDSGNQKNFLT |
| SEQ ID NO: 511 (Kabat) | LCDR2 | WASTRES |
| SEQ ID NO: 512 (Kabat) | LCDR3 | QNDYSYPYT |
| SEQ ID NO: 513 (Chothia) | LCDR1 | SQSLLDSGNQKNF |
| SEQ ID NO: 514 (Chothia) | LCDR2 | WAS |
| SEQ ID NO: 515 (Chothia) | LCDR3 | DYSYPY |
| SEQ ID NO: 520 | VL | EIVLTQSPATLSLSPGERATLSCKSSQSLLDSGNQKNFLTWYQQKP GQAPRLLIYWASTRESGVPSRFSGSGSGTDFTFTISSLEAEDAATYY CQNDYSYPYTFGQGTKVEIK |
| SEQ ID NO: 521 | DNA VL | GAGATCGTCCTGACTCAGTCACCCGCTACCCTGAGCCTGAGCCC TGGCGAGCGGGCTACACTGAGCTGTAAATCTAGTCAGTCACTG CTGGATAGCGGTAATCAGAAGAACTTCCTGACCTGGTATCAGC AGAAGCCCGGTCAAGCCCCTAGACTGCTGATCTACTGGGCCTCT ACTAGAGAATCAGGCGTGCCCTCTAGGTTTAGCGGTAGCGGTA GTGGCACCGACTTCACCTTCACTATCTCTAGCCTGGAAGCCGAG GACGCCGCTACCTACTACTGTCAGAACGACTATAGCTACCCCTA CACCTTCGGTCAAGGCACTAAGGTCGAGATTAAG |
| SEQ ID NO: 522 | Light chain | EIVLTQSPATLSLSPGERATLSCKSSQSLLDSGNQKNFLTWYQQKP GQAPRLLIYWASTRESGVPSRFSGSGSGTDFTFTISSLEAEDAATYY CQNDYSYPYTFGQGTKVEIKRTVAAPSVFIFPPSDEQLKSGTASVV CLLNNFYPREAKVQWKVDNALQSGNSQESVTEQDSKDSTYSLSST LTLSKADYEKHKVYACEVTHQGLSSPVTKSFNRGEC |
| SEQ ID NO: 523 | DNA light chain | GAGATCGTCCTGACTCAGTCACCCGCTACCCTGAGCCTGAGCCC TGGCGAGCGGGCTACACTGAGCTGTAAATCTAGTCAGTCACTG CTGGATAGCGGTAATCAGAAGAACTTCCTGACCTGGTATCAGC AGAAGCCCGGTCAAGCCCCTAGACTGCTGATCTACTGGGCCTCT ACTAGAGAATCAGGCGTGCCCTCTAGGTTTAGCGGTAGCGGTA GTGGCACCGACTTCACCTTCACTATCTCTAGCCTGGAAGCCGAG GACGCCGCTACCTACTACTGTCAGAACGACTATAGCTACCCCTA CACCTTCGGTCAAGGCACTAAGGTCGAGATTAAGCGTACGGTG GCCGCTCCCAGCGTGTTCATCTTCCCCCCCAGCGACGAGCAGCT GAAGAGCGGCACCGCCAGCGTGGTGTGCCTGCTGAACAACTTC TACCCCCGGGAGGCCAAGGTGCAGTGGAAGGTGGACAACGCCC TGCAGAGCGGCAACAGCCAGGAGAGCGTCACCGAGCAGGACA GCAAGGACTCCACCTACAGCCTGAGCAGCACCCTGACCCTGAG CAAGGCCGACTACGAGAAGCATAAGGTGTACGCCTGCGAGGTG ACCCACCAGGGCCTGTCCAGCCCCGTGACCAAGAGCTTCAACA GGGGCGAGTGC |
| BAP049-Clone-B HC | | |
| SEQ ID NO: 524 (Kabat) | HCDR1 | ACCTACTGGATGCAC |
| SEQ ID NO: 525 (Kabat) | HCDR2 | AATATCTACCCCGGCACCGGCGGCTCTAACTTCGACGAGAAGT TTAAGAAT |

TABLE 5-continued

| Amino acid and nucleotide sequences of exemplary anti-PD-1 antibody molecules | | |
|---|---|---|
| SEQ ID NO: 526 (Kabat) | HCDR3 | TGGACTACCGGCACAGGCGCCTAC |
| SEQ ID NO: 527 (Chothia) | HCDR1 | GGCTACACCTTCACTACCTAC |
| SEQ ID NO: 528 (Chothia) | HCDR2 | TACCCCGGCACCGGCGGC |
| SEQ ID NO: 526 (Chothia) | HCDR3 | TGGACTACCGGCACAGGCGCCTAC |
| BAP049-Clone-B LC | | |
| SEQ ID NO: 529 (Kabat) | LCDR1 | AAATCTAGTCAGTCACTGCTGGATAGCGGTAATCAGAAGAACT TCCTGACC |
| SEQ ID NO: 530 (Kabat) | LCDR2 | TGGGCCTCTACTAGAGAATCA |
| SEQ ID NO: 531 (Kabat) | LCDR3 | CAGAACGACTATAGCTACCCCTACACC |
| SEQ ID NO: 532 (Chothia) | LCDR1 | AGTCAGTCACTGCTGGATAGCGGTAATCAGAAGAACTTC |
| SEQ ID NO: 533 (Chothia) | LCDR2 | TGGGCCTCT |
| SEQ ID NO: 534 (Chothia) | LCDR3 | GACTATAGCTACCCCTAC |
| BAP049-Clone-E HC | | |
| SEQ ID NO: 524 (Kabat) | HCDR1 | ACCTACTGGATGCAC |
| SEQ ID NO: 525 (Kabat) | HCDR2 | AATATCTACCCCGGCACCGGCGGCTCTAACTTCGACGAGAAGT TTAAGAAT |
| SEQ ID NO: 526 (Kabat) | HCDR3 | TGGACTACCGGCACAGGCGCCTAC |
| SEQ ID NO: 527 (Chothia) | HCDR1 | GGCTACACCTTCACTACCTAC |
| SEQ ID NO: 528 (Chothia) | HCDR2 | TACCCCGGCACCGGCGGC |
| SEQ ID NO: 526 (Chothia) | HCDR3 | TGGACTACCGGCACAGGCGCCTAC |
| BAP049-Clone-E LC | | |
| SEQ ID NO: 529 (Kabat) | LCDR1 | AAATCTAGTCAGTCACTGCTGGATAGCGGTAATCAGAAGAACT TCCTGACC |
| SEQ ID NO: 530 (Kabat) | LCDR2 | TGGGCCTCTACTAGAGAATCA |
| SEQ ID NO: 531 (Kabat) | LCDR3 | CAGAACGACTATAGCTACCCCTACACC |
| SEQ ID NO: 532 (Chothia) | LCDR1 | AGTCAGTCACTGCTGGATAGCGGTAATCAGAAGAACTTC |
| SEQ ID NO: 533 (Chothia) | LCDR2 | TGGGCCTCT |
| SEQ ID NO: 534 (Chothia) | LCDR3 | GACTATAGCTACCCCTAC |

Other Exemplary PD-1 Inhibitors

In one embodiment, the anti-PD-1 antibody molecule is Nivolumab (Bristol-Myers Squibb), also known as MDX-1106, MDX-1106-04, ONO-4538, BMS-936558, or OPDIVO®. Nivolumab (clone 5C4) and other anti-PD-1 antibodies are disclosed in U.S. Pat. No. 8,008,449 and WO 2006/121168, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Nivolumab, e.g., as disclosed in Table 6.

In one embodiment, the anti-PD-1 antibody molecule is Pembrolizumab (Merck & Co), also known as Lambrolizumab, MK-3475, MK03475, SCH-900475, or KEYTRUDA®. Pembrolizumab and other anti-PD-1 antibodies are disclosed in Hamid, O. et al. (2013) *New England Journal of Medicine* 369 (2): 134-44, U.S. Pat. No. 8,354, 509, and WO 2009/114335, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pembrolizumab, e.g., as disclosed in Table 6.

In one embodiment, the anti-PD-1 antibody molecule is Pidilizumab (CureTech), also known as CT-011. Pidilizumab and other anti-PD-1 antibodies are disclosed in Rosenblatt, J. et al. (2011) *J Immunotherapy* 34(5): 409-18, U.S. Pat. Nos. 7,695,715, 7,332,582, and 8,686,119, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pidilizumab, e.g., as disclosed in Table 6.

In one embodiment, the anti-PD-1 antibody molecule is MEDI0680 (Medimmune), also known as AMP-514. MEDI0680 and other anti-PD-1 antibodies are disclosed in U.S. Pat. No. 9,205,148 and WO 2012/145493, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of MEDI0680.

In one embodiment, the anti-PD-1 antibody molecule is REGN2810 (Regeneron). In one embodiment, the anti-PD-1 antibody molecule comprises one or more of the CDR sequences (or collectively all of the CDR sequences), the heavy chain or light chain variable region sequence, or the heavy chain or light chain sequence of REGN2810.

In one embodiment, the anti-PD-1 antibody molecule is PF-06801591 (Pfizer). In one embodiment, the anti-PD-1 antibody molecule comprises one or more of the CDR sequences (or collectively all of the CDR sequences), the heavy chain or light chain variable region sequence, or the heavy chain or light chain sequence of PF-06801591.

In one embodiment, the anti-PD-1 antibody molecule is BGB-A317 or BGB-108 (Beigene). In one embodiment, the anti-PD-1 antibody molecule comprises one or more of the CDR sequences (or collectively all of the CDR sequences), the heavy chain or light chain variable region sequence, or the heavy chain or light chain sequence of BGB-A317 or BGB-108.

In one embodiment, the anti-PD-1 antibody molecule is INCSHR1210 (Incyte), also known as INCSHR01210 or SHR-1210. In one embodiment, the anti-PD-1 antibody molecule comprises one or more of the CDR sequences (or collectively all of the CDR sequences), the heavy chain or light chain variable region sequence, or the heavy chain or light chain sequence of INCSHR1210.

In one embodiment, the anti-PD-1 antibody molecule is TSR-042 (Tesaro), also known as ANB011. In one embodiment, the anti-PD-1 antibody molecule comprises one or more of the CDR sequences (or collectively all of the CDR sequences), the heavy chain or light chain variable region sequence, or the heavy chain or light chain sequence of TSR-042.

Further known anti-PD-1 antibodies include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety.

In one embodiment, the anti-PD-1 antibody is an antibody that competes for binding with, and/or binds to the same epitope on PD-1 as, one of the anti-PD-1 antibodies described herein.

In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

TABLE 6

| Amino acid sequences of other exemplary anti-PD-1 antibody molecules | | |
|---|---|---|
| Nivolumab | | |
| SEQ ID NO: 535 | Heavy chain | QVQLVESGGGVVQPGRSLRLDCKASGITFSNSGMHWVRQAPGKGLEWVAV IWYDGSKRYYADSVKGRFTISRDNSKNTLFLQMNSLRAEDTAVYYCATND DYWGQGTLVTVSSASTKGPSVFPLAPCSRSTSESTAALGCLVKDYFPEPVTV SWNSGALTSGVHTFPAVLQSSGLYSLSSVVTVPSSSLGTKTYTCNVDHKPSN TKVDKRVESKYGPPCPPCPAPEFLGGPSVFLFPPKPKDTLMISRTPEVTCVVV DVSQEDPEVQFNWYVDGVEVHNAKTKPREEQFNSTYRVVSVLTVLHQDW LNGKEYKCKVSNKGLPSSIEKTISKAKGQPREPQVYTLPPSQEEMTKNQVSL TCLVKGFYPSDIAVEWESNGQPENNYKTTPPVLDSDGSFFLYSRLTVDKSR WQEGNVFSCSVMHEALHNHYTQKSLSLSLGK |
| SEQ ID NO: 536 | Light chain | EIVLTQSPATLSLSPGERATLSCRASQSVSSYLAWYQQKPGQAPRLLIYDASN RATGIPARFSGSGSGTDFTLTISSLEPEDFAVYYCQQSSNWPRTFGQGTKVEI KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSF NRGEC |
| Pembrolizumab | | |
| SEQ ID NO: 537 | Heavy chain | QVQLVQSGVEVKKPGASVKVSCKASGYTFTNYYMYWVRQAPGQGLEWM GGINPSNGGTNFNEKFKNRVTLTTDSSTTTAYMELKSLQFDDTAVYYCARR DYRFDMGFDYWGQGTTVTVSSASTKGPSVFPLAPCSRSTSESTAALGCLVK DYFPEPVTVSWNSGALTSGVHTFPAVLQSSGLYSLSSVVTVPSSSLGTKTYT CNVDHKPSNTKVDKRVESKYGPPCPPCPAPEFLGGPSVFLFPPKPKDTLMISR TPEVTCVVVDVSQEDPEVQFNWYVDGVEVHNAKTKPREEQFNSTYRVVSV |

TABLE 6-continued

| Amino acid sequences of other exemplary anti-PD-1 antibody molecules | |
|---|---|
| | LTVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLGK |
| SEQ ID NO: 538 Light chain | EIVLTQSPATLSLSPGERATLSCRASKGVSTSGYSYLHWYQQKPGQAPRLLI YLASYLESGVPARFSGSGSGTDFTLTISSLEPEDFAVYYCQHSRDLPLTFGGG TKVEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPV TKSFNRGEC |
| Pidilizumab | |
| SEQ ID NO: 539 Heavy chain | QVQLVQSGSELKKPGASVKISCKASGYTFTNYGMNWVRQAPGQGLQWMG WINTDSGESTYAEEFKGRFVFSLDTSVNTAYLQITSLTAEDTGMYFCVRVGY DALDYWGQGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHK PSNTKVDKRVEPKSCDKTHTCPPCPAPELLGGPSVFLFPPKPKDTLMISRTPE VTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSREEM TKNQVSLTCLVKGFYPSDIAVEWESNGQPENNYKTTPPVLDSDGSFFLYSKL TVDKSRWQQGNVFSCSVMHEALHNHYTQKSLSLSPGK |
| SEQ ID NO: 540 Light chain | EIVLTQSPSSLSASVGDRVTITCSARSSVSYMHWIFQQKPGKAPKLWIYRTSN LASGVPSRFSGSGSGTSYCLTINSLQPEDFATYYCQQRSSFPLTFGGGTKLEIK RTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFN RGEC |

Exemplary PD-L1 Inhibitors

In certain embodiments, the anti-CD73 antibody molecule described herein is administered in combination with a PD-L1 inhibitor. The PD-L1 inhibitor may be an antibody, an antigen binding fragment thereof, an immunoadhesin, a fusion protein, or an oligopeptide. In some embodiments, the PD-L1 inhibitor is chosen from FAZ053 (Novartis), Atezolizumab (Genentech/Roche), Avelumab (Merck Serono and Pfizer), Durvalumab (MedImmune/AstraZeneca), or BMS-936559 (Bristol-Myers Squibb).

Exemplary Anti-PD-L1 Antibody Molecules In one embodiment, the PD-L1 inhibitor is an anti-PD-L1 antibody molecule. In one embodiment, the PD-L1 inhibitor is an anti-PD-L1 antibody molecule as disclosed in US 2016/0108123, published on Apr. 21, 2016, entitled "Antibody Molecules to PD-L1 and Uses Thereof," incorporated by reference in its entirety.

In one embodiment, the anti-PD-L1 antibody molecule comprises at least one, two, three, four, five or six complementarity determining regions (CDRs) (or collectively all of the CDRs) from a heavy and light chain variable region comprising an amino acid sequence shown in Table 7 (e.g., from the heavy and light chain variable region sequences of BAP058-Clone O or BAP058-Clone N disclosed in Table 7), or encoded by a nucleotide sequence shown in Table 7. In some embodiments, the CDRs are according to the Kabat definition (e.g., as set out in Table 7). In some embodiments, the CDRs are according to the Chothia definition (e.g., as set out in Table 7). In some embodiments, the CDRs are according to the combined CDR definitions of both Kabat and Chothia (e.g., as set out in Table 7). In one embodiment, the combination of Kabat and Chothia CDR of VH CDR1 comprises the amino acid sequence GYTFTSYWMY (SEQ ID NO: 647). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 7, or encoded by a nucleotide sequence shown in Table 7.

In one embodiment, the anti-PD-L1 antibody molecule comprises a heavy chain variable region (VH) comprising a VHCDR1 amino acid sequence of SEQ ID NO: 601, a VHCDR2 amino acid sequence of SEQ ID NO: 602, and a VHCDR3 amino acid sequence of SEQ ID NO: 603; and a light chain variable region (VL) comprising a VLCDR1 amino acid sequence of SEQ ID NO: 609, a VLCDR2 amino acid sequence of SEQ ID NO: 610, and a VLCDR3 amino acid sequence of SEQ ID NO: 611, each disclosed in Table 7.

In one embodiment, the anti-PD-L1 antibody molecule comprises a VH comprising a VHCDR1 encoded by the nucleotide sequence of SEQ ID NO: 628, a VHCDR2 encoded by the nucleotide sequence of SEQ ID NO: 629, and a VHCDR3 encoded by the nucleotide sequence of SEQ ID NO: 630; and a VL comprising a VLCDR1 encoded by the nucleotide sequence of SEQ ID NO: 633, a VLCDR2 encoded by the nucleotide sequence of SEQ ID NO: 634, and a VLCDR3 encoded by the nucleotide sequence of SEQ ID NO: 635, each disclosed in Table 7.

In one embodiment, the anti-PD-L1 antibody molecule comprises a VH comprising the amino acid sequence of SEQ ID NO: 606, or an amino acid sequence having at least about 85%, 90%, 95%, or 99% sequence identity to SEQ ID NO: 606. In one embodiment, the anti-PD-L1 antibody molecule comprises a VL comprising the amino acid sequence of SEQ ID NO: 616, or an amino acid sequence having at least about 85%, 90%, 95%, or 99% sequence identity or higher to SEQ ID NO: 616. In one embodiment, the anti-PD-L1 antibody molecule comprises a VH comprising the amino acid sequence of SEQ ID NO: 620, or an amino acid sequence having at least about 85%, 90%, 95%, or 99% sequence identity to SEQ ID NO: 620. In one embodiment, the anti-PD-L1 antibody molecule comprises a VL comprising the amino acid sequence of SEQ ID NO: 624, or an amino acid sequence having at least about 85%, 90%, 95%, or 99% sequence identity to SEQ ID NO: 624. In one embodiment, the anti-PD-L1 antibody molecule comprises a VH comprising the amino acid sequence of SEQ ID NO: 606 and a VL comprising the amino acid sequence of SEQ ID NO: 616. In one embodiment, the anti-PD-L1 antibody molecule comprises a VH comprising the amino acid sequence of SEQ ID NO: 620 and a VL comprising the amino acid sequence of SEQ ID NO: 624.

In one embodiment, the antibody molecule comprises a VH encoded by the nucleotide sequence of SEQ ID NO: 607, or a nucleotide sequence having at least about 85%, 90%, 95%, or 99% sequence identity to SEQ ID NO: 607. In one embodiment, the antibody molecule comprises a VL encoded by the nucleotide sequence of SEQ ID NO: 617, or a nucleotide sequence having at least about 85%, 90%, 95%, or 99% sequence identity to SEQ ID NO: 617. In one embodiment, the antibody molecule comprises a VH encoded by the nucleotide sequence of SEQ ID NO: 621, or a nucleotide sequence having at least about 85%, 90%, 95%, or 99% sequence identity to SEQ ID NO: 621. In one embodiment, the antibody molecule comprises a VL encoded by the nucleotide sequence of SEQ ID NO: 625, or a nucleotide sequence having at least about 85%, 90%, 95%, or 99% sequence identity to SEQ ID NO: 625. In one embodiment, the antibody molecule comprises a VH encoded by the nucleotide sequence of SEQ ID NO: 607 and a VL encoded by the nucleotide sequence of SEQ ID NO: 617. In one embodiment, the antibody molecule comprises a VH encoded by the nucleotide sequence of SEQ ID NO: 621 and a VL encoded by the nucleotide sequence of SEQ ID NO: 625.

In one embodiment, the anti-PD-L1 antibody molecule comprises a heavy chain comprising the amino acid sequence of SEQ ID NO: 608, or an amino acid sequence having at least about 85%, 90%, 95%, or 99% sequence identity to SEQ ID NO: 608. In one embodiment, the anti-PD-L1 antibody molecule comprises a light chain comprising the amino acid sequence of SEQ ID NO: 618, or an amino acid sequence having at least about 85%, 90%, 95%, or 99% sequence identity to SEQ ID NO: 618. In one embodiment, the anti-PD-L1 antibody molecule comprises a heavy chain comprising the amino acid sequence of SEQ ID NO: 622, or an amino acid sequence having at least about 85%, 90%, 95%, or 99% sequence identity to SEQ ID NO: 622. In one embodiment, the anti-PD-L1 antibody molecule comprises a light chain comprising the amino acid sequence of SEQ ID NO: 626, or an amino acid sequence having at least about 85%, 90%, 95%, or 99% sequence identity to SEQ ID NO: 626. In one embodiment, the anti-PD-L1 antibody molecule comprises a heavy chain comprising the amino acid sequence of SEQ ID NO: 608 and a light chain comprising the amino acid sequence of SEQ ID NO: 618. In one embodiment, the anti-PD-L1 antibody molecule comprises a heavy chain comprising the amino acid sequence of SEQ ID NO: 622 and a light chain comprising the amino acid sequence of SEQ ID NO: 626.

In one embodiment, the antibody molecule comprises a heavy chain encoded by the nucleotide sequence of SEQ ID NO: 615, or a nucleotide sequence having at least about 85%, 90%, 95%, or 99% sequence identity to SEQ ID NO: 615. In one embodiment, the antibody molecule comprises a light chain encoded by the nucleotide sequence of SEQ ID NO: 619, or a nucleotide sequence having at least about 85%, 90%, 95%, or 99% sequence identity to SEQ ID NO: 619. In one embodiment, the antibody molecule comprises a heavy chain encoded by the nucleotide sequence of SEQ ID NO: 623, or a nucleotide sequence having at least about 85%, 90%, 95%, or 99% sequence identity to SEQ ID NO: 623. In one embodiment, the antibody molecule comprises a light chain encoded by the nucleotide sequence of SEQ ID NO: 627, or a nucleotide sequence having at least about 85%, 90%, 95%, or 99% sequence identity to SEQ ID NO: 627. In one embodiment, the antibody molecule comprises a heavy chain encoded by the nucleotide sequence of SEQ ID NO: 615 and a light chain encoded by the nucleotide sequence of SEQ ID NO: 619. In one embodiment, the antibody molecule comprises a heavy chain encoded by the nucleotide sequence of SEQ ID NO: 623 and a light chain encoded by the nucleotide sequence of SEQ ID NO: 627.

The antibody molecules described herein can be made by vectors, host cells, and methods described in US 2016/0108123, incorporated by reference in its entirety.

TABLE 7

| Amino acid and nucleotide sequences of exemplary anti-PD-L1 antibody molecules | | |
|---|---|---|
| BAP058-Clone O HC | | |
| SEQ ID NO: 601 (Kabat) | HCDR1 | SYWMY |
| SEQ ID NO: 602 (Kabat) | HCDR2 | RIDPNSGSTKYNEKFKN |
| SEQ ID NO: 603 (Kabat) | HCDR3 | DYRKGLYAMDY |
| SEQ ID NO: 604 (Chothia) | HCDR1 | GYTFTSY |
| SEQ ID NO: 605 (Chothia) | HCDR2 | DPNSGS |
| SEQ ID NO: 603 (Chothia) | HCDR3 | DYRKGLYAMDY |
| SEQ ID NO: 606 | VH | EVQLVQSGAEVKKPGATVKISCKVSGYTFTSYWMYWVRQARGQ<br>RLEWIGRIDPNSGSTKYNEKFKNRFTISRDNSKNTLYLQMNSLRA<br>EDTAVYYCARDYRKGLYAMDYWGQGTTVTVSS |
| SEQ ID NO: 607 | DNA VH | GAAGTGCAGCTGGTGCAGTCAGGCGCCGAAGTGAAGAAACCC<br>GGCGCTACCGTGAAGATTAGCTGTAAAGTCTCAGGCTACACCT<br>TCACTAGCTACTGGATGTACTGGGTCCGACAGGCTAGAGGGCA<br>AAGACTGGAGTGGATCGGTAGAATCGACCCTAATAGCGGCTC<br>TACTAAGTATAACGAGAAGTTTAAGAATAGGTTCACTATTAGT<br>AGGGATAACTCTAAGAACACCCTGTACCTGCAGATGAATAGC<br>CTGAGAGCCGAGGACACCGCCGTCTACTACTGCGCTAGAGACT |

TABLE 7-continued

| Amino acid and nucleotide sequences of exemplary anti-PD-L1 antibody molecules | | |
|---|---|---|
| | | ATAGAAAGGGCCTGTACGCTATGGACTACTGGGGTCAAGGCA CTACCGTGACCGTGTCTTCA |
| SEQ ID NO: 608 | Heavy chain | EVQLVQSGAEVKKPGATVKISCKVSGYTFTSYWMYWVRQARGQ RLEWIGRIDPNSGSTKYNEKFKNRFTISRDNSKNTLYLQMNSLRA EDTAVYYCARDYRKGLYAMDYWGQGTTVTVSSASTKGPSVFPL APCSRSTSESTAALGCLVKDYFPEPVTVSWNSGALTSGVHTFPAV LQSSGLYSLSSVVTVPSSSLGTKTYTCNVDHKPSNTKVDKRVESK YGPPCPPCPAPEFLGGPSVFLFPPKPKDTLMISRTPEVTCVVVDVS QEDPEVQFNWYVDGVEVHNAKTKPREEQFNSTYRVVSVLTVLH QDWLNGKEYKCKVSNKGLPSSIEKTISKAKGQPREPQVYTLPPSQ EEMTKNQVSLTCLVKGFYPSDIAVEWESNGQPENNYKTTPPVLD SDGSFFLYSRLTVDKSRWQEGNVFSCSVMHEALHNHYTQKSLSL SLG |
| SEQ ID NO: 615 | DNA heavy chain | GAAGTGCAGCTGGTGCAGTCAGGCGCCGAAGTGAAGAAACCC GGCGCTACCGTGAAGATTAGCTGTAAAGTCTCAGGCTACACCT TCACTAGCTACTGGATGTACTGGGTCCGACAGGCTAGAGGGCA AAGACTGGAGTGGATCGGTAGAATCGACCCTAATAGCGGCTC TACTAAGTATAACGAGAAGTTTAAGAATAGGTTCACTATTAGT AGGGATAACTCTAAGAACACCCTGTACCTGCAGATGAATAGC CTGAGAGCCGAGGACACCGCCGTCTACTACTGCGCTAGAGACT ATAGAAAGGGCCTGTACGCTATGGACTACTGGGGTCAAGGCA CTACCGTGACCGTGTCTTCAGCTAGCACTAAGGGCCCGTCCGT GTTCCCCCTGGCACCTTGTAGCCGGAGCACTAGCGAATCCACC GCTGCCCTCGGCTGCCTGGTCAAGGATTACTTCCCGGAGCCCG TGACCGTGTCCTGGAACAGCGGAGCCCTGACCTCCGGAGTGCA CACCTTCCCCGCTGTGCTGCAGAGCTCCGGGCTGTACTCGCTG TCGTCGGTGGTCACGGTGCCTTCATCTAGCCTGGGTACCAAGA CCTACACTTGCAACGTGGACCACAAGCCTTCCAACACTAAGGT GGACAAGCGCGTCGAATCGAAGTACGGCCCACCGTGCCCGCC TTGTCCCGCGCCGGAGTTCCTCGGCGGTCCCTCGGTCTTTCTGT TCCCACCGAAGCCCAAGGACACTTTGATGATTTCCCGCACCCC TGAAGTGACATGCGTGGTCGTGGACGTGTCACAGGAAGATCC GGAGGTGCAGTTCAATTGGTACGTGGATGGCGTCGAGGTGCA CAACGCCAAAACCAAGCCGAGGGAGGAGCAGTTCAACTCCAC TTACCGCGTCGTGTCCGTGCTGACGGTGCTGCATCAGGACTGG CTGAACGGGAAGGAGTACAAGTGCAAAGTGTCCAACAAGGGA CTTCCTAGCTCAATCGAAAAGACCATCTCGAAAGCCAAGGGA CAGCCCCGGGAACCCCAAGTGTATACCCTGCCACCGAGCCAG GAAGAAATGACTAAGAACCAAGTCTCATTGACTTGCCTTGTGA AGGGCTTCTACCCATCGGATATCGCCGTGGAATGGGAGTCCAA CGGCCAGCCGGAAAACAACTACAAGACCACCCCTCCGGTGCT GGACTCAGACGGATCCTTCTTCCTCTACTCGCGGCTGACCGTG GATAAGAGCAGATGGCAGGAGGGAAATGTGTTCAGCTGTTCT GTGATGCATGAAGCCCTGCACAACCACTACACTCAGAAGTCCC TGTCCCTCTCCCTGGGA |
| BAP058-Clone O LC | | |
| SEQ ID NO: 609 (Kabat) | LCDR1 | KASQDVGTAVA |
| SEQ ID NO: 610 (Kabat) | LCDR2 | WASTRHT |
| SEQ ID NO: 611 (Kabat) | LCDR3 | QQYNSYPLT |
| SEQ ID NO: 612 (Chothia) | LCDR1 | SQDVGTA |
| SEQ ID NO: 613 (Chothia) | LCDR2 | WAS |
| SEQ ID NO: 614 (Chothia) | LCDR3 | YNSYPL |
| SEQ ID NO: 616 | VL | AIQLTQSPSSLSASVGDRVTITCKASQDVGTAVAWYLQKPGQSPQ LLIYWASTRHTGVPSRFSGSGSGTDFTFTISSLEAEDAATYYCQQY NSYPLTFGQGTKVEIK |
| SEQ ID NO: 617 | DNA VL | GCTATTCAGCTGACTCAGTCACCTAGTAGCCTGAGCGCTAGTG TGGGCGATAGAGTGACTATCACCTGTAAAGCCTCTCAGGACGT GGGCACCGCCGTGGCCTGGTATCTGCAGAAGCCTGGTCAATCA CCTCAGCTGCTGATCTACTGGGCCTCTACTAGACACACCGGCG TGCCCTCTAGGTTTAGCGGTAGCGGTAGTGGCACCGACTTCAC CTTCACTATCTCTTCACTGGAAGCCGAGGACGCCGCTACCTAC TACTGTCAGCAGTATAATAGCTACCCCCTGACCTTCGGTCAAG GCACTAAGGTCGAGATTAAG |

TABLE 7-continued

| Amino acid and nucleotide sequences of exemplary anti-PD-L1 antibody molecules | | |
|---|---|---|
| SEQ ID NO: 618 | Light chain | AIQLTQSPSSLSASVGDRVTITCKASQDVGTAVAWYLQKPGQSPQ LLIYWASTRHTGVPSRFSGSGSGTDFTFTISSLEAEDAATYYCQQY NSYPLTFGQGTKVEIKRTVAAPSVFIFPPSDEQLKSGTASVVCLLN NFYPREAKVQWKVDNALQSGNSQESVTEQDSKDSTYSLSSTLTL SKADYEKHKVYACEVTHQGLSSPVTKSFNRGEC |
| SEQ ID NO: 619 | DNA light chain | GCTATTCAGCTGACTCAGTCACCTAGTAGCCTGAGCGCTAGTG TGGGCGATAGAGTGACTATCACCTGTAAAGCCTCTCAGGACGT GGGCACCGCCGTGGCCTGGTATCTGCAGAAGCCTGGTCAATCA CCTCAGCTGCTGATCTACTGGGCCTCTACTAGACACACCGGCG TGCCCTCTAGGTTTAGCGGTAGCGGTAGTGGCACCGACTTCAC CTTCACTATCTCTTCACTGGAAGCCGAGGACGCCGCTACCTAC TACTGTCAGCAGTATAATAGCTACCCCCTGACCTTCGGTCAAG GCACTAAGGTCGAGATTAAGCGTACGGTGGCCGCTCCCAGCGT GTTCATCTTCCCCCCCAGCGACGAGCAGCTGAAGAGCGGCACC GCCAGCGTGGTGTGCCTGCTGAACAACTTCTACCCCCGGGAGG CCAAGGTGCAGTGGAAGGTGGACAACGCCCTGCAGAGCGGCA ACAGCCAGGAGAGCGTCACCGAGCAGGACAGCAAGGACTCCA CCTACAGCCTGAGCAGCACCCTGACCCTGAGCAAGGCCGACT ACGAGAAGCATAAGGTGTACGCCTGCGAGGTGACCCACCAGG GCCTGTCCAGCCCCGTGACCAAGAGCTTCAACAGGGGCGAGT GC |
| BAP058-Clone N HC | | |
| SEQ ID NO: 601 (Kabat) | HCDR1 | SYWMY |
| SEQ ID NO: 602 (Kabat) | HCDR2 | RIDPNSGSTKYNEKFKN |
| SEQ ID NO: 603 (Kabat) | HCDR3 | DYRKGLYAMDY |
| SEQ ID NO: 604 (Chothia) | HCDR1 | GYTFTSY |
| SEQ ID NO: 605 (Chothia) | HCDR2 | DPNSGS |
| SEQ ID NO: 603 (Chothia) | HCDR3 | DYRKGLYAMDY |
| SEQ ID NO: 620 | VH | EVQLVQSGAEVKKPGATVKISCKVSGYTFTSYWMYWVRQATGQ GLEWMGRIDPNSGSTKYNEKFKNRVTITADKSTSTAYMELSSLRS EDTAVYYCARDYRKGLYAMDYWGQGTTVTVSS |
| SEQ ID NO: 621 | DNA VH | GAAGTGCAGCTGGTGCAGTCAGGCGCCGAAGTGAAGAAACCC GGCGCTACCGTGAAGATTAGCTGTAAAGTCTCAGGCTACACCT TCACTAGCTACTGGATGTACTGGGTCCGACAGGCTACCGGTCA AGGCCTGGAGTGGATGGGTAGAATCGACCCTAATAGCGGCTC TACTAAGTATAACGAGAAGTTTAAGAATAGAGTGACTATCACC GCCGATAAGTCTACTAGCACCGCCTATATGGAACTGTCTAGCC TGAGATCAGAGGACACCGCCGTCTACTACTGCGCTAGAGACTA TAGAAAGGGCCTGTACGCTATGGACTACTGGGGTCAAGGCAC TACCGTGACCGTGTCTTCA |
| SEQ ID NO: 622 | Heavy chain | EVQLVQSGAEVKKPGATVKISCKVSGYTFTSYWMYWVRQATGQ GLEWMGRIDPNSGSTKYNEKFKNRVTITADKSTSTAYMELSSLRS EDTAVYYCARDYRKGLYAMDYWGQGTTVTVSSASTKGPSVFPL APCSRSTSESTAALGCLVKDYFPEPVTVSWNSGALTSGVHTFPAV LQSSGLYSLSSVVTVPSSSLGTKTYTCNVDHKPSNTKVDKRVESK YGPPCPPCPAPEFLGGPSVFLFPPKPKDTLMISRTPEVTCVVVDVS QEDPEVQFNWYVDGVEVHNAKTKPREEQFNSTYRVVSVLTVLH QDWLNGKEYKCKVSNKGLPSSIEKTISKAKGQPREPQVYTLPPSQ EEMTKNQVSLTCLVKGFYPSDIAVEWESNGQPENNYKTTPPVLD SDGSFFLYSRLTVDKSRWQEGNVFSCSVMHEALHNHYTQKSLSL SLG |
| SEQ ID NO: 623 | DNA heavy chain | GAAGTGCAGCTGGTGCAGTCAGGCGCCGAAGTGAAGAAACCC GGCGCTACCGTGAAGATTAGCTGTAAAGTCTCAGGCTACACCT TCACTAGCTACTGGATGTACTGGGTCCGACAGGCTACCGGTCA AGGCCTGGAGTGGATGGGTAGAATCGACCCTAATAGCGGCTC TACTAAGTATAACGAGAAGTTTAAGAATAGAGTGACTATCACC GCCGATAAGTCTACTAGCACCGCCTATATGGAACTGTCTAGCC TGAGATCAGAGGACACCGCCGTCTACTACTGCGCTAGAGACTA TAGAAAGGGCCTGTACGCTATGGACTACTGGGGTCAAGGCAC TACCGTGACCGTGTCTTCAGCTAGCACTAAGGGCCCGTCCGTG TTCCCCCTGGCACCTTGTAGCCGGAGCACTAGCGAATCCACCG CTGCCCTCGGCTGCCTGGTCAAGGATTACTTCCCGGAGCCCGT GACCGTGTCCTGGAACAGCGGAGCCCTGACCTCCGGAGTGCA |

TABLE 7-continued

Amino acid and nucleotide sequences of exemplary anti-PD-L1 antibody molecules

| | | |
|---|---|---|
| | | CACCTTCCCCGCTGTGCTGCAGAGCTCCGGGCTGTACTCGCTG<br>TCGTCGGTGGTCACGGTGCCTTCATCTAGCCTGGGTACCAAGA<br>CCTACACTTGCAACGTGGACCACAAGCCTTCCAACACTAAGGT<br>GGACAAGCGCGTCGAATCGAAGTACGGCCCACCGTGCCCGCC<br>TTGTCCCGCGCCGGAGTTCCTCGGCGGTCCCTCGGTCTTTCTGT<br>TCCCACCGAAGCCCAAGGACACTTTGATGATTTCCCGCACCCC<br>TGAAGTGACATGCGTGGTCGTGGACGTGTCACAGGAAGATCC<br>GGAGGTGCAGTTCAATTGGTACGTGGATGGCGTCGAGGTGCA<br>CAACGCCAAAACCAAGCCGAGGGAGGAGCAGTTCAACTCCAC<br>TTACCGCGTCGTGTCCGTGCTGACGGTGCTGCATCAGGACTGG<br>CTGAACGGGAAGGAGTACAAGTGCAAAGTGTCCAACAAGGGA<br>CTTCCTAGCTCAATCGAAAAGACCATCTCGAAAGCCAAGGGA<br>CAGCCCCGGGAACCCCAAGTGTATACCCTGCCACCGAGCCAG<br>GAAGAAATGACTAAGAACCAAGTCTCATTGACTTGCCTTGTGA<br>AGGGCTTCTACCCATCGGATATCGCCGTGGAATGGGAGTCCAA<br>CGGCCAGCCGGAAAACAACTACAAGACCACCCCTCCGGTGCT<br>GGACTCAGACGGATCCTTCTTCCTCTACTCGCGGCTGACCGTG<br>GATAAGAGCAGATGGCAGGAGGGAAATGTGTTCAGCTGTTCT<br>GTGATGCATGAAGCCCTGCACAACCACTACACTCAGAAGTCCC<br>TGTCCCTCTCCCTGGGA |
| BAP058-Clone N LC | | |
| SEQ ID NO: 609 (Kabat) | LCDR1 | KASQDVGTAVA |
| SEQ ID NO: 610 (Kabat) | LCDR2 | WASTRHT |
| SEQ ID NO: 611 (Kabat) | LCDR3 | QQYNSYPLT |
| SEQ ID NO: 612 (Chothia) | LCDR1 | SQDVGTA |
| SEQ ID NO: 613 (Chothia) | LCDR2 | WAS |
| SEQ ID NO: 614 (Chothia) | LCDR3 | YNSYPL |
| SEQ ID NO: 624 | VL | DVVMTQSPLSLPVTLGQPASISCKASQDVGTAVAWYQQKPGQAP<br>RLLIYWASTRHTGVPSRFSGSGSGTEFTLTISSLQPDDFATYYCQQ<br>YNSYPLTFGQGTKVEIK |
| SEQ ID NO: 625 | DNA VL | GACGTCGTGATGACTCAGTCACCCCTGAGCCTGCCCGTGACCC<br>TGGGGCAGCCCGCCTCTATTAGCTGTAAAGCCTCTCAGGACGT<br>GGGCACCGCCGTGGCCTGGTATCAGCAGAAGCCAGGGCAAGC<br>CCCTAGACTGCTGATCTACTGGGCCTCTACTAGACACACCGGC<br>GTGCCCTCTAGGTTTAGCGGTAGCGGTAGTGGCACCGAGTTCA<br>CCCTGACTATCTCTTCACTGCAGCCCGACGACTTCGCTACCTAC<br>TACTGTCAGCAGTATAATAGCTACCCCCTGACCTTCGGTCAAG<br>GCACTAAGGTCGAGATTAAG |
| SEQ ID NO: 626 | Light chain | DVVMTQSPLSLPVTLGQPASISCKASQDVGTAVAWYQQKPGQAP<br>RLLIYWASTRHTGVPSRFSGSGSGTEFTLTISSLQPDDFATYYCQQ<br>YNSYPLTFGQGTKVEIKRTVAAPSVFIFPPSDEQLKSGTASVVCLL<br>NNFYPREAKVQWKVDNALQSGNSQESVTEQDSKDSTYSLSSTLT<br>LSKADYEKHKVYACEVTHQGLSSPVTKSFNRGEC |
| SEQ ID NO: 627 | DNA light chain | GACGTCGTGATGACTCAGTCACCCCTGAGCCTGCCCGTGACCC<br>TGGGGCAGCCCGCCTCTATTAGCTGTAAAGCCTCTCAGGACGT<br>GGGCACCGCCGTGGCCTGGTATCAGCAGAAGCCAGGGCAAGC<br>CCCTAGACTGCTGATCTACTGGGCCTCTACTAGACACACCGGC<br>GTGCCCTCTAGGTTTAGCGGTAGCGGTAGTGGCACCGAGTTCA<br>CCCTGACTATCTCTTCACTGCAGCCCGACGACTTCGCTACCTAC<br>TACTGTCAGCAGTATAATAGCTACCCCCTGACCTTCGGTCAAG<br>GCACTAAGGTCGAGATTAAGCGTACGGTGGCCGCTCCCAGCGT<br>GTTCATCTTCCCCCCCAGCGACGAGCAGCTGAAGAGCGGCACC<br>GCCAGCGTGGTGTGCCTGCTGAACAACTTCTACCCCCGGGAGG<br>CCAAGGTGCAGTGGAAGGTGGACAACGCCCTGCAGAGCGGCA<br>ACAGCCAGGAGAGCGTCACCGAGCAGGACAGCAAGGACTCCA<br>CCTACAGCCTGAGCAGCACCCTGACCCTGAGCAAGGCCGACT<br>ACGAGAAGCATAAGGTGTACGCCTGCGAGGTGACCCACCAGG<br>GCCTGTCCAGCCCCGTGACCAAGAGCTTCAACAGGGGCGAGT<br>GC |

TABLE 7-continued

Amino acid and nucleotide sequences of exemplary anti-PD-L1 antibody molecules

BAP058-Clone O HC

| | | | |
|---|---|---|---|
| SEQ ID NO: 628 (Kabat) | HCDR1 | agctactggatgtac | |
| SEQ ID NO: 629 (Kabat) | HCDR2 | agaatcgaccctaatagcggctctactaagtataacgagaagtttaagaat | |
| SEQ ID NO: 630 (Kabat) | HCDR3 | gactatagaaagggcctgtacgctatggactac | |
| SEQ ID NO: 631 (Chothia) | HCDR1 | ggctacaccttcactagctac | |
| SEQ ID NO: 632 (Chothia) | HCDR2 | gaccctaatagcggctct | |
| SEQ ID NO: 630 (Chothia) | HCDR3 | gactatagaaagggcctgtacgctatggactac | |

BAP058-Clone O LC

| | | | |
|---|---|---|---|
| SEQ ID NO: 633 (Kabat) | LCDR1 | aaagcctctcaggacgtgggcaccgccgtggcc | |
| SEQ ID NO: 634 (Kabat) | LCDR2 | tgggcctctactagacacacc | |
| SEQ ID NO: 635 (Kabat) | LCDR3 | cagcagtataatagctaccccctgacc | |
| SEQ ID NO: 636 (Chothia) | LCDR1 | tctcaggacgtgggcaccgcc | |
| SEQ ID NO: 637 (Chothia) | LCDR2 | tgggcctct | |
| SEQ ID NO: 638 (Chothia) | LCDR3 | tataatagctaccccctg | |

BAP058-Clone N HC

| | | | |
|---|---|---|---|
| SEQ ID NO: 628 (Kabat) | HCDR1 | agctactggatgtac | |
| SEQ ID NO: 629 (Kabat) | HCDR2 | agaatcgaccctaatagcggctctactaagtataacgagaagtttaagaat | |
| SEQ ID NO: 630 (Kabat) | HCDR3 | gactatagaaagggcctgtacgctatggactac | |
| SEQ ID NO: 631 (Chothia) | HCDR1 | ggctacaccttcactagctac | |
| SEQ ID NO: 632 (Chothia) | HCDR2 | gaccctaatagcggctct | |
| SEQ ID NO: 630 (Chothia) | HCDR3 | gactatagaaagggcctgtacgctatggactac | |

BAP058-Clone N LC

| | | | |
|---|---|---|---|
| SEQ ID NO: 633 (Kabat) | LCDR1 | aaagcctctcaggacgtgggcaccgccgtggcc | |
| SEQ ID NO: 634 (Kabat) | LCDR2 | tgggcctctactagacacacc | |
| SEQ ID NO: 635 (Kabat) | LCDR3 | cagcagtataatagctaccccctgacc | |
| SEQ ID NO: 636 (Chothia) | LCDR1 | tctcaggacgtgggcaccgcc | |
| SEQ ID NO: 637 (Chothia) | LCDR2 | tgggcctct | |
| SEQ ID NO: 638 (Chothia) | LCDR3 | tataatagctaccccctg | |

Other Exemplary PD-L Inhibitors

In one embodiment, the anti-PD-L1 antibody molecule is Atezolizumab (Genentech/Roche), also known as MPDL3280A, RG7446, RO5541267, YW243.55.S70, or TECENTRIQ™. Atezolizumab and other anti-PD-L1 antibodies are disclosed in U.S. Pat. No. 8,217,149, incorporated by reference in its entirety. In one embodiment, the anti-PD-L1 antibody molecule comprises one or more of the CDR sequences (or collectively all of the CDR sequences), the heavy chain or light chain variable region sequence, or the heavy chain or light chain sequence of Atezolizuma, e.g., as disclosed in Table 8.

In one embodiment, the anti-PD-L1 antibody molecule is Avelumab (Merck Serono and Pfizer), also known as MSB0010718C. Avelumab and other anti-PD-L1 antibodies are disclosed in WO 2013/079174, incorporated by reference in its entirety. In one embodiment, the anti-PD-L1 antibody molecule comprises one or more of the CDR sequences (or collectively all of the CDR sequences), the heavy chain or light chain variable region sequence, or the heavy chain or light chain sequence of Avelumab, e.g., as disclosed in Table 8.

In one embodiment, the anti-PD-L1 antibody molecule is Durvalumab (MedImmune/AstraZeneca), also known as MEDI4736. Durvalumab and other anti-PD-L1 antibodies are disclosed in U.S. Pat. No. 8,779,108, incorporated by reference in its entirety. In one embodiment, the anti-PD-L1 antibody molecule comprises one or more of the CDR sequences (or collectively all of the CDR sequences), the heavy chain or light chain variable region sequence, or the heavy chain or light chain sequence of Durvalumab, e.g., as disclosed in Table 8.

In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081158, incorporated by reference in their entirety. In one embodiment, the anti-PD-L1 antibody molecule comprises one or more of the CDR sequences (or collectively all of the CDR sequences), the heavy chain or light chain variable region sequence, or the heavy chain or light chain sequence of BMS-936559, e.g., as disclosed in Table 8.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 20121145493, WO 2015/112805, WO 2015/109124, WO 2015/195163, U.S. Pat. Nos. 8,168,179, 8,552,154, 8,460,927, and 9,175,082, incorporated by reference in their entirety.

In one embodiment, the anti-PD-L1 antibody is an antibody that competes for binding with, and/or binds to the same epitope on PD-L1 as, one of the anti-PD-L1 antibodies described herein.

TABLE 8

Amino acid sequences of other exemplary anti-PD-L1 antibody molecules

| | | |
|---|---|---|
| Atezolizumab | | |
| SEQ ID NO: 639 | Heavy chain | EVQLVESGGGLVQPGGSLRLSCAASGFTFSDSWIHWVRQAPGKGLEWVAWI<br>SPYGGSTYYADSVKGRFTISADTSKNTAYLQMNSLRAEDTAVYYCARRHWP<br>GGFDYWGQGTLVTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHKP<br>SNTKVDKKVEPKSCDKTHTCPPCPAPELLGGPSVFLFPPKPKDTLMISRTPEVT<br>CVVVDVSHEDPEVKFNWYVDGVEVHNAKTKPREEQYASTYRVVSVLTVLH<br>QDWLNGKEYKCKVSNKALPAPIEKTISKAKGQPREPQVYTLPPSREEMTKNQ<br>VSLTCLVKGFYPSDIAVEWESNGQPENNYKTTPPVLDSDGSFFLYSKLTVDKS<br>RWQQGNVFSCSVMHEALHNHYTQKSLSLSPGK |
| SEQ ID NO: 640 | Light chain | DIQMTQSPSSLSASVGDRVTITCRASQDVSTAVAWYQQKPGKAPKLLIYSASF<br>LYSGVPSRFSGSGSGTDFTLTISSLQPEDFATYYCQQYLYHPATFGQGTKVEIK<br>RTVAAPSVFIFPPSDEQLKSGTASVVCLLNNFYPREAKVQWKVDNALQSGNS<br>QESVTEQDSKDSTYSLSSTLTLSKADYEKHKVYACEVTHQGLSSPVTKSFNR<br>GEC |
| Avelumab | | |
| SEQ ID NO: 641 | Heavy chain | EVQLLESGGGLVQPGGSLRLSCAASGFTFSSYIMMWVRQAPGKGLEWVSSIY<br>PSGGITFYADTVKGRFTISRDNSKNTLYLQMNSLRAEDTAVYYCARIKLGTV<br>TTVDYWGQGTLVTVSSASTKGPSVFPLAPSSKSTSGGTAALGCLVKDYFPEP<br>VTVSWNSGALTSGVHTFPAVLQSSGLYSLSSVVTVPSSSLGTQTYICNVNHKP<br>SNTKVDKKVEPKSCDKTHTCPPCPAPELLGGPSVFLFPPKPKDTLMISRTPEVT<br>CVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTVDKS<br>RWQQGNVFSCSVMHEALHNHYTQKSLSLSPGK |
| SEQ ID NO: 642 | Light chain | QSALTQPASVSGSPGQSITISCTGTSSDVGGYNYVSWYQQHPGKAPKLMIYD<br>VSNRPSGVSNRFSGSKSGNTASLTISGLQAEDEADYYCSSYTSSSTRVFGTGT<br>KVTVLGQPKANPTVTLFPPSSEELQANKATLVCLISDFYPGAVTVAWKADGS<br>PVKAGVETTKPSKQSNNKYAASSYLSLTPEQWKSHRSYSCQVTHEGSTVEKT<br>VAPTECS |
| Durvalumab | | |
| SEQ ID NO: 643 | Heavy chain | EVQLVESGGGLVQPGGSLRLSCAASGFTFSRYWMSWVRQAPGKGLEWVANI<br>KQDGSEKYYVDSVKGRFTISRDNAKNSLYLQMNSLRAEDTAVYYCAREGG<br>WFGELAFDYWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICNV<br>NHKPSNTKVDKRVEPKSCDKTHTCPPCPAPEFEGGPSVFLFPPKPKDTLMISR<br>TPEVTCVVVDVSHEDPEVKFNWYVDGVEVHNAKTKPREEQYNSTYRVVSV<br>LTVLHQDWLNGKEYKCKVSNKALPASIEKTISKAKGQPREPQVYTLPPSREE<br>MTKNQVSLTCLVKGFYPSDIAVEWESNGQPENNYKTTPPVLDSDGSFFLYSK<br>LTVDKSRWQQGNVFSCSVMHEALHNHYTQKSLSLSPGK |

TABLE 8-continued

| Amino acid sequences of other exemplary anti-PD-L1 antibody molecules | | |
|---|---|---|
| SEQ ID NO: 644 | Light chain | EIVLTQSPGTLSLSPGERATLSCRASQRVSSSYLAWYQQKPGQAPRLLIYDAS SRATGIPDRFSGSGSGTDFTLTISRLEPEDFAVYYCQQYGSLPWTFGQGTKVEI KRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNR GEC |
| BMS-936559 | | |
| SEQ ID NO: 645 | VH | QVQLVQSGAEVKKPGSSVKVSCKTSGDTFSTYAISWVRQAPGQGLEWMGGII PIFGKAHYAQKFQGRVTITADESTSTAYMELSSLRSEDTAVYFCARKFHFVSG SPFGMDVWGQGTTVTVSS |
| SEQ ID NO: 646 | VL | EIVLTQSPATLSLSPGERATLSCRASQSVSSYLAWYQQKPGQAPRLLIYDASN RATGIPARFSGSGSGTDFTLTISSLEPEDFAVYYCQQRSNWPTFGQGTKVEIK |

Exemplary LAG-3 Inhibitors

In certain embodiments, the anti-CD73 molecule described herein is administered in combination with a LAG-3 inhibitor known in the art. The LAG-3 inhibitor may be an antibody, an antigen binding fragment thereof, an immunoadhesin, a fusion protein, or oligopeptide. In some embodiments, the LAG-3 inhibitor is chosen from LAG525 (Novartis), BMS-986016 (Bristol-Myers Squibb), TSR-033 (Tesaro), MK-4280 (Merck & Co), or REGN3767 (Regeneron).

Exemplary Anti-LAG-3 Antibody Molecules

In one embodiment, the LAG-3 inhibitor is an anti-LAG-3 antibody molecule. In one embodiment, the LAG-3 inhibitor is an anti-LAG-3 antibody molecule as disclosed in US 2015/0259420, published on Sep. 17, 2015, entitled "Antibody Molecules to LAG-3 and Uses Thereof," incorporated by reference in its entirety.

In one embodiment, the anti-LAG-3 antibody molecule comprises at least one, two, three, four, five or six complementarity determining regions (CDRs) (or collectively all of the CDRs) from a heavy and light chain variable region comprising an amino acid sequence shown in Table 9 (e.g., from the heavy and light chain variable region sequences of BAP050-Clone I or BAP050-Clone J disclosed in Table 9), or encoded by a nucleotide sequence shown in Table 9. In some embodiments, the CDRs are according to the Kabat definition (e.g., as set out in Table 9). In some embodiments, the CDRs are according to the Chothia definition (e.g., as set out in Table 5). In some embodiments, the CDRs are according to the combined CDR definitions of both Kabat and Chothia (e.g., as set out in Table 9). In one embodiment, the combination of Kabat and Chothia CDR of VH CDR1 comprises the amino acid sequence GFTLTNYGMN (SEQ ID NO: 766). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 9, or encoded by a nucleotide sequence shown in Table 9.

In one embodiment, the anti-LAG-3 antibody molecule comprises a heavy chain variable region (VH) comprising a VHCDR1 amino acid sequence of SEQ ID NO: 701, a VHCDR2 amino acid sequence of SEQ ID NO: 702, and a VHCDR3 amino acid sequence of SEQ ID NO: 703; and a light chain variable region (VL) comprising a VLCDR1 amino acid sequence of SEQ ID NO: 710, a VLCDR2 amino acid sequence of SEQ ID NO: 711, and a VLCDR3 amino acid sequence of SEQ ID NO: 712, each disclosed in Table 9.

In one embodiment, the anti-LAG-3 antibody molecule comprises a VH comprising a VHCDR1 encoded by the nucleotide sequence of SEQ ID NO: 736 or 737, a VHCDR2 encoded by the nucleotide sequence of SEQ ID NO: 738 or 739, and a VHCDR3 encoded by the nucleotide sequence of SEQ ID NO: 740 or 741; and a VL comprising a VLCDR1 encoded by the nucleotide sequence of SEQ ID NO: 746 or 747, a VLCDR2 encoded by the nucleotide sequence of SEQ ID NO: 748 or 749, and a VLCDR3 encoded by the nucleotide sequence of SEQ ID NO: 750 or 751, each disclosed in Table 9. In one embodiment, the anti-LAG-3 antibody molecule comprises a VH comprising a VHCDR1 encoded by the nucleotide sequence of SEQ ID NO: 758 or 737, a VHCDR2 encoded by the nucleotide sequence of SEQ ID NO: 759 or 739, and a VHCDR3 encoded by the nucleotide sequence of SEQ ID NO: 760 or 741; and a VL comprising a VLCDR1 encoded by the nucleotide sequence of SEQ ID NO: 746 or 747, a VLCDR2 encoded by the nucleotide sequence of SEQ ID NO: 748 or 749, and a VLCDR3 encoded by the nucleotide sequence of SEQ ID NO: 750 or 751, each disclosed in Table 9.

In one embodiment, the anti-LAG-3 antibody molecule comprises a VH comprising the amino acid sequence of SEQ ID NO: 706, or an amino acid sequence having at least about 85%, 90%, 95%, or 99% sequence identity to SEQ ID NO: 706. In one embodiment, the anti-LAG-3 antibody molecule comprises a VL comprising the amino acid sequence of SEQ ID NO: 718, or an amino acid sequence having at least about 85%, 90%, 95%, or 99% sequence identity to SEQ ID NO: 718. In one embodiment, the anti-LAG-3 antibody molecule comprises a VH comprising the amino acid sequence of SEQ ID NO: 724, or an amino acid sequence having at least about 85%, 90%, 95%, or 99% sequence identity to SEQ ID NO: 724. In one embodiment, the anti-LAG-3 antibody molecule comprises a VL comprising the amino acid sequence of SEQ ID NO: 730, or an amino acid sequence having at least about 85%, 90%, 95%, or 99% sequence identity to SEQ ID NO: 730. In one embodiment, the anti-LAG-3 antibody molecule comprises a VH comprising the amino acid sequence of SEQ ID NO: 706 and a VL comprising the amino acid sequence of SEQ ID NO: 718. In one embodiment, the anti-LAG-3 antibody molecule comprises a VH comprising the amino acid sequence of SEQ ID NO: 724 and a VL comprising the amino acid sequence of SEQ ID NO: 730.

In one embodiment, the antibody molecule comprises a VH encoded by the nucleotide sequence of SEQ ID NO: 707 or 708, or a nucleotide sequence having at least about 85%, 90%, 95%, or 99% sequence identity to SEQ ID NO: 707 or 708. In one embodiment, the antibody molecule comprises a VL encoded by the nucleotide sequence of SEQ ID NO:

719 or 720, or a nucleotide sequence having at least about 85%, 90%, 95%, or 99% sequence identity to SEQ ID NO: 719 or 720. In one embodiment, the antibody molecule comprises a VH encoded by the nucleotide sequence of SEQ ID NO: 725 or 726, or a nucleotide sequence having at least about 85%, 90%, 95%, or 99% sequence identity to SEQ ID NO: 725 or 726. In one embodiment, the antibody molecule comprises a VL encoded by the nucleotide sequence of SEQ ID NO: 731 or 732, or a nucleotide sequence having at least about 85%, 90%, 95%, or 99% sequence identity to SEQ ID NO: 731 or 732. In one embodiment, the antibody molecule comprises a VH encoded by the nucleotide sequence of SEQ ID NO: 707 or 708 and a VL encoded by the nucleotide sequence of SEQ ID NO: 719 or 720. In one embodiment, the antibody molecule comprises a VH encoded by the nucleotide sequence of SEQ ID NO: 725 or 726 and a VL encoded by the nucleotide sequence of SEQ ID NO: 731 or 732.

In one embodiment, the anti-LAG-3 antibody molecule comprises a heavy chain comprising the amino acid sequence of SEQ ID NO: 709, or an amino acid sequence having at least about 85%, 90%, 95%, or 99% sequence identity to SEQ ID NO: 709. In one embodiment, the anti-LAG-3 antibody molecule comprises a light chain comprising the amino acid sequence of SEQ ID NO: 721, or an amino acid sequence having at least about 85%, 90%, 95%, or 99% sequence identity to SEQ ID NO: 721. In one embodiment, the anti-LAG-3 antibody molecule comprises a heavy chain comprising the amino acid sequence of SEQ ID NO: 727, or an amino acid sequence having at least about 85%, 90%, 95%, or 99% sequence identity to SEQ ID NO: 727. In one embodiment, the anti-LAG-3 antibody molecule comprises a light chain comprising the amino acid sequence of SEQ ID NO: 733, or an amino acid sequence having at least about 85%, 90%, 95%, or 99% sequence identity to SEQ ID NO: 733. In one embodiment, the anti-LAG-3 antibody molecule comprises a heavy chain comprising the amino acid sequence of SEQ ID NO: 709 and a light chain comprising the amino acid sequence of SEQ ID NO: 721. In one embodiment, the anti-LAG-3 antibody molecule comprises a heavy chain comprising the amino acid sequence of SEQ ID NO: 727 and a light chain comprising the amino acid sequence of SEQ ID NO: 733.

In one embodiment, the antibody molecule comprises a heavy chain encoded by the nucleotide sequence of SEQ ID NO: 716 or 717, or a nucleotide sequence having at least about 85%, 90%, 95%, or 99% sequence identity to SEQ ID NO: 716 or 717. In one embodiment, the antibody molecule comprises a light chain encoded by the nucleotide sequence of SEQ ID NO: 722 or 723, or a nucleotide sequence having at least about 85%, 90%, 95%, or 99% sequence identity to SEQ ID NO: 722 or 723. In one embodiment, the antibody molecule comprises a heavy chain encoded by the nucleotide sequence of SEQ ID NO: 728 or 729, or a nucleotide sequence having at least about 85%, 90%, 95%, or 99% sequence identity to SEQ ID NO: 728 or 729. In one embodiment, the antibody molecule comprises a light chain encoded by the nucleotide sequence of SEQ ID NO: 734 or 735, or a nucleotide sequence having at least about 85%, 90%, 95%, or 99% sequence identity to SEQ ID NO: 734 or 735. In one embodiment, the antibody molecule comprises a heavy chain encoded by the nucleotide sequence of SEQ ID NO: 716 or 717 and a light chain encoded by the nucleotide sequence of SEQ ID NO: 722 or 723. In one embodiment, the antibody molecule comprises a heavy chain encoded by the nucleotide sequence of SEQ ID NO: 728 or 729 and a light chain encoded by the nucleotide sequence of SEQ ID NO: 734 or 735.

The antibody molecules described herein can be made by vectors, host cells, and methods described in US 2015/0259420, incorporated by reference in its entirety.

TABLE 9

| Amino acid and nucleotide sequences of exemplary anti-LAG-3 antibody molecules | | |
|---|---|---|
| BAP050-Clone I HC | | |
| SEQ ID NO: 701 (Kabat) | HCDR1 | NYGMN |
| SEQ ID NO: 702 (Kabat) | HCDR2 | WINTDTGEPTYADDFKG |
| SEQ ID NO: 703 (Kabat) | HCDR3 | NPPYYYGTNNAEAMDY |
| SEQ ID NO: 704 (Chothia) | HCDR1 | GFTLTNY |
| SEQ ID NO: 705 (Chothia) | HCDR2 | NTDTGE |
| SEQ ID NO: 703 (Chothia) | HCDR3 | NPPYYYGTNNAEAMDY |
| SEQ ID NO: 706 | VH | QVQLVQSGAEVKKPGASVKVSCKASGFTLTNYGMNWVRQARGQ<br>RLEWIGWINTDTGEPTYADDFKGRFVFSLDTSVSTAYLQISSLKAE<br>DTAVYYCARNPPYYYGTNNAEAMDYWGQGTTVTVSS |
| SEQ ID NO: 707 | DNA VH | CAAGTGCAGCTGGTGCAGTCGGGAGCCGAAGTGAAGAAGCCTG<br>GAGCCTCGGTGAAGGTGTCGTGCAAGGCATCCGGATTCACCCT<br>CACCAATTACGGGATGAACTGGGTCAGACAGGCCCGGGGTCAA<br>CGGCTGGAGTGGATCGGATGGATTAACACCGACACCGGGGAGC<br>CTACCTACGCGGACGATTTCAAGGGACGGTTCGTGTTCTCCCTC<br>GACACCTCCGTGTCCACCGCCTACCTCCAAATCTCCTCACTGAA<br>AGCGGAGGACACCGCCGTGTACTATTGCGCGAGGAACCCGCCC<br>TACTACTACGGAACCAACAACGCCGAAGCCATGGACTACTGGG<br>GCCAGGGCACCACTGTGACTGTGTCCAGC |
| SEQ ID NO: 708 | DNA VH | CAGGTGCAGCTGGTGCAGTCTGGCGCCGAAGTGAAGAAACCTG<br>GCGCCTCCGTGAAGGTGTCCTGCAAGGCCTCTGGCTTCACCCTG |

TABLE 9-continued

| Amino acid and nucleotide sequences of exemplary anti-LAG-3 antibody molecules | | |
|---|---|---|
| | | ACCAACTACGGCATGAACTGGGTGCGACAGGCCAGGGGCCAGC<br>GGCTGGAATGGATCGGCTGGATCAACACCGACACCGGCGAGCC<br>TACCTACGCCGACGACTTCAAGGGCAGATTCGTGTTCTCCCTGG<br>ACACCTCCGTGTCCACCGCCTACCTGCAGATCTCCAGCCTGAAG<br>GCCGAGGATACCGCCGTGTACTACTGCGCCCGGAACCCCCCTT<br>ACTACTACGGCACCAACAACGCCGAGGCCATGGACTATTGGGG<br>CCAGGGCACCACCGTGACCGTGTCCTCT |
| SEQ ID NO: 709 | Heavy chain | QVQLVQSGAEVKKPGASVKVSCKASGFTLTNYGMNWVRQARGQ<br>RLEWIGWINTDTGEPTYADDFKGRFVFSLDTSVSTAYLQISSLKAE<br>DTAVYYCARNPPYYYGTNNAEAMDYWGQGTTVTVSSASTKGPS<br>VFPLAPCSRSTSESTAALGCLVKDYFPEPVTVSWNSGALTSGVHTF<br>PAVLQSSGLYSLSSVVTVPSSSLGTKTYTCNVDHKPSNTKVDKRV<br>ESKYGPPCPPCPAPEFLGGPSVFLFPPKPKDTLMISRTPEVTCVVVD<br>VSQEDPEVQFNWYVDGVEVHNAKTKPREEQFNSTYRVVSVLTVL<br>HQDWLNGKEYKCKVSNKGLPSSIEKTISKAKGQPREPQVYTLPPS<br>QEEMTKNQVSLTCLVKGFYPSDIAVEWESNGQPENNYKTTPPVLD<br>SDGSFFLYSRLTVDKSRWQEGNVFSCSVMHEALHNHYTQKSLSLS<br>LG |
| SEQ ID NO: 716 | DNA heavy chain | CAAGTGCAGCTGGTGCAGTCGGGAGCCGAAGTGAAGAAGCCTG<br>GAGCCTCGGTGAAGGTGTCGTGCAAGGCATCCGGATTCACCCT<br>CACCAATTACGGGATGAACTGGGTCAGACAGGCCCGGGGTCAA<br>CGGCTGGAGTGGATCGGATGGATTAACACCGACACCGGGGAGC<br>CTACCTACGCGGACGATTTCAAGGGACGGTTCGTGTTCTCCCTC<br>GACACCTCCGTGTCCACCGCCTACCTCCAAATCTCCTCACTGAA<br>AGCGGAGGACACCGCCGTGTACTATTGCGCGAGGAACCCGCCC<br>TACTACTACGGAACCAACAACGCCGAAGCCATGGACTACTGGG<br>GCCAGGGCACCACTGTGACTGTGTCCAGCGCGTCCACTAAGGG<br>CCCGTCCGTGTTCCCCCTGGCACCTTGTAGCCGGAGCACTAGCG<br>AATCCACCGCTGCCCTCGGCTGCCTGGTCAAGGATTACTTCCCG<br>GAGCCCGTGACCGTGTCCTGGAACAGCGGAGCCCTGACCTCCG<br>GAGTGCACACCTTCCCCGCTGTGCTGCAGAGCTCCGGGCTGTAC<br>TCGCTGTCGTCGGTGGTCACGGTGCCTTCATCTAGCCTGGGTAC<br>CAAGACCTACACTTGCAACGTGGACCACAAGCCTTCCAACACT<br>AAGGTGGACAAGCGCGTCGAATCGAAGTACGGCCCACCGTGCC<br>CGCCTTGTCCCGCGCCGGAGTTCCTCGGCGGTCCCTCGGTCTTT<br>CTGTTCCCACCGAAGCCCAAGGACACTTTGATGATTTCCCGCAC<br>CCCTGAAGTGACATGCGTGGTCGTGGACGTGTCACAGGAAGAT<br>CCGGAGGTGCAGTTCAATTGGTACGTGGATGGCGTCGAGGTGC<br>ACAACGCCAAAACCAAGCCGAGGGAGGAGCAGTTCAACTCCAC<br>TTACCGCGTCGTGTCCGTGCTGACGGTGCTGCATCAGGACTGGC<br>TGAACGGGAAGGAGTACAAGTGCAAAGTGTCCAACAAGGGAC<br>TTCCTAGCTCAATCGAAAAGACCATCTCGAAAGCCAAGGGACA<br>GCCCCGGGAACCCCAAGTGTATACCCTGCCACCGAGCCAGGAA<br>GAAATGACTAAGAACCAAGTCTCATTGACTTGCCTTGTGAAGG<br>GCTTCTACCCATCGGATATCGCCGTGGAATGGGAGTCCAACGG<br>CCAGCCGGAAAACAACTACAAGACCACCCCTCCGGTGCTGGAC<br>TCAGACGGATCCTTCTTCCTCTACTCGCGGCTGACCGTGGATAA<br>GAGCAGATGGCAGGAGGGAAATGTGTTCAGCTGTTCTGTGATG<br>CATGAAGCCCTGCACAACCACTACACTCAGAAGTCCCTGTCCCT<br>CTCCCTGGGA |
| SEQ ID NO: 717 | DNA heavy chain | CAGGTGCAGCTGGTGCAGTCTGGCGCCGAAGTGAAGAAACCTG<br>GCGCCTCCGTGAAGGTGTCCTGCAAGGCCTCTGGCTTCACCCTG<br>ACCAACTACGGCATGAACTGGGTGCGACAGGCCAGGGGCCAGC<br>GGCTGGAATGGATCGGCTGGATCAACACCGACACCGGCGAGCC<br>TACCTACGCCGACGACTTCAAGGGCAGATTCGTGTTCTCCCTGG<br>ACACCTCCGTGTCCACCGCCTACCTGCAGATCTCCAGCCTGAAG<br>GCCGAGGATACCGCCGTGTACTACTGCGCCCGGAACCCCCCTT<br>ACTACTACGGCACCAACAACGCCGAGGCCATGGACTATTGGGG<br>CCAGGGCACCACCGTGACCGTGTCCTCTGCTTCTACCAAGGGGC<br>CCAGCGTGTTCCCCCTGGCCCCCTGCTCCAGAAGCACCAGCGA<br>GAGCACAGCCGCCCTGGGCTGCCTGGTGAAGGACTACTTCCCC<br>GAGCCCGTGACCGTGTCCTGGAACAGCGGAGCCCTGACCAGCG<br>GCGTGCACACCTTCCCCGCCGTGCTGCAGAGCAGCGGCCTGTA<br>CAGCCTGAGCAGCGTGGTGACCGTGCCCAGCAGCAGCCTGGGC<br>ACCAAGACCTACACCTGTAACGTGGACCACAAGCCCAGCAACA<br>CCAAGGTGGACAAGAGGGTGGAGAGCAAGTACGGCCCACCCT<br>GCCCCCCCTGCCCAGCCCCCGAGTTCCTGGGCGGACCCAGCGT<br>GTTCCTGTTCCCCCCCAAGCCCAAGGACACCCTGATGATCAGCA<br>GAACCCCCGAGGTGACCTGTGTGGTGGTGGACGTGTCCCAGGA<br>GGACCCCGAGGTCCAGTTCAACTGGTACGTGGACGGCGTGGAG<br>GTGCACAACGCCAAGACCAAGCCCAGAGAGGAGCAGTTTAACA<br>GCACCTACCGGGTGGTGTCCGTGCTGACCGTGCTGCACCAGGA<br>CTGGCTGAACGGCAAAGAGTACAAGTGTAAGGTCTCCAACAAG<br>GGCCTGCCAAGCAGCATCGAAAAGACCATCAGCAAGGCCAAG<br>GGCCAGCCTAGAGAGCCCCAGGTCTACACCCTGCCACCCAGCC |

TABLE 9-continued

| Amino acid and nucleotide sequences of exemplary anti-LAG-3 antibody molecules | | |
|---|---|---|
| | | AAGAGGAGATGACCAAGAACCAGGTGTCCCTGACCTGTCTGGT GAAGGGCTTCTACCCAAGCGACATCGCCGTGGAGTGGGAGAGC AACGGCCAGCCCGAGAACAACTACAAGACCACCCCCCCAGTGC TGGACAGCGACGGCAGCTTCTTCCTGTACAGCAGGCTGACCGT GGACAAGTCCAGATGGCAGGAGGGCAACGTCTTTAGCTGCTCC GTGATGCACGAGGCCCTGCACAACCACTACACCCAGAAGAGCC TGAGCCTGTCCCTGGGC |
| BAP050-Clone I LC | | |
| SEQ ID NO: 710 (Kabat) | LCDR1 | SSSQDISNYLN |
| SEQ ID NO: 711 (Kabat) | LCDR2 | YTSTLHL |
| SEQ ID NO: 712 (Kabat) | LCDR3 | QQYYNLPWT |
| SEQ ID NO: 713 (Chothia) | LCDR1 | SQDISNY |
| SEQ ID NO: 714 (Chothia) | LCDR2 | YTS |
| SEQ ID NO: 715 (Chothia) | LCDR3 | YYNLPW |
| SEQ ID NO: 718 | VL | DIQMTQSPSSLSASVGDRVTITCSSSQDISNYLNWYLQKPGQSPQL LIYYTSTLHLGVPSRFSGSGSGTEFTLTISSLQPDDFATYYCQQYYN LPWTFGQGTKVEIK |
| SEQ ID NO: 719 | DNA VL | GATATTCAGATGACTCAGTCACCTAGTAGCCTGAGCGCTAGTGT GGGCGATAGAGTGACTATCACCTGTAGCTCTAGTCAGGATATCT CTAACTACCTGAACTGGTATCTGCAGAAGCCCGGTCAATCACCT CAGCTGCTGATCTACTACACTAGCACCCTGCACCTGGGCGTGCC CTCTAGGTTTAGCGGTAGCGGTAGTGGCACCGAGTTCACCCTGA CTATCTCTAGCCTGCAGCCCGACGACTTCGCTACCTACTACTGT CAGCAGTACTATAACCTGCCCTGGACCTTCGGTCAAGGCACTA AGGTCGAGATTAAG |
| SEQ ID NO: 720 | DNA VL | GACATCCAGATGACCCAGTCCCCCTCCAGCCTGTCTGCTTCCGT GGGCGACAGAGTGACCATCACCTGTTCCTCCAGCCAGGACATC TCCAACTACCTGAACTGGTATCTGCAGAAGCCCGGCCAGTCCCC TCAGCTGCTGATCTACTACACCTCCACCCTGCACCTGGGCGTGC CCTCCAGATTTTCCGGCTCTGGCTCTGGCACCGAGTTTACCCTG ACCATCAGCTCCCTGCAGCCCGACGACTTCGCCACCTACTACTG CCAGCAGTACTACAACCTGCCCTGGACCTTCGGCCAGGGCACC AAGGTGGAAATCAAG |
| SEQ ID NO: 721 | Light chain | DIQMTQSPSSLSASVGDRVTITCSSSQDISNYLNWYLQKPGQSPQL LIYYTSTLHLGVPSRFSGSGSGTEFTLTISSLQPDDFATYYCQQYYN LPWTFGQGTKVEIKRTVAAPSVFIFPPSDEQLKSGTASVVCLLNNF YPREAKVQWKVDNALQSGNSQESVTEQDSKDSTYSLSSTLTLSKA DYEKHKVYACEVTHQGLSSPVTKSFNRGEC |
| SEQ ID NO: 722 | DNA light chain | GATATTCAGATGACTCAGTCACCTAGTAGCCTGAGCGCTAGTGT GGGCGATAGAGTGACTATCACCTGTAGCTCTAGTCAGGATATCT CTAACTACCTGAACTGGTATCTGCAGAAGCCCGGTCAATCACCT CAGCTGCTGATCTACTACACTAGCACCCTGCACCTGGGCGTGCC CTCTAGGTTTAGCGGTAGCGGTAGTGGCACCGAGTTCACCCTGA CTATCTCTAGCCTGCAGCCCGACGACTTCGCTACCTACTACTGT CAGCAGTACTATAACCTGCCCTGGACCTTCGGTCAAGGCACTA AGGTCGAGATTAAGCGTACGGTGGCCGCTCCCAGCGTGTTCAT CTTCCCCCCCAGCGACGAGCAGCTGAAGAGCGGCACCGCCAGC GTGGTGTGCCTGCTGAACAACTTCTACCCCCGGGAGGCCAAGG TGCAGTGGAAGGTGGACAACGCCCTGCAGAGCGGCAACAGCCA GGAGAGCGTCACCGAGCAGGACAGCAAGGACTCCACCTACAGC CTGAGCAGCACCCTGACCCTGAGCAAGGCCGACTACGAGAAGC ATAAGGTGTACGCCTGCGAGGTGACCCACCAGGGCCTGTCCAG CCCCGTGACCAAGAGCTTCAACAGGGGCGAGTGC |
| SEQ ID NO: 723 | DNA light chain | GACATCCAGATGACCCAGTCCCCCTCCAGCCTGTCTGCTTCCGT GGGCGACAGAGTGACCATCACCTGTTCCTCCAGCCAGGACATC TCCAACTACCTGAACTGGTATCTGCAGAAGCCCGGCCAGTCCCC TCAGCTGCTGATCTACTACACCTCCACCCTGCACCTGGGCGTGC CCTCCAGATTTTCCGGCTCTGGCTCTGGCACCGAGTTTACCCTG ACCATCAGCTCCCTGCAGCCCGACGACTTCGCCACCTACTACTG CCAGCAGTACTACAACCTGCCCTGGACCTTCGGCCAGGGCACC AAGGTGGAAATCAAGCGTACGGTGGCCGCTCCCAGCGTGTTCA TCTTCCCCCCAAGCGACGAGCAGCTGAAGAGCGGCACCGCCAG |

TABLE 9-continued

| Amino acid and nucleotide sequences of exemplary anti-LAG-3 antibody molecules | | |
|---|---|---|
| | | CGTGGTGTGTCTGCTGAACAACTTCTACCCCAGGGAGGCCAAG GTGCAGTGGAAGGTGGACAACGCCCTGCAGAGCGGCAACAGCC AGGAGAGCGTCACCGAGCAGGACAGCAAGGACTCCACCTACA GCCTGAGCAGCACCCTGACCCTGAGCAAGGCCGACTACGAGAA GCACAAGGTGTACGCCTGTGAGGTGACCCACCAGGGCCTGTCC AGCCCCGTGACCAAGAGCTTCAACAGGGGCGAGTGC |
| BAP050-Clone J HC | | |
| SEQ ID NO: 701 (Kabat) | HCDR1 | NYGMN |
| SEQ ID NO: 702 (Kabat) | HCDR2 | WINTDTGEPTYADDFKG |
| SEQ ID NO: 703 (Kabat) | HCDR3 | NPPYYYGTNNAEAMDY |
| SEQ ID NO: 704 (Chothia) | HCDR1 | GFTLTNY |
| SEQ ID NO: 705 (Chothia) | HCDR2 | NTDTGE |
| SEQ ID NO: 703 (Chothia) | HCDR3 | NPPYYYGTNNAEAMDY |
| SEQ ID NO: 724 | VH | QVQLVQSGAEVKKPGASVKVSCKASGFTLTNYGMNWVRQAPGQ GLEWMGWINTDTGEPTYADDFKGRFVFSLDTSVSTAYLQISSLKA EDTAVYYCARNPPYYYGTNNAEAMDYWGQGTTVTVSS |
| SEQ ID NO: 725 | DNA VH | CAGGTGCAGCTGGTGCAGTCAGGCGCCGAAGTGAAGAAACCCG GCGCTAGTGTGAAAGTCAGCTGTAAAGCTAGTGGCTTCACCCT GACTAACTACGGGATGAACTGGGTCCGCCAGGCCCCAGGTCAA GGCCTCGAGTGGATGGGCTGGATTAACACCGACACCGGCGAGC CTACCTACGCCGACGACTTTAAGGGCAGATTCGTGTTTAGCCTG GACACTAGTGTGTCTACCGCCTACCTGCAGATCTCTAGCCTGAA GGCCGAGGACACCGCCGTCTACTACTGCGCTAGAAACCCCCCC TACTACTACGGCACTAACAACGCCGAGGCTATGGACTACTGGG GTCAAGGCACTACCGTGACCGTGTCTAGC |
| SEQ ID NO: 726 | DNA VH | CAGGTGCAGCTGGTGCAGTCTGGCGCCGAAGTGAAGAAACCTG GCGCCTCCGTGAAGGTGTCCTGCAAGGCCTCTGGCTTCACCCTG ACCAACTACGGCATGAACTGGGTGCGACAGGCCCCTGGACAGG GCCTGGAATGGATGGGCTGGATCAACACCGACACCGGCGAGCC TACCTACGCCGACGACTTCAAGGGCAGATTCGTGTTCTCCCTGG ACACCTCCGTGTCCACCGCCTACCTGCAGATCTCCAGCCTGAAG GCCGAGGATACCGCCGTGTACTACTGCGCCCGGAACCCCCCTT ACTACTACGGCACCAACAACGCCGAGGCCATGGACTATTGGGG CCAGGGCACCACCGTGACCGTGTCCTCT |
| SEQ ID NO: 727 | Heavy chain | QVQLVQSGAEVKKPGASVKVSCKASGFTLTNYGMNWVRQAPGQ GLEWMGWINTDTGEPTYADDFKGRFVFSLDTSVSTAYLQISSLKA EDTAVYYCARNPPYYYGTNNAEAMDYWGQGTTVTVSSASTKGP SVFPLAPCSRSTSESTAALGCLVKDYFPEPVTVSWNSGALTSGVHT FPAVLQSSGLYSLSSVVTVPSSSLGTKTYTCNVDHKPSNTKVDKRV ESKYGPPCPPCPAPEFLGGPSVFLFPPKPKDTLMISRTPEVTCVVVD VSQEDPEVQFNWYVDGVEVHNAKTKPREEQFNSTYRVVSVLTVL HQDWLNGKEYKCKVSNKGLPSSIEKTISKAKGQPREPQVYTLPPS QEEMTKNQVSLTCLVKGFYPSDIAVEWESNGQPENNYKTTPPVLD SDGSFFLYSRLTVDKSRWQEGNVFSCSVMHEALHNHYTQKSLSLS LG |
| SEQ ID NO: 728 | DNA heavy chain | CAGGTGCAGCTGGTGCAGTCAGGCGCCGAAGTGAAGAAACCCG GCGCTAGTGTGAAAGTCAGCTGTAAAGCTAGTGGCTTCACCCT GACTAACTACGGGATGAACTGGGTCCGCCAGGCCCCAGGTCAA GGCCTCGAGTGGATGGGCTGGATTAACACCGACACCGGCGAGC CTACCTACGCCGACGACTTTAAGGGCAGATTCGTGTTTAGCCTG GACACTAGTGTGTCTACCGCCTACCTGCAGATCTCTAGCCTGAA GGCCGAGGACACCGCCGTCTACTACTGCGCTAGAAACCCCCCC TACTACTACGGCACTAACAACGCCGAGGCTATGGACTACTGGG GTCAAGGCACTACCGTGACCGTGTCTAGCGCTAGCACTAAGGG CCCGTCCGTGTTCCCCCTGGCACCTTGTAGCCGGAGCACTAGCG AATCCACCGCTGCCCTCGGCTGCCTGGTCAAGGATTACTTCCCG GAGCCCGTGACCGTGTCCTGGAACAGCGGAGCCCTGACCTCCG GAGTGCACACCTTCCCCGCTGTGCTGCAGAGCTCCGGGCTGTAC TCGCTGTCGTCGGTGGTCACGGTGCCTTCATCTAGCCTGGGTAC CAAGACCTACACTTGCAACGTGGACCACAAGCCTTCCAACACT AAGGTGGACAAGCGCGTCGAATCGAAGTACGGCCCACCGTGCC CGCCTTGTCCCGCGCCGGAGTTCCTCGGCGGTCCCTCGGTCTTT CTGTTCCCACCGAAGCCCAAGGACACTTTGATGATTTCCCGCAC |

TABLE 9-continued

| Amino acid and nucleotide sequences of exemplary anti-LAG-3 antibody molecules | | |
|---|---|---|
| | | CCCTGAAGTGACATGCGTGGTCGTGGACGTGTCACAGGAAGAT CCGGAGGTGCAGTTCAATTGGTACGTGGATGGCGTCGAGGTGC ACAACGCCAAAACCAAGCCGAGGGAGGAGCAGTTCAACTCCAC TTACCGCGTCGTGTCCGTGCTGACGGTGCTGCATCAGGACTGGC TGAACGGGAAGGAGTACAAGTGCAAAGTGTCCAACAAGGGAC TTCCTAGCTCAATCGAAAAGACCATCTCGAAAGCCAAGGGACA GCCCCGGGAACCCCAAGTGTATACCCTGCCACCGAGCCAGGAA GAAATGACTAAGAACCAAGTCTCATTGACTTGCCTTGTGAAGG GCTTCTACCCATCGGATATCGCCGTGGAATGGGAGTCCAACGG CCAGCCGGAAAACAACTACAAGACCACCCCTCCGGTGCTGGAC TCAGACGGATCCTTCTTCCTCTACTCGCGGCTGACCGTGGATAA GAGCAGATGGCAGGAGGGAAATGTGTTCAGCTGTTCTGTGATG CATGAAGCCCTGCACAACCACTACACTCAGAAGTCCCTGTCCCT CTCCCTGGGA |
| SEQ ID NO: 729 | DNA heavy chain | CAGGTGCAGCTGGTGCAGTCTGGCGCCGAAGTGAAGAAACCTG GCGCCTCCGTGAAGGTGTCCTGCAAGGCCTCTGGCTTCACCCTG ACCAACTACGGCATGAACTGGGTGCGACAGGCCCCTGGACAGG GCCTGGAATGGATGGGCTGGATCAACACCGACACCGGCGAGCC TACCTACGCCGACGACTTCAAGGGCAGATTCGTGTTCTCCCTGG ACACCTCCGTGTCCACCGCCTACCTGCAGATCTCCAGCCTGAAG GCCGAGGATACCGCCGTGTACTACTGCGCCCGGAACCCCCCTT ACTACTACGGCACCAACAACGCCGAGGCCATGGACTATTGGGG CCAGGGCACCACCGTGACCGTGTCCTCTGCTTCTACCAAGGGGC CCAGCGTGTTCCCCCTGGCCCCCTGCTCCAGAAGCACCAGCGA GAGCACAGCCGCCCTGGGCTGCCTGGTGAAGGACTACTTCCCC GAGCCCGTGACCGTGTCCTGGAACAGCGGAGCCCTGACCAGCG GCGTGCACACCTTCCCCGCCGTGCTGCAGAGCAGCGGCCTGTA CAGCCTGAGCAGCGTGGTGACCGTGCCCAGCAGCAGCCTGGGC ACCAAGACCTACACCTGTAACGTGGACCACAAGCCCAGCAACA CCAAGGTGGACAAGAGGGTGGAGAGCAAGTACGGCCCACCCT GCCCCCCCTGCCCAGCCCCCGAGTTCCTGGGCGGACCCAGCGT GTTCCTGTTCCCCCCCAAGCCCAAGGACACCCTGATGATCAGCA GAACCCCCGAGGTGACCTGTGTGGTGGTGGACGTGTCCCAGGA GGACCCCGAGGTCCAGTTCAACTGGTACGTGGACGGCGTGGAG GTGCACAACGCCAAGACCAAGCCCAGAGAGGAGCAGTTTAACA GCACCTACCGGGTGGTGTCCGTGCTGACCGTGCTGCACCAGGA CTGGCTGAACGGCAAAGAGTACAAGTGTAAGGTCTCCAACAAG GGCCTGCCAAGCAGCATCGAAAAGACCATCAGCAAGGCCAAG GGCCAGCCTAGAGAGCCCCAGGTCTACACCCTGCCACCCAGCC AAGAGGAGATGACCAAGAACCAGGTGTCCCTGACCTGTCTGGT GAAGGGCTTCTACCCAAGCGACATCGCCGTGGAGTGGGAGAGC AACGGCCAGCCCGAGAACAACTACAAGACCACCCCCCCAGTGC TGGACAGCGACGGCAGCTTCTTCCTGTACAGCAGGCTGACCGT GGACAAGTCCAGATGGCAGGAGGGCAACGTCTTTAGCTGCTCC GTGATGCACGAGGCCCTGCACAACCACTACACCCAGAAGAGCC TGAGCCTGTCCCTGGGC |
| BAP050-Clone J LC | | |
| SEQ ID NO: 710 (Kabat) | LCDR1 | SSSQDISNYLN |
| SEQ ID NO: 711 (Kabat) | LCDR2 | YTSTLHL |
| SEQ ID NO: 712 (Kabat) | LCDR3 | QQYYNLPWT |
| SEQ ID NO: 713 (Chothia) | LCDR1 | SQDISNY |
| SEQ ID NO: 714 (Chothia) | LCDR2 | YTS |
| SEQ ID NO: 715 (Chothia) | LCDR3 | YYNLPW |
| SEQ ID NO: 730 | VL | DIQMTQSPSSLSASVGDRVTITCSSSQDISNYLNWYQQKPGKAPKL LIYYTSTLHLGIPPRFSGSGYGTDFTLTINNIESEDAAYYFCQQYYN LPWTFGQGTKVEIK |
| SEQ ID NO: 731 | DNA VL | GATATTCAGATGACTCAGTCACCTAGTAGCCTGAGCGCTAGTGT GGGCGATAGAGTGACTATCACCTGTAGCTCTAGTCAGGATATCT CTAACTACCTGAACTGGTATCAGCAGAAGCCCGGTAAAGCCCC TAAGCTGCTGATCTACTACACTAGCACCCTGCACCTGGGAATCC CCCCTAGGTTTAGCGGTAGCGGCTACGGCACCGACTTCACCCTG ACTATTAACAATATCGAGTCAGAGGACGCCGCCTACTACTTCTG TCAGCAGTACTATAACCTGCCCTGGACCTTCGGTCAAGGCACTA AGGTCGAGATTAAG |

TABLE 9-continued

| Amino acid and nucleotide sequences of exemplary anti-LAG-3 antibody molecules | | |
|---|---|---|
| SEQ ID NO: 732 | DNA VL | GACATCCAGATGACCCAGTCCCCCTCCAGCCTGTCTGCTTCCGT GGGCGACAGAGTGACCATCACCTGTTCCTCCAGCCAGGACATC TCCAACTACCTGAACTGGTATCAGCAGAAGCCCGGCAAGGCCC CCAAGCTGCTGATCTACTACACCTCCACCCTGCACCTGGGCATC CCCCCTAGATTCTCCGGCTCTGGCTACGGCACCGACTTCACCCT GACCATCAACAACATCGAGTCCGAGGACGCCGCCTACTACTTC TGCCAGCAGTACTACAACCTGCCCTGGACCTTCGGCCAGGGCA CCAAGGTGGAAATCAAG |
| SEQ ID NO: 733 | Light chain | DIQMTQSPSSLSASVGDRVTITCSSSQDISNYLNWYQQKPGKAPKL LIYYTSTLHLGIPPRFSGSGYGTDFTLTINNIESEDAAYYFCQQYYN LPWTFGQGTKVEIKRTVAAPSVFIFPPSDEQLKSGTASVVCLLNNF YPREAKVQWKVDNALQSGNSQESVTEQDSKDSTYSLSSTLTLSKA DYEKHKVYACEVTHQGLSSPVTKSFNRGEC |
| SEQ ID NO: 734 | DNA light chain | GATATTCAGATGACTCAGTCACCTAGTAGCCTGAGCGCTAGTGT GGGCGATAGAGTGACTATCACCTGTAGCTCTAGTCAGGATATCT CTAACTACCTGAACTGGTATCAGCAGAAGCCCGGTAAAGCCCC TAAGCTGCTGATCTACTACACTAGCACCCTGCACCTGGGAATCC CCCCTAGGTTTAGCGGTAGCGGCTACGGCACCGACTTCACCCTG ACTATTAACAATATCGAGTCAGAGGACGCCGCCTACTACTTCTG TCAGCAGTACTATAACCTGCCCTGGACCTTCGGTCAAGGCACTA AGGTCGAGATTAAGCGTACGGTGGCCGCTCCCAGCGTGTTCAT CTTCCCCCCCAGCGACGAGCAGCTGAAGAGCGGCACCGCCAGC GTGGTGTGCCTGCTGAACAACTTCTACCCCCGGGAGGCCAAGG TGCAGTGGAAGGTGGACAACGCCCTGCAGAGCGGCAACAGCCA GGAGAGCGTCACCGAGCAGGACAGCAAGGACTCCACCTACAGC CTGAGCAGCACCCTGACCCTGAGCAAGGCCGACTACGAGAAGC ATAAGGTGTACGCCTGCGAGGTGACCCACCAGGGCCTGTCCAG CCCCGTGACCAAGAGCTTCAACAGGGGCGAGTGC |
| SEQ ID NO: 735 | DNA light chain | GACATCCAGATGACCCAGTCCCCCTCCAGCCTGTCTGCTTCCGT GGGCGACAGAGTGACCATCACCTGTTCCTCCAGCCAGGACATC TCCAACTACCTGAACTGGTATCAGCAGAAGCCCGGCAAGGCCC CCAAGCTGCTGATCTACTACACCTCCACCCTGCACCTGGGCATC CCCCCTAGATTCTCCGGCTCTGGCTACGGCACCGACTTCACCCT GACCATCAACAACATCGAGTCCGAGGACGCCGCCTACTACTTC TGCCAGCAGTACTACAACCTGCCCTGGACCTTCGGCCAGGGCA CCAAGGTGGAAATCAAGCGTACGGTGGCCGCTCCCAGCGTGTT CATCTTCCCCCCAAGCGACGAGCAGCTGAAGAGCGGCACCGCC AGCGTGGTGTGTCTGCTGAACAACTTCTACCCCAGGGAGGCCA AGGTGCAGTGGAAGGTGGACAACGCCCTGCAGAGCGGCAACA GCCAGGAGAGCGTCACCGAGCAGGACAGCAAGGACTCCACCTA CAGCCTGAGCAGCACCCTGACCCTGAGCAAGGCCGACTACGAG AAGCACAAGGTGTACGCCTGTGAGGTGACCCACCAGGGCCTGT CCAGCCCCGTGACCAAGAGCTTCAACAGGGGCGAGTGC |
| BAP050-Clone I HC | | |
| SEQ ID NO: 736 (Kabat) | HCDR1 | AATTACGGGATGAAC |
| SEQ ID NO: 737 (Kabat) | HCDR1 | AACTACGGCATGAAC |
| SEQ ID NO: 738 (Kabat) | HCDR2 | TGGATTAACACCGACACCGGGGAGCCTACCTACGCGGACGATT TCAAGGGA |
| SEQ ID NO: 739 (Kabat) | HCDR2 | TGGATCAACACCGACACCGGCGAGCCTACCTACGCCGACGACT TCAAGGGC |
| SEQ ID NO: 740 (Kabat) | HCDR3 | AACCCGCCCTACTACTACGGAACCAACAACGCCGAAGCCATGG ACTAC |
| SEQ ID NO: 741 (Kabat) | HCDR3 | AACCCCCCTTACTACTACGGCACCAACAACGCCGAGGCCATGG ACTAT |
| SEQ ID NO: 742 (Chothia) | HCDR1 | GGATTCACCCTCACCAATTAC |
| SEQ ID NO: 743 (Chothia) | HCDR1 | GGCTTCACCCTGACCAACTAC |
| SEQ ID NO: 744 (Chothia) | HCDR2 | AACACCGACACCGGGGAG |
| SEQ ID NO: 745 (Chothia) | HCDR2 | AACACCGACACCGGCGAG |

TABLE 9-continued

| Amino acid and nucleotide sequences of exemplary anti-LAG-3 antibody molecules | | |
|---|---|---|
| SEQ ID NO: 740 (Chothia) | HCDR3 | AACCCGCCCTACTACTACGGAACCAACAACGCCGAAGCCATGGACTAC |
| SEQ ID NO: 741 (Chothia) | HCDR3 | AACCCCCCTTACTACTACGGCACCAACAACGCCGAGGCCATGGACTAT |
| BAP050-Clone I LC | | |
| SEQ ID NO: 746 (Kabat) | LCDR1 | AGCTCTAGTCAGGATATCTCTAACTACCTGAAC |
| SEQ ID NO: 747 (Kabat) | LCDR1 | TCCTCCAGCCAGGACATCTCCAACTACCTGAAC |
| SEQ ID NO: 748 (Kabat) | LCDR2 | TACACTAGCACCCTGCACCTG |
| SEQ ID NO: 749 (Kabat) | LCDR2 | TACACCTCCACCCTGCACCTG |
| SEQ ID NO: 750 (Kabat) | LCDR3 | CAGCAGTACTATAACCTGCCCTGGACC |
| SEQ ID NO: 751 (Kabat) | LCDR3 | CAGCAGTACTACAACCTGCCCTGGACC |
| SEQ ID NO: 752 (Chothia) | LCDR1 | AGTCAGGATATCTCTAACTAC |
| SEQ ID NO: 753 (Chothia) | LCDR1 | AGCCAGGACATCTCCAACTAC |
| SEQ ID NO: 754 (Chothia) | LCDR2 | TACACTAGC |
| SEQ ID NO: 755 (Chothia) | LCDR2 | TACACCTCC |
| SEQ ID NO: 756 (Chothia) | LCDR3 | TACTATAACCTGCCCTGG |
| SEQ ID NO: 757 (Chothia) | LCDR3 | TACTACAACCTGCCCTGG |
| BAP050-Clone J HC | | |
| SEQ ID NO: 758 (Kabat) | HCDR1 | AACTACGGGATGAAC |
| SEQ ID NO: 737 (Kabat) | HCDR1 | AACTACGGCATGAAC |
| SEQ ID NO: 759 (Kabat) | HCDR2 | TGGATTAACACCGACACCGGCGAGCCTACCTACGCCGACGACTTTAAGGGC |
| SEQ ID NO: 739 (Kabat) | HCDR2 | TGGATCAACACCGACACCGGCGAGCCTACCTACGCCGACGACTTCAAGGGC |
| SEQ ID NO: 760 (Kabat) | HCDR3 | AACCCCCCCTACTACTACGGCACTAACAACGCCGAGGCTATGGACTAC |
| SEQ ID NO: 741 (Kabat) | HCDR3 | AACCCCCCTTACTACTACGGCACCAACAACGCCGAGGCCATGGACTAT |
| SEQ ID NO: 761 (Chothia) | HCDR1 | GGCTTCACCCTGACTAACTAC |
| SEQ ID NO: 743 (Chothia) | HCDR1 | GGCTTCACCCTGACCAACTAC |
| SEQ ID NO: 744 (Chothia) | HCDR2 | AACACCGACACCGGGGAG |
| SEQ ID NO: 745 (Chothia) | HCDR2 | AACACCGACACCGGCGAG |

TABLE 9-continued

| Amino acid and nucleotide sequences of exemplary anti-LAG-3 antibody molecules | | |
|---|---|---|
| SEQ ID NO: 760 (Chothia) | HCDR3 | AACCCCCCCTACTACTACGGCACTAACAACGCCGAGGCTATGG ACTAC |
| SEQ ID NO: 741 (Chothia) | HCDR3 | AACCCCCCTTACTACTACGGCACCAACAACGCCGAGGCCATGG ACTAT |
| BAP050-Clone J LC | | |
| SEQ ID NO: 746 (Kabat) | LCDR1 | AGCTCTAGTCAGGATATCTCTAACTACCTGAAC |
| SEQ ID NO: 747 (Kabat) | LCDR1 | TCCTCCAGCCAGGACATCTCCAACTACCTGAAC |
| SEQ ID NO: 748 (Kabat) | LCDR2 | TACACTAGCACCCTGCACCTG |
| SEQ ID NO: 749 (Kabat) | LCDR2 | TACACCTCCACCCTGCACCTG |
| SEQ ID NO: 750 (Kabat) | LCDR3 | CAGCAGTACTATAACCTGCCCTGGACC |
| SEQ ID NO: 751 (Kabat) | LCDR3 | CAGCAGTACTACAACCTGCCCTGGACC |
| SEQ ID NO: 752 (Chothia) | LCDR1 | AGTCAGGATATCTCTAACTAC |
| SEQ ID NO: 753 (Chothia) | LCDR1 | AGCCAGGACATCTCCAACTAC |
| SEQ ID NO: 754 (Chothia) | LCDR2 | TACACTAGC |
| SEQ ID NO: 755 (Chothia) | LCDR2 | TACACCTCC |
| SEQ ID NO: 756 (Chothia) | LCDR3 | TACTATAACCTGCCCTGG |
| SEQ ID NO: 757 (Chothia) | LCDR3 | TACTACAACCTGCCCTGG |

Other Exemplary LAG-3 Inhibitors

In one embodiment, the anti-LAG-3 antibody molecule is BMS-986016 (Bristol-Myers Squibb), also known as BMS986016. BMS-986016 and other anti-LAG-3 antibodies are disclosed in WO 2015/116539 and U.S. Pat. No. 9,505,839, incorporated by reference in their entirety. In one embodiment, the anti-LAG-3 antibody molecule comprises one or more of the CDR sequences (or collectively all of the CDR sequences), the heavy chain or light chain variable region sequence, or the heavy chain or light chain sequence of BMS-986016, e.g., as disclosed in Table 10.

In one embodiment, the anti-LAG-3 antibody molecule is TSR-033 (Tesaro). In one embodiment, the anti-LAG-3 antibody molecule comprises one or more of the CDR sequences (or collectively all of the CDR sequences), the heavy chain or light chain variable region sequence, or the heavy chain or light chain sequence of TSR-033.

In one embodiment, the anti-LAG-3 antibody molecule is MK-4280 (Merck & Co). In one embodiment, the anti-LAG-3 antibody molecule comprises one or more of the CDR sequences (or collectively all of the CDR sequences), the heavy chain or light chain variable region sequence, or the heavy chain or light chain sequence of MK-4280.

In one embodiment, the anti-LAG-3 antibody molecule is REGN3767 (Regeneron). In one embodiment, the anti-LAG-3 antibody molecule comprises one or more of the CDR sequences (or collectively all of the CDR sequences), the heavy chain or light chain variable region sequence, or the heavy chain or light chain sequence of REGN3767.

In one embodiment, the anti-LAG-3 antibody molecule is IMP731 or GSK2831781 (GSK and Prima BioMed). IMP731 and other anti-LAG-3 antibodies are disclosed in WO 2008/132601 and U.S. Pat. No. 9,244,059, incorporated by reference in their entirety. In one embodiment, the anti-LAG-3 antibody molecule comprises one or more of the CDR sequences (or collectively all of the CDR sequences), the heavy chain or light chain variable region sequence, or the heavy chain or light chain sequence of IMP731, e.g., as disclosed in Table 10. In one embodiment, the anti-LAG-3 antibody molecule comprises one or more of the CDR sequences (or collectively all of the CDR sequences), the heavy chain or light chain variable region sequence, or the heavy chain or light chain sequence of GSK2831781.

In one embodiment, the anti-LAG-3 antibody molecule is IMP761 (Prima BioMed). In one embodiment, the anti-LAG-3 antibody molecule comprises one or more of the CDR sequences (or collectively all of the CDR sequences), the heavy chain or light chain variable region sequence, or the heavy chain or light chain sequence of IMP761.

Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, incorporated by reference in their entirety.

In one embodiment, the anti-LAG-3 antibody is an antibody that competes for binding with, and/or binds to the same epitope on LAG-3 as, one of the anti-LAG-3 antibodies described herein.

In one embodiment, the anti-LAG-3 inhibitor is a soluble LAG-3 protein, e.g., IMP321 (Prima BioMed), e.g., as disclosed in WO 2009/044273, incorporated by reference in its entirety.

TABLE 10

| Amino acid sequences of other exemplary anti-LAG-3 antibody molecules | |
|---|---|
| BMS-986016 | |
| SEQ ID NO: 762 Heavy chain | QVQLQQWGAGLLKPSETLSLTCAVYGGSFSDYYWNWIRQPPGKGLE WIGEINHRGSTNSNPSLKSRVTLSLDTSKNQFSLKLRSVTAADTAVYYC AFGYSDYEYNWFDPWGQGTLVTVSSASTKGPSVFPLAPCSRSTSESTA ALGCLVKDYFPEPVTVSWNSGALTSGVHTFPAVLQSSGLYSLSSVVTV PSSSLGTKTYTCNVDHKPSNTKVDKRVESKYGPPCPPCPAPEFLGGPSV FLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKT ISKAKGQPREPQVYTLPPSQEEMTKNQVSLTCLVKGFYPSDIAVEWES NGQPENNYKTTPPVLDSDGSFFLYSRLTVDKSRWQEGNVFSCSVMHE ALHNHYTQKSLSLSLGK |
| SEQ ID NO: 763 Light chain | EIVLTQSPATLSLSPGERATLSCRASQSISSYLAWYQQKPGQAPRLLIYD ASNRATGIPARFSGSGSGTDFTLTISSLEPEDFAVYYCQQRSNWPLTFG QGTNLEIKRTVAAPSVFIFPPSDEQLKSGTASVVCLLNNFYPREAKVQW KVDNALQSGNSQESVTEQDSKDSTYSLSSTLTLSKADYEKHKVYACE VTHQGLSSPVTKSFNRGEC |
| IMP731 | |
| SEQ ID NO: 764 Heavy chain | QVQLKESGPGLVAPSQSLSITCTVSGFSLTAYGVNWVRQPPGKGLEWL GMIWDDGSTDYNSALKSRLSISKDNSKSQVFLKMNSLQTDDTARYYC AREGDVAFDYWGQGTTLTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTI SKAKGQPREPQVYTLPPSRDELTKNQVSLTCLVKGFYPSDIAVEWESN GQPENNYKTTPPVLDSDGSFFLYSKLTVDKSRWQQGNVFSCSVMHEA LHNHYTQKSLSLSPGK |
| SEQ ID NO: 765 Light chain | DIVMTQSPSSLAVSVGQKVTMSCKSSQSLLNGSNQKNYLAWYQQKPG QSPKLLVYFASTRDSGVPDRFIGSGSGTDFTLTISSVQAEDLADYFCLQ HFGTPPTFGGGTKLEIKRTVAAPSVFIFPPSDEQLKSGTASVVCLLNNFY PREAKVQWKVDNALQSGNSQESVTEQDSKDSTYSLSSTLTLSKADYE KHKVYACEVTHQGLSSPVTKSFNRGEC |

Exemplary TIM-3 Inhibitors

In certain embodiments, the anti-CD73 antibody molecule described herein is administered in combination with a TIM-3 inhibitor. The TIM-3 inhibitor may be an antibody, an antigen binding fragment thereof, an immunoadhesin, a fusion protein, or an oligopeptide. In some embodiments, the TIM-3 inhibitor is chosen from MGB453 (Novartis), TSR-022 (Tesaro), or LY3321367 (Eli Lilly).

Exemplary Anti-TIM-3 Antibody Molecules

In one embodiment, the TIM-3 inhibitor is an anti-TIM-3 antibody molecule. In one embodiment, the TIM-3 inhibitor is an anti-TIM-3 antibody molecule as disclosed in US 2015/0218274, published on Aug. 6, 2015, entitled "Antibody Molecules to TIM-3 and Uses Thereof," incorporated by reference in its entirety.

In one embodiment, the anti-TIM-3 antibody molecule comprises at least one, two, three, four, five or six complementarity determining regions (CDRs) (or collectively all of the CDRs) from a heavy and light chain variable region comprising an amino acid sequence shown in Table 11 (e.g., from the heavy and light chain variable region sequences of ABTIM3-hum11 or ABTIM3-hum03 disclosed in Table 11), or encoded by a nucleotide sequence shown in Table 11. In some embodiments, the CDRs are according to the Kabat definition (e.g., as set out in Table 11). In some embodiments, the CDRs are according to the Chothia definition (e.g., as set out in Table 11). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 11, or encoded by a nucleotide sequence shown in Table 11.

In one embodiment, the anti-TIM-3 antibody molecule comprises a heavy chain variable region (VH) comprising a VHCDR1 amino acid sequence of SEQ ID NO: 801, a VHCDR2 amino acid sequence of SEQ ID NO: 802, and a VHCDR3 amino acid sequence of SEQ ID NO: 803; and a light chain variable region (VL) comprising a VLCDR1 amino acid sequence of SEQ ID NO: 810, a VLCDR2 amino acid sequence of SEQ ID NO: 811, and a VLCDR3 amino acid sequence of SEQ ID NO: 812, each disclosed in Table 11. In one embodiment, the anti-TIM-3 antibody molecule comprises a heavy chain variable region (VH) comprising a VHCDR1 amino acid sequence of SEQ ID NO: 801, a VHCDR2 amino acid sequence of SEQ ID NO: 820, and a VHCDR3 amino acid sequence of SEQ ID NO: 803; and a light chain variable region (VL) comprising a VLCDR1 amino acid sequence of SEQ ID NO: 810, a VLCDR2 amino acid sequence of SEQ ID NO: 811, and a VLCDR3 amino acid sequence of SEQ ID NO: 812, each disclosed in Table 11.

In one embodiment, the anti-TIM-3 antibody molecule comprises a VH comprising the amino acid sequence of SEQ ID NO: 806, or an amino acid sequence having at least about 85%, 90%, 95%, or 99% sequence identity to SEQ ID NO: 806. In one embodiment, the anti-TIM-3 antibody molecule comprises a VL comprising the amino acid sequence of SEQ ID NO: 816, or an amino acid sequence having at least about 85%, 90%, 95%, or 99% sequence identity to SEQ ID NO: 816. In one embodiment, the anti-TIM-3 antibody molecule comprises a VH comprising the amino acid sequence of SEQ ID NO: 822, or an amino acid sequence having at least about 85%, 90%, 95%, or 99% sequence identity to SEQ ID NO:

822. In one embodiment, the anti-TIM-3 antibody molecule comprises a VL comprising the amino acid sequence of SEQ ID NO: 826, or an amino acid sequence having at least about 85%, 90%, 95%, or 99% sequence identity to SEQ ID NO: 826. In one embodiment, the anti-TIM-3 antibody molecule comprises a VH comprising the amino acid sequence of SEQ ID NO: 806 and a VL comprising the amino acid sequence of SEQ ID NO: 816. In one embodiment, the anti-TIM-3 antibody molecule comprises a VH comprising the amino acid sequence of SEQ ID NO: 822 and a VL comprising the amino acid sequence of SEQ ID NO: 826.

In one embodiment, the antibody molecule comprises a VH encoded by the nucleotide sequence of SEQ ID NO: 807, or a nucleotide sequence having at least about 85%, 90%, 95%, or 99% sequence identity to SEQ ID NO: 807. In one embodiment, the antibody molecule comprises a VL encoded by the nucleotide sequence of SEQ ID NO: 817, or a nucleotide sequence having at least about 85%, 90%, 95%, or 99% sequence identity to SEQ ID NO: 817. In one embodiment, the antibody molecule comprises a VH encoded by the nucleotide sequence of SEQ ID NO: 823, or a nucleotide sequence having at least about 85%, 90%, 95%, or 99% sequence identity to SEQ ID NO: 823. In one embodiment, the antibody molecule comprises a VL encoded by the nucleotide sequence of SEQ ID NO: 827, or a nucleotide sequence having at least about 85%, 90%, 95%, or 99% sequence identity to SEQ ID NO: 827. In one embodiment, the antibody molecule comprises a VH encoded by the nucleotide sequence of SEQ ID NO: 807 and a VL encoded by the nucleotide sequence of SEQ ID NO: 817. In one embodiment, the antibody molecule comprises a VH encoded by the nucleotide sequence of SEQ ID NO: 823 and a VL encoded by the nucleotide sequence of SEQ ID NO: 827.

In one embodiment, the anti-TIM-3 antibody molecule comprises a heavy chain comprising the amino acid sequence of SEQ ID NO: 808, or an amino acid sequence having at least about 85%, 90%, 95%, or 99% sequence identity to SEQ ID NO: 808. In one embodiment, the anti-TIM-3 antibody molecule comprises a light chain comprising the amino acid sequence of SEQ ID NO: 818, or an amino acid sequence having at least about 85%, 90%, 95%, or 99% sequence identity to SEQ ID NO: 818. In one embodiment, the anti-TIM-3 antibody molecule comprises a heavy chain comprising the amino acid sequence of SEQ ID NO: 824, or an amino acid sequence having at least about 85%, 90%, 95%, or 99% sequence identity to SEQ ID NO: 824. In one embodiment, the anti-TIM-3 antibody molecule comprises a light chain comprising the amino acid sequence of SEQ ID NO: 828, or an amino acid sequence having at least about 85%, 90%, 95%, or 99% sequence identity to SEQ ID NO: 828. In one embodiment, the anti-TIM-3 antibody molecule comprises a heavy chain comprising the amino acid sequence of SEQ ID NO: 808 and a light chain comprising the amino acid sequence of SEQ ID NO: 818. In one embodiment, the anti-TIM-3 antibody molecule comprises a heavy chain comprising the amino acid sequence of SEQ ID NO: 824 and a light chain comprising the amino acid sequence of SEQ ID NO: 828.

In one embodiment, the antibody molecule comprises a heavy chain encoded by the nucleotide sequence of SEQ ID NO: 809, or a nucleotide sequence having at least about 85%, 90%, 95%, or 99% sequence identity to SEQ ID NO: 809. In one embodiment, the antibody molecule comprises a light chain encoded by the nucleotide sequence of SEQ ID NO: 819, or a nucleotide sequence having at least about 85%, 90%, 95%, or 99% sequence identity to SEQ ID NO: 819. In one embodiment, the antibody molecule comprises a heavy chain encoded by the nucleotide sequence of SEQ ID NO: 825, or a nucleotide sequence having at least about 85%, 90%, 95%, or 99% sequence identity to SEQ ID NO: 825. In one embodiment, the antibody molecule comprises a light chain encoded by the nucleotide sequence of SEQ ID NO: 829, or a nucleotide sequence having at least about 85%, 90%, 95%, or 99% sequence identity to SEQ ID NO: 829. In one embodiment, the antibody molecule comprises a heavy chain encoded by the nucleotide sequence of SEQ ID NO: 809 and a light chain encoded by the nucleotide sequence of SEQ ID NO: 819. In one embodiment, the antibody molecule comprises a heavy chain encoded by the nucleotide sequence of SEQ ID NO: 825 and a light chain encoded by the nucleotide sequence of SEQ ID NO: 829.

The antibody molecules described herein can be made by vectors, host cells, and methods described in US 2015/0218274, incorporated by reference in its entirety.

TABLE 11

Amino acid and nucleotide sequences of exemplary anti-TIM-3 antibody molecules

| | | |
|---|---|---|
| ABTIM3-hum11 | | |
| SEQ ID NO: 801 (Kabat) | HCDR1 | SYNMH |
| SEQ ID NO: 802 (Kabat) | HCDR2 | DIYPGNGDTSYNQKFKG |
| SEQ ID NO: 803 (Kabat) | HCDR3 | VGGAFPMDY |
| SEQ ID NO: 804 (Chothia) | HCDR1 | GYTFTSY |
| SEQ ID NO: 805 (Chothia) | HCDR2 | YPGNGD |
| SEQ ID NO: 803 (Chothia) | HCDR3 | VGGAFPMDY |
| SEQ ID NO: 806 | VH | QVQLVQSGAEVKKPGSSVKVSCKASGYTFTSYNMHWVRQAPG<br>QGLEWMGDIYPGNGDTSYNQKFKGRVTITADKSTSTVYMELSS<br>LRSEDTAVYYCARVGGAFPMDYWGQGTTVTVSS |
| SEQ ID NO: 807 | DNA VH | CAGGTGCAGCTGGTGCAGTCAGGCGCCGAAGTGAAGAAACC<br>CGGCTCTAGCGTGAAAGTTTCTTGTAAAGCTAGTGGCTACAC<br>CTTCACTAGCTATAATATGCACTGGGTTCGCCAGGCCCCAGG<br>GCAAGGCCTCGAGTGGATGGGCGATATCTACCCCGGGAACGG<br>CGACACTAGTTATAATCAGAAGTTTAAGGGTAGAGTCACTAT<br>CACCGCCGATAAGTCTACTAGCACCGTCTATATGGAACTGAG |

TABLE 11-continued

| Amino acid and nucleotide sequences of exemplary anti-TIM-3 antibody molecules | | |
|---|---|---|
| | | TTCCCTGAGGTCTGAGGACACCGCCGTCTACTACTGCGCTAG AGTGGGCGGAGCCTTCCCTATGGACTACTGGGGTCAAGGCAC TACCGTGACCGTGTCTAGC |
| SEQ ID NO: 808 | Heavy chain | QVQLVQSGAEVKKPGSSVKVSCKASGYTFTSYNMHWVRQAPG QGLEWMGDIYPGNGDTSYNQKFKGRVTITADKSTSTVYMELSS LRSEDTAVYYCARVGGAFPMDYWGQGTTVTVSSASTKGPSVFP LAPCSRSTSESTAALGCLVKDYFPEPVTVSWNSGALTSGVHTFP AVLQSSGLYSLSSVVTVPSSSLGTKTYTCNVDHKPSNTKVDKRV ESKYGPPCPPCPAPEFLGGPSVFLFPPKPKDTLMISRTPEVTCVVV DVSQEDPEVQFNWYVDGVEVHNAKTKPREEQFNSTYRVVSVLT VLHQDWLNGKEYKCKVSNKGLPSSIEKTISKAKGQPREPQVYTL PPSQEEMTKNQVSLTCLVKGFYPSDIAVEWESNGQPENNYKTTP PVLDSDGSFFLYSRLTVDKSRWQEGNVFSCSVMHEALHNHYTQ KSLSLSLG |
| SEQ ID NO: 809 | DNA heavy chain | CAGGTGCAGCTGGTGCAGTCAGGCGCCGAAGTGAAGAAACC CGGCTCTAGCGTGAAAGTTTCTTGTAAAGCTAGTGGCTACAC CTTCACTAGCTATAATATGCACTGGGTTCGCCAGGCCCCAGG GCAAGGCCTCGAGTGGATGGGCGATATCTACCCCGGGAACGG CGACACTAGTTATAATCAGAAGTTTAAGGGTAGAGTCACTAT CACCGCCGATAAGTCTACTAGCACCGTCTATATGGAACTGAG TTCCCTGAGGTCTGAGGACACCGCCGTCTACTACTGCGCTAG AGTGGGCGGAGCCTTCCCTATGGACTACTGGGGTCAAGGCAC TACCGTGACCGTGTCTAGCGCTAGCACTAAGGGCCCGTCCGT GTTCCCCCTGGCACCTTGTAGCCGGAGCACTAGCGAATCCAC CGCTGCCCTCGGCTGCCTGGTCAAGGATTACTTCCCGGAGCC CGTGACCGTGTCCTGGAACAGCGGAGCCCTGACCTCCGGAGT GCACACCTTCCCCGCTGTGCTGCAGAGCTCCGGGCTGTACTC GCTGTCGTCGGTGGTCACGGTGCCTTCATCTAGCCTGGGTACC AAGACCTACACTTGCAACGTGGACCACAAGCCTTCCAACACT AAGGTGGACAAGCGCGTCGAATCGAAGTACGGCCCACCGTG CCCGCCTTGTCCCGCGCCGGAGTTCCTCGGCGGTCCCTCGGTC TTTCTGTTCCCACCGAAGCCCAAGGACACTTTGATGATTTCCC GCACCCCTGAAGTGACATGCGTGGTCGTGGACGTGTCACAGG AAGATCCGGAGGTGCAGTTCAATTGGTACGTGGATGGCGTCG AGGTGCACAACGCCAAAACCAAGCCGAGGGAGGAGCAGTTC AACTCCACTTACCGCGTCGTGTCCGTGCTGACGGTGCTGCATC AGGACTGGCTGAACGGGAAGGAGTACAAGTGCAAAGTGTCC AACAAGGGACTTCCTAGCTCAATCGAAAAGACCATCTCGAAA GCCAAGGGACAGCCCCGGGAACCCCAAGTGTATACCCTGCCA CCGAGCCAGGAAGAAATGACTAAGAACCAAGTCTCATTGACT TGCCTTGTGAAGGGCTTCTACCCATCGGATATCGCCGTGGAA TGGGAGTCCAACGGCCAGCCGGAAAACAACTACAAGACCAC CCCTCCGGTGCTGGACTCAGACGGATCCTTCTTCCTCTACTCG CGGCTGACCGTGGATAAGAGCAGATGGCAGGAGGGAAATGT GTTCAGCTGTTCTGTGATGCATGAAGCCCTGCACAACCACTA CACTCAGAAGTCCCTGTCCCTCTCCCTGGGA |
| SEQ ID NO: 810 (Kabat) | LCDR1 | RASESVEYYGTSLMQ |
| SEQ ID NO: 811 (Kabat) | LCDR2 | AASNVES |
| SEQ ID NO: 812 (Kabat) | LCDR3 | QQSRKDPST |
| SEQ ID NO: 813 (Chothia) | LCDR1 | SESVEYYGTSL |
| SEQ ID NO: 814 (Chothia) | LCDR2 | AAS |
| SEQ ID NO: 815 (Chothia) | LCDR3 | SRKDPS |
| SEQ ID NO: 816 | VL | AIQLTQSPSSLSASVGDRVTITCRASESVEYYGTSLMQWYQQKP GKAPKLLIYAASNVESGVPSRFSGSGSGTDFTLTISSLQPEDFATY FCQQSRKDPSTFGGGTKVEIK |
| SEQ ID NO: 817 | DNA VL | GCTATTCAGCTGACTCAGTCACCTAGTAGCCTGAGCGCTAGT GTGGGCGATAGAGTGACTATCACCTGTAGAGCTAGTGAATCA GTCGAGTACTACGGCACTAGCCTGATGCAGTGGTATCAGCAG AAGCCCGGGAAAGCCCCTAAGCTGCTGATCTACGCCGCCTCT AACGTGGAATCAGGCGTGCCCTCTAGGTTTAGCGGTAGCGGT AGTGGCACCGACTTCACCCTGACTATCTCTAGCCTGCAGCCC GAGGACTTCGCTACCTACTTCTGTCAGCAGTCTAGGAAGGAC CCTAGCACCTTCGGCGGAGGCACTAAGGTCGAGATTAAG |

TABLE 11-continued

| Amino acid and nucleotide sequences of exemplary anti-TIM-3 antibody molecules | | |
|---|---|---|
| SEQ ID NO: 818 | Light chain | AIQLTQSPSSLSASVGDRVTITCRASESVEYYGTSLMQWYQQKP GKAPKLLIYAASNVESGVPSRFSGSGSGTDFTLTISSLQPEDFATY FCQQSRKDPSTFGGGTKVEIKRTVAAPSVFIFPPSDEQLKSGTAS VVCLLNNFYPREAKVQWKVDNALQSGNSQESVTEQDSKDSTYS LSSTLTLSKADYEKHKVYACEVTHQGLSSPVTKSFNRGEC |
| SEQ ID NO: 819 | DNA light chain | GCTATTCAGCTGACTCAGTCACCTAGTAGCCTGAGCGCTAGT GTGGGCGATAGAGTGACTATCACCTGTAGAGCTAGTGAATCA GTCGAGTACTACGGCACTAGCCTGATGCAGTGGTATCAGCAG AAGCCCGGGAAAGCCCCTAAGCTGCTGATCTACGCCGCCTCT AACGTGGAATCAGGCGTGCCCTCTAGGTTTAGCGGTAGCGGT AGTGGCACCGACTTCACCCTGACTATCTCTAGCCTGCAGCCC GAGGACTTCGCTACCTACTTCTGTCAGCAGTCTAGGAAGGAC CCTAGCACCTTCGGCGGAGGCACTAAGGTCGAGATTAAGCGT ACGGTGGCCGCTCCCAGCGTGTTCATCTTCCCCCCCAGCGAC GAGCAGCTGAAGAGCGGCACCGCCAGCGTGGTGTGCCTGCTG AACAACTTCTACCCCCGGGAGGCCAAGGTGCAGTGGAAGGTG GACAACGCCCTGCAGAGCGGCAACAGCCAGGAGAGCGTCAC CGAGCAGGACAGCAAGGACTCCACCTACAGCCTGAGCAGCA CCCTGACCCTGAGCAAGGCCGACTACGAGAAGCATAAGGTGT ACGCCTGCGAGGTGACCCACCAGGGCCTGTCCAGCCCCGTGA CCAAGAGCTTCAACAGGGGCGAGTGC |
| ABTIM3-hum03 | | |
| SEQ ID NO: 801 (Kabat) | HCDR1 | SYNMH |
| SEQ ID NO: 820 (Kabat) | HCDR2 | DIYPGQGDTSYNQKFKG |
| SEQ ID NO: 803 (Kabat) | HCDR3 | VGGAFPMDY |
| SEQ ID NO: 804 (Chothia) | HCDR1 | GYTFTSY |
| SEQ ID NO: 821 (Chothia) | HCDR2 | YPGQGD |
| SEQ ID NO: 803 (Chothia) | HCDR3 | VGGAFPMDY |
| SEQ ID NO: 822 | VH | QVQLVQSGAEVKKPGASVKVSCKASGYTFTSYNMHWVRQAPG QGLEWIGDIYPGQGDTSYNQKFKGRATMTADKSTSTVYMELSS LRSEDTAVYYCARVGGAFPMDYWGQGTLVTVSS |
| SEQ ID NO: 823 | DNA VH | CAGGTGCAGCTGGTGCAGTCAGGCGCCGAAGTGAAGAAACC CGGCGCTAGTGTGAAAGTTAGCTGTAAAGCTAGTGGCTATAC TTTCACTTCTTATAATATGCACTGGGTCCGCCAGGCCCCAGGT CAAGGCCTCGAGTGGATCGGCGATATCTACCCCGGTCAAGGC GACACTTCCTATAATCAGAAGTTTAAGGGTAGAGCTACTATG ACCGCCGATAAGTCTACTTCTACCGTCTATATGGAACTGAGTT CCCTGAGGTCTGAGGACACCGCCGTCTACTACTGCGCTAGAG TGGGCGGAGCCTTCCCAATGGACTACTGGGGTCAAGGCACCC TGGTCACCGTGTCTAGC |
| SEQ ID NO: 824 | Heavy chain | QVQLVQSGAEVKKPGASVKVSCKASGYTFTSYNMHWVRQAPG QGLEWIGDIYPGQGDTSYNQKFKGRATMTADKSTSTVYMELSS LRSEDTAVYYCARVGGAFPMDYWGQGTLVTVSSASTKGPSVFP LAPCSRSTSESTAALGCLVKDYFPEPVTVSWNSGALTSGVHTFP AVLQSSGLYSLSSVVTVPSSSLGTKTYTCNVDHKPSNTKVDKRV ESKYGPPCPPCPAPEFLGGPSVFLFPPKPKDTLMISRTPEVTCVVV DVSQEDPEVQFNWYVDGVEVHNAKTKPREEQFNSTYRVVSVLT VLHQDWLNGKEYKCKVSNKGLPSSTEKTTSKAKGQPREPQVYTL PPSQEEMTKNQVSLTCLVKGFYPSDIAVEWESNGQPENNYKTTP PVLDSDGSFFLYSRLTVDKSRWQEGNVFSCSVMHEALHNHYTQ KSLSLSLG |
| SEQ ID NO: 825 | DNA heavy chain | CAGGTGCAGCTGGTGCAGTCAGGCGCCGAAGTGAAGAAACC CGGCGCTAGTGTGAAAGTTAGCTGTAAAGCTAGTGGCTATAC TTTCACTTCTTATAATATGCACTGGGTCCGCCAGGCCCCAGGT CAAGGCCTCGAGTGGATCGGCGATATCTACCCCGGTCAAGGC GACACTTCCTATAATCAGAAGTTTAAGGGTAGAGCTACTATG ACCGCCGATAAGTCTACTTCTACCGTCTATATGGAACTGAGTT CCCTGAGGTCTGAGGACACCGCCGTCTACTACTGCGCTAGAG TGGGCGGAGCCTTCCCAATGGACTACTGGGGTCAAGGCACCC TGGTCACCGTGTCTAGCGCTAGCACTAAGGGCCCGTCCGTGT TCCCCCTGGCACCTTGTAGCCGGAGCACTAGCGAATCCACCG CTGCCCTCGGCTGCCTGGTCAAGGATTACTTCCCGGAGCCCGT GACCGTGTCCTGGAACAGCGGAGCCCTGACCTCCGGAGTGCA CACCTTCCCCGCTGTGCTGCAGAGCTCCGGGCTGTACTCGCTG TCGTCGGTGGTCACGGTGCCTTCATCTAGCCTGGGTACCAAG ACCTACACTTGCAACGTGGACCACAAGCCTTCCAACACTAAG |

TABLE 11-continued

| Amino acid and nucleotide sequences of exemplary anti-TIM-3 antibody molecules | | | |
|---|---|---|---|
| | | | GTGGACAAGCGCGTCGAATCGAAGTACGGCCCACCGTGCCCG<br>CCTTGTCCCGCGCCGGAGTTCCTCGGCGGTCCCTCGGTCTTTC<br>TGTTCCCACCGAAGCCCAAGGACACTTTGATGATTTCCCGCA<br>CCCCTGAAGTGACATGCGTGGTCGTGGACGTGTCACAGGAAG<br>ATCCGGAGGTGCAGTTCAATTGGTACGTGGATGGCGTCGAGG<br>TGCACAACGCCAAAACCAAGCCGAGGGAGGAGCAGTTCAAC<br>TCCACTTACCGCGTCGTGTCCGTGCTGACGGTGCTGCATCAGG<br>ACTGGCTGAACGGGAAGGAGTACAAGTGCAAAGTGTCCAAC<br>AAGGGACTTCCTAGCTCAATCGAAAAGACCATCTCGAAAGCC<br>AAGGGACAGCCCCGGGAACCCCAAGTGTATACCCTGCCACCG<br>AGCCAGGAAGAAATGACTAAGAACCAAGTCTCATTGACTTGC<br>CTTGTGAAGGGCTTCTACCCATCGGATATCGCCGTGGAATGG<br>GAGTCCAACGGCCAGCCGGAAAACAACTACAAGACCACCCC<br>TCCGGTGCTGGACTCAGACGGATCCTTCTTCCTCTACTCGCGG<br>CTGACCGTGGATAAGAGCAGATGGCAGGAGGGAAATGTGTT<br>CAGCTGTTCTGTGATGCATGAAGCCCTGCACAACCACTACAC<br>TCAGAAGTCCCTGTCCCTCTCCCTGGGA |
| SEQ ID NO: 810 | (Kabat) | LCDR1 | RASESVEYYGTSLMQ |
| SEQ ID NO: 811 | (Kabat) | LCDR2 | AASNVES |
| SEQ ID NO: 812 | (Kabat) | LCDR3 | QQSRKDPST |
| SEQ ID NO: 813 | (Chothia) | LCDR1 | SESVEYYGTSL |
| SEQ ID NO: 814 | (Chothia) | LCDR2 | AAS |
| SEQ ID NO: 815 | (Chothia) | LCDR3 | SRKDPS |
| SEQ ID NO: 826 | | VL | DIVLTQSPDSLAVSLGERATINCRASESVEYYGTSLMQWYQQKP<br>GQPPKLLIYAASNVESGVPDRFSGSGSGTDFTLTISSLQAEDVAV<br>YYCQQSRKDPSTFGGGTKVEIK |
| SEQ ID NO: 827 | | DNA VL | GATATCGTCCTGACTCAGTCACCCGATAGCCTGGCCGTCAGC<br>CTGGGCGAGCGGGCTACTATTAACTGTAGAGCTAGTGAATCA<br>GTCGAGTACTACGGCACTAGCCTGATGCAGTGGTATCAGCAG<br>AAGCCCGGTCAACCCCCTAAGCTGCTGATCTACGCCGCCTCT<br>AACGTGGAATCAGGCGTGCCCGATAGGTTTAGCGGTAGCGGT<br>AGTGGCACCGACTTCACCCTGACTATTAGTAGCCTGCAGGCC<br>GAGGACGTGGCCGTCTACTACTGTCAGCAGTCTAGGAAGGAC<br>CCTAGCACCTTCGGCGGAGGCACTAAGGTCGAGATTAAG |
| SEQ ID NO: 828 | | Light chain | DIVLTQSPDSLAVSLGERATINCRASESVEYYGTSLMQWYQQKP<br>GQPPKLLIYAASNVESGVPDRFSGSGSGTDFTLTISSLQAEDVAV<br>YYCQQSRKDPSTFGGGTKVEIKRTVAAPSVFIFPPSDEQLKSGTA<br>SVVCLLNNFYPREAKVQWKVDNALQSGNSQESVTEQDSKDSTY<br>SLSSTLTLSKADYEKHKVYACEVTHQGLSSPVTKSFNRGEC |
| SEQ ID NO: 829 | | DNA light chain | GATATCGTCCTGACTCAGTCACCCGATAGCCTGGCCGTCAGC<br>CTGGGCGAGCGGGCTACTATTAACTGTAGAGCTAGTGAATCA<br>GTCGAGTACTACGGCACTAGCCTGATGCAGTGGTATCAGCAG<br>AAGCCCGGTCAACCCCCTAAGCTGCTGATCTACGCCGCCTCT<br>AACGTGGAATCAGGCGTGCCCGATAGGTTTAGCGGTAGCGGT<br>AGTGGCACCGACTTCACCCTGACTATTAGTAGCCTGCAGGCC<br>GAGGACGTGGCCGTCTACTACTGTCAGCAGTCTAGGAAGGAC<br>CCTAGCACCTTCGGCGGAGGCACTAAGGTCGAGATTAAGCGT<br>ACGGTGGCCGCTCCCAGCGTGTTCATCTTCCCCCCCAGCGAC<br>GAGCAGCTGAAGAGCGGCACCGCCAGCGTGGTGTGCCTGCTG<br>AACAACTTCTACCCCCGGGAGGCCAAGGTGCAGTGGAAGGTG<br>GACAACGCCCTGCAGAGCGGCAACAGCCAGGAGAGCGTCAC<br>CGAGCAGGACAGCAAGGACTCCACCTACAGCCTGAGCAGCA<br>CCCTGACCCTGAGCAAGGCCGACTACGAGAAGCATAAGGTGT<br>ACGCCTGCGAGGTGACCCACCAGGGCCTGTCCAGCCCCGTGA<br>CCAAGAGCTTCAACAGGGGCGAGTGC |

Other Exemplary TIM-3 Inhibitors

In one embodiment, the anti-TIM-3 antibody molecule is TSR-022 (AnaptysBio/Tesaro). In one embodiment, the anti-TIM-3 antibody molecule comprises one or more of the CDR sequences (or collectively all of the CDR sequences), the heavy chain or light chain variable region sequence, or the heavy chain or light chain sequence of TSR-022. In one embodiment, the anti-TIM-3 antibody molecule comprises one or more of the CDR sequences (or collectively all of the CDR sequences), the heavy chain or light chain variable region sequence, or the heavy chain or light chain sequence of APE5137 or APE5121, e.g., as disclosed in Table 12. APE5137, APE5121, and other anti-TIM-3 antibodies are disclosed in WO 2016/161270, incorporated by reference in its entirety.

In one embodiment, the anti-TIM-3 antibody molecule is LY3321367 (Eli Lilly). In one embodiment, the anti-TIM-3 antibody molecule comprises one or more of the CDR sequences (or collectively all of the CDR sequences), the heavy chain or light chain variable region sequence, or the heavy chain or light chain sequence of LY3321367.

In one embodiment, the anti-TIM-3 antibody molecule is the antibody clone F38-2E2. In one embodiment, the anti-TIM-3 antibody molecule comprises one or more of the CDR sequences (or collectively all of the CDR sequences), the heavy chain or light chain variable region sequence, or the heavy chain or light chain sequence of F38-2E2.

Further known anti-TIM-3 antibodies include those described, e.g., in WO 2016/111947, WO 2016/071448, WO 2016/144803, U.S. Pat. Nos. 8,552,156, 8,841,418, and 9,163,087, incorporated by reference in their entirety.

In one embodiment, the anti-TIM-3 antibody is an antibody that competes for binding with, and/or binds to the same epitope on TIM-3 as, one of the anti-TIM-3 antibodies described herein.

TABLE 12

Amino acid sequences of other exemplary anti-TIM-3 antibody molecules

| | | |
|---|---|---|
| APE5137 | | |
| SEQ ID NO: 830 | VH | EVQLLESGGGLVQPGGSLRLSCAAASGFTFSSYDMSWVRQAPGKGLDWVS TISGGGTYTYYQDSVKGRFTISRDNSKNTLYLQMNSLRAEDTAVYYCASMD YWGQGTTVTVSSA |
| SEQ ID NO: 831 | VL | DIQMTQSPSSLSASVGDRVTITCRASQSIRRYLNWYHQKPGKAPKLLIYGAS TLQSGVPSRFSGSGSGTDFTLTISSLQPEDFAVYYCQQSHSAPLTFGGGTKVE IKR |
| APE5121 | | |
| SEQ ID NO: 832 | VH | EVQVLESGGGLVQPGGSLRLYCVASGFTFSGSYAMSWVRQAPGKGLEWVS AISGSGGSTYYADSVKGRFTISRDNSKNTLYLQMNSLRAEDTAVYYCAKKY YVGPADYWGQGTLVTVSSG |
| SEQ ID NO: 833 | VL | DIVMTQSPDSLAVSLGERATINCKSSQSVLYSSNNKNYLAWYQHKPGQPPK LLIYWASTRESGVPDRFSGSGSGTDFTLTISSLQAEDVAVYYCQQYYSSPLTF GGGTKIEVK |

Exemplary CTLA-4 Inhibitors

In certain embodiments, the anti-CD73 antibody molecule described herein is administered in combination with a CTLA-4 inhibitor. The CTLA-4 inhibitor may be an antibody, an antigen binding fragment thereof, an immunoadhesin, a fusion protein, or an oligopeptide. In some embodiments, the CTLA-4 inhibitor is Ipilimumab (Yervoy®, Bristol-Myers Squibb) or Tremelimumab (Pfizer). The antibody Ipilimumab and other anti-CTLA-4 antibodies are disclosed in U.S. Pat. No. 6,984,720, herein incorporated by reference. The antibody Tremelimumab and other anti-CTLA-4 antibodies are disclosed in U.S. Pat. No. 7,411,057, herein incorporated by reference.

Exemplary GITR Agonists

In certain embodiments, the anti-CD73 antibody molecule described herein is administered in combination with a GITR agonist. The GITR agonist may be an antibody, an antigen binding fragment thereof, an immunoadhesin, a fusion protein, or an oligopeptide. In some embodiments, the GITR agonist is GWN323 (Novartis), BMS-986156 (BMS), MK-4166 or MK-1248 (Merck), TRX518 (Leap Therapeutics), INCAGN1876 (Incyte/Agenus), AMG 228 (Amgen), or INBRX-110 (Inhibrx).

Exemplary Anti-GITR Antibody Molecules

In one embodiment, the GITR agonist is an anti-GITR antibody molecule. In one embodiment, the GITR agonist is an anti-GITR antibody molecule as described in WO 2016/057846, published on Apr. 14, 2016, entitled "Compositions and Methods of Use for Augmented Immune Response and Cancer Therapy," incorporated by reference in its entirety.

In one embodiment, the anti-GITR antibody molecule comprises at least one, two, three, four, five or six complementarity determining regions (CDRs) (or collectively all of the CDRs) from a heavy and light chain variable region comprising an amino acid sequence shown in Table 13 (e.g., from the heavy and light chain variable region sequences of MAB7 disclosed in Table 13), or encoded by a nucleotide sequence shown in Table 13. In some embodiments, the CDRs are according to the Kabat definition (e.g., as set out in Table 13). In some embodiments, the CDRs are according to the Chothia definition (e.g., as set out in Table 13). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table 13, or encoded by a nucleotide sequence shown in Table 13.

In one embodiment, the anti-GITR antibody molecule comprises a heavy chain variable region (VH) comprising a VHCDR1 amino acid sequence of SEQ ID NO: 909, a VHCDR2 amino acid sequence of SEQ ID NO: 911, and a VHCDR3 amino acid sequence of SEQ ID NO: 913; and a light chain variable region (VL) comprising a VLCDR1 amino acid sequence of SEQ ID NO: 914, a VLCDR2 amino acid sequence of SEQ ID NO: 916, and a VLCDR3 amino acid sequence of SEQ ID NO: 918, each disclosed in Table 13.

In one embodiment, the anti-GITR antibody molecule comprises a VH comprising the amino acid sequence of SEQ ID NO: 901, or an amino acid sequence at least 85%, 90%, 95%, or 99% identical or higher to SEQ ID NO: 901. In one embodiment, the anti-GITR antibody molecule comprises a VL comprising the amino acid sequence of SEQ ID NO: 902, or an amino acid sequence at least 85%, 90%, 95%, or 99% identical or higher to SEQ ID NO: 902. In one embodiment, the anti-GITR antibody molecule comprises a VH comprising the amino acid sequence of SEQ ID NO: 901 and a VL comprising the amino acid sequence of SEQ ID NO: 902.

In one embodiment, the antibody molecule comprises a VH encoded by the nucleotide sequence of SEQ ID NO: 905, or a nucleotide sequence at least 85%, 90%, 95%, or 99% identical or higher to SEQ ID NO: 905. In one embodiment, the antibody molecule comprises a VL encoded by the nucleotide sequence of SEQ ID NO: 906, or a nucleotide sequence at least 85%, 90%, 95%, or 99% identical or higher to SEQ ID NO: 906. In one embodiment, the antibody molecule comprises a VH encoded by the nucleotide sequence of SEQ ID NO: 905 and a VL encoded by the nucleotide sequence of SEQ ID NO: 906.

In one embodiment, the anti-GITR antibody molecule comprises a heavy chain comprising the amino acid sequence of SEQ ID NO: 903, or an amino acid sequence at least 85%, 90%, 95%, or 99% identical or higher to SEQ ID NO: 903. In one embodiment, the anti-GITR antibody molecule comprises a light chain comprising the amino acid sequence of SEQ ID NO: 904, or an amino acid sequence at least 85%, 90%, 95%, or 99% identical or higher to SEQ ID NO: 904. In one embodiment, the anti-GITR antibody molecule comprises a heavy chain comprising the amino acid sequence of SEQ ID NO: 903 and a light chain comprising the amino acid sequence of SEQ ID NO: 904.

In one embodiment, the antibody molecule comprises a heavy chain encoded by the nucleotide sequence of SEQ ID NO: 907, or a nucleotide sequence at least 85%, 90%, 95%, or 99% identical or higher to SEQ ID NO: 907. In one embodiment, the antibody molecule comprises a light chain encoded by the nucleotide sequence of SEQ ID NO: 908, or a nucleotide sequence at least 85%, 90%, 95%, or 99% identical or higher to SEQ ID NO: 908. In one embodiment, the antibody molecule comprises a heavy chain encoded by the nucleotide sequence of SEQ ID NO: 907 and a light chain encoded by the nucleotide sequence of SEQ ID NO: 908.

The antibody molecules described herein can be made by vectors, host cells, and methods described in WO 2016/057846, incorporated by reference in its entirety.

TABLE 13

Amino acid and nucleotide sequences of exemplary anti-GITR antibody molecule

| MAB7 | | |
|---|---|---|
| SEQ ID NO: 901 | VH | EVQLVESGGGLVQSGGSLRLSCAASGFSLSSYGVDWVRQAP<br>GKGLEWVGVIWGGGGTYYASSLMGRFTISRDNSKNTLYLQ<br>MNSLRAEDTAVYYCARHAYGHDGGFAMDYWGQGTLVTVSS |
| SEQ ID NO: 902 | VL | EIVMTQSPATLSVSPGERATLSCRASESVSSNVAWYQQRPGQ<br>APRLLIYGASNRATGIPARFSGSGSGTDFTLTISRLEPEDFAVY<br>YCGQSYSYPFTFGQGTKLEIK |
| SEQ ID NO: 903 | Heavy Chain | EVQLVESGGGLVQSGGSLRLSCAASGFSLSSYGVDWVRQAP<br>GKGLEWVGVIWGGGGTYYASSLMGRFTISRDNSKNTLYLQ<br>MNSLRAEDTAVYYCARHAYGHDGGFAMDYWGQGTLVTVS<br>SASTKGPSVFPLAPSSKSTSGGTAALGCLVKDYFPEPVTVSW<br>NSGALTSGVHTFPAVLQSSGLYSLSSVVTVPSSSLGTQTYICN<br>VNHKPSNTKVDKRVEPKSCDKTHTCPPCPAPELLGGPSVFLF<br>PPKPKDTLMISRTPEVTCVVVDVSHEDPEVKFNWYVDGVEV<br>HNAKTKPREEQYNSTYRVVSVLTVLHQDWLNGKEYKCKVS<br>NKALPAPIEKTISKAKGQPREPQVYTLPPSREEMTKNQVSLTC<br>LVKGFYPSDIAVEWESNGQPENNYKTTPPVLDSDGSFFLYSK<br>LTVDKSRWQQGNVFSCSVMHEALHNHYTQKSLSLSPGK |
| SEQ ID NO: 904 | Light Chain | EIVMTQSPATLSVSPGERATLSCRASESVSSNVAWYQQRPGQ<br>APRLLIYGASNRATGIPARFSGSGSGTDFTLTISRLEPEDFAVY<br>YCGQSYSYPFTFGQGTKLEIKRTVAAPSVFIFPPSDEQLKSGT<br>ASVVCLLNNFYPREAKVQWKVDNALQSGNSQESVTEQDSK<br>DSTYSLSSTLTLSKADYEKHKVYACEVTHQGLSSPVTKSFNR<br>GEC |
| SEQ ID NO: 905 | DNA VH | GAGGTGCAGCTGGTGGAATCTGGCGGCGGACTGGTGCAG<br>TCCGGCGGCTCTCTGAGACTGTCTTGCGCTGCCTCCGGCTT<br>CTCCCTGTCCTCTTACGGCGTGGACTGGGTGCGACAGGCC<br>CCTGGCAAGGGCCTGGAATGGGTGGGAGTGATCTGGGGC<br>GGAGGCGGCACCTACTACGCCTCTTCCCTGATGGGCCGGT<br>TCACCATCTCCCGGGACAACTCCAAGAACACCCTGTACCT<br>GCAGATGAACTCCCTGCGGGCCGAGGACACCGCCGTGTAC<br>TACTGCGCCAGACACGCCTACGGCCACGACGGCGGCTTCG<br>CCATGGATTATTGGGGCCAGGGCACCCTGGTGACAGTGTC<br>CTCC |
| SEQ ID NO: 906 | DNA VL | GAGATCGTGATGACCCAGTCCCCCGCCACCCTGTCTGTGT<br>CTCCCGGCGAGAGAGCCACCCTGAGCTGCAGAGCCTCCGA<br>GTCCGTGTCCTCCAACGTGGCCTGGTATCAGCAGAGACCT<br>GGTCAGGCCCCTCGGCTGCTGATCTACGGCGCCTCTAACC<br>GGGCCACCGGCATCCCTGCCAGATTCTCCGGCTCCGGCAG<br>CGGCACCGACTTCACCCTGACCATCTCCCGGCTGGAACCC<br>GAGGACTTCGCCGTGTACTACTGCGGCCAGTCCTACTCAT<br>ACCCCTTCACCTTCGGCCAGGGCACCAAGCTGGAAATCAAG |
| SEQ ID NO: 907 | DNA Heavy Chain | GAGGTGCAGCTGGTGGAATCTGGCGGCGGACTGGTGCAG<br>TCCGGCGGCTCTCTGAGACTGTCTTGCGCTGCCTCCGGCTT<br>CTCCCTGTCCTCTTACGGCGTGGACTGGGTGCGACAGGCC<br>CCTGGCAAGGGCCTGGAATGGGTGGGAGTGATCTGGGGC<br>GGAGGCGGCACCTACTACGCCTCTTCCCTGATGGGCCGGT |

TABLE 13-continued

Amino acid and nucleotide sequences of exemplary anti-GITR antibody molecule

MAB7

| | | |
|---|---|---|
| | | TCACCATCTCCCGGGACAACTCCAAGAACACCCTGTACCT GCAGATGAACTCCCTGCGGGCCGAGGACACCGCCGTGTAC TACTGCGCCAGACACGCCTACGGCCACGACGGCGGCTTCG CCATGGATTATTGGGGCCAGGGCACCCTGGTGACAGTGTC CTCCGCTAGCACCAAGGGCCCAAGTGTGTTTCCCCTGGCC CCCAGCAGCAAGTCTACTTCCGGCGGAACTGCTGCCCTGG GTTGCCTGGTGAAGGACTACTTCCCCGAGCCCGTGACAGT GTCCTGGAACTCTGGGGCTCTGACTTCCGGCGTGCACACC TTCCCCGCCGTGCTGCAGAGCAGCGGCCTGTACAGCCTGA GCAGCGTGGTGACAGTGCCCTCCAGCTCTCTGGGAACCCA GACCTATATCTGCAACGTGAACCACAAGCCCAGCAACACC AAGGTGGACAAGAGAGTGGAGCCCAAGAGCTGCGACAAG ACCCACACCTGCCCCCCCTGCCCAGCTCCAGAACTGCTGG GAGGGCCTTCCGTGTTCCTGTTCCCCCCCAAGCCCAAGGA CACCCTGATGATCAGCAGGACCCCCGAGGTGACCTGCGTG GTGGTGGACGTGTCCCACGAGGACCCAGAGGTGAAGTTC AACTGGTACGTGGACGGCGTGGAGGTGCACAACGCCAAG ACCAAGCCCAGAGAGGAGCAGTACAACAGCACCTACAGG GTGGTGTCCGTGCTGACCGTGCTGCACCAGGACTGGCTGA ACGGCAAAGAATACAAGTGCAAAGTCTCCAACAAGGCCC TGCCAGCCCCAATCGAAAAGACAATCAGCAAGGCCAAGG GCCAGCCACGGGAGCCCCAGGTGTACACCCTGCCCCCCAG CCGGGAGGAGATGACCAAGAACCAGGTGTCCCTGACCTG TCTGGTGAAGGGCTTCTACCCCAGCGATATCGCCGTGGAG TGGGAGAGCAACGGCCAGCCCGAGAACAACTACAAGACC ACCCCCCCAGTGCTGGACAGCGACGGCAGCTTCTTCCTGT ACAGCAAGCTGACCGTGGACAAGTCCAGGTGGCAGCAGG GCAACGTGTTCAGCTGCAGCGTGATGCACGAGGCCCTGCA CAACCACTACACCCAGAAGTCCCTGAGCCTGAGCCCCGGC AAG |
| SEQ ID NO: 908 | DNA Light Chain | GAGATCGTGATGACCCAGTCCCCCGCCACCCTGTCTGTGT CTCCCGGCGAGAGAGCCACCCTGAGCTGCAGAGCCTCCGA GTCCGTGTCCTCCAACGTGGCCTGGTATCAGCAGAGACCT GGTCAGGCCCCTCGGCTGCTGATCTACGGCGCCTCTAACC GGGCCACCGGCATCCCTGCCAGATTCTCCGGCTCCGGCAG CGGCACCGACTTCACCCTGACCATCTCCCGGCTGGAACCC GAGGACTTCGCCGTGTACTACTGCGGCCAGTCCTACTCAT ACCCCTTCACCTTCGGCCAGGGCACCAAGCTGGAAATCAA GCGTACGGTGGCCGCTCCCAGCGTGTTCATCTTCCCCCCC AGCGACGAGCAGCTGAAGAGCGGCACCGCCAGCGTGGTG TGCCTGCTGAACAACTTCTACCCCCGGGAGGCCAAGGTGC AGTGGAAGGTGGACAACGCCCTGCAGAGCGGCAACAGCC AGGAGAGCGTCACCGAGCAGGACAGCAAGGACTCCACCT ACAGCCTGAGCAGCACCCTGACCCTGAGCAAGGCCGACT ACGAGAAGCATAAGGTGTACGCCTGCGAGGTGACCCACC AGGGCCTGTCCAGCCCCGTGACCAAGAGCTTCAACAGGG GCGAGTGC |
| SEQ ID NO: 909 (KABAT) | HCDR1 | SYGVD |
| SEQ ID NO: 910 (CHOTHIA) | HCDR1 | GFSLSSY |
| SEQ ID NO: 911 (KABAT) | HCDR2 | VIWGGGGTYYASSLMG |
| SEQ ID NO: 912 (CHOTHIA) | HCDR2 | WGGGG |
| SEQ ID NO: 913 (KABAT) | HCDR3 | HAYGHDGGFAMDY |
| SEQ ID NO: 913 (CHOTHIA) | HCDR3 | HAYGHDGGFAMDY |
| SEQ ID NO: 914 (KABAT) | LCDR1 | RASESVSSNVA |
| SEQ ID NO: 915 (CHOTHIA) | LCDR1 | SESVSSN |
| SEQ ID NO: 916 (KABAT) | LCDR2 | GASNRAT |
| SEQ ID NO: 917 (CHOTHIA) | LCDR2 | GAS |
| SEQ ID NO: 918 (KABAT) | LCDR3 | GQSYSYPFT |
| SEQ ID NO: 919 (CHOTHIA) | LCDR3 | SYSYPF |

Other Exemplary GITR Agonists

In one embodiment, the anti-GITR antibody molecule is BMS-986156 (Bristol-Myers Squibb), also known as BMS 986156 or BMS986156. BMS-986156 and other anti-GITR antibodies are disclosed, e.g., in U.S. Pat. No. 9,228,016 and WO 2016/196792, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of BMS-986156, e.g., as disclosed in Table 14.

In one embodiment, the anti-GITR antibody molecule is MK-4166 or MK-1248 (Merck). MK-4166, MK-1248, and other anti-GITR antibodies are disclosed, e.g., in U.S. Pat. No. 8,709,424, WO 2011/028683, WO 2015/026684, and Mahne et al. *Cancer Res*. 2017; 77(5):1108-1118, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of MK-4166 or MK-1248.

In one embodiment, the anti-GITR antibody molecule is TRX518 (Leap Therapeutics). TRX518 and other anti-GITR antibodies are disclosed, e.g., in U.S. Pat. Nos. 7,812,135, 8,388,967, 9,028,823, WO 2006/105021, and Ponte J et al. (2010) *Clinical Immunology;* 135:S96, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of TRX518.

In one embodiment, the anti-GITR antibody molecule is INCAGN1876 (Incyte/Agenus). INCAGN1876 and other anti-GITR antibodies are disclosed, e.g., in US 2015/0368349 and WO 2015/184099, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of INCAGN1876.

In one embodiment, the anti-GITR antibody molecule is AMG 228 (Amgen). AMG 228 and other anti-GITR antibodies are disclosed, e.g., in U.S. Pat. No. 9,464,139 and WO 2015/031667, incorporated by reference in their entirety. In one embodiment, the anti-GITR antibody molecule comprises one or more of the CDR sequences (or collectively all of the CDR sequences), the heavy chain or light chain variable region sequence, or the heavy chain or light chain sequence of AMG 228.

In one embodiment, the anti-GITR antibody molecule is INBRX-110 (Inhibrx). INBRX-110 and other anti-GITR antibodies are disclosed, e.g., in US 2017/0022284 and WO 2017/015623, incorporated by reference in their entirety. In one embodiment, the GITR agonist comprises one or more of the CDR sequences (or collectively all of the CDR sequences), the heavy chain or light chain variable region sequence, or the heavy chain or light chain sequence of INBRX-110.

In one embodiment, the GITR agonist (e.g., a fusion protein) is MEDI 1873 (MedImmune), also known as MEDI1873. MEDI 1873 and other GITR agonists are disclosed, e.g., in US 2017/0073386, WO 2017/025610, and Ross et al. *Cancer Res* 2016; 76(14 Suppl): Abstract nr 561, incorporated by reference in their entirety. In one embodiment, the GITR agonist comprises one or more of an IgG Fc domain, a functional multimerization domain, and a receptor binding domain of a glucocorticoid-induced TNF receptor ligand (GITRL) of MEDI 1873.

Further known GITR agonists (e.g., anti-GITR antibodies) include those described, e.g., in WO 2016/054638, incorporated by reference in its entirety.

In one embodiment, the anti-GITR antibody is an antibody that competes for binding with, and/or binds to the same epitope on GITR as, one of the anti-GITR antibodies described herein.

In one embodiment, the GITR agonist is a peptide that activates the GITR signaling pathway. In one embodiment, the GITR agonist is an immunoadhesin binding fragment (e.g., an immunoadhesin binding fragment comprising an extracellular or GITR binding portion of GITRL) fused to a constant region (e.g., an Fc region of an immunoglobulin sequence).

TABLE 14

| Amino acid sequences of other exemplary anti-GITR antibody molecules | |
|---|---|
| BMS-986156 | |
| SEQ ID NO: 920 VH | QVQLVESGGGVVQPGRSLRLSCAASGFTFSSYGMHWVRQAPGKGL EWVAVIWYEGSNKYYADSVKGRFTISRDNSKNTLYLQMNSLRAED TAVYYCARGGSMVRGDYYYGMDVWGQGTTVTVSS |
| SEQ ID NO: 921 VL | AIQLTQSPSSLSASVGDRVTITCRASQGISSALAWYQQKPGKAPKLLI YDASSLESGVPSRFSGSGSGTDFTLTISSLQPEDFATYYCQQFNSYPY TFGQGTKLEIK |

Exemplary Anti-CD3 Multispecific Antibody Molecules

In certain embodiments, the anti-CD73 antibody molecule described herein is administered in combination with an anti-CD3 multispecific antibody molecule (e.g., an anti-CD3 bispecific antibody molecule). In one embodiment, the anti-CD3 multispecific antibody molecule binds to CD3 and a target tumor antigen (TTA). In one embodiment, the TTA is chosen from CD19, CD20, CD38, or CD123. In one embodiment, the anti-CD3 multispecific antibody molecule is in a format disclosed in FIGS. 1A, 1B, 1C, and 125 of WO 2016/182751, herein incorporated by reference in its entirety.

In one embodiment, the anti-CD3 multispecific antibody molecule is an anti-CD3×anti-CD123 bispecific antibody molecule, e.g., XENP14045 (e.g., as set out in Table 15) or an anti-CD3×anti-CD123 bispecific antibody molecule disclosed in WO 2016/086189 or WO 2016/182751, herein incorporated by reference in their entirety. In one embodiment, the anti-CD3×anti-CD123 bispecific antibody molecule comprises one or more of the CDR sequences (or collectively all of the CDR sequences), the heavy chain or light chain variable region sequence, or the heavy chain or light chain sequence of XENP14045, or an amino acid sequence substantially identical thereto (e.g., a sequence having at least about 85%, 90%, or 95% sequence identity thereto).

In one embodiment, the anti-CD3 multispecific antibody is an anti-CD3×anti-CD20 bispecific antibody molecule, e.g., XENP13676 (e.g., as set out in Table 15) or an anti-CD3×anti-CD20 bispecific antibody molecule disclosed in WO 2016/086189 or WO 2016/182751, herein incorporated by reference in their entirety. In one embodiment, the anti-CD3×anti-CD20 bispecific antibody molecule comprises one or more of the CDR sequences (or collectively all of the CDR sequences), the heavy chain or light chain variable region sequence, or the heavy chain or light chain sequence of XENP13676, or an amino acid sequence substantially identical thereto (e.g., a sequence having at least about 85%, 90%, or 95% sequence identity thereto).

TABLE 15

| Amino acid sequences of exemplary anti-CD3 bispecific antibody molecules | | |
|---|---|---|
| XENP14045 (anti-CD123 × anti-CD3 Fab-scFv-Fc) | | |
| SEQ ID NO: 177 | Heavy chain 1 (anti-CD123 Fab-Fc) | QVQLQQSGAEVKKPGASVKVSCKASGYTFTDYYMKWVKQSHGKSLEWMGDIIPSNGATFYNQKFKGKATLTVDRSTSTAYMELSSLRSEDTAVYYCARSHLLRASWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK |
| SEQ ID NO: 178 | Heavy chain 2 (anti-CD3 scFv-Fc) | EVQLVESGGGLVQPGGSLRLSCAASGFTFSTYAMNWVRQAPGKGLEWVGRIRSKYNNYATYYADSVKGRFTISRDDSKNTLYLQMNSLRAEDTAVYYCVRHGNFGDSYVSWFAYWGQGTLVTVSSGKPGSGKPGSGKPGSGKPGSQAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGGGTKLTVLEPKSSDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 179 | Light chain | DFVMTQSPDSLAVSLGERATINCKSSQSLLNTGNQKNYLTWYQQKPGQPPKLLIYWASTRESGVPDRFTGSGSGTDFTLTISSLQAEDVAVYYCQNDYSYPYTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| XENP13676 (anti-CD20 × anti-CD3 Fab-scFv-Fc) | | |
| SEQ ID NO: 180 | Heavy chain 1 (Fab-Fc) | QVQLVQSGAEVKKPGASVKVSCKASGYTFTSYNMHWVRQAPGQGLEWMGAIYPGNGDTSYNQKFQGRVTITADKSISTAYMELSSLRSEDTAVYYCARSTYYGGDWYFNVWGAGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK |
| SEQ ID NO: 181 | Heavy chain 2 (scFv-Fc) | EVQLVESGGGLVQPGGSLRLSCAASGFTFSTYAMNWVRQAPGKGLEWVGRIRSKYNNYATYYADSVKGRFTISRDDSKNTLYLQMNSLRAEDTAVYYCVRHGNFGDSYVSWFAYWGQGTLVTVSSGKPGSGKPGSGKPGSGKPGSQAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGGGTKLTVLEPKSSDKTHTCPPCPAPPVAGPSVFLFPPKPKDTLMISRTPEVTCVVVDVKHEDPEVKFNWYVDGVEVHNAKTKPREEQYNSTYRVVSVLTVLHQDWLNGKEYKCKVSNKALPAPIEKTISKAKGQPREPQVYTLPPSREQMTKNQVKLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 182 | Light chain | QIVLTQSPSSLSASVGDRVTITCRASSSVSYIHWFQQKPGKSPKPLIYATSNLASGVPVRFSGSGSGTDYTLTISSLQPEDFATYYCQQWTSNPPTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

Exemplary IL15/IL-15Ra Complexes

In certain embodiments, the anti-CD73 antibody molecule described herein is administered in combination with an IL-15/IL-15Ra complex. In some embodiments, the IL-15/IL-15Ra complex is chosen from NIZ985 (Novartis), ATL-803 (Altor) or CYPO150 (Cytune).

Exemplary IL-15/IL-15Ra Complexes

In one embodiment, the IL-15/IL-15Ra complex comprises human IL-15 complexed with a soluble form of human IL-15Ra. The complex may comprise IL-15 covalently or noncovalently bound to a soluble form of IL-15Ra. In a particular embodiment, the human IL-15 is noncovalently bonded to a soluble form of IL-15Ra. In a particular embodiment, the human IL-15 of the composition comprises an amino acid sequence of SEQ ID NO: 183 in Table 16 and the soluble form of human IL-15Ra comprises an amino acid sequence of SEQ ID NO: 184 in Table 16, as described in WO 2014/066527, incorporated by reference in its entirety. The molecules described herein can be made by vectors, host cells, and methods described in WO 2007/084342, incorporated by reference in its entirety.

TABLE 16

| Amino acid and nucleotide sequences of exemplary IL-15/IL-15Ra complexes NIZ985 | | |
|---|---|---|
| SEQ ID NO: 183 | Human IL-15 | NWVNVISDLKKIEDLIQSMHIDATLYTESDVHPSCKVTAMKCFLLEL QVISLESGDASIHDTVENLIILANNSLSSNGNVTESGCKECEELEEKNI KEFLQSFVHIVQMFINTS |
| SEQ ID NO: 184 | Human Soluble IL-15Ra | ITCPPPMSCVEHADIWVKSYSLYSRERYICNSGFKRKAGTSSLTECVLN KATNVAHWTTPSLKCIRDPALVHQRPAPPSTVTTAGVTPQPESLSPSG KEPAASSPSSNNTAATTAAIVPGSQLMPSKSPSTGTTEISSHESSHGTPS QTTAKNWELTASASHQPPGVYPQG |

Other Exemplary IL-15/IL-15Ra Complexes

In one embodiment, the IL-15/IL-15Ra complex is ALT-803, an IL-15/IL-15Ra Fc fusion protein (IL-15N72D:IL-15RaSu/Fc soluble complex). ALT-803 is disclosed in WO 2008/143794, incorporated by reference in its entirety. In one embodiment, the IL-15/IL-15Ra Fc fusion protein comprises the sequences as disclosed in Table 17.

In one embodiment, the IL-15/IL-15Ra complex comprises IL-15 fused to the sushi domain of IL-15Ra (CYP0150, Cytune). The sushi domain of IL-15Ra refers to a domain beginning at the first cysteine residue after the signal peptide of IL-15Ra, and ending at the fourth cysteine residue after said signal peptide. The complex of IL-15 fused to the sushi domain of IL-15Ra is disclosed in WO 2007/04606 and WO 2012/175222, incorporated by reference in their entirety. In one embodiment, the IL-15/IL-15Ra sushi domain fusion comprises the sequences as disclosed in Table 17.

TABLE 17

| Amino acid sequences of other exemplary IL-15/IL-15Ra complexes | | |
|---|---|---|
| ALT-803 (Altor) | | |
| SEQ ID NO: 185 | IL-15N72D | NWVNVISDLKKIEDLIQSMHIDATLYTESDVHPSCKVTAMKCFLLEL QVISLESGDASIHDTVENLIILANDSLSSNGNVTESGCKECEELEEKNI KEFLQSFVHIVQMFINTS |
| SEQ ID NO: 186 | IL-15RaSu/Fc | ITCPPPMSVEHADIWVKSYSLYSRERYICNSGFKRKAGTSSLTECVLN KATNVAHWTTPSLKCIREPKSCDKTHTCPPCPAPELLGGPSVFLFPPK PKDTLMISRTPEVTCVVVDVSHEDPEVKFNWYVDGVEVHNAKTKPR EEQYNSTYRVVSVLTVLHQDWLNGKEYKCKVSNKALPAPIEKTISKA KGQPREPQVYTLPPSRDELTKNQVSLTCLVKGFYPSDIAVEWESNGQ PENNYKTTPPVLDSDGSFFLYSKLTVDKSRWQQGNVFSCSVMHEAL HNHYTQKSLSLSPGK |
| IL-15/IL-15Ra sushi domain fusion (Cytune) | | |
| SEQ ID NO: 187 | Human IL-15 | NWVNVISDLKKIEDLIQSMHIDATLYTESDVHPSCKVTAMKCFLLEL QVISLESGDASIHDTVENLIILANNSLSSNGNVTESGCKECEELEXKNI KEFLQSFVHIVQMFINTS Where X is E or K |
| SEQ ID NO: 188 | Human IL-15Ra sushi and hinge domains | ITCPPPMSVEHADIWVKSYSLYSRERYICNSGFKRKAGTSSLTECVLN KATNVAHWTTPSLKCIRDPALVHQRPAPP |

Exemplary STING Agonists

In certain embodiments, the anti-CD73 antibody molecule described herein is administered in combination with a STING agonist. In some embodiments, the combination is used to treat a cancer, e.g., a cancer described herein e.g., a solid tumor (e.g., a breast cancer, a squamous cell carcinoma, a melanoma, an ovarian cancer, a fallopian tube carcinoma, a peritoneal carcinoma, a soft tissue sarcoma, an esophageal cancer, a head and neck cancer, an endometrial cancer, a cervical cancer, or a basal cell carcinoma), e.g., a hematologic malignancy (e.g., a leukemia (e.g., a chronic lymphocytic leukemia (CLL), or a lymphoma (e.g., a marginal zone B-cell lymphoma, a small lymphocytic lymphoma, a follicular lymphoma, Hodgkin lymphoma, non-Hodgkin lymphoma)). In some embodiments, the cancer is chosen from a head and neck cancer (e.g., a head and neck squamous cell carcinoma (HNSCC), a skin cancer (e.g., melanoma), a lung cancer (e.g., a non-small cell lung cancer (NSCLC)), or a breast cancer (e.g., a triple negative breast cancer (TNBC)).

In some embodiments, the STING agonist is cyclic dinucleotide, e.g., a cyclic dinucleotide comprising purine or pyrimidine nucleobases (e.g., adenosine, guanine, uracil, thymine, or cytosine nucleobases). In some embodiments, the nucleobases of the cyclic dinucleotide comprise the same nucleobase or different nucleobases.

In some embodiments, the STING agonist comprises an adenosine or a guanosine nucleobase. In some embodiments, the STING agonist comprises one adenosine nucleobase and one guanosine nucleobase. In some embodiments, the STING agonist comprises two adenosine nucleobases or two guanosine nucleobases.

In some embodiments, the STING agonist comprises a modified cyclic dinucleotide, e.g., comprising a modified nucleobase, a modified ribose, or a modified phosphate linkage. In some embodiments, the modified cyclic dinucleotide comprises a modified phosphate linkage, e.g., a thiophosphate.

In some embodiments, the STING agonist comprises a cyclic dinucleotide (e.g., a modified cyclic dinucleotide) with 2',5' or 3',5' phosphate linkages. In some embodiments, the STING agonist comprises a cyclic dinucleotide (e.g., a modified cyclic dinucleotide) with Rp or Sp stereochemistry around the phosphate linkages.

In some embodiments, the STING agonist is Rp,Rp dithio 2',3' c-di-AMP (e.g., Rp,Rp-dithio c-[A(2',5')pA(3',5')p]), or a cyclic dinucleotide analog thereof. In some embodiments, the STING agonist is a compound depicted in U.S. Patent Publication No. US2015/0056224 (e.g., a compound in FIG. 2*c*, e.g., compound 21 or compound 22). In some embodiments, the STING agonist is c-[G(2',5'pG(3',5')p], a dithio ribose O-substituted derivative thereof, or a compound depicted in FIG. 4 of PCT Publication Nos. WO 2014/189805 and WO 2014/189806. In some embodiments, the STING agonist is c-[A(2',5')pA(3',5')p] or a dithio ribose O-substituted derivative thereof, or is a compound depicted in FIG. 5 of PCT Publication Nos. WO 2014/189805 and WO 2014/189806. In some embodiments, the STING agonist is c-[G(2',5)pA(3',5)p], or a dithio ribose O-substituted derivative thereof, or is a compound depicted in FIG. 5 of PCT Publication Nos. WO 2014/189805 and WO 2014/189806. In some embodiments, the STING agonist is 2'-O-propargyl-cyclic-[A(2',5')pA(3',5')p] (2'-O-propargyl-ML-CDA) or a compound depicted in FIG. 7 of PCT Publication No. WO 2014/189806.

Other exemplary STING agonists are disclosed, e.g., in PCT Publication Nos. WO 2014/189805 and WO 2014/189806, and U.S. Publication No. 2015/0056225.

Exemplary CSF-1/1R Binding Agents

In certain embodiments, the anti-CD73 antibody molecule described herein is administered in combination with a CSF-1/1R binding agent. In some embodiments, the combination is used to treat a cancer, e.g., a cancer described herein, e.g., a solid tumor (e.g., a prostate cancer, a breast cancer, or pigmented villonodular synovitis (PVNS)).

In some embodiments, the CSF-1/1R binding agent is an inhibitor of macrophage colony-stimulating factor (M-CSF). M-CSF is also sometimes known as CSF-1.

In another embodiment, the CSF-1/1R binding agent is a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224. In some embodiments, the cancer is chosen from a brain cancer (e.g., glioblastoma multiforme (GBM)), a pancreatic cancer, or a breast cancer (e.g., a triple-negative breast cancer (TNBC)).

In some embodiments, the CSF-1/1R binding agent (e.g., a CSF-1R tyrosine kinase inhibitor), 4-((2-(((R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered in combination with a CD73 inhibitor (e.g., an anti-CD73 antibody molecule).

In certain embodiments, the CSF-1/1R binding agent (e.g., a CSF-1R tyrosine kinase inhibitor), 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered in combination with the CD73 inhibitor (e.g., the anti-CD73 antibody molecule) to treat a cancer, e.g., a solid tumor (e.g., an advanced solid tumor), e.g., a brain cancer (e.g., glioblastoma multiforme (GBM), e.g., recurrent glioblastoma), a breast cancer (e.g., a triple-negative breast cancer (e.g., NTBC)), or a pancreatic cancer (e.g., advanced pancreatic cancer).

In some embodiments, the CSF-1/1R binding agent is an M-CSF inhibitor, Compound A33, or a binding agent to CSF-1 disclosed in PCT Publication No. WO 2004/045532 or PCT Publication No WO 2005/068503 including RX 1 or 5H4 (e.g., an antibody molecule or Fab fragment against M-CSF). In some embodiments, the cancer is chosen from an endometrial cancer, a skin cancer (e.g., melanoma), a pancreatic cancer, or a breast cancer (e.g., a triple negative breast cancer (TNBC)).

In some embodiments, the CSF-1/1R binding agent is a CSF1R inhibitor or 4-(2-((1R, 2R)-2-hydroxycyclohexylamino)benzothiazol-6-yloxy)-N-methylpicolinamide. 4-(2-((1R, 2R)-2-hydroxycyclohexylamino)benzothiazol-6-yloxy)-N-methylpicolinamide is disclosed as example 157 at page 117 of PCT Publication No. WO 2007/121484.

In some embodiments, the CSF-1/1R binding agent is pexidartinib (CAS Registry Number 1029044-16-3). Pexidrtinib is also known as PLX3397 or 5-((5-chloro-1H-pyrrolo[2,3-b]pyridin-3-yl)methyl)-N-((6-(trifluoromethyl)pyridin-3-yl)methyl)pyridin-2-amine. Pexidartinib is a small-molecule receptor tyrosine kinase (RTK) inhibitor of KIT, CSF1R and FLT3. In some embodiments, the CSF-1/1R binding agent, e.g., pexidartinib, is used in combination with a CD73 inhibitor, e.g., an anti-CD73 antibody molecule described herein.

In some embodiments, the CSF-1/1R binding agent is emactuzumab. Emactuzumab is also known as RG7155 or R05509554. Emactuzumab is a humanized IgG1 mAb targeting CSF1R. In some embodiments, the CSF-1/1R binding agent, e.g., pexidartinib, is used in combination with a CD73 inhibitor, e.g., an anti-CD73 antibody molecule described herein.

In some embodiments, the CSF-1/1R binding agent is FPA008. FPA008 is a humanized mAb that inhibits CSF1R. In some embodiments, the CSF-1/1R binding agent, e.g., FPA008, is used in combination with a CD73 inhibitor, e.g., an anti-CD73 antibody molecule described herein.

Exemplary IDO/TDO Inhibitors

In certain embodiments, the anti-CD73 antibody molecule described herein is administered in combination with an inhibitor of indoleamine 2,3-dioxygenase (IDO) and/or tryptophan 2,3-dioxygenase (TDO). In some embodiments, the combination is used to treat a cancer, e.g., a cancer described herein, e.g., a solid tumor (e.g., melanoma, non-small cell lung cancer, colon cancer, squamous cell head and neck cancer, ovarian cancer, peritoneal cancer, fallopian tube cancer, breast cancer (e.g., metastatic or HER2-negative breast cancer)), e.g., a hematologic malignancy (e.g., a lymphoma, e.g., a non-Hodgkin's lymphoma or a Hodgkin's lymphoma (e.g., a diffuse large B-cell lymphoma (DLBCL))).

In some embodiments, the IDO/TDO inhibitor is chosen from (4E)-4-[(3-chloro-4-fluoroanilino)-nitrosomethylidene]-1,2,5-oxadiazol-3-amine (also known as INCB24360), indoximod (1-methyl-D-tryptophan), or α-cyclohexyl-5H-Imidazo[5,1-a]isoindole-5-ethanol (also known as NLG919).

In some embodiments, the IDO/TDO inhibitor is epacadostat (CAS Registry Number: 1204669-58-8). Epacadostat is also known as INCB24360 or INCB024360 (Incyte). Epacadostat is a potent and selective indoleamine 2,3-dioxygenase (IDO1) inhibitor with IC50 of 10 nM, highly selective over other related enzymes such as IDO2 or tryptophan 2,3-dioxygenase (TDO).

In some embodiments, the IDO/TDO inhibitor is indoximod (New Link Genetics). Indoximod, the D isomer of 1-methyl-tryptophan, is an orally administered small-molecule indoleamine 2,3-dioxygenase (IDO) pathway inhibitor that disrupts the mechanisms by which tumors evade immune-mediated destruction.

In some embodiments, the IDO/TDO inhibitor is NLG919 (New Link Genetics). NLG919 is a potent IDO (indoleamine-(2,3)-dioxygenase) pathway inhibitor with Ki/EC50 of 7 nM/75 nM in cell-free assays.

In some embodiments, the IDO/TDO inhibitor is F001287 (Flexus/BMS). F001287 is a small molecule inhibitor of indoleamine 2,3-dioxygenase 1 (IDO1).

Exemplary TGF-β Inhibitors

In certain embodiments, the anti-CD73 antibody molecule described herein is administered in combination with a transforming growth factor beta (TGF-β) inhibitor. In some embodiments, the combination is used to treat a cancer, e.g., a cancer described herein, e.g., a solid tumor (e.g., a brain cancer (e.g., a glioma), a melanoma, a kidney cancer (e.g., a renal cell carcinoma), a pleural malignant mesothelioma (e.g., a relapsed pleural malignant mesothelioma), or a breast cancer (e.g., a metastatic breast cancer)). In certain embodiments, the cancer is chosen from a colorectal cancer (e.g., a microsatelliate stable colorectal cancer (MSS CRC), a liver cancer (e.g., a hepatocellular carcinoma), a lung cancer (e.g., a non-small cell lung cancer (HSCLC)), a breast cancer (e.g., a triple negative breast cancer (TNBC)), a TGF-β-expressing cancer, a pancreatic cancer, a prostate cancer, or a renal cancer (e.g., a renal cell carcinoma).

TGF-β belongs to a large family of structurally-related cytokines including, e.g., bone morphogenetic proteins (BMPs), growth and differentiation factors, activins and inhibins. In some embodiments, the TGF-β inhibitors described herein can bind and/or inhibit one or more isoforms of TGF-β (e.g., one, two, or all of TGF-β1, TGF-β2, or TGF-β3).

In some embodiments, the TGF-β inhibitor is fresolimumab (CAS Registry Number: 948564-73-6). Fresolimumab is also known as GC1008. Fresolimumab is a human monoclonal antibody that binds to and inhibits TGF-beta isoforms 1, 2 and 3.

The heavy chain of fresolimumab has the amino acid sequence of:

```
                                   (SEQ ID NO: 172)
QVQLVQSGAEVKKPGSSVKVSCKASGYTFSSNVISWVRQAPGQGLEWMGG

VIPIVDIANYAQRFKGRVTITADESTSTTYMELSSLRSEDTAVYYCASTL

GLVLDAMDYWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPSCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK.
```

The light chain of fresolimumab has the amino acid sequence of:

```
                                   (SEQ ID NO: 173)
ETVLTQSPGTLSLSPGERATLSCRASQSLGSSYLAWYQQKPGQAPRLLIY

GASSRAPGIPDRFSGSGSGTDFTLTISRLEPEDFAVYYCQQYADSPITFG

QGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC.
```

Fresolimumab is disclosed, e.g., in WO 2006/086469, U.S. Pat. Nos. 8,383,780, and 8,591,901.

In some embodiments, the TGF-β inhibitor is XOMA 089. XOMA 089 is also known as XPA.42.089. XOMA 089 is a fully human monoclonal antibody that binds and neutralizes TGF-beta 1 and 2 ligands.

The heavy chain variable region of XOMA 089 has the amino acid sequence of:

```
                                   (SEQ ID NO: 174)
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCARGL

WEVRALPSVYWGQGTLVTVSS
```

(disclosed as SEQ ID NO: 6 in WO 2012/167143).

The light chain variable region of XOMA 089 has the amino acid sequence of:

```
                                          (SEQ ID NO: 175)
SYELTQPPSVSVAPGQTARITCGANDIGSKSVHWYQQKAGQAPVLVVSED

IIRPSGIPERISGSNSGNTATLTISRVEAGDEADYYCQVWDRDSDQYVFG

TGTKVTVLG
```

(disclosed as SEQ ID NO: 8 in WO 2012/167143).

In certain embodiments, the combination includes an inhibitor of CD73 (e.g., an anti-CD73 antibody molecule described herein) and a TGF-β inhibitor (e.g., a TGF-β inhibitor described herein).

In one embodiment, the combination includes a TGF-β inhibitor, XOMA 089, or a compound disclosed in PCT Publication No. WO 2012/167143, and an inhibitor of CD73 (e.g., an anti-CD73 antibody described herein).

In one embodiment, the TGF-β inhibitor, XOMA 089, or a compound disclosed in PCT Publication No. WO 2012/167143, is administered in combination with an inhibitor of CD73 (e.g., an anti-CD73 antibody molecule) to treat a pancreatic cancer, a colorectal cancer (e.g., a microsatellite stable colorectal cancer (MSS-CRC)), a lung cancer (e.g., a non-small cell lung cancer), a breast cancer (e.g., a triple negative breast cancer), a liver cancer (e.g., a hepatocellular carcinoma), a prostate cancer, or a renal cancer (e.g., a clear cell renal cell carcinoma).

Exemplary VEGFR Inhibitors

In certain embodiments, the anti-CD73 antibody molecule described herein is administered in combination with a vascular endothelial growth factor (VEGF) receptor inhibitor (e.g., an inhibitor of one or more of VEGFR (e.g., VEGFR-1, VEGFR-2, or VEGFR-3) or VEGF). In some embodiments, the combination is used to treat a cancer, e.g., a cancer described herein, e.g., a solid tumor (e.g., a melanoma, a breast cancer, a colon cancer, an esophageal cancer, a gastrointestinal stromal tumor (GIST), a kidney cancer (e.g., a renal cell cancer), a liver cancer, a non-small cell lung cancer (NSCLC), an ovarian cancer, a pancreatic cancer, a prostate cancer, or a stomach cancer), e.g., a hematologic malignancy (e.g., a lymphoma).

In some embodiments, the VEGFR inhibitor is vatalanib succinate (Compound A47) or a compound disclosed in EP 296122.

In some embodiment, the VEGFR inhibitor is an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377.

Other exemplary VEGFR pathway inhibitors that can be used in the combinations disclosed herein include, e.g., bevacizumab (AVASTIN®), axitinib (INLYTA®); brivanib alaninate (BMS-582664, (S)—((R)-1-(4-(4-Fluoro-2-methyl-1H-indol-5-yloxy)-5-methylpyrrolo[2, 1-f][1,2,4]triazin-6-yloxy)propan-2-yl)2-aminopropanoate); sorafenib (NEXAVAR®); pazopanib (VOTRIENT®); sunitinib malate (SUTENT®); cediranib (AZD2171, CAS 288383-20-1); vargatef (BIBF1120, CAS 928326-83-4); Foretinib (GSK1363089); telatinib (BAY57-9352, CAS 332012-40-5); apatinib (YN968D1, CAS 811803-05-1); imatinib (GLEEVEC®); ponatinib (AP24534, CAS 943319-70-8); tivozanib (AV951, CAS 475108-18-0); regorafenib (BAY73-4506, CAS 755037-03-7); vatalanib dihydrochloride (PTK787, CAS 212141-51-0); brivanib (BMS-540215, CAS 649735-46-6); vandetanib (CAPRELSA® or AZD6474); motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); linfanib (ABT869, CAS 796967-16-3); cabozantinib (XL184, CAS 849217-68-1); lestaurtinib (CAS 111358-88-4); N-[5-[[[5-(1,1-dimethylethyl)-2-oxazolyl]methyl]thio]-2-thiazolyl]-4-piperidinecarboxamide (BMS38703, CAS 345627-80-7); (3R,4R)-4-amino-1-((4-((3-methoxyphenyl)amino)pyrrolo[2, 1-f][1,2,4]triazin-5-yl)methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); aflibercept (EYLEA®), and endostatin (ENDOSTAR®).

Exemplary anti-VEGF antibodies that can be used in the combinations disclosed herein include, e.g., a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) *Cancer Res.* 57:4593-4599. In one embodiment, the anti-VEGF antibody is Bevacizumab (BV), also known as rhuMAb VEGF or AVASTIN®. It comprises mutated human IgG1 framework regions and antigen-binding complementarity-determining regions from the murine anti-hVEGF monoclonal antibody A.4.6.1 that blocks binding of human VEGF to its receptors. Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, the contents of these patent applications are expressly incorporated herein by reference. For additional antibodies, see U.S. Pat. Nos. 7,060,269, 6,582,959, 6,703,020, 6,054,297, WO98/45332, WO 96/30046, WO94/10202, EP 0666868B1, U.S. Patent Application Publication Nos. 2006/009360, 2005/0186208, 2003/0206899, 2003/0190317, 2003/0203409, and 2005/0112126; and Popkov et al, *Journal of Immunological Methods* 288: 149-164 (2004). Other antibodies include those that bind to a functional epitope on human VEGF comprising of residues F17, Ml 8, D19, Y21, Y25, Q89, 191, K101, El 03, and C104 or, alternatively, comprising residues F17, Y21, Q22, Y25, D63, 183 and Q89.

Exemplary c-MET Inhibitors

In certain embodiments, the anti-CD73 antibody molecule described herein is administered in combination with an inhibitor of c-MET. In some embodiments, the combination is used to treat a cancer, e.g., a cancer described herein, e.g., a solid tumor (e.g., a non-small cell lung cancer, a pancreatic cancer, a liver cancer, a thyroid cancer (e.g., anaplastic thyroid carcinoma), a brain tumor (e.g., a glioblastoma), a kidney cancer (e.g., a renal cell carcinoma), or a head and neck cancer (e.g., a head and neck squamous cell carcinoma). In certain embodiments, the cancer is a liver cancer, e.g., a hepatocellular carcinoma (HCC) (e.g., a c-MET-expressing HCC).

In some embodiments, the c-MET inhibitor is Compound A17 or a compound described in U.S. Pat. Nos. 7,767,675 and 8,420,645).

In some embodiments, the c-MET inhibitor is JNJ-38877605. JNJ-38877605 is an orally available, small molecule inhibitor of c-Met. JNJ-38877605 selectively binds to c-MET, thereby inhibiting c-MET phosphorylation and disrupting c-Met signal transduction pathways.

In some embodiments, the c-Met inhibitor is AMG 208. AMG 208 is a selective small-molecule inhibitor of c-MET. AMG 208 inhibits the ligand-dependent and ligand-independent activation of c-MET, inhibiting its tyrosine kinase activity, which may result in cell growth inhibition in tumors that overexpress c-Met.

In some embodiments, the c-Met inhibitor is AMG 337. AMG 337 is an orally bioavailable inhibitor of c-Met. AMG 337 selectively binds to c-MET, thereby disrupting c-MET signal transduction pathways.

In some embodiments, the c-Met inhibitor is LY2801653. LY2801653 is an orally available, small molecule inhibitor of c-Met. LY2801653 selectively binds to c-MET, thereby inhibiting c-MET phosphorylation and disrupting c-Met signal transduction pathways.

In some embodiments, c-Met inhibitor is MSC2156119J. MSC2156119J is an orally bioavailable inhibitor of c-Met. MSC2156119J selectively binds to c-MET, which inhibits c-MET phosphorylation and disrupts c-Met-mediated signal transduction pathways.

In some embodiments, the c-MET inhibitor is capmatinib. Capmatinib is also known as INCB028060. Capmatinib is an orally bioavailable inhibitor of c-MET. Capmatinib selectively binds to c-Met, thereby inhibiting c-Met phosphorylation and disrupting c-Met signal transduction pathways.

In some embodiments, the c-MET inhibitor is crizotinib. Crizotinib is also known as PF-02341066. Crizotinib is an orally available aminopyridine-based inhibitor of the receptor tyrosine kinase anaplastic lymphoma kinase (ALK) and the c-Met/hepatocyte growth factor receptor (HGFR). Crizotinib, in an ATP-competitive manner, binds to and inhibits ALK kinase and ALK fusion proteins. In addition, crizotinib inhibits c-Met kinase, and disrupts the c-Met signaling pathway. Altogether, this agent inhibits tumor cell growth.

In some embodiments, the c-MET inhibitor is golvatinib. Golvatinib is an orally bioavailable dual kinase inhibitor of c-MET and VEGFR-2 with potential antineoplastic activity. Golvatinib binds to and inhibits the activities of both c-MET and VEGFR-2, which may inhibit tumor cell growth and survival of tumor cells that overexpress these receptor tyrosine kinases.

In some embodiments, the c-MET inhibitor is tivantinib. Tivantinib is also known as ARQ 197. Tivantinib is an orally bioavailable small molecule inhibitor of c-MET. Tivantinib binds to the c-MET protein and disrupts c-Met signal transduction pathways, which may induce cell death in tumor cells overexpressing c-MET protein or expressing constitutively activated c-Met protein.

Exemplary IAP Inhibitors

In certain embodiments, the anti-CD73 antibody molecule described herein is administered in combination with an inhibitor of Inhibitor of Apoptosis Protein (IAP). In some embodiments, the combination is used to treat a cancer, e.g., a cancer described herein, e.g., a solid tumor (e.g., a colorectal cancer (CRC), a lung cancer (e.g., a non-small cell lung cancer (NSCLC)), a breast cancer (e.g., a triple negative breast cancer (TNBC)), an ovarian cancer, or a pancreatic cancer), e.g., a hematologic malignancy (e.g., a multiple myeloma).

In some embodiments, the IAP inhibitor is (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003.

In some embodiments, the combination described herein includes an IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, and an inhibitor of an immune checkpoint molecule, e.g., an inhibitor of CD73 (e.g., an anti-CD73 antibody molecule).

Exemplary EGFR Inhibitors

In certain embodiments, the anti-CD73 antibody molecule described herein is administered in combination with an inhibitor of Epidermal Growth Factor Receptor (EGFR). In some embodiments, the combination is used to treat a cancer, e.g., a cancer described herein, e.g., a solid tumor (e.g., a lung cancer (e.g., a non-small cell lung cancer), a pancreatic cancer, a breast cancer (e.g., a triple negative breast cancer (TNBC)), or a colon cancer). In certain embodiments, the cancer is chosen from a colorectal cancer (e.g., a microsatellite stable colorectal cancer (MSS CRC)), a lung cancer (e.g., a non-small cell lung cancer), or a breast cancer (e.g., a triple negative lung cancer (TNBC)).

In some embodiments, the EGFR inhibitor is (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757.

In some embodiments, the combination described herein includes an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, and an inhibitor of an immune checkpoint molecule, e.g., an inhibitor of CD73 (e.g., an anti-CD73 antibody molecule).

In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered in combination with an inhibitor of CD73 (e.g., an anti-CD73 antibody molecule) to treat a colorectal cancer (CRC) (e.g., an MSS-CRC), a lung cancer (e.g., a non-small cell lung cancer (NSCLC)), or a breast cancer (e.g., a triple negative breast cancer (TNBC)).

In some embodiments, the EGFR inhibitor is chosen from one of more of erlotinib, gefitinib, cetuximab, panitumumab, necitumumab, PF-00299804, nimotuzumab, or R05083945.

Exemplary mTOR Inhibitors

In certain embodiments, the anti-CD73 antibody molecule described herein is administered in combination with an inhibitor of target of rapamycin (mTOR). In some embodiments, the combination is used to treat a cancer, e.g., a cancer described herein, e.g., a solid tumor (e.g., a prostate cancer, a breast cancer, a brain cancer, a bladder cancer, a pancreatic cancer, a renal cancer, or a liver cancer, a lung cancer (e.g., a small cell lung cancer or a non-small cell lung cancer), a respiratory/thoracic cancer, a sarcoma, a bone cancer, a non-small cell lung cancer, an endocrine cancer, an astrocytoma, a cervical cancer, a neurologic cancer, a gastric cancer, or a melanoma), e.g., a hematologic malignancy (e.g., a leukemia (e.g., lymphocytic leukemia), e.g., a lymphoma, or e.g., a multiple myeloma). In certain embodiments, the cancer is chosen from a colorectal cancer (e.g., a microsatellite stable colorectal cancer (MSS CRC)), a lung cancer (e.g., a non-small cell lung cancer), or a breast cancer (e.g., a triple negative lung cancer (TNBC)).

In some embodiments, the mTOR inhibitor is 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41).

In some embodiments, the mTOR inhibitor is everolimus (also known as AFINITOR®; Compound A36) or a compound disclosed in PCT Publication No. WO 2014/085318.

In some embodiments, the combination described herein includes the mTOR inhibitor, everolimus (Compound A36), or a compound disclosed in PCT Publication No. WO 2014/085318, and an inhibitor of an immune checkpoint molecule, e.g., an inhibitor of CD73 (e.g., an anti-CD73 antibody molecule).

In some embodiments, the mTOR inhibitor, Everolimus (Compound A36), or a compound disclosed in PCT Publication No. WO 2014/085318, is administered in combination with the CD73 inhibitor (e.g., the anti-CD73 antibody molecule) to treat a colorectal cancer, a lung cancer (e.g., a non-small cell lung cancer (NSCLC)), or a breast cancer (e.g., a triple negative breast cancer (NTBC)).

In some embodiments, the mTOR inhibitor is chosen from one or more of rapamycin, temsirolimus (TORISEL®), AZD8055, BGT226, XL765, PF-4691502, GDC0980, SF1126, OSI-027, GSK1059615, KU-0063794, WYE-354, Palomid 529 (P529), PF-04691502, or PKI-587. ridaforolimus (formally known as deferolimus, (1R,2R,4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.04,9] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (AFINITOR® or RAD001); rapamycin (AY22989, SIROLIMUS®); simapimod (CAS Registry Number: 164301-51-3); (5-{2,4-Bis[(3S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS Registry Number: 1013101-36-4); N2-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine (SEQ ID NO: 176) inner salt (SF1126, CAS Registry Number: 936487-67-1), or XL765 (SAR245409).

Other exemplary mTOR Inhibitors include, but are not limited to, temsirolimus; ridaforolimus (1R,2R,4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.$0^{4,9}$] hexatriaconta-16,24,26,28-tetraen-12-yl]propyl]-2-methoxycyclohexyl dimethylphosphinate, also known as AP23573 and MK8669; everolimus (RAD001); rapamycin (AY22989); simapimod; (5-(2,4-bis[(3S)-3-methylmorpholin-4-yl]pyrido[2,3-d]pyrimidin-7-yl)-2-methoxyphenyl)methanol (AZD8055); 2-mmino-8-[trans-4-(2-hydroxyethoxy)cyclohexyl]-6-(6-methoxy-3-pyridinyl)-4-methyl-pyrido[2,3-d]pyrimidin-7(8H)-one (PF04691502); and $N^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-(SEQ ID NO: 176), inner salt (SF1126); and XL765.

Exemplary PI3K-γ, -δ Inhibitors

In certain embodiments, the anti-CD73 antibody molecule described herein is administered in combination with an inhibitor of phosphatidylinositol-4,5-bisphosphate 3-kinase (PI3K), e.g., phosphatidylinositol-4,5-bisphosphate 3-kinase gamma and/or delta (PI3K-γ,δ). In some embodiments, the combination is used to treat a cancer, e.g., a cancer described herein, e.g., a solid tumor (e.g., a prostate cancer, a breast cancer, a brain cancer, a bladder cancer, a pancreatic cancer, a renal cancer, a solid tumor, a liver cancer, a non-small cell lung cancer, an endocrine cancer, an ovarian cancer, a melanoma, a female reproductive system cancer, a digestive/gastrointestinal cancer, a glioblastoma multiforme, a head and neck cancer, or a colon cancer), e.g., a hematologic malignancy (e.g., a leukemia (e.g., a lymphocytic leukemia, e.g., chronic lymphocytic leukemia (CLL) (e.g., relapsed CLL)), e.g., a lymphoma (e.g., non-Hodgkin lymphoma (e.g., relapsed follicular B-cell non-Hodgkin lymphoma (FL) or relapsed small lymphocytic lymphoma (SLL)), or e.g., a multiple myeloma).

In some embodiments, the PI3K inhibitor is an inhibitor of delta and gamma isoforms of PI3K. Exemplary PI3K inhibitors that can be used in combination are described in, e.g., WO 2010/036380, WO 2010/006086, WO 09/114870, WO 05/113556, GSK 2126458, GDC-0980, GDC-0941, Sanofi XL147, XL756, XL147, PF-46915032, BKM 120, CAL-101, CAL 263, SF1126, PX-886, and a dual PI3K inhibitor.

In some embodiments, the PI3K-γ,δ inhibitor is idelalisib (CAS Registry Number: 870281-82-6). Idelalisib is also known as ZYDELIG®, GS-1101, CAL-101, or 5-Fluoro-3-phenyl-2-[(1S)-1-(7H-purin-6-ylamino)propyl]-4(3H)-quinazolinone. Idelalisib blocks P1108, the delta isoform of PI3K. Idelalisib is disclosed, e.g., in Wu et al. *Journal of Hematology & Oncology* (2013) 6: 36.

In some embodiments, the PI3K-γ,δ inhibitor is 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41).

In some embodiments, the PI3K-γ,δ inhibitor is buparlisib (Compound A6) or a compound disclosed in PCT Publication No. WO 2007/084786.

Other exemplary PI3K-γ,δ inhibitors that can be used in the combination include, e.g., pictilisib (GDC-0941), LY294002, pilaralisib (XL147), PI-3065, PI-103, VS-5584 (SB2343), CZC24832, duvelisib (IPI-145, INK 1197), TG100-115, CAY 10505, GSK1059615, PF-04691502, AS-605240, voxtalisib (SAR245409, XL765), IC-87114, omipalisib (GSK2126458, GSK458), TG100713, gedatolisib (PF-05212384, PKI-587), PKI-402, XL147 analogue, PIK-90, PIK-293, PIK-294, 3-Methyladenine (3-MA), AS-252424, AS-604850, or apitolisib (GDC-0980, RG7422).

In some embodiments, the PI3K inhibitor is Compound A8 or a compound described in PCT Publication No. WO2010/029082.

In some embodiments, the PI3K inhibitor is a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826.

Exemplary PI3K-γ, -δ inhibitors include, but are not limited to, duvelisib and idelalisib. Idelalisib (also called GS-1101 or CAL-101; Gilead) is a small molecule that blocks the delta isoform of PI3K. The structure of idelalisib (5-Fluoro-3-phenyl-2-[(1S)-1-(7H-purin-6-ylamino)propyl]-4(3H)-quinazolinone) is shown below.

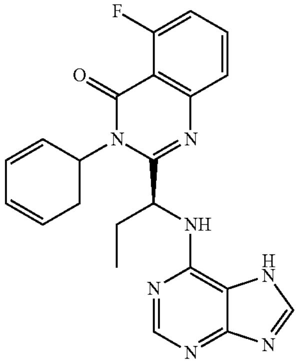 [SMILES: CC[C@H](Nc1ncnc2nc[nH]c12)c1nc2cccc(F)c2c(=O)n1C1C=CC=CC1]

Duvelisib (also called IPI-145; Infinity Pharmaceuticals and Abbvie) is a small molecule that blocks PI3K-δ,γ. The structure of duvelisib (8-Chloro-2-phenyl-3-[(1S)-1-(9H-purin-6-ylamino)ethyl]-1(2H)-isoquinolinone) is shown below.

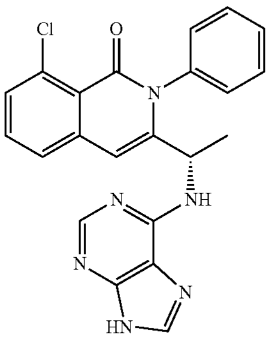 [SMILES: C[C@H](Nc1ncnc2[nH]cnc12)c1cc2cccc(Cl)c2c(=O)n1-c1ccccc1]

In one embodiment, the inhibitor is a dual phosphatidylinositol 3-kinase (PI3K) and mTOR inhibitor selected from 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502); N-[4-[[4-(Dimethylamino)-1-piperidinyl]carbonyl]phenyl]-N'-[4-(4,6-di-4-morpholinyl-1,3,5-triazin-2-yl)phenyl]urea (PF-05212384, PKI-587); apitolisib (GDC-0980, RG7422); 2,4-Difluoro-N-{2-(methyloxy)-5-[4-(4-pyridazinyl)-6-quinolinyl]-3-pyridinyl}benzenesulfonamide (GSK2126458); 8-(6-methoxypyridin-3-yl)-3-methyl-1-(4-(piperazin-1-yl)-3-(trifluoromethyl)phenyl)-1H-imidazo[4,5-c]quinolin-2(3H)-one Maleic acid (NVP-BGT226); 3-[4-(4-Morpholinylpyrido[3',2':4,5]furo[3,2-d]pyrimidin-2-yl]phenol (PI-103); 5-(9-isopropyl-8-methyl-2-morpholino-9H-purin-6-yl)pyrimidin-2-amine (VS-5584, SB2343); or N-[2-[(3,5-Dimethoxyphenyl)amino]quinoxalin-3-yl]-4-[(4-methyl-3-methoxyphenyl)carbonyl]aminophenylsulfonamide (XL765).

Exemplary JAK Inhibitors

In certain embodiments, the anti-CD73 antibody molecule described herein is administered in combination with an inhibitor of Janus kinase (JAK). In some embodiments, the combination is used to treat a cancer, e.g., a cancer described herein, e.g., a solid tumor (e.g., a colon cancer, a prostate cancer, a lung cancer, a breast cancer, or a pancreatic cancer), e.g., a hematologic malignancy (e.g., a leukemia (e.g., a myeloid leukemia or a lymphocytic leukemia), e.g., a lymphoma (e.g., a non-Hodgkin lymphoma), or a multiple myeloma.

In some embodiments, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514.

In some embodiment, the JAK inhibitor is ruxolitinib phosphate (also known as JAKAFI; Compound A18) or a compound disclosed in PCT Publication No. WO 2007/070514.

Exemplary Cell Therapies

Anti-CD73 antibody molecules can also be combined with a cell therapy, e.g., a chimeric antigen receptor (CAR) therapy, a T cell therapy, a natural killer (NK) cell therapy, or a dendritic cell therapy.

Combinations with CAR Therapies

The anti-CD73 antibody molecules described herein can be administered in combination with a second therapeutic, e.g., a cell comprising a chimeric antigen receptor (CAR). The CAR may comprise i) an extracellular antigen binding domain, ii) a transmembrane domain, and iii) an intracellular signaling domain (which may comprise one or both of a primary signaling domain and a costimulatory domain). The CAR may further comprise a leader sequence and/or a hinge sequence. In specific embodiments, the CAR construct comprises a scFv domain, wherein the scFv may be preceded by an optional leader sequence, and followed by an optional hinge sequence, a transmembrane region, and an intracellular signaling domain, e.g., wherein the domains are contiguous with and in the same reading frame to form a single fusion protein.

In some embodiments, the CAR molecule comprises a CD19 CAR molecule described herein, e.g., a CD19 CAR molecule described in US 2015/0283178, e.g., CTL019. In embodiments, the CD19 CAR comprises an amino acid, or has a nucleotide sequence shown in US 2015/0283178, incorporated herein by reference in its entirety, or a sequence substantially identical thereto (e.g., a sequence having at least about 85%, 90%, or 95% sequence identity thereto).

In one embodiment, the CAR T cell that binds to CD19 has the USAN designation TISAGENLECLEUCEL-T. CTL019 is made by a gene modification of T cells mediated by stable insertion via transduction with a self-inactivating, replication deficient lentiviral (LV) vector containing the CTL019 transgene under the control of the EF-1 alpha promoter. CTL019 can be a mixture of transgene positive and negative T cells that are delivered to the subject on the basis of percent transgene positive T cells.

In one embodiment, the CD19 CAR comprises an amino acid sequence provided as SEQ ID NO: 12 in PCT publication WO2012/079000. In embodiment, the amino acid sequence is:

MALPVTALLLPLALLLHAARPdiqmtqttsslsaslgdrvtiscrasqdiskylnwyqqkpdgtvkliyhtsrlhsgvpsrfsgsgsgtdysltisnleqediatyfcqqgntlpytfgggtkleitggggsggggsggggsevklqesgpgvapsqssvtctvsgvspdygvswi rqpprkglewlgviwgsettyynsalksrltiikdnsksqvflkmnslqtddtaiyycakhyyyggsyamdywgqgtsvtvssttpaprpptpapt iasqplslrpeacrpaaggavhtrgldfacdiyiwaplagtcgvlllsivitlyckrgrkklyifkqpfmrpvqttqeedgcscrfpeeeeggcelrvkf srsadapaykqgqnqlynelnlgrreeydvldkrrgrdpemggkprrknpqeglynelqkdkmaeayseigmkgerrrgkghdglyqglstatk dtydalhmqalppr (SEQ ID NO: 132), or a sequence substantially identical thereto (e.g., a sequence having at least about 85%, 90%, or 95% sequence identity thereto), with or without the signal peptide sequence indicated in capital letters.

In one embodiment, the amino acid sequence is: diqmtqttsslsaslgdrvtiscrasqdisky-lnwyqqkpdgtvklliyhtsrlhsgvpsrfsgsgsgtdysltisnleqedi-atyfcqqgntl pytfgggtkleitggggsggggsggggsevklqesgpglvap-sqslsvtctvsgvslpdygvswirqpprkglewlgviwgsettyynsalksrltii kdnsksqvflkmnslqtddtaiyy-cakhyyyggsyamdywgqgtsvtvssttpaprpptpaptiasqpslrpeacr-paaggavhtrgldfacdiy iwaplagtcgvylllsvitlyckrgrkklly-ifkqpfmrpvqttqeedgcscrfpeeeeggcelrvkfsrsadapaykqgqnqly-nelnigrreeydvld krrgrdpemggkprrknpqeglynelqkdkmaeaysei-gmkgerrrgkghdglyqglstatkdtydalhmqalppr (SEQ ID NO: 133), or a sequence substantially homologous thereto (e.g., a sequence having at least about 85%, 90%, or 95% sequence identity thereto).

Antigen Binding Domain of a Chimeric Antigen Receptor (CAR)

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, a T cell receptor (TCR), or a fragment there of, e.g., single chain TCR, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

In some embodiments, the antigen binding domain of the CAR is a scFv antibody fragment that is humanized compared to the murine sequence of the scFv from which it is derived.

In some embodiments, the antigen binding domain binds a tumor antigen described herein. In embodiments, the tumor antigen is chosen from: CD19; CD123; CD22; CD30; CD171; CS-1 (also referred to as CD2 subset 1, CRACC, SLAMF7, CD319, and 19A24); C-type lectin-like molecule-1 (CLL-1 or CLECL); CD33; epidermal growth factor receptor variant III (EGFRvIII); ganglioside G2 (GD2); ganglioside GD3 (aNeu5Ac(2-8)aNeu5Ac(2-3)bDGalp(1-4)bDGlcp(1-1)Cer); TNF receptor family member B cell maturation (BCMA); Tn antigen ((Tn Ag) or (GalNAcα-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GMI; sialyl Lewis adhesion molecule (sLe); ganglioside GM3 (aNeu5Ac(2-3)bDGalp(1-4)bDGlcp(1-1)Cer); transglutaminase 5 (TGS5); high molecular weight-melanoma-associated antigen (HMWMAA); o-acetyl-GD2 ganglioside (OAcGD2); Folate receptor beta; tumor endothelial marker 1 (TEMi/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC 1); hexasaccharide portion of globoH glycoceramide (GloboH); mammary gland differentiation antigen (NY-BR-1); uroplakin 2 (UPK2); Hepatitis A virus cellular receptor 1 (HAVCR 1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA 17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYPIB 1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU 1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLECI2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In one embodiment, the CAR molecule comprises a BCMA CAR molecule, e.g., a BCMA CAR described in US 2016/0046724 or WO 2016/014565, incorporated herein by reference. In embodiments, the BCMA CAR comprises an amino acid, or has a nucleotide sequence of a CAR molecule, or an antigen binding domain according to US 2016/0046724, or Table 1 or 16, SEQ ID NO: 271 or SEQ ID NO: 273 of WO 2016/014565, incorporated herein by reference, or a sequence substantially identical to any of the aforesaid sequences (e.g., having at least about 85%, 90%, or 95% sequence identity to any of the aforesaid BCMA CAR sequences). The amino acid and nucleotide sequences encoding the BCMA CAR molecules and antigen binding domains (e.g., including one, two, three VH CDRs; and one, two, three VL CDRs according to Kabat or Chothia), are specified in WO 2016/014565.

Transmembrane Domain of a Chimeric Antigen Receptor (CAR)

With respect to the transmembrane domain, in various embodiments, a CAR can be designed to comprise a transmembrane domain that is attached to the extracellular domain of the CAR.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain may include at least the transmembrane region(s) of e.g., the alpha, beta or zeta chain of the T-cell receptor, CD28, CD27, CD3 epsilon, CD45, CD4, CD5, CD8, CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R $\alpha$, ITGA1, VLA1, CD49a, ITGA4, IA4, CD49D, ITGA6, VLA-6, CD49f, ITGAD, CD1 d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, or NKG2C.

In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge (e.g., an IgG4 hinge, an IgD hinge), a GS linker (e.g., a GS linker described herein), a KIR2DS2 hinge or a CD8a hinge.

Intracellular Signaling Domain of a Chimeric Antigen Receptor (CAR)

The cytoplasmic domain or region of the CAR includes an intracellular signaling domain. An intracellular signaling domain is generally responsible for activation of at least one of the normal effector functions of the immune cell in which the CAR has been introduced.

Examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains include those of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In one embodiment, a CAR comprises an intracellular signaling domain, e.g., a primary signaling domain of CD3-zeta.

The intracellular signaling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that binds to CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3): 696-706). Further examples of such costimulatory molecules include CDS, ICAM-1, GITR, BAFFR, HVEM (LIGHTR), SLAMF7, NKp80 (KLRF), NKp44, NKp30, NKp46, CD160, CD19, CD4, CD8alpha, CD8beta, IL2R beta, IL2R gamma, IL7R alpha, ITGA4, VLA, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

Activation and Expansion of Immune Effector Cells (e.g., T Cells)

Immune effector cells such as T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 2006/0121005, incorporated herein by reference.

Examples of immune effector cells include T cells, e.g., alpha/beta T cells and gamma/delta T cells, B cells, natural killer (NK) cells, natural killer T (NKT) cells, mast cells, and myeloid-derived phagocytes.

Methods of making CAR-expressing cells are described, e.g., in US 2016/0185861, incorporated herein by reference.

Exemplary Cancer Vaccines

Anti-CD73 antibody molecules can be combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, tumor cells transfected to express the cytokine GM-CSF, DNA-based vaccines, RNA-based vaccines, and viral transduction-based vaccines. The cancer vaccine may be prophylactic or therapeutic.

CD73 blockade can be used in conjunction with a collection of recombinant proteins and/or peptides expressed in a tumor in order to generate an immune response to these proteins.

Other tumor vaccines may include the proteins from viruses implicated in human cancers such a Human Papilloma Viruses (HPV), Hepatitis Viruses (HBV and HCV), Kaposi's Herpes Sarcoma Virus (KHSV), and Epstein-Barr virus (EBV). Another form of tumor specific antigen which may be used in conjunction with CD73 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269: 1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with CD73 blockade to activate more potent anti-tumor responses.

Exemplary Oncolytic Viruses

Anti-CD73 antibody molecules can be administered in combination with oncolytic viruses. In embodiments, oncolytic viruses are capable of selectively replicating in and triggering the death of or slowing the growth of a cancer cell. In some cases, oncolytic viruses have no effect or a minimal effect on non-cancer cells. In some embodiments, the combination is used to treat a cancer, e.g., a cancer described herein. In certain embodiments, the cancer is a brain cancer, e.g., a glioblastoma (GBM). An oncolytic virus includes, but is not limited to, an oncolytic adenovirus, oncolytic Herpes Simplex Viruses, oncolytic retrovirus, oncolytic parvovirus, oncolytic vaccinia virus, oncolytic Sindbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

Exemplary oncolytic viruses include but are not limited to the following: Group B Oncolytic Adenovirus (ColoAd1) (PsiOxus Therapeutics Ltd.) (see, e.g., Clinical Trial Identifier: NCT02053220);

ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);

VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);

Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759);

Celyvir, which comprises bone marrow-derived autologous mesenchymal stem cells (MSCs) infected with ICOVIRS, an oncolytic adenovirus (Hospital Infantil Universitario Niño Jesús, Madrid, Spain/Ramon Alemany) (see, e.g., Clinical Trial Identifier: NCT01844661);

CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, an oncolytic virus described herein is administering by injection, e.g., subcutaneous, intraarterial, intravenous, intramuscular, intrathecal, or intraperitoneal injection. In embodiments, an oncolytic virus described herein is administered intratumorally, transdermally, transmucosally, orally, intranasally, or via pulmonary administration.

Additional Exemplary Cancer Therapies

Exemplary combinations of anti-CD73 antibody molecules (alone or in combination with other stimulatory agents) and standard of care for cancer, include at least the following. In certain embodiments, the anti-CD73 antibody molecule, e.g., the anti-CD73 antibody molecule described herein, is used in combination with a standard of cancer care chemotherapeutic agent including, but not limited to, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), vinorelbine (Navelbine®), Ibrutinib, idelalisib, and brentuximab vedotin.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellencem); idarubicin (Idamycin®, Idamycin PFS®); mitomycin C (Mutamycin®); geldanamycin; herbimycin; ravidomycin; and desacetylravidomycin. Exemplary vinca alkaloids that can be used in combination with the anti-CD73 antibody molecules, include, but are not limited to, vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®).

Exemplary proteosome inhibitors that can be used in combination with the anti-CD73 antibody molecules include, but are not limited to, bortezomib (Velcade®); carfilzomib (PX-171-007, (S)-4-Methyl-N—((S)-1-(((S)-4-methyl-1-((R)-2-methyloxiran-2-yl)-1-oxopentan-2-yl) amino)-1-oxo-3-phenylpropan-2-yl)-2-((S)-2-(2-morpholinoacetamido)-4-phenylbutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912).

In some embodiments, the anti-CD73 antibody molecule, e.g., the anti-CD73 antibody molecule described herein, is used, in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-ß inhibitor)), a RAF-1 inhibitor, a KIT inhibitor and a RET inhibitor. In some embodiments, the anti-cancer agent used in combination with the hedgehog inhibitor is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU 11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CP 673451, CYC 16, E7080, Ki8751, masitinib (AB1010), MGCD-265, motesanib diphosphate (AMG-706), MP-470, OSI-930, Pazopanib Hydrochloride, PD 173074, Sorafenib Tosylate (Bay 43-9006), SU 5402, TSU-68(SU6668), vatalanib, XL880 (GSK1363089, EXEL-2880). Selected tyrosine kinase inhibitors are chosen from sunitinib, erlotinib, gefitinib, or sorafenib.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as 1-125, 1-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide (s), e.g., a solution of I-125 or I-131, or a radioactive fluid can be produced using a slurry of a suitable fluid containing small particles of solid radionuclides, such as Au-198, Y-90.

CD73 blockade may also be effectively combined with chemotherapeutic regimes. In these instances, it may be possible to reduce the dose of chemotherapeutic reagent administered.

Exemplary cytotoxic agents that can be administered in combination with an anti-CD73 antibody molecule include antimicrotubule agents, topoisomerase inhibitors, anti-metabolites, mitotic inhibitors, alkylating agents, anthracyclines, vinca alkaloids, intercalating agents, agents capable of interfering with a signal transduction pathway, agents that promote apoptosis, proteosome inhibitors, and radiation (e.g., local or whole body irradiation).

In certain embodiments, any of the combinations disclosed herein, alternatively or in combination, further includes one or more of the agents described in Table 18.

TABLE 18

Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A1 | Sotrastaurin | 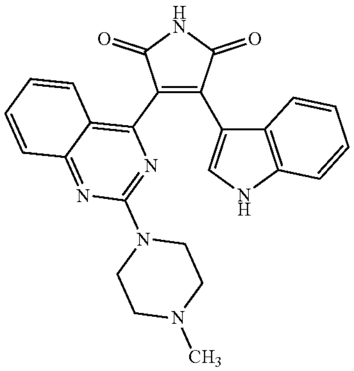 [SMILES: CN1CCN(c2nc(C3=C(c4c[nH]c5ccccc45)C(=O)NC3=O)c3ccccc3n2)CC1] | EP 1682103<br>US 2007/142401<br>WO 2005/039549 |
| A2 | Nilotinib<br>HCl<br>monohydrate<br>TASIGNA ® | 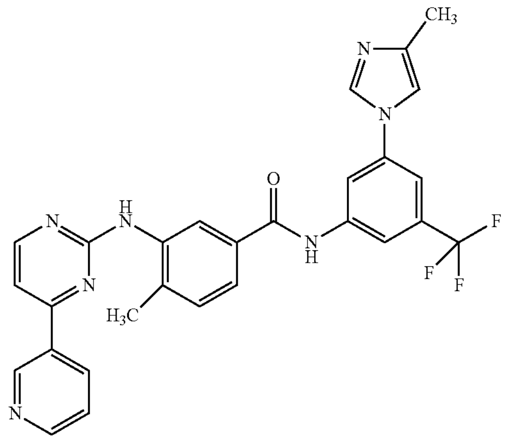 [SMILES: Cc1cn(-c2cc(NC(=O)c3ccc(C)c(Nc4nccc(-c5cccnc5)n4)c3)cc(C(F)(F)F)c2)cn1]<br>$HCl \cdot H_2O$ | WO 2004/005281<br>US 7,169,791 |

TABLE 18-continued

Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A7 | | 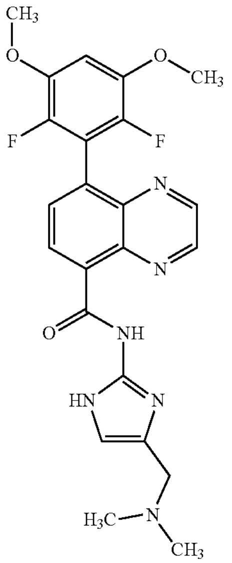 [SMILES: COc1cc(OC)c(F)c(-c2ccc(C(=O)Nc3nc(CN(C)C)c[nH]3)c3nccnc23)c1F] | WO 2009/141386<br>US 2010/0105667 |
| A8 | | 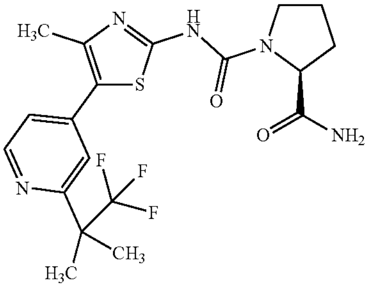 [SMILES: Cc1nc(NC(=O)N2CCC[C@H]2C(N)=O)sc1-c1ccnc(C(C)(C)C(F)(F)F)c1] | WO 2010/029082 |
| A10 | | 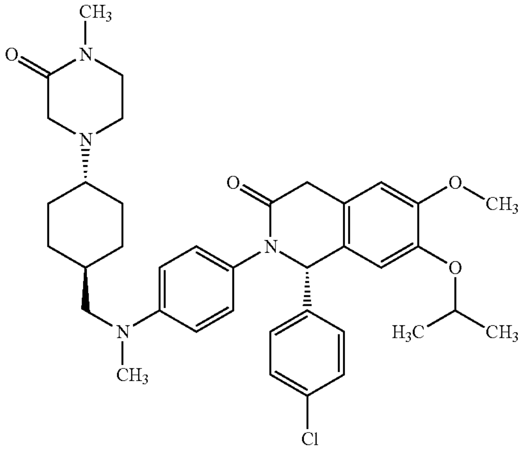 [SMILES: COc1cc2c(cc1OC(C)C)[C@H](c1ccc(Cl)cc1)N(c1ccc(N(C)C[C@H]3CC[C@H](N4CCN(C)C(=O)C4)CC3)cc1)C(=O)C2] | WO 2011/076786 |

TABLE 18-continued

Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A11 | Deferasirox EXJADE ® | 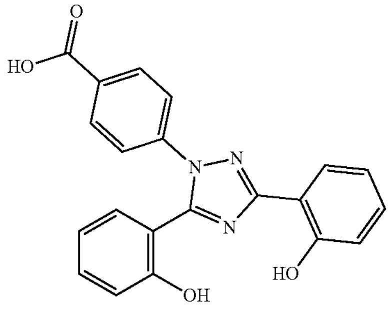 [SMILES: O=C(O)c1ccc(-n2nc(-c3ccccc3O)nc2-c2ccccc2O)cc1] | WO 1997/049395 |
| A12 | Letrozole FEMARA ® | 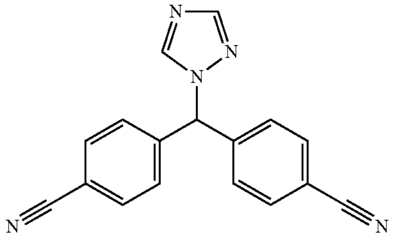 [SMILES: N#Cc1ccc(C(c2ccc(C#N)cc2)n2cncn2)cc1] | US 4,978,672 |
| A13 | | 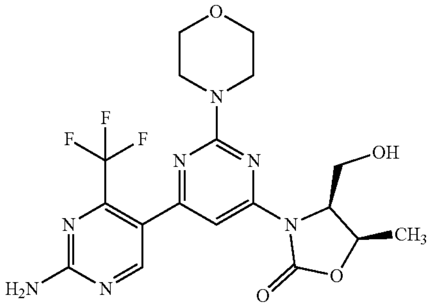 [SMILES: C[C@H]1OC(=O)N(c2cc(-c3cnc(N)nc3C(F)(F)F)nc(N3CCOCC3)n2)[C@H]1CO] | WO 2013/124826<br>US 2013/0225574 |
| A14 | | 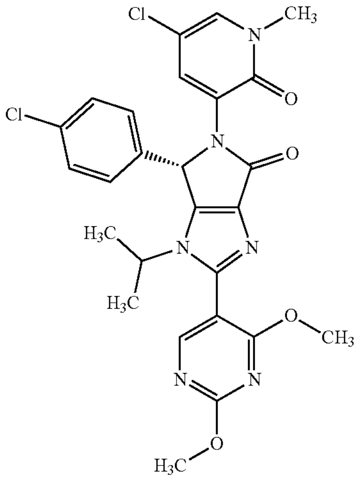 [SMILES: COc1ncc(-c2nc3c(n2C(C)C)[C@H](c2ccc(Cl)cc2)N(c2cc(Cl)cn(C)c2=O)C3=O)c(OC)n1] | WO 2013/111105 |

TABLE 18-continued

| Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein. | | | |
|---|---|---|---|
| Compound Designation | Generic Name Tradename | Compound Structure | Patents/Patent Application Publications |
| A15 | | 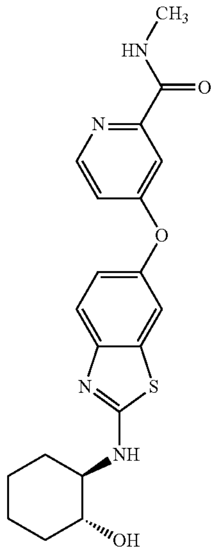 [SMILES: CNC(=O)c1cc(Oc2ccc3nc(N[C@@H]4CCCC[C@H]4O)sc3c2)ccn1] | WO 2005/073224 |
| A16 | Imatinib mesylate GLEEVEC ® | 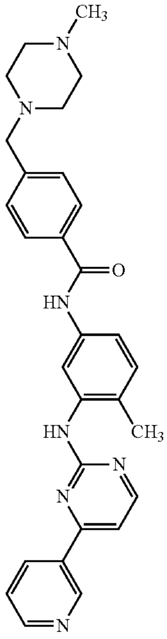 [SMILES: Cc1ccc(NC(=O)c2ccc(CN3CCN(C)CC3)cc2)cc1Nc1nccc(-c2cccnc2)n1] Mesylate | WO 1999/003854 |

TABLE 18-continued

| Compound Designation | Generic Name Tradename | Compound Structure | Patents/Patent Application Publications |
|---|---|---|---|
| Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein. | | | |
| A17 | | 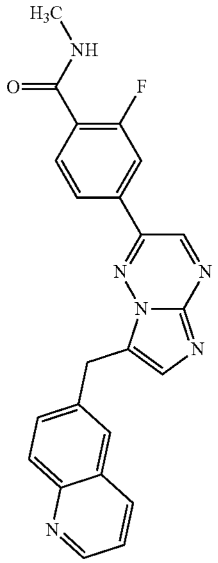 [SMILES: CNC(=O)c1ccc(-c2cnc3ncc(Cc4ccc5ncccc5c4)n3n2)cc1F] Dihydrochloric salt | EP 2099447<br>US 7,767,675<br>US 8,420,645 |
| A18 | Ruxolitinib Phosphate JAKAFI ® | 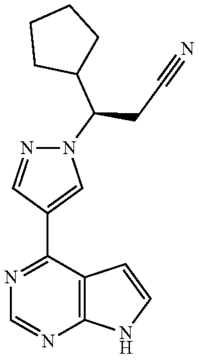 [SMILES: N#CC[C@H](C1CCCC1)n1cc(-c2ncnc3[nH]ccc23)cn1] $H_3PO_4$ | WO 2007/070514<br>EP 2474545<br>US 7,598,257<br>WO 2014/018632 |
| A19 | Panobinostat | 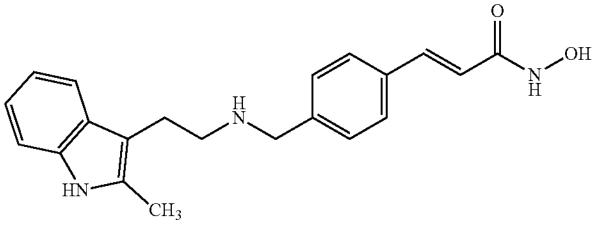 [SMILES: Cc1[nH]c2ccccc2c1CCNCc1ccc(/C=C/C(=O)NO)cc1] | WO 2014/072493<br>WO 2002/022577<br>EP 1870399 |

TABLE 18-continued

Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A20 | Osilodrostat | 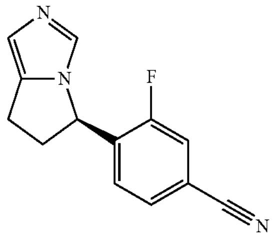 [SMILES: N#Cc1ccc([C@H]2CCc3cncn32)c(F)c1] | WO 2007/024945 |
| A21 | | 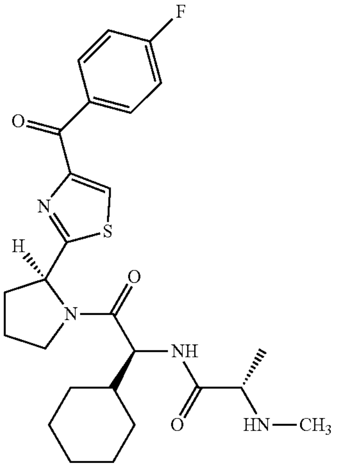 [SMILES: CN[C@@H](C)C(=O)N[C@H](C(=O)N1CCC[C@H]1c1nc(C(=O)c2ccc(F)cc2)cs1)C1CCCCC1] | WO 2008/016893<br>EP 2051990<br>US 8,546,336 |
| A23 | ceritinib<br>ZYKADIA ™ | 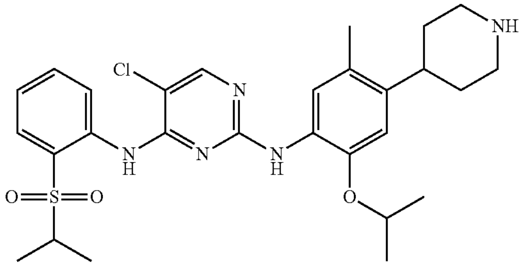 [SMILES: Cc1cc(Nc2ncc(Cl)c(Nc3ccccc3S(=O)(=O)C(C)C)n2)c(OC(C)C)cc1C1CCNCC1] | WO 2008/073687<br>US 8,039,479 |
| A24 | | 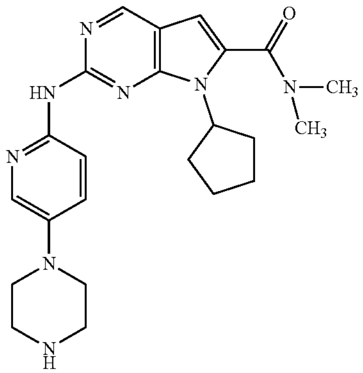 [SMILES: CN(C)C(=O)c1cc2cnc(Nc3ccc(N4CCNCC4)cn3)nc2n1C1CCCC1] | US 8,415,355<br>US 8,685,980 |

TABLE 18-continued

Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A25 | | 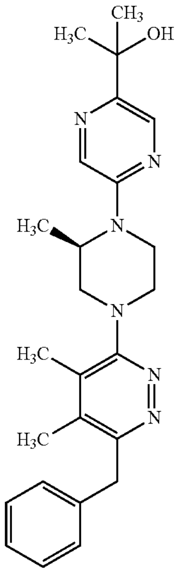 [SMILES: Cc1c(Cc2ccccc2)nnc(N2CCN(c3cnc(C(C)(C)O)cn3)[C@H](C)C2)c1C] | WO 2010/007120 |
| A26 | | Human monoclonal antibody to PRLR | US 7,867,493 |
| A27 | | 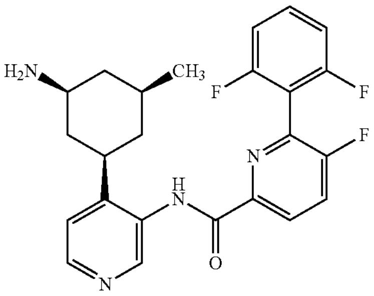 [SMILES: C[C@@H]1C[C@H](N)C[C@H](c2ccncc2NC(=O)c2ccc(F)c(-c3c(F)cccc3F)n2)C1] | WO 2010/026124<br>EP 2344474<br>US 2010/0056576<br>WO2008/106692 |
| A28 | | 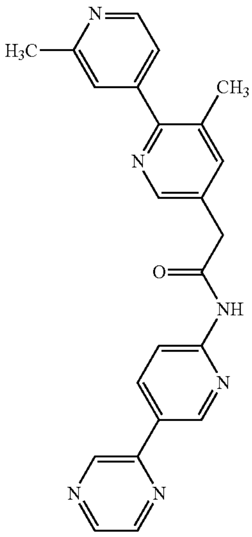 [SMILES: Cc1cc(-c2ncc(CC(=O)Nc3ccc(-c4cnccn4)cn3)cc2C)ccn1] | WO 2010/101849 |

TABLE 18-continued

| Compound Designation | Generic Name Tradename | Compound Structure | Patents/Patent Application Publications |
|---|---|---|---|
| | | Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein. | |
| A30 | | 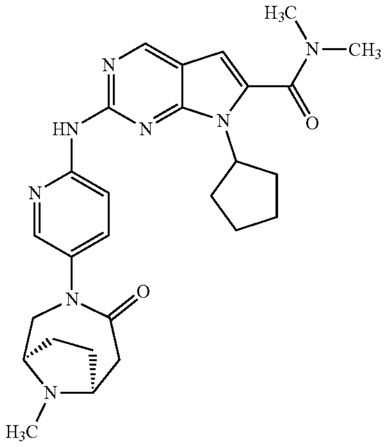 [SMILES: CN(C)C(=O)c1cc2cnc(Nc3ccc(N4C[C@H]5CC[C@@H](CC4=O)N5C)cn3)nc2n1C1CCCC1] | WO 2011/101409 |
| A31 | | Human monoclonal antibody to HER3 | WO 2012/022814<br>EP 2606070<br>US 8,735,551 |
| A32 | | Antibody Drug Conjugate (ADC) | WO 2014/160160<br>Ab: 12425 (see Table 1, paragraph [00191])<br>Linker: SMCC (see paragraph [00117]<br>Payload: DM1 (see paragraph [00111]<br>See also Claim 29 |
| A33 | | Monoclonal antibody or Fab to M-CSF | WO 2004/045532 |
| A35 | Midostaurin | 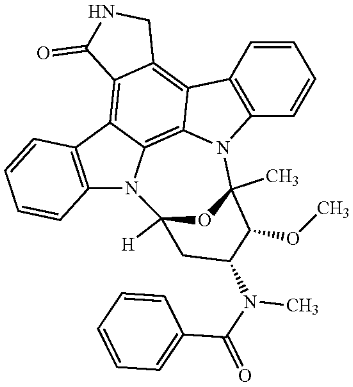 [SMILES: CO[C@@H]1[C@H](N(C)C(=O)c2ccccc2)C[C@H]2O[C@]1(C)n1c3ccccc3c3c4c(c5c6ccccc6n2c5c31)C(=O)NC4] | WO 2003/037347<br>EP 1441737<br>US 2012/252785 |

TABLE 18-continued

| Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein. | | | |
|---|---|---|---|
| Compound Designation | Generic Name Tradename | Compound Structure | Patents/Patent Application Publications |
| A36 | Everolimus AFINITOR ® | 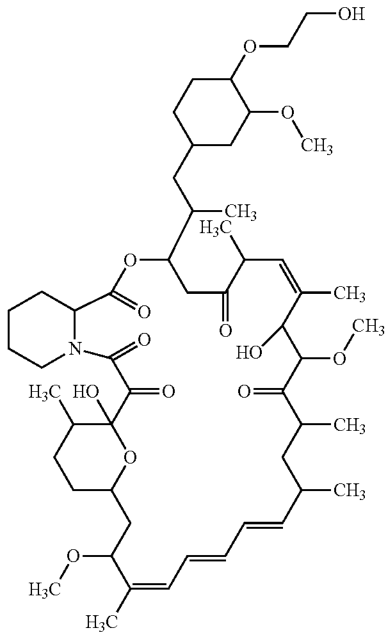 [SMILES: COC1CC2CCC(C)C(O)(O2)C(=O)C(=O)N2CCCCC2C(=O)OC(C(C)CC2CCC(OCCO)C(OC)C2)CC(=O)C(C)/C=C(/C)C(O)C(OC)C(=O)C(C)CC(C)/C=C/C=C/C=C\1C] | WO 2014/085318 |
| A37 | | 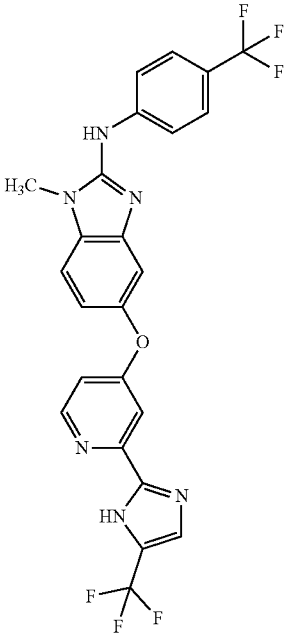 [SMILES: Cn1c(Nc2ccc(C(F)(F)F)cc2)nc2cc(Oc3ccnc(-c4ncc(C(F)(F)F)[nH]4)c3)ccc21] | WO 2007/030377 US 7,482,367 |

TABLE 18-continued

| Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein. | | | |
|---|---|---|---|
| Compound Designation | Generic Name Tradename | Compound Structure | Patents/Patent Application Publications |
| A38 | Pasireotide diaspartate SIGNIFOR ® | 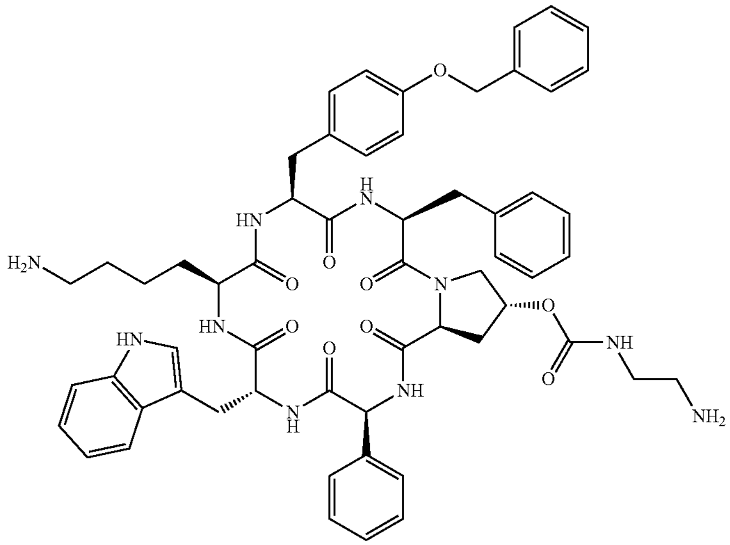 [SMILES: NCCCC[C@@H]1NC(=O)[C@@H](Cc2c[nH]c3ccccc23)NC(=O)[C@H](c2ccccc2)NC(=O)[C@@H]2C[C@@H](OC(=O)NCCN)CN2C(=O)[C@H](Cc2ccccc2)NC(=O)[C@H](Cc2ccc(OCc3ccccc3)cc2)NC1=O] | WO2002/010192<br>US 7,473,761 |
| A40 | | 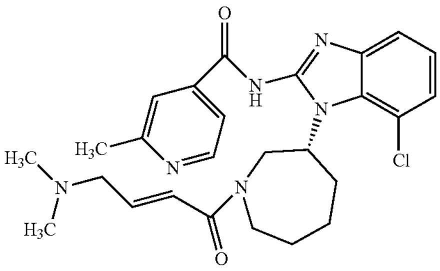 [SMILES: Cc1cc(C(=O)Nc2nc3cccc(Cl)c3n2[C@@H]2CCCCN(C(=O)/C=C/CN(C)C)C2)ccn1] | WO 2013/184757 |
| A41 | | 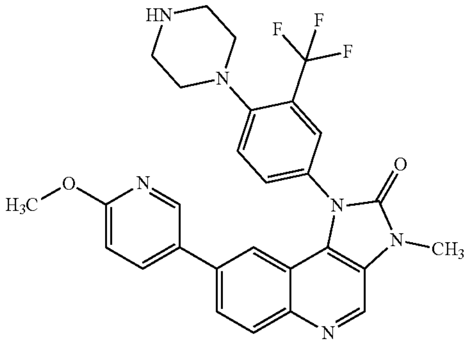 | WO 2006/122806 |

TABLE 18-continued

| Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein. | | | |
|---|---|---|---|
| Compound Designation | Generic Name Tradename | Compound Structure | Patents/Patent Application Publications |
| A42 | | 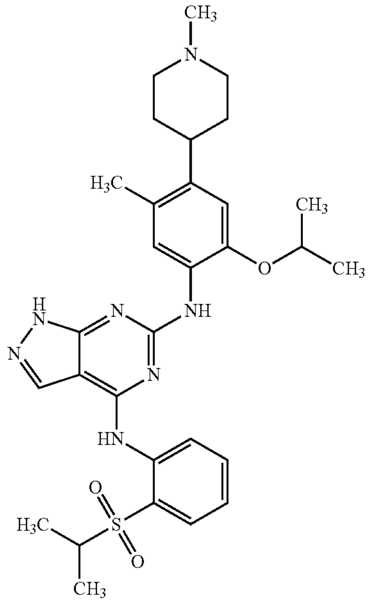 [SMILES: Cc1cc(Nc2nc(Nc3ccccc3S(=O)(=O)C(C)C)c3cn[nH]c3n2)c(OC(C)C)cc1C1CCN(C)CC1] | WO 2008/073687<br>US 8,372,858 |
| A43 | | 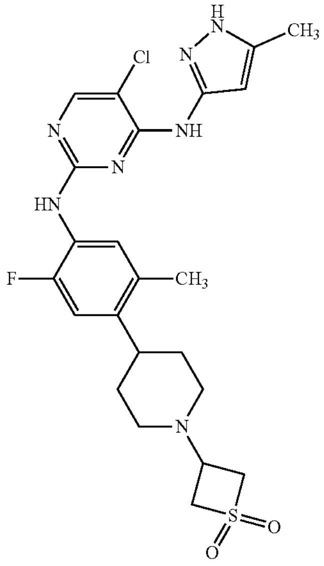 [SMILES: Cc1cc(Nc2nc(Nc3cc(C)c(C4CCN(C5CS(=O)(=O)C5)CC4)cc3F)ncc2Cl)n[nH]1] | WO 2010/002655<br>US 8,519,129 |

TABLE 18-continued

| Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein. | | | |
|---|---|---|---|
| Compound Designation | Generic Name Tradename | Compound Structure | Patents/Patent Application Publications |
| A44 | | 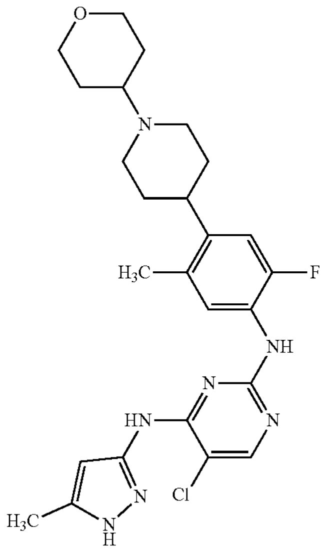 [SMILES: Cc1cc(Nc2nc(Nc3cc(C)c(C4CCN(C5CCOCC5)CC4)cc3F)ncc2Cl)n[nH]1] | WO 2010/002655 US 8,519,129 |
| A45 | | 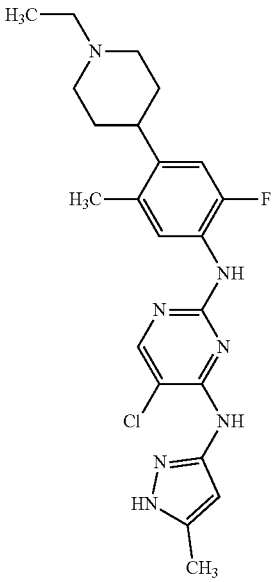 [SMILES: CCN1CCC(c2cc(F)c(Nc3ncc(Cl)c(Nc4cc(C)[nH]n4)n3)cc2C)CC1] | WO 2010/002655 |

TABLE 18-continued

Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A46 | Valspodar AMDRAY ™ | 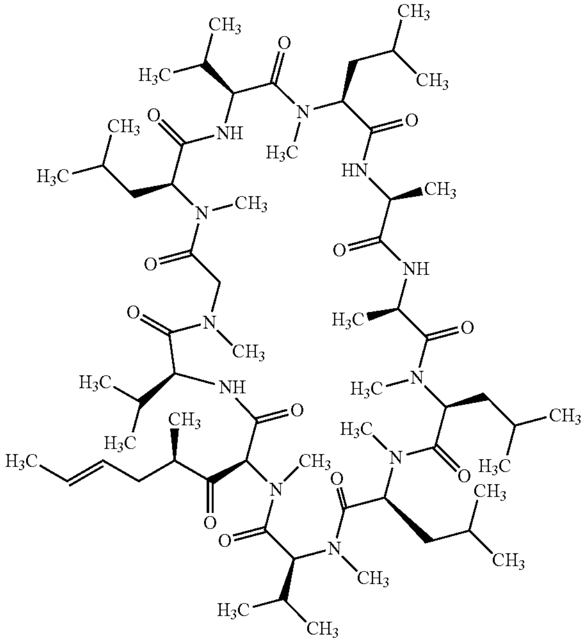 [SMILES: C/C=C/C[C@@H](C)C(=O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C] | EP 296122 |
| A47 | Vatalanib succinate | 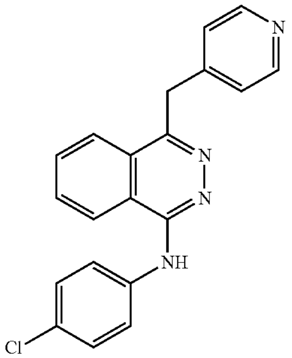 [SMILES: Clc1ccc(Nc2nnc(Cc3ccncc3)c3ccccc23)cc1] succinate | WO 98/35958 |
| A48 | | IDH inhibitor | WO2014/141104 |
| A49 | | 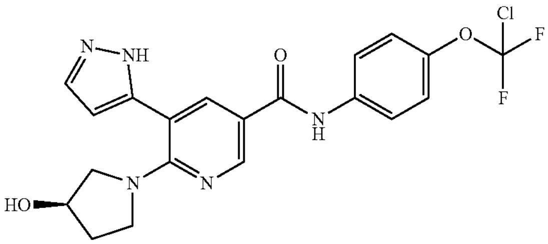 [SMILES: O=C(Nc1ccc(OC(F)(F)Cl)cc1)c1cnc(N2CC[C@@H](O)C2)c(-c2ccn[nH]2)c1] BCR-ABL inhibitor | WO2013/171639 WO2013/171640 WO2013/171641 WO2013/171642 |

TABLE 18-continued

Selected therapeutic agents that can be administered in combination with the anti-CD73 antibody molecules, e.g., as a single agent or in combination with other immunomodulators described herein. Each publication listed in this Table is herein incorporated by reference in its entirety, including all structural formulae therein.

| Compound Designation | Generic Name Tradename | Compound Structure | Patents/Patent Application Publications |
|---|---|---|---|
| A50 | | cRAF inhibitor | WO2014/151616 |
| A51 | | ERK ½ ATP competitive inhibitor | WO2015/066188 |

In some embodiments, the additional therapeutic agent is chosen from one or more of: 1) a protein kinase C (PKC) inhibitor; 2) a heat shock protein 90 (HSP90) inhibitor; 3) an inhibitor of a phosphoinositide 3-kinase (PI3K) and/or target of rapamycin (mTOR); 4) an inhibitor of cytochrome P450 (e.g., a CYP17 inhibitor or a 17alpha-Hydroxylase/C17-20 Lyase inhibitor); 5) an iron chelating agent; 6) an aromatase inhibitor; 7) an inhibitor of p53, e.g., an inhibitor of a p53/Mdm2 interaction; 8) an apoptosis inducer; 9) an angiogenesis inhibitor; 10) an aldosterone synthase inhibitor; 11) a smoothened (SMO) receptor inhibitor; 12) a prolactin receptor (PRLR) inhibitor; 13) a Wnt signaling inhibitor; 14) a CDK4/6 inhibitor; 15) a fibroblast growth factor receptor 2 (FGFR2)/fibroblast growth factor receptor 4 (FGFR4) inhibitor; 16) an inhibitor of macrophage colony-stimulating factor (M-CSF); 17) an inhibitor of one or more of c-KIT, histamine release, Flt3 (e.g., FLK2/STK1) or PKC; 18) an inhibitor of one or more of VEGFR-2 (e.g., FLK-1/KDR), PDGFRbeta, c-KIT or Raf kinase C; 19) a somatostatin agonist and/or a growth hormone release inhibitor; 20) an anaplastic lymphoma kinase (ALK) inhibitor; 21) an insulin-like growth factor 1 receptor (IGF-1R) inhibitor; 22) a P-Glycoprotein 1 inhibitor; 23) a vascular endothelial growth factor receptor (VEGFR) inhibitor; 24) a BCR-ABL kinase inhibitor; 25) an FGFR inhibitor; 26) an inhibitor of CYP11B2; 27) a HDM2 inhibitor, e.g., an inhibitor of the HDM2-p53 interaction; 28) an inhibitor of a tyrosine kinase; 29) an inhibitor of c-MET; 30) an inhibitor of JAK; 31) an inhibitor of DAC; 32) an inhibitor of 11β-hydroxylase; 33) an inhibitor of IAP; 34) an inhibitor of PIM kinase; 35) an inhibitor of Porcupine; 36) an inhibitor of BRAF, e.g., BRAF V600E or wild-type BRAF; 37) an inhibitor of HER3; 38) an inhibitor of MEK; or 39) an inhibitor of a lipid kinase, e.g., as described herein and in Table 18.

Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-ß inhibitor)), a RAF-1 inhibitor, a KIT inhibitor and a RET inhibitor.

In one embodiment, the combination, e.g., a combination comprising an anti-CD73 antibody molecule as described herein, includes or is used in combination with a PKC inhibitor, Sotrastaurin (Compound A1), or a compound disclosed in PCT Publication No. WO 2005/039549, to treat a disorder, e.g., a disorder described herein. In one embodiment, the PKC inhibitor is Sotrastaurin (Compound A1) or a compound disclosed in PCT Publication No. WO 2005/039549. In one embodiment, an anti-CD73 antibody molecule is used in combination with Sotrastaurin (Compound A1), or a compound as described in PCT Publication No. WO 2005/039549, to treat a disorder such as a cancer, a melanoma, a non-Hodgkin lymphoma, an inflammatory bowel disease, transplant rejection, an ophthalmic disorder, or psoriasis.

In one embodiment, the combination, e.g., a combination comprising an anti-CD73 antibody molecule as described herein, includes or is used in combination with a BCR-ABL inhibitor, TASIGNA (Compound A2), or a compound disclosed in PCT Publication No. WO 2004/005281, to treat a disorder, e.g., a disorder described herein. In one embodiment, the BCR-ABL inhibitor is TASIGNA, or a compound disclosed in PCT Publication No. WO 2004/005281. In one embodiment, an anti-CD73 antibody molecule is used in combination with TASIGNA (Compound A2), or a compound as described in PCT Publication No. WO 2004/005281, to treat a disorder such as a lymphocytic leukemia, Parkinson's Disease, a neurologic cancer, a melanoma, a digestive/gastrointestinal cancer, a colorectal cancer, a myeloid leukemia, a head and neck cancer, or pulmonary hypertension.

In another embodiment, the combination, e.g., a combination comprising an anti-CD73 antibody molecule as described herein, includes or is used in combination with an HSP90 inhibitor, to treat a disorder, e.g., a disorder described herein, e.g., a cancer, a multiple myeloma, a non-small cell lung cancer, a lymphoma, a gastric cancer, a breast cancer, a digestive/gastrointestinal cancer, a pancreatic cancer, a colorectal cancer, a solid tumor, or a hematopoiesis disorder.

In another embodiment, the combination, e.g., a combination comprising an anti-CD73 antibody molecule as described herein, is used in combination with an inhibitor of PI3K and/or mTOR, 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), to treat a disorder, e.g., a disorder described herein. In one embodiment, the PI3K and/or mTOR inhibitor is 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41). In one embodiment, an anti-CD73 antibody molecule is used in combination with 8-(6-Methoxy-pyridin-3-yl)-3-methyl-1-(4-piperazin-1-yl-3-trifluoromethyl-phenyl)-1,3-dihydro-imidazo[4,5-c]quinolin-2-one (Compound A41), to treat a disorder such as a cancer, a prostate cancer, a leukemia (e.g., lymphocytic leukemia), a breast cancer, a brain cancer, a bladder cancer, a pancreatic cancer, a renal cancer, a solid tumor, or a liver cancer.

In another embodiment, the combination, e.g., a combination comprising an anti-CD73 antibody molecule as described herein, includes or is used in combination with an FGFR inhibitor, 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002, to treat a disorder, e.g., a disorder described herein. In one embodiment, the FGFR inhibitor is 3-(2,6-dichloro-3,5-dimethoxyphenyl)-1-(6-((4-(4-ethylpiperazin-1-yl)phenyl)amino)pyrimidin-4-yl)-1-methylurea (Compound A5) or a compound disclosed in U.S. Pat. No. 8,552,002. In one embodiment, an anti-CD73 antibody molecule is used in combination with Compound A5, or a compound as described in U.S. Pat. No. 8,552,002, to treat a disorder such as a digestive/gastrointestinal cancer, a hematological cancer, or a solid tumor. Compound A5 has the following structure:

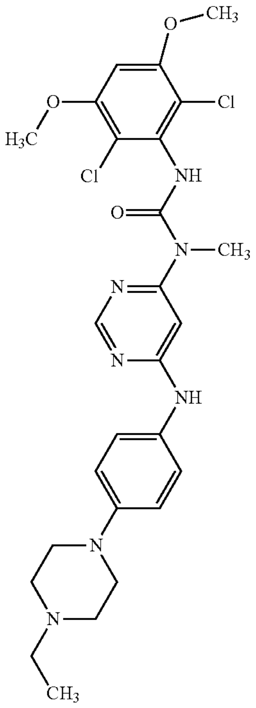

In another embodiment, the combination, e.g., a combination comprising an anti-CD73 antibody molecule as described herein, includes or is used in combination with a PI3K inhibitor, Buparlisib (Compound A6), or a compound disclosed in PCT Publication No. WO 2007/084786, to treat a disorder, e.g., a disorder described herein. In one embodiment, the PI3K inhibitor is Buparlisib (Compound A6) or a compound disclosed in PCT Publication No. WO 2007/084786. In one embodiment, an anti-CD73 antibody molecule is used in combination with Buparlisib (Compound A6), or a compound disclosed in PCT Publication No. WO 2007/084786, to treat a disorder such as, a prostate cancer, a non-small cell lung cancer, an endocrine cancer, a leukemia, an ovarian cancer, a melanoma, a bladder cancer, a breast cancer, a female reproductive system cancer, a digestive/gastrointestinal cancer, a colorectal cancer, a glioblastoma multiforme, a solid tumor, a non-Hodgkin lymphoma, a hematopoiesis disorder, or a head and neck cancer. Compound A6 has the following structure:

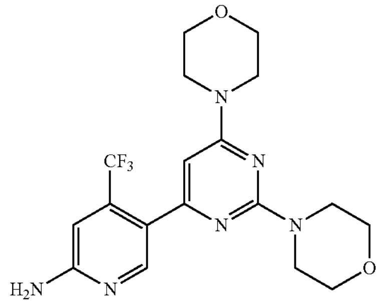 [SMILES: Nc1cc(C(F)(F)F)c(-c2cc(N3CCOCC3)nc(N3CCOCC3)n2)cn1]

In another embodiment, the combination, e.g., a combination comprising an anti-CD73 antibody molecule as described herein, includes or is used in combination with an FGFR inhibitor, 8-(2,6-difluoro-3,5-dimethoxyphenyl)-N-(4-((dimethylamino)methyl)-1H-imidazol-2-yl)quinoxaline-5-carboxamide (Compound A7) or a compound disclosed in PCT Publication No. WO 2009/141386 to treat a disorder, e.g., a disorder described herein. In one embodiment, the FGFR inhibitor is 8-(2,6-difluoro-3,5-dimethoxyphenyl)-N-(4-((dimethylamino)methyl)-1H-imidazol-2-yl) quinoxaline-5-carboxamide (Compound A7) or a compound disclosed in a PCT Publication No. WO 2009/141386. In one embodiment, the FGFR inhibitor is 8-(2,6-difluoro-3,5-dimethoxyphenyl)-N-(4-((dimethylamino)methyl)-1H-imidazol-2-yl)quinoxaline-5-carboxamide (Compound A7). In one embodiment, an anti-CD73 antibody molecule is used in combination with 8-(2,6-difluoro-3,5-dimethoxyphenyl)-N-(4-((dimethylamino)methyl)-1H-imidazol-2-yl)quinoxaline-5-carboxamide (Compound A7), or a compound disclosed in PCT Publication No. WO 2009/141386, to treat a disorder such as a cancer characterized by angiogenesis.

In another embodiment the combination, e.g., a combination comprising an anti-CD73 antibody molecule as described herein, includes or is used in combination with a PI3K inhibitor, (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082 to treat a disorder, e.g., a disorder described herein. In one embodiment, the PI3K inhibitor is (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8) or a compound disclosed PCT Publication No. WO 2010/029082. In one embodiment, an anti-CD73 antibody molecule is used in combination with (S)—N1-(4-methyl-5-(2-(1,1,1-trifluoro-2-methylpropan-2-yl)pyridin-4-yl)thiazol-2-yl)pyrrolidine-1,2-dicarboxamide (Compound A8), or a compound disclosed PCT Publication No. WO 2010/029082, to treat a disorder such as a gastric cancer, a breast cancer, a pancreatic cancer, a digestive/gastrointestinal cancer, a solid tumor, and a head and neck cancer.

In another embodiment, the combination, e.g., a combination comprising an anti-CD73 antibody molecule as described herein, includes or is used in combination with an inhibitor of cytochrome P450 (e.g., a CYP17 inhibitor) or a compound disclosed in PCT Publication No. WO 2010/149755, to treat a disorder, e.g., a disorder described herein. In one embodiment, the cytochrome P450 inhibitor (e.g., the CYP17 inhibitor) is CFG920 or a compound disclosed in PCT Publication No. WO 2010/149755; U.S. Pat. No. 8,263,635 B2; or EP 2445903 B1. In one embodiment, an anti-CD73 antibody molecule is used in combination with a compound disclosed in PCT Publication No. WO 2010/149755, to treat prostate cancer.

In another embodiment, the combination, e.g., a combination comprising an anti-CD73 antibody molecule as described herein, includes or is used in combination with an HDM2 inhibitor, (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786 to treat a disorder, e.g., a disorder described herein). In one embodiment, the HDM2 inhibitor is (S)-1-(4-chlorophenyl)-7-isopropoxy-6-methoxy-2-(4-(methyl(((1r,4S)-4-(4-methyl-3-oxopiperazin-1-yl)cyclohexyl)methyl)amino)phenyl)-1,2-dihydroisoquinolin-3(4H)-one (Compound A10) or a compound disclosed in PCT Publication No. WO 2011/076786. In one embodiment, an anti-CD73 antibody molecule is used in combination with (S)-1-(4-chlorophenyl)-7-isopropoxy-6-methoxy-2-(4-(methyl(((1 r,4S)-4-(4-methyl-3-oxopiperazin-1-yl)cyclohexyl)methyl)amino)phenyl)-1,2-dihydroisoquinolin-3(4H)-one (Compound A10), or a compound disclosed in PCT Publication No. WO 2011/076786, to treat a disorder such as a solid tumor.

In another embodiment, the combination, e.g., a combination comprising an anti-CD73 antibody molecule as described herein, includes or is used in combination with an iron chelating agent, Deferasirox (also known as EXJADE; Compound A11), or a compound disclosed in PCT Publication No. WO 1997/049395 to treat a disorder, e.g., a disorder described herein. In one embodiment, the iron chelating agent is Deferasirox or a compound disclosed in PCT Publication No. WO 1997/049395. In one embodiment, the iron chelating agent is Deferasirox (Compound A11). In one embodiment, an anti-CD73 antibody molecule is used in combination with Deferasirox (Compound A11), or a compound disclosed in PCT Publication No. WO 1997/049395, to treat iron overload, hemochromatosis, or myelodysplasia.

In another embodiment, the combination, e.g., a combination comprising an anti-CD73 antibody molecule as described herein, includes or is used in combination with an aromatase inhibitor, Letrozole (also known as FEMARA; Compound A12), or a compound disclosed in U.S. Pat. No. 4,978,672 to treat a disorder, e.g., a disorder described herein. In one embodiment, the aromatase inhibitor is Letrozole (Compound A12) or a compound disclosed in U.S. Pat. No. 4,978,672. In one embodiment, an anti-CD73 antibody molecule is used in combination with Letrozole (Compound A12), or a compound disclosed in U.S. Pat. No. 4,978,672, to treat a disorder such as a cancer, a leiomyosarcoma, an endometrium cancer, a breast cancer, a female reproductive system cancer, or a hormone deficiency.

In another embodiment, the combination, e.g., a combination comprising an anti-CD73 antibody molecule as described herein, includes or is used in combination with a PI3K inhibitor, e.g., a pan-PI3K inhibitor, (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826 to treat a disorder, e.g., a disorder described herein. In one embodiment, the PI3K inhibitor is (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13) or a compound disclosed in PCT Publication No. WO2013/124826. In one embodiment, an anti-CD73 antibody molecule is used in combination with (4S,5R)-3-(2'-amino-2-morpholino-4'-(trifluoromethyl)-[4,5'-bipyrimidin]-6-yl)-4-(hydroxymethyl)-5-methyloxazolidin-2-one (Compound A13), or a compound disclosed in PCT Publication No. WO2013/124826, to treat a disorder such as a cancer or an advanced solid tumor.

In another embodiment, the combination, e.g., a combination comprising an anti-CD73 antibody molecule as described herein, includes or is used in combination with an inhibitor of p53 and/or a p53/Mdm2 interaction, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105 to treat a disorder, e.g., a disorder described herein. In one embodiment, the p53 and/or a p53/Mdm2 interaction inhibitor is (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14) or a compound disclosed in PCT Publication No. WO2013/111105. In one embodiment, an anti-CD73 antibody molecule is used in combination with (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one (Compound A14), or a compound disclosed in PCT Publication No. WO2013/111105, to treat a disorder such as a cancer or a soft tissue sarcoma.

In another embodiment, the combination, e.g., a combination comprising an anti-CD73 antibody molecule as described herein, includes or is used in combination with a CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224 to treat a disorder, e.g., a disorder described herein. In one embodiment, the CSF-1R tyrosine kinase inhibitor is 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224. In one embodiment, an anti-CD73 antibody molecule is used in combination with 4-((2-(((1R,2R)-2-hydroxycyclohexyl)amino)benzo[d]thiazol-6-yl)oxy)-N-methylpicolinamide (Compound A15) or a compound disclosed in PCT Publication No. WO 2005/073224, to treat a disorder such as cancer.

In certain embodiments, the CSF-1R tyrosine kinase inhibitor, 4-((2-(((1R,2R)-2-hydroxycyclohexyl)amino)benzo[d]thiazol-6-yl)oxy)-N-methylpicolinamide (Compound A15), or a compound disclosed in PCT Publication No. WO 2005/073224, is administered in combination with the CD73 inhibitor (e.g., the anti-CD73 antibody molecule) to treat a cancer, e.g., a solid tumor (e.g., an advanced solid tumor). Exemplary cancers that can be treated by the combination include, but are not limited to, a brain cancer (e.g., glioblastoma multiforme (GBM), e.g., recurrent glioblastoma), a breast cancer (e.g., a triple-negative breast cancer (e.g., NTBC)), or a pancreatic cancer (e.g., advanced pancreatic cancer). The common features of these cancers include, e.g., a tumor biology characterized by high levels of TAMs in the tumor microenvironment that may contribute to immune evasion and immune suppression. In some embodiments, blockade of CSF-1R in conjunction with an anti-CD73 therapy can, e.g., promote re-programming of TAMs and/or remove immune suppression of tumor infiltrating lymphocytes (TIL).

In another embodiment, the combination, e.g., a combination comprising an anti-CD73 antibody molecule as described herein, includes or is used in combination with an apoptosis inducer and/or an angiogenesis inhibitor, such as Imatinib mesylate (also known as GLEEVEC®; Compound A16) or a compound disclosed in PCT Publication No. WO1999/003854 to treat a disorder, e.g., a disorder described. In one embodiment, the apoptosis inducer and/or an angiogenesis inhibitor is Imatinib mesylate (Compound A16) or a compound disclosed in PCT Publication No. WO1999/003854. In one embodiment, an anti-CD73 antibody molecule is used in combination with Imatinib mesylate (Compound A16), or a compound disclosed in PCT Publication No. WO1999/003854, to treat a disorder such as a cancer, a multiple myeloma, a prostate cancer, a non-small cell lung cancer, a lymphoma, a gastric cancer, a melanoma, a breast cancer, a pancreatic cancer, a digestive/gastrointestinal cancer, a colorectal cancer, a glioblastoma multiforme, a liver cancer, a head and neck cancer, asthma, multiple sclerosis, allergy, Alzheimer's dementia, amyotrophic lateral sclerosis, or rheumatoid arthritis.

In another embodiment, the combination, e.g., a combination comprising an anti-CD73 antibody molecule as described herein, includes or is used in combination with a JAK inhibitor, 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514, to treat a disorder, e.g., a disorder described herein. In one embodiment, the JAK inhibitor is 2-fluoro-N-methyl-4-(7-(quinolin-6-ylmethyl)imidazo[1,2-b][1,2,4]triazin-2-yl)benzamide (Compound A17), or a dihydrochloric salt thereof, or a compound disclosed in PCT Publication No. WO 2007/070514. In one embodiment, an anti-CD73 antibody molecule is used in combination with 2-fluoro-N-methyl-4-(7-(quinolin-6-ylmethyl)imidazo[1,2-b][1,2,4]triazin-2-yl) benzamide (Compound A17), or a dihydrochloric salt thereof, or a compound disclosed in PCT Publication No. WO 2007/070514, to treat a disorder such as colorectal cancer, myeloid leukemia, hematological cancer, autoimmune disease, non-Hodgkin lymphoma, or thrombocythemia.

In another embodiment, the combination, e.g., a combination comprising an anti-CD73 antibody molecule as described herein, includes or is used in combination with a JAK inhibitor, Ruxolitinib Phosphate (also known as JAKAFI; Compound A18) or a compound disclosed in PCT Publication No. WO 2007/070514 to treat a disorder, e.g., a disorder described herein. In one embodiment, the JAK inhibitor is Ruxolitinib Phosphate (Compound A18) or a compound disclosed in PCT Publication No. WO 2007/070514. In one embodiment, an anti-CD73 antibody molecule is used in combination with Ruxolitinib Phosphate (Compound A18), or a compound disclosed in PCT Publication No. WO 2007/070514, to treat a disorder such as a prostate cancer, a lymphocytic leukemia, a multiple myeloma, a lymphoma, a lung cancer, a leukemia, cachexia, a breast cancer, a pancreatic cancer, rheumatoid arthritis, psoriasis, a colorectal cancer, a myeloid leukemia, a hematological cancer, an autoimmune disease, a non-Hodgkin lymphoma, or thrombocythemia.

In another embodiment, the combination, e.g., a combination comprising an anti-CD73 antibody molecule as described herein, includes or is used in combination with a deacetylase (DAC) inhibitor, Panobinostat (Compound A19), or a compound disclosed in PCT Publication No. WO 2014/072493 to treat a disorder, e.g., a disorder described herein. In one embodiment, the DAC inhibitor is Panobinostat (Compound A19) or a compound disclosed in PCT Publication No. WO 2014/072493. In one embodiment, an anti-CD73 antibody molecule is used in combination with Panobinostat (Compound A19), a compound disclosed in PCT Publication No. WO 2014/072493, to treat a disorder such as a colorectal cancer, a small cell lung cancer, a respiratory/thoracic cancer, a prostate cancer, a multiple myeloma, myelodysplastic syndrome, a bone cancer, a non-small cell lung cancer, an endocrine cancer, a lymphoma, a neurologic cancer, a leukemia, HIV/AIDS, an immune disorder, transplant rejection, a gastric cancer, a melanoma, a breast cancer (e.g., a triple negative breast cancer (TNBC)), a pancreatic cancer, a colorectal cancer, a glioblastoma multiforme, a myeloid leukemia, a hematological cancer, a renal cancer, a non-Hodgkin lymphoma, a head and neck cancer, a hematopoiesis disorders, or a liver cancer. In some embodiments, the cancer is chosen from a colorectal cancer (e.g., a microsatellite stable colorectal cancer (MSS CRC), a lung cancer (e.g., a non-small cell lung cancer), or a breast cancer (e.g., a triple negative lung cancer (TNBC)).

In some embodiments, the combination described herein includes a deacetylase (DAC) inhibitor, Panobinostat (Compound A19), or a compound disclosed in PCT Publication No. WO 2014/072493, and an inhibitor of an immune checkpoint molecule, e.g., an inhibitor of CD73 (e.g., an anti-CD73 antibody molecule).

In one embodiment, the DAC inhibitor, Panobinostat (Compound A19), or a compound disclosed in PCT Publication No. WO 2014/072493, is administered in combination with the CD73 inhibitor (e.g., the anti-CD73 antibody molecule) to treat a colorectal cancer (e.g., an MSS CRC), a lung cancer (e.g., a non-small cell lung cancer (NSCLC), or a breast cancer (e.g., a triple negative breast cancer (TNBC)).

In another embodiment, the combination, e.g., a combination comprising an anti-CD73 antibody molecule as described herein, includes or is used in combination with an inhibitor of one or more of cytochrome P450 (e.g., 11B2), aldosterone or angiogenesis, Osilodrostat (Compound A20), or a compound disclosed in PCT Publication No. WO2007/024945 to treat a disorder, e.g., a disorder described herein. In one embodiment, the inhibitor of one or more of cytochrome P450 (e.g., 11B2), aldosterone or angiogenesis is Osilodrostat (Compound A20) or a compound disclosed in PCT Publication No. WO2007/024945. In one embodiment, an anti-CD73 antibody molecule is used in combination with Osilodrostat (Compound A20), or a compound disclosed in PCT Publication No. WO2007/024945, to treat a disorder such as Cushing's syndrome, hypertension, or heart failure therapy.

In another embodiment, the combination, e.g., a combination comprising an anti-CD73 antibody molecule as described herein, includes or is used in combination with a IAP inhibitor, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003 to treat a disorder, e.g., a disorder described herein. In one embodiment, the IAP inhibitor is (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21) or a compound disclosed in U.S. Pat. No. 8,552,003. In one embodiment, an anti-CD73 antibody molecule is used in combination with (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide (Compound A21), or a compound disclosed in U.S. Pat. No. 8,552,003, to treat a disorder such as a multiple myeloma, a colorectal cancer (CLC), a lung cancer (e.g., non-small cell lung cancer (NSCLC), a breast cancer (e.g., a triple-negative breast cancer (TNBC)), an ovarian cancer, a pancreatic cancer, or a hematopoiesis disorder. In some embodiments, the cancer is chosen from a colorectal cancer (e.g., a microsatellite stable colorectal cancer (MSS CRC), a lung cancer (e.g., a non-small cell lung cancer), or a breast cancer (e.g., a triple negative lung cancer (TNBC)).

In another embodiment, the combination, e.g., a combination comprising an anti-CD73 antibody molecule as described herein, includes or is used in combination a Smoothened (SMO) inhibitor, (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2010/007120 to treat a disorder, e.g., a disorder described herein. In one embodiment, the SMO inhibitor is (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2010/007120. In one embodiment, an anti-CD73 antibody molecule is used in combination with (R)-2-(5-(4-(6-benzyl-4,5-dimethylpyridazin-3-yl)-2-methylpiperazin-1-yl)pyrazin-2-yl)propan-2-ol (Compound A25), or a compound disclosed in PCT Publication No. WO 2010/007120 to treat a disorder such as a cancer, a medulloblastoma, a small cell lung cancer, a prostate cancer, a basal cell carcinoma, a pancreatic cancer, or an inflammation.

In another embodiment, the combination, e.g., a combination comprising an anti-CD73 antibody molecule as described herein, includes or is used in combination with an Alk inhibitor, ceritinib (also known as ZYKADIA; Compound A23) to treat a disorder, e.g., a disorder described herein. In one embodiment, the Alk inhibitor is ceritinib (Compound A23). In one embodiment, an anti-CD73 antibody molecule is used in combination with ceritinib (Compound A23), to treat a disorder such as non-small cell lung cancer or solid tumors.

In another embodiment, the combination, e.g., a combination comprising an anti-CD73 antibody molecule as described herein, includes or is used in combination with a JAK and/or CDK4/6 inhibitor, 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. Nos. 8,415,355 or 8,685,980 to treat a disorder, e.g., a disorder described herein. In one embodiment, the JAK and/or CDK4/6 inhibitor is 7-cyclopentyl-N,N-dimethyl-2-((5-(piperazin-1-yl)pyridin-2-yl)amino)-7H-pyrrolo[2,3-d]pyrimidine-6-carboxamide (Compound A24) or a compound disclosed in U.S. Pat. Nos. 8,415,355 or 8,685,980. In one embodiment, an anti-CD73 antibody molecule is used in combination with 7-cyclopentyl-N,N-dimethyl-2-((5-(piperazin-1-yl)pyridin-2-yl)amino)-7H-pyrrolo[2,3-d]pyrimidine-6-carboxamide (Compound A24), or a compound disclosed in U.S. Pat. Nos. 8,415,355 or 8,685,980, to treat a disorder such as a lymphoma, a neurologic cancer, a melanoma, a breast cancer, or a solid tumor.

In another embodiment, the combination, e.g., a combination comprising an anti-CD73 antibody molecule as described herein, includes or is used in combination a prolactin receptor (PRLR) inhibitor, a human monoclonal antibody molecule (Compound A26) as disclosed in U.S. Pat. No. 7,867,493), to treat a disorder, e.g., a disorder described herein. In one embodiment, the PRLR inhibitor is a human monoclonal antibody (Compound A26) disclosed in U.S. Pat. No. 7,867,493. In one embodiment, an anti-CD73 antibody molecule is used in combination with human monoclonal antibody molecule (Compound A26) described in U.S. Pat. No. 7,867,493 to treat a disorder such as, a cancer, a prostate cancer, or a breast cancer.

In another embodiment, the combination, e.g., a combination comprising an anti-CD73 antibody molecule as described herein, includes or is used in combination with a PIM Kinase inhibitor, N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124 to treat a disorder, e.g., a disorder described herein. In one embodiment, the PIM Kinase inhibitor is N-(4-((1R,3S,5S)-3-amino-5-methylcyclohexyl)pyridin-3-yl)-6-(2,6-difluorophenyl)-5-fluoropicolinamide (Compound A27) or a compound disclosed in PCT Publication No. WO 2010/026124. In one embodiment, an anti-CD73 antibody molecule is used in combination with N-(4-((1R,3S,5S)-3-amino-5-methylcyclohexyl)pyridin-3-yl)-6-(2,6-difluorophenyl)-5-fluoropicolinamide (Compound A27), or a compound disclosed in PCT Publication No. WO 2010/026124, to treat a disorder such as a multiple myeloma, myelodysplastic syndrome, a myeloid leukemia, or a non-Hodgkin lymphoma.

In another embodiment, the combination, e.g., a combination comprising an anti-CD73 antibody molecule as described herein, includes or is used in combination a Wnt signaling inhibitor, 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849 to treat a disorder, e.g., a disorder described herein. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28) or a compound disclosed in PCT publication No. WO 2010/101849. In one embodiment, the Wnt signaling inhibitor is 2-(2',3-dimethyl-[2,4'-bipyridin]-5-yl)-N-(5-(pyrazin-2-yl)pyridin-2-yl)acetamide (Compound A28). In one embodiment, an anti-CD73 antibody molecule is used in combination with 2-(2',3-dimethyl-[2,4'-bipyridin]-5-yl)-N-(5-(pyrazin-2-yl)pyridin-2-yl)acetamide (Compound A28), or a compound disclosed in PCT publication No. WO 2010/101849, to treat a disorder such as a solid tumor (e.g., a head and neck cancer, a squamous cell carcinoma, a breast cancer, a pancreatic cancer, or a colon cancer). In certain embodiments, the cancer is chosen from a skin cancer (e.g., a melanoma), a microsatellite instability-high (MSI-high) solid tumor, a pancreatic cancer, or a breast cancer (e.g., a triple negative breast cancer (TNBC)).

In another embodiment, the combination, e.g., a combination comprising an anti-CD73 antibody molecule as described herein, includes or is used in combination with a BRAF inhibitor, to treat a disorder, e.g., a disorder described herein, e.g., a non-small cell lung cancer, a melanoma, or a colorectal cancer.

In another embodiment, the combination, e.g., a combination comprising an anti-CD73 antibody molecule as described herein, includes or is used in combination a CDK4/6 inhibitor, 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30), or a compound disclosed in PCT publication No. WO 2011/101409 to treat a disorder, e.g., a disorder described herein. In one embodiment, the CDK4/6 inhibitor is 7-cyclopentyl-N,N-dimethyl-2-((5-((1R,6S)-9-methyl-4-oxo-3,9-diazabicyclo[4.2.1]nonan-3-yl)pyridin-2-yl)amino)-7H-pyrrolo[2,3-d]pyrimidine-6-carboxamide (Compound A30) or a compound disclosed in PCT publication No. WO 2011/101409. In one embodiment, an anti-CD73 antibody molecule is used in combination with 7-cyclopentyl-N,N-dimethyl-2-((5-((1R,6S)-9-methyl-4-oxo-3,9-diazabicyclo[4.2.1]nonan-3-yl)pyridin-2-yl) amino)-7H-pyrrolo[2,3-d]pyrimidine-6-carboxamide (Compound A30), or a compound disclosed in PCT publication No. WO 2011/101409, to treat a disorder such as a cancer, a mantle cell lymphoma, a liposarcoma, a non-small cell lung cancer, a melanoma, a squamous cell esophageal cancer, or a breast cancer.

In another embodiment, the combination, e.g., a combination comprising an anti-CD73 antibody molecule as described herein, includes or is used in combination with a HER3 inhibitor, Compound A31, or a compound disclosed in PCT Publication No. WO 2012/022814, to treat a disorder, e.g., a disorder described herein. In one embodiment, the HER3 inhibitor is Compound A31 or a compound disclosed in PCT Publication WO 2012/022814. In one embodiment, an anti-CD73 antibody molecule is used in combination with Compound A31, or a compound disclosed in PCT Publication WO 2012/022814, to treat a disorder such as a gastric cancer, an esophageal cancer, a head and neck cancer, a squamous cell carcinoma, a stomach cancer, a breast cancer (e.g., metastatic breast cancer), or a digestive/gastrointestinal cancer.

In another embodiment, the combination, e.g., a combination comprising an anti-CD73 antibody molecule as described herein, includes or is used in combination an FGFR2 and/or FGFR4 inhibitor, Compound A32, or a compound disclosed in a publication PCT Publication No. WO 2014/160160 (e.g., an antibody molecule drug conjugate against an FGFR2 and/or FGFR4, e.g., mAb 12425), to treat a disorder, e.g., a disorder described herein. In one embodiment, the FGFR2 and/or FGFR4 inhibitor is Compound A32 or a compound disclosed in a publication PCT Publication No. WO 2014/160160. In one embodiment, an anti-CD73 antibody molecule is used in combination with Compound A32, or a compound as described in Table 18, to treat a disorder such as a cancer, a gastric cancer, a breast cancer, a rhabdomyosarcoma, a liver cancer, an adrenal cancer, a lung cancer, an esophageal cancer, a colon cancer, or an endometrial cancer.

In some embodiments, Compound A32 is an antibody molecule drug conjugate against an FGFR2 and/or FGFR4, e.g., mAb 12425.

In another embodiment, the combination, e.g., a combination comprising an anti-CD73 antibody molecule as described herein, includes or is used in combination an M-CSF inhibitor, Compound A33, or a compound disclosed in PCT Publication No. WO 2004/045532 (e.g., an antibody molecule or Fab fragment against M-CSF), to treat a disorder, e.g., a disorder described herein. In one embodiment, the M-CSF inhibitor is Compound A33 or a compound disclosed in PCT Publication No. WO 2004/045532. In one embodiment, an anti-CD73 antibody molecule is used in combination with Compound A33, or a compound as described in PCT Publication No. WO 2004/045532, to treat a disorder such as a cancer, a prostate cancer, a breast cancer, or pigmented villonodular synovitis (PVNS).

In another embodiment, the combination, e.g., a combination comprising an anti-CD73 antibody molecule as described herein, includes or is used in combination with a MEK inhibitor, to treat a disorder such as a non-small cell lung cancer, a multisystem genetic disorder, a melanoma, an ovarian cancer, a digestive/gastrointestinal cancer, a rheumatoid arthritis, or a colorectal cancer.

In another embodiment, the combination, e.g., a combination comprising an anti-CD73 antibody molecule as described herein, includes or is used in combination an inhibitor of one or more of c-KIT, histamine release, Flt3 (e.g., FLK2/STK1) or PKC, Midostaurin (Compound A35) or a compound disclosed in PCT Publication No. WO 2003/037347 to treat a disorder, e.g., a disorder described herein.

In one embodiment, the inhibitor is Midostaurin (Compound A35) or compound disclosed in PCT Publication No. WO 2003/037347. In one embodiment, the inhibitor of one or more of c-KIT, histamine release, Flt3 (e.g., FLK2/STK1) or PKC is Midostaurin. In one embodiment, an anti-CD73 antibody molecule is used in combination with Midostaurin (Compound A35), or compound disclosed in PCT Publication No. WO 2003/037347, to treat a disorder such as a cancer, a colorectal cancer, a myeloid leukemia, myelodysplastic syndrome, an age-related macular degeneration, a diabetic complication, or a dermatologic disorder.

In another embodiment, the combination, e.g., a combination comprising an anti-CD73 antibody molecule as described herein, includes or is used in combination with a TOR inhibitor (e.g., mTOR inhibitor), Everolimus (also known as AFINITOR; Compound A36) or a Compound disclosed in PCT Publication No. WO 2014/085318 to treat a disorder, e.g., a disorder described herein). In one embodiment, the TOR inhibitor is Everolimus (Compound A36) or a Compound disclosed in PCT Publication No. WO 2014/085318. In one embodiment, an anti-CD73 antibody molecule is used in combination with Everolimus (Compound A36) to treat a disorder such as a colorectal cancer, an interstitial lung disease, a small cell lung cancer, a respiratory/thoracic cancer, a prostate cancer, a multiple myeloma, a sarcoma, an age-related macular degeneration, a bone cancer, tuberous sclerosis, a non-small cell lung cancer, an endocrine cancer, a lymphoma, a neurologic disorders, an astrocytoma, a cervical cancer, a neurologic cancer, a leukemia, an immune disorders, transplant rejection, a gastric cancer, a melanoma, epilepsy, a breast cancer (e.g., a triple-negative breast cancer (TNBC), or a bladder cancer. In some embodiments, the cancer is chosen from a colorectal cancer (e.g., a microsatellite stable colorectal cancer (MSS CRC), a lung cancer (e.g., a non-small cell lung cancer), or a breast cancer (e.g., a triple negative lung cancer (TNBC)).

In some embodiments, the combination described herein includes the mTOR inhibitor, everolimus (Compound A36), or a compound disclosed in PCT Publication No. WO 2014/085318, and an inhibitor of an immune checkpoint molecule, e.g., an inhibitor of CD73 (e.g., an anti-CD73 antibody molecule).

In another embodiment, the combination, e.g., a combination comprising an anti-CD73 antibody molecule as described herein, includes or is used in combination an inhibitor of one or more of VEGFR-2, PDGFRbeta, KIT or Raf kinase C, 1-methyl-5-((2-(5-(trifluoromethyl)-1H-imidazol-2-yl)pyridin-4-yl)oxy)-N-(4-(trifluoromethyl)phenyl)-1H-benzo[d]imidazol-2-amine (Compound A37) or a compound disclosed in PCT Publication No. WO 2007/030377 to treat a disorder, e.g., a disorder described herein.

In one embodiment, the inhibitor of one or more of VEGFR-2, PDGFRbeta, KIT or Raf kinase C is 1-methyl-5-((2-(5-(trifluoromethyl)-1H-imidazol-2-yl)pyridin-4-yl) oxy)-N-(4-(trifluoromethyl)phenyl)-1H-benzo[d]imidazol-2-amine (Compound A37) or a compound disclosed in PCT Publication No. WO 2007/030377. In one embodiment, an anti-CD73 antibody molecule is used in combination with 1-methyl-5-((2-(5-(trifluoromethyl)-1H-imidazol-2-yl)pyridin-4-yl)oxy)-N-(4-(trifluoromethyl)phenyl)-1H-benzo[d] imidazol-2-amine (Compound A37), or a compound disclosed in PCT Publication No. WO 2007/030377, to treat a disorder such as a cancer, a melanoma, or a solid tumor.

In another embodiment, the combination, e.g., a combination comprising an anti-CD73 antibody molecule as described herein, includes or is used in combination a somatostatin agonist and/or growth hormone release inhibitor, Pasireotide diaspartate (also known as SIGNIFOR; Compound A38) or a compound disclosed in PCT Publication No. WO2002/010192 or U.S. Pat. No. 7,473,761 to treat a disorder, e.g., a disorder described herein. In one embodiment, the somatostatin agonist and/or growth hormone release inhibitor is Pasireotide diaspartate (Compound A38) or a compound disclosed in PCT Publication No. WO2002/010192 or U.S. Pat. No. 7,473,761. In one embodiment, an anti-CD73 antibody molecule is used in combination with Pasireotide diaspartate (Compound A38), or a compound disclosed in PCT Publication No. WO2002/010192 or U.S. Pat. No. 7,473,761, to treat a disorder such as a prostate cancer, an endocrine cancer, a nurologic cancer, a neuroendocrine tumor (NET) (e.g., an atypical pulmonary carcinoid tumor), a skin cancer (e.g., a melanoma or Merkel cell carcinoma), a pancreatic cancer, a liver cancer, Cushing's syndrome, a gastrointestinal disorder, acromegaly, a liver and biliary tract disorder, or liver cirrhosis.

In another embodiment, the combination, e.g., a combination comprising an anti-CD73 antibody molecule as described herein, includes or is used in combination a signal transduction modulator and/or angiogenesis inhibitor, e.g., to treat a disorder such as a cancer, a respiratory/thoracic cancer, a multiple myeloma, a prostate cancer, a non-small cell lung cancer, an endocrine cancer, or a neurological genetic disorder.

In another embodiment, the combination, e.g., a combination comprising an anti-CD73 antibody molecule as described herein, includes or is used in combination with an EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40) or a compound disclosed in PCT Publication No. WO 2013/184757 to treat a disorder, e.g., a disorder described herein. In one embodiment, the EGFR inhibitor is (R,E)-N-(7-chloro-1-(1-(4-(dimethylamino) but-2-enoyl)azepan-3-yl)-1H-benzo[d]imidazol-2-yl)-2-methylisonicotinamide (Compound A40) or a compound disclosed in PCT Publication No. WO 2013/184757. In one embodiment, an anti-CD73 antibody molecule is used in combination with (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, to treat a disorder such as a cancer, e.g., a solid tumor.

In some embodiments, the EGFR inhibitor, (R,E)-N-(7-chloro-1-(1-(4-(dimethylamino)but-2-enoyl)azepan-3-yl)-1H-benzo[d]imidazol-2-yl)-2-methylisonicotinamide (Compound A40), or a compound disclosed in PCT Publication No. WO 2013/184757, is administered in combination with an inhibitor of CD73 (e.g., an anti-CD73 antibody molecule) to treat a colorectal cancer (CRC), a lung cancer (e.g., a non-small cell lung cancer (NSCLC)), or a breast cancer (e.g., a triple negative breast cancer (TNBC)).

In another embodiment, the combination, e.g., a combination comprising an anti-CD73 antibody molecule as described herein, includes or is used in combination an ALK inhibitor, $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687 to treat a disorder, e.g., a disorder described herein. In one embodiment, the ALK inhibitor is $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42) or a compound disclosed in PCT Publication No. WO 2008/073687. In one embodiment, an anti-CD73 antibody molecule is used in combination with $N^6$-(2-isopropoxy-5-methyl-4-(1-methylpiperidin-4-yl)phenyl)-$N^4$-(2-(isopropylsulfonyl)phenyl)-1H-pyrazolo[3,4-d]pyrimidine-4,6-diamine (Compound A42), or a compound disclosed in PCT Publication No. WO 2008/073687, to treat a disorder such as a cancer, an anaplastic large-cell lymphoma (ALCL), a non-small cell lung carcinoma (NSCLC), or a neuroblastoma.

In another embodiment, the combination, e.g., a combination comprising an anti-CD73 antibody molecule as described herein, includes or is used in combination an IGF-1R inhibitor, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-$N^4$-(5-methyl-1H-pyrazol-3-yl)pyrimidine-2,4-diamine (Compound A44), or 5-chloro-N2-(4-(1-ethylpiperidin-4-yl)-2-fluoro-5-methylphenyl)-N-(5-methyl-1H-pyrazol-3-yl)pyrimidine-2,4-diamine (Compound A45) or a compound disclosed in PCT Publication No. WO 2010/002655 to treat a disorder, e.g., a disorder described. In one embodiment, the IGF-1R inhibitor is 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-N-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-N-(5-methyl-1H-pyrazol-3-yl)pyrimidine-2,4-diamine (Compound A45), or a compound disclosed in PCT Publication No. WO 2010/002655. In one embodiment, an anti-CD73 antibody molecule is used in combination with 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide (Compound A43), 5-chloro-$N^2$-(2-fluoro-5-methyl-4-(1-(tetrahydro-2H-pyran-4-yl)piperidin-4-yl)phenyl)-N-(5-methyl-1H-pyrazol-3-yl)pyrimidine-2,4-diamine (Compound A44), 5-chloro-N2-(4-(1-ethylpiperidin-4-yl)-2-fluoro-5-methylphenyl)-N-(5-methyl-1H-pyrazol-3-yl)pyrimidine-2,4-diamine (Compound A45), or a compound disclosed in PCT Publication No.

WO 2010/002655, to treat a disorder such as a cancer or a sarcoma.

In another embodiment, the combination, e.g., a combination comprising an anti-CD73 antibody molecule as described herein, includes or is used in combination a P-Glycoprotein 1 inhibitor, Valspodar (also known as AMDRAY; Compound A46) or a compound disclosed in EP 296122 to treat a disorder, e.g., a disorder described herein. In one embodiment, the P-Glycoprotein 1 inhibitor is Valspodar (Compound A46) or a compound disclosed in EP 296122. In one embodiment, an anti-CD73 antibody molecule is used in combination with Valspodar (Compound A46), or a compound disclosed in EP 296122, to treat a disorder such as a cancer or a drug-resistant tumor.

In another embodiment, the combination, e.g., a combination comprising an anti-CD73 antibody molecule as described herein, includes or is used in combination one or more of a VEGFR inhibitor, Vatalanib succinate (Compound A47) or a compound disclosed in EP 296122 to treat a disorder, e.g., a disorder described herein. In one embodiment, the VEGFR inhibitor is Vatalanib succinate (Compound A47) or a compound disclosed in EP 296122. In one embodiment, an anti-CD73 antibody molecule is used in combination with Vatalanib succinate (Compound A47), or a compound disclosed in EP 296122, to treat cancer.

In another embodiment, the combination, e.g., a combination comprising an anti-CD73 antibody molecule as described herein, includes or is used in combination with an IDH inhibitor or a compound disclosed in WO2014/141104 to treat a disorder, e.g., a disorder described herein. In one embodiment, the IDH inhibitor is a compound disclosed in PCT Publication No. WO2014/141104. In one embodiment, an anti-CD73 antibody molecule is used in combination with a compound disclosed in WO2014/141104 to treat a disorder such as a cancer.

In another embodiment, the combination, e.g., a combination comprising an anti-CD73 antibody molecule as described herein, includes or is used in combination with a BCL-ABL inhibitor or a compound disclosed in PCT Publication No. WO2013/171639, WO2013/171640, WO2013/171641, or WO2013/171642 to treat a disorder, e.g., a disorder described herein. In one embodiment, the BCL-ABL inhibitor is a compound disclosed in PCT Publication No. WO2013/171639, WO2013/171640, WO2013/171641, or WO2013/171642. In one embodiment, an anti-CD73 antibody molecule is used in combination with a compound disclosed in PCT Publication No. WO2013/171639, WO2013/171640, WO2013/171641, or WO2013/171642 to treat a disorder such as a cancer.

In another embodiment, the combination, e.g., a combination comprising an anti-CD73 antibody molecule as described herein, includes or is used in combination with a c-RAF inhibitor or a compound disclosed in PCT Publication No. WO2014/151616 to treat a disorder, e.g., a disorder described herein. In one embodiment, the c-RAF inhibitor is Compound A50 or a compound disclosed in PCT Publication No. WO2014/151616. In some embodiments, the c-RAF inhibitor or Compound A50 is a compound of formula (I):

(I)

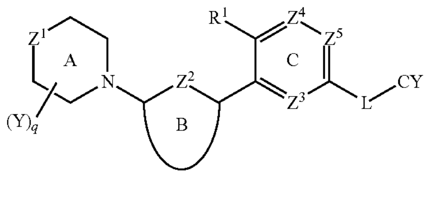

or a pharmaceutically acceptable salt thereof, wherein:

$Z^1$ is O, S, S(=O) or $SO_2$;

$Z^2$ is N, S or $CR^a$, where $R^a$ is H, halo, $C_{1-4}$ alkyl or $C_{1-4}$ haloalkyl;

$R^1$ is CN, halo, OH, $C_{1-4}$ alkoxy, or $C_{1-4}$ alkyl that is optionally substituted with one to three groups selected from halo, $C_{1-4}$ alkoxy, CN, and hydroxyl;

Ring B is selected from phenyl, pyridine, pyrimidine, pyrazine, pyridazine, pyridone, pyrimidone, pyrazinone, pyridazinone, and thiazole, each of which is optionally substituted with up to two groups selected from halo, OH, CN, $C_{1-4}$ alkyl, $C_{2-4}$ alkenyl, —O—($C_{1-4}$ alkyl), $NH_2$, NH—($C_{1-4}$ alkyl), —N($C_{1-4}$ alkyl)$_2$, —$SO_2R^2$, $NHSO_2R^2$, NHC(O)$R^2$, $NHCO_2R^2$, $C_{3-6}$ cycloalkyl, 5-6 membered heteroaryl, —O—$C_{3-6}$ cycloalkyl, —O-(5-6-membered heteroaryl), $C_{4-8}$ heterocycloalkyi, and —O-(4-8 membered heterocycloalkyi), where each heterocycloalkyi and heteroaryl contains up to three heteroatoms selected from N, O and S as ring members, where each $C_{1-4}$ alkyl, $C_{2-4}$ alkenyl, $C_{3-6}$ cycloalkyl, 5-6 membered heteroaryl, and 4-8 membered heterocycloalkyi is each optionally substituted with up to three groups selected from oxo, hydroxyl, halo, $C_{1-4}$ alkyl, $C_{1-4}$ haloalkyl, $C_{1-4}$ alkoxy, and —$(CH_2)_{1-2}Q$ where Q is OH, $C_{1-4}$ alkoxy, —CN, $NH_2$, —$NHR^3$, —$N(R^3)_2$, —$SO_2R^3$, $NHSO_2R^3$, NHC(O)O$R^3$, or NHC(O)$R^3$;

each $R^2$ and $R^3$ is independently $C_{1-4}$ alkyl; and

Ring B is optionally fused to a 5-6 membered aromatic or nonaromatic ring containing up to two heteroatoms selected from N, O and S, where the 5-6 membered ring can be substituted with halo, $C_{1-4}$ alkyl, $C_{1-4}$ haloalkyl, or $C_{1-4}$ alkoxy, and if the fused ring is non-aromatic the substituent options can further include oxo;

each Y is independently selected from $C_{1-4}$ alkyl, $C_{1-4}$ alkoxy, CN, halo, oxo, —$(CH_2)_pOR^4$, —$(CH_2)$p $N(R^4)_2$, —$(CH_2)$pNHC(O)$R^4$, —$(CH_2)_p$NHCOO($C_{1-4}$ alkyl), and imidazole, or two Y groups on Ring A are optionally taken together to form a ring fused to or bridging Ring A, where said fused or bridging ring optionally contains a heteroatom selected from N, O and S as a ring member, and is optionally substituted with up to two groups selected from $C_{1-4}$ alkyl, $C_{1-4}$ alkoxy, CN, halo, oxo, —$(CH_2)_pOR^4$, —$(CH_2)_p$ $N(R^4)_2$, —$(CH_2)_p$NHC(O)$R^4$, and —$(CH_2)_p$NHCOO($C_{1-4}$ alkyl);

each $R^4$ is independently H or $C_{1-4}$ alkyl;

each p is independently 0, 1, or 2;

q is 0, 1 or 2;

$Z^3$, $Z^4$, and $Z^5$ are independently selected from CH and N and optionally NO;

L is —C(=O)—$NR^4$—[CY] or —$NR^4$—C(=O)—[CY], where [CY] indicates which atom of L is attached to CY; and CY is an aromatic ring selected from phenyl, pyridine, pyrimidine, pyrazine, pyridazine, pyridone, thiazole, isothiazole, oxazole, pyrazole, and isoxazole, wherein the ring is optionally fused to a thiophene, imidazole, oxazolone, or pyrrole ring;

and CY is substituted with up to two groups selected from halo, CN, $R^5$, $OR^5$, $SO_2R^5$, —S(=NH)(=O)$R^5$, OH, $NH_2$, $NHR^5$, and —$N(R^5)_2$, wherein each $R^5$ is independently $C_{1-4}$ alkyl, $C_{2-4}$ alkenyl, $C_{2-6}$ heterocyclyl, 5-membered heteroaryl containing up to three heteroatoms selected from N, O and S as ring members, or $C_{3-8}$ cycloalkyl, and $R^5$ is optionally substituted with up to four groups selected from oxo, halo, CN, $R^6$, OH, $OR^6$, $SO_2R^6$, $NH_2$, $NHR^6$, $N(R^6)_2$, $NHSO_2R^6$, $NHCOOR^6$, NHC(=O)$R^6$, —$CH_2OR^7$, —$CH_2N(R^7)_2$, wherein each $R^6$ is independently $C_{1-4}$ alkyl, and each $R^7$ is independently H or $C_{1-4}$ alkyl;

and two $R^4$, $R^5$, $R^6$, or $R^7$ on the same nitrogen atom can be taken together to form a 5-6 membered heterocyclic ring optionally containing an additional N, O or S as a ring member and optionally substituted with up to two groups selected from $C_{1-4}$ alkyl, oxo, halo, OH, and $C_{1-4}$ alkoxy.

Methods of administering the antibody molecules are known in the art and are described below. Suitable dosages of the molecules used will depend on the age and weight of the subject and the particular drug used. Dosages and therapeutic regimens of the anti-CD73 antibody molecule can be determined by a skilled artisan.

In certain embodiments, the anti-CD73 antibody molecule is administered by injection (e.g., intravenously) at a dose (e.g., a flat dose) of about 60 mg to 2400 mg, e.g., about 100 mg to 2400 mg, about 100 mg to 2200 mg, about 100 mg to 2000 mg, about 100 mg to 1800 mg, about 100 mg to 1600 mg, about 100 mg to 1400 mg, about 100 mg to 1200 mg, about 100 mg to 1000 mg, about 100 mg to 800 mg, about 100 mg to 600 mg, about 100 mg to 400 mg, about 100 mg to 200 mg, or about 100 mg, about 180 mg, or about 200 mg. The dosing schedule can vary from e.g., once a week to once every 2, 3, or 4 weeks. In some embodiments, the anti-CD73 antibody molecule is administered at a dose of about 100 mg once every two weeks by intravenous infusion. In some embodiments, the anti-CD73 antibody molecule is administered at a dose of at least about 180 mg once every two weeks by intravenous infusion. In some embodiments, the anti-CD73 antibody molecule is administered at a dose of about 200 mg once every two weeks by intravenous infusion.

In some embodiments, an anti-CD73 antibody molecule disclosed herein is administered by injection (e.g., subcutaneously or intravenously) at a dose (e.g., a flat dose) of about 5 mg to 100 mg, about 100 mg to 500 mg, about 500 mg to 1000 mg, about 1000 mg to 1500 mg, about 1500 mg to 2000 mg, about 2000 mg to 2500 mg, about 2500 mg to 3000 mg, about 3000 mg to 3500 mg, or about 3500 mg to 4000 mg, e.g., once every week (QW), once every two weeks (Q2W), or once every four weeks (Q4W). In certain embodiments, the antibody molecule is administered, e.g., intravenously, at a dose of about 6 mg, about 20 mg, about 60 mg, about 200 mg, about 600 mg, about 1200 mg, about 2400 mg, about 3000 mg, or about 3600 mg, e.g., QW, Q2W, or Q4W. In certain embodiments, the antibody molecule is administered, e.g., intravenously, at a dose of about 60 mg Q2W. In certain embodiments, the antibody molecule is administered, e.g., intravenously, at a dose of about 200 mg Q2W. In certain embodiments, the antibody molecule is administered, e.g., intravenously, at a dose of about 600 mg Q2W. In certain embodiments, the antibody molecule is administered, e.g., intravenously, at a dose of about 1200 mg Q2W. In certain embodiments, the antibody molecule is administered, e.g., intravenously, at a dose of about 2400 mg Q2W. In certain embodiments, the antibody molecule is administered, e.g., intravenously, at a dose of about 3000 mg Q2W. In certain embodiments, the antibody molecule is administered, e.g., intravenously, at a dose of about 3600 mg Q2W.

In certain embodiments, the anti-CD73 antibody molecule is administered by injection (e.g., intravenously) at a dose of about 1 to 30 mg/kg, e.g., about 5 to 25 mg/kg, about 10 to 20 mg/kg, about 1 to 5 mg/kg, or about 3 mg/kg. In some embodiments, the anti-CD73 antibody molecule is administered at a dose of about 1 mg/kg, about 3 mg/kg, or 10 mg/kg, about 20 mg/kg, about 30 mg/kg, or about 40 mg/kg. In some embodiments, the anti-CD73 antibody molecule is administered at a dose of about 1-3 mg/kg, or about 3-10 mg/kg. In some embodiments, the anti-CD73 antibody molecule is administered at a dose of about 0.5-2, 2-4, 2-5, 5-15, or 5-20 mg/kg. The dosing schedule can vary from e.g., once a week to once every 2, 3, or 4 weeks. In one embodiment, the anti-CD73 antibody molecule is administered at a dose of about 10 to 20 mg/kg every other week.

The antibody molecules can be used in unconjugated forms or conjugated to a second agent, e.g., a cytotoxic drug, radioisotope, or a protein, e.g., a protein toxin or a viral protein. This method includes: administering the antibody molecule, alone or conjugated to a cytotoxic drug, to a subject requiring such treatment. The antibody molecules can be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g., via a viral coat protein), or mixtures thereof.

Diagnostic Uses

In one aspect, the present invention provides a diagnostic method for detecting the presence of a CD73 protein in vitro (e.g., in a biological sample, such as a tissue biopsy, e.g., from a cancerous tissue) or in vivo (e.g., in vivo imaging in a subject). The method includes: (i) contacting the sample with an antibody molecule described herein, or administering to the subject, the antibody molecule; (optionally) (ii) contacting a reference sample, e.g., a control sample (e.g., a control biological sample, such as plasma, tissue, biopsy) or a control subject)); and (iii) detecting formation of a complex between the antibody molecule, and the sample or subject, or the control sample or subject, wherein a change, e.g., a statistically significant change, in the formation of the complex in the sample or subject relative to the control sample or subject is indicative of the presence of CD73 in the sample. The antibody molecule can be directly or indirectly labeled with a detectable substance to facilitate detection of the bound or unbound antibody. Suitable detectable substances include various enzymes, prosthetic groups, fluorescent materials, luminescent materials and radioactive materials, as described above and described in more detail below.

The term "sample," as it refers to samples used for detecting polypeptides includes, but is not limited to, cells, cell lysates, proteins or membrane extracts of cells, body fluids, or tissue samples.

Complex formation between the antibody molecule and CD73 can be detected by measuring or visualizing either the binding molecule bound to the CD73 antigen or unbound binding molecule. Conventional detection assays can be used, e.g., an enzyme-linked immunosorbent assays (ELISA), a radioimmunoassay (RIA) or tissue immunohistochemistry. Alternative to labeling the antibody molecule, the presence of CD73 can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of CD73 in the sample is inversely proportional to the amount of labeled standard bound to the antibody molecule.

Nucleic Acids

The invention also features nucleic acids comprising nucleotide sequences that encode heavy and light chain variable regions and CDRs or hypervariable loops of the anti-CD73 antibody molecules, as described herein. For example, the invention features a first and second nucleic acid encoding heavy and light chain variable regions, respectively, of an anti-CD73 antibody molecule chosen from one or more of the antibody molecules disclosed herein. The nucleic acid can comprise a nucleotide sequence as set forth in Table 1, or a sequence substantially identical thereto (e.g., a sequence having at least about 85%, 90%, 95%, or 99% sequence identity thereto, or which differs by no more than 3, 6, 15, 30, or 45 nucleotides from the sequences shown in Table 1).

In certain embodiments, the nucleic acid can comprise a nucleotide sequence encoding at least one, two, or three CDRs or hypervariable loops from a heavy chain variable region having an amino acid sequence as set forth in Table 1, or a sequence substantially homologous thereto (e.g., a sequence having at least about 85%, 90%, 95%, or 99% sequence identity thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in Table 1, or a sequence substantially homologous thereto (e.g., a sequence having at least about 85%, 90%, 95%, or 99% sequence identity thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in Table 1, or a sequence substantially homologous thereto (e.g., a sequence having at least about 85%, 90%, 95%, or 99% sequence identity thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in Table 1, a sequence substantially homologous thereto (e.g., a sequence having at least about 85%, 90%, 95%, or 99% sequence identity thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in Table 1, or a sequence substantially homologous thereto (e.g., a sequence having at least about 85%, 90%, 95%, or 99% sequence identity thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in Table 1, or a sequence substantially homologous thereto (e.g., a sequence having at least about 85%, 90%, 95%, or 99% sequence identity thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail herein below.

Vectors

Further provided herein are vectors comprising nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity. Methods and conditions for culturing the resulting transfected cells and for recovering the antibody molecule produced are known to those skilled in the art, and may be varied or optimized depending upon the specific expression vector and mammalian host cell employed, based upon the present description.

Cells

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells (e.g., CHO-C8TD cells), HEK293 cells, BHK cells and MDCKII cells. Suitable insect cells include, but are not limited to, Sf9 cells.

EXAMPLES

The Examples below are set forth to aid in the understanding of the inventions but are not intended to, and should not be construed to limit its scope in any way.

Example 1: Generation and Characterization of Anti-CD73 Antibodies

Selection and Optimization of Anti-CD73 Antibodies from Synthetic Yeast Antibody Libraries Anti-CD73 monoclonal antibodies representing five distinct epitope bins were selected from eight naïve human synthetic yeast libraries using methods described below.

Materials and Methods

Antigens were biotinylated using the EZ-Link Sulfo-NHS-Biotinylation Kit from Pierce. Goat $F(ab')_2$ anti-human kappa-FITC (LC-FITC), ExtrAvidin-PE (EA-PE) and Streptavidin-AF633 (SA-633) were obtained from Southern Biotech, Sigma, and Molecular Probes, respectively. Streptavidin MicroBeads and MACS LC separation columns were purchased from Miltenyi Biotec. Goat anti-human IgG-PE (Human-PE) was obtained from Southern Biotech.

Primary Discovery

Eight naïve human synthetic yeast libraries each of $\sim 10^9$ diversity were propagated as previously described (see, e.g., Y. Xu et al, Addressing polyspecificity of antibodies selected from an in vitro yeast presentation system: a FACS-based, high-throughput selection and analytical tool. *PEDS* 26.10, 663-70 (2013); WO2009036379; WO2010105256; and WO2012009568, incorporated by reference herein in their entireties). For the first two rounds of selection, a magnetic bead sorting technique utilizing the Miltenyi MACS system was performed, as previously described (see, e.g., Siegel et al, High efficiency recovery and epitope-specific sorting of an scFv yeast display library. *J Immunol Methods* 286(1-2), 141-153 (2004), herein incorporated by reference in its entirety). Briefly, yeast cells ($\sim 10^{10}$ cells/library) were incubated with 3 ml of 100 nM biotinylated antigen for 30 min at 30° C. in wash buffer (phosphate-buffered saline (PBS)/0.1% bovine serum albumin (BSA)). After washing once with 40 ml ice-cold wash buffer, the cell pellet was resuspended in 20 mL wash buffer, and Streptavidin MicroBeads (500 μl) were added to the yeast and incubated for 15 min at 4° C. Next, the yeast cells were pelleted, resuspended in 20 mL wash buffer, and loaded onto a Miltenyi LS column. After the 20 mL was loaded, the column was washed 3 times with 3 ml wash buffer. The column was then removed from the magnetic field, and the yeast cells were eluted with 5 mL of growth media and then grown overnight. The following rounds of selection were performed using flow cytometry. Approximately $2\times10^7$ yeast cells were pelleted, washed three times with wash buffer, and incubated at 30° C. with either decreasing concentrations of biotinylated antigen (100 to 1 nM) under equilibrium conditions, 30 nM biotinylated antigens of different species in order to obtain species cross-reactivity, or with a poly-specificity depletion reagent (PSR) to remove non-specific antibodies from the selection. For the PSR depletion, the libraries were incubated with a 1:10 dilution of biotinylated PSR reagent as previously described (see, e.g., Y. Xu et al, Addressing polyspecificity of antibodies selected from an in vitro yeast presentation system: a FACS-based, high-throughput selection and analytical tool. *PEDS* 26.10, 663-70 (2013), herein incorporated by reference in its entirety). Yeast cells were then washed twice with wash buffer and stained with LC-FITC (diluted 1:100) and either SA-633 (diluted 1:500) or EAPE (diluted 1:50) secondary reagents for 15 min at 4° C. After washing twice with wash buffer, the cell pellets were resuspended in 0.3 mL wash buffer and transferred to strainer-capped sort tubes. Sorting was performed using a FACS ARIA sorter (BD Biosciences) and sort gates were determined to select for antibodies with desired characteristics. Selection rounds were repeated until a population with all of the desired characteristics was obtained. After the final round of sorting, yeast cells were plated and individual colonies were picked for characterization.

Light chain diversification protocol was used during the primary discovery phase for further discovery and improvement of antibodies.

Light chain batch diversification protocol: Heavy chain plasmids from a naïve selection output were extracted from the yeast via smash and grab, propagated in and subsequently purified from *E. coli*, and transformed into a light chain library with a diversity of $5\times10^6$. Selections were performed with one round of MACS and four rounds of FACS employing the same conditions as the naïve discovery.

Antibody Optimization

Optimization of antibodies was performed by introducing diversities into the heavy chain and light chain variable regions as described below.

CDRH1 and CDRH2 selection: The CDRH3 of a single antibody was recombined into a premade library with CDRH1 and CDRH2 variants of a diversity of $1\times10^8$ and selections were performed with one round of MACS and four rounds of FACS as described in the naïve discovery. In the different FACS rounds the libraries were looked at for PSR binding, species cross-reactivity, and affinity pressure by titration or parental Fab pre-complexing, and sorting was performed in order to obtain a population with the desired characteristics.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

ForteBio $K_D$ Measurements

ForteBio affinity measurements were performed on an Octet RED384 generally as previously described (see, e.g., Estep et al, High throughput solution-based measurement of antibody-antigen affinity and epitope binning. *Mabs* 5(2), 270-278 (2013), herein incorporated by reference in its entirety). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. All kinetics were analyzed using the 1:1 binding model. Antigens used were:

Human CD73-His: Recombinant Human 5'-Nucleotidase/CD73 Protein, CF from R&D Systems Cat: 5795-EN Mouse CD73-His: Recombinant Mouse 5'-Nucleotidase/CD73 Protein, CF from R&D Systems Cat: 4488-EN Cynomolgus CD73-His: Cynomolgus CD73/NT5E Protein (His Tag) from Sino Biological Cat: 90192-C08H-50

ForteBio Epitope Binning/Ligand Blocking

Epitope binning/ligand blocking was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Additional binding by the second antibody or ligand after antigen association indicates an unoccupied epitope (non-competitor), while no binding indicates epitope blocking (competitor or ligand blocking).

MSD-SET Kinetic Assay

Equilibrium affinity measurements performed as previously described (Estep et al., 2013). Solution equilibrium titrations (SET) were performed in PBS+0.1% IgG-Free BSA (PBSF) with antigen held constant at 10-100 μM and incubated with 3-to 5-fold serial dilutions of antibody starting at 5-100 nM (experimental condition is sample dependent). Antibodies (20 nM in PBS) were coated onto standard bind MSD-ECL plates overnight at 4° C. or at room temperature for 30 min. Plates were then blocked for 30 min with shaking at 700 rpm, followed by three washes with wash buffer (PBSF+0.05% Tween 20). SET samples were applied and incubated on the plates for 150s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

Cell Binding Analysis

Approximately 100,000 cells overexpressing the antigen were washed with wash buffer and incubated with 100 µl 100 nM IgG for 5 minutes at room temperature. Cells were then washed twice with wash buffer and incubated with 100 µl of 1:100 Human-PE for 15 minutes on ice. Cells were then washed twice with wash buffer and analyzed on a FACS Canto II analyzer (BD Biosciences).

Results

Yeast cells expressing a library of human antibodies on their surface were screened for binding to human CD73. Two antibodies from epitope bin 4, 918 and 930, bound well to CD73 and inhibited the enzymatic activity of CD73 (data not shown). These two antibodies were subjected to affinity maturation which produced two lineages of related antibodies, referred to as lineage 1 and lineage 3, respectively (Table 19). These anti-CD73 antibodies were expressed in three different formats: IgG1 antibodies (referred to as .C constructs, e.g., 350.C), IgG4 antibodies comprising an S228P mutation in the Fc region (IgG4 S228P, referred to as .A constructs, e.g., 350.A), or IgG4 antibodies comprising S228P and L235E mutations in the Fc region (IgG4 S228P/L235E, referred to as .B constructs, e.g., 350.B), numbered according to Eu numbering. The sequences of these antibodies are disclosed in Table 1. For the antibody 350.A, two lots of antibodies were produced, referred to hereafter as 350.A1 and 350.A2.

TABLE 19

Two lineages of anti-CD73 antibodies

| | Antibody | IgG1 format | IgG4 S228P format | IgG4 S228P/ L235E format |
|---|---|---|---|---|
| Lineage 1 | | | | |
| Parent | 918 | 918.C | 918.A | 918.B |
| Child | 350 | 350.C | 350.A1, 350.A2 | 350.B |
| Child | 356 | 356.C | 356.A | 356.B |
| Child | 358 | 358.C | 358.A | 358.B |
| Lineage 3 | | | | |
| Parent | 930 | 930.C | 930.A | 930.B |
| Child | 373 | 373.C | 373.A | 373.B |
| Child | 374 | 374.C | 374.A | 374.B |
| Child | 376 | 376.C | 376.A | 376.B |
| Child | 377 | 377.C | 377.A | 377.B |
| Child | 379 | 379.C | 379.A | 379.B |

All the anti-CD73 antibodies tested bind to human and cynomolgus CD73. The Lineage 1 antibodies also bind to murine CD73. Table 20 provides $K_d$ values of these antibodies measured using Octet as described above.

TABLE 20

Affinities of anti-CD73 antibodies

| mAb | Human ForteBio Whole IgG Kd (M) | Cyno ForteBio Whole IgG Kd (M) | Murine ForteBio Whole IgG Kd (M) |
|---|---|---|---|
| 918.C | 1.53E−09 | Not Determined | 8.88E−09 |
| 350.C | 2.48E−10* | 6.35E−10 | 4.09E−10* |
| 356.C | 2.43E−10* | 6.93E−10 | 4.01E−10 |
| 358.C | 3.17E−10 | 8.14E−10 | 3.51E−09 |
| 930.C | 1.83E−09 | Not Determined | Not Bound |
| 373.C | 6.21E−10 | 9.14E−10 | Not Bound |
| 374.C | 3.58E−10 | 1.03E−10 | Not Bound |
| 376.C | 3.01E−10 | Not Determined | Not Bound |
| 377.C | 5.72E−10 | 1.42E−09 | Not Bound |
| 379.C | 5.50E−10 | 1.62E−09 | Not Bound |

*Value approaching upper limit for $K_d$ measurement

Next, using epitope binning/ligand blocking studies, it was shown that the parental antibody 918 competed for binding to CD73 with the progeny antibodies 350, 356, and 358. Similarly, the parental antibody 930 competed for binding to CD73 with the progeny antibodies 373, 374, 376, 377, and 379. Both 918 and 930 were shown to compete with an internal reference anti-CD73 antibody, suggesting that these antibodies share the same epitope bin.

Fab and Antibody Affinity Measurement Using Surface Plasmon Resonance

Fabs of mAbs 350 and 373 were generated by engineering a stop between the two proline residues above the core hinge region of the heavy chain of 350 and 373. Both were expressed in Expi293F (ThermoFisher) cells and purified using CaptureSelect IgG CH1 Affinity resin (ThermoFisher).

Biacore was used to measure cross-species affinity for the Fab materials of mAbs 350 and 373. Proteins used were as follows: recombinant human CD73 (R&D Systems 5795-EN); recombinant cynomolgus monkey CD73 (Sino Biological 90912-C08H); recombinant mouse CD73 (R&D Systems 4488-EN); and recombinant rat CD73 (Sino Biological 80375-R08H). Anti-human Fab (GE Healthcare Life Sciences) was immobilized on all 4 flow cells (Fc) on a CM5 chip (GE). Fabs 350 and 373 were captured on Fc2 and Fc4, at ~20 RU. 0.01 nM to 90 nM CD73 (3-fold dilution series) was flown over all 4 Fcs. All samples were diluted in running buffer HBS-EP+(pH 7.4, 0.01 M HEPES, 150 mM NaCl, 3 mM EDTA and 0.05% (v/v) P20).

Shown in Table 21 are results for $K_d$ (M) affinity for cross-species binding of 350 and 373 Fabs.

TABLE 21

Affinities of anti-CD73 Fabs

| Fab | Antigen | $K_d$ (M) |
|---|---|---|
| Fab 350 | hCD73 | ≤1E−10 |
| Fab 350 | cCD73 | ≤1E−10 |
| Fab 350 | mCD73 | 1.728E−8 |
| Fab 350 | rCD73 | 2.829E−8 |
| Fab 373 | hCD73 | 1.304E−8 |
| Fab 373 | cCD73 | 9.465E−9 |
| Fab 373 | mCD73 | No Binding |
| Fab 373 | rCD73 | No Binding |

In a separate study, the affinity of the full-length antibody 373.A or Fab fragments of 373.A to human, cynomolgus monkey, mouse and rat CD73 was determined using an anti-histidine (His) antibody capture Biacore method utilizing surface plasmon resonance (SPR). The anti-His Ab was directly immobilized onto a CM5 chip surface by amine coupling. The His-tagged human CD73/His, cynomolgus monkey CD73/His, mouse CD73/His or rat CD73/His was flowed over and captured at a desired resonance unit (RU) for an Rmax of 20. Antibody analyte concentrations in serial dilutions of IgG or Fab were flowed over at 60 μL/min. The sensorgrams were analyzed using the manufacturer's software for a 1:1 binding model. Binding to mouse CD73/His protein and rat CD73/His protein was undetectable for 373.A and 373.A Fab, demonstrating that 373.A is not rodent cross-reactive.

Affinities were established for human and cynomolgus monkey CD73 with both 373.A and 373.A Fab. Hydrogen-deuterium mass spectrometry and size exclusion chromatography studies support a model of conformational locking of the CD73-dimer by 373.A into the open-open (inactive-inactive) conformation, supporting a 1:1 bidentate binding of 1 Ab:1 CD73 dimer (see Example 2). Therefore, given that 1:1 bidentate binding will favor avidity, the whole Ab affinities were used rather than Fab measurements. The full length antibody 373.A binds recombinant human CD73 with a $K_d$ of 0.991±0.267 nM and cross-reacts with recombinant cynomolgus monkey CD73 with a $K_d$ of 0.068±0.009 nM as determined by Biacore kinetic binding studies.

Whole Blood Target Engagement by Anti-CD73 Antibodies

Whole blood target engagement was assessed by flow cytometry using whole blood from healthy human donors. Briefly, biotinylated antibodies were incubated with whole blood for 30 minutes prior to red blood cell lysis and fixation. Fixed cells were stained for CD3 and CD8 to identify CD8+ T cells, and streptavidin-APC to detect biotin. After staining, the cell were washed and subjected to flow cytometry analysis.

Dose dependent binding, as measured by median fluorescence intensity (MFI) of APC signal, was observed for the anti-CD73 antibodies tested (FIG. 1). A biotinylated isotype control antibody did not show binding to CD8+ T cells (FIG. 1).

CD73 Target Occupancy on Human Whole Blood Samples

Figure 24A:
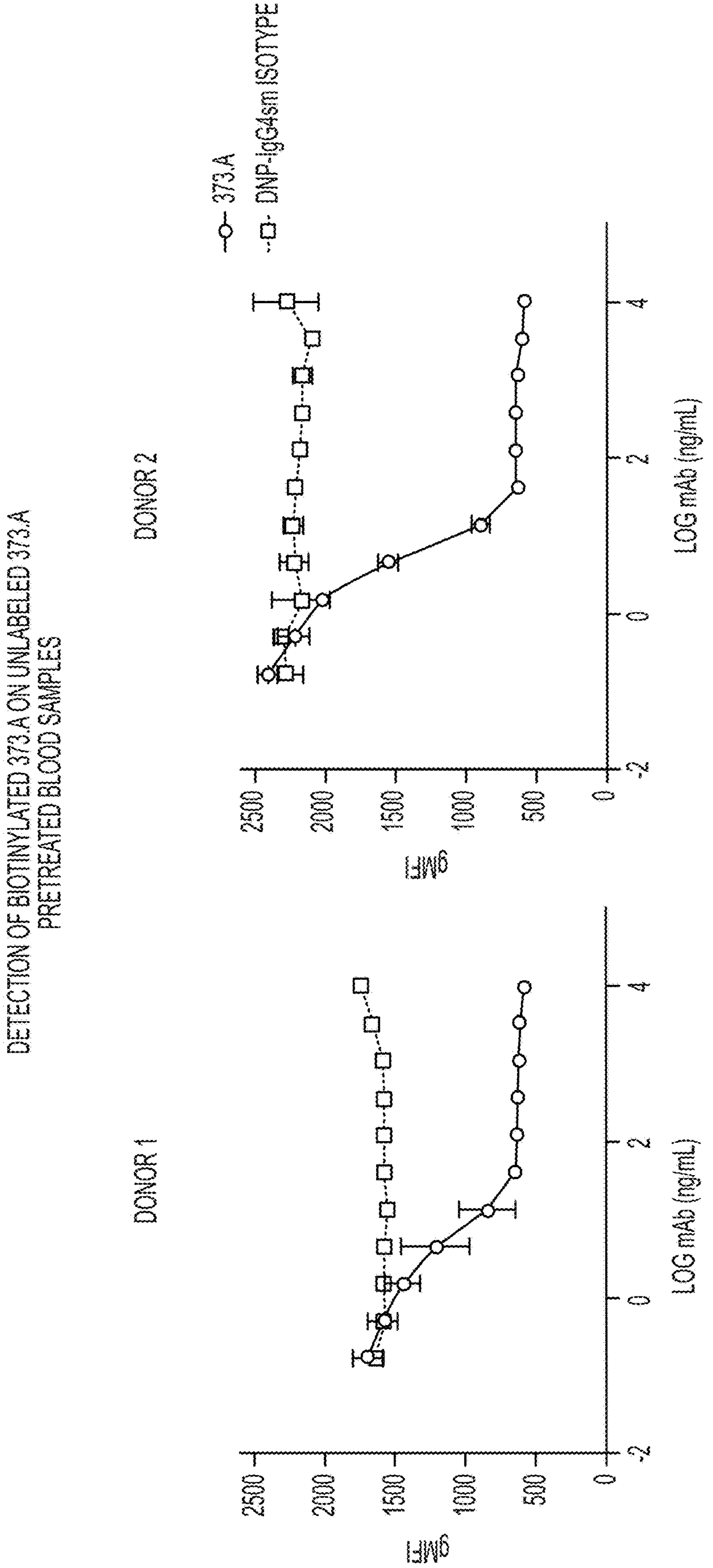
FIG. 24A is a pair of graphs showing detection of biotinylated 373.A on unlabeled 373.A pretreated blood samples from two donors.
Figure 24B:
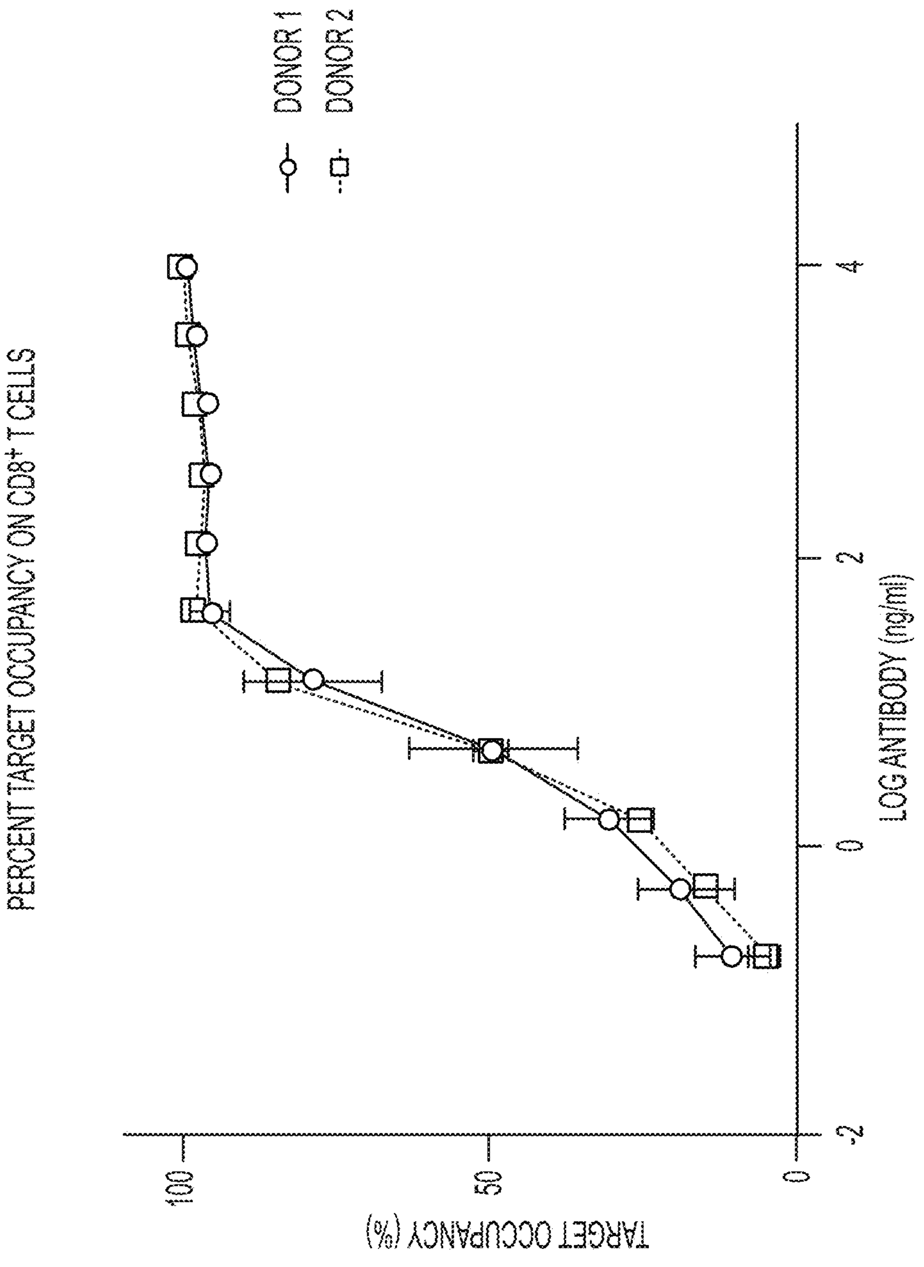
FIG. 24B is a graph showing percent target occupancy on CD8+ T cells by the antibody 373.A.

Conceptual demonstration of the target occupancy (TO) of CD73 on human whole blood samples was performed by treating donor blood ex vivo with unlabeled 373.A. A titration of 373.A or DNP-IgG4sm isotype control from 10 μg/mL to 0.17 ng/mL was performed. As shown in FIG. 24A, samples from the two donors that were treated with unlabeled 373.A at higher doses (10 μg/mL to ~0.0.1 μg/mL) prevented biotinylated 373.A from binding to the cells, reducing the geometric mean fluorescence intensity (gMFI) values to a plateau at the background level of fluorescence (~550 gMFI for both donors). This is indicative of full CD73 target occupancy. In contrast, gMFI values for cells that were pretreated with lower amounts of unlabeled 373.A (0.17 ng/mL and 0.51 ng/mL) were similar to samples that were pretreated with DNP-IgG4sm isotype control (~1600 gMFI for donor 1 and ~2200 gMFI for donor 2). Isotype control treated samples mimicked blood that had zero target occupancy. The resultant % TO values are shown in FIG. 24B.

Inhibition of the Enzymatic Activity of Soluble Recombinant CD73

5' ectonucleotidase CD73 is the rate limiting step in the conversion of AMP to adenosine. The ability of anti-CD73 antibodies to inhibit the enzymatic activity of CD73 was measured using a malachite green phosphate assay. Briefly, 25 ng/ml recombinant human CD73 was incubated with a dose titration of the substrate adenosine monophosphate (AMP) (0-500 μM) with buffer alone, or in the presence of an isotype control antibody at 1 μg/ml or the anti-CD73 antibody 350.C at 1, 0.3, or 0.1 μg/ml. Release of inorganic phosphate (Pi) was measured using a malachite green phosphate assay kit (Enzo Life Sciences, Catalog #BML-AK 11).

Figure 2A:
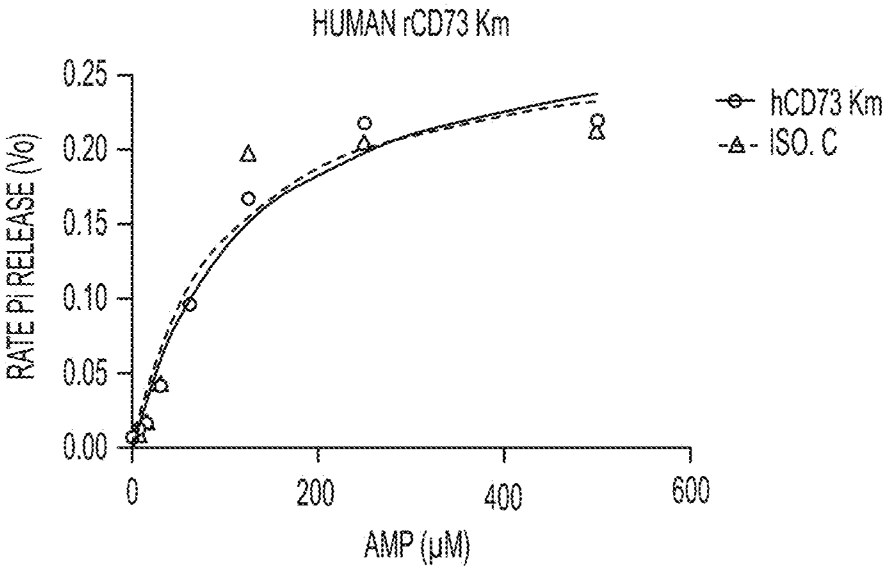
FIGS. 2A and 2B are graphs showing results from a malachite green inorganic phosphate assay testing the ability of anti-CD73 antibody to inhibit human CD73-medicated conversion of adenosine monophosphate (AMP) to adenosine. Rate of inorganic phosphate (Pi) release is plotted against AMP concentrations tested.
Figure 2B:
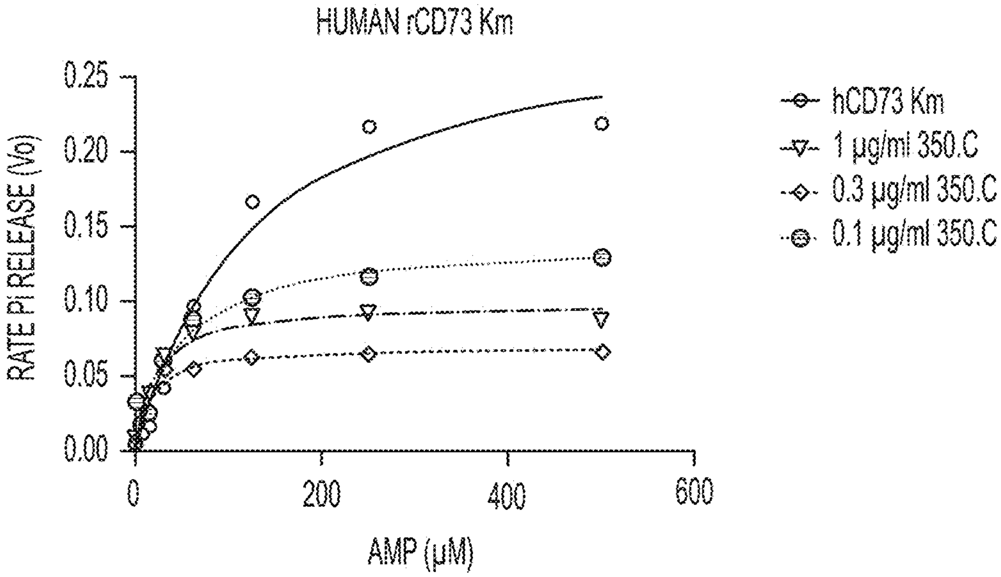

As shown in FIG. 2A, the control antibody at the tested concentration had no effect on the Michaelis constant ($K_m$) of recombinant human CD73. In contrast, the anti-CD73 antibody 350.C caused dose-dependent reduction of $V_{max}$ on $K_m$ curves (FIG. 2B), indicating that the antibody 350.C is a non-competitive inhibitor of human CD73.

Next, the anti-CD73 antibodies 350, 356, 373, and 374, expressed in either the .A or .B format, were tested for their ability to inhibit the enzymatic activity of recombinant human and cynomolgus monkey CD73 using a similar malachite green phosphate assay as described above. In brief, anti-CD73 antibodies were incubated for 10 minutes with 25 ng/ml recombinant human or cynomolgus CD73 in the presence of 25 μM AMP. Release of inorganic phosphate (Pi) was measured using a malachite green phosphate assay kit (Enzo Life Sciences, Catalog #BML-AK 11). Normalized percent inhibition (% INH) was determined using time zero control as 100% INH and no antibody control as 0% INH.

Figure 3A:
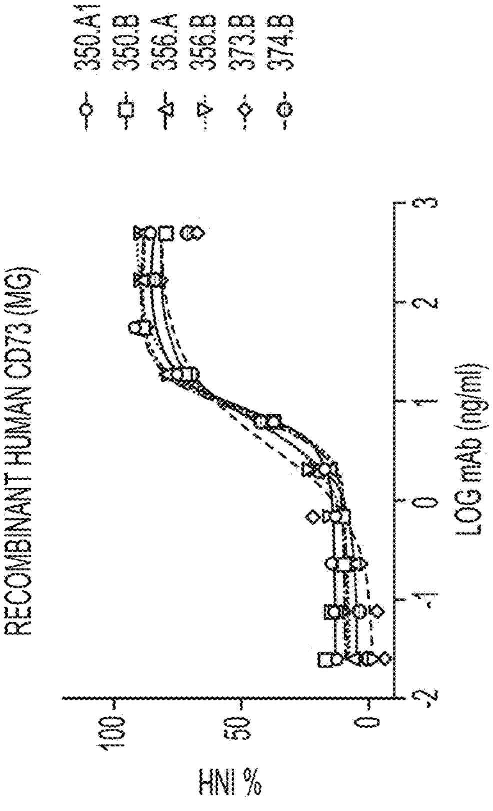
FIGS. 3A, 3B, and 3C are graphs showing results from a malachite green (MG) phosphate assay testing the ability of anti-CD73 antibody to inhibit the enzymatic activity of recombinant soluble human or cynomolgus CD73. % INH phosphate formation is plotted against anti-CD73 antibody concentrations for the studies using recombinant human CD73 (FIGS. 3A and 3B) or cynomolgus CD73 (FIG. 3C). The antibodies tested are the anti-CD73 antibodies 350, 356, 373, and 374, expressed in either the .A or .B format.
Figure 3B:
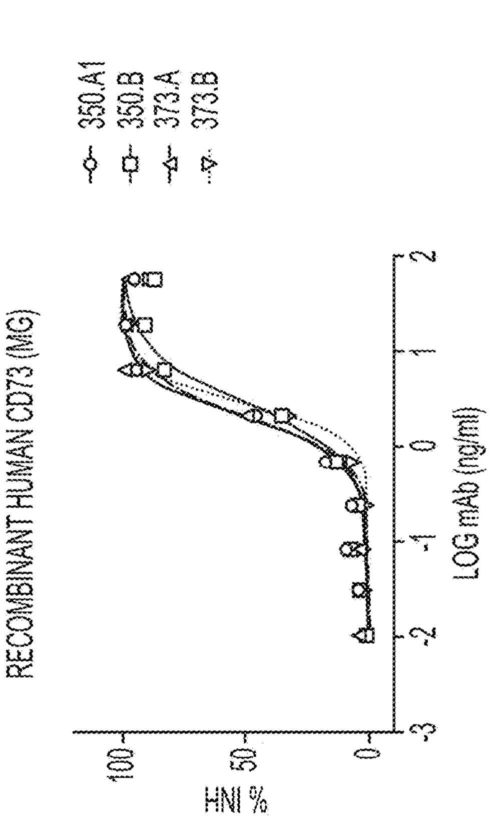
Figure 3C:
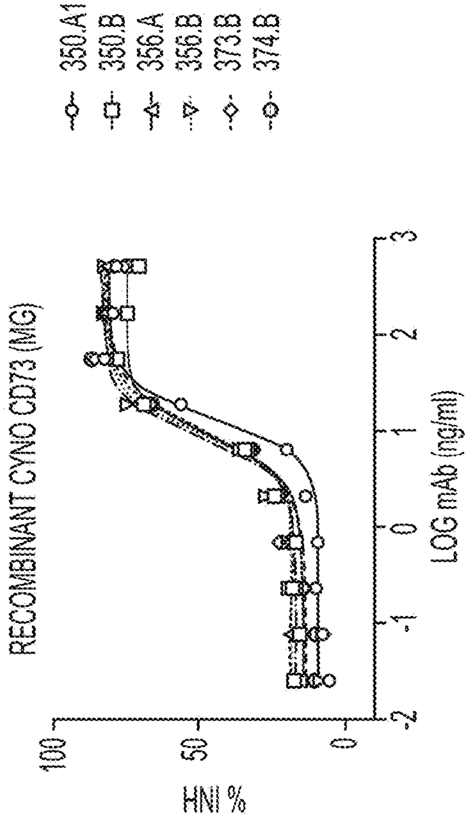

As shown in FIGS. 3A-3C, all the anti-CD73 antibodies tested inhibited the enzymatic activity of soluble recombinant human and cynomolgus CD73.

Inhibition of the Enzymatic Activity of Soluble Endogenous CD73

Further, the enzyme inhibition activity of anti-CD73 antibodies was tested against soluble endogenous CD73, for example, CD73 shed from the cell surface.

In a first study, anti-CD73 antibodies 350 and 373, expressed in either the .A or .B format, or isotype control antibodies were incubated for 240 minutes with MDA-MB-231 (a human breast cancer cell line) conditioned serum free media in the presence of 100 μM AMP. Disappearance of AMP was measured by a modified Cell Titer Glo (CTG) assay (Promega, Cat# G9242/3). AMP inhibits the luciferase signal in the CTG kit. The luciferase signal increases as the added AMP is enzymatically consumed by CD73. Normalized percent inhibition (% INH) was determined using time zero control as 100% INH and no antibody control as 0% INH.

Figure 4:
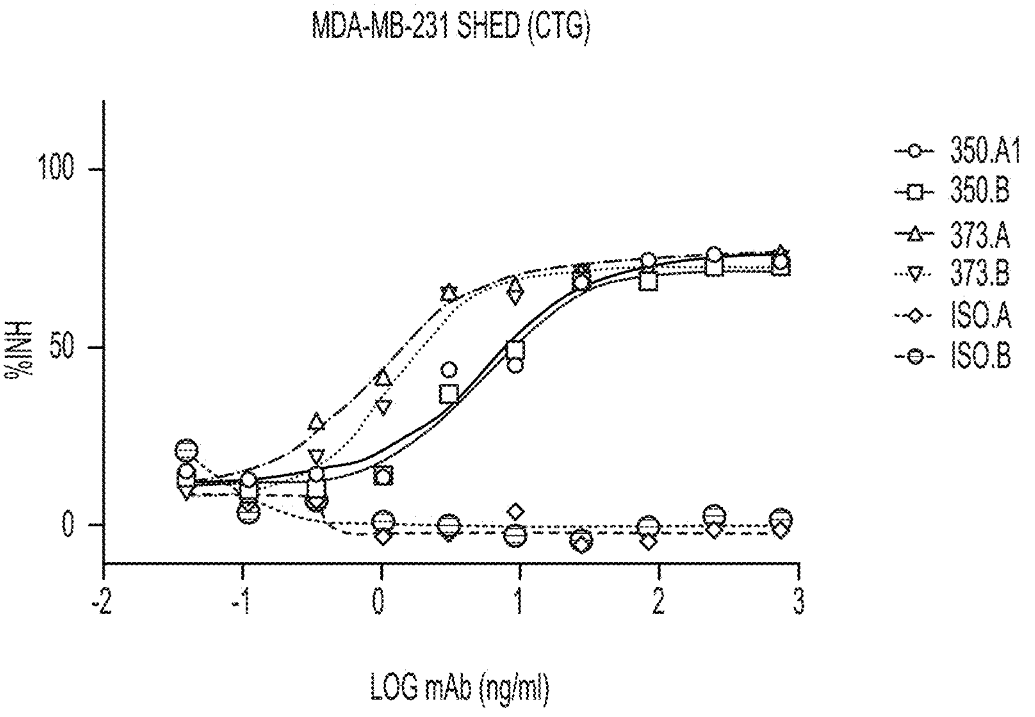
FIG. 4 is a graph showing results from a modified Cell Titer Glo (CTG) assay examining the enzyme inhibition activity of anti-CD73 antibodies against CD73 shed from a breast cancer cell line MDA-MB-231. % INH is plotted against a range of anti-CD73 antibody concentrations. The antibodies tested are the anti-CD73 antibodies 350 and 373, expressed in either the .A or .B format, an IgG4 S228P isotype control antibody ("ISO.A"), and an IgG4 S228P/L235E isotype control antibody ("ISO.B").

As shown in FIG. 4, the anti-CD73 antibodies dose-dependently inhibited the enzymatic activity of CD73 shed from the breast cancer cell line MDA-MB-231.

In a second study, anti-CD73 antibodies 350, 356, 358, 373, 374, 377, and 379, all expressed in the .B format, were incubated for 60 minutes with diluted (12.5% v:v in PBS) serum from a pancreatic cancer patient in the presence of 100 μM AMP. Similar to the first study, disappearance of AMP was measured by the modified Cell Titer Glo (CTG) assay and normalized percent inhibition (% INH) was determined using time zero control as 100% INH and no antibody control as 0% INH.

Figure 5:
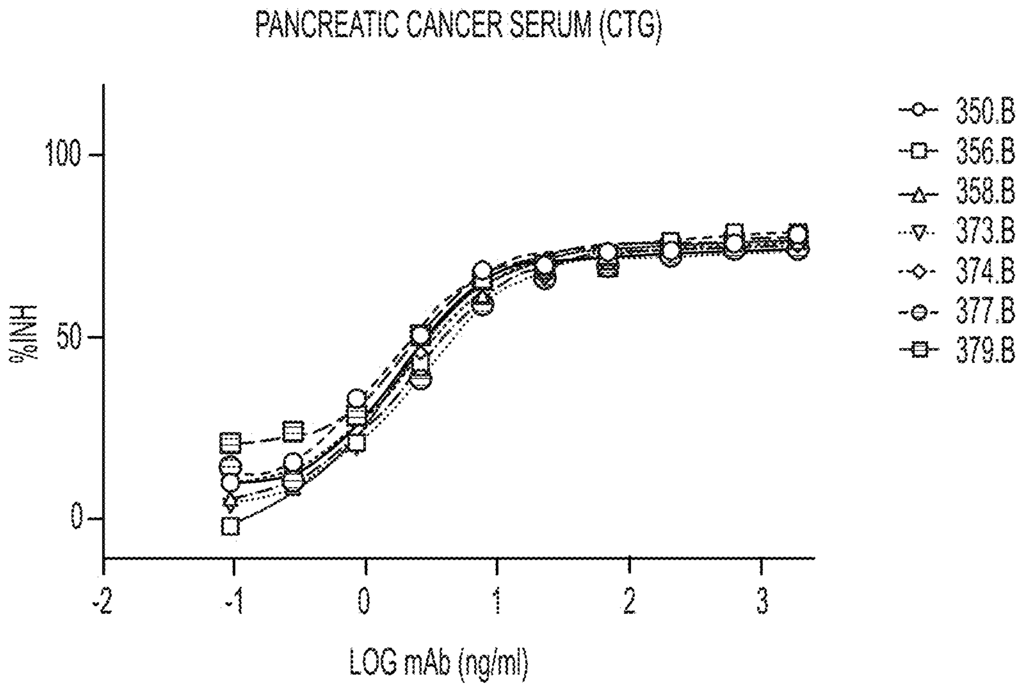
FIG. 5 is a graph showing results from a modified Cell Titer Glo (CTG) assay examining the ability of anti-CD73 antibodies to inhibit the enzymatic activity of CD73 in the serum from a pancreatic cancer patient. % INH AMP conversion is plotted against anti-CD73 antibody concentrations. The anti-CD73 antibodies tested are 350, 356, 358, 373, 374, 377, and 379, all expressed in the .B format.

Anti-CD73 antibodies also inhibited CD73 enzymatic activity in the serum from the pancreatic cancer patient in a dose-dependent manner (FIG. 5).

Inhibition of the Enzymatic Activity of CD73 Expressed on the Cell Surface

First, a malachite green phosphate assay was used to examine the ability of anti-CD73 antibodies 350, 356, 358, 373, 374, 377, and 379 (all in the .B format) to inhibit CD73 expressed on a breast cancer cell line MDA-MB-231. Briefly, antibodies were incubated for 180 minutes with cells in the presence of 100 μM AMP. Release of inorganic phosphate from AMP was measured using a malachite green phosphate assay kit (Enzo Life Sciences, Catalog #BML-AK111). Normalized percent inhibition (% INH) was determined using time zero control as 100% INH and no antibody control as 0% INH.

Figure 6:
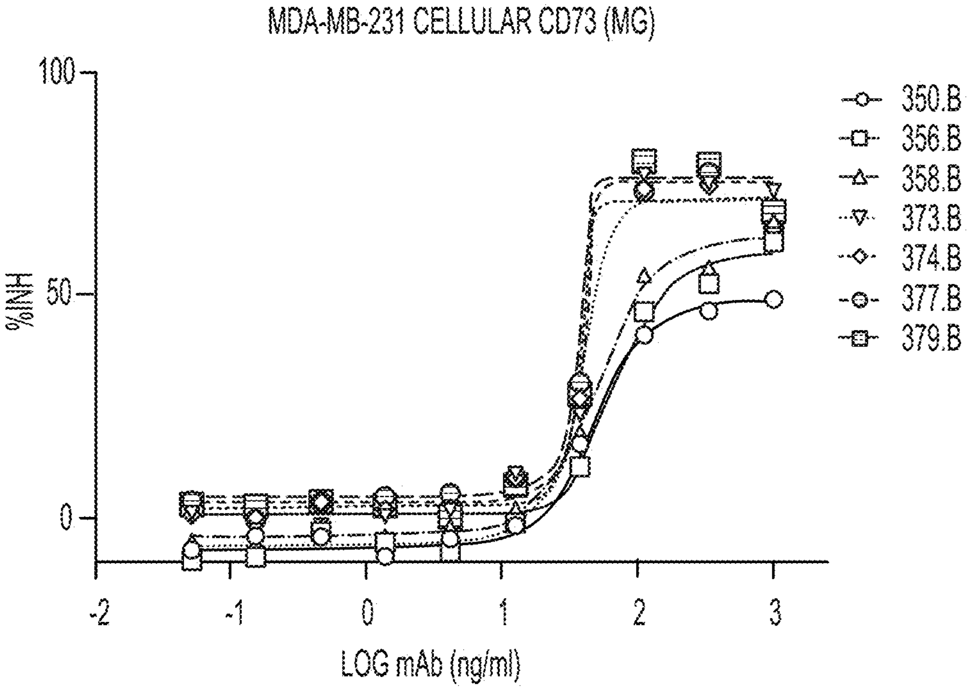
FIG. 6 is a graph showing inhibition of CD73 expressed on the surface of a breast cancer cell line MDA-MB-231, measured using a malachite green phosphate assay. % INH AMP conversion is plotted over a range of anti-CD73 antibody concentrations. The anti-CD73 antibodies tested are 350, 356, 358, 373, 374, 377, and 379, all in the .B format.

As shown in FIG. 6, all the anti-CD73 antibodies tested inhibited CD73 enzymatic activity expressed on the surface of the breast cancer cell line MDA-MB-231.

Next, since the Lineage 1 antibodies cross-react with mouse CD73 whereas the Lineage 3 antibodies do not, antibodies from both lineages were tested against CD73 expressed on the surface of a human or murine breast cancer cell line. Anti-CD73 antibodies were incubated for 240 minutes with a human breast cancer cell line MDA-MB-231 or a murine breast cancer cell line 4T1 in the presence of 100 μM AMP. Disappearance of AMP was measured by the modified Cell Titer Glo (CTG) assay described above and normalized percent inhibition (% INH) was determined using time zero control as 100% INH and no antibody control as 0% INH.

Figure 7A:
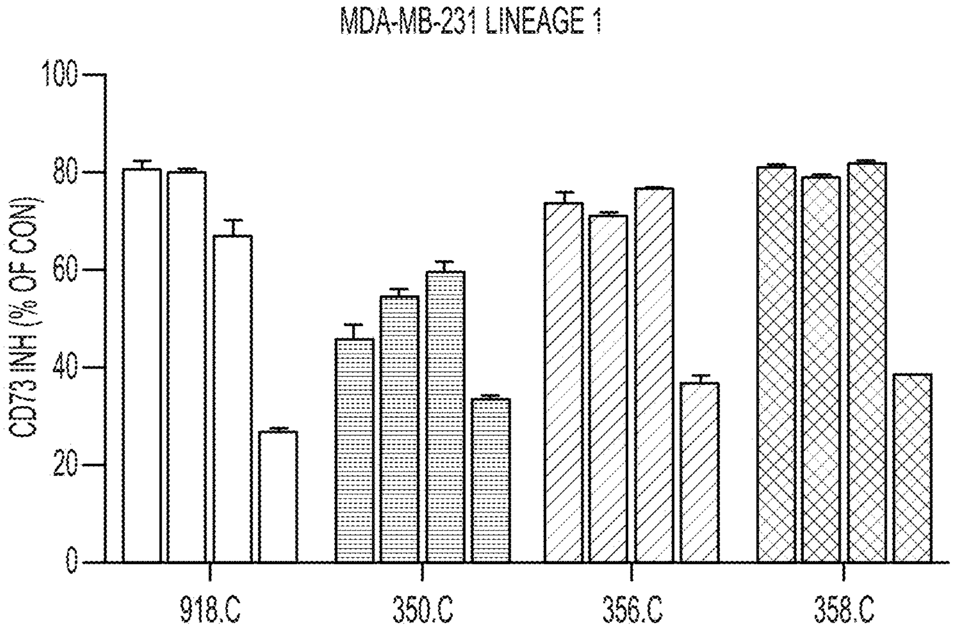
FIGS. 7A, 7B, 7C, and 7D are bar graphs showing results from a modified Cell Titer Glo (CTG) assay testing the ability of anti-CD73 antibodies to inhibit the enzymatic activity of CD73 expressed on the surface of a human breast cancer cell line MDA-MB-231 (FIGS. 7A and 7C) or a murine breast cancer cell line 4T1 (FIGS. 7B and 7D). The y-axis shows percentage of inhibition relative to the no antibody (full conversion) control and the time zero (no conversion) control. For each antibody, the bars from left to right represent 10, 3, 1, and 0.3 μg/ml doses. The antibodies tested are the Lineage 1 antibodies 918, 350, 356, and 358 (FIGS. 7A and 7B) and the Lineage 3 antibodies 930, 373, 374, 376, 377, and 379 (FIGS. 7C and 7D).
Figure 7B:
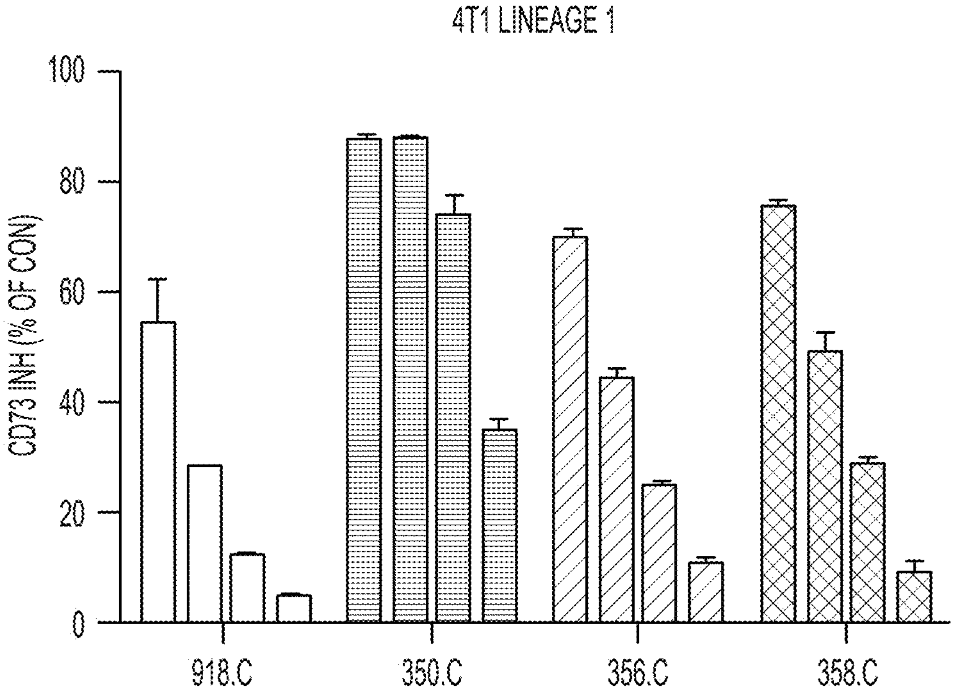
Figure 7C:
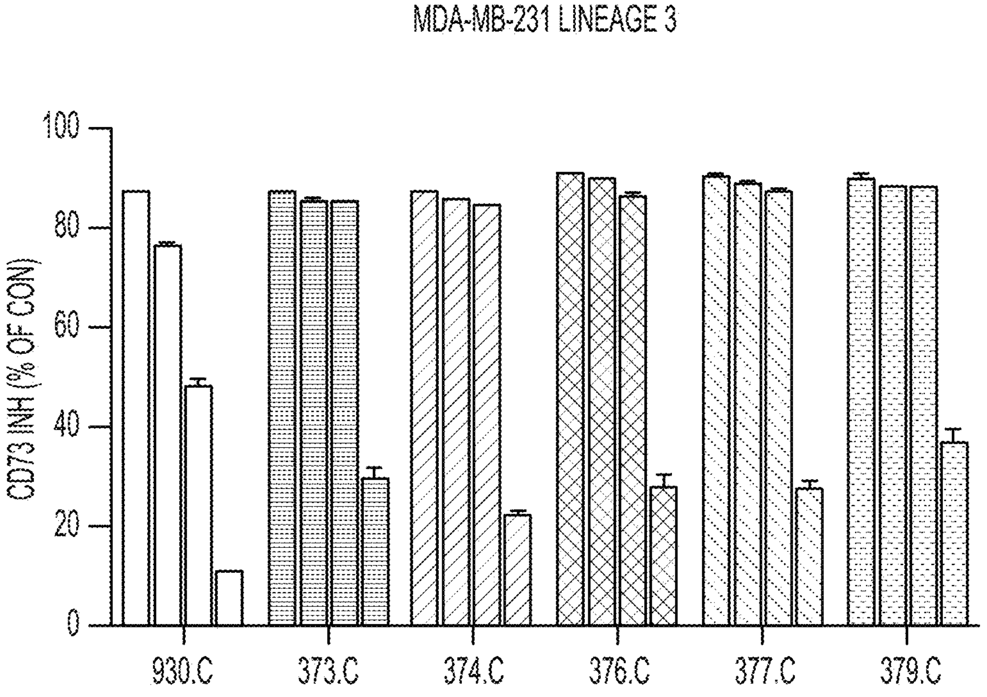
Figure 7D:
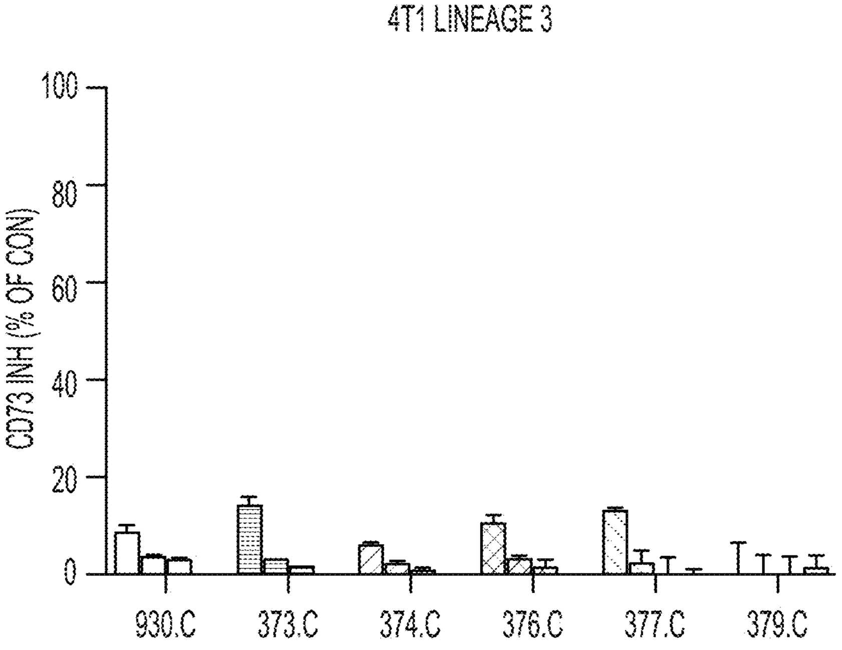
Figure 8A:
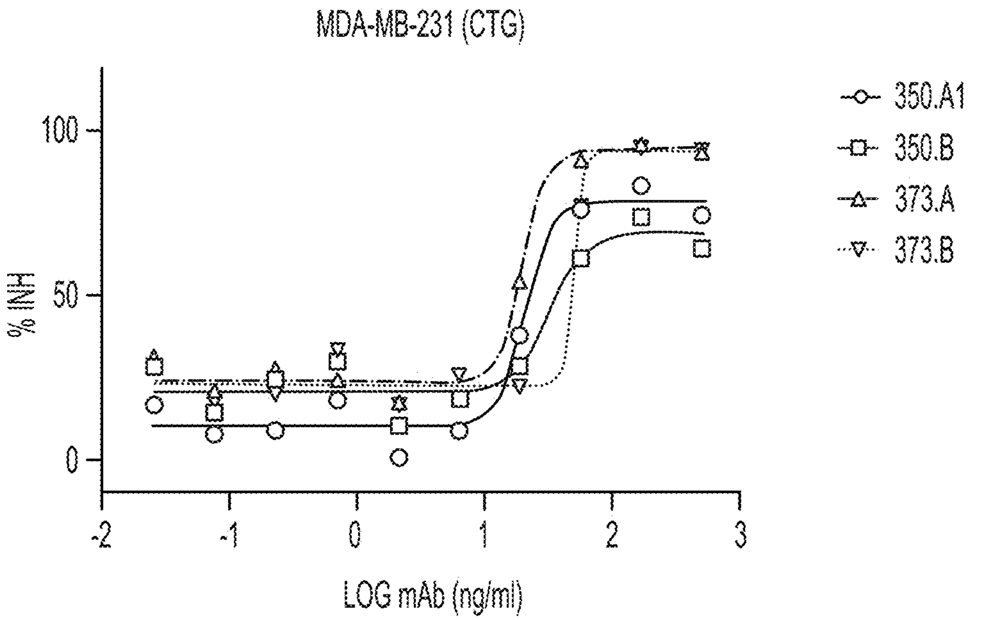
FIGS. 8A and 8B are graphs showing the enzyme inhibition activity of anti-CD73 antibodies against surface CD73 expressed on a human breast cancer cell line MDA-MB-231 or a human ovarian cancer cell line SKOV3, measured by a modified Cell Titer Glo (CTG) assay. % INH is plotted against anti-CD73 antibody concentrations. The anti-CD73 antibodies tested are 350 and 373, expressed in either the .A or .B format.
Figure 8B:
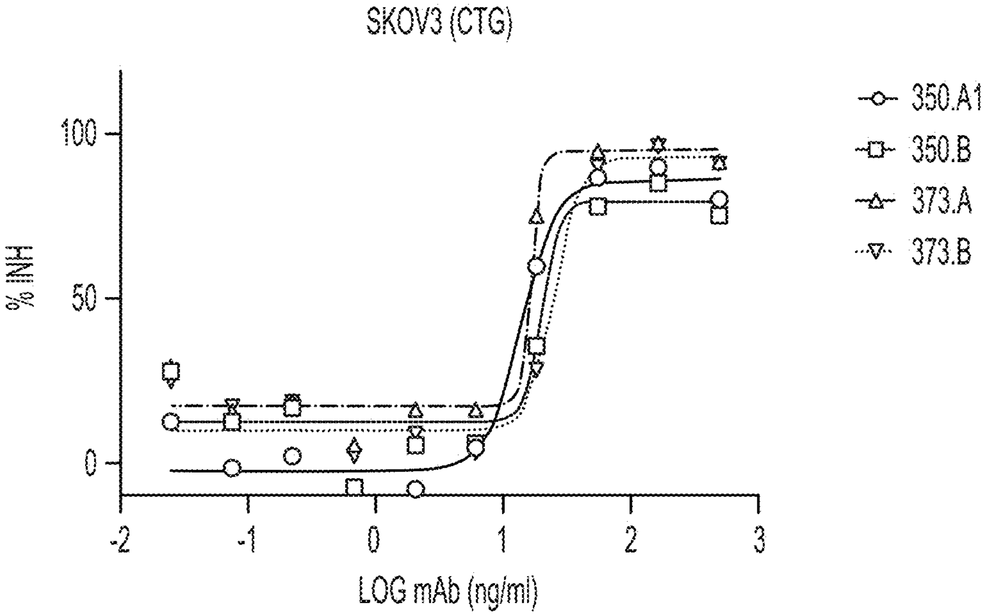
Figure 9A:
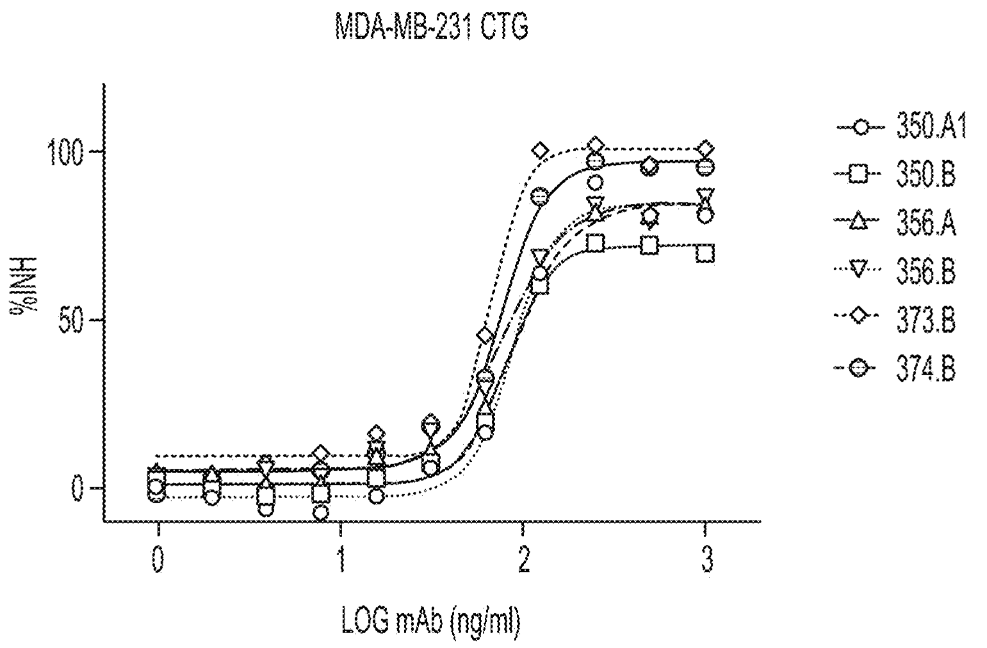
FIGS. 9A and 9B are graphs similar to FIGS. 8A and 8B. The antibodies tested are the anti-CD73 antibodies 350, 356, 373, and 374, in the .A or .B format.
Figure 9B:
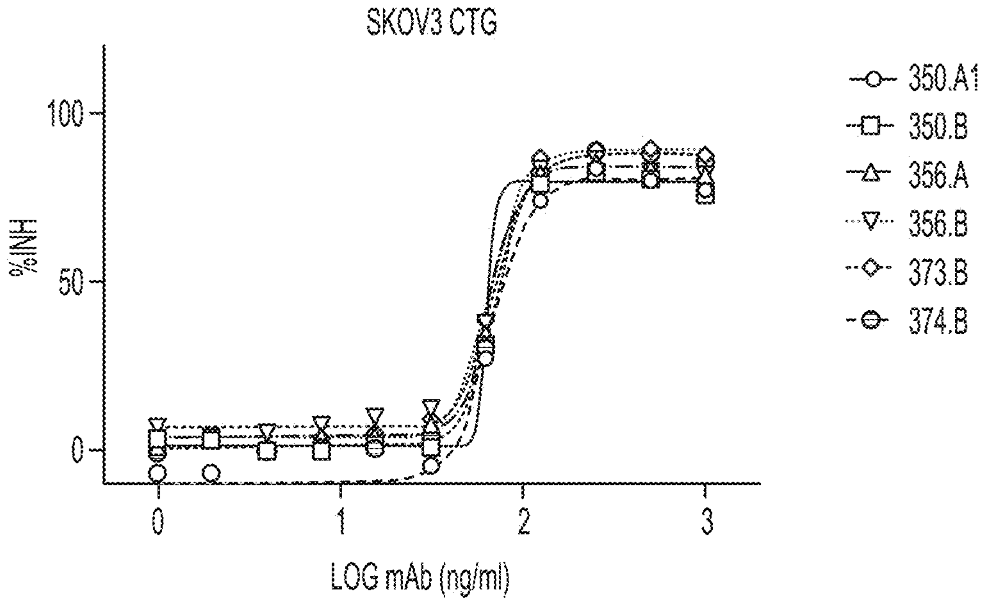

Consistent with their binding profiles, the Lineage 1 antibodies 918, 350, 356, and 358 inhibited both human and murine CD73 (FIGS. 7A and 7B), whereas the Lineage 3 antibodies 930, 373, 374, 376, 377, and 379 inhibited human, but not murine, CD73 (FIGS. 7C and 7D).

Furthermore, two modified Cell Titer Glo (CTG) assays were conducted to test the enzyme inhibition activity of anti-CD73 antibodies against CD73 expressed on a human breast cancer cell line MDA-MB-231 or a human ovarian cancer cell line SKOV3. In both studies, 1000 ng/ml anti-CD73 antibodies were incubated for 240 minutes with 20,000 cells/ml cells in the presence of 100 μM AMP at 37° C. Disappearance of AMP was measured by the modified Cell Titer Glo (CTG) assay described above and normalized percent inhibition (% INH) was determined using time zero control as 100% INH and no antibody control as 0% INH.

In both studies, all the anti-CD73 antibodies tested were able to inhibit surface CD73 expressed on the human breast cancer cell line MDA-MB-231 or the human ovarian cancer cell line SKOV3 (FIGS. 8A, 8B, 9A, and 9B).

Next, a similar Cell Titer Glo (CTG) assay was performed to examine the ability of anti-CD73 antibodies to inhibit human CD73 expressed on a HEK 293 cell line. Briefly, a HEK 293 cell line was engineered to stably overexpress human CD73 and incubated with anti-CD73 antibodies for 150 minutes in the presence of 100 μM AMP. Disappearance of AMP was measured by the modified Cell Titer Glo (CTG) assay described above and normalized percent inhibition (% INH) was determined using time zero control as 100% INH and no antibody control as 0% INH.

Figure 10:
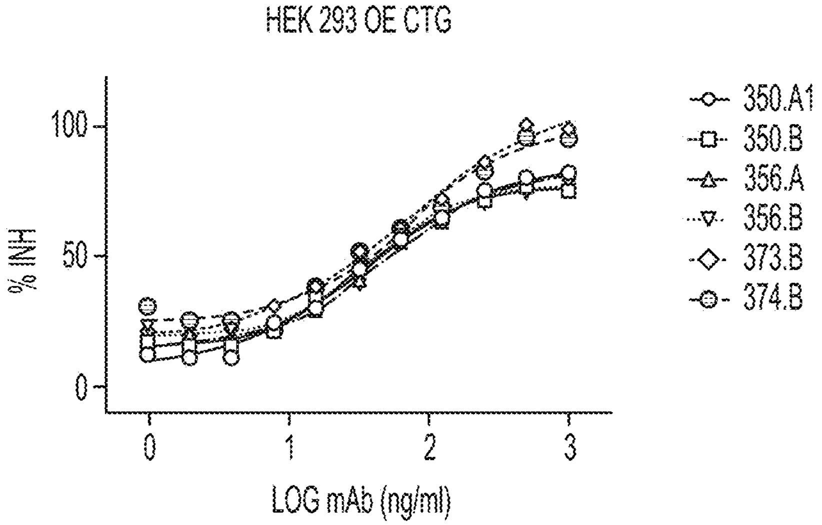
FIG. 10 is a graph showing inhibition of human CD73 over-expressed on HEK 293 cells by anti-CD73 antibodies, measured by a modified Cell Titer Glo (CTG) assay. % INH AMP conversion is plotted against a range of anti-CD73 antibody concentrations. The antibodies tested are the anti-CD73 antibodies 350, 356, 373, and 374, in the .A or .B format.

As shown in FIG. 10, the anti-CD73 antibodies 350, 356, 373, and 374, in the .A or .B format, inhibited membrane-bound human CD73 in a dose-dependent manner.

In addition, the enzyme inhibition activity of anti-CD73 antibodies were also examined using human PBMCs. In brief, primary human PBMCs were isolated from two separate donors and incubated with anti-CD73 antibodies for 480 minutes in the presence of 25 μM AMP. Disappearance of AMP was measured by the modified Cell Titer Glo (CTG) assay described above and normalized percent inhibition (% INH) was determined using time zero control as 100% INH and no antibody control as 0% INH.

Figure 11A:
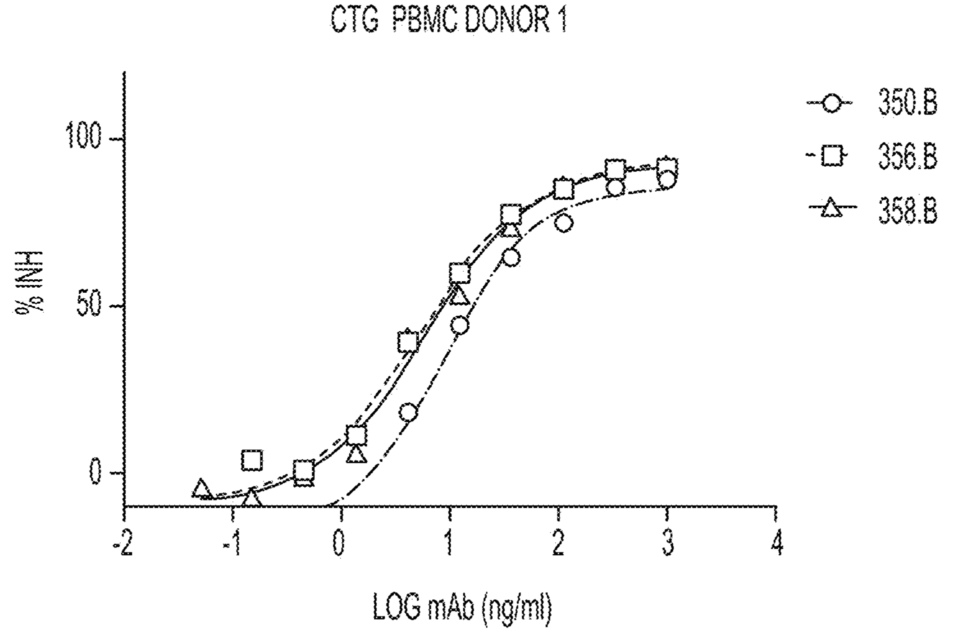
FIGS. 11A and 11B are graphs showing inhibition of CD73 expressed on primary human PBMCs isolated from two separate donors by anti-CD73 antibodies, measured by a modified Cell Titer Glo (CTG) assay. % INH is plotted against a range of anti-CD73 antibody concentrations. The anti-CD73 antibodies tested are 350, 356, and 358, all in the .B format.
Figure 11B:
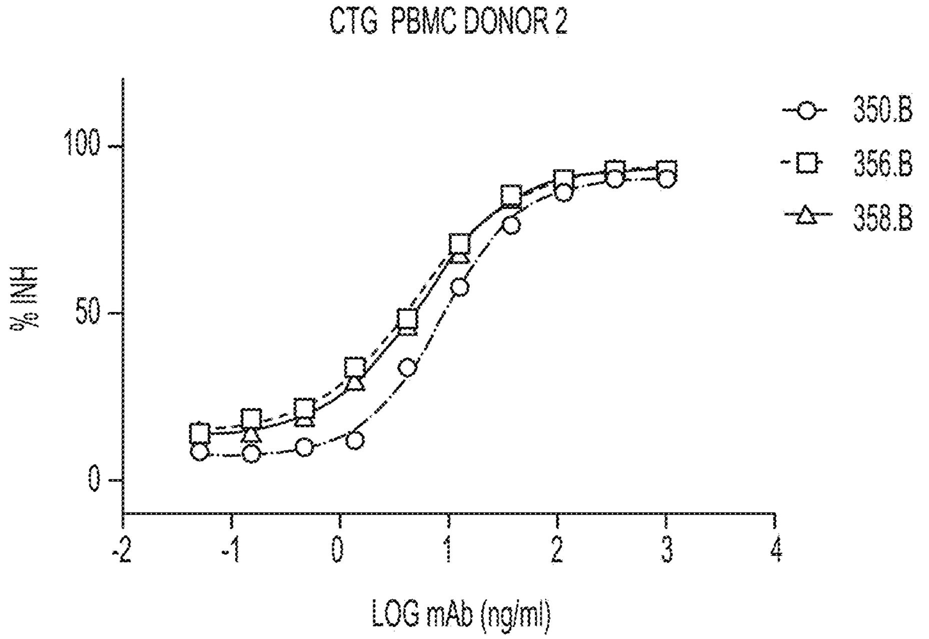

As shown in FIGS. 11A and 11B, the anti-CD73 antibodies tested inhibited the enzymatic activity of CD73 expressed on primary human PBMCs from both donors.

Restoration of CD4+ and CD8+ T Cell Proliferation in the Presence of AMP

Next, anti-CD73 antibodies were tested for their ability to relieve AMP-mediated inhibition of CD4+ T cells. Briefly, CD4+ T cells were isolated from healthy human donor pooled Peripheral Blood Mononuclear Cells (PBMC). Prior to stimulation with anti-CD3/28 beads in the presence of 800 μM AMP, CD4+ T cells were stained with CellTrace Violet (CTV) (Thermo Fisher Scientific, Cat# C34557) to track cell division. On day 4, proliferation was determined by CTV dilution using flow cytometry. Cells stained with CTV lose approximately half of their fluorescence signal as measured on the flow cytometer with each division. Proliferation index was calculated as a measure of the level of T cell division for each condition where 100 represents maximal proliferation and 0 represents no proliferation.

As shown in FIGS. 12A and 12B, all the anti-CD73 antibodies tested were able to restore CD4+ T cell proliferation in the presence of AMP.

Figure 25A:
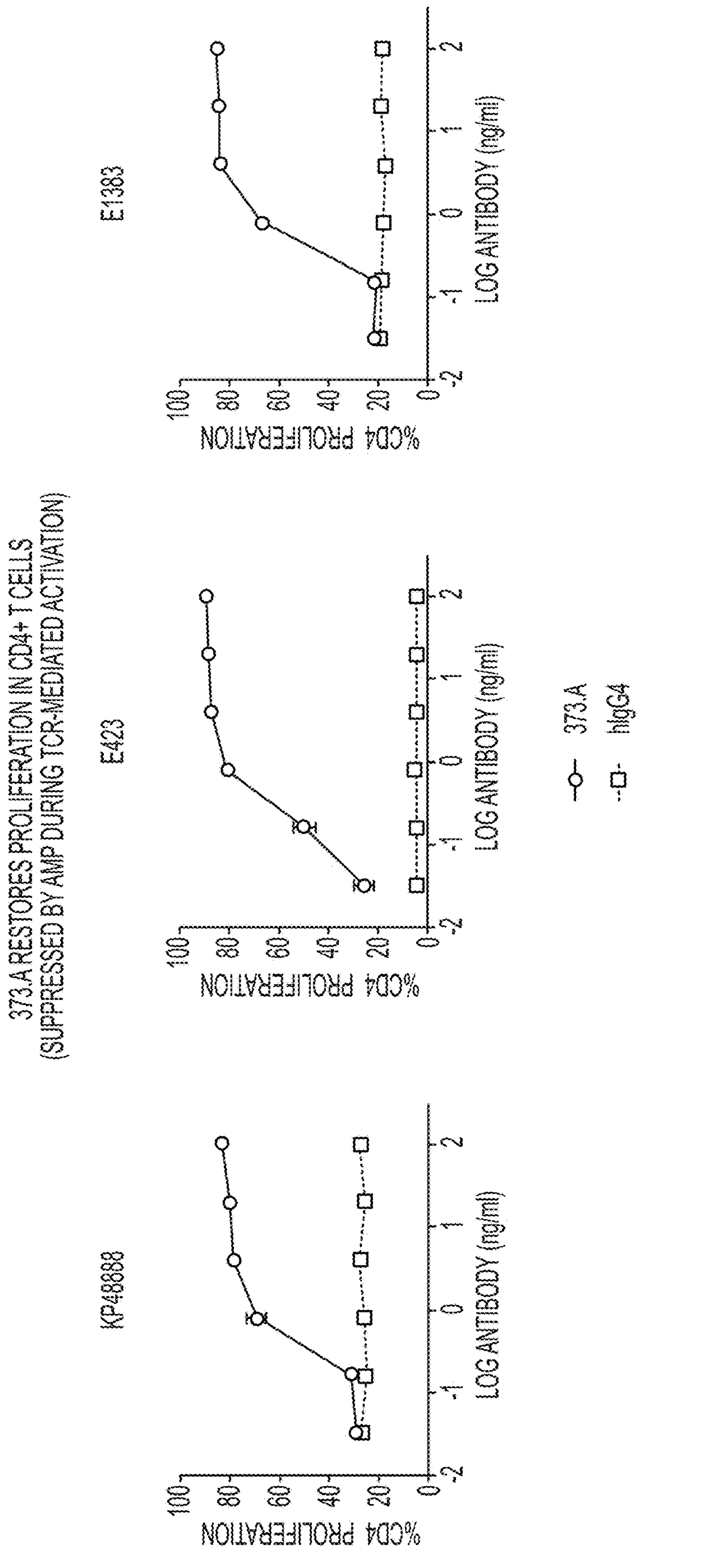
FIGS. 25A and 25B are a panel of graphs showing that proliferation of CD4+ and CD8+ T cells was suppressed by AMP during TCR-mediated activation, and this suppression could be restored by the antibody 373.A.
Figure 25B:
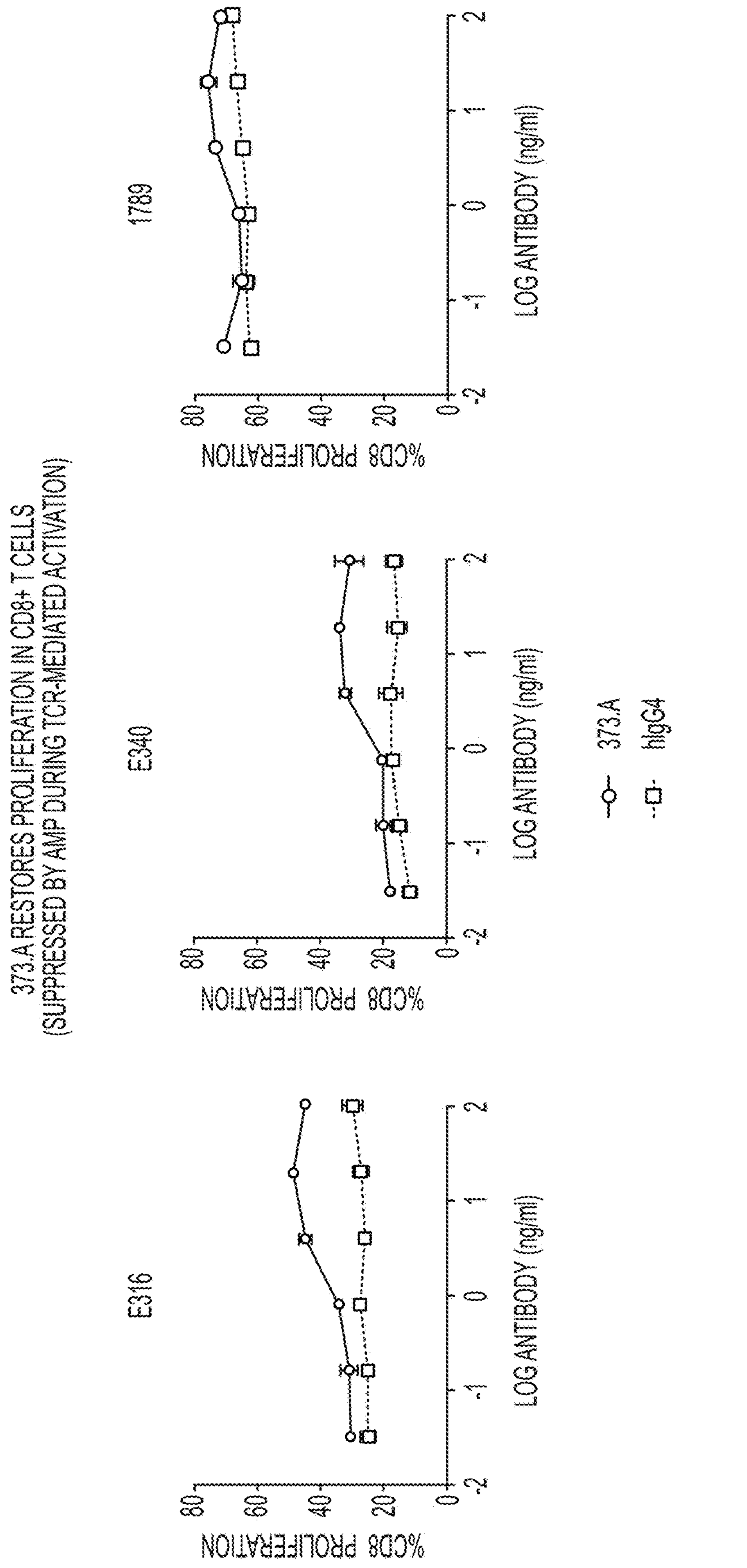

In a separate study, both CD4+ and CD8+ T cells were tested. Briefly, CD4+ and CD8+ T cells were purified from peripheral blood mononuclear cells (PBMC) isolated from healthy human donors and labeled with carboxyfluorescein succinimidyl ester (CFSE). CFSE-labeled CD4+ or CD8+ T cells were activated for 4 days with anti-CD3/CD28 T cell activator beads (1 bead/16 cells) in the presence of 800 □M AMP and serial dilutions of either isotype control hIgG4 or 373.A. Representative data from three donors each are shown for CD4+ T cells (FIG. 25A) and CD8+ T cells (FIG. 25B). Data are represented as percent CD4+(FIG. 25A) or CD8+(FIG. 25B) T cell proliferation where isotype control demonstrates that maximal proliferation is suppressed in the presence of AMP, and the presence of 373.A restores proliferation in a dose-dependent manner. While the magnitude of the response varies across donors, in all three CD4+ T cell donors represented in (FIG. 25A) and 2/3 donors shown for CD8+ T cells (FIG. 25B), 373.A demonstrates in vitro activity in restoring T cell proliferation.

Inhibition of the Enzymatic Activity of CD73 In Vivo

Furthermore, anti-CD73 antibodies were examined for their enzyme inhibition activity in vivo. Athymic nude, female mice (6-8 weeks of age) were implanted with high CD73-expressing MDA-MB231 breast cancer cell line (ATCC HTB-26) at $10\times10^6$ cells/mouse/200 μl. Five mice per group were randomized when tumors were 200 $mm^3$ and treated intraperitoneally with either 20 or 200 μg/mouse of control polyclonal human IgG or a panel of anti-CD73 mAbs. The antibodies tested are the anti-CD73 antibodies 350, 356, 373, and 374, expressed in either the .A or .B format.

Plasma was collected three days post-dose at a ratio of one portion of plasma into five portions of methanol by volume. The methanol quenched samples were stored at −80'C before use, at which time the samples were centrifuged. The precipitations were discarded and the supernatants were transferred to new Eppendorf tubes. Stock solutions of internal standards (IS, C-13 labeled adenosine and N-15 labeled Inosine, Cambridge Isotope Laboratories, MA) were added to the final concentration of 50 nM. The prepared samples were then analyzed using an LC/MS system of API-6500 QTrap (AB Sciex, US) coupled with a Shimadzu LC pump (LC-20AD) and a CTC auto sampler with DLW wash. For each sample, 5 μL was injected and separated using a SeQuant ZIC-pHILIC column (5 μm, 150×2.1 mm, Millipore, Mass.) maintained at 40° C. A binary gradient was used for the elution, where mobile phase B is 100% acetonitrile with no additives and mobile phase A is 12 mM ammonium formate and 12 mM formic acid in 1:1 (v/v) mix of water and acetonitrile. The elution was programmed as (0, 85, 0.6), (0.5, 85, 0.4), (2, 10, 0.4), (4.5, 10, 0.4), (5, 85, 0.4), (5.5, 85, 0.6), where values in the parentheses are time in minutes, percent of mobile phase B and flow rate in mL/min in order. Adenosine and C13-Adenosine were monitored from 0.5 to 4.5 minutes at ESI positive mode and mass transitions 268->136 and 273->136 respectively. Inosine and N15-Inosine were monitored from 0.5 to 4.5 minutes at ESI negative mode and mass transitions 267->135 and 271->139 respectively. Results were reported as nM adenosine or inosine.

Figure 13:
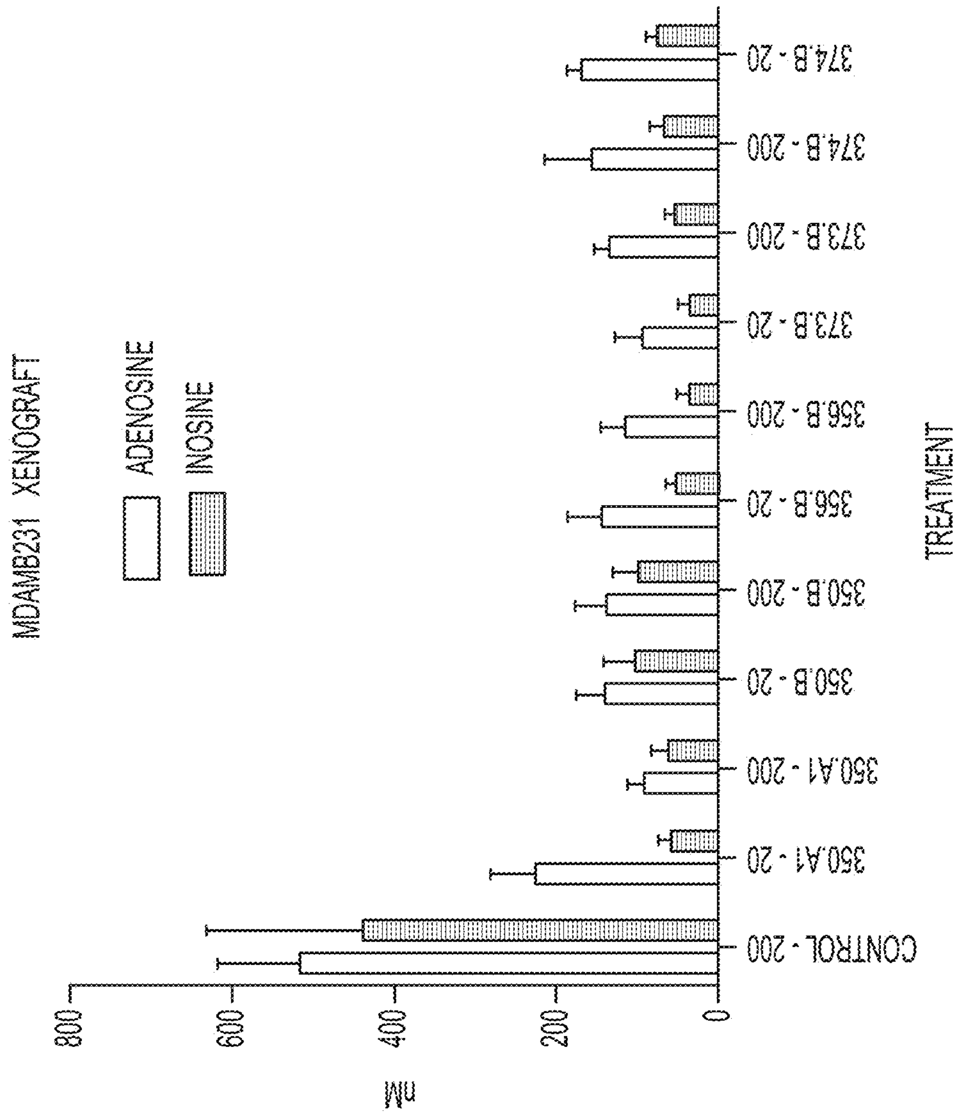
FIG. 13 is a bar graph showing the results of a xenograft study testing the ability of anti-CD73 antibody to inhibit the enzymatic activity of CD73 in vivo. The y-axis shows adenosine and inosine levels in the serum of immunocompromised mice implanted with a high-CD73 expressing breast cancer cell line (MDA-MB-231) as measured by mass spectrometry. The anti-CD73 antibodies 350, 356, 373, and 374, expressed in either the .A or .B format, were administered intraperitoneally at 20 or 200 μg/mouse. The control polyclonal human IgG antibody was administered at 200 μg/mouse.

All the anti-CD73 antibodies tested effectively reduced the accumulation of adenosine and inosine in the serum of immunocompromised mice implanted with the high CD73-expressing MDA-MB231 breast cancer cell line (FIG. 13).

Example 2: Determination of the Epitope and Binding Mode of Anti-CD73 Antibodies In this example, the epitope and binding mode of anti-CD73 antibodies 350.A2, 350.B, 373.A, and 373.B were determined by fragmentation amide hydrogen/deuterium exchange (HDx) and size exclusion chromatography (SEC).

Methods

Fragmentation Hydrogen Deuterium-Exchange Mass Spectrometry (HDx-MS)

HDx-MS experiments were performed as previously described (Park I H, et al., J. Chem. Inf. Model; 55(9): 1914-1925 (2015); Chalmers M J, et al., Anal. Chem.; 78(4): 1005-14 (2006)). Antibody antigen complexes were prepared and used in a 1:1 molar ratio by overnight incubation at 4° C. It is important to note that this means that there is a 2-fold excess of Fab binding sites present in the complex mixtures.

Room temperature on-exchange experiments were performed by manual addition of 50 µL of in-exchange buffer (50 mM phosphate, 150 mM NaCl, pH 7.1, in $D_2O$) to 10 µL of 0.5 mg/ml rhCD73 protein (R&D systems, Catalog #5795, Trp27-Lys547 of AAH65937 fused to a C-terminal 6-His tag (SEQ ID NO: 922)) or a molar equivalent amount of a CD73-mAb complex (50 mM phosphate, 150 mM NaCl, pH 7.1). Samples were quenched after 60s of in-exchange at room temperature by addition of 250 µL quench buffer (4M guanidinium hydrochloride, 0.5M Tris(2-carboxyethyl)phosphine hydrochloride (TCEP-HCl), 0.2M phosphate, pH 2.5, 0° C.) and after 30s further diluted with 300 µL of ice cold storage buffer (20% glycerol, 0.25% formic acid in water) before flash freezing with liquid nitrogen and storage at −80° C. until use or transfer into a −70° C. drawer attached to the rail of a liquid handler (PAL HTS, LEAP Technologies, Carrboro, N.C.) located inside a 0° C. enclosure. The frozen samples were thawed for 120s by flowing N2 gas over the sample vial (facilitated by the liquid handler in conjunction with a thaw fixture) and loaded into the sample loop of the injection valve (Valco, Houston, Tex.). Loading of samples (load buffer 0.05% Trifluoroacetic acid (TFA), 500 µL/min) onto the pre-column of the chromatographic system and online pepsin digestion (immobilized pepsin on Poros AL20, 2.1×150 mm, maintained at 15° C.) was performed with a dual pump system (2×, Accela 1250, Thermo Scientific, Waltham Mass.) that allowed admixing of a second flow of 550 µL/min (0.05% TFA, 500 µL/min) of load buffer post digestion through a mixing tee. The combined flow was directed into the chromatographic system maintained at 0° C. for desalting and gradient LC separation at a flow rate of 15 µL/min (Dionex UltiMate 3000, Thermo Scientific, Waltham, Mass.) and concurrent mass spectrometric analysis (QExactive, Thermo Scientific, Waltham, Mass.) of the chromatographic effluent. The chromatographic system consisted of a valve (15kPSI Valco, Houston, Tex.), a 4 µL EXP Halo C18 reversed-phase trap cartridge (Optimize Technologies Inc., Oregon City, Oreg.), and an analytical column (2.1×10 mm ID, Prozap 1.5 µm C18, Grace). Gradient separation was from 0% to 40% B over 20 min followed by 40% to 75% B over 5 min using buffer compositions A: 99.75:0.25% v/v (H20: formic acid) and B: 99.75:0.25% v/v (acetonitrile:formic acid).

MS scans were acquired at a resolution of 70,000 over the m/z range of 350-2000 for MS, and 35,000 for MS/MS. The instrument parameters used for all experiments including spray voltage of 2.5 kV, a maximum injection time of 120 ms, AGC target for MS of 500,000 ions were maintained the same for all runs. Sample were analyzed in triplicate.

Peptide identification was performed by converting raw data to .mgf format using Proteome Discoverer 1.4, searched against the construct sequence using MASCOT 2.4 (Matrix Science, London, UK), and filtered using Scaffold 1.4. Filtered results were imported into HDExaminer (v1.3, Sierra Analytics, Modesto, Calif.) together with raw data files for quantitation of deuteration. Deuteration values were exported into Microsoft Excel for calculation of deuteration differences, and normalization of deuterium incorporation by the number of observable amides (number of residues minus 2, further subtracting the number of prolines in the sequence excluding the N-terminus and penultimate residues) in a peptide. For compression of peptide difference data onto the sequence the normalized difference deuteration values were averaged for each primary sequence residue over the peptide observations in which the respective amide was observable.

Water, deuterium oxide, guanidine hyrdochloride, sodium chloride, glycerol, formic acid, trifluoroacetic acid (TFA), trifluoroethanol (TFE), acetonitrile (ACN) were from Sigma Chemical Company (St. Louis, Mo.). Tris-(2-carboxyethyl) phosphine) TCEP was from Gold Biotechnology Inc (St. Louis, Mo.).

Size Exclusion Chromatography (SEC)

An equimolar amount of rhCD73 (3.2 µL, 1.6 mg/mL) was mixed with mAb (2.6 µL, 5 mg/mL) and allowed to complex overnight at 4° C. Samples were run using an Agilent Autosampler connected to an Agilent 1200 series pump with an Agilent UV detector. The system was controlled by Agilent Chemstation software. Column used was Shodex Protein KW-803 column (8×300 mm ID). Mobile Phase: 90% 2×PBS, 10% isopropanol by volume. Flow rate: 500 µL/min. Injection volume: 8 µL. Detection wavelength: 220 nm. Run time: 30 min.

Antibody antigen complexes were prepared and used in a 1:1 ratio using supplied concentration values by overnight incubation at 4° C. It is important to note that this means that there is a nominally 2-fold excess of Fab binding sites in the complex mixtures.

Structure Data

Structural data used for interpretation was retrieved from the Protein Data Bank (www.rcsb.org) and consisted of the entries 4H2F, 4H21, and 4H1S. Alignments of the various models and visualization was performed with PyMOL (PyMOL Molecular Graphics System, Version 1.8 Schrödinger, LLC).

Results

Hydrogen Exchange Data

The HDx MS protection profiles of 373.A and 373.B as shown in FIG. 14 overlap over the full sequence of CD73. This demonstrates the equivalence of the antibodies in terms of their epitope.

The HDx MS protection profiles of 350.A2 and 350.B as shown in FIG. 15 are in excellent agreement with each other over the full sequence of CD73. This demonstrates the equivalence of the antibodies in terms of their epitope.

Figure 16A:
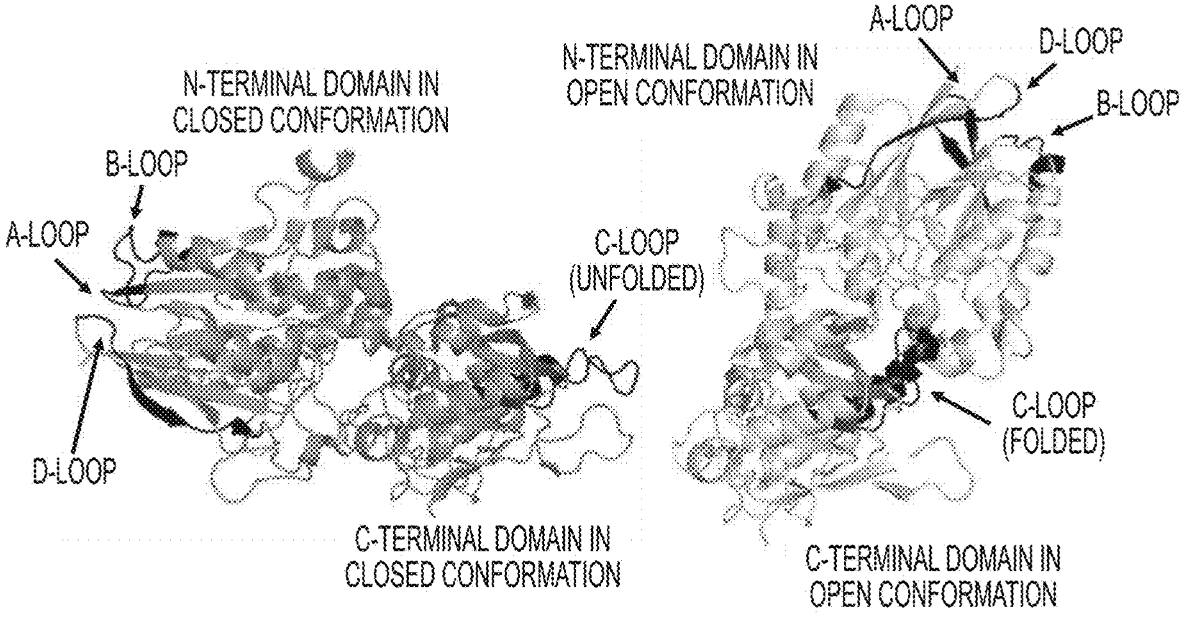
FIG. 16A is a graph showing conformational change of CD73 between closed/active (Protein data bank (PDB) 4H2I) and open/inactive conformation (PDB 4H2F).
Figure 16B:
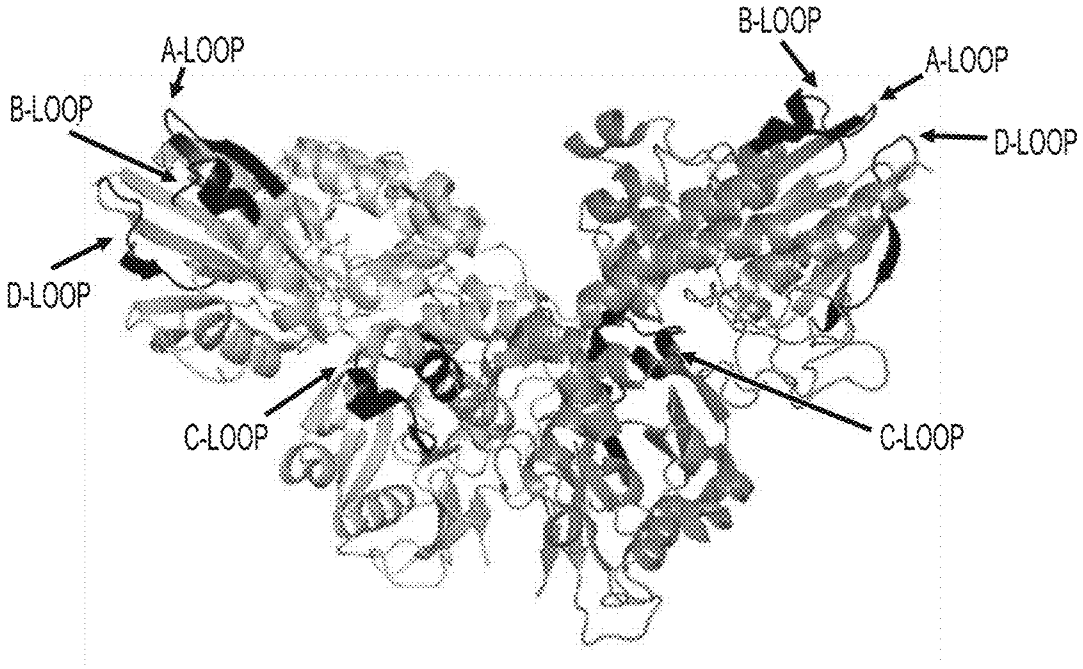
FIG. 16B is a graph showing open/open conformation of CD73 dimer constructed from two units of PDB 4H2F after alignment of c-terminal domains with PDB 4H1S.

The sequences on which the strongest protection is observed are annotated in the figures and mostly correspond to loop regions of CD73. Their relative spatial arrangement is depicted in the structure models shown in FIGS. 16A and 16B. Whereas protection observed for the sequences of A-, B-, and D-loop is attributable to antibody-CD73 interactions, the protective effects observed for the sequence annotated as C-loop likely arise from conformational locking. The C-loop is folded in the open/inactive conformation of CD73 and unfolded in the closed/active conformation (FIG. 16A). Soluble as well as membrane bound CD73 forms a dimer through the C-terminal domains (FIG. 16B). An equilibrium between open and closed conformations exists as the N-terminal domain rotates by about 90 degrees to convert from open to closed form. The C-loop reports back on that equilibrium. If upon antibody binding to CD73, the equilibrium is shifted more toward the open conformation, a larger fraction of the C-loops will be folded, which is a protected state. On the other hand, if the equilibrium is shifted more toward the closed conformation on antibody binding to CD73, then a deprotective effect is expected. The unusually strong protection observed for 373.A and 373.B at the C-loop (FIG. 14) suggests that these are most efficient in maintaining CD73 in the inactive conformation and/or do so by a distinct mechanism.

From the profiles it is inferred that the maximally protected sequences are residue range 158-172, YLPYKVLPVGDEVVG (SEQ ID NO: 108) assigned as A-loop, residue range 206-215, KLKTLNVNKI (SEQ ID NO: 109) assigned as B-loop, and residue range 368-387, MINNNLRHADETFWNHVSMC (SEQ ID NO: 110) assigned as C-loop in all the figures, numbered according to SEQ ID NO: 105.

For the antibodies 373.A and 373.B, residues in the A- and B-loop regions seem to be equally important for the epitope as indicated by comparable amounts of protection observed in FIG. 14. In the case of the antibodies 350.A2 and 350.B, mostly A-loop residues appear important for the epitope even so some B-loop protection is observed but it is not clear if this should be interpreted as direct engagement of the antibody with residues in that range or is just an indirect effect due to the proximity to the A-loop.

Size Exclusion Data

The size exclusion data correlate well with the HDx data discussed above. The equivalence of the antibodies 373.A and 373.B is seen in the similarity of their size exclusion chromatography (SEC) profiles, which reflects the oligomerization state distribution (FIGS. 17A and 17B). The same assessment holds for the antibodies 350.A2 and 350.B (FIGS. 18A and 18B).

Features around 17 min correspond to CD73 dimer and free antibody in agreement with the molecular weight scale based on the calibrants, which are shown for reference. The feature at about 14.8 min or about 300 kDa is consistent with a CD73 dimer/mAb complex. Around 12.4 min a feature of approximately 600 kDa consistent with a composition of two CD73 dimers+2 mAbs (2×CD73 dimer/2×mAb) is observed. Additional features above 600 kDa are affected by the exclusion limit of the column. Nevertheless, they can be assigned to higher oligomeric states meaning complexes consisting of 3 or more CD73 dimers in addition to 3 or more mAbs ($3^{+}$×CD73 dimer/$3^{+}$×mAb).

The dominant species in the CD73-373.A and CD73-373.B profiles shown in FIGS. 17A and 17B is the CD73 dimer/mAb complex. Only a minor amount of 2×CD73 dimer/2×mAb species is observed. This is consistent with a preferred bidentate binding mode of one antibody with a CD73 dimer.

Figure 18A:
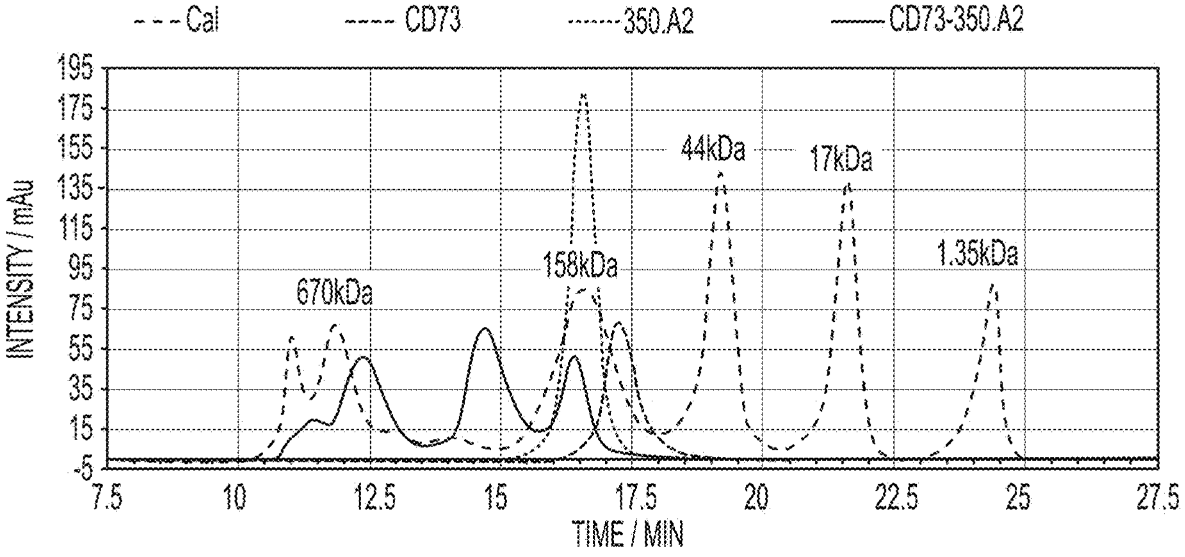
FIGS. 18A and 18B are graphs showing SEC profiles of CD73-350.A2 and CD73-350.B complexes, respectively.
Figure 18B:
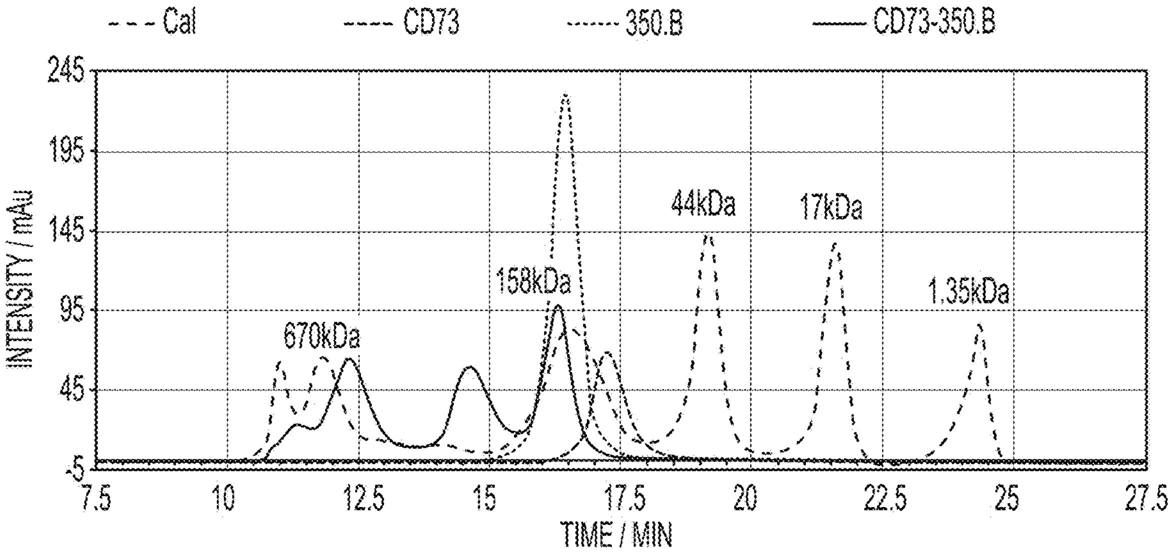

The SEC profiles for CD73-350.A2 and CD73-350.B shown in FIGS. 18A and 18B show comparable abundances for the CD73 dimer/mAb species and 2×CD73 dimer/2×mAb species. A shoulder at shorter elution times indicates the presence of some higher oligomers. This shows that 350.A2 and 350.B are capable of binding CD73 like 373.A and 373.B in bidentate fashion but this mode is not necessarily the thermodynamically favored one at least at high concentrations as used in the experiment.

Figure 19:
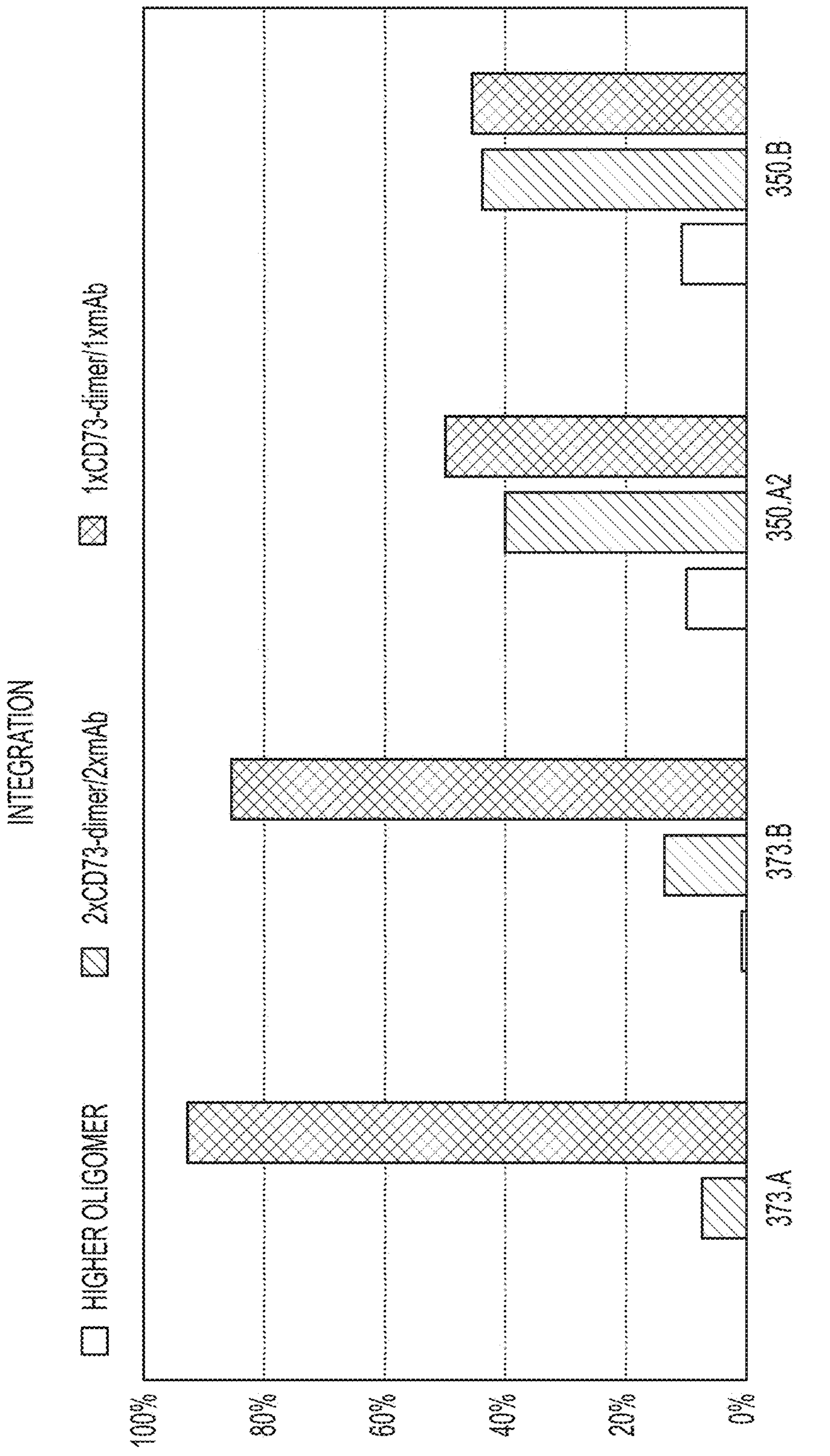
FIG. 19 is a graph showing the relative percentages of CD73/mAb species calculated using the integration method.

The percentages of anti-CD73 antibodies that formed a 1×CD73 dimer/1×mAb complex, a 2×CD73 dimer/2×mAb complex, or a higher oligomer were estimated by integration of the SEC profiles over the distinguishable species (FIG. 19). A zero baseline was used for all integrations with integration intervals from 10.5 min to 11.65 min for higher oligomers and 11.65 min to 13.5 min for 2×CD73 dimer/2×mAb complex consistently used for all samples. The integration intervals for the 1×CD73 dimer/1×mAb complex species varied slightly and were chosen as 13.5 min to 16.2 min for CD73-373.A, 13.5 min to 16 min for CD73-373.B, 13.5 min to 15.75 min for CD73-350. A2, and 13.5 min to 15.75 min for CD73-350.B to obtain optimal separation from the free antibody signal that was not integrated as it is not relevant for the analysis (antibodies were used in pseudo-excess as about twice the number of Fab binding sites to CD73 binding sites were present in the complex mixtures).

CONCLUSION AND DISCUSSION

The above HDx and SEC data provide convincing evidence for the equivalence of 373.A and 373.B as well as 350.A2 and 350.B in terms of their mode of interaction with CD73. This was expected considering that the only sequence difference between the pairs is a single mutation (L235E to ablate residual FcR interactions) in the constant region.

Figure 20:
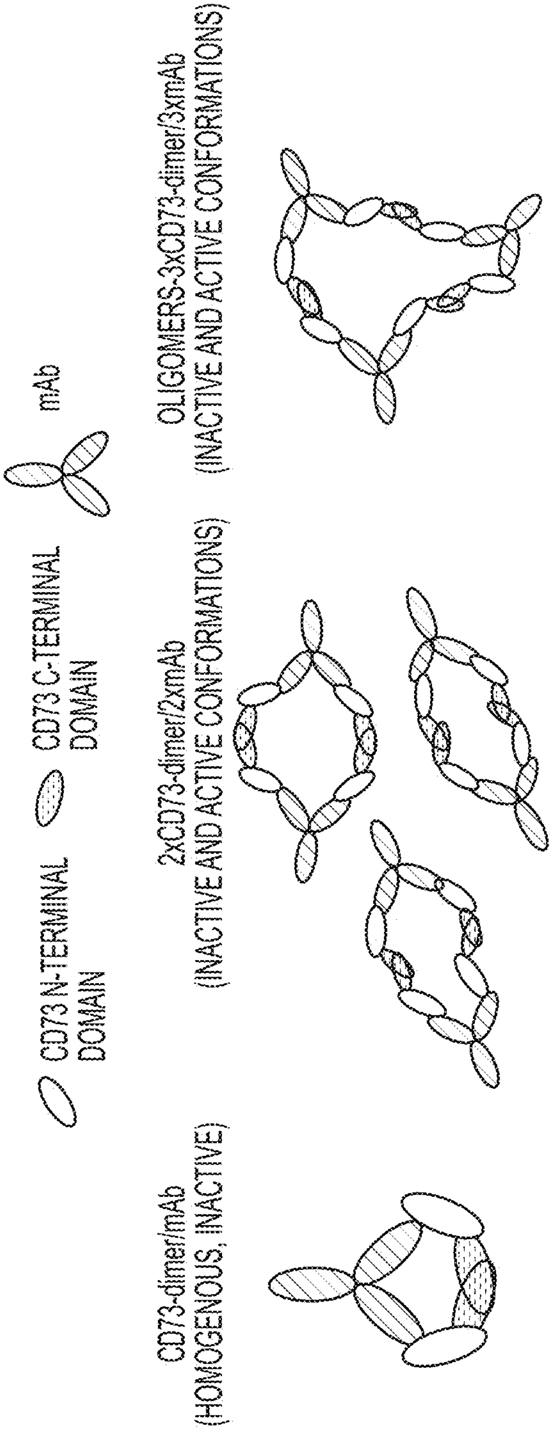
FIG. 20 is a schematic graph showing an oligomerization model for unifying HDx and SEC interpretations.

The data from HDx and SEC experiments are consistent and fully support the model presented in FIG. 20. According to the model, the epitopes for all the antibodies are on the N-terminal domains. The antibodies 373.A and 373.B interact with the CD73 dimer to form almost exclusively the homogeneous species illustrated on the left of FIG. 20. In that species, both active sites of the CD73 dimer are locked into the inactive conformation. Further, in this conformation both N-terminal domains of the CD73 dimer are directed away from the cell surface in the case of membrane bound CD73, allowing 373.A and 373.B to inhibit soluble and membrane bound versions of the target with equal efficiency.

The antibodies 350.A2 and 350.B can form the bidentate homogeneous complex on the left but do not show preference for that form over the 2×CD73 dimer/2×mAb species shown in the middle of FIG. 20. Higher oligomeric species illustrated on the right of FIG. 20 are also observed. Presumably the distribution of species will shift toward the homogeneous bidentate complex in the case of membrane bound CD73 or at low concentrations of antibody and antigen, which is the likely scenario in vivo. The antibodies 350.A2 and 350.B are expected to be able to efficiently inhibit all forms of CD73 by the inactive site locking mechanism. It is understood that even in the active conformation, the target could still be catalytically inactive due to antibody binding due to other allosteric inhibition mechanisms.

Based on the model, one would expect that an anti-CD73 antibody that preferentially forms oligomeric species illustrated in the middle and right of FIG. 20 would be less efficient in inhibiting soluble and membrane bound CD73, especially at low concentrations. The reason for this is a large fraction of CD73 will be always in the active conformation and even though the antibody might inhibit catalysis under those circumstances by an indirect mechanism, any detachment of the antibody will immediately produce catalytically active CD73. Further, as total concentration of antigen and antibody go toward zero, two antibody molecules will be required to inhibit a single CD73 dimer, whereas for the 373 and 350 antibodies, a single molecule would still suffice.

Summary

The putative binding sites of antibodies 373.A, 373.B, 350.A2, and 350.B on rhCD73, as well as their modes of interaction with the rhCD73 dimer were determined. The epitopes were characterized as likely discontinuous and consisting of residues found in the sequence ranges 158-172 YLPYKVLPVGDEVVG (SEQ ID NO: 108) and 206-215 KLKTLNVNKI (SEQ ID NO: 109) of human CD73, numbered according to SEQ ID NO: 105. If one considers a model that requires locking of CD73 into the inactive conformation for inhibition, then based on the experimental observations from HDx MS and SEC, one would predict that 373.A, 373.B, 350.A2, and 350.B are able to inhibit soluble and membrane bound forms of CD73.

Example 3: Up-Regulation of CD73 in Stromal Cells Upon TGFβ Blockade In Vivo

CD73 expression in cancer has been reported not only in cancer cells but also in the stromal elements that make up the tumor microenvironment. Additionally, several stromal factors, including TGFβ, have been suggested to provide potential amplification mechanisms for adenosine generation in tissue microenvironment. In this example, a study was conducted to determine whether TGFβ blockade in vivo may prompt changes in expression of CD73 in tumor stromal cells.

Figure 21A:
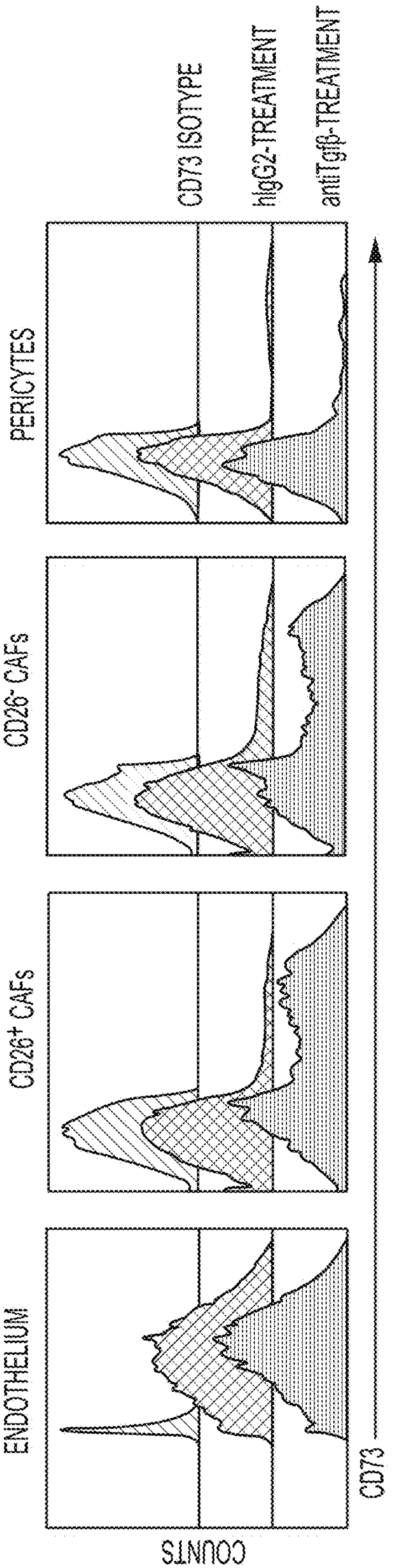
FIGS. 21A and 21B are graphs showing expression of CD73 in stromal cell subsets analyzed by flow cytometry in 4T1 tumors from mice treated with a pan anti-TGFβ antibody or hIgG2 isotype control.
Figure 21B:
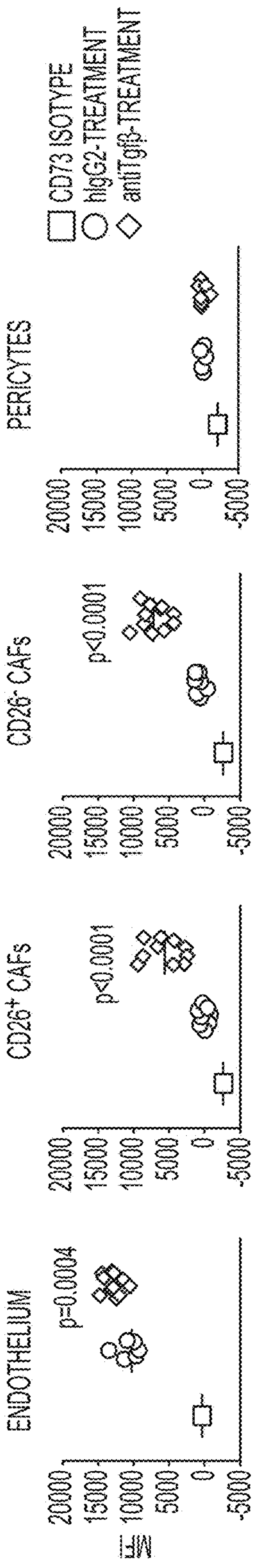

To this end, a humanized IgG2 monoclonal antibody that binds to human and murine TGFβ1 and TGFβ2 with high affinity and to TGFβ3 with lower affinity was utilized. This antibody has been demonstrated to possess neutralizing activity against TGFβ isoforms in vitro and in vivo. Immunocompetent, BALB/c, female mice (6-8 weeks of age) were implanted in the right flank with 4T1 murine triple-negative breast cancer cell line at $10\times10^4$ cells/mouse/100 μl. Ten mice per group were treated intraperitoneally, every other day with either a pan TGFβ-blocking antibody or isotype control (hIgG2), both at a final concentration of 10 mg/kg of body weight. Tumors were allowed to grow for 14 days, after which animals were euthanized and tumors collected and subjected to flow cytometric analysis. Briefly, tumors were excised from mice and digested using a combination of physical and enzymatic dissociation (DNaseI, CollagenaseP, Dispase). Single cell suspensions were Fc-blocked for 30 minutes to prevent nonspecific antibody binding, and stained with a panel of antibodies that bind to specific cell surface markers including CD45 (to exclude hematopoietic cells). CD31 (endothelial cells), CD90 (pan mesenchymal marker), CD26 and podoplanin, to allow identification of stromal cell populations. CD73 expression was assessed using an eFluor450-conjugated anti-CD73 antibody (eBioscience #48-0731-82), as compared to isotype-controlled stained samples (eFluor 450-conjugated Rat IgG1, eBioscience #48-4301-82). After staining for 40 minutes at 4° C., samples were washed with FACS buffer (PBS, 5 mM EDTA, 2% Fetal Bovine Serum), fixed with Fix/Perm solution (eBioscience #00-5523) following the manufacturer's instructions, and analyzed on a BD LSRFortessa™ flow cytometer. CD73 was highly expressed in endothelial cells in isotype control-treated mice, while minimal expression was detected in mesenchymal stromal cells (CD26+ and CD26-CAFs, and pericytes) (FIGS. 21A and 21B). Strikingly, treatment of mice with TGFβ-neutralizing antibodies prompted a significant up-regulation of CD73 in cancer associated fibroblasts (CAFs), independently of CD26 expression (FIGS. 21A and 21B). Up-regulation of CD73 was also noticeable in endothelial cells, although to a lesser extent, while no up-regulation was observed in pericytes (FIGS. 21A and 21B). Altogether, these data indicate that neutralizing TGFβ in the tumor microenvironment elicits expression of CD73 in stromal cells, suggesting that up-regulation of CD73 and adenosine production by tumor fibroblasts may provide an alternative mechanism co-opted by tumors to maintain immune quiescent upon TGFβ blockade.

Example 4: Impact of Anti-CD73 Antibodies on B Cells

Figure 22A:
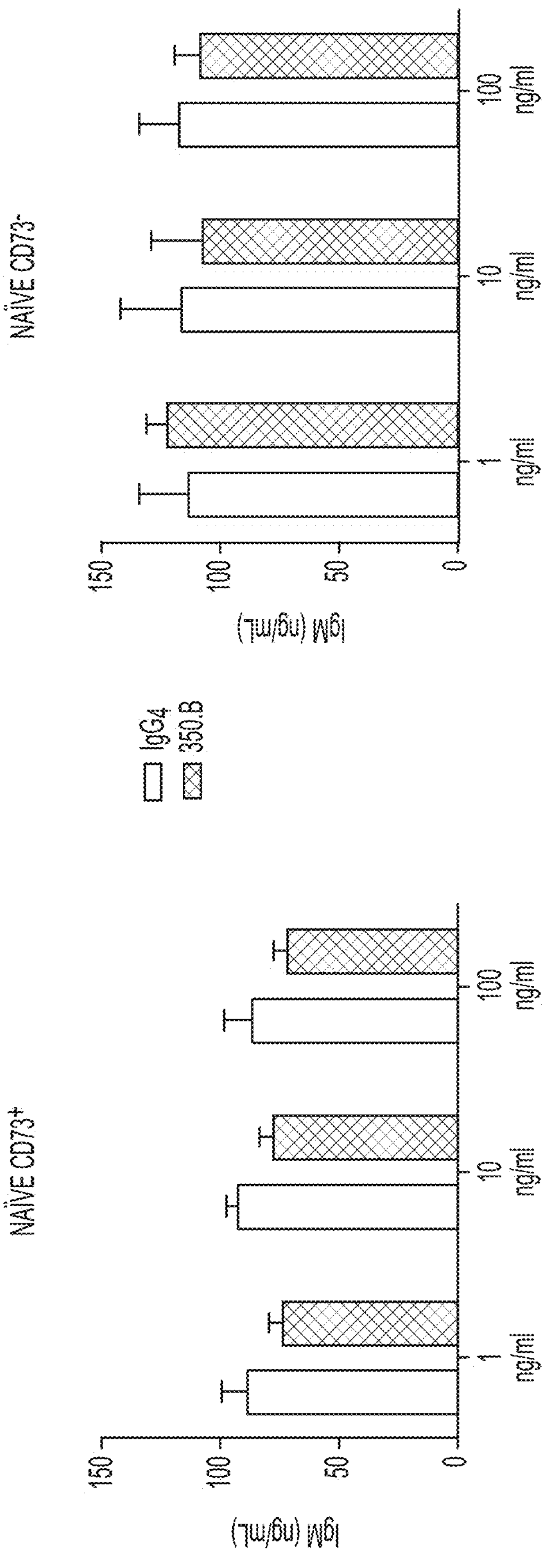
FIGS. 22A, 22B, and 22C are graphs showing results from an assay assessing the impact of an anti-CD73 antibody on class switch recombination in B cells. Naive ($CD19^+CD27^-IgM^+IgD^+$) $CD73^+$ and $CD73^-$ B cells were isolated from peripheral blood of healthy donors, labelled with CFSE and stimulated in vitro with CpG 2006, anti-CD40, IL-2, IL-21 and tranferrin. Cells were cultured in the presence of the anti-CD73 antibody 350.B or an isotype control antibody (IgG4) at three different concentrations: 1, 10 and 100 ng/mL.
Figure 22B:
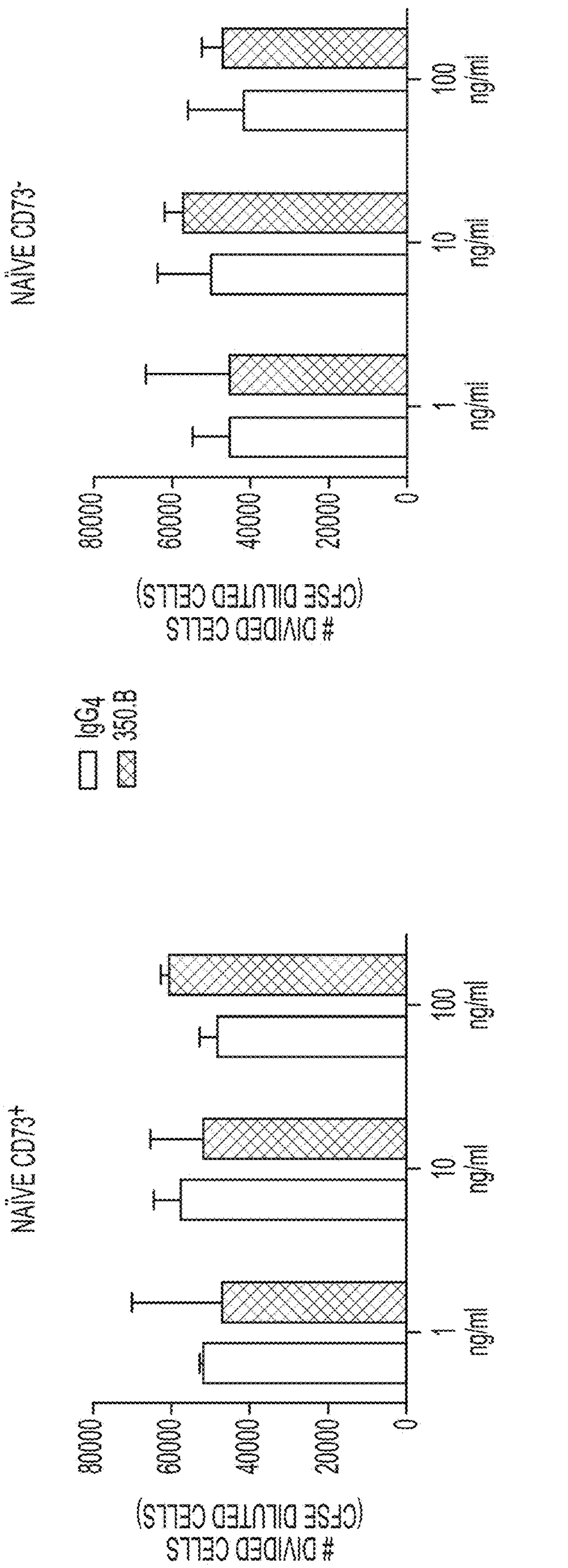
Figure 22C:
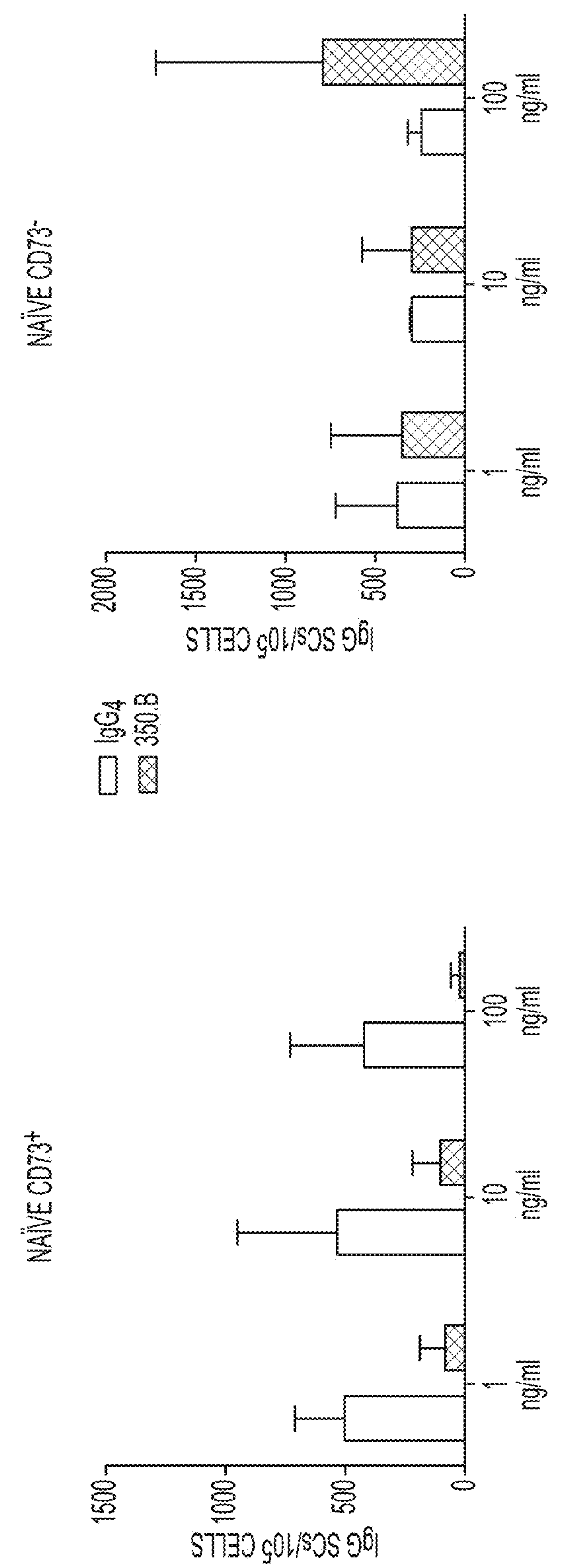

To assess whether blockade of CD73-dependent adenosine generation could specifically inhibit class switch recombination (CSR) without impacting B cell response efficiency, the anti-CD73 antibody 350.B was tested. Naive B (CD19+ CD27−IgM+IgD+) cells were purified from peripheral blood of two healthy donors, based on CD73 expression, and stimulated with a TLR9 agonist, an anti-CD40 antibody, and cytokines (IL-2 and IL-21) in the presence of the antibody 350.B. Three different concentrations of the antibody were tested—1 ng/ml, 10 ng/ml and 100 ng/ml—along with an IgG4 isotype control. IgM secretion was measured at day 7 in culture supernatants, and no differences were observed compared to the isotype control (FIG. 22A). Notably, inhibition of CD73-enzymatic activity with 350.B treatment resulted in decreased differentiation of IgG secreting cells, as measured by an ELISPOT assay to detect IgG secreting plasma cells (Millipore MSIPS4510 plates, coated with 10 μg/ml goat anti-human IgG, Southern Biotechnologies), with a strong effect at the concentration of 100 ng/ml (FIG. 22C). The number of viable cells was also evaluated, and no differences were observed (FIG. 22B), ruling out the link between low survival rate and poor CSR efficiency observed in the naive CD73+ B cells after treatment with 350.B. As a control, naive CD73− cells were equally stimulated, and no differences were observed (FIGS. 22A-C). Finally, the evaluation of CSR in the isotype control conditions confirmed increased number of IgG ISCs in the naive CD73+ compartment (FIG. 22C). Taken together, these results demonstrated that blockade of CD73 enzymatic activity has an impact on class switch recombination without altering the IgM response.

Example 5: Anti-CD73 and Anti-PD-1 Co-Blockade in Syngeneic Mouse Tumor Models To determine the role of co-blockade of the CD73 and PD-1 pathways in tumor-bearing mice, anti-PD-1 and anti- CD73 (350.B) antibodies were administered to immunocompetent mice inoculated with a syngeneic colon carcinoma cell line, CT-26. BALB/c mice aged 6-10 weeks each were inoculated on the flank with $1\times10^5$ CT-26 tumor cells. On day 2 after inoculation, mice (n=10/group) were treated intraperitoneally with either isotype control antibody, 350.B 600 μg for 1 dose followed by 400 μg for 4 doses; anti-PD-1 300 μg for 5 doses (low dose); anti-PD-1 600 μg for 5 doses (high dose); a combination of high-dose anti-PD-1+350.B; or a combination of low-dose anti-PD-1+350.B. Tumor dimensions and body weights were recorded three times in a week with a gap of 2 to 3 days in between measurements, and each animal was euthanized when the tumor size reached >2000 $mm^3$, if the mouse was moribund, or if the tumor was ulcerated. Percent tumor growth inhibition through day 25 was calculated (because the control group was euthanized on day 26).

Figure 23:
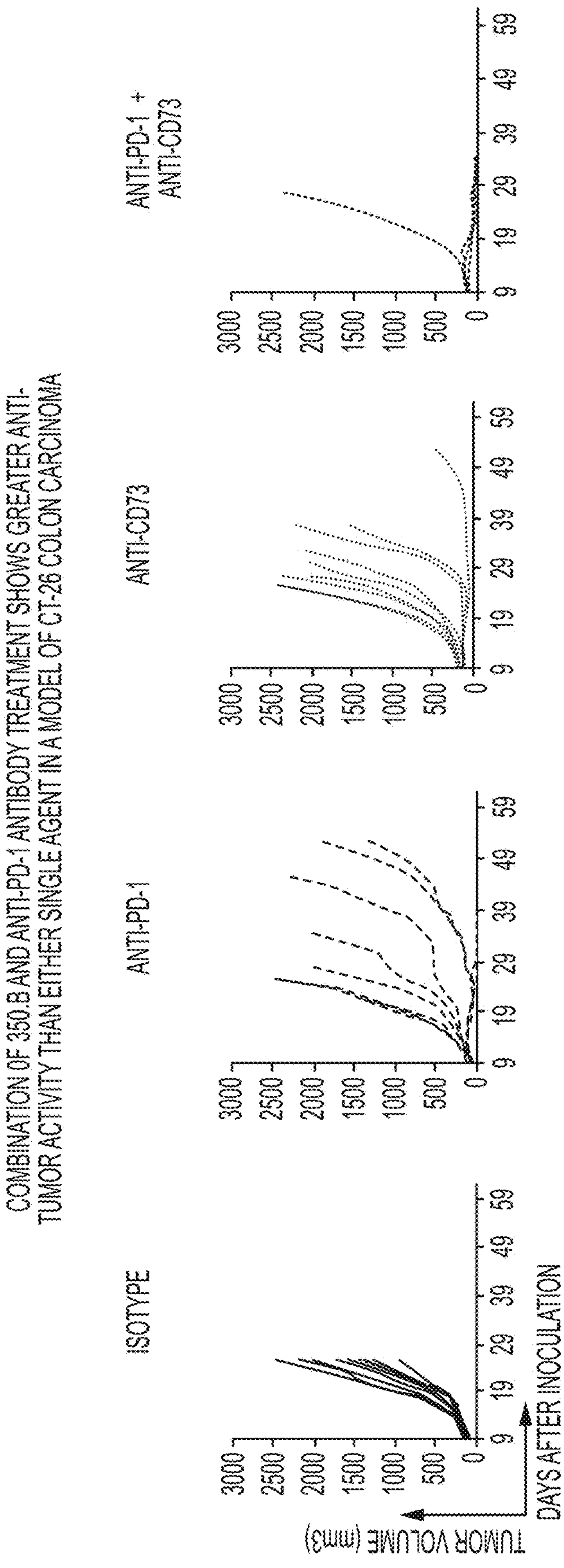
FIG. 23 is a panel of graphs showing individual tumor volumes for the indicated groups. Isotype control mice were euthanized on Day 25. In the anti-PD-1-treated group, mice received 300 μg/mouse for all doses. In the 350.B-treated group, mice received 600 μg/mouse for the first dose, followed by 400 μg/mouse for the four remaining doses. The same dosing schemes were administered for the combination group. All mice were treated on Days 2, 5, 9, 12 and 17.

Treatment with 350.B or low-dose anti-PD-1 alone (300 μg) showed partial tumor growth inhibition (30.96% and 52.04%, respectively) on day 25. In contrast, low-dose anti-PD-1+350.B in combination resulted in 88.41% tumor growth inhibition (FIG. 23). Tumor control with a high dose of anti-PD-1 alone was sufficient such that additional benefit with 350.B was not observed. No notable loss in body weights was observed in any of the groups, and there were no significant clinical observations for the animals on study. These data demonstrate that combination treatment of sub-optimal doses of anti-CD73 and anti-PD-1 antibodies can lead to enhanced tumor growth inhibition in the CT-26 syngeneic tumor model.

Example 6: Pharmacokinetics and Toxicology Study of the Anti-CD73 Antibody 373.A in Cynomolgus Monkeys As a single agent, the anti-CD73 antibody 373.A was well tolerated when intravenously administered once weekly over four weeks to cynomolgus monkeys at doses as high as 100 mg/kg. There were no effects on cardiac function as assessed by electrocardiogram nor were there any toxicologically meaningful effects on clinical pathology, immunophenotyping or histopathological findings. Therefore, the no observed adverse effect level (NOAEL) for 373.A in cynomolgus monkeys is 100 mg/kg, whereas the highest non-severely toxic dose (HNSTD) is >100 mg/kg.

In a Non GLP single dose toxicology study, cynomolgous monkeys were administered single IV doses of control, 3, 30 or 100 mg/kg of the antibody 373.A. After IV injection, 373.A declined rapidly in the 3 mg/kg group likely due to target-mediated drug disposition. In the 30 mg/kg and 100 mg/kg group decline was generally in a multi-exponential manner. No sex differences in 373.A Cmax and $AUC_{0\text{-}168\ hr}$ values were observed. Exposure, assessed by 373.A mean Cmax and $AUC_{0\text{-}168\ hr}$ values, increased with the increase in dose levels from 3 to 100 mg/kg. The increases in 373.A mean Cmax and $AUC_{0\text{-}168\ hr}$ values were generally dose proportional, with the exception of the $AUC_{0\text{-}168\ hr}$ between dose levels of 3 and 30 mg/kg. In the 100 mg/kg dose cohort, mean Cmax and $AUC_{0\text{-}168\ hr}$ were 2540 μg/mL and 173,000 μg·hr/mL, respectively. Anti-drug antibody (ADA) incidence in this study did not affect the PK.

In a GLP toxicology study, monkeys were administered four weekly IV doses of control, 10, 30 or 100 mg/kg of 373.A. Sex differences in 373.A Cmax and $AUC_{0\text{-}168\ hr}$ were minimal (between 0.7 to 1.2 fold). Exposure, as assessed by mean Cmax and $AUC_{0\text{-}168\ hr}$ increased proportionally from 10 to 100 mg/kg. After IV bolus injection, 373.A PK declined in a bi-exponential manner, with a mean elimination phase $t_{1/2}$ value of 266 hours following the recovery phase on Day 22 in the 100 mg/kg group. In the 100 mg/kg dose cohort, mean Cmax and $AUC_{0\text{-}168\ hr}$ after the day 22 dose, were 5030 μg/mL and 365,000 μg·hr/mL, respectively. ADA incidence decreased exposure in one animal in the 30 mg/kg group.

In a separate study, the cytokine release was assessed in an in-vitro soluble assay format following a 24-hour stimulation of human whole blood with 373.A, at 50, 100, 500 and 1000 μg/mL.

Blood samples were collected from ten healthy human donors. For each sample, negative (whole blood and whole blood with medium) and positive (anti-human CD3) controls were included. Cytokine levels were measured using a Luminex multiplex method for IL-13, IL-2, IL-6, IL-8, IL-10, IFNγ, and TNFα. Results obtained with the Buffer control were similar to the results obtained with the negative control (blood only) and no trend towards a decrease or an increase in cytokine release was noted with the diluent (0.5% Dextrose). For all donors, there was cytokine release induction with the anti-CD3 positive controls for all cytokines, indicating that the stimulation was appropriate and cytokine release could be induced in all samples. Cytokine levels obtained following stimulation with 373.A were similar to the levels measured in the negative controls. In conclusion, in-vitro stimulation of human whole blood with 373.A did not induce cytokine release at concentrations as high as 1000 μg/mL.

Example 7: A Phase I/Ib Study of the Anti-CD73 Antibody 373.A as a Single Agent and in Combination with BAP049-Clone-E and/or PBF509 in Patients with Advanced Malignancies During the last decade, immunotherapies that target different immune checkpoints (e.g., PD-1, PD-L1 and CTLA-4) have shown efficacy in a numbers of cancer indications. However, while some patients achieve objective and long lasting responses to checkpoint blockade, the majority of patients show modest or no clinical benefit, indicating that tumors use alternative immunosuppressive mechanisms to achieve immune escape (Allard et al., Clin Cancer Res. 2013; 19(20):5626-35; Vesely et al., Annu Rev Immunol 2011; 29:235-271). Thus, concomitant blockade of multiple immune suppressive pathways may be required to induce clinically meaningful responses in a larger number of patients.

Over the past years, adenosine generation and signaling have emerged as potential therapeutic targets in cancer treatment. Adenosine creates an immunosuppressive tumor microenvironment by reducing the cytotoxic anti-tumor immune response, enhancing the proliferation and polarization of immune suppressive cells, and by increasing neovascularization (Young et al., Cancer Discovery 2014; 4(8): 879-88). Preclinical data demonstrate that CD73 blockade can significantly delay primary tumor growth and inhibit the development of lung metastases in an immune-competent syngeneic mouse model (Stagg et al 2010). Similar results were observed in a study where genetic deletion of A2aR in the host resulted in rejection of the established immunogenic tumors in A2aR deficient mice with no rejection seen in control wild type mice (Ohta et al., PNAS 2006; 103(35): 13132-37).

A phase I/Ib, open-label, multi-center study has been designed to evaluate the safety, tolerability, preliminary anti-tumor activity, pharmacokinetics (PK) and pharmacodynamics (PD) of the anti-CD73 antibody 373.A as a single agent and in combination with the $A2a_AR$ antagonist PBF509 and/or the anti-PD-1 antibody BAP049-Clone-E in patients with advanced malignancies. The primary objectives are to characterize the safety and tolerability, and to determine the recommended dose (RD) for 373.A as a single agent and in combination with PBF509 and/or BAP049-Clone-E. The secondary objectives are to assess the preliminary anti-tumor activity and PK of 373.A as a single agent and in combination with PBF509 and/or BAP049-Clone-E, assess the immunogenicity of 373.A and BAP049-Clone-E, and to characterize changes in the immune infiltrate in tumors following treatment, e.g., change from baseline in tumor infiltrating lymphocytes (TILs), tumor associated macrophages (TAMs), CD8+ T-cells, and PDL-expression.

BAP049-Clone-E is a high-affinity, ligand-blocking, humanized anti-programmed death-1 (PD-1) IgG4 antibody that blocks the binding of PD-L and PD-L2 to PD-1. BAP049-Clone-E is being tested in a phase I/II study in advanced malignancies. PBF509, a new, non-xanthine-based compound, is a potent oral adenosine $A2a_AR$ antagonist. The sequence of BAP049-Clone-E is disclosed in Table 5.

Two ongoing Phase I/Ib and Phase II studies evaluate PBF509 as a single agent and/or in combination with BAP049-Clone-E in patients with advanced non-small cell lung cancer (NSCLC) and solid tumors and non-Hodgkin lymphoma, respectively.

This I/Ib study will initially enroll adult patients with advanced malignancies that have progressed or are intolerant to standard therapy in indications where moderate to high CD73 expression has been associated with poorer outcome, indicating adenosine-mediated immune escape (Wu et al., Journal of Surgical Oncology 2012, 106(2): 130-137; Gaudreau et al., Oncoimmunology; 2016, 5(5): e1127496; Inoue et al., Oncotarget.; 2017, 8(5):8738-8751). These indications include non-small cell lung cancer (NSCLC), triple negative breast cancer (TNBC), pancreatic cancer (PDAC), renal cell carcinoma (RCC), ovarian cancer, and micro-satellite stable (MSS) colorectal cancer, though additional indications may be enrolled based on emerging clinical data (e.g. efficacy data or proven pathway activation).

The study consists of two parts: (1) a dose escalation part for single agent 373.A, doublet combinations 373.A/PBF509 and 373.A/BAP049-Clone-E, or a triplet combination 373.A/PBF509/BAP049-Clone-E, which leads to declaration of recommended doses (RDs) for each treatment, and (2) a dose expansion part where patients will be treated at the RDs for single agent, doublet combinations, and triplet combination. The escalation part will enroll patients with advanced NSCLC, TNBC, PDAC, RCC, ovarian cancer, and colorectal cancer (MSS); and there is no restriction on the number of prior treatments. The expansion part will enroll patients with advanced malignancies having received up to 3 lines of prior treatment.

In the expansion part, patients in each indication will be equally randomized to the combination treatment arms. Randomization will be performed per indication, and further stratified within certain indications by prior PD-1/PD-L1 treatment (naive or resistant).

Dose and Regimen Selection

373.A Monotherapy

The starting dose of 60 mg flat dose 373.A, administered intravenously every 2 weeks (Q2W), was selected based upon preclinical safety, tolerability, and PK data observed in cynomolgus monkey as well as published case histories of CD73 deficient patients.

The 60 mg dose is considered to be a minimally pharmacological active dose (mPAD) as it is predicted to provide (1) approximately 20 hrs of >90% CD8+ T-cell CD73 occupancy, (2) approximately 22 hrs of >90% adenosine inhibition, (3) approximately 17 hrs of >90% imputed overall CD73 occupancy.

Based on modeling of TK data from the cynomolgus monkey Toxicology studies, ex-vivo CD8+ T cell CD73 occupancy data and in-vitro data on inhibition of adenosine formation, a dose ≥1200 mg Q2W is predicted to achieve >90% target occupancy on CD8+ T cells throughout the dosing interval and a dose ≥600 mg Q2W is predicted to achieve >90% inhibition of adenosine production.

The dose of 373.A will be escalated in sequential cohorts, guided by a Bayesian Logistic Regression model (BLRM) coupled with overdose control (EWOC) criterion, until a maximum tolerated dose (MTD) or recommended dose (RD) for expansion is identified. Preclinical data and modeling suggest that there may be a high antigen sink and that high doses (e.g. ≥1200 mg Q2W) may be needed to achieve continuous target occupancy throughout the dose interval. Dose escalation will primarily be performed with a Q2W regimen. However, if this regimen shows rapid 373.A elimination and lack of target saturation within the dosing interval, a more frequent QW regimen may be tested. If on the other hand, a Q4W regimen is predicted to have no rapid elimination within the dosing interval, Q4W regimen may be explored instead.

373.A/PBF509 Combination

The maximum starting doses for the 373.A/PBF509 doublet combination will be 200 mg Q2W 373.A and 80 mg BID PBF509.

200 mg Q2W 373.A is a low dose of 373.A that is predicted to achieve ~2.3 days of >90% target occupancy on CD8+ T cells. The 200 mg Q2W 373.A dose is 16% of the 1200 mg Q2W dose that is anticipated to achieve >90% CD8+ T cell target occupancy throughout the dosing interval.

PBF509 has been tested as a single-agent up to 640 mg BID with no safety issues in advanced/metastatic NSCLC (only 1 DLT out of 5 evaluable patients at the 640 mg BID dose). In the same study, PBF509 has shown single-agent activity in the range of 80 mg BID to 480 mg BID, with 2 partial responses (PRs) and 6 with stable disease (SD), in a total of 18 dosed patients.

A dose-escalation approach of 373.A and PBF509 will be undertaken in order to determine the appropriate dose of each drug in combination, guided by Bayesian Logistic Regression modeling (BLRM) coupled with overdose control (EWOC) principle criteria.

373.A/BAP049-Clone-E Combination

The maximum starting dose for the 373.A/BAP049-Clone-E doublet combination will be 200 mg Q2W 373.A and 400 mg Q4W BAP049-Clone-E.

The rationale for 200 mg Q2W 373.A has been described above. The 200 mg Q2W 373.A will be combined with the RD for BAP049-Clone-E which is 400 mg Q4W, which has been shown to be safe and efficacious.

373.A dose level will be escalated sequentially with a fixed dose of BAP049-Clone-E, guided by Bayesian Logistic Regression modeling (BLRM) coupled with overdose control (EWOC) principle criteria.

373.A/BAP049-Clone-E/PBF509 Combination

The maximum starting dose for the 373.A/BAP049-Clone-E/PBF509 triplet combination will be 200 mg Q2W 373.A, 400 mg Q4W BAP049-Clone-E and 80 mg BID PBF509.

PBF509 has been safely administered up to 160 mg BID in combination with 400 mg Q4W BAP049-Clone-E (only 1 DLT out of 6 evaluable patients), with combination activity on efficacy: 2 PRs and 6 SDs, out of a total of 10 patients. The 160 mg BID PBF509 and 400 mg Q4W BAP049-Clone-E dose is currently being used in the Ph2 study.

A dose-escalation approach for 373.A/BAP049-Clone-E/PBF509 with a fixed dose of BAP049-Clone-E will be undertaken in order to determine the appropriate dose of 373.A and PBF509 in the triplet combination, guided by a Bayesian Logistic Regression model (BLRM) coupled with overdose control (EWOC) criterion.

The antibody 373.A (100 mg powder for solution for infusion) will be administered intravenously as a 1 hr infusion (up to 2 hours if clinically indicated). BAP049-Clone-E (100 mg powder for solution for infusion) will be administered intravenously as a 30 minute infusion (up to 2 hours, if clinically indicated). When given in combination, 373.A and BAP049-Clone-E are to be administered on the same day using separate infusion materials (bag, lines, filters) for each infusion. The same access site may be used for both infusions. 373.A will be infused first followed by a 30 minute break before infusing BAP049-Clone-E. PBF509 (40 mg and/or 80 mg and/or 160 mg capsule for oral use) will be taken orally twice daily (BID) continuously. On the visits where 373.A and/or BAP049-Clone-E will be administered, the dose of PBF509 will be taken first followed by the 373.A infusion. A break between PBF509 administration and the 373.A infusion is not required. The 373.A infusion should be started as soon as possible and not more than 60 minutes after PBF509 is given.

Tables 22-25 describe the starting dose and the dose levels that may be evaluated during this trial. Patients treated with 373.A single agent or 373.A in combination with BAP049-Clone-E and/or PBF509 will begin study treatment on Cycle 1 Day 1. Each cycle will consist of 28 days. 373.A Q2W will be administered on Day 1 and 15 of a cycle. 373.A QW will be administered on Day 1, 8, 15, and 22 of a cycle. 373.A Q4W will be administered on Day 1 of a cycle. BAP049-Clone-E Q4W will be administered on Day 1 of a cycle. PBF509 BID will be taken every day of a cycle.

TABLE 22

Provisional dose levels for 373.A

| Dose level | Proposed dosing regimen* | Increment from previous dose |
|---|---|---|
| −2** | 6 mg Q2W | −233% |
| −1** | 20 mg Q2W | −200% |
| 1 | 60 mg Q2W | (starting dose) |
| 2 | 200 mg Q2W | 233% |
| 3 | 600 mg Q2W | 200% |
| 4 | 1200 mg Q2W | 100% |
| 5 | 2400 mg Q2W | 100% |
| 6 | 3600 mg Q2W | 50% |

*It is possible for additional and/or intermediate dose levels to be added during the course of the study Cohorts may be added at any dose level below the MTD in order to better understand safety, PK or PD.

**Dose level −1 and −2 represent treatment doses for patients requiring a dose reduction from the starting dose level. No dose reduction below dose level −2 is permitted for this study.

TABLE 23

Provisional dose levels for 373.A in combination with PBF509

| Dose level | Proposed dose 373.A* | Increment from previous dose 373.A | Proposed dose PBF509* | Increment from previous dose PBF509 |
|---|---|---|---|---|
| −2** | 20 mg Q2W | −200% | 40 mg BID | 0% |
| −1** | 60 mg Q2W | −233% | 40 mg BID | −100% |
| 1 | 200 mg Q2W | (starting dose) | 80 mg BID | (starting dose) |
| 2 | 200 mg Q2W | 0% | 160 mg BID | 100% |
| 3 | 600 mg Q2W | 200% | 160 mg BID | 0% |
| 4 | 1200 mg Q2W | 100% | 160 mg BID | 0% |
| 5 | 2400 mg Q2W | 100% | 160 mg BID | 0% |
| 6 | 2400 mg Q2W | 100% | 320 mg BID | 100% |
| 7 | 2400 mg Q2W | | 480 mg BID | |
| 8 | 2400 mg Q2W | | 620 mg BID | |
| 9 | 3600 mg Q2W | | 320 mg BID | |
| 10 | 3600 mg Q2W | | 480 mg BID | |
| 11 | 3600 mg Q2W | | 620 mg BID | |

*It is possible for additional and/or intermediate dose levels to be added during the course of the study Cohorts may be added at any dose level below the MTD in order to better understand safety, PK or PD.

**Dose level −1 and −2 represent treatment doses for patients requiring a dose reduction from the starting dose level. No dose reduction below dose level −2 is permitted for this study.

TABLE 24

Provisional dose levels for 373.A in combination with BAP049-Clone-E

| Dose level | Proposed dose 373.A* | Increment from previous dose 373.A | Proposed dose BAP049-Clone-E | Increment from previous dose BAP049-Clone-E |
|---|---|---|---|---|
| −2** | 20 mg Q2W | −200% | 400 mg Q4w | 0% |
| −1** | 60 mg Q2W | −233% | 400 mg Q4w | 0% |
| 1 | 200 mg Q2W | (starting dose) | 400 mg Q4w | (starting dose) |
| 2 | 600 mg Q2W | 200% | 400 mg Q4w | 0% |
| 3 | 1200 mg Q2W | 100% | 400 mg Q4w | 0% |
| 4 | 2400 mg Q2W | 100% | 400 mg Q4w | 0% |
| 5 | 3600 mg Q2W | 50% | 400 mg Q4W | 0% |

*It is possible for additional and/or intermediate dose levels to be added during the course of the study Cohorts may be added at any dose level below the MTD in order to better understand safety, PK or PD.

**Dose level −1 and −2 represent treatment doses for patients requiring a dose reduction from the starting dose level. No dose reduction below dose level −2 is permitted for this study.

TABLE 25

Provisional dose levels for PBF509 in combination with 373.A and BAP049-Clone-E

| Dose level | Proposed dose 373.A* | Increment from previous dose 373.A | Proposed dose BAP049-Clone-E | Increment from previous dose BAP049-Clone-E | Proposed dose PBF509* | Increment from previous dose PBF509 |
|---|---|---|---|---|---|---|
| −2** | 20 mg Q2W | −200% | 400 mg Q4W | 0% | 40 mg BID | 0% |
| −1** | 60 mg Q2W | −233% | 400 mg Q4W | 0% | 40 mg BID | −100% |
| 1 | 200 mg Q2W | (starting dose) | 400 mg Q4W | (starting dose) | 80 mg BID | (starting dose) |
| 2 | 200 mg Q2W | 0% | 400 mg Q4W | 0% | 160 mg BID | 100% |
| 3 | 600 mg Q2W | 200% | 400 mg Q4W | 0% | 160 mg BID | 0% |
| 4 | 1200 mg Q2W | 100% | 400 mg Q4W | 0% | 160 mg BID | 0% |
| 5 | 2400 mg Q2W | 100% | 400 mg Q4W | 0% | 160 mg BID | 0% |
| 6 | 2400 mg Q2W | | 400 mg Q4W | | 320 mg BID | |
| 7 | 2400 mg Q2W | | 400 mg Q4W | | 480 mg BID | |
| 8 | 2400 mg Q2W | | 400 mg Q4W | | 620 mg BID | |
| 9 | 3600 mg Q2W | | 400 mg Q4W | | 320 mg BID | |
| 10 | 3600 mg Q2W | | 400 mg Q4W | | 480 mg BID | |
| 11 | 3600 mg Q2W | | 400 mg Q4W | | 620 mg BID | |

*It is possible for additional and/or intermediate dose levels to be added during the course of the study Cohorts may be added at any dose level below the MTD in order to better understand safety, PK or PD.
**Dose level −1 and −2 represent treatment doses for patients requiring a dose reduction from the starting dose level. No dose reduction below dose level −2 is permitted for this study.

Example 8. Crystal Structure Analysis

Cloning

The Fab fragment of 350.A2 was generated by engineering a stop codon between the two proline residues above the core hinge region of the heavy chain of 350.A2 antibody. 350.A2 Fab comprises a heavy chain comprising the amino acid sequence of SEQ ID NO: 331 and a light chain comprising the amino acid sequence of SEQ ID NO: 23. The CD73 ECD with his-tag (SEQ ID NO: 171) was cloned into pRS5a vector.

Expression and Purification

Expi293F cells were transfected at 1:1 350.A2 to CD73 ECD ratio and five days post-transfection cells were pelleted at 2000 rpm. During this time, the Fab:CD73 complex was secreted into the supernatant. The supernatant was filtered through a 0.2 μm SteriFlip filter. Pelleted cell debris was discarded. The Fab-ECD complex was purified using a protein L column followed by a Mono Q column. After elution from a MonoQ column, the complex (captured in the flow-through) was re-purified using a Protein L column. The purified sample was dialyzed against 10 mM tris, pH 7.5, 100 mM NaCl and analyzed by SEC-MALS for purity. It was subsequently concentrated to 9 mg/ml.

Crystallization, Cryopreservation and Data Collection

The 350.A2 Fab-CD73 complex was crystallized using the hanging-drop method. Prior to setting up crystallization trays, the purified complex was spun at 14,000 rpm for 10m minutes to remove aggregated protein and debris. Following this, 1.0 μl of complex at 9 mg/ml was mixed with 1.0 μl of protein precipitant consisting of 0.2M $Li_2SO_4$, 1.2M $NaH_2PO_4$, 0.8M $K_2HPO_4$, 0.1M Glycine, pH 10.5, and then suspended over a well of 300 μl of protein precipitant. Crystals grew in approximately 3-4 days. Crystals were harvested and then cryopreserved using a solution of protein precipitant combined with 25% (v:v) of glycerol. X-ray diffraction data was collected at the Advanced Light Source, beamline 5.0.1. Diffraction data was usable to approximately 2.85 Angstroms.

Structure Solution and Refinement

The structure of 350.A2 was modeled using the Fab fragment of AL-57 (RCSB accession code 3HI5) as a template using the MOE modeling suite. The co-structure was solved using the program PHASER and the dimeric structure of glycosylated human CD73 (RCSB 4H1S) and the Fab homology model as search models. Briefly, the dimeric structure of human CD73 was used as the first search model, locating the position of two dimers of human CD73 in the asymmetric unit. This initial structure was refined using Phenix-Refine. Subsequently, the homology model of the heavy and light chain were used as separate search models, thereby locating the position of the two Fabs in relation to the two dimers of human CD73. The completed structure was refined to convergence over multiple rounds of refinement and real-space rebuilding. The final R-factor and free-R factor were 22.78% and 27.12%, respectively. The electron density maps reveal that each CD73 monomer is glycosylated on asparagine-311. However, this glycosylation is heterogonous and thus it is not possible to determine the exact chemical structure of the glycosylation event. Because of this, the glycosylation is not included in the structural model.

The 350.A2 Fab-CD73 co-crystal structure reveals the interactions of the antibody with CD73. These interactions can be divided into direct enthalpic interactions, such as hydrogen-bonding or electrostatic interactions, and Van der Waal and hydrophobic interactions which are driven by shape complementarity between the antibody and CD73.

The key enthalpic and VDW/hydrophobic interactions identified by the co-crystal structure are as follows. The following interactions occur between the Fab heavy chain and CD73. The Fab heavy chain residues are numbered according to Kabat numbering and highlighted in FIGS. 26C and 26D (bold, italic, and single-underlined). The CD73 residues are numbered according to SEQ ID NO: 105 and highlighted in FIGS. 26A and 26B (bold, italic, and single-underlined).

R54 of the Fab heavy chain is positioned for electrostatic interactions with the backbone carbonyls of Y110 and K136 in CD73.

R31 of the Fab heavy chain is positioned for electrostatic interactions with the backbone carbonyls of L132 and L157 of CD73.

The S99 backbone carbonyl, R31 backbone carbonyl, and the E95 sidechain of the Fab heavy chain are positioned for an electrostatic interaction with the K162 sidechain of CD73.

The E98 sidechain of the Fab heavy chain is positioned to hydrogen-bond with the sidechain of S155 in CD73.

Shape complementarity and Van der Waal interactions between amino acids 33, 50, 52, 56, 97, 98, 100, and 100a of the Fab heavy chain and amino acids 155-170 of CD73.

Shape complementarity and Van der Waal interactions between amino acids 30-31 of the Fab heavy chain and amino acids 136-138 of CD73.

The following interactions occur between the Fab light chain and CD73. The Fab light chain residues are numbered according to Kabat numbering and highlighted in FIGS. 26G and 26H (bold, italic, and single-underlined). The CD73 residues are numbered according to SEQ ID NO: 105 and highlighted in FIGS. 26E and 26F (bold, italic, and single-underlined).

The W32 sidechain of the Fab light chain is positioned to hydrogen-bond with the T209 sidechain of CD73.

Shape complementarity and Van der Waal interactions between amino acids 30 and 32 of the Fab light chain and amino acids 209-210 of CD73.

Example 9. Epitope Mapping Using Tandem Mass Tag (TMT) Isotope Labeling

Antibody comparisons using TMT isotope coding reagents were principally conducted as described in John D. et al., Analytical Chemistry 2015 87 (15), 7540-7544, herein incorporated by reference in its entirety.

Methods

TMT Labeling

Antibodies in DPBS had the following concentrations and were used without further processing: 374 (1.37 mg/mL), 377.B (2.25 mg/mL), 379.B (2.82 mg/mL), 373 (1 mg/mL), and 350 (1 mg/mL). CD73 (R&D Systems, Cat #5795-EN) was buffer exchanged into 100 mM triethylammonium bicarbonate buffer (TEAB), pH 8 and concentrated to 5 mg/ml to remove free amine in the received material and condition sample for TMT labeling using 10 kDa molecular weight cutoff micro-concentrators (Millipore Amicon Ultra). Antigen/antibody complexes (CD73/anti-CD73 mAb complexes) were prepared by combining 10 μg of CD73 with 12.8 μg of mAb (equinormal amounts or 2:1 molar ratio of CD73:mAb or 1:1 by binding site equivalents) at approximately 2 μM concentration with respect to CD73 in 100 mM TEAB, pH 8 buffer and equilibration for 30 min at room temperature. Labeling was performed by addition of 5 μl of 35 mM TMT reagent. A CD73 only control was prepared for labeling in a similar manner. Labeling time was 30s and 300s, respectively, after which labeling reactions were quenched by addition of 50 μL of 5% hydroxylamine solution. All reactions were prepared in duplicate.

Digestion

Samples were combined 15 min post hydroxylamine quench in a spin-concentrator and the total volume reduced to ~30 μL. This was followed by deglycosylation with PNGase F and reducing/denaturing SDS PAGE separation by standard methods.

The bands containing CD73 were excised from the gel for in-gel digestion. Gel processing followed standard procedures for destaining, reduction, alkylation, and dehydration. For conditioning prior to elastase digestion, dehydrated gel pieces were rehydrated with 50 mM Tris-buffer pH8, whereas for pepsin digestion, 1% formic acid was used in the last rehydration step before complete dehydration in vacuum.

Elastase digest samples were rehydrated for 1 hr on ice by addition of 25 μL of 12.5 ng/μL of elastase in 50 mM Tris pH8. Pepsin digest samples were rehydrated for 1 hr on ice by addition of 25 μl of 10 ng/μL pepsin in 1% formic acid.

After rehydration with enzymes, excess enzyme solution was discarded and 50 μl of the respective digestion buffer added before digesting for 4 hrs at 37° C. Following digestion, peptide recovery followed again standard in-gel digestion methodology.

LCMSMS

LCMSMS was performed using an Orbitrap Lumos mass spectrometer (Thermo Scientific, Waltham, Mass.) coupled to an Easy-nLC 1200 chromatography system (Thermo Scientific, Waltham, Mass.). The separation column was a 75 μm capillary with pulled tip packed with 15 cm of ReproSil-Pur 120 C18 AQ 3 μm (catalog # r13.aq). Proteolytic fragments were eluted using a segmented gradient from 0-35% B in 120 min, 35-63% B in 30 min, 63-100% B in 5 min, 100% B hold for 5 min, 100-0% B in 2 min, 0% B hold for 2 min at a flow rate of 500 nL/min using elution buffers A=0.1% formic acid water and B=0.1% formic acid in 80%-MCN.

The data acquisition method used the manufacturer's default method parameters for a TMT experiment with MSMS detection.

Data Reduction and Analysis

Raw data was searched against the CD73 protein sequence using MASCOT 2.5.1 (MatrixScience, UK) using MASCOT Daemon (MatrixScienc, UK) and ExtractMSn (Thermo Scientific, Waltham, Mass.) for conversion and merging of elastase and pepsin raw files to .mgf peak lists. For quantitation the default TMT10plex method build into MASCOT was used. Search results including the TMT reporter ion intensities were exported as .csv and further refined/curated to remove outliers before calculating intensity weighed reporter ion intensities averages across peptide spectral matches (PSMs) for a given lysine residue of the primary sequence using Microsoft Excel. Only PSMs of peptides containing a single lysine residue were used in the analysis to avoid ambiguity in labeling site.

Results

Intensity weighed CD73 normalized reporter ion intensity ratios covering observable lysine residues of the primary sequence are plotted as the difference between the ratio of CD73/anti-CD73 mAb complex and CD73 (1 by definition of normalization). Plotting the ratio in this fashion allows straightforward assessment of the changes in labeling rates occurring as a result of complex formation. Negative differences are indicative of reduced labeling in the antibody/antigen complexes and are interpreted similarly to HDX data as protection. The expectation is that the strongest protective effects are reflective of the shielding of the protein surface of the antigen from the reagent by the antibody. Besides the direct shielding at the protein-protein interface, changes elsewhere are not unexpected as the protein fold as a whole and the conformational ensemble in total can be disturbed by complex formation. Despite the complexities, this facilitates interpretation of the molecular events at an absolute scale. It is likely that antibodies showing similar overall effects (labeling profiles) upon complex formation will have similar epitopes and exert their effector function by similar molecular mechanisms. All the residues shown in this example are numbered according to SEQ ID NO: 105.

Figure 27A:
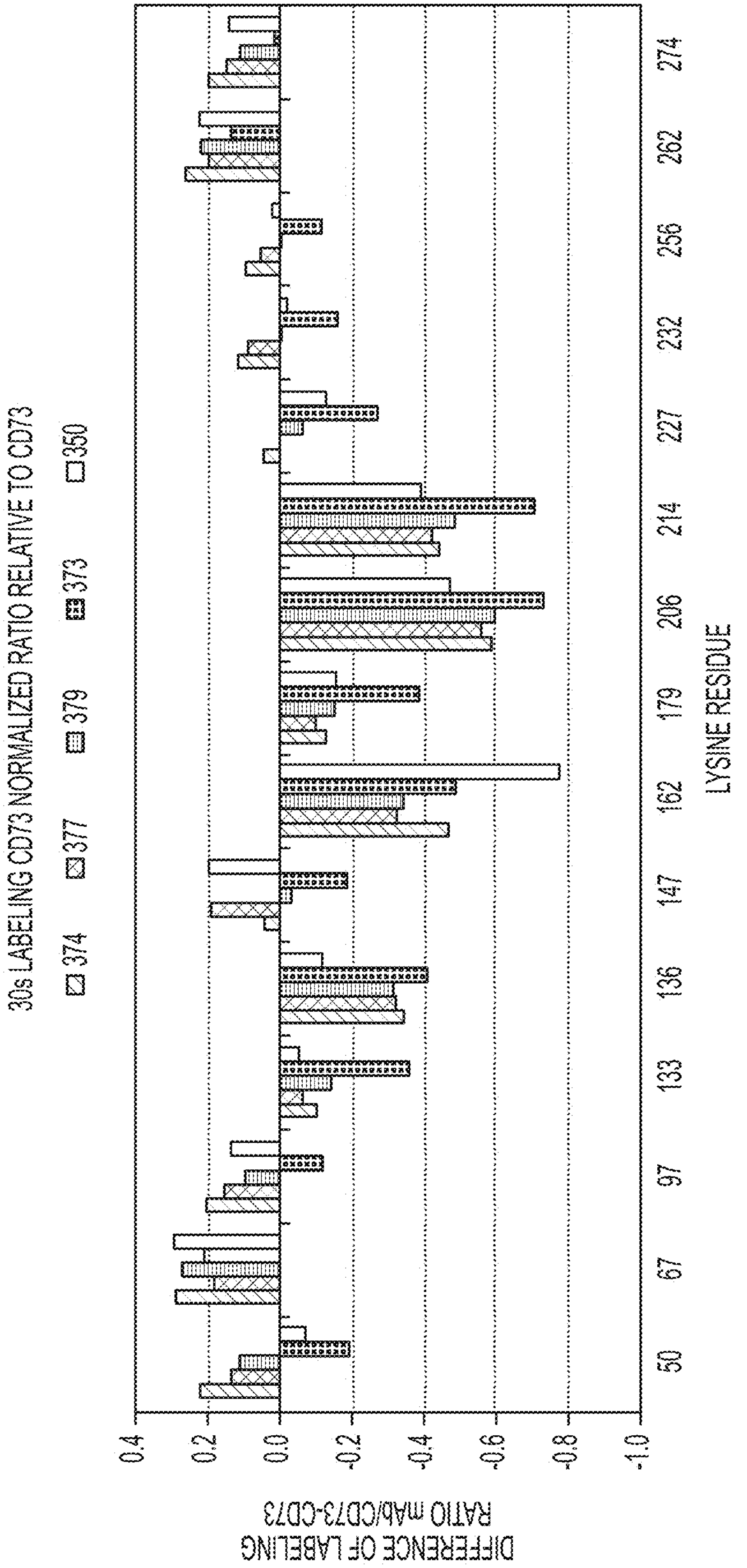
FIGS. 27A and 27B are graphs showing the difference between the labeling ratios observed for the CD73/mAb complexes and CD73 alone after a 30s labeling pulse.
Figure 27B:
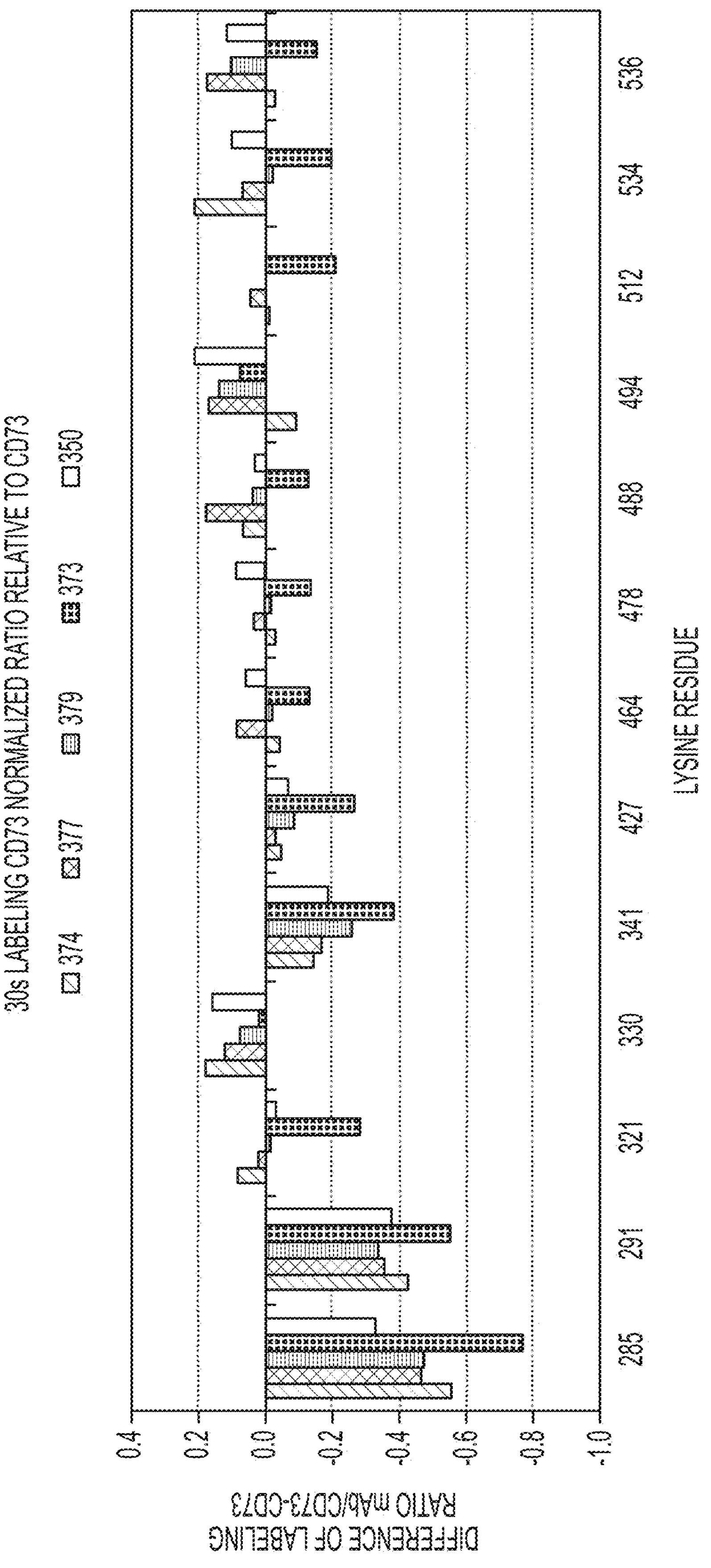

FIGS. 27A and 27B show the difference of ratios for 29 of the 35 lysines in the primary sequence of CD73 as observed at 30s labeling. Protection at lysines K162, K206 and K214 (FIG. 27A) correlates well with the prior HDX interpretation of the epitope of 373 (Example 2). Specifically, the HDX study assigned residues 158-172 (YLPYKVLPVGDEVVG, SEQ ID NO: 108, A-loop), which encompass K162; and residues 206-215 (KLKTLNVNKI, SEQ ID NO: 109, B-loop), which encompass K206 and K214, as part of the epitope of 373. Protection at lysines K285 and K291 (FIG. 27B) is consistent with the minor protection observed in the prior HDX data in the area around residue 300 (FIG. 14 and Example 2). K262 and K274 are located on the opposing sides of the N-terminal domain with respect to the epitope (K162, K206, and K214) and the increase in labeling at these two residues (FIG. 27A) may reflect the "destabilization" in that region as a consequence of mAb engagement. K136 is spatially close to K162 but located more to the center of the dimer. Protection at K136 for antibodies 374, 377, 379, and 373 (FIG. 27A) is consistent with the bidentate binding mode described for 373 in Example 2. This data suggests that antibodies 374, 377, 379, and 373 may form a highly homogeneous group. K341 is located in the N/C-terminal domain interface and close to the dimer interface.

Figure 28A:
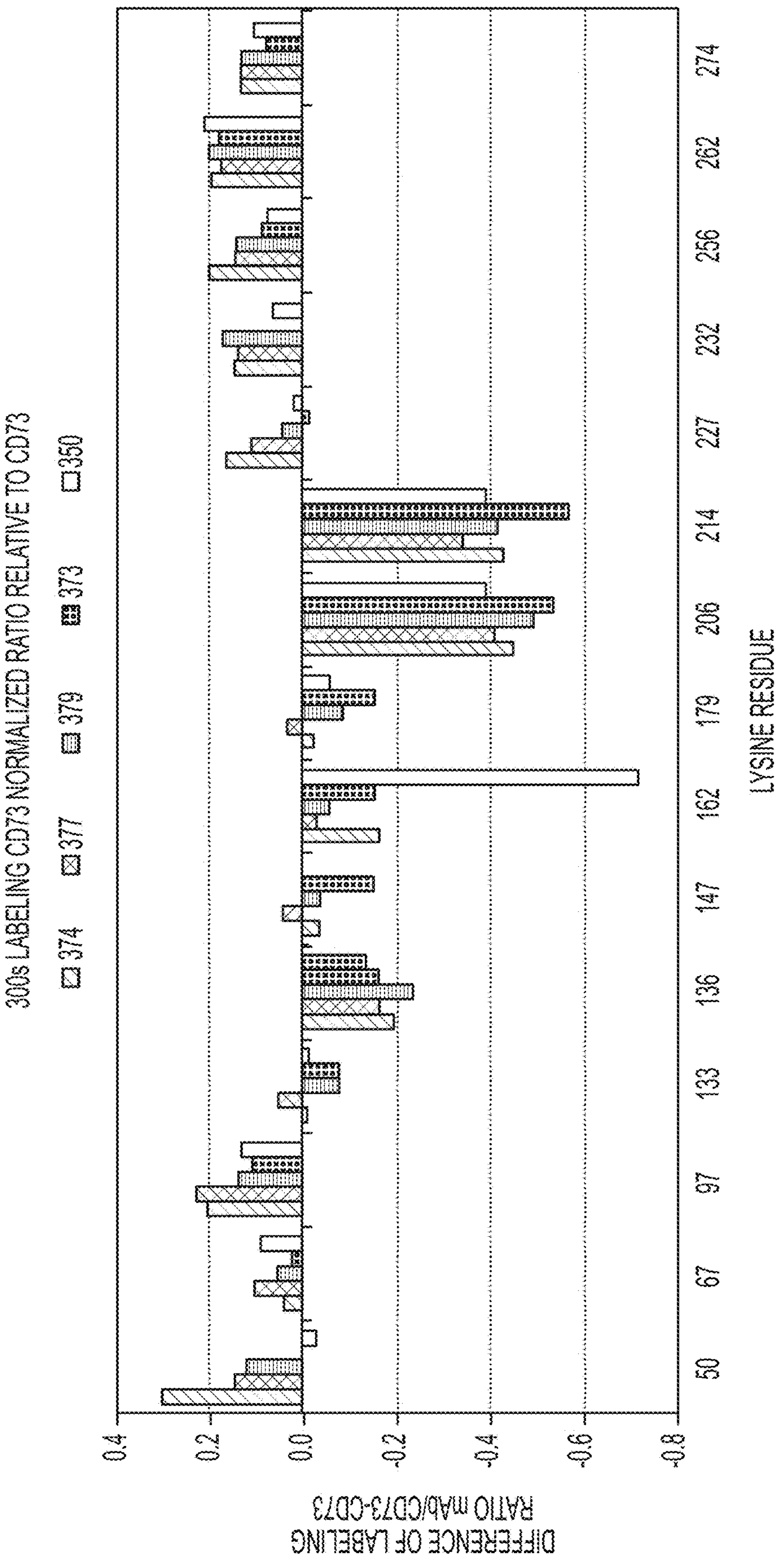
FIGS. 28A and 28B are graphs showing the difference between the labeling ratios observed for the CD73/mAb complexes and CD73 alone after labeling for 300s.
Figure 28B:
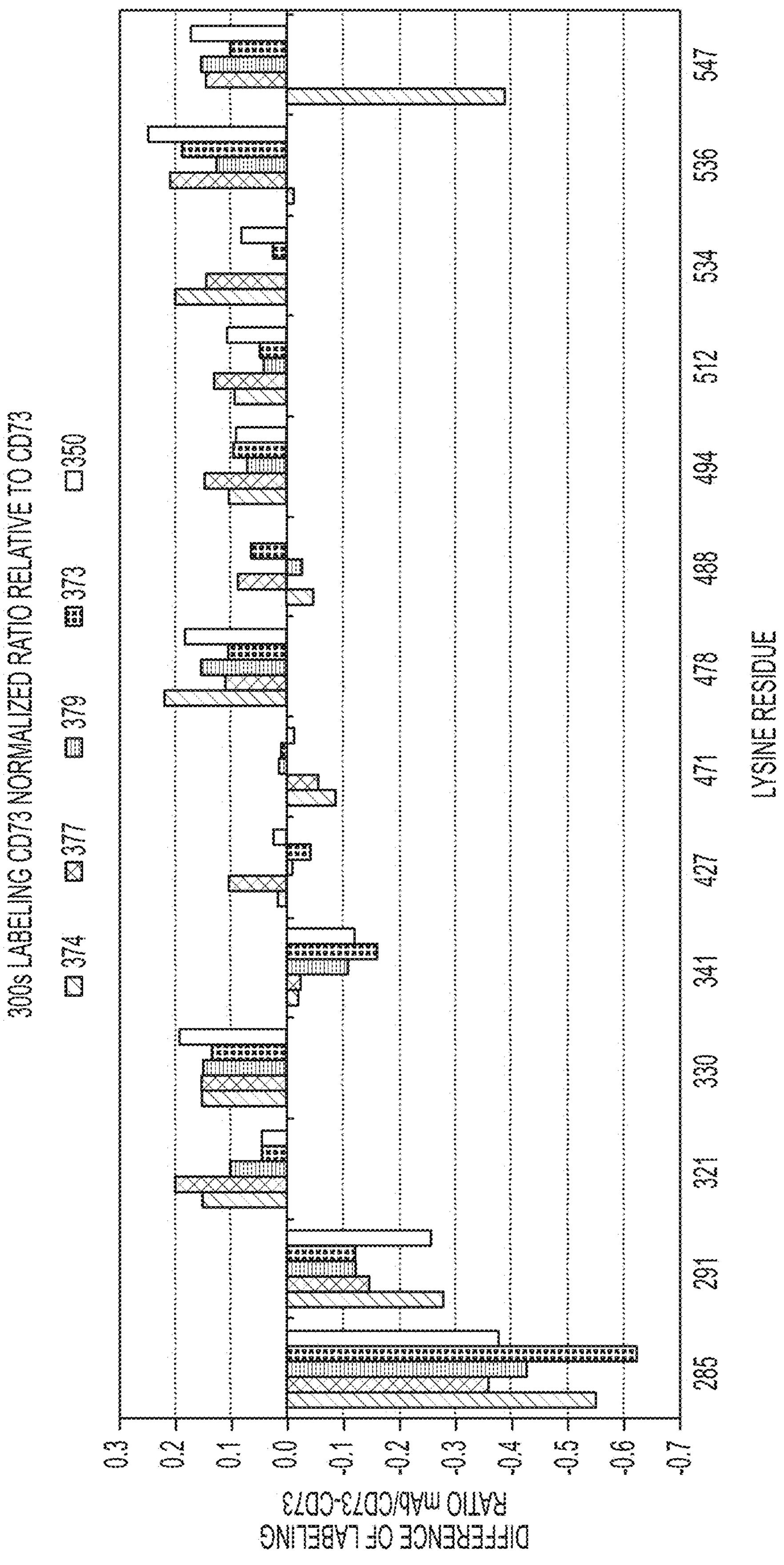

FIGS. 28A and 28B show the difference of ratios for 29 of the 35 lysines in the primary sequence of CD73 as observed at 300s labeling. Protection at K162 is no longer observable for mAbs 374, 377, 379, and 373, whereas protection is still strong for 350. In contrast, protection at K206 and K214 is unchanged. This provides further evidence of the highly homologous nature of antibodies 374, 377, 379, and 373 as assessed by their spatio-temporal labeling patterns.

Notably, for all these antibodies, protection at K206 is comparable to protection at K214 (FIGS. 27A and 28A).

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. An antibody molecule that binds to human CD73, comprising:

(a) (i) a heavy chain variable region (VH) comprising a heavy chain complementarity determining region 1 (VHCDR1) amino acid sequence of SEQ ID NO: 88, a VHCDR2 amino acid sequence of SEQ ID NO: 89, and a VHCDR3 amino acid sequence of SEQ ID NO: 37; and (ii) a light chain variable region (VL) comprising a light chain complementarity determining region 1 (VLCDR1) amino acid sequence of SEQ ID NO: 48, a VLCDR2 amino acid sequence of SEQ ID NO: 49, and a VLCDR3 amino acid sequence of SEQ ID NO: 50; or (b) (i) a VH comprising a VHCDR1 amino acid sequence of SEQ ID NO: 189, a VHCDR2 amino acid sequence of SEQ ID NO: 89, and a VHCDR3 amino acid sequence of SEQ ID NO: 43; and (ii) a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

2. The antibody molecule of claim 1, comprising:

(i) a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(ii) a VH comprising a VHCDR1 amino acid sequence of SEQ ID NO: 72, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(iii) a VH comprising a VHCDR1 amino acid sequence of SEQ ID NO: 38, a VHCDR2 amino acid sequence of SEQ ID NO: 71, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(iv) a VH comprising a VHCDR1 amino acid sequence of SEQ ID NO: 137, a VHCDR2 amino acid sequence of SEQ ID NO: 136, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(v) a VH comprising a VHCDR1 amino acid sequence of SEQ ID NO: 137, a VHCDR2 amino acid sequence of SEQ ID NO: 146, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(vi) a VH comprising a VHCDR1 amino acid sequence of SEQ ID NO: 137, a VHCDR2 amino acid sequence of SEQ ID NO: 154, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(vii) a VH comprising a VHCDR1 amino acid sequence of SEQ ID NO: 190, a VHCDR2 amino acid sequence of SEQ ID NO: 36, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(viii) a VH comprising a VHCDR1 amino acid sequence of SEQ ID NO: 191, a VHCDR2 amino acid sequence of SEQ ID NO: 71, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(ix) a VH comprising a VHCDR1 amino acid sequence of SEQ ID NO: 192, a VHCDR2 amino acid sequence of SEQ ID NO: 71, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(x) a VH comprising a VHCDR1 amino acid sequence of SEQ ID NO: 193, a VHCDR2 amino acid sequence of SEQ ID NO: 136, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;

(xi) a VH comprising a VHCDR1 amino acid sequence of SEQ ID NO: 194, a VHCDR2 amino acid sequence of SEQ ID NO: 146, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50; or (xii) a VH comprising a VHCDR1 amino acid sequence of SEQ ID NO: 195, a VHCDR2 amino acid sequence of SEQ ID NO: 154, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

3. The antibody molecule of claim 1, wherein:

(i) the antibody molecule is a human antibody, a full length antibody, a bispecific antibody, Fab, F(ab')2, Fv, or a single chain Fv fragment (scFv);

(ii) the antibody molecule comprises a heavy chain constant region selected from IgG1, IgG2, IgG3, and IgG4, and a light chain constant region chosen from the light chain constant regions of kappa or lambda; or (iii) the antibody molecule comprises a heavy chain constant region comprising an amino acid sequence selected from the group consisting of SEQ ID NOs: 92-103, 119, and 120, and/or a light chain constant region comprising the amino acid sequence of SEQ ID NO: 104.

4. A composition comprising a plurality of the antibody molecules of claim 1, wherein the antibody molecules bind to a human CD73 dimer, said dimer consisting of a first CD73 monomer and a second CD73 monomer, each monomer comprising the amino acid sequence of residues 27-547 of SEQ ID NO: 105, wherein when the antibody molecules in the plurality each comprises the same first antigen binding domain and the same second antigen binding domain, (i) at least 30%, 35%, or 40% of the antibody molecules in said composition bind to the CD73 dimer to form a complex, wherein each of said complex consists of one antibody molecule and one CD73 dimer; or (ii) at most 60%, 65%, or 70% of the antibody molecules in said composition bind to the CD73 dimer to form a complex, wherein each of said complex comprises two or more antibody molecules and two or more CD73 dimers.

5. A pharmaceutical composition comprising the antibody molecule of claim 1 and a pharmaceutically acceptable carrier, excipient or stabilizer.

6. The antibody molecule of claim 1, comprising a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

7. The antibody molecule of claim 1, comprising a heavy chain variable region comprising the amino acid sequence of SEQ ID NO: 44 and a light chain variable region comprising the amino acid sequence of SEQ ID NO: 55.

8. The antibody molecule of claim 1, comprising a heavy chain comprising the amino acid sequence of SEQ ID NO: 46, wherein residue 451 of SEQ ID NO: 46 is K, and a light chain comprising the amino acid sequence of SEQ ID NO: 57.

9. The antibody molecule of claim 1, comprising a heavy chain comprising the amino acid sequence of SEQ ID NO: 114, wherein residue 451 of SEQ ID NO: 114 is K, and a light chain comprising the amino acid sequence of SEQ ID NO: 57.

10. The antibody molecule of claim 1, wherein the antibody molecule comprises a heavy chain constant region of IgG4 and a light chain constant region of kappa.

11. The antibody molecule of claim 1, comprising:
(i) a human IgG4 heavy chain constant region with a mutation at position 228 according to EU numbering;
(ii) a human IgG4 heavy chain constant region with a Serine to Proline mutation at position 228 according to EU numbering; or
(iii) a heavy chain constant region comprising the amino acid sequence of SEQ ID NO: 92 or 93.

12. The antibody molecule of claim 1, comprising:
(i) a heavy chain variable region comprising the amino acid sequence of SEQ ID NO: 44, 77, 84, 142, 151, or 159, or an amino acid sequence having at least about 85%, 90%, 95%, or 99% sequence identity to SEQ ID NO: 44, 77, 84, 142, 151, or 159;
(ii) a light chain variable region comprising the amino acid sequence of SEQ ID NO: 55, or an amino acid sequence having at least about 85%, 90%, 95%, or 99% sequence identity to SEQ ID NO: 55;
(iii) a heavy chain comprising the amino acid sequence of SEQ ID NO: 46, 79, 86, 114, 116, or 117, or an amino acid sequence having at least about 85%, 90%, 95%, or 99% sequence identity to SEQ ID NO: 46, 79, 86, 114, 116, or 117;
(iv) a light chain comprising the amino acid sequence of SEQ ID NO: 57, or an amino acid sequence having at least about 85%, 90%, 95%, or 99% sequence identity to SEQ ID NO: 57;
(v) a heavy chain variable region comprising the amino acid sequence of SEQ ID NO: 44, or a sequence having at least about 85%, 90%, 95%, or 99% sequence identity thereto, and a light chain variable region comprising the amino acid sequence of SEQ ID NO: 55, or a sequence having at least about 85%, 90%, 95%, or 99% sequence identity thereto;
(vi) a heavy chain variable region comprising the amino acid sequence of SEQ ID NO: 77, or a sequence having at least about 85%, 90%, 95%, or 99% sequence identity thereto, and a light chain variable region comprising the amino acid sequence or SEQ ID NO: 55, or a sequence having at least about 85%, 90%, 95%, or 99% sequence identity thereto;
(vii) a heavy chain variable region comprising the amino acid sequence of SEQ ID NO: 84, or a sequence having at least about 85%, 90%, 95%, or 99% sequence identity thereto and a light chain variable region comprising the amino acid sequence of SEQ ID NO: 55, or a sequence having at least about 85%, 90%, 95%, or 99% sequence identity thereto;
(viii) a heavy chain variable region comprising the amino acid sequence of SEQ ID NO: 142, or a sequence having at least about 85%, 90%, 95%, or 99% sequence identity thereto, and a light chain variable region comprising the amino acid sequence of SEQ ID NO: 55, or a sequence having at least about 85%, 90%, 95%, or 99% sequence identity thereto;
(ix) a heavy chain variable region comprising the amino acid sequence of SEQ ID NO: 151, or a sequence having at least about 85%, 90%, 95%, or 99% sequence identity thereto, and a light chain variable region comprising the amino acid sequence of SEQ ID NO: 55, or a sequence having at least about 85%, 90%, 95%, or 99% sequence identity thereto;
(x) a heavy chain variable region comprising the amino acid sequence of SEQ ID NO: 159, or a sequence having at least about 85%, 90%, 95%, or 99% sequence identity thereto, and a light chain variable region comprising the amino acid sequence of SEQ ID NO: 55, or a sequence having at least about 85%, 90%, 95%, or 99% sequence identity thereto; or
(xi) a heavy chain variable region comprising the amino acid sequence of SEQ ID NO: 44 and a light chain variable region comprising the amino acid sequence of SEQ ID NO: 55.

13. The antibody molecule of claim 1, comprising:
(i) a heavy chain comprising the amino acid sequence of SEQ ID NO: 46, or a sequence having at least about 85%, 90%, 95%, or 99% sequence identity thereto, and a light chain comprising the amino acid sequence of SEQ ID NO: 57, or a sequence having at least about 85%, 90%, 95%, or 99% sequence identity thereto;
(ii) a heavy chain comprising the amino acid sequence of SEQ ID NO: 114, or a sequence having at least about 85%, 90%, 95%, or 99% sequence identity thereto, and a light chain comprising the amino acid sequence of SEQ ID NO: 57, or a sequence having at least about 85%, 90%, 95%, or 99% sequence identity thereto;
(iii) a heavy chain comprising the amino acid sequence of SEQ ID NO: 79, or a sequence having at least about 85%, 90%, 95%, or 99% sequence identity thereto, and a light chain comprising the amino acid sequence of SEQ ID NO: 57, or a sequence having at least about 85%, 90%, 95%, or 99% sequence identity thereto;
(iv) a heavy chain comprising the amino acid sequence of SEQ ID NO: 116, or a sequence having at least about 85%, 90%, 95%, or 99% sequence identity thereto, and a light chain comprising the amino acid sequence of SEQ ID NO: 57, or a sequence having at least about 85%, 90%, 95%, or 99% sequence identity thereto;
(v) a heavy chain comprising the amino acid sequence of SEQ ID NO: 86, or a sequence having at least about 85%, 90%, 95%, or 99% sequence identity thereto, and a light chain comprising the amino acid sequence of SEQ ID NO: 57, or a sequence having at least about 85%, 90%, 95%, or 99% sequence identity thereto;
(vi) a heavy chain comprising the amino acid sequence of SEQ ID NO: 117, or a sequence having at least about 85%, 90%, 95%, or 99% sequence identity thereto, and a light chain comprising the amino acid sequence of SEQ ID NO: 57, or a sequence having at least about 85%, 90%, 95%, or 99% sequence identity thereto; or
(vii) a heavy chain comprising the amino acid sequence of SEQ ID NO: 46 and a light chain comprising the amino acid sequence of SEQ ID NO: 57.

14. An antibody molecule that binds to human CD73, comprising:
(a) a heavy chain variable region (VH) comprising a heavy chain complementarity determining region 1 (VHCDR1) amino acid sequence of SEQ ID NO: 38, a VHCDR2 amino acid sequence of SEQ ID NO: 36, and a VHCDR3 amino acid sequence of SEQ ID NO: 37; and a light chain variable region (VL) comprising a light chain complementarity determining region 1 (VLCDR1) amino acid sequence of SEQ ID NO: 48, a VLCDR2 amino acid sequence of SEQ ID NO: 49, and a VLCDR3 amino acid sequence of SEQ ID NO: 50;
(b) a VH comprising a VHCDR1 amino acid sequence of SEQ ID NO: 35, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50;
(c) a VH comprising a VHCDR1 amino acid sequence of SEQ ID NO: 39, a VHCDR2 amino acid sequence of SEQ ID NO: 40, and a VHCDR3 amino acid sequence of SEQ ID NO: 37; and a VL comprising a VLCDR1 amino acid sequence of SEQ ID NO: 51, a VLCDR2 amino acid sequence of SEQ ID NO: 52, and a VLCDR3 amino acid sequence of SEQ ID NO: 53;

(d) a VH comprising a VHCDR1 amino acid sequence of SEQ ID NO: 41, a VHCDR2 amino acid sequence of SEQ ID NO: 42, and a VHCDR3 amino acid sequence of SEQ ID NO: 43; and a VL comprising a VLCDR1 amino acid sequence of SEQ ID NO: 54, a VLCDR2 amino acid sequence of SEQ ID NO: 52, and a VLCDR3 amino acid sequence of SEQ ID NO: 50; or (e) a VH comprising a VHCDR1 amino acid sequence of SEQ ID NO: 190, a VHCDR2 amino acid sequence of SEQ ID NO: 36, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

15. The antibody molecule of claim 14, comprising a VH comprising a VHCDR1 amino acid sequence of SEQ ID NO: 38, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

16. The antibody molecule of claim 14, comprising a VH comprising a VHCDR1 amino acid sequence of SEQ ID NO: 35, a VHCDR2 amino acid sequence of SEQ ID NO: 36, and a VHCDR3 amino acid sequence of SEQ ID NO: 37; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

17. The antibody molecule of claim 14, comprising a VH comprising a VHCDR1 amino acid sequence of SEQ ID NO: 39, a VHCDR2 amino acid sequence of SEQ ID NO: 40, and a VHCDR3 amino acid sequence of SEQ ID NO: 37; and a VL comprising a VLCDR1 amino acid sequence of SEQ ID NO: 51, a VLCDR2 amino acid sequence of SEQ ID NO: 52, and a VLCDR3 amino acid sequence of SEQ ID NO: 53.

18. The antibody molecule of claim 14, comprising a VH comprising a VHCDR1 amino acid sequence of SEQ ID NO: 41, a VHCDR2 amino acid sequence of SEQ ID NO: 42, and a VHCDR3 amino acid sequence of SEQ ID NO: 43; and a VL comprising a VLCDR1 amino acid sequence of SEQ ID NO: 54, a VLCDR2 amino acid sequence of SEQ ID NO: 52, and a VLCDR3 amino acid sequence of SEQ ID NO: 50.

19. The antibody molecule of claim 14, comprising a VH comprising a VHCDR1 amino acid sequence of SEQ ID NO: 190, a VHCDR2 amino acid sequence of SEQ ID NO: 36, and a VHCDR3 amino acid sequence of SEQ ID NO: 43; and a VL comprising a VLCDR1 amino acid sequence of SEQ ID NO: 48, a VLCDR2 amino acid sequence of SEQ ID NO: 49, and a VLCDR3 amino acid sequence of SEQ ID NO: 50.

20. The antibody molecule of claim 14, comprising a heavy chain variable region comprising the amino acid sequence of SEQ ID NO: 44, and a light chain variable region comprising the amino acid sequence of SEQ ID NO: 55.

21. The antibody molecule of claim 14, comprising:

(i) a heavy chain comprising the amino acid sequence of SEQ ID NO: 46, wherein residue 451 of SEQ ID NO: 46 is K, and a light chain comprising the amino acid sequence of SEQ ID NO: 57; or (ii) a heavy chain comprising the amino acid sequence of SEQ ID NO: 114, wherein residue 451 of SEQ ID NO: 114 is K, and a light chain comprising the amino acid sequence of SEQ ID NO: 57.

22. A pharmaceutical composition comprising the antibody molecule of claim 14 and a pharmaceutically acceptable carrier, excipient, or stabilizer.

23. An antibody molecule that binds to human CD73, comprising a heavy chain variable region comprising the amino acid sequence of SEQ ID NO: 44, and a light chain variable region comprising the amino acid sequence of SEQ ID NO: 55.

24. A pharmaceutical composition comprising the antibody molecule of claim 23 and a pharmaceutically acceptable carrier, excipient, or stabilizer.

25. An antibody molecule that binds to human CD73, comprising a heavy chain comprising the amino acid sequence of SEQ ID NO: 46, wherein residue 451 of SEQ ID NO: 46 is K, and a light chain comprising the amino acid sequence of SEQ ID NO: 57.

26. A pharmaceutical composition comprising the antibody molecule of claim 25 and a pharmaceutically acceptable carrier, excipient, or stabilizer.

* * * * *

UNITED STATES PATENT AND TRADEMARK OFFICE

CERTIFICATE OF CORRECTION

PATENT NO. : 11,312,783 B2
APPLICATION NO. : 16/014744
DATED : April 26, 2022
INVENTOR(S) : Prinz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 628 days.

Signed and Sealed this
Eleventh Day of February, 2025

Coke Morgan Stewart
*Acting Director of the United States Patent and Trademark Office*